(12) United States Patent
Gude et al.

(10) Patent No.: US 8,114,867 B2
(45) Date of Patent: Feb. 14, 2012

(54) OXAZOLIDINONE ANTIBIOTIC DERIVATIVES

(75) Inventors: Markus Gude, Allschwil (CH);
Christian Hubschwerlen, Durmenach (FR); Georg Rueedi, Allschwil (CH);
Jean-Philippe Surivet, Kembs (FR);
Cornelia Zumbrunn-Acklin, Basel (CH)

(73) Assignee: Actelion Pharmaceuticals Ltd, Allschwil (CH)

( * ) Notice: Subject to any disclaimer, the term of this patent is extended or adjusted under 35 U.S.C. 154(b) by 180 days.

(21) Appl. No.: 12/595,711

(22) PCT Filed: Apr. 10, 2008

(86) PCT No.: PCT/IB2008/051356
§ 371 (c)(1),
(2), (4) Date: Oct. 13, 2009

(87) PCT Pub. No.: WO2008/126024
PCT Pub. Date: Oct. 23, 2008

(65) Prior Publication Data
US 2010/0137290 A1    Jun. 3, 2010

(30) Foreign Application Priority Data

Apr. 11, 2007  (WO) .................. PCT/IB2007/051292
Feb. 29, 2008  (WO) .................. PCT/IB2008/050746

(51) Int. Cl.
C07D 471/04   (2006.01)
C07D 413/14   (2006.01)
C07D 417/14   (2006.01)
A61K 31/4375  (2006.01)

(52) U.S. Cl. ....... 514/224.2; 544/51; 544/354; 544/284; 544/105; 546/155; 546/122; 514/300; 514/312; 514/249; 514/266.24; 514/230.5

(58) Field of Classification Search .................... 544/51, 544/354, 105, 284; 514/224.2, 300, 312, 514/249, 266.24, 230.5; 546/122, 155
See application file for complete search history.

(56) References Cited

U.S. PATENT DOCUMENTS
2007/0060558 A1   3/2007  Sanchez et al.

FOREIGN PATENT DOCUMENTS

| DE | 103 16 081 | 10/2004 |
|---|---|---|
| EP | 1 484 304 | 12/2004 |
| WO | WO 96/33195 | 10/1996 |
| WO | WO 99/58533 | 11/1999 |
| WO | WO 00/40554 | 7/2000 |
| WO | WO 00/78748 | 12/2000 |
| WO | WO 01/00615 | 1/2001 |
| WO | WO 02/08224 | 1/2002 |
| WO | WO 02/50040 | 6/2002 |
| WO | WO 02/096907 | 12/2002 |
| WO | WO 03/087098 | 10/2003 |
| WO | WO 2004/002490 | 1/2004 |
| WO | WO 2004/002992 | 1/2004 |
| WO | WO 2004/035569 | 4/2004 |
| WO | WO 2004/050036 | 6/2004 |
| WO | WO 2004/058144 | 7/2004 |
| WO | WO 2004/089947 | 10/2004 |
| WO | WO 2006/002047 | 1/2006 |
| WO | WO 2006/010831 | 2/2006 |

(Continued)

OTHER PUBLICATIONS

Bal et al., Tetrahedron, Great Britain vol. 37, pp. 2091-2096 (1981).

(Continued)

*Primary Examiner* — Kahsay T Habte
(74) *Attorney, Agent, or Firm* — Hunton & Williams LLP

(57) ABSTRACT

The invention relates to antibacterial compounds of formula I

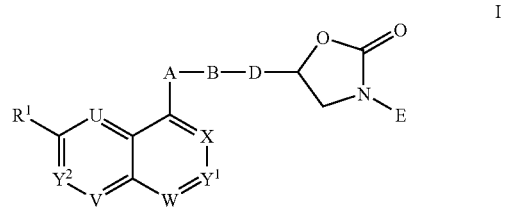

wherein $R^1$ is hydrogen, halogen, hydroxy, alkoxy or cyano; $Y^1$ and $Y^2$ each represent CH, one or two of U, V, W and X represent(s) N and the remaining each represent CH or, in the case of X, may also represent $CR^a$, $R^a$ being halogen, and, in the case of W, may also represent $CR^b$, or each of U, V, W, X, $Y^1$ and $Y^2$ represents CH, or each of U, V, W, X and $Y^1$ represents CH and $Y^2$ represents N, or also one or, provided $R^1$ is hydrogen, two of U, V, W, X, $Y^1$ and $Y^2$ represent(s) CRC and the remaining each represent CH, $R^b$ being alkoxy, alkoxycarbonyl or alkoxyalkoxy and $R^c$ being, each time it occurs, independently represents hydroxy or alkoxy; A-B-D represents a chain of 4 to 6 atoms, which 4 to 6 atoms are selected from carbon, oxygen and nitrogen and may be substituted; E is one of the following groups:

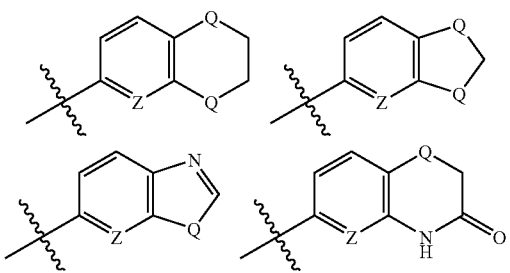

in which Z is CH or N and Q is O or S, or E is a phenyl group which is substituted once or twice in the meta and/or para position(s); and to salts of such compounds.

11 Claims, No Drawings

FOREIGN PATENT DOCUMENTS

| | | |
|---|---|---|
| WO | WO 2006/021448 | 3/2006 |
| WO | WO 2006/032466 | 3/2006 |
| WO | WO 2006/046552 | 5/2006 |
| WO | WO 2006/058700 | 6/2006 |
| WO | WO 2006/010831 | 8/2006 |
| WO | WO 2006/093253 | 9/2006 |
| WO | WO 2006/105289 | 10/2006 |
| WO | WO 2007/016610 | 2/2007 |
| WO | WO 2007/069555 | 6/2007 |
| WO | WO 2007/086016 | 8/2007 |

OTHER PUBLICATIONS

Cha et al., Chemical Reviews—American Chemical Society, vol. 95, No. 6, pp. 1761-1795 (1995).
Chen et al., Organic Letters, vol. 8, No. 24, pp. 5609-5612, Sep. 2006.
Fatiadi, Synthesis—Reviews, pp. 85-111, Feb. 1987.
Greene, T.W., "Protection for the Amino Group", Protecting Groups in Organic Synthesis, 3$^{rd}$ Ed (1999), pp. 494-653.
Kolb et al., Chemical Reviews—American Chemical Society, vol. 94, No. 8, pp. 2483-2547 (1994).
Larock, Comprehensive Organic Transformations—A guide to Functional Group Preparations, pp. 779-784, © 1999.
Mancuso et al., Journal of Organic Chemistry, vol. 43, No. 12 pp. 2480-2482, (1978).
Margolis et al., Journal of Organic Chemistry, vol. 72, pp. 2232-2235, Oct. 2006.
Martin, The Journal of Organic Chemistry, vol. 48, No. 22, pp. 4155-4156, Nov. 1983.
Schaus et al., Journal of the American Chemical Society, vol. 124, No. 7, pp. 1307-1315 (2002).
Shi, Accounts of Chemical Research—Articles, vol. 37, No. 8, pp. 488-496, Mar. 2004.
Tokunaga et al., Science, vol. 277, pp. 936-938, Aug. 1997, www.sciencemag.org.
Toto et al., Tetrahedron Letters, vol. 47, pp. 1181-1186 (2006) www.sciencedirect.com.
Vanrheenen et al., Tetrahedron Letters, Pergamon Press, Great Britain, No. 23, pp. 1973-1976 (1976).
Walters et al., Journal of Combinatorial Chemistry, vol. 4, No. 2, pp. 125-130 (2002).
Asensio, et al., "Epoxidation of Primary and Secondary Alkenylammonium Salts with Dimethyldioxirane, Methyl(trifluoromethyl)dioxirane, and m-Chloroperbenzoic Acid. A General Synthetic Route to Epoxyalkylamines," J. Org. Chem (1995), 60:3692-3699 .
Belanger, et al., "New Approach to Aphidicolin and Total Asymmetric Synthesis of Unnatural (11R)-(−)-8-Epi-11-hydroxyaphidicolin by Tandem Transannular Diels-Alder/Aldol Reactions," J. Org. Chem. (2000), 65:7070-7074.
Benz, G., "Synthesis of Amides and Related Compounds, Comprehensive Organic Synthesis." Comprehensive Organic Synthesis—Selectivity, Strategy and Efficiency in Modern Organic Chemistry, vol. 6, Section 2:2.3, edited by: Trost, Barry M.; Fleming, Ian © 1991 Elsevier, Pergamon Press, NY, p. 381-417 (1991).
Chang, et al., "Triazolinones as Nonpeptides Angiotensin II Antagonists. 1. Synthesis and Evaluation of Potent 2,4,5-Trisubstituted Triazolinones,". J. Med. Chem (1993), 36:2558-2568.
Chincilla, et al., "The Sonogashira Reaction: A Booming Methodology in Synthetic Organic Chemistry," Chem. Rev. (2007), 107(3) 874-922.
Corey and Fuchs, "A Synthetic Method for Formyl→Ethynyl Conversion (RCHO→ RC≡CH or RC≡CR')," Tetrahedron Letters (1972), 36:3769-3772.
Denmark, et al., "Lewis Base Activation of Lew Acids: Catalytic, Enantioselective Addition of Silyl Ketene Acetals to Aldehydes," J. Am. Chem. Soc. (2005), 127:3774-3789.
Diederich and Stang, edited, "Metal-Catalyzed Cross-coupling Reactions," Contents pages, Wiley-VCH: Weinheim, Germany, 1998.
Echavarren, et al., "Palladium-Catalyzed Coupling of Aryl Triflates with Organostannenes," J. Am. Chem. Soc. (1987), 109:5478-5486.

Fernandez, et al., "Synthesis of enantiomerically pure (+)- and (−)-protected 5-aminomethy1-1,3-oxazolidin-2-one derivatives from allylamine and carbon dioxide," Tetrahedron: Asymmetry (2006), 17:2548-2557.
Fukuyama, et al., "2- and 4-Nitrobenzenesulfonamides: Exceptionally Versatile Means for Preparation of Secondary Amines and Protection of Amines," Tetrahedron Lett. (1995), 36(36):6373-6374.
Georgalis, et al., "Ordering of Fractal Clusters in Crystallizing Lysozyme Solutions," J. Chem. Soc., (1999), 121(8):1627-1630.
Gooding, et al., "Synthesis of Some Carbocyclic Nucleoside Analogues Based on a Bicyclo[3.1.0]hexane Ring System," J. Chem. Soc., (1994), 1891-1892.
Gould, "Salt selection for basic drugs," Int. J. Pharm. (1986), 33:201-217.
Green & Wuts, Section 2: "Protection for the Hydroxyl Group, Including 1,2- and 1,3-Diols," Protecting Groups in Organic Synthesis 3rd Ed; 1999, pp. 23-245 (specifically 23-147, 133-139 and 142-143), John Wiley and Sons, Inc. Publisher, New York, NY.
Green & Wuts, Section 5: "Protection for the Carboxyl Group," Protecting Groups in Organic Synthesis 3rd Ed; 1999, pp. 369-453, John Wiley and Sons, Inc. Publisher New York, N. Y.
Heck, Richard, "Palladium-Catalyzed Vinylation of Organic Halides," Organic Reactions, (1982) 27:345-390.
Johnson, et al., "Cyclization Studies in the Quinoline Series. A New Synthesis of 4-Aminoquinolines," J. Am. Chem. Soc. (1949), 71(6):1901-1905.
Kanth & Brown, "Hydroboration. 97. Synthesis of New Exceptional Chloroborane-Lewis Base Adducts for Hydroboration. Dioxane-Monochloroborane as a Superior Reagent for the Selective Hydroboration of Terminal Alkenes," J. Org. Chem., 66:5359-5365 (2001).
Kotsuki, et al., "Stereoselective Reduction of Bicyclic Ketals. A New, Enantioselective Synthesis of Isolaurepinnacin and Lauthisan Skeletons," J. Org. Chem. (1989), 54(21), 5153-5161.
Langford, et al., "A Three Component Metalloporphyrin Assembly," Aust. J. Chem. (2004), 57:29-32.
Larock, R.C., Comprehensive Organic Transformation, A guide to Functional Group Preparations; 2nd Edition, Wiley-VC; New York, Chichester, Weinheim, Brisbane, Singapore, Toronto, 1999, Nitriles, Carboxylic Acids and Derivatives, Section 1, pp. 1646-1648 and 1653-1655; Section 9, pp. 1941-1949 and pages of Contents, Literature and Chemical Abbreviations.
Liu, et al., "Facile synthesis of versatile functionalized amino caprolactams using RCM reactions of α-amino acrylamide," Tetrahedron Lett. (2006), 47:3295-3298.
Meijere, Armin de and Meyer, Frank E, "Fine Feathers Make Fine Birds: The Heck Reaction in Modern Garb," Angew. Chem. Int. Ed. Engl. (1994), 33(23-24), 2379-2411.
Mislow and Koepfli, "The Synthesis of Potential Antimalarials. Some 2-Substituted 8-(3-Diethylaminopropylamine)-quinolines," J. Am. Chem. Soc. (1946), 1553-1556.
Nicolaou, et al., "Total Synthesis of the Originally Proposed and Revised Structures of Palmerolide A," Angew. Chem. Int. Ed. (2007), 46(31):5896-5900.
Panek & Liu, Total Synthesis of the Actin-Depolymeri zing Agent (−)-Mycalolide A: Application of Chiral Silane-Based Bond Construction Methodology, J. Am. Chem. Soc., vol. 122 (45):11090-11097 (2000).
Payne, et al., "Synthesis and protein conjugation studies of vitamin K analogues," Bioorg. & Med. Chem. (2004), 12:5785-5791.
Pelter, et al. "4.1 Oxidation of Carbon-Boron Bonds," Comprehensive Organic Synthesis, Edited by Trost, and Fleming, Pergamon Press: New York (1991), vol. 7, p. 593-611.
Perrault, et al., "The Synthesis of N-Aryl-5(S)-aminomethyl-2-oxazolidinone Antibacterials and Derivatives in One Step from Aryl Carbamates," Org. Process Research and Development (2003), 7:533-546.
Reddy, et al., "A Highly Effective Catalyst System for the Pd-Catalyzed Amination of Vinyl Bromides and Chlorides," Org. Lett. (2005), 7(20):4427-4430.
Remington, The Science and Practice of Pharmacy, 21st Edition, Contents pages (2005), published by Lippincott Williams & Wilkins.

Sato, et al., "One-pot reductive amination of aldehydes and ketones with α-picoline-borane in methanol, in water, and in neat conditions," *Tetrahedron* (2004), 60:7899-7906.

Smith & Pelter., "Hydroboration of C=C and C≡C," Comprehensive Organic Synthesis—Selectivity, Strategy and Efficiency in Modern Organic Chemistry, vol. 8, Section 3.10, edited by: Trost and Fleming, Pergamon Press: New York (1991), p. 703-731.

Soffer, et al., "High Moleccular Weight Hydrocarbons. II. Five New Hydrocarbons Derived from Sebacic Acid," *J. Chem. Soc.* (1946), 1684-1688.

Taillier, et al., "Synthesis of 3-Oxoazacyclohept-4-enes by Ring-Closing Metathesis. Application to the Synthesis of an Inhibitor of Cathepsin K," *Heterocycles* (2006), 67(2), 549-554.

Takeuchi, et al. "Iridium Complex-Catalyzed Allylic Amination of Allylic Esters," *J. Am. Chem. Soc.* (2001), 123:9525-9534.

Turner, James A., "A general approach to the synthesis of 1,6-, 1,7-, and 1,8-naphthyridines," *J. Org. Chem.*, 1990, 55 (15):4744-4750.

Walsh, et al., "Asymmetric Dihydroxylation (AD)/Cyclization of N-DiBoc Allylic and Homoallylic Amines: Selective Differentiation of the Hydroxyl Groups," *Tetrahedron Lett.* (1993), 34(35):5545-5548.

OXAZOLIDINONE ANTIBIOTIC DERIVATIVES

CROSS-REFERENCE TO RELATED APPLICATIONS

This application is the U.S. National Stage filing of International Application No. PCT/IB2008/051356, filed Apr. 10, 2008, which claims priority to International Application No. PCT/IB2007/051292, filed Apr. 11, 2007, and International Application No. PCT/IB2008/050746, filed Feb. 29, 2008, the disclosures of which is hereby incorporated by reference in their entirety.

BACKGROUND OF THE INVENTION

The intensive use of antibiotics has exerted a selective evolutionary pressure on micro-organisms to produce genetically based resistance mechanisms. Modern medicine and socio-economic behaviour exacerbates the problem of resistance development by creating slow growth situations for pathogenic microbes, e.g. in artificial joints, and by supporting long-term host reservoirs, e.g. in immuno-compromised patients.

In hospital settings, an increasing number of strains of *Staphylococcus aureus, Streptococcus pneumoniae, Enterococcus* spp., and *Pseudomonas aeruginosa*, major sources of infections, are becoming multi-drug resistant and therefore difficult if not impossible to treat:

- *S. aureus* is resistant to β-lactams, quinolones and now even to vancomycin;
- *S. pneumoniae* is becoming resistant to penicillin or quinolone antibiotics and even to new macrolides;
- *Enteroccocci* are quinolone and vancomycin resistant and β-lactam antibiotics are inefficacious against these strains;
- Enterobacteriacea are cephalosporin and quinolone resistant;
- *P. aeruginosa* are β-lactam and quinolone resistant.

Further new emerging organisms like *Acinetobacter* spp. or *C. difficile*, which have been selected during therapy with the currently used antibiotics, are becoming a real problem in hospital settings.

In addition, microorganisms that are causing persistent infections are increasingly being recognized as causative agents or cofactors of severe chronic diseases like peptic ulcers or heart diseases.

WO 2006/010831 describes inter alia substituted 4-quinoline derivatives which do however notably not possess the oxazolidinone motif of the invention compounds.

WO 02/50040 discloses inter alia substituted 4-quinoline derivatives compounds which could have the oxazolidinone motif but always include a piperazine ring in their middle chain.

Besides, WO 2006/032466 discloses antibacterial compounds that possess certain motifs of the instant invention, i.e. the alkoxy-substituted quinoline, naphthyridine, quinoxaline or quinazoline and the benzofused bicyclic system at both ends of the molecule, but not the oxazolidinone motif attached to said benzofused bicyclic system.

BRIEF SUMMARY OF THE INVENTION

The present invention concerns novel oxazolidinone antibiotic derivatives, a pharmaceutical antibacterial composition containing them and the use of these compounds in the manufacture of a medicament for the treatment of infections (e.g. bacterial infections). These compounds are useful antimicrobial agents effective against a variety of human and veterinary pathogens including among others Gram positive and Gram negative aerobic and anaerobic bacteria and mycobacteria.

DETAILED DESCRIPTION OF THE INVENTION

Various embodiments of the invention are presented hereafter:

i) The invention firstly relates to compounds of formula I

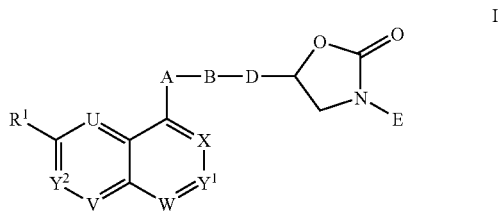

wherein $R^1$ is hydrogen, halogen, hydroxy, alkoxy or cyano;

$Y^1$ and $Y^2$ each represent CH and one or two of U, V, W and X represent(s) N and the remaining each represent CH or, in the case of X, may also represent $CR^a$, and, in the case of W, may also represent $CR^b$, or each of U, V, W, X, $Y^1$ and $Y^2$ represents CH or each of U, V, W, X and $Y^1$ represents CH and $Y^2$ represents N, or also one or, provided $R^1$ is hydrogen, two of U, V, W, X, $Y^1$ and $Y^2$ represent(s) $CR^c$ and the remaining each represent CH;

$R^a$ represents halogen;

$R^b$ represents alkoxy, alkoxycarbonyl or alkoxyalkoxy;

$R^c$, each time it occurs, independently represents hydroxy or alkoxy;

A is $CH_2CH(OH)$, $CH_2CH(NH_2)$, $CH(OH)CH(NH_2)$ or $CH(NH_2)CH_2$, B is $CH_2CH_2$, $CH_2NH$ or CONH and D is $CH_2$, or A is $CH(OH)CH_2$ and either B is $CH_2CH_2$, $CH_2NH$, $N(R^2)$CO, CONH or $N(R^2)CH_2$ and D is $CH_2$ or B is $N(R^{2a})CH_2$ and D is CH(OH), or A is CH(OH)CH(OH), B is $CH_2NH$ or CONH and D is $CH_2$, or A is $CH_2CH_2$ and either B is $CH_2CH_2$, $NR^{4a}CH_2$, $CH_2NR^3$, NHCO, $CONR^4$, $CH_2O$, $CH(OH)CH_2$, $CH_2CH(OH)$, $CH(NHR^{3a})CH_2$, $COCH_2$ or $CH_2CH_2NH$ and D is $CH_2$ or B is $CH_2NH$ and D is CO, or also A is $CH_2CH_2$, B is $NR^{4b}CH_2$ or $CH_2CH_2$ and D is CH(OH), or A is CH=CH, B is $CH_2NR^5$, $CONR^6$ or $CH_2O$ and D is $CH_2$, or A is C≡C, B is $CH_2NH$ and D is CO, or A is $CH_2CO$, B is $NHCH_2$ and D is $CH_2$, or A is $COCH_2$, B is $CH_2CH_2$ or CONH and D is $CH_2$, or A is $CH_2N(R^7)$ and either B is $CH_2CH_2$, $COCH_2$ or $CH_2CH(OH)$ (and notably $CH_2CH_2$ or $COCH_2$) and D is $CH_2$ or B is $CH_2CH_2$ or $CH_2CH(OH)$ and D is CH(OH) or $CH(NH_2)$, or A is CONH or $CH_2O$, B is $CH_2CH_2$ and D is $CH_2$, or A is $NHCH_2$ and either B is $CH_2CH_2$ or $CH_2NH$ and D is $CH_2$, or B is $CH_2NH$ and D is CO, or A is NHCO, B is $CH(R^8)NH$ or $CH_2CH_2$ and D is $CH_2$, or A is $OCH_2$, B is $CH_2$, $CH_2CH_2$, CH=CH or CONH and D is $CH_2$;

$R^2$ is hydrogen or alkyl;

$R^{2a}$ is hydrogen or alkyl;

R³ is hydrogen, phenylalkyl, CO—(CH₂)$_p$—COOR³', (CH₂)$_p$—COOR³', acyl or aminoalkyl, or also R³ is alkyl which may be substituted once or twice by hydroxy groups, p being an integer from 1 to 4 and R³' being hydrogen or alkyl;

R$^{3a}$ is hydrogen, acyl or alkylsulfonyl;

R⁴ is hydrogen or alkyl;

R$^{4a}$ is hydrogen or (CH₂)$_q$—COOR$^{4a'}$, or also R$^{4a}$ is alkyl which may be substituted once or twice by hydroxy groups, q being an integer from 1 to 4 and R$^{4a'}$ being hydrogen or alkyl;

R$^{4b}$ is hydrogen or alkyl;

R⁵ is hydrogen or acyl;

R⁶ is hydrogen, alkyl or phenylalkyl;

R⁷ is hydrogen or (CH₂)$_r$—COOR⁷', or also R⁷ is alkyl which may be substituted once or twice by groups independently selected from hydroxy, halogen, amino and dimethylamino (and notably from hydroxy, halogen and dimethylamino), r being an integer from 1 to 4 and R⁷' being hydrogen or alkyl;

R⁸ is hydrogen or alkyl;

E is one of the following groups:

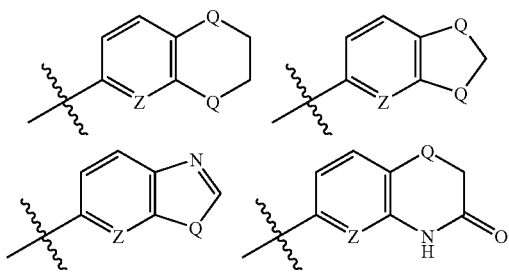

wherein Z is CH or N and Q is O or S, or

E is a phenyl group which is substituted once or twice in the meta and/or para position(s) by substituents each independently selected from the group consisting of halogen, (C₁-C₃) alkyl, (C₁-C₃)alkoxy, trifluoromethyl and trifluoromethoxy (and preferably each independently selected from the group consisting of halogen, (C₁-C₃)alkyl and trifluoromethyl);

and to salts (in particular pharmaceutically acceptable salts) of compounds of formula I.

The compounds of formula I may contain one or more stereogenic or asymmetric centers, such as one or more asymmetric carbon atoms. Substituents at a double bond may be present in the Z- or E-configuration unless indicated otherwise. The compounds of formula I may thus be present as mixtures of stereoisomers or preferably as pure stereoisomers. Mixtures of stereoisomers may be separated in a manner known to a person skilled in the art.

The following paragraphs provide definitions of the various chemical moieties for the compounds according to the invention and are intended to apply uniformly throughout the specification and claims, unless an otherwise expressly set out definition provides a broader or narrower definition:

The term "alkyl", used alone or in combination, refers to a straight or branched chain alkyl group, containing from one to six and preferably one to four carbon atoms. Representative examples of alkyl groups include, but are not limited to, methyl, ethyl, propyl, iso-propyl, n-butyl, iso-butyl, sec-butyl, tert-butyl, n-pentyl, iso-pentyl, n-hexyl or 2,2-dimethylbutyl. The term "(C₁-C$_x$)alkyl" (x being an integer) refers to a straight or branched chain alkyl group of 1 to x carbon atoms.

The term "alkoxy", used alone or in combination, refers to a straight or branched chain alkoxy group, containing from one to six and preferably one to four carbon atoms. Representative examples of alkoxy groups include, but are not limited to, methoxy, ethoxy, propoxy, iso-propoxy, n-butoxy, iso-butoxy, sec-butoxy, tert-butoxy or n-hexyloxy. The term "(C₁-C$_x$)alkoxy" refers to a straight or branched chain alkoxy group of 1 to x carbon atoms.

The term "alkoxycarbonyl" refers to an ester group wherein the alkoxy group is a straight or branched chain alkoxy group containing from one to four carbon atoms. Representative examples of alkoxycarbonyl include, but are not limited to, methoxycarbonyl and ethoxycarbonyl.

The term "alkoxyalkoxy" refers to a straight or branched chain alkoxy group of one to four carbon atoms wherein one hydrogen atom has been replaced by a straight or branched chain alkoxy group of one to four carbon atoms. Representative examples of alkoxyalkoxy include, but are not limited to, methoxyethoxy and methoxymethoxy.

The term "halogen" refers to fluorine, chlorine, bromine or iodine, preferably to fluorine or bromine and more preferably to fluorine.

The term "acyl" refers to a straight or branched chain acyl group, containing from two to seven and preferably two to five carbon atoms. Representative examples of acyl groups include, but are not limited to, acetyl, propionyl, butyryl, pentanoyl, hexanoyl or 3,3-dimethypentanoyl.

The term "phenylalkyl" refers to an alkyl group wherein one of the hydrogen atoms has been replaced by an unsubstituted phenyl group. Representative examples of phenylalkyl include, but are not limited to, benzyl, 2-phenylethyl and 3-phenylpropyl.

The term "alkylsulfonyl" refers to an alkylsulfonyl group wherein the alkyl group is a straight or branched chain alkyl group containing from one to four carbon atoms. Representative examples of alkylsulfonyl include, but are not limited to, methylsulfonyl and ethylsulfonyl.

In this patent application, a bond interrupted by a wavy line shows the point of attachment of the radical drawn. For example, the radical drawn below

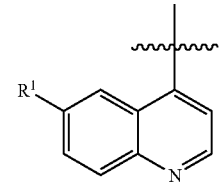

wherein R¹ represents methoxy is the 6-methoxy-quinolin-4-yl group.

When in the formula

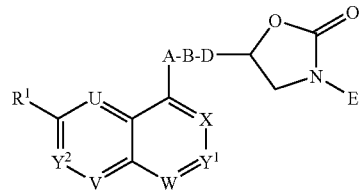

B represents the radical NHCH$_2$, this means specifically that the nitrogen atom of the latter radical is attached to the A group whereas the carbon atom bearing the two hydrogen atoms is attached to the D group.

This is applicable mutatis mutandis to all radicals that make A or B radicals. As a further example, in the substructure B, if it is stated that B represents CH$_2$NH, it is thereby meant that the nitrogen atom of the CH$_2$NH radical is attached to the D group and that the carbon atom of the CH$_2$NH radical is attached to the A group. In other words, the left part of a radical is always attached to the right part of the radical that is next to the left.

In the nomenclature of the molecules, the use of two mentions "R*" means that the configurations at the two relevant carbons are either both "R" or both "S", whereas the use of a mention "R*" in conjunction with a mention "S*" means that the configuration at the first relevant carbon is "R" whereas the configuration at the second relevant carbon is "S" or vice versa.

Besides, the term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

ii) The invention relates notably to compounds of formula I as defined in embodiment i) that are also compounds of formula $I_{P1}$

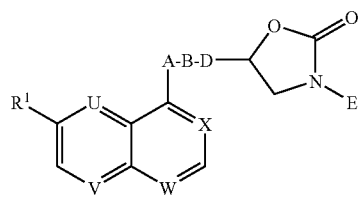

wherein
R$^1$ is hydrogen, halogen, alkoxy or cyano;
one or two of U, V, W and X represent(s) N and the remaining each represent CH or, in the case of X, may also represent CR$^a$;
R$^a$ represents halogen;
A is CH$_2$CH(OH), CH$_2$CH(NH$_2$), CH(OH)CH(NH$_2$) or CH(NH$_2$)CH$_2$, B is CH$_2$CH$_2$, CH$_2$NH or CONH and D is CH$_2$, or
A is CH(OH)CH$_2$, B is CH$_2$CH$_2$, CH$_2$NH, N(R$^2$)CO or CONH and D is CH$_2$, or
A is CH(OH)CH(OH), B is CH$_2$NH or CONH and D is CH$_2$, or
A is CH$_2$CH$_2$ and either B is NHCH$_2$, CH$_2$NR$^3$, NHCO or CONR$^4$ and D is CH$_2$ or B is CH$_2$NH and D is CO, or
A is CH=CH, B is CH$_2$NR$^5$ or CONR$^6$ and D is CH$_2$, or
A is C≡C, B is CH$_2$NH and D is CO, or
A is CH$_2$CO, B is NHCH$_2$ and D is CH$_2$, or
A is COCH$_2$, B is CH$_2$CH$_2$ or CONH and D is CH$_2$, or
A is CH$_2$N(R$^7$), B is CH$_2$CH$_2$ or COCH$_2$ and D is CH$_2$, or
A is CONH, B is CH$_2$CH$_2$ and D is CH$_2$, or
A is NHCH$_2$ and either B is CH$_2$CH$_2$ or CH$_2$NH and D is CH$_2$, or B is CH$_2$NH and D is CO, or
A is NHCO, B is CH(R$^8$)NH or CH$_2$CH$_2$ and D is CH$_2$;
R$^2$ is hydrogen or alkyl;
R$^3$ is hydrogen, alkyl, phenylalkyl, CO—(CH$_2$)$_p$—COOH, acyl or aminoalkyl,
p being an integer from 1 to 4;
R$^4$ is hydrogen or alkyl;
R$^5$ is hydrogen or acyl;
R$^6$ is hydrogen, alkyl or phenylalkyl;
R$^7$ is hydrogen or alkyl;
R$^8$ is hydrogen or alkyl;
E is a group of the formula

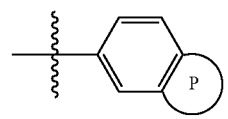

wherein P is a ring selected from the group consisting of the following rings:

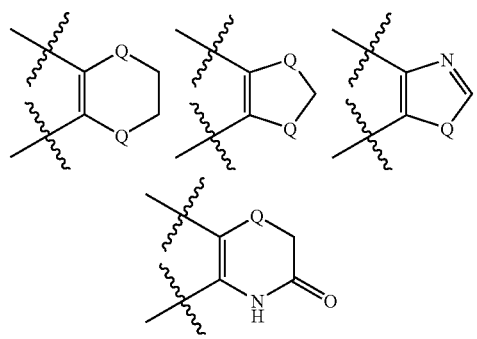

in which Q is O or S, or
E is a phenyl group which is substituted once or twice in the meta and/or para position(s) by substituents each independently selected from the group consisting of halogen, (C$_1$-C$_3$) alkyl, (C$_1$-C$_3$)alkoxy, trifluoromethyl and trifluoromethoxy (and preferably each independently selected from the group consisting of halogen, (C$_1$-C$_3$)alkyl and trifluoromethyl);
and to salts (in particular pharmaceutically acceptable salts) of compounds of formula I.

iii) In particular, the invention relates to compounds of formula I as defined in embodiment i) that are also compounds of formula $I_{CE}$

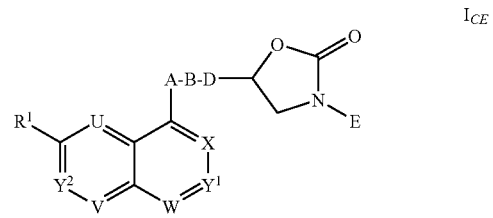

wherein
R$^1$ is hydrogen, halogen, hydroxy, alkoxy or cyano;
Y$^1$, Y$^2$ and V each represent CH, X represents CH or CR$^a$ and U and W each represent N, or Y$^1$, Y$^2$ and X each represent CH, W represents CH or CR$^b$ and U and V each represent N, or $Y^1$, $Y^2$, U and V each represent CH and W and X each represent N, or $Y^1$, $Y^2$, U and V each represent CH, X represents CH or $CR^a$ and W represents N, or $Y^1$, $Y^2$, U, W each represent CH, X represents CH or $CR^a$ and V represents N, or $Y^1$, $Y^2$, V and W each represent CH, X represents CH or $CR^a$ and U represents N, or $Y^1$, $Y^2$, X and V each represent CH, W represents $CR^{b'}$ and U represents N, or each of U, V, W, X, $Y^1$ and $Y^2$ represents CH, or each of U, V, W, X and $Y^1$ represents CH and $Y^2$ represents N, or also each of U, V, X, $Y^1$ and $Y^2$ represents CH and W represents $CR^c$, or each of U, V, W, $Y^1$ and $Y^2$ represents CH and X represents $CR^c$, or each of U, V, W and $Y^2$ represents CH and X and $Y^1$ each represent $CR^c$;

$R^a$ represents halogen (especially florine);
$R^b$ represents alkoxyalkoxy;
$R^{b'}$ represents alkoxycarbonyl;
$R^c$, each time it occurs, independently represents hydroxy or alkoxy (and preferably hydroxy or methoxy);

A is $CH_2CH(OH)$, $CH_2CH(NH_2)$, $CH(OH)CH(NH_2)$ or $CH(NH_2)CH_2$, B is $CH_2CH_2$, $CH_2NH$ or CONH and D is $CH_2$ (it being understood that when A is $CH_2CH(OH)$, $CH_2CH(NH_2)$, $CH(OH)CH(NH_2)$ or $CH(NH_2)CH_2$, B is $CH_2CH_2$, $CH_2NH$ or CONH and D is $CH_2$, the cases wherein A is $CH_2CH(OH)$, B is CONH and D is $CH_2$, A is $CH_2CH(NH_2)$, B is $CH_2NH$ or CONH and D is $CH_2$, A is $CH(OH)CH(NH_2)$, B is CONH and D is $CH_2$ or A is $CH(NH_2)CH_2$, B is $CH_2CH_2$, $CH_2NH$ or CONH and D is $CH_2$ will be preferred), or A is $CH(OH)CH_2$ and either B is $CH_2CH_2$, $CH_2NH$, $N(R^2)CO$, CONH or $N(R^2)CH_2$ and D is $CH_2$ or B is $N(R^{2a})CH_2$ and D is $CH(OH)$, or A is $CH(OH)CH(OH)$, B is $CH_2NH$ or CONH and D is $CH_2$, or A is $CH_2CH_2$ and either B is $CH_2CH_2$, $NR^{4a}CH_2$, $CH_2NR^3$, NHCO, $CONR^4$, $CH_2O$, $CH(OH)CH_2$, $CH_2CH(OH)$, $CH(NHR^{3a})CH_2$, $COCH_2$ or $CH_2CH_2NH$ and D is $CH_2$ or B is $CH_2NH$ and D is CO, or also A is $CH_2CH_2$, B is $NR^{4b}CH_2$ or $CH_2CH_2$ and D is CH(OH), or A is CH=CH, B is $CH_2NR^5$, $CONR^6$ or $CH_2O$ and D is $CH_2$, or A is C≡C, B is $CH_2NH$ and D is CO, or
A is $CH_2CO$, B is $NHCH_2$ and D is $CH_2$, or
A is $COCH_2$, B is $CH_2CH_2$ or CONH and D is $CH_2$, or
A is $CH_2N(R^7)$ and either B is $CH_2CH_2$, $COCH_2$ or $CH_2CH(OH)$ (and notably $CH_2CH_2$ or $COCH_2$) and D is $CH_2$ or B is $CH_2CH_2$ or $CH_2CH(OH)$ and D is CH(OH) or $CH(NH_2)$, or A is CONH or $CH_2O$, B is $CH_2CH_2$ and D is $CH_2$, or
A is $NHCH_2$ and either B is $CH_2CH_2$ or $CH_2NH$ and D is $CH_2$, or B is $CH_2NH$ and D is CO, or A is NHCO, B is $CH(R^8)NH$ or $CH_2CH_2$ and D is $CH_2$, or
A is $OCH_2$, B is $CH_2$, $CH_2CH_2$, CH=CH or CONH and D is $CH_2$;

$R^2$ is hydrogen or alkyl;
$R^{2a}$ is hydrogen or alkyl;
$R^3$ is hydrogen, phenylalkyl, CO—$(CH_2)_p$—$COOR^{3'}$, $(CH_2)_p$—$COOR^{3'}$, acyl or aminoalkyl, or also $R^3$ is alkyl which may be substituted once or twice by hydroxy groups, p being an integer from 1 to 4 and $R^{3'}$ being hydrogen or alkyl;
$R^{3a}$ is hydrogen, acyl or alkylsulfonyl;
$R^4$ is hydrogen or alkyl;
$R^{4a}$ is hydrogen or $(CH_2)_q$—$COOR^{4a'}$, or also $R^{4a}$ is alkyl which may be substituted once or twice by hydroxy groups, q being an integer from 1 to 4 and $R^{4a'}$ being hydrogen or alkyl (and preferably alkyl);
$R^{4b}$ is hydrogen or alkyl;
$R^5$ is hydrogen or acyl;
$R^6$ is hydrogen, alkyl or phenylalkyl;

$R^7$ is hydrogen or $(CH_2)_r$—$COOR^{7'}$, or also $R^7$ is alkyl which may be substituted once or twice by groups independently selected from hydroxy, halogen, amino and dimethylamino (and notably from hydroxy, halogen and dimethylamino), r being an integer from 1 to 4 and $R^{7'}$ being hydrogen or alkyl;

$R^8$ is hydrogen or alkyl (in particular hydrogen or methyl);
E is one of the following groups

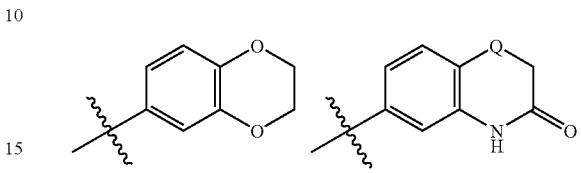

in which Q is O or S, or

E is a phenyl group which is substituted once or twice in the meta and/or para position(s) by substituents each independently selected from the group consisting of halogen, $(C_1$-$C_3)$alkyl, $(C_1$-$C_3)$alkoxy, trifluoromethyl and trifluoromethoxy (and preferably each independently selected from the group consisting of halogen, $(C_1$-$C_3)$alkyl and trifluoromethyl);

and to salts (in particular pharmaceutically acceptable salts) of compounds of formula $I_{CE}$.

iv) In particular, the invention relates to compounds of formula $I_{CE}$ as defined in embodiment iii) that are also compounds of formula $I_{CEP1}$

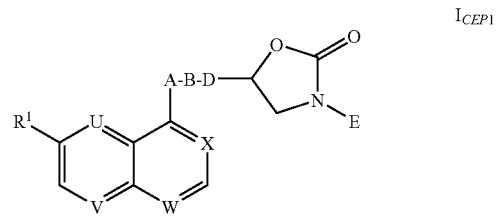

wherein
$R^1$ is hydrogen, halogen, alkoxy (in particular methoxy) or cyano;
U and W each represent N and V and X each represent CH, or W and X each represent N and U and V each represent CH, or U represents N and V, W and X each represent CH, or V represents N and U, W and X each represent CH, or V represents N, U and W each represent CH and X represents $CR^a$, or U and W each represent N, V represents CH and X represents $CR^a$, or U and V each represent N and W and X each represent CH, or W represents N and U, V and X each represent CH, or W represents N, U and V each represent CH and X represents $CR^a$;
$R^a$ represents halogen (especially fluorine);
A is $CH_2CH(NH_2)$ or $CH(OH)CH(OH)$, B is $CH_2NH$ or CONH and D is $CH_2$, or
A is $CH(OH)CH_2$, B is $CH_2CH_2$, $CH_2NH$, $N(R^2)CO$ or CONH and D is $CH_2$, or
A is $CH_2CH(OH)$ or $CH(OH)CH(NH_2)$, B is CONH and D is $CH_2$, or
A is $CH_2CH_2$ and either B is $NHCH_2$, $CH_2NR^3$, NHCO or $CONR^4$ and D is $CH_2$ or B is $CH_2NH$ and D is CO, or
A is CH=CH and B is $CH_2NR^5$ or $CONR^6$ and D is $CH_2$, or
A is C≡C, B is $CH_2NH$ and D is CO, or
A is $CH_2CO$, B is $NHCH_2$ and D is $CH_2$, or A is COCH$_2$, B is CH$_2$CH$_2$ or CONH and D is CH$_2$, or
A is CH$_2$NH, B is CH$_2$CH$_2$ and D is CH$_2$, or
A is CH$_2$N(R$^7$), B is COCH$_2$ and D is CH$_2$, or
A is CONH, B is CH$_2$CH$_2$ and D is CH$_2$, or
A is NHCH$_2$ and either B is CH$_2$CH$_2$ or CH$_2$NH and D is CH$_2$, or B is CH$_2$NH and D is CO, or
A is NHCO, B is CH(R$^8$)NH or CH$_2$CH$_2$ and D is CH$_2$;
R$^2$ is alkyl (especially methyl);
R$^3$ is hydrogen, alkyl, phenylalkyl, CO—(CH$_2$)$_p$—COOH, acyl or aminoalkyl,
  p being an integer from 1 to 4;
R$^4$ is hydrogen or alkyl;
R$^5$ is hydrogen or acyl;
R$^6$ is hydrogen, alkyl or phenylalkyl;
R$^7$ is hydrogen or alkyl;
R$^8$ is hydrogen or alkyl;
E is a group of the formula

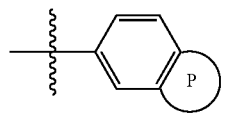

wherein P is a ring selected from the group consisting of the following rings:

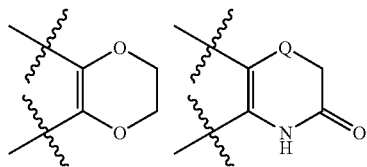

in which Q is O or S, or

E is a phenyl group which is substituted once or twice in the meta and/or para position(s) by substituents each independently selected from the group consisting of halogen, (C$_1$-C$_3$) alkyl and trifluoromethyl;

and to salts (in particular pharmaceutically acceptable salts) of compounds of formula I$_{CE}$.

v) According to a preferred embodiment of this invention, the compounds of formula I as defined in one of embodiments i) to iv) above or their salts (among which the pharmaceutically acceptable salts will be preferred) will be such that R$^1$ is alkoxy (preferably (C$_1$-C$_3$)alkoxy and in particular methoxy).

vi) According to another embodiment of this invention, the compounds of formula I as defined in one of embodiments i) to iv) above or their salts (among which the pharmaceutically acceptable salts will be preferred) will be such that:
  R$^1$ is hydrogen, halogen, hydroxy, alkoxy or cyano (and in particular methoxy);
  Y$^1$, Y$^2$ and V each represent CH, X represents CH or CR$^a$ and U and W each represent N, or Y$^1$, Y$^2$ and X each represent CH, W represents CH or CR$^b$ and U and V each represent N, or Y$^1$, Y$^2$, U and V each represent CH and W and X each represent N, or Y$^1$, Y$^2$, U and V each represent CH, X represents CH or CR$^a$ and W represents N, or Y$^1$, Y$^2$, U, W each represent CH, X represents CH or CR$^a$ and V represents N, or Y$^1$, Y$^2$, V and W each represent CH, X represents CH or CR$^a$ and U represents N, or Y$^1$, Y$^2$, X and V each represent CH, W represents CR$^{b'}$ and U represents N, or each of U, V, W, X, Y$^1$ and Y$^2$ represents CH, or each of U, V, W, X and Y$^1$ represents CH and Y$^2$ represents N, or also
  each of U, V, X, Y$^1$ and Y$^2$ represents CH and W represents CR$^c$, or each of U, V, W, Y$^1$ and Y$^2$ represents CH and X represents CR$^c$, or each of U, V, W and Y$^2$ represents CH and X and Y$^1$ each represent CR$^c$;
  R$^a$ represents halogen (especially fluorine);
  R$^b$ represents alkoxyalkoxy;
  R$^{b'}$ represents alkoxycarbonyl; and
  R$^c$, each time it occurs, independently represents hydroxy or alkoxy (and preferably hydroxy or methoxy).

vii) Another preferred embodiment of this invention relates to the compounds of formula I as defined in one of embodiments i) to vi) above or their salts (among which the pharmaceutically acceptable salts will be preferred) wherein U and W each represent N, Y$^1$, Y$^2$ and V each represent CH and X represents CH or CF.

viii) Yet another preferred embodiment of this invention relates to the compounds of formula I as defined in one of embodiments i) to vi) above or their salts (among which the pharmaceutically acceptable salts will be preferred) wherein Y$^1$, Y$^2$, U and V each represent CH, W represents N and X represents CH or CF.

ix) Yet another preferred embodiment of this invention relates to the compounds of formula I as defined in one of embodiments i) to vi) above or their salts (among which the pharmaceutically acceptable salts will be preferred) wherein Y$^1$, Y$^2$, U and W each represent CH, V represents N and X represents CH or CF.

x) Yet another preferred embodiment of this invention relates to the compounds of formula I as defined in embodiments i) to vi) above or their salts (among which the pharmaceutically acceptable salts will be preferred) wherein Y$^1$, Y$^2$, U and V each represent CH and W and X each represent N.

xi) Yet another preferred embodiment of this invention relates to the compounds of formula I as defined in one of embodiments i) to vi) above or their salts (among which the pharmaceutically acceptable salts will be preferred) wherein Y$^1$, Y$^2$, U and V each represent N and W and X each represent CH.

xii) A further preferred embodiment of this invention relates to the compounds of formula I as defined in one of embodiments i) to vi) above or their salts (among which the pharmaceutically acceptable salts will be preferred) wherein U and W each represent N, Y$^1$, Y$^2$, V each represent CH and X represents CH or CF, or Y$^1$, Y$^2$, U and V each represent CH, W represents N and X represents CH or CF, or Y$^1$, Y$^2$, U and W each represent CH, V represents N and X represents CH or CF, or Y$^1$, Y$^2$, U and V each represent CH and W and X each represent N, or U and V each represent N and Y$^1$, Y$^2$, W and X each represent CH.

xiii) A further embodiment of this invention relates to the compounds of formula I as defined in one of embodiments i), iii), v) or vi) above or their salts (among which the pharmaceutically acceptable salts will be preferred) wherein Y$^1$, Y$^2$, U, V, W and X each represent CH.

xiv) Yet a further embodiment of this invention relates to the compounds of formula I as defined in one of embodiments i), iii), v) or vi) above or their salts (among which the pharmaceutically acceptable salts will be preferred) wherein each of U, V, W, X and Y$^1$ represents CH and Y$^2$ represents N.

xv) Yet another embodiment of this invention relates to the compounds of formula I as defined in one of embodiments i), iii), v) or vi) above or their salts (among which the pharmaceutically acceptable salts will be preferred) wherein each of U, V, X, Y$^1$ and Y$^2$ represents CH and W represents CR$^c$, or each of U, V, W, Y$^1$ and Y$^2$ represents CH and X represents $CR^c$, or each of U, V, W and $Y^2$ represents CH and X and $Y^1$ each represent $CR^c$, whereby $R^c$, each time it occurs, independently represents hydroxy or alkoxy (and preferably hydroxy or methoxy).

xvi) Still another embodiment of this invention relates to the compounds of formula I as defined in one of embodiments i), iii), v) or vi) above or their salts (among which the pharmaceutically acceptable salts will be preferred) wherein $Y^1$, $Y^2$ and X each represent CH, W represents CH or $CR^b$ and U and V each represent N, $R^b$ representing alkoxyalkoxy.

xvii) Still another embodiment of this invention relates to the compounds of formula I as defined in one of embodiments i), iii), v) or vi) above or their salts (among which the pharmaceutically acceptable salts will be preferred) wherein $Y^1$, $Y^2$, X and V each represent CH, W represents $CR^{b'}$ and U represents N, $R^{b'}$ representing alkoxycarbonyl.

xviii) Preferably, the compounds of formula I as defined in one of embodiments i) to xvii) above or their salts (among which the pharmaceutically acceptable salts will be preferred) will be such that $R^2$, when present, represents hydrogen or methyl (and in particular hydrogen).

xix) Preferably, the compounds of formula I as defined in one of embodiments i) to xviii) above or their salts (among which the pharmaceutically acceptable salts will be preferred) will be such that $R^{2a}$, when present, represents hydrogen or methyl.

xx) Preferably, the compounds of formula I as defined in one of embodiments i) to xix) above or their salts (among which the pharmaceutically acceptable salts will be preferred) will be such that $R^3$, when present, represents hydrogen, methyl, ethyl, acetyl, 3-propionyl, 2-amino-ethyl, 2,3-dihydroxy-propyl or benzyl, whereby the compounds and salts wherein $R^3$, when present, represents hydrogen, methyl, ethyl, acetyl, 3-propionyl, 2-amino-ethyl or benzyl (in particular hydrogen or methyl and notably hydrogen) constitute a particular variant.

xxi) More preferably, the compounds of formula I as defined in one of embodiments i) to xx) above or their salts (among which the pharmaceutically acceptable salts will be preferred) will be such that $R^3$, when present, represents hydrogen, methyl or 2,3-dihydroxy-propyl.

xxii) Preferably, the compounds of formula I as defined in one of embodiments i) to xxi) above or their salts (among which the pharmaceutically acceptable salts will be preferred) will be such that $R^{3a}$, when present, represents hydrogen, acetyl or methylsulfonyl (and notably hydrogen).

xxiii) Preferably, the compounds of formula I as defined in one of embodiments i) to xxii) above or their salts (among which the pharmaceutically acceptable salts will be preferred) will be such that $R^4$, when present, represents hydrogen or methyl (and in particular hydrogen).

xxiv) Preferably, the compounds of formula I as defined in one of embodiments i) to xxiii) above or their salts (among which the pharmaceutically acceptable salts will be preferred) will be such that $R^{4a}$, when present, represents hydrogen or $(CH_2)_q$—$COOR^{4a'}$, or also $R^{4a}$ is alkyl which may be substituted once or twice by hydroxy groups, q being an integer from 1 to 4 and $R^{4a'}$ being alkyl (and notably hydrogen or alkyl substituted once or twice by hydroxy groups, in particular hydrogen or 2,3-dihydroxy-propyl).

xxv) Preferably, the compounds of formula I as defined in one of embodiments i) to xxiv) above or their salts (among which the pharmaceutically acceptable salts will be preferred) will be such that $R^5$, when present, represents hydrogen or acetyl (and in particular hydrogen).

xxvi) Preferably, the compounds of formula I as defined in one of embodiments i) to xxv) above or their salts (among which the pharmaceutically acceptable salts will be preferred) will be such that $R^6$, when present, represents hydrogen, methyl or benzyl (in particular hydrogen or methyl and notably hydrogen).

xxvii) Preferably, the compounds of formula I as defined in one of embodiments i) to xxvi) above or their salts (among which the pharmaceutically acceptable salts will be preferred) will be such that $R^7$, when present, represents hydrogen or $(CH_2)_r$—$COOR^{7'}$, or also $R^7$ is alkyl which may be substituted once or twice by groups independently selected from hydroxy, halogen, amino and dimethylamino (and notably from hydroxy, halogen and dimethylamino), r being an integer from 1 to 4 and $R^{7'}$ being alkyl (for example such that $R^7$, when present, represents hydrogen or methyl, in particular hydrogen).

xxviii) More preferably, the compounds of formula I as defined in one of embodiments i) to xxvii) above or their salts (among which the pharmaceutically acceptable salts will be preferred) will be such that $R^7$, when present, represents hydrogen or alkyl which may be substituted once or twice by groups independently selected from hydroxy and halogen (notably hydrogen or alkyl which is substituted once or twice by groups independently selected from hydroxy and halogen, and in particular hydrogen, 2-hydroxy-ethyl or 2,3-dihydroxy-propyl).

xxix) Preferably, the compounds of formula I as defined in one of embodiments i) to xxviii) above or their salts (among which the pharmaceutically acceptable salts will be preferred) will be such that $R^8$, when present, represents hydrogen or methyl (and in particular hydrogen).

xxx) According to a first main variant of this invention, the compounds of formula I as defined in one of embodiments i) to xxix) above or their salts (among which the pharmaceutically acceptable salts will be preferred) will be such that A is $CH_2CH_2$, CH=CH or $NHCH_2$, B is $CH_2NH$ and D is CO.

xxxi) According to a second main variant of this invention, the compounds of formula I as defined in one of embodiments i) to xxix) above or their salts (among which the pharmaceutically acceptable salts will be preferred) will be such that:
A is $CH(OH)CH_2$, B is $CH_2NH$ and D is $CH_2$;
A is $CH_2CH_2$, B is $CH_2NR^3$ and D is $CH_2$;
A is $NHCH_2$, B is $CH_2NH$ and D is $CH_2$;
A is CH=CH, B is $CH_2NR^5$ and D is $CH_2$;
A is $CH(OH)CH(OH)$ B is $CH_2NH$ and D is $CH_2$; or
A is $CH_2CH(NH_2)$, B is $CH_2NH$ and D is $CH_2$.

xxxii) According to a sub-embodiment of embodiment xxxi) above, the compounds of formula I or their salts (among which the pharmaceutically acceptable salts will be preferred) will be such that A is $CH(OH)CH_2$, $CH_2CH_2$, $NHCH_2$, CH=CH, $CH(OH)CH(OH)$ or $CH_2CH(NH_2)$, B is $CH_2NH$ and D is $CH_2$.

xxxiii) Preferably, the compounds of formula I as defined in sub-embodiment xxxii) above or their salts (among which the pharmaceutically acceptable salts will be preferred) will be such that A is $CH(OH)CH_2$, $CH_2CH_2$, $NHCH_2$ or CH=CH, B is $CH_2NH$ and D is $CH_2$.

xxxiv) More preferably, the compounds of formula I as defined in sub-embodiment xxxii) above or their salts (among which the pharmaceutically acceptable salts will be preferred) will be such that A is $CH_2CH_2$ or CH=CH, B is $CH_2NH$ and D is $CH_2$.

xxxv) According to a third main variant of this invention, the compounds of formula I as defined in one of embodiments i) to xxix) above or their salts (among which the pharmaceutically acceptable salts will be preferred) will be such that A is $CH_2N(R^7)$, NHCO, CONH, $COCH_2$ or $NHCH_2$, B is $CH_2CH_2$ and D is $CH_2$.

xxxvi) According to a sub-embodiment of embodiment xxxv) above, the compounds of formula I or their salts (among which the pharmaceutically acceptable salts will be preferred) will be such that A is $CH_2NH$, NHCO, CONH, $COCH_2$ or $NHCH_2$, B is $CH_2CH_2$ and D is $CH_2$.

xxxvii) Preferably, the compounds of formula I as defined in sub-embodiment xxxvi) above or their salts (among which the pharmaceutically acceptable salts will be preferred) will be such that A is $CH_2NH$, NHCO or $COCH_2$, B is $CH_2CH_2$ and D is $CH_2$.

xxxviii) More preferably, the compounds of formula I as defined in sub-embodiment xxxvi) above or their salts (among which the pharmaceutically acceptable salts will be preferred) will be such that A is $CH_2NH$ or NHCO, B is $CH_2CH_2$ and D is $CH_2$.

xxxix) According to a fourth main variant of this invention, the compounds of formula I as defined in one of embodiments i) to xxix) above or their salts (among which the pharmaceutically acceptable salts will be preferred) will be such that A is CH=CH, $CH_2CH_2$, CH(OH)CH(OH), CH(OH)CH($NH_2$) or CH(OH)$CH_2$, B is CONH and D is $CH_2$.

xl) Preferably, the compounds of formula I as defined in embodiment xxxix) above or their salts (among which the pharmaceutically acceptable salts will be preferred) will be such that A is CH=CH, B is CONH and D is $CH_2$.

xli) According to a fifth main variant of this invention, the compounds of formula I as defined in one of embodiments i) to xxix) above or their salts (in particular their pharmaceutically acceptable salts) will be such that A is $CH_2CH_2$, B is $NR^{4a}CH_2$ and D is $CH_2$ or such that A is $CH_2CO$, B is $NHCH_2$ and D is $CH_2$ (and notably such that A is $CH_2CH_2$ or $CH_2CO$, B is $NHCH_2$ and D is $CH_2$).

xlii) Preferably, the compounds of formula I as defined in embodiment xli) above or their salts (in particular their pharmaceutically acceptable salts) will be such that A is $CH_2CH_2$, B is $NR^{4a}CH_2$, and D is $CH_2$, $R^{4a}$ being hydrogen or alkyl substituted once or twice by hydroxy groups, in particular hydrogen or 2,3-dihydroxy-propyl (said compounds or salts being for example such that A is $CH_2CH_2$, B is $NHCH_2$ and D is $CH_2$).

xliii) According to a sixth main variant of this invention, the compounds of formula I as defined in one of embodiments i) to xxix) above or their salts (among which the pharmaceutically acceptable salts will be preferred) will be such that A is NHCO, B is CH($R^8$)NH and D is $CH_2$, $R^8$ being hydrogen or alkyl (and preferably hydrogen or methyl).

xliv) Preferably, the compounds of formula I as defined in embodiment xliii) above or their salts (among which the pharmaceutically acceptable salts will be preferred) will be such that A is NHCO, B is $CH_2NH$ and D is $CH_2$.

xlv) According to a seventh main variant of this invention, the compounds of formula I as defined in one of embodiments i) to xxix) above or their salts (among which the pharmaceutically acceptable salts will be preferred) will be such that A is $CH_2CH_2$, B is NHCO and D is $CH_2$.

xlvi) According to an eighth main variant of this invention, the compounds of formula I as defined in one of embodiments i), iii) and v) to xxix) above or their salts (among which the pharmaceutically acceptable salts will be preferred) will be such that A is CH=CH or $CH_2CH_2$, B is $CH_2O$ and D is $CH_2$, or such that A is $OCH_2$, B is $CH_2$ or $CH_2CH_2$ and D is $CH_2$.

xlvii) According to a ninth main variant of this invention, the compounds of formula I as defined in one of embodiments i), iii) and v) to xxix) above or their salts (among which the pharmaceutically acceptable salts will be preferred) will be such that:

A is CH(OH)$CH_2$, B is N($R^{2a}$)$CH_2$ and D is CH(OH);
A is $CH_2CH_2$, B is $NR^{4b}CH_2$ or $CH_2CH_2$ and D is CH(OH); or
A is $CH_2N(R^7)$, B is $CH_2CH_2$ or $CH_2CH(OH)$ and D is CH(OH).

xlviii) Preferably, the compounds of formula I as defined in embodiment xlvii) above or their salts (in particular their pharmaceutically acceptable salts) will be such that A is $CH_2CH_2$, B is $NR^{4b}CH_2$ and D is CH(OH), $R^{4b}$ being hydrogen or methyl (and in particular hydrogen).

il) According to a tenth main variant of this invention, the compounds of formula I as defined in one of embodiments i) to xxix) above or their salts (among which the pharmaceutically acceptable salts will be preferred) will be such that A is $CH_2N(R^7)$, B is $CH_2CH_2$ or $CH_2CH(OH)$ and D is CH($NH_2$).

l) In a general manner, the compounds of formula I as defined in one of embodiments i), iii) and v) to xxix) above or their salts (among which the pharmaceutically acceptable salts will be preferred) will preferably be such that:

$R^1$ is hydrogen or alkoxy (notably hydrogen or methoxy);
$Y^1$, $Y^2$ and V each represent CH, X represents CH or CF and U and W each represent N, or $Y^1$, $Y^2$ and X each represent CH, W represents CH or $CR^b$ and U and V each represent N, or $Y^1$, $Y^2$, U and V each represent CH, X represents CH or CF and W represents N, or $Y^1$, $Y^2$, U, W each represent CH, X represents CH or CF and V represents N, or $Y^1$, $Y^2$, V and W each represent CH, X represents CH or CF and U represents N, or also
each of U, V, W, X, $Y^1$ and $Y^2$ represents CH,
$R^b$ representing alkoxyalkoxy;
A is CH(OH)$CH_2$, B is N($R^2$)CO and D is $CH_2$, $R^3$ being hydrogen or methyl, or A is $CH_2CH_2$, B is $CH_2CH_2$, $NR^{4a}CH_2$, $CH_2NR^3$, NHCO or CH(OH)$CH_2$ and D is $CH_2$, or A is $CH_2CH_2$, B is $NHCH_2$ and D is CH(OH), $R^3$ being hydrogen or alkyl which may be substituted once or twice by hydroxy groups (notably hydrogen, methyl or 2,3-dihydroxy-propyl) and $R^{4a}$ being hydrogen or alkyl which may be substituted once or twice by hydroxy groups (notably hydrogen or alkyl substituted once or twice by hydroxy groups, and in particular hydrogen or 2,3-dihydroxy-propyl), or A is CH=CH, B is $CH_2NH$ or $CONR^6$ and D is $CH_2$, $R^6$ being hydrogen or methyl, or A is $CH_2N(R^7)$, B is $CH_2CH_2$ and D is $CH_2$, or A is $CH_2NH$, B is $CH_2CH_2$ or $CH_2CH(OH)$ and D is CH(OH), $R^7$ representing hydrogen or alkyl which may be substituted once or twice by hydroxy, or
A is $NHCH_2$, B is $CH_2NH$ and D is $CH_2$, or also
A is NHCO, B is $CH_2NH$ or $CH_2CH_2$ and D is $CH_2$;
E is one of the groups drawn below (and preferably the right one)

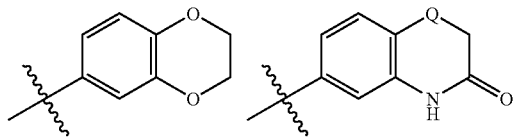

in which Q is O or S;

li) In a general manner, the compounds of formula I as defined in one of embodiments i), iii) and v) to xxix) above or their salts (among which the pharmaceutically acceptable salts will be preferred) will more preferably be such that:

$R^1$ is hydrogen or methoxy;
$Y^1$, $Y^2$ and V each represent CH, X represents CH or CF and U and W each represent N, or $Y^1$, $Y^2$, U and V each represent CH, X represents CH or CF and W represents N, or $Y^1$, $Y^2$, U, W each represent CH, X represents CH or CF and V represents N, or $Y^1$, $Y^2$, V and W each represent CH, X represents CH or CF and U represents N, or also each of U, V, W, X, $Y^1$ and $Y^2$ represents CH;

A is $CH_2CH_2$, B is $NHCH_2$, $CH_2NR^3$ or $CH(OH)CH_2$ and D is $CH_2$, $R^3$ being hydrogen or alkyl which is substituted once or twice by hydroxy groups (notably hydrogen or 2,3-dihydroxy-propyl), or A is CH=CH, B is CONH and D is $CH_2$, or A is $CH_2N(R^7)$, B is $CH_2CH_2$ and D is $CH_2$, or A is $CH_2NH$, B is $CH_2CH_2$ and D is CH(OH), $R^7$ representing hydrogen or alkyl which may be substituted once or twice by hydroxy (notably hydrogen or 2,3-dihydroxy-propyl), or also A is $NHCH_2$, B is $CH_2NH$ and D is $CH_2$;

E is the group

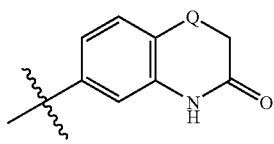

in which Q is O or S;

lii) According to a particular embodiment of the invention, the compounds of formula I as defined in one of embodiments i) to il) above or their salts (among which the pharmaceutically acceptable salts will be preferred) will be such that E is one of the following groups:

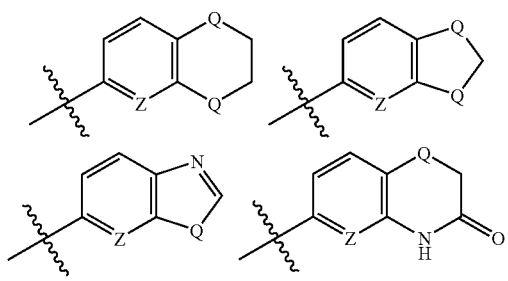

wherein P and Z are as defined in embodiment i), Z being in particular CH (or as defined in embodiment ii) when compounds of formula $I_{P1}$ as defined in embodiment ii) are concerned, or as defined in embodiment iii) when compounds of formula $I_{CE}$ as defined in embodiment iii) are concerned, or as defined in embodiment iv) when compounds of formula $I_{CEP1}$ as defined in embodiment iv) are concerned).

liii) Preferably, the compounds of formula I as defined in embodiment lii) above or their salts (among which the pharmaceutically acceptable salts will be preferred) will be such that Z is CH and E is one of the following groups:

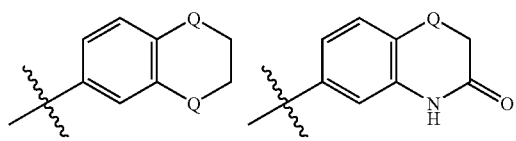

wherein Q is O or S.

liv) According to one particular variant of embodiment liii) above, the compounds of formula I as defined in embodiment lii) above or their salts (among which the pharmaceutically acceptable salts will be preferred) will be such that E is 2,3-dihydro-benzo[1,4]dioxin-6-yl.

lv) According to another particular variant of embodiment liii) above, the compounds of formula I as defined in embodiment lii) above or their salts (among which the pharmaceutically acceptable salts will be preferred) will be such that E is 3-oxo-3,4-dihydro-2H-benzo[1,4]thiazine-6-yl or 3-oxo-3,4-dihydro-2H-benzo[1,4]oxazine-6-yl.

lvi) According to another particular embodiment of the invention, the compounds of formula I as defined in one of embodiments i) to il) above or their salts (among which the pharmaceutically acceptable salts will be preferred) will be such that E is a phenyl group which is substituted as mentioned in embodiment i).

lvii) Preferably, the compounds of formula I as defined in embodiment lvi) above or their salts (among which the pharmaceutically acceptable salts will be preferred) will be such that E is a phenyl group substituted in para position by halogen or $(C_1-C_3)$alkyl, and in meta position by halogen, $(C_1-C_3)$alkyl or trifluoromethyl.

lviii) More preferably, the compounds of formula I as defined in embodiment lvi) above or their salts (among which the pharmaceutically acceptable salts will be preferred) will be such that E is phenyl substituted in para position by $(C_1-C_3)$alkyl (especially by methyl or ethyl), and in meta position by halogen (this halogen being in particular fluorine), $(C_1-C_3)$alkyl or trifluoromethyl.

lix) Even more preferably, the compounds of formula I as defined in embodiment lvi) above or their salts (among which the pharmaceutically acceptable salts will be preferred) will be such that E is 3-fluoro-4-methyl-phenyl, 4-methyl-3-trifluoromethyl-phenyl or 3-bromo-4-methyl-phenyl.

lx) According to a further particular (and preferred) embodiment, the compounds of formula I as defined in one of embodiments i) to lix) above or their salts (among which the pharmaceutically acceptable salts will be preferred) will be such that they possess the following stereochemistry:

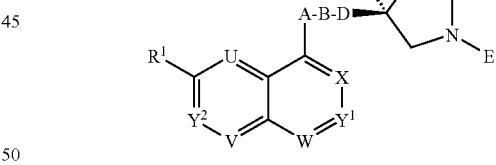

lxi) According to yet a further particular embodiment, the compounds of formula I as defined in one of embodiments i) to lix) above or their salts (among which the pharmaceutically acceptable salts will be preferred) will be such that they possess the following stereochemistry:

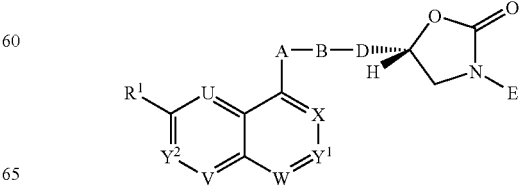

lxii) Particularly preferred are the following compounds of formula I as defined in embodiment i) or ii):

(E)-[(S)-3-(2,3-dihydro-benzo[1,4]dioxin-6-yl)-2-oxo-oxazolidin-5-ylmethyl]-3-(6-methoxy-[1,5]naphthyridin-4-yl)-acrylamide;

(E)-[(S)-3-(2,3-dihydro-benzo[1,4]dioxin-6-yl)-2-oxo-oxazolidin-5-ylmethyl]-3-(6-methoxy-quinolin-4-yl)-acrylamide;

(E)-[(R)-3-(2,3-dihydro-benzo[1,4]dioxin-6-yl)-2-oxo-oxazolidin-5-ylmethyl]-3-(6-methoxy-[1,5]naphthyridin-4-yl)-acrylamide;

(E)-3-(6-methoxy-[1,5]naphthyridin-4-yl)-N-[(R)-2-oxo-3-(3-oxo-3,4-dihydro-2H-benzo[1,4]thiazin-6-yl)-oxazolidin-5-ylmethyl]-acrylamide;

(E)-N-[(R)-3-(2,3-dihydro-benzo[1,4]dioxin-6-yl)-2-oxo-oxazolidin-5-ylmethyl]-3-(3-methoxy-quinoxalin-5-yl)-acrylamide;

(E)-N-[(R)-3-(2,3-dihydro-benzo[1,4]dioxin-6-yl)-2-oxo-oxazolidin-5-ylmethyl]-3-(3-methoxy-quinolin-5-yl)-acrylamide;

(E)-N-[(R)-3-(2,3-dihydro-benzo[1,4]dioxin-6-yl)-2-oxo-oxazolidin-5-ylmethyl]-N-ethyl-3-(6-methoxy-[1,5]naphthyridin-4-yl)-acrylamide;

(E)-N-benzyl-N-[3-(2,3-dihydro-benzo[1,4]dioxin-6-yl)-2-oxo-oxazolidin-5-ylmethyl]-3-(6-methoxy-[1,5]naphthyridin-4-yl)-acrylamide;

(E)-3-(3-methoxy-quinoxalin-5-yl)-N-[(R)-2-oxo-3-(3-oxo-3,4-dihydro-2H-benzo[1,4]thiazin-6-yl)-oxazolidin-5-ylmethyl]-acrylamide;

(E)-3-(3-methoxy-quinolin-5-yl)-N-[(R)-2-oxo-3-(3-oxo-3,4-dihydro-2H-benzo[1,4]thiazin-6-yl)-oxazolidin-5-ylmethyl]-acrylamide;

(E)-3-(6-methoxy-[1,5]naphthyridin-4-yl)-N-methyl-N-[(R)-2-oxo-3-(3-oxo-3,4-dihydro-2H-benzo[1,4]thiazin-6-yl)-oxazolidin-5-ylmethyl]-acrylamide;

(E)-N-[(R)-3-(3-fluoro-4-methyl-phenyl)-2-oxo-oxazolidin-5-ylmethyl]-3-(6-methoxy-[1,5]naphthyridin-4-yl)-acrylamide;

(E)-N-[(R)-3-(3-fluoro-4-methyl-phenyl)-2-oxo-oxazolidin-5-ylmethyl]-3-(6-methoxy-[1,5]naphthyridin-4-yl)-N-methyl-acrylamide;

(E)-N-[(R)-3-(4-ethyl-phenyl)-2-oxo-oxazolidin-5-ylmethyl]-3-(6-methoxy-[1,5]naphthyridin-4-yl)-N-methyl-acrylamide;

(E)-3-(6-methoxy-[1,5]naphthyridin-4-yl)-N-methyl-N-[(R)-2-oxo-3-(4-propyl-phenyl)-oxazolidin-5-ylmethyl]-acrylamide;

(E)-3-(2-cyano-quinolin-8-yl)-N-[(R)-3-(2,3-dihydro-benzo[1,4]dioxin-6-yl)-2-oxo-oxazolidin-5-ylmethyl]-acrylamide;

(E)-N-[(R)-3-(2,3-dihydro-benzo[1,4]dioxin-6-yl)-2-oxo-oxazolidin-5-ylmethyl]-3-(6-fluoro-quinolin-4-yl)-acrylamide;

(E)-N-[(R)-3-(2,3-dihydro-benzo[1,4]dioxin-6-yl)-2-oxo-oxazolidin-5-ylmethyl]-3-(2-methoxy-quinolin-8-yl)-acrylamide;

(E)-3-(6-methoxy-[1,5]naphthyridin-4-yl)-N-methyl-N-[(R)-3-(4-methyl-3-trifluoromethyl-phenyl)-2-oxo-oxazolidin-5-ylmethyl]-acrylamide;

(E)-N-[(R)-3-(3-bromo-4-methyl-phenyl)-2-oxo-oxazolidin-5-ylmethyl]-3-(6-methoxy-[1,5]naphthyridin-4-yl)-N-methyl-acrylamide;

(E)-N-[(R)-3-(4-bromo-3-methyl-phenyl)-2-oxo-oxazolidin-5-ylmethyl]-3-(6-methoxy-[1,5]naphthyridin-4-yl)-N-methyl-acrylamide;

(E)-N-[(R)-3-(4-bromo-3-fluoro-phenyl)-2-oxo-oxazolidin-5-ylmethyl]-3-(6-methoxy-[1,5]naphthyridin-4-yl)-N-methyl-acrylamide;

(E)-N-[(S)-3-(3-fluoro-4-methyl-phenyl)-2-oxo-oxazolidin-5-ylmethyl]-3-(6-methoxy-[1,5]naphthyridin-4-yl)-N-methyl-acrylamide;

(E)-3-(6-methoxy-[1,5]naphthyridin-4-yl)-N-methyl-N-[(S)-2-oxo-3-(3-oxo-3,4-dihydro-2H-benzo[1,4]thiazin-6-yl)-oxazolidin-5-ylmethyl]-acrylamide;

(E)-N-[(S)-3-(2,3-dihydro-benzo[1,4]dioxin-6-yl)-2-oxo-oxazolidin-5-ylmethyl]-3-(6-methoxy-[1,5]naphthyridin-4-yl)-N-methyl-acrylamide;

(E)-N-[(S)-3-(4-ethyl-phenyl)-2-oxo-oxazolidin-5-ylmethyl]-3-(3-methoxy-quinoxalin-5-yl)-N-methyl-acrylamide;

N-[(R)-3-(2,3-dihydro-benzo[1,4]dioxin-6-yl)-2-oxo-oxazolidin-5-ylmethyl]-3-(6-methoxy-[1,5]naphthyridin-4-yl)-propionamide;

3-(3-methoxy-quinolin-5-yl)-N-[(R)-2-oxo-3-(3-oxo-3,4-dihydro-2H-benzo[1,4]thiazin-6-yl)-oxazolidin-5-ylmethyl]-propionamide;

(R)-3-(2,3-dihydro-benzo[1,4]dioxin-6-yl)-5-{[(E)-3-(6-methoxy-[1,5]naphthyridin-4-yl)-allylamino]-methyl}-oxazolidin-2-one;

(R)-3-(2,3-dihydro-benzo[1,4]dioxin-6-yl)-5-{[3-(6-methoxy-[1,5]naphthyridin-4-yl)-propylamino]-methyl}-oxazolidin-2-one;

N-[(R)-3-(2,3-dihydro-benzo[1,4]dioxin-6-yl)-2-oxo-oxazolidin-5-ylmethyl]-N-[(E)-3-(6-methoxy-[1,5]naphthyridin-4-yl)-allyl]-acetamide;

6-((R)-5-{[(E)-3-(6-methoxy-[1,5]naphthyridin-4-yl)-allylamino]-methyl}-2-oxo-oxazolidin-3-yl)-4H-benzo[1,4]thiazin-3-one;

6-((R)-5-{[3-(6-methoxy-[1,5]naphthyridin-4-yl)-propylamino]-methyl}-2-oxo-oxazolidin-3-yl)-4H-benzo[1,4]thiazin-3-one;

6-(5-{[3-(6-methoxy-[1,5]naphthyridin-4-yl)-propylamino]-methyl}-2-oxo-3-yl)-4H-benzo[1,4]oxazin-3-one;

6-((R)-5-{[3-(3-methoxy-quinolin-5-yl)-propylamino]-methyl}-2-oxo-oxazolidin-3-yl)-4H-benzo[1,4]thiazin-3-one;

N-[(R)-3-(2,3-dihydro-benzo[1,4]dioxin-6-yl)-2-oxo-oxazolidin-5-ylmethyl]-N-[3-(6-methoxy-[1,5]naphthyridin-4-yl)-propyl]-acetamide;

N-[3-(6-methoxy-[1,5]naphthyridin-4-yl)-propyl]-N-[(R)-2-oxo-3-(3-oxo-3,4-dihydro-2H-benzo[1,4]thiazin-6-yl)-oxazolidin-5-ylmethyl]-succinamic acid;

N-[3-(6-methoxy-[1,5]naphthyridin-4-yl)-propyl]-N-[(R)-2-oxo-3-(3-oxo-3,4-dihydro-2H-benzo[1,4]thiazin-6-yl)-oxazolidin-5-ylmethyl]-propionamide;

(R)-3-(2,3-dihydro-benzo[1,4]dioxin-6-yl)-5-({ethyl-[3-(6-methoxy-[1,5]naphthyridin-4-yl)-propyl]-amino}-methyl)-oxazolidin-2-one;

5-({benzyl-[3-(6-methoxy-[1,5]naphthyridin-4-yl)-propyl]-amino}-methyl)-3-(2,3-dihydro-benzo[1,4]dioxin-6-yl)-oxazolidin-2-one;

(R)-5-({(2-amino-ethyl)-[3-(6-methoxy-[1,5]naphthyridin-4-yl)-propyl]-amino}-methyl)-3-(2,3-dihydro-benzo[1,4]dioxin-6-yl)-oxazolidin-2-one;

6-[(R)-5-({[3-(3-methoxy-quinolin-5-yl)-propyl]-methyl-amino}-methyl)-2-oxo-oxazolidin-3-yl]-4H-benzo[1,4]thiazin-3-one;

(R)-3-(3-fluoro-4-methyl-phenyl)-5-({[3-(3-methoxy-quinolin-5-yl)-propyl]-methyl-amino}-methyl)-oxazolidin-2-one;

(R)-5-({[3-(3-methoxy-quinolin-5-yl)-propyl]-methyl-amino}-methyl)-3-(4-methyl-3-trifluoromethyl-phenyl)-oxazolidin-2-one;
(R)-3-(4-ethyl-phenyl)-5-({[3-(3-methoxy-quinolin-5-yl)-propyl]-methyl-amino}-methyl)-oxazolidin-2-one;
(R)-5-({[3-(3-methoxy-quinolin-5-yl)-propyl]-methyl-amino}-methyl)-3-(4-propyl-phenyl)-oxazolidin-2-one;
(R)-3-(3-bromo-4-methyl-phenyl)-5-({[3-(3-methoxy-quinolin-5-yl)-propyl]-methyl-amino}-methyl)-oxazolidin-2-one;
(R)-3-(4-bromo-3-methyl-phenyl)-5-({[3-(3-methoxy-quinolin-5-yl)-propyl]-methyl-amino}-methyl)-oxazolidin-2-one;
(R)-3-(4-bromo-3-fluoro-phenyl)-5-({[3-(3-methoxy-quinolin-5-yl)-propyl]-methyl-amino}-methyl)-oxazolidin-2-one;
(S)-3-(3-fluoro-4-methyl-phenyl)-5-({[3-(3-methoxy-quinolin-5-yl)-propyl]-methyl-amino}-methyl)-oxazolidin-2-one;
(S)-3-(2,3-dihydro-benzo[1,4]dioxin-6-yl)-2-oxo-oxazolidine-5-carboxylic acid [3-(6-methoxy-[1,5]naphthyridin-4-yl)-propyl]-amide;
6-(5-{[2,3-dihydroxy-3-(6-methoxy-[1,5]naphthyridin-4-yl)-propylamino]-methyl}-2-oxo-oxazolidin-3-yl)-4H-benzo[1,4]thiazin-3-one;
(2S,3R)-N-[(S)-3-(2,3-dihydro-benzo[1,4]dioxin-6-yl)-2-oxo-oxazolidin-5-ylmethyl]-2,3-dihydroxy-3-(6-methoxy-[1,5]naphthyridin-4-yl)-propionamide;
(2R,3S)-2,3-dihydroxy-3-(6-methoxy-[1,5]naphthyridin-4-yl)-N-[(R)-2-oxo-3-(oxo-3,4-dihydro-2H-benzo[1,4]thiazin-6-yl)-oxazolidin-5-ylmethyl]-propionamide;
(2S,3R)-2,3-dihydroxy-3-(6-methoxy-[1,5]naphthyridin-4-yl)-N-[(R)-2-oxo-3-(3-oxo-3,4-dihydro-2H-benzo[1,4]thiazin-6-yl)-oxazolidin-5-ylmethyl]-propionamide;
N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-propionamide;
(R)-N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-propionamide;
(S)-N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-propionamide;
(Z)-N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-acrylamide;
(R)-3-(2,3-dihydro-benzo[1,4]dioxin-6-yl)-5-{[3-hydroxy-3-(6-methoxy-[1,5]naphthyridin-4-yl)-propylamino]-methyl}-oxazolidin-2-one;
3-(2,3-dihydro-benzo[1,4]dioxin-6-yl)-5-[5-hydroxy-5-(6-methoxy-[1,5]naphthyridin-4-yl)-pentyl]-oxazolidin-2-one;
3-(2,3-dihydro-benzo[1,4]dioxin-6-yl)-5-[5-(3-fluoro-6-methoxy-[1,5]naphthyridin-4-yl)-5-hydroxy-pentyl]-oxazolidin-2-one;
(R)-3-(2,3-dihydro-benzo[1,4]dioxin-6-yl)-5-[5-(6-methoxy-[1,5]naphthyridin-4-yl)-5-oxo-pentyl]-oxazolidin-2-one;
(S)-3-(2,3-dihydro-benzo[1,4]dioxin-6-yl)-5-[5-(6-methoxy-[1,5]naphthyridin-4-yl)-5-oxo-pentyl]-oxazolidin-2-one;
5-[(5-amino-5-(6-methoxy-[1,5]naphthyridin-4-yl)-pentyl]-3-(2,3-dihydro-benzo[1,4]dioxin-6-yl)-oxazolidin-2-one;
3-(2,3-dihydro-benzo[1,4]dioxin-6-yl)-5-[4-(6-methoxy-quinazolin-4-ylamino)-butyl]-oxazolidin-2-one;
N-[(R)-3-(2,3-dihydro-benzo[1,4]dioxin-6-yl)-2-oxo-oxazolidin-5-ylmethyl]-2-hydroxy-3-(6-methoxy-[1,5]naphthyridin-4-yl)-propionamide;
2-hydroxy-3-(6-methoxy-[1,5]naphthyridin-4-yl)-N-[(R)-2-oxo-3-(3-oxo-3,4-dihydro-2H-benzo[1,4]thiazin-6-yl)-oxazolidin-5-ylmethyl]-propionamide;
2-amino-N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-propionamide;
2-amino-N-[(R)-3-(2,3-dihydro-benzo[1,4]dioxin-6-yl)-2-oxo-oxazolidin-5-ylmethyl]-3-(6-methoxy-[1,5]naphthyridin-4-yl)-propionamide;
(5R)-5-{[2-amino-3-(6-methoxy-[1,5]naphthyridin-4-yl)-propylamino]-methyl}-3-(2,3-dihydro-benzo[1,4]dioxin-6-yl)-oxazolidin-2-one;
(S)-3-(2,3-dihydro-benzo[1,4]dioxin-6-yl)-2-oxo-oxazolidine-5-carboxylic acid [3-(6-methoxy-[1,5]naphthyridin-4-yl)-prop-2-ynyl]-amide;
(R)-3-(2,3-dihydro-benzo[1,4]dioxin-6-yl)-5-{2-[2-(6-methoxy-[1,5]naphthyridin-4-yl)-ethylamino]-ethyl}-oxazolidin-2-one;
6-(5-{2-[2-(6-methoxy-[1,5]naphthyridin-4-yl)-ethylamino]-ethyl}-2-oxo-oxazolidin-3-yl)-4H-benzo[1,4]thiazin-3-one;
6-(5-{2-[2-(3-fluoro-6-methoxy-[1,5]naphthyridin-4-yl)-ethylamino]-ethyl}-oxo-oxazolidin-3-yl)-4H-benzo[1,4]thiazin-3-one;
N-{2-[3-(2,3-dihydro-benzo[1,4]dioxin-6-yl)-2-oxo-oxazolidin-5-yl]-ethyl}-2-(3-methoxy-quinoxalin-5-yl)-acetamide;
6-methoxy-quinoline-4-carboxylic acid {3-[2-oxo-3-(3-oxo-3,4-dihydro-2H-benzo[1,4]thiazin-6-yl)-oxazolidin-5-yl]-propyl}-amide;
6-(5-{3-[(6-methoxy-[1,5]naphthyridin-4-ylmethyl)-amino]-propyl}-2-oxo-oxazolidin-3-yl)-4H-benzo[1,4]thiazin-3-one;
6-(5-{3-[(3-fluoro-6-methoxy-[1,5]naphthyridin-4-ylmethyl)-amino]-propyl}-2-oxo-oxazolidin-3-yl)-4H-benzo[1,4]thiazin-3-one;
6-(5-{3-[(3-fluoro-6-methoxy-quinolin-4-ylmethyl)-amino]-propyl}-2-oxo-oxazolidin-3-yl)-4H-benzo[1,4]thiazin-3-one;
N-(6-methoxy-[1,5]naphthyridin-4-yl)-4-[2-oxo-3-(3-oxo-3,4-dihydro-2H-benzo[1,4]thiazin-6-yl)-oxazolidin-5-yl]-butyramide;
(S)-3-(2,3-dihydro-benzo[1,4]dioxin-6-yl)-5-{[2-(6-methoxy-[1,5]naphthyridin-4-ylamino)-ethylamino]-methyl}-oxazolidin-2-one;
(S)-3-(2,3-dihydro-benzo[1,4]dioxin-6-yl)-2-oxo-oxazolidine-5-carboxylic acid [2-(6-methoxy-[1,5]naphthyridin-4-ylamino)-ethyl]-amide;
(S)-2-{[(R)-3-(2,3-dihydro-benzo[1,4]dioxin-6-yl)-2-oxo-oxazolidin-5-ylmethyl]-amino}-N-(6-methoxy-[1,5]naphthyridin-4-yl)-propionamide;
2-{[(R)-3-(2,3-dihydro-benzo[1,4]dioxin-6-yl)-2-oxo-oxazolidin-5-ylmethyl]amino}-N-(6-methoxy-[1,5]naphthyridin-4-yl)-acetamide;
2-[(R)-3-(2,3-dihydro-benzo[1,4]dioxin-6-yl)-2-oxo-oxazolidin-5-yl]-N-[2-(6-methoxy-quinolin-4-yl)-ethyl]-acetamide;
(S)-3-(2,3-dihydro-benzo[1,4]dioxin-6-yl)-5-({[3-(3-methoxy-quinolin-5-yl)-propyl]-methyl-amino}-methyl)-oxazolidin-2-one;
N-[(R)-3-(3-fluoro-4-methyl-phenyl)-2-oxo-oxazolidin-5-ylmethyl]-3-(3-methoxy-quinolin-5-yl)-N-methyl-propionamide;

2-[(R)-3-(2,3-dihydro-benzo[1,4]dioxin-6-yl)-2-oxo-oxazolidin-5-yl]-N-[(R)-2-hydroxy-2-(3-methoxy-quinoxalin-5-yl)-ethyl]-N-methyl-acetamide;

6-((R)-5-{[2-amino-3-(6-methoxy-[1,5]naphthyridin-4-yl)-propylamino]-methyl}-2-oxo-oxazolidin-3-yl)-4H-benzo[1,4]thiazin-3-one;

6-(5-{3-[(6-fluoro-quinolin-5-ylmethyl)-amino]-propyl}-2-oxo-oxazolidin-3-yl)-4H-benzo[1,4]thiazin-3-one;

N-(6-methoxy-[1,5]naphthyridin-4-yl)-2-{[(R)-2-oxo-3-(3-oxo-3,4-dihydro-2H-benzo[1,4]thiazin-6-yl)-oxazolidin-5-ylmethyl]-amino}-acetamide;

(R*)-3-(2,3-dihydro-benzo[1,4]dioxin-6-yl)-5-{2-[(R*)-2-hydroxy-2-(3-methoxy-quinoxalin-5-yl)-ethylamino]-ethyl}-oxazolidin-2-one;

N-[(R)-2-hydroxy-2-(6-methoxy-[1,5]naphthyridin-4-yl)-ethyl]-N-methyl-2-[(R)-2-oxo-3-(3-oxo-3,4-dihydro-2H-benzo[1,4]thiazin-6-yl)-oxazolidin-5-yl]-acetamide;

(S)-3-(2,3-dihydro-benzo[1,4]dioxin-6-yl)-5-[3-(6-methoxy-[1,5]naphthyridin-4-yl)-propoxymethyl]-oxazolidin-2-one;

3-(2,3-dihydro-benzo[1,4]dioxin-6-yl)-5-[(E)-3-(6-methoxy-[1,5]naphthyridin-4-yl)-allyloxymethyl]-oxazolidin-2-one;

N-[2-(6-methoxy-[1,5]naphthyridin-4-yl)-ethyl]-2-[(R)-2-oxo-3-(3-oxo-3,4-dihydro-2H-benzo[1,4]thiazin-6-yl)-oxazolidin-5-yl]-acetamide;

(R*)-3-(2,3-dihydro-benzo[1,4]dioxin-6-yl)-5-{(R*)-1-hydroxy-2-[2-(6-methoxy-[1,5]naphthyridin-4-yl)-ethylamino]-ethyl}-oxazolidin-2-one;

(R*)-3-(2,3-dihydro-benzo[1,4]dioxin-6-yl)-5-{(R*)-1-hydroxy-2-[2-(6-methoxy-quinolin-4-yl)-ethylamino]-ethyl}-oxazolidin-2-one;

(R*)-3-(2,3-dihydro-benzo[1,4]dioxin-6-yl)-5-((R*)-1-hydroxy-2-{[2-(6-methoxy-[1,5]naphthyridin-4-yl)-ethyl]-methyl-amino}-ethyl)-oxazolidin-2-one;

(R*)-3-(2,3-dihydro-benzo[1,4]dioxin-6-yl)-(R*)-5-(1-hydroxy-2-{[2-hydroxy-2-(3-methoxy-quinoxalin-5-yl)-ethyl]-methyl-amino}-ethyl)-oxazolidin-2-one;

6-((S)-5-{(S)-1-hydroxy-2-[2-(6-methoxy-[1,5]naphthyridin-4-yl)-ethylamino]-ethyl}-2-oxo-oxazolidin-3-yl)-4H-benzo[1,4]thiazin-3-one;

(S)-3-(2,3-dihydro-benzo[1,4]dioxin-6-yl)-5-{(S)-1-hydroxy-2-[2-hydroxy-2-(3-methoxy-quinoxalin-5-yl)-ethylamino]-ethyl}-oxazolidin-2-one;

6-((R*)-5-{(R*)-1-hydroxy-3-[(6-methoxy-[1,5]naphthyridin-4-ylmethyl)-amino]-propyl}-2-oxo-oxazolidin-3-yl)-4H-benzo[1,4]thiazin-3-one;

6-((R*)-5-{(R*)-3-[(3-fluoro-6-methoxy-[1,5]naphthyridin-4-ylmethyl)-amino]-1-hydroxy-propyl}-2-oxo-oxazolidin-3-yl)-4H-benzo[1,4]thiazin-3-one;

(R*)-3-(2,3-dihydro-benzo[1,4]dioxin-6-yl)-5-{(R*)-3-[(3-fluoro-6-methoxy-[1,5]naphthyridin-4-ylmethyl)-amino]-1-hydroxy-propyl}-oxazolidin-2-one;

(S*)-3-(2,3-dihydro-benzo[1,4]dioxin-6-yl)-5-{(R*)-3-[(3-fluoro-6-methoxy-[1,5]naphthyridin-4-ylmethyl)-amino]-1-hydroxy-propyl}-oxazolidin-2-one;

(S*)-5-{(R*)-1-amino-3-[(3-fluoro-6-methoxy-[1,5]naphthyridin-4-ylmethyl)-amino]-propyl}-3-(2,3-dihydro-benzo[1,4]dioxin-6-yl)-oxazolidin-2-one;

(R)-3-(2,3-dihydro-benzo[1,4]dioxin-6-yl)-5-[(E)-4-(6-methoxy-quinolin-4-yloxy)-but-2-enyl]-oxazolidin-2-one;

3-(2,3-dihydro-benzo[1,4]dioxin-6-yl)-5-[4-(6-methoxy-quinolin-4-yloxy)-butyl]-oxazolidin-2-one;

3-[3-(2,3-dihydro-benzo[1,4]dioxin-6-yl)-2-oxo-oxazolidin-5-yl]-N-(3-methoxy-quinoxalin-5-ylmethyl)-N-methyl-propionamide;

(R*)-3-(2,3-dihydro-benzo[1,4]dioxin-6-yl)-5-[(R*)-1-hydroxy-5-(6-methoxy-[1,5]naphthyridin-4-yl)-pentyl]-oxazolidin-2-one;

(R)-3-(2,3-dihydro-benzo[1,4]dioxin-6-yl)-5-{[4-(6-methoxy-[1,5]naphthyridin-4-yl)-butylamino]-methyl}-oxazolidin-2-one;

6-((R)-5-{[4-(6-methoxy-[1,5]naphthyridin-4-yl)-butylamino]-methyl}-2-oxo-oxazolidin-3-yl)-4H-benzo[1,4]thiazin-3-one;

3-(2,3-dihydro-benzo[1,4]dioxin-6-yl)-5-[3-hydroxy-5-(6-methoxy-[1,5]naphthyridin-4-yl)-pentyl]-oxazolidin-2-one;

3-(2,3-dihydro-benzo[1,4]dioxin-6-yl)-5-[5-(6-methoxy-[1,5]naphthyridin-4-yl)-3-oxo-pentyl]-oxazolidin-2-one;

5-[3-amino-5-(6-methoxy-[1,5]naphthyridin-4-yl)-pentyl]-3-(2,3-dihydro-benzo[1,4]dioxin-6-yl)-oxazolidin-2-one;

N-[1-{2-[3-(2,3-dihydro-benzo[1,4]dioxin-6-yl)-2-oxo-oxazolidin-5-yl]-ethyl}-3-(6-methoxy-[1,5]naphthyridin-4-yl)-propyl]-methanesulfonamide;

N-[1-{2-[3-(2,3-dihydro-benzo[1,4]dioxin-6-yl)-2-oxo-oxazolidin-5-yl]-ethyl}-3-(6-methoxy-[1,5]naphthyridin-4-yl)-propyl]-acetamide;

3-(2,3-dihydro-benzo[1,4]dioxin-6-yl)-5-[3-(7-fluoro-2-methoxy-quinolin-8-ylmethoxy)-propyl]-oxazolidin-2-one;

3-(2,3-dihydro-benzo[1,4]dioxin-6-yl)-5-[3-(6-methoxy-quinolin-4-ylmethoxy)-propyl]-oxazolidin-2-one;

3-(2,3-dihydro-benzo[1,4]dioxin-6-yl)-5-[3-(6-methoxy-quinazolin-4-yloxy)-propyl]-oxazolidin-2-one;

6-{5-[3-hydroxy-5-(6-methoxy-[1,5]naphthyridin-4-yl)-pentyl]-2-oxo-oxazolidin-3-yl}-4H-benzo[1,4]thiazin-3-one;

3-(2,3-dihydro-benzo[1,4]dioxin-6-yl)-5-[2-hydroxy-5-(6-methoxy-[1,5]naphthyridin-4-yl)-pentyl]-oxazolidin-2-one;

3-(2,3-dihydro-benzo[1,4]dioxin-6-yl)-5-[5-(6-methoxy-[1,5]naphthyridin-4-yl)-pentyl]-oxazolidin-2-one;

6-{(R)-5-[5-(6-methoxy-[1,5]naphthyridin-4-yl)-pentyl]-2-oxo-oxazolidin-3-yl}-4H-benzo[1,4]thiazin-3-one;

6-(5-{2-[2-(6-methoxy-[1,5]naphthyridin-4-yl)-ethylamino]-ethyl}-2-oxo-oxazolidin-3-yl)-4H-benzo[1,4]oxazin-3-one;

6-[5-(2-{((R)-2,3-dihydroxy-propyl)-[2-(6-methoxy-[1,5]naphthyridin-4-yl)ethyl]-amino}-ethyl)-2-oxo-oxazolidin-3-yl]-4H-benzo[1,4]oxazin-3-one;

{{2-[3-(2,3-dihydro-benzo[1,4]dioxin-6-yl)-2-oxo-oxazolidin-5-yl]-ethyl}-[2-(6-methoxy-[1,5]naphthyridin-4-yl)-ethyl]-amino}-acetic acid tert-butyl ester;

3-{{2-[3-(2,3-dihydro-benzo[1,4]dioxin-6-yl)-2-oxo-oxazolidin-5-yl]-ethyl}-[2-(6-methoxy-[1,5]naphthyridin-4-yl)-ethyl]-amino}-propionic acid methyl ester;

4-{{2-[3-(2,3-dihydro-benzo[1,4]dioxin-6-yl)-2-oxo-oxazolidin-5-yl]-ethyl}-[2-(6-methoxy-[1,5]naphthyridin-4-yl)-ethyl]-amino}-butyric acid ethyl ester;

6-((R)-5-{[3-(6-methoxy-[1,5]naphthyridin-4-yl)-propylamino]-methyl}-2-oxo-oxazolidin-3-yl)-4H-benzo[1,4]oxazin-3-one;

6-((R)-5-{[3-(3-fluoro-6-methoxy-[1,5]naphthyridin-4-yl)-propylamino]-methyl}-2-oxo-oxazolidin-3-yl)-4H-benzo[1,4]oxazin-3-one;

6-((R)-5-{[3-(3-fluoro-6-methoxy-[1,5]naphthyridin-4-yl)-propylamino]-methyl}-2-oxo-oxazolidin-3-yl)-4H-benzo[1,4]thiazin-3-one;

(R)-3-(2,3-dihydro-benzo[1,4]dioxin-6-yl)-5-{[3-(3-fluoro-6-methoxy-[1,5]naphthyridin-4-yl)-propylamino]-methyl}-oxazolidin-2-one;

(R)-3-(2,3-dihydro-benzo[1,4]dioxin-6-yl)-5-({((S)-2,3-dihydroxy-propyl)-[3-(3-fluoro-6-methoxy-[1,5]naphthyridin-4-yl)-propyl]-amino}-methyl)-oxazolidin-2-one;

6-[(R)-5-({((S)-2,3-dihydroxy-propyl)-[3-(3-fluoro-6-methoxy-[1,5]naphthyridin-4-yl)-propyl]-amino}-methyl)-2-oxo-oxazolidin-3-yl]-4H-benzo[1,4]thiazin-3-one;

6-[(R)-5-({((R)-2,3-dihydroxy-propyl)-[3-(3-fluoro-6-methoxy-[1,5]naphthyridin-4-yl)-propyl]-amino}-methyl)-2-oxo-oxazolidin-3-yl]-4H-benzo[1,4]oxazin-3-one;

6-[(R)-5-({((R)-2,3-dihydroxy-propyl)-[3-(6-methoxy-[1,5]naphthyridin-4-yl)-propyl]-amino}-methyl)-2-oxo-oxazolidin-3-yl]-4H-benzo[1,4]oxazin-3-one;

{[(R)-3-(2,3-dihydro-benzo[1,4]dioxin-6-yl)-2-oxo-oxazolidin-5-ylmethyl]-[3-(6-methoxy-[1,5]naphthyridin-4-yl)-propyl]-amino}-acetic acid tert-butyl ester;

3-{[(R)-3-(2,3-dihydro-benzo[1,4]dioxin-6-yl)-2-oxo-oxazolidin-5-ylmethyl]-[3-(6-methoxy-[1,5]naphthyridin-4-yl)-propyl]-amino}-propionic acid methyl ester;

4-{[(R)-3-(2,3-dihydro-benzo[1,4]dioxin-6-yl)-2-oxo-oxazolidin-5-ylmethyl]-[3-(6-methoxy-[1,5]naphthyridin-4-yl)-propyl]-amino}-butyric acid ethyl ester;

{[(R)-3-(2,3-dihydro-benzo[1,4]dioxin-6-yl)-2-oxo-oxazolidin-5-ylmethyl]-[3-(6-methoxy-[1,5]naphthyridin-4-yl)-propyl]-amino}-acetic acid;

3-{[(R)-3-(2,3-dihydro-benzo[1,4]dioxin-6-yl)-2-oxo-oxazolidin-5-ylmethyl]-[3-(6-methoxy-[1,5]naphthyridin-4-yl)-propyl]-amino}-propionic acid;

6-(5-{3-[(6-methoxy-[1,5]naphthyridin-4-ylmethyl)-amino]-propyl}-2-oxo-oxazolidin-3-yl)-4H-benzo[1,4]oxazin-3-one;

6-(5-{3-[(3-methoxy-quinoxalin-5-ylmethyl)-amino]-propyl}-2-oxo-oxazolidin-3-yl)-4H-benzo[1,4]oxazin-3-one;

6-(5-{3-[(6-methoxy-quinolin-4-ylmethyl)-amino]-propyl}-2-oxo-oxazolidin-3-yl)-4H-benzo[1,4]oxazin-3-one;

2-methoxy-8-({3-[2-oxo-3-(3-oxo-3,4-dihydro-2H-benzo[1,4]oxazin-6-yl)-oxazolidin-5-yl]-propylamino}-methyl)-quinoline-5-carboxylic acid methyl ester;

6-(5-{3-[(3-fluoro-6-methoxy-quinolin-4-ylmethyl)-amino]-propyl}-2-oxo-oxazolidin-3-yl)-4H-benzo[1,4]oxazin-3-one;

6-(5-{3-[(3-fluoro-6-methoxy-[1,5]naphthyridin-4-ylmethyl)-amino]-propyl}-2-oxo-oxazolidin-3-yl)-4H-benzo[1,4]oxazin-3-one;

6-(5-{3-[(7-fluoro-2-methoxy-quinolin-8-ylmethyl)-amino]-propyl}-2-oxo-oxazolidin-3-yl)-4H-benzo[1,4]oxazin-3-one;

6-(5-{3-[((R)-2,3-dihydroxy-propyl)-(3-fluoro-6-methoxy-[1,5]naphthyridin-4-ylmethyl)-amino]-propyl}-2-oxo-oxazolidin-3-yl)-4H-benzo[1,4]thiazin-3-one;

6-(5-{3-[((R)-3-chloro-2-hydroxy-propyl)-(3-fluoro-6-methoxy-[1,5]naphthyridin-4-ylmethyl)-amino]-propyl}-2-oxo-oxazolidin-3-yl)-4H-benzo[1,4]thiazin-3-one;

6-(5-{3-[((S)-3-dimethylamino-2-hydroxy-propyl)-(3-fluoro-6-methoxy-[1,5]naphthyridin-4-ylmethyl)-amino]-propyl}-2-oxo-oxazolidin-3-yl)-4H-benzo[1,4]thiazin-3-one;

6-(2-oxo-5-{3-[(quinolin-4-ylmethyl)-amino]-propyl}-oxazolidin-3-yl)-4H-benzo[1,4]thiazin-3-one;

6-(5-{3-[(naphthalen-1-ylmethyl)-amino]-propyl}-2-oxo-oxazolidin-3-yl)-4H-benzo[1,4]thiazin-3-one;

2-methoxy-8-({3-[2-oxo-3-(3-oxo-3,4-dihydro-2H-benzo[1,4]thiazin-6-yl)-oxazolidin-5-yl]-propylamino}-methyl)-quinoline-5-carboxylic acid methyl ester;

6-[5-(3-{[3-methoxy-8-(2-methoxy-ethoxy)-quinoxalin-5-ylmethyl]-amino}-propyl)-2-oxo-oxazolidin-3-yl]-4H-benzo[1,4]thiazin-3-one;

6-(5-{3-[(6-fluoro-quinolin-4-ylmethyl)-amino]-propyl}-2-oxo-oxazolidin-3-yl)-4H-benzo[1,4]thiazin-3-one;

6-(5-{3-[(3-methoxy-quinoxalin-5-ylmethyl)-amino]-propyl}-2-oxo-oxazolidin-3-yl)-4H-benzo[1,4]thiazin-3-one;

6-(5-{3-[(6-methoxy-quinolin-4-ylmethyl)-amino]-propyl}-2-oxo-oxazolidin-3-yl)-4H-benzo[1,4]thiazin-3-one;

6-(5-{3-[(isoquinolin-5-ylmethyl)-amino]-propyl}-2-oxo-oxazolidin-3-yl)-4H-benzo[1,4]thiazin-3-one;

6-(5-{3-[(4-methoxy-naphthalen-1-ylmethyl)-amino]-propyl}-2-oxo-oxazolidin-3-yl)-4H-benzo[1,4]thiazin-3-one;

6-(2-oxo-5-{3-[(quinolin-5-ylmethyl)-amino]-propyl}-oxazolidin-3-yl)-4H-benzo[1,4]thiazin-3-one;

6-(2-oxo-5-{3-[(quinolin-8-ylmethyl)-amino]-propyl}-oxazolidin-3-yl)-4H-benzo[1,4]thiazin-3-one;

6-(5-{3-[(4-hydroxy-naphthalen-1-ylmethyl)-amino]-propyl}-2-oxo-oxazolidin-3-yl)-4H-benzo[1,4]thiazin-3-one;

6-(5-{3-[(2-hydroxy-naphthalen-1-ylmethyl)-amino]-propyl}-2-oxo-oxazolidin-3-yl)-4H-benzo[1,4]thiazin-3-one;

6-(5-{3-[(7-fluoro-2-methoxy-quinolin-8-ylmethyl)-amino]-propyl}-2-oxo-oxazolidin-3-yl)-4H-benzo[1,4]thiazin-3-one;

6-(5-{3-[(2,3-dimethoxy-naphthalen-1-ylmethyl)-amino]-propyl}-2-oxo-oxazolidin-3-yl)-4H-benzo[1,4]thiazin-3-one;

6-(5-{3-[(4,7-dimethoxy-naphthalen-1-ylmethyl)-amino]-propyl}-2-oxo-oxazolidin-3-yl)-4H-benzo[1,4]thiazin-3-one;

((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-acetic acid tert-butyl ester;

3-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-propionic acid methyl ester;

4-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-butyric acid ethyl ester;

((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-acetic acid;

3-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-propionic acid;

4-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-butyric acid;

6-((R)-5-{3-[(3-fluoro-6-methoxy-[1,5]naphthyridin-4-ylmethyl)-amino]-propyl}-2-oxo-oxazolidin-3-yl)-4H-benzo[1,4]oxazin-3-one;

6-((R)-5-{3-[((S)-2,3-dihydroxy-propyl)-(3-fluoro-6-methoxy-[1,5]naphthyridin-4-ylmethyl)-amino]-propyl}-2-oxo-oxazolidin-3-yl)-4H-benzo[1,4]oxazin-3-one;

6-((R)-5-{3-[((R)-2,3-dihydroxy-propyl)-(3-fluoro-6-methoxy-[1,5]naphthyridin-4-ylmethyl)-amino]-propyl}-2-oxo-oxazolidin-3-yl)-4H-benzo[1,4]oxazin-3-one;

6-((R)-5-{3-[(3-fluoro-6-methoxy-[1,5]naphthyridin-4-ylmethyl)-(2-hydroxy-ethyl)-amino]-propyl}-2-oxo-oxazolidin-3-yl)-4H-benzo[1,4]oxazin-3-one;

(S)-3-(2,3-dihydro-benzo[1,4]dioxin-6-yl)-5-{(1R,2S)-1,2-dihydroxy-3-[(6-methoxy-[1,5]naphthyridin-4-ylmethyl)-amino]-propyl}-oxazolidin-2-one;

(S)-3-(2,3-dihydro-benzo[1,4]dioxin-6-yl)-5-{(1R,2S)-3-[(3-fluoro-6-methoxy-quinolin-4-ylmethyl)-amino]-1,2-dihydroxy-propyl}-oxazolidin-2-one;

(S)-3-(2,3-dihydro-benzo[1,4]dioxin-6-yl)-5-{(1R,2S)-1,2-dihydroxy-3-[(3-methoxy-quinoxalin-5-ylmethyl)-amino]-propyl}-oxazolidin-2-one;

(R)-3-(2,3-dihydro-benzo[1,4]dioxin-6-yl)-5-{(1R,2S)-1,2-dihydroxy-3-[(6-methoxy-[1,5]naphthyridin-4-ylmethyl)-amino]-propyl}-oxazolidin-2-one;

(R)-3-(2,3-dihydro-benzo[1,4]dioxin-6-yl)-5-{(1R,2S)-3-[(3-fluoro-6-methoxy-[1,5]naphthyridin-4-ylmethyl)-amino]-1,2-dihydroxy-propyl}-oxazolidin-2-one;

6-((S)-5-{(1R,2S)-1,2-dihydroxy-3-[(6-methoxy-[1,5]naphthyridin-4-ylmethyl)-amino]-propyl}-2-oxo-oxazolidin-3-yl)-4H-benzo[1,4]thiazin-3-one;

6-((S)-5-{(1R,2S)-3-[(3-fluoro-6-methoxy-[1,5]naphthyridin-4-ylmethyl)-amino]-1,2-dihydroxy-propyl}-2-oxo-oxazolidin-3-yl)-4H-benzo[1,4]thiazin-3-one;

6-((S)-5-{(1R,2S)-3-[(3-fluoro-6-methoxy-quinolin-4-ylmethyl)-amino]-1,2-dihydroxy-propyl}-2-oxo-oxazolidin-3-yl)-4H-benzo[1,4]thiazin-3-one;

(R)-3-(2,3-dihydro-benzo[1,4]dioxin-6-yl)-5-{(1S,2R)-1,2-dihydroxy-3-[(6-methoxy-[1,5]naphthyridin-4-ylmethyl)-amino]-propyl}-oxazolidin-2-one;

(R)-3-(2,3-dihydro-benzo[1,4]dioxin-6-yl)-5-{(1S,2R)-3-[(3-fluoro-6-methoxy-[1,5]naphthyridin-4-ylmethyl)-amino]-1,2-dihydroxy-propyl}-oxazolidin-2-one;

(S)-3-(2,3-dihydro-benzo[1,4]dioxin-6-yl)-5-{(1S,2R)-1,2-dihydroxy-3-[(6-methoxy-[1,5]naphthyridin-4-ylmethyl)-amino]-propyl}-oxazolidin-2-one;

6-((R)-5-{(1S,2R)-1,2-dihydroxy-3-[(6-methoxy-[1,5]naphthyridin-4-ylmethyl)amino]-propyl}-2-oxo-oxazolidin-3-yl)-4H-benzo[1,4]thiazin-3-one;

6-((R)-5-{(1S,2R)-1,2-dihydroxy-3-[(3-methoxy-quinoxalin-5-ylmethyl)-amino]-propyl}-2-oxo-oxazolidin-3-yl)-4H-benzo[1,4]thiazin-3-one;

6-((R)-5-{(1S,2R)-3-[(3-fluoro-6-methoxy-[1,5]naphthyridin-4-ylmethyl)-amino]-1,2-dihydroxy-propyl}-2-oxo-oxazolidin-3-yl)-4H-benzo[1,4]thiazin-3-one;

6-((R)-5-{(1S,2R)-3-[(3-fluoro-6-methoxy-quinolin-4-ylmethyl)-amino]-1,2-dihydroxy-propyl}-2-oxo-oxazolidin-3-yl)-4H-benzo[1,4]thiazin-3-one;

6-((S)-5-{(1S,2R)-3-[(3-fluoro-6-methoxy-[1,5]naphthyridin-4-ylmethyl)-amino]-1,2-dihydroxy-propyl}-2-oxo-oxazolidin-3-yl)-4H-benzo[1,4]thiazin-3-one;

6-((R)-5-{(1S,2R)-3-[(3-fluoro-6-methoxy-[1,5]naphthyridin-4-ylmethyl)-amino]-1,2-dihydroxy-propyl}-2-oxo-oxazolidin-3-yl)-4H-benzo[1,4]oxazin-3-one;

6-((R)-5-{(1S,2R)-3-[(3-fluoro-6-methoxy-quinolin-4-ylmethyl)-amino]-1,2-dihydroxy-propyl}-2-oxo-oxazolidin-3-yl)-4H-benzo[1,4]oxazin-3-one;

6-((S)-5-{(1S,2R)-3-[(3-fluoro-6-methoxy-[1,5]naphthyridin-4-ylmethyl)-amino]-1,2-dihydroxy-propyl}-2-oxo-oxazolidin-3-yl)-4H-benzo[1,4]oxazin-3-one;

2-(6-methoxy-[1,5]naphthyridin-4-yloxy)-N-[(R)-2-oxo-3-(3-oxo-3,4-dihydro-2H-benzo[1,4]thiazin-6-yl)-oxazolidin-5-ylmethyl]-acetamide;

3-(3-fluoro-4-methyl-phenyl)-5-{2-[2-hydroxy-2-(3-methoxy-quinoxalin-5-yl)-ethylamino]-ethyl}-oxazolidin-2-one;

6-((R)-5-{[2-(6-methoxy-[1,5]naphthyridin-4-ylamino)-ethylamino]-methyl}-2-oxo-oxazolidin-3-yl)-4H-benzo[1,4]thiazin-3-one;

6-((R)-5-{[2-(6-methoxy-[1,5]naphthyridin-4-ylamino)-ethylamino]-methyl}-2-oxo-oxazolidin-3-yl)-4H-benzo[1,4]oxazin-3-one;

6-((S)-5-{3-[(3-fluoro-6-methoxy-[1,5]naphthyridin-4-ylmethyl)-amino]-propyl}-2-oxo-oxazolidin-3-yl)-4H-benzo[1,4]oxazin-3-one;

6-((R)-5-{[3-(6-methoxy-[1,5]naphthyridin-4-yl)-propylamino]-methyl}-2-oxo-oxazolidin-3-yl)-4H-pyrido[3,2-b][1,4]oxazin-3-one;

3-(2,3-dihydro-benzo[1,4]dioxin-6-yl)-5-{[(3-fluoro-6-methoxy-[1,5]naphthyridin-4-ylmethyl)-amino]-2-hydroxy-propyl}-oxazolidin-2-one;

6-((R)-5-{3-[(3-amino-propyl)-(3-fluoro-6-methoxy-[1,5]naphthyridin-4-ylmethyl)-amino]-propyl}-2-oxo-oxazolidin-3-yl)-4H-benzo[1,4]oxazin-3-one;

6-((R)-5-{3-[(3-fluoro-6-methoxy-[1,5]naphthyridin-4-ylmethyl)-(3-hydroxy-propyl)-amino]-propyl}-2-oxo-oxazolidin-3-yl)-4H-benzo[1,4]oxazin-3-one;

6-((S*)-5-{(S*)-3-[(3-fluoro-6-methoxy-[1,5]naphthyridin-4-ylmethyl)-amino]-1-hydroxy-propyl}-2-oxo-oxazolidin-3-yl)-4H-benzo[1,4]oxazin-3-one;

(S*)-5-{(S*)-1-amino-3-[(3-fluoro-6-methoxy-[1,5]naphthyridin-4-ylmethyl)-amino]-propyl}-3-(2,3-dihydro-benzo[1,4]dioxin-6-yl)-oxazolidin-2-one;

6-(5-{3-[(3-fluoro-6-methoxy-[1,5]naphthyridin-4-ylmethyl)-amino]-2-hydroxy-propyl}-2-oxo-oxazolidin-3-yl)-4H-benzo[1,4]thiazin-3-one;

6-(5-{3-[(3-fluoro-6-methoxy-quinolin-4-ylmethyl)-amino]-2-hydroxy-propyl}-2-oxo-oxazolidin-3-yl)-4H-benzo[1,4]thiazin-3-one;

6-(5-{3-[(3-fluoro-6-methoxy-[1,5]naphthyridin-4-ylmethyl)-amino]-2-hydroxy-propyl}-2-oxo-oxazolidin-3-yl)-4H-benzo[1,4]oxazin-3-one;

6-(5-{3-[(3-fluoro-6-methoxy-quinolin-4-ylmethyl)-amino]-2-hydroxy-propyl}-2-oxo-oxazolidin-3-yl)-4H-benzo[1,4]oxazin-3-one;

6-(5-{3-[(7-fluoro-2-methoxy-quinolin-8-ylmethyl)-amino]-2-hydroxy-propyl}-2-oxo-oxazolidin-3-yl)-4H-benzo[1,4]oxazin-3-one;

and the salts (in particular pharmaceutically acceptable salts) thereof, whereby the first 92 compounds in the list above (counted from the top of the list) and their salts (in particular their pharmaceutically acceptable salts) constitute a particular sub-embodiment and the first 203 compounds in the list above (counted from the top of the list) and their salts (in particular their pharmaceutically acceptable salts) constitute another particular sub-embodiment.

lxiii) Furthermore, the following compounds of formula I as defined in embodiment i) or ii) are particularly preferred:

(E)-[(S)-3-(2,3-dihydro-benzo[1,4]dioxin-6-yl)-2-oxo-oxazolidin-5-ylmethyl]-3-(6-methoxy-[1,5]naphthyridin-4-yl)-acrylamide;

(E)-[(S)-3-(2,3-dihydro-benzo[1,4]dioxin-6-yl)-2-oxo-oxazolidin-5-ylmethyl]-3-(6-methoxy-quinolin-4-yl)-acrylamide;

(E)-[(R)-3-(2,3-dihydro-benzo[1,4]dioxin-6-yl)-2-oxo-oxazolidin-5-ylmethyl]-3-(6-methoxy-[1,5]naphthyridin-4-yl)-acrylamide;

(E)-3-(6-methoxy-[1,5]naphthyridin-4-yl)-N-[(R)-2-oxo-3-(3-oxo-3,4-dihydro-2H-benzo[1,4]thiazin-6-yl)-oxazolidin-5-ylmethyl]-acrylamide;

(E)-N-[(R)-3-(2,3-dihydro-benzo[1,4]dioxin-6-yl)-2-oxo-oxazolidin-5-ylmethyl]-3-(3-methoxy-quinoxalin-5-yl)-acrylamide;

(E)-N-[(R)-3-(2,3-dihydro-benzo[1,4]dioxin-6-yl)-2-oxo-oxazolidin-5-ylmethyl]-3-(3-methoxy-quinolin-5-yl)-acrylamide;

(E)-N-[(R)-3-(2,3-dihydro-benzo[1,4]dioxin-6-yl)-2-oxo-oxazolidin-5-ylmethyl]-N-ethyl-3-(6-methoxy-[1,5]naphthyridin-4-yl)-acrylamide;

(E)-N-benzyl-N-[(R)-3-(2,3-dihydro-benzo[1,4]dioxin-6-yl)-2-oxo-oxazolidin-5-ylmethyl]-3-(6-methoxy-[1,5]naphthyridin-4-yl)-acrylamide;

(E)-N-benzyl-N-[(S)-3-(2,3-dihydro-benzo[1,4]dioxin-6-yl)-2-oxo-oxazolidin-5-ylmethyl]-3-(6-methoxy-[1,5]naphthyridin-4-yl)-acrylamide;

(E)-3-(3-methoxy-quinoxalin-5-yl)-N-[(R)-2-oxo-3-(3-oxo-3,4-dihydro-2H-benzo[1,4]thiazin-6-yl)-oxazolidin-5-ylmethyl]-acrylamide;

(E)-3-(3-methoxy-quinolin-5-yl)-N-[(R)-2-oxo-3-(3-oxo-3,4-dihydro-2H-benzo[1,4]thiazin-6-yl)-oxazolidin-5-ylmethyl]-acrylamide;

(E)-3-(6-methoxy-[1,5]naphthyridin-4-yl)-N-methyl-N-[(R)-2-oxo-3-(3-oxo-3,4-dihydro-2H-benzo[1,4]thiazin-6-yl)-oxazolidin-5-ylmethyl]-acrylamide;

(E)-N-[(R)-3-(3-fluoro-4-methyl-phenyl)-2-oxo-oxazolidin-5-ylmethyl]-3-(6-methoxy-[1,5]naphthyridin-4-yl)-acrylamide;

(E)-N-[(R)-3-(3-fluoro-4-methyl-phenyl)-2-oxo-oxazolidin-5-ylmethyl]-3-(6-methoxy-[1,5]naphthyridin-4-yl)-N-methyl-acrylamide;

(E)-N-[(R)-3-(4-ethyl-phenyl)-2-oxo-oxazolidin-5-ylmethyl]-3-(6-methoxy-[1,5]naphthyridin-4-yl)-N-methyl-acrylamide;

(E)-3-(6-methoxy-[1,5]naphthyridin-4-yl)-N-methyl-N-[(R)-2-oxo-3-(4-propyl-phenyl)-oxazolidin-5-ylmethyl]-acrylamide;

(E)-3-(2-cyano-quinolin-8-yl)-N-[(R)-3-(2,3-dihydro-benzo[1,4]dioxin-6-yl)-2-oxo-oxazolidin-5-ylmethyl]-acrylamide;

(E)-N-[(R)-3-(2,3-dihydro-benzo[1,4]dioxin-6-yl)-2-oxo-oxazolidin-5-ylmethyl]-3-(6-fluoro-quinolin-4-yl)-acrylamide;

(E)-N-[(R)-3-(2,3-dihydro-benzo[1,4]dioxin-6-yl)-2-oxo-oxazolidin-5-ylmethyl]-3-(2-methoxy-quinolin-8-yl)-acrylamide;

(E)-3-(6-methoxy-[1,5]naphthyridin-4-yl)-N-methyl-N-[(R)-3-(4-methyl-3-trifluoromethyl-phenyl)-2-oxo-oxazolidin-5-ylmethyl]-acrylamide;

(E)-N-[(R)-3-(3-bromo-4-methyl-phenyl)-2-oxo-oxazolidin-5-ylmethyl]-3-(6-methoxy-[1,5]naphthyridin-4-yl)-N-methyl-acrylamide;

(E)-N-[(R)-3-(4-bromo-3-methyl-phenyl)-2-oxo-oxazolidin-5-ylmethyl]-3-(6-methoxy-[1,5]naphthyridin-4-yl)-N-methyl-acrylamide;

(E)-N-[(R)-3-(4-bromo-3-fluoro-phenyl)-2-oxo-oxazolidin-5-ylmethyl]-3-(6-methoxy-[1,5]naphthyridin-4-yl)-N-methyl-acrylamide;

(E)-N-[(S)-3-(3-fluoro-4-methyl-phenyl)-2-oxo-oxazolidin-5-ylmethyl]-3-(6-methoxy-[1,5]naphthyridin-4-yl)-N-methyl-acrylamide;

(E)-3-(6-methoxy-[1,5]naphthyridin-4-yl)-N-methyl-N-[(S)-2-oxo-3-(3-oxo-3,4-dihydro-2H-benzo[1,4]thiazin-6-yl)-oxazolidin-5-ylmethyl]-acrylamide;

(E)-N-[(S)-3-(2,3-dihydro-benzo[1,4]dioxin-6-yl)-2-oxo-oxazolidin-5-ylmethyl]-3-(6-methoxy-[1,5]naphthyridin-4-yl)-N-methyl-acrylamide;

(E)-N-[(S)-3-(4-ethyl-phenyl)-2-oxo-oxazolidin-5-ylmethyl]-3-(3-methoxy-quinoxalin-5-yl)-N-methyl-acrylamide;

N-[(R)-3-(2,3-dihydro-benzo[1,4]dioxin-6-yl)-2-oxo-oxazolidin-5-ylmethyl]-3-(6-methoxy-[1,5]naphthyridin-4-yl)-propionamide;

3-(3-methoxy-quinolin-5-yl)-N-[(R)-2-oxo-3-(3-oxo-3,4-dihydro-2H-benzo[1,4]thiazin-6-yl)-oxazolidin-5-ylmethyl]-propionamide;

(R)-3-(2,3-dihydro-benzo[1,4]dioxin-6-yl)-5-{[(E)-3-(6-methoxy-[1,5]naphthyridin-4-yl)allylamino]-methyl}-oxazolidin-2-one;

(R)-3-(2,3-dihydro-benzo[1,4]dioxin-6-yl)-5-{[3-(6-methoxy-[1,5]naphthyridin-4-yl)-propylamino]-methyl}-oxazolidin-2-one;

N-[(R)-3-(2,3-dihydro-benzo[1,4]dioxin-6-yl)-2-oxo-oxazolidin-5-ylmethyl]-N-[(E)-3-(6-methoxy-[1,5]naphthyridin-4-yl)-allyl]-acetamide;

6-((R)-5-{[(E)-3-(6-methoxy-[1,5]naphthyridin-4-yl)-allylamino]-methyl}-2-oxo-oxazolidin-3-yl)-4H-benzo[1,4]thiazin-3-one;

6-((R)-5-{[3-(6-methoxy-[1,5]naphthyridin-4-yl)-propylamino]-methyl}-2-oxo-oxazolidin-3-yl)-4H-benzo[1,4]thiazin-3-one;

6-((R)-5-{[3-(6-methoxy-[1,5]naphthyridin-4-yl)-propylamino]-methyl}-2-oxo-oxazolidin-3-yl)-4H-benzo[1,4]oxazin-3-one;

6-((S)-5-{[3-(6-methoxy-[1,5]naphthyridin-4-yl)-propylamino]-methyl}-2-oxo-oxazolidin-3-yl)-4H-benzo[1,4]oxazin-3-one;

6-((R)-5-{[3-(3-methoxy-quinolin-5-yl)-propylamino]-methyl}-2-oxo-oxazolidin-3-yl)-4H-benzo[1,4]thiazin-3-one;

N-[(R)-3-(2,3-dihydro-benzo[1,4]dioxin-6-yl)-2-oxo-oxazolidin-5-ylmethyl]-N-[3-(6-methoxy-[1,5]naphthyridin-4-yl)-propyl]-acetamide;

N-[3-(6-methoxy-[1,5]naphthyridin-4-yl)-propyl]-N-[(R)-2-oxo-3-(3-oxo-3,4-dihydro-2H-benzo[1,4]thiazin-6-yl)-oxazolidin-5-ylmethyl]-succinamic acid;

N-[3-(6-methoxy-[1,5]naphthyridin-4-yl)-propyl]-N-[(R)-2-oxo-3-(3-oxo-3,4-dihydro-2H-benzo[1,4]thiazin-6-yl)-oxazolidin-5-ylmethyl]-propionamide;

(R)-3-(2,3-dihydro-benzo[1,4]dioxin-6-yl)-5-({ethyl-[3-(6-methoxy-[1,5]naphthyridin-4-yl)-propyl]-amino}-methyl)-oxazolidin-2-one;

(R)-5-({benzyl-[3-(6-methoxy-[1,5]naphthyridin-4-yl)-propyl]-amino}-methyl)-3-(2,3-dihydro-benzo[1,4]dioxin-6-yl)-oxazolidin-2-one;

(S)-5-({benzyl-[3-(6-methoxy-[1,5]naphthyridin-4-yl)-propyl]-amino}-methyl)-3-(2,3-dihydro-benzo[1,4]dioxin-6-yl)-oxazolidin-2-one;

(R)-5-({(2-amino-ethyl)-[3-(6-methoxy-[1,5]naphthyridin-4-yl)-propyl]-amino}-methyl)-3-(2,3-dihydro-benzo[1,4]dioxin-6-yl)-oxazolidin-2-one;

6-[(R)-5-({[3-(3-methoxy-quinolin-5-yl)-propyl]-methyl-amino}-methyl)-2-oxo-oxazolidin-3-yl]-4H-benzo[1,4]thiazin-3-one;

(R)-3-(3-fluoro-4-methyl-phenyl)-5-({[3-(3-methoxy-quinolin-5-yl)-propyl]-methyl-amino}-methyl)-oxazolidin-2-one;

(R)-5-({[3-(3-methoxy-quinolin-5-yl)-propyl]-methyl-amino}-methyl)-3-(4-methyl-3-trifluoromethyl-phenyl)-oxazolidin-2-one;

(R)-3-(4-ethyl-phenyl)-5-({[3-(3-methoxy-quinolin-5-yl)-propyl]-methyl-amino}-methyl)-oxazolidin-2-one;

(R)-5-({[3-(3-methoxy-quinolin-5-yl)-propyl]-methyl-amino}-methyl)-3-(4-propyl-phenyl)-oxazolidin-2-one;

(R)-3-(3-bromo-4-methyl-phenyl)-5-({[3-(3-methoxy-quinolin-5-yl)-propyl]-methyl-amino}-methyl)-oxazolidin-2-one;

(R)-3-(4-bromo-3-methyl-phenyl)-5-({[3-(3-methoxy-quinolin-5-yl)-propyl]-methyl-amino}-methyl)-oxazolidin-2-one;

(R)-3-(4-bromo-3-fluoro-phenyl)-5-({[3-(3-methoxy-quinolin-5-yl)-propyl]-methyl-amino}-methyl)-oxazolidin-2-one;

(S)-3-(3-fluoro-4-methyl-phenyl)-5-({[3-(3-methoxy-quinolin-5-yl)-propyl]-methyl-amino}-methyl)-oxazolidin-2-one;

(S)-3-(2,3-dihydro-benzo[1,4]dioxin-6-yl)-2-oxo-oxazolidine-5-carboxylic acid [3-(6-methoxy-[1,5]naphthyridin-4-yl)-propyl]-amide;

6-((R)-5-{[(2R,3R)-2,3-dihydroxy-3-(6-methoxy-[1,5]naphthyridin-4-yl)-propylamino]-methyl}-2-oxo-oxazolidin-3-yl)-4H-benzo[1,4]thiazin-3-one;

6-((R)-5-{[(2S,3S)-2,3-dihydroxy-3-(6-methoxy-[1,5]naphthyridin-4-yl)-propylamino]-methyl}-2-oxo-oxazolidin-3-yl)-4H-benzo[1,4]thiazin-3-one;

6-((S)-5-{[(2R,3R)-2,3-dihydroxy-3-(6-methoxy-[1,5]naphthyridin-4-yl)-propylamino]-methyl}-2-oxo-oxazolidin-3-yl)-4H-benzo[1,4]thiazin-3-one;

6-((S)-5-{[(2S,3S)-2,3-dihydroxy-3-(6-methoxy-[1,5]naphthyridin-4-yl)-propylamino]-methyl}-2-oxo-oxazolidin-3-yl)-4H-benzo[1,4]thiazin-3-one;

(2S,3R)-N-[(S)-3-(2,3-dihydro-benzo[1,4]dioxin-6-yl)-2-oxo-oxazolidin-5-ylmethyl]-2,3-dihydroxy-3-(6-methoxy-[1,5]naphthyridin-4-yl)-propionamide;

(2R,3S)-2,3-dihydroxy-3-(6-methoxy-[1,5]naphthyridin-4-yl)-N-[(R)-2-oxo-3-(3-oxo-3,4-dihydro-2H-benzo[1,4]thiazin-6-yl)-oxazolidin-5-ylmethyl]-propionamide;

(2S,3R)-2,3-dihydroxy-3-(6-methoxy-[1,5]naphthyridin-4-yl)-N-[(R)-2-oxo-3-(3-oxo-3,4-dihydro-2H-benzo[1,4]thiazin-6-yl)-oxazolidin-5-ylmethyl]-propionamide;

N-[(R)-3-(2,3-dihydro-benzo[1,4]dioxin-6-yl)-2-oxo-oxazolidin-5-ylmethyl]-(3R)-3-hydroxy-3-(6-methoxy-[1,5]naphthyridin-4-yl)-propionamide;

N-[(R)-3-(2,3-dihydro-benzo[1,4]dioxin-6-yl)-2-oxo-oxazolidin-5-ylmethyl]-(3S)-3-hydroxy-3-(6-methoxy-[1,5]naphthyridin-4-yl)-propionamide;

(R)-N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-propionamide;

(S)-N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-propionamide;

(Z)-N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-acrylamide;

(R)-3-(2,3-dihydro-benzo[1,4]dioxin-6-yl)-5-{[(3R)-3-hydroxy-3-(6-methoxy-[1,5]naphthyridin-4-yl)-propylamino]-methyl}-oxazolidin-2-one;

(R)-3-(2,3-dihydro-benzo[1,4]dioxin-6-yl)-5-{[(3S)-3-hydroxy-3-(6-methoxy-[1,5]naphthyridin-4-yl)-propylamino]-methyl}-oxazolidin-2-one;

3-(2,3-dihydro-benzo[1,4]dioxin-6-yl)-(5R)-5-[(5R)-5-hydroxy-5-(6-methoxy-[1,5]naphthyridin-4-yl)-pentyl]-oxazolidin-2-one;

3-(2,3-dihydro-benzo[1,4]dioxin-6-yl)-(5R)-5-[(5S)-5-hydroxy-5-(6-methoxy-[1,5]naphthyridin-4-yl)-pentyl]-oxazolidin-2-one;

3-(2,3-dihydro-benzo[1,4]dioxin-6-yl)-(5S)-5-[(5R)-5-hydroxy-5-(6-methoxy-[1,5]naphthyridin-4-yl)-pentyl]-oxazolidin-2-one;

3-(2,3-dihydro-benzo[1,4]dioxin-6-yl)-(5S)-5-[(5S)-5-hydroxy-5-(6-methoxy-[1,5]naphthyridin-4-yl)-pentyl]-oxazolidin-2-one;

3-(2,3-dihydro-benzo[1,4]dioxin-6-yl)-(5R)-5-[(5R)-5-(3-fluoro-6-methoxy-[1,5]naphthyridin-4-yl)-5-hydroxy-pentyl]-oxazolidin-2-one;

3-(2,3-dihydro-benzo[1,4]dioxin-6-yl)-(5R)-5-[(5S)-5-(3-fluoro-6-methoxy-[1,5]naphthyridin-4-yl)-5-hydroxy-pentyl]-oxazolidin-2-one;

3-(2,3-dihydro-benzo[1,4]dioxin-6-yl)-(5S)-5-[(5R)-5-(3-fluoro-6-methoxy-[1,5]naphthyridin-4-yl)-5-hydroxy-pentyl]-oxazolidin-2-one;

3-(2,3-dihydro-benzo[1,4]dioxin-6-yl)-(5S)-5-[(5S)-5-(3-fluoro-6-methoxy-[1,5]naphthyridin-4-yl)-5-hydroxy-pentyl]-oxazolidin-2-one;

(R)-3-(2,3-dihydro-benzo[1,4]dioxin-6-yl)-5-[5-(6-methoxy-[1,5]naphthyridin-4-yl)-5-oxo-pentyl]-oxazolidin-2-one;

(S)-3-(2,3-dihydro-benzo[1,4]dioxin-6-yl)-5-[5-(6-methoxy-[1,5]naphthyridin-4-yl)-5-oxo-pentyl]-oxazolidin-2-one;

(5R)-5-[(5R)-5-amino-5-(6-methoxy-[1,5]naphthyridin-4-yl)-pentyl]-3-(2,3-dihydro-benzo[1,4]dioxin-6-yl)-oxazolidin-2-one;

(5R)-5-[(5S)-5-amino-5-(6-methoxy-[1,5]naphthyridin-4-yl)-pentyl]-3-(2,3-dihydro-benzo[1,4]dioxin-6-yl)-oxazolidin-2-one;

(5S)-5-[(5R)-5-amino-5-(6-methoxy-[1,5]naphthyridin-4-yl)-pentyl]-3-(2,3-dihydro-benzo[1,4]dioxin-6-yl)-oxazolidin-2-one;

(5S)-5-[(5S)-5-amino-5-(6-methoxy-[1,5]naphthyridin-4-yl)-pentyl]-3-(2,3-dihydro-benzo[1,4]dioxin-6-yl)-oxazolidin-2-one;

(R)-3-(2,3-dihydro-benzo[1,4]dioxin-6-yl)-5-[4-(6-methoxy-quinazolin-4-ylamino)-butyl]-oxazolidin-2-one;

(S)-3-(2,3-dihydro-benzo[1,4]dioxin-6-yl)-5-[4-(6-methoxy-quinazolin-4-ylamino)-butyl]-oxazolidin-2-one;

N-[(R)-3-(2,3-dihydro-benzo[1,4]dioxin-6-yl)-2-oxo-oxazolidin-5-ylmethyl]-(2R)-2-hydroxy-3-(6-methoxy-[1,5]naphthyridin-4-yl)-propionamide;

N-[(R)-3-(2,3-dihydro-benzo[1,4]dioxin-6-yl)-2-oxo-oxazolidin-5-ylmethyl]-(2S)-2-hydroxy-3-(6-methoxy-[1,5]naphthyridin-4-yl)-propionamide;

(2R)-2-hydroxy-3-(6-methoxy-[1,5]naphthyridin-4-yl)-N-[(R)-2-oxo-3-(3-oxo-3,4-dihydro-2H-benzo[1,4]thiazin-6-yl)-oxazolidin-5-ylmethyl]-propionamide;

(2S)-2-hydroxy-3-(6-methoxy-[1,5]naphthyridin-4-yl)-N-[(R)-2-oxo-3-(3-oxo-3,4-dihydro-2H-benzo[1,4]thiazin-6-yl)-oxazolidin-5-ylmethyl]-propionamide;

(2R,3R)-2-amino-N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-propionamide;

(2R,3S)-2-amino-N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-propionamide;

(2S,3R)-2-amino-N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-propionamide;

(2S,3S)-2-amino-N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-propionamide;

(2R)-2-amino-N-[(R)-3-(2,3-dihydro-benzo[1,4]dioxin-6-yl)-2-oxo-oxazolidin-5-ylmethyl]-3-(6-methoxy-[1,5]naphthyridin-4-yl)-propionamide;

(2S)-2-amino-N-[(R)-3-(2,3-dihydro-benzo[1,4]dioxin-6-yl)-2-oxo-oxazolidin-5-ylmethyl]-3-(6-methoxy-[1,5]naphthyridin-4-yl)-propionamide;

(5R)-5-{[(2R)-2-amino-3-(6-methoxy-[1,5]naphthyridin-4-yl)-propylamino]-methyl}-3-(2,3-dihydro-benzo[1,4]dioxin-6-yl)-oxazolidin-2-one;

(5R)-5-{[(2S)-2-amino-3-(6-methoxy-[1,5]naphthyridin-4-yl)-propylamino]-methyl}-3-(2,3-dihydro-benzo[1,4]dioxin-6-yl)-oxazolidin-2-one;

(S)-3-(2,3-dihydro-benzo[1,4]dioxin-6-yl)-2-oxo-oxazolidine-5-carboxylic acid [3-(6-methoxy-[1,5]naphthyridin-4-yl)-prop-2-ynyl]-amide;

(R)-3-(2,3-dihydro-benzo[1,4]dioxin-6-yl)-5-{2-[2-(6-methoxy-[1,5]naphthyridin-4-yl)-ethylamino]-ethyl}-oxazolidin-2-one;

(S)-3-(2,3-dihydro-benzo[1,4]dioxin-6-yl)-5-{2-[2-(6-methoxy-[1,5]naphthyridin-4-yl)-ethylamino]-ethyl}-oxazolidin-2-one;
6-((R)-5-{2-[2-(6-methoxy-[1,5]naphthyridin-4-yl)-ethylamino]-ethyl}-2-oxo-oxazolidin-3-yl)-4H-benzo[1,4]thiazin-3-one;
6-((S)-5-{2-[2-(6-methoxy-[1,5]naphthyridin-4-yl)-ethylamino]-ethyl}-2-oxo-oxazolidin-3-yl)-4H-benzo[1,4]thiazin-3-one;
6-((R)-5-{2-[2-(3-fluoro-6-methoxy-[1,5]naphthyridin-4-yl)-ethylamino]-ethyl}-2-oxo-oxazolidin-3-yl)-4H-benzo[1,4]thiazin-3-one;
6-((S)-5-{2-[2-(3-fluoro-6-methoxy-[1,5]naphthyridin-4-yl)-ethylamino]-ethyl}-2-oxo-oxazolidin-3-yl)-4H-benzo[1,4]thiazin-3-one;
N-{2-[(R)-3-(2,3-dihydro-benzo[1,4]dioxin-6-yl)-2-oxo-oxazolidin-5-yl]-ethyl}-2-(3-methoxy-quinoxalin-5-yl)-acetamide;
N-{2-[(S)-3-(2,3-dihydro-benzo[1,4]dioxin-6-yl)-2-oxo-oxazolidin-5-yl]-ethyl}-2-(3-methoxy-quinoxalin-5-yl)-acetamide;
6-methoxy-quinoline-4-carboxylic acid {3-[(R)-2-oxo-3-(3-oxo-3,4-dihydro-2H-benzo[1,4]thiazin-6-yl)-oxazolidin-5-yl]-propyl}-amide;
6-methoxy-quinoline-4-carboxylic acid {3-[(S)-2-oxo-3-(3-oxo-3,4-dihydro-2H-benzo[1,4]thiazin-6-yl)-oxazolidin-5-yl]-propyl}-amide;
6-((R)-5-{3-[(6-methoxy-[1,5]naphthyridin-4-ylmethyl)-amino]-propyl}-2-oxo-oxazolidin-3-yl)-4H-benzo[1,4]thiazin-3-one;
6-((S)-5-{3-[(6-methoxy-[1,5]naphthyridin-4-ylmethyl)-amino]-propyl}-2-oxo-oxazolidin-3-yl)-4H-benzo[1,4]thiazin-3-one;
6-((R)-5-{3-[(3-fluoro-6-methoxy-[1,5]naphthyridin-4-ylmethyl)-amino]-propyl}-2-oxo-oxazolidin-3-yl)-4H-benzo[1,4]thiazin-3-one;
6-((S)-5-{3-[(3-fluoro-6-methoxy-[1,5]naphthyridin-4-ylmethyl)-amino]-propyl}-2-oxo-oxazolidin-3-yl)-4H-benzo[1,4]thiazin-3-one;
6-((R)-5-{3-[(3-fluoro-6-methoxy-quinolin-4-ylmethyl)-amino]-propyl}-2-oxo-oxazolidin-3-yl)-4H-benzo[1,4]thiazin-3-one;
6-((S)-5-{3-[(3-fluoro-6-methoxy-quinolin-4-ylmethyl)-amino]-propyl}-2-oxo-oxazolidin-3-yl)-4H-benzo[1,4]thiazin-3-one;
N-(6-methoxy-[1,5]naphthyridin-4-yl)-4-[(R)-2-oxo-3-(3-oxo-3,4-dihydro-2H-benzo[1,4]thiazin-6-yl)-oxazolidin-5-yl]-butyramide;
N-(6-methoxy-[1,5]naphthyridin-4-yl)-4-[(S)-2-oxo-3-(3-oxo-3,4-dihydro-2H-benzo[1,4]thiazin-6-yl)-oxazolidin-5-yl]-butyramide;
(S)-3-(2,3-dihydro-benzo[1,4]dioxin-6-yl)-5-{[2-(6-methoxy-[1,5]naphthyridin-4-ylamino)-ethylamino]-methyl}-oxazolidin-2-one;
(S)-3-(2,3-dihydro-benzo[1,4]dioxin-6-yl)-2-oxo-oxazolidine-5-carboxylic acid [2-(6-methoxy-[1,5]naphthyridin-4-ylamino)-ethyl]-amide;
(S)-2-{[(R)-3-(2,3-dihydro-benzo[1,4]dioxin-6-yl)-2-oxo-oxazolidin-5-ylmethyl]-amino}-N-(6-methoxy-[1,5]naphthyridin-4-yl)-propionamide;
2-{[(R)-3-(2,3-dihydro-benzo[1,4]dioxin-6-yl)-2-oxo-oxazolidin-5-ylmethyl]-amino}-N-(6-methoxy-[1,5]naphthyridin-4-yl)-acetamide;
2-[(R)-3-(2,3-dihydro-benzo[1,4]dioxin-6-yl)-2-oxo-oxazolidin-5-yl]-N-[2-(6-methoxy-quinolin-4-yl)-ethyl]-acetamide;
(S)-3-(2,3-dihydro-benzo[1,4]dioxin-6-yl)-5-({[3-(3-methoxy-quinolin-5-yl)-propyl]-methyl-amino}-methyl)-oxazolidin-2-one;
N-[(R)-3-(3-fluoro-4-methyl-phenyl)-2-oxo-oxazolidin-5-ylmethyl]-3-(3-methoxy-quinolin-5-yl)-N-methyl-propionamide;
2-[(R)-3-(2,3-dihydro-benzo[1,4]dioxin-6-yl)-2-oxo-oxazolidin-5-yl]-N-[(R)-2-hydroxy-2-(3-methoxy-quinoxalin-5-yl)-ethyl]-N-methyl-acetamide;
6-((R)-5-{[(2R)-2-amino-3-(6-methoxy-[1,5]naphthyridin-4-yl)-propylamino]-methyl}-2-oxo-oxazolidin-3-yl)-4H-benzo[1,4]thiazin-3-one;
6-((R)-5-{[(2S)-2-amino-3-(6-methoxy-[1,5]naphthyridin-4-yl)-propylamino]-methyl}-2-oxo-oxazolidin-3-yl)-4H-benzo[1,4]thiazin-3-one;
6-((R)-5-{3-[(6-fluoro-quinolin-5-ylmethyl)-amino]-propyl}-2-oxo-oxazolidin-4-yl)-4H-benzo[1,4]thiazin-3-one;
6-((S)-5-{3-[(6-fluoro-quinolin-5-ylmethyl)-amino]-propyl}-2-oxo-oxazolidin-3-yl)-4H-benzo[1,4]thiazin-3-one;
N-(6-methoxy-[1,5]naphthyridin-4-yl)-2-{[(R)-2-oxo-3-(3-oxo-3,4-dihydro-2H-benzo[1,4]thiazin-6-yl)-oxazolidin-5-ylmethyl]-amino}-acetamide;
(R*)-3-(2,3-dihydro-benzo[1,4]dioxin-6-yl)-5-{2-[(R*)-2-hydroxy-2-(3-methoxy-quinoxalin-5-yl)-ethylamino]-ethyl}-oxazolidin-2-one;
N-[(R)-2-hydroxy-2-(6-methoxy-[1,5]naphthyridin-4-yl)-ethyl]-N-methyl-2-[(R)-2-oxo-3-(3-oxo-3,4-dihydro-2H-benzo[1,4]thiazin-6-yl)-oxazolidin-5-yl]-acetamide;
(S)-3-(2,3-dihydro-benzo[1,4]dioxin-6-yl)-5-[3-(6-methoxy-[1,5]naphthyridin-4-yl)-propoxymethyl]-oxazolidin-2-one;
(R)-3-(2,3-dihydro-benzo[1,4]dioxin-6-yl)-5-[(E)-3-(6-methoxy-[1,5]naphthyridin-4-yl)-allyloxymethyl]-oxazolidin-2-one;
(S)-3-(2,3-dihydro-benzo[1,4]dioxin-6-yl)-5-[(E)-3-(6-methoxy-[1,5]naphthyridin-4-yl)-allyloxymethyl]-oxazolidin-2-one;
N-[2-(6-methoxy-[1,5]naphthyridin-4-yl)-ethyl]-2-[(R)-2-oxo-3-(3-oxo-3,4-dihydro-2H-benzo[1,4]thiazin-6-yl)-oxazolidin-5-yl]-acetamide;
(R)-3-(2,3-dihydro-benzo[1,4]dioxin-6-yl)-5-{(R)-1-hydroxy-2-[2-(6-methoxy-[1,5]naphthyridin-4-yl)-ethylamino]-ethyl}-oxazolidin-2-one;
(S)-3-(2,3-dihydro-benzo[1,4]dioxin-6-yl)-5-{(S)-1-hydroxy-2-[2-(6-methoxy-[1,5]naphthyridin-4-yl)-ethylamino]-ethyl}-oxazolidin-2-one;
(R)-3-(2,3-dihydro-benzo[1,4]dioxin-6-yl)-5-{(R)-1-hydroxy-2-[2-(6-methoxy-quinolin-4-yl)-ethylamino]-ethyl}-oxazolidin-2-one;
(S)-3-(2,3-dihydro-benzo[1,4]dioxin-6-yl)-5-{(S)-1-hydroxy-2-[2-(6-methoxy-quinolin-4-yl)-ethylamino]-ethyl}-oxazolidin-2-one;
(R)-3-(2,3-dihydro-benzo[1,4]dioxin-6-yl)-5-((R)-1-hydroxy-2-{[2-(6-methoxy-[1,5]naphthyridin-4-yl)-ethyl]-methyl-amino}-ethyl)-oxazolidin-2-one;
(S)-3-(2,3-dihydro-benzo[1,4]dioxin-6-yl)-5-((S)-1-hydroxy-2-{[2-(6-methoxy-[1,5]naphthyridin-4-yl)-ethyl]-methyl-amino}-ethyl)-oxazolidin-2-one;
(R)-3-(2,3-dihydro-benzo[1,4]dioxin-6-yl)-(R)-5-(1-hydroxy-2-{[(R)-2-hydroxy-2-(3-methoxy-quinoxalin-5-yl)-ethyl]-methyl-amino}-ethyl)-oxazolidin-2-one;
(R)-3-(2,3-dihydro-benzo[1,4]dioxin-6-yl)-(R)-5-(1-hydroxy-2-{[(S)-2-hydroxy-2-(3-methoxy-quinoxalin-5-yl)-ethyl]-methyl-amino}-ethyl)-oxazolidin-2-one;

(S)-3-(2,3-dihydro-benzo[1,4]dioxin-6-yl)-(S)-5-(1-hydroxy-2-{[(R)-2-hydroxy-2-(3-methoxy-quinoxalin-5-yl)-ethyl]-methyl-amino}-ethyl)-oxazolidin-2-one;
(S)-3-(2,3-dihydro-benzo[1,4]dioxin-6-yl)-(S)-5-(1-hydroxy-2-{[(S)-2-hydroxy-2-(3-methoxy-quinoxalin-5-yl)-ethyl]-methyl-amino}-ethyl)-oxazolidin-2-one;
6-((S)-5-{(S)-1-hydroxy-2-[2-(6-methoxy-[1,5]naphthyridin-4-yl)-ethylamino]-ethyl}-2-oxo-oxazolidin-3-yl)-4H-benzo[1,4]thiazin-3-one;
(S)-3-(2,3-dihydro-benzo[1,4]dioxin-6-yl)-5-{(S)-1-hydroxy-2-[(R)-2-hydroxy-2-(3-methoxy-quinoxalin-5-yl)-ethylamino]-ethyl}-oxazolidin-2-one;
(S)-3-(2,3-dihydro-benzo[1,4]dioxin-6-yl)-5-{(S)-1-hydroxy-2-[(S)-2-hydroxy-2-(3-methoxy-quinoxalin-5-yl)-ethylamino]-ethyl}-oxazolidin-2-one;
6-((R)-5-{(R)-1-hydroxy-3-[(6-methoxy-[1,5]naphthyridin-4-ylmethyl)-amino]-propyl}-2-oxo-oxazolidin-3-yl)-4H-benzo[1,4]thiazin-3-one;
6-((S)-5-{(S)-1-hydroxy-3-[(6-methoxy-[1,5]naphthyridin-4-ylmethyl)-amino]-propyl}-2-oxo-oxazolidin-3-yl)-4H-benzo[1,4]thiazin-3-one;
6-((R)-5-{(R)-3-[(3-fluoro-6-methoxy-[1,5]naphthyridin-4-ylmethyl)-amino]-1-hydroxy-propyl}-2-oxo-oxazolidin-3-yl)-4H-benzo[1,4]thiazin-3-one;
6-((S)-5-{(S)-3-[(3-fluoro-6-methoxy-[1,5]naphthyridin-4-ylmethyl)-amino]-1-hydroxy-propyl}-2-oxo-oxazolidin-3-yl)-4H-benzo[1,4]thiazin-3-one;
(R)-3-(2,3-dihydro-benzo[1,4]dioxin-6-yl)-5-{(R)-3-[(3-fluoro-6-methoxy-[1,5]naphthyridin-4-ylmethyl)-amino]-1-hydroxy-propyl}-oxazolidin-2-one;
(S)-3-(2,3-dihydro-benzo[1,4]dioxin-6-yl)-5-{(S)-3-[(3-fluoro-6-methoxy-[1,5]naphthyridin-4-ylmethyl)-amino]-1-hydroxy-propyl}-oxazolidin-2-one;
(S)-3-(2,3-dihydro-benzo[1,4]dioxin-6-yl)-5-{(R)-3-[(3-fluoro-6-methoxy-[1,5]naphthyridin-4-ylmethyl)-amino]-1-hydroxy-propyl}-oxazolidin-2-one;
(R)-3-(2,3-dihydro-benzo[1,4]dioxin-6-yl)-5-{(S)-3-[(3-fluoro-6-methoxy-[1,5]naphthyridin-4-ylmethyl)-amino]-1-hydroxy-propyl}-oxazolidin-2-one;
(S)-5-{(R)-1-amino-3-[(3-fluoro-6-methoxy-[1,5]naphthyridin-4-ylmethyl)-amino]-propyl}-3-(2,3-dihydro-benzo[1,4]dioxin-6-yl)-oxazolidin-2-one;
(R)-5-{(S)-1-amino-3-[(3-fluoro-6-methoxy-[1,5]naphthyridin-4-ylmethyl)-amino]-propyl}-3-(2,3-dihydro-benzo[1,4]dioxin-6-yl)-oxazolidin-2-one;
(R)-3-(2,3-dihydro-benzo[1,4]dioxin-6-yl)-5-[(E)-4-(6-methoxy-quinolin-4-yloxy)-but-2-enyl]-oxazolidin-2-one;
(R)-3-(2,3-dihydro-benzo[1,4]dioxin-6-yl)-5-[4-(6-methoxy-quinolin-4-yloxy)-butyl]-oxazolidin-2-one;
(S)-3-(2,3-dihydro-benzo[1,4]dioxin-6-yl)-5-[4-(6-methoxy-quinolin-4-yloxy)-butyl]-oxazolidin-2-one;
(R)-3-[3-(2,3-dihydro-benzo[1,4]dioxin-6-yl)-2-oxo-oxazolidin-5-yl]-N-(3-quinoxalin-5-ylmethyl)-N-methyl-propionamide;
(S)-3-[3-(2,3-dihydro-benzo[1,4]dioxin-6-yl)-2-oxo-oxazolidin-5-yl]-N-(3-methoxy-quinoxalin-5-ylmethyl)-N-methyl-propionamide;
(R)-3-(2,3-dihydro-benzo[1,4]dioxin-6-yl)-5-[(R)-1-hydroxy-5-(6-methoxy-(6-methoxy-[1,5]naphthyridin-4-yl)-pentyl]-oxazolidin-2-one;
(S)-3-(2,3-dihydro-benzo[1,4]dioxin-6-yl)-5-[(S)-1-hydroxy-5-(6-methoxy-[1,5]naphthyridin-4-yl)-pentyl]-oxazolidin-2-one;
(R)-3-(2,3-dihydro-benzo[1,4]dioxin-6-yl)-5-{[4-(6-methoxy-[1,5]naphthyridin-4-yl)-butylamino]-methyl}-oxazolidin-2-one;
6-((R)-5-{[4-(6-methoxy-[1,5]naphthyridin-4-yl)-butylamino]-methyl}-2-oxo-oxazolidin-3-yl)-4H-benzo[1,4]thiazin-3-one;
(R)-3-(2,3-dihydro-benzo[1,4]dioxin-6-yl)-5-[(R)-3-hydroxy-5-(6-methoxy-[1,5]naphthyridin-4-yl)-pentyl]-oxazolidin-2-one;
(R)-3-(2,3-dihydro-benzo[1,4]dioxin-6-yl)-5-[(S)-3-hydroxy-5-(6-methoxy-[1,5]naphthyridin-4-yl)-pentyl]-oxazolidin-2-one;
(S)-3-(2,3-dihydro-benzo[1,4]dioxin-6-yl)-5-[(R)-3-hydroxy-5-(6-methoxy-[1,5]naphthyridin-4-yl)-pentyl]-oxazolidin-2-one;
(S)-3-(2,3-dihydro-benzo[1,4]dioxin-6-yl)-5-[(S)-3-hydroxy-5-(6-methoxy-[1,5]naphthyridin-4-yl)-pentyl]-oxazolidin-2-one;
(R)-3-(2,3-dihydro-benzo[1,4]dioxin-6-yl)-5-[5-(6-methoxy-[1,5]naphthyridin-4-yl)-3-oxo-pentyl]-oxazolidin-2-one;
(S)-3-(2,3-dihydro-benzo[1,4]dioxin-6-yl)-5-[5-(6-methoxy-[1,5]naphthyridin-4-yl)-3-oxo-pentyl]-oxazolidin-2-one;
(R)-5-[(R)-3-amino-5-(6-methoxy-[1,5]naphthyridin-4-yl)-pentyl]-3-(2,3-dihydro-benzo[1,4]dioxin-6-yl)-oxazolidin-2-one;
(R)-5-[(S)-3-amino-5-(6-methoxy-[1,5]naphthyridin-4-yl)-pentyl]-3-(2,3-dihydro-benzo[1,4]dioxin-6-yl)-oxazolidin-2-one;
(S)-5-[(R)-3-amino-5-(6-methoxy-[1,5]naphthyridin-4-yl)-pentyl]-3-(2,3-dihydro-benzo[1,4]dioxin-6-yl)-oxazolidin-2-one;
(S)-5-[(S)-3-amino-5-(6-methoxy-[1,5]naphthyridin-4-yl)-pentyl]-3-(2,3-dihydro-benzo[1,4]dioxin-6-yl)-oxazolidin-2-one;
(R)-N-[(R)-1-{2-[3-(2,3-dihydro-benzo[1,4]dioxin-6-yl)-2-oxo-oxazolidin-5-yl]-ethyl}-3-(6-methoxy-[1,5]naphthyridin-4-yl)-propyl]-methanesulfonamide;
(R)-N-[(S)-1-{2-[3-(2,3-dihydro-benzo[1,4]dioxin-6-yl)-2-oxo-oxazolidin-5-yl]-ethyl}-3-(6-methoxy-[1,5]naphthyridin-4-yl)-propyl]-methanesulfonamide;
(S)-N-[(R)-1-{2-[3-(2,3-dihydro-benzo[1,4]dioxin-6-yl)-2-oxo-oxazolidin-5-yl]-ethyl}-3-(6-methoxy-[1,5]naphthyridin-4-yl)-propyl]-methanesulfonamide;
(S)-N-[(S)-1-{2-[3-(2,3-dihydro-benzo[1,4]dioxin-6-yl)-2-oxo-oxazolidin-5-yl]-ethyl}-3-(6-methoxy-[1,5]naphthyridin-4-yl)-propyl]-methanesulfonamide;
N-[(R)-1-{2-[(R)-3-(2,3-dihydro-benzo[1,4]dioxin-6-yl)-2-oxo-oxazolidin-5-yl]-ethyl}-3-(6-methoxy-[1,5]naphthyridin-4-yl)-propyl]-acetamide;
N-[(R)-1-{2-[(S)-3-(2,3-dihydro-benzo[1,4]dioxin-6-yl)-2-oxo-oxazolidin-5-yl]-ethyl}-3-(6-methoxy-[1,5]naphthyridin-4-yl)-propyl]-acetamide;
N-[(S)-1-{2-[(R)-3-(2,3-dihydro-benzo[1,4]dioxin-6-yl)-2-oxo-oxazolidin-5-yl]-ethyl}-3-(6-methoxy-[1,5]naphthyridin-4-yl)-propyl]-acetamide;
N-[(S)-1-{2-[(S)-3-(2,3-dihydro-benzo[1,4]dioxin-6-yl)-2-oxo-oxazolidin-5-yl]-ethyl}-3-(6-methoxy-[1,5]naphthyridin-4-yl)-propyl]-acetamide;
(R)-3-(2,3-dihydro-benzo[1,4]dioxin-6-yl)-5-[3-(7-fluoro-2-methoxy-quinolin-8-ylmethoxy)-propyl]-oxazolidin-2-one;
(S)-3-(2,3-dihydro-benzo[1,4]dioxin-6-yl)-5-[3-(7-fluoro-2-methoxy-quinolin-8-ylmethoxy)-propyl]-oxazolidin-2-one;
(R)-3-(2,3-dihydro-benzo[1,4]dioxin-6-yl)-5-[3-(6-methoxy-quinolin-4-ylmethoxy)-propyl]-oxazolidin-2-one;
(S)-3-(2,3-dihydro-benzo[1,4]dioxin-6-yl)-5-[3-(6-methoxy-quinolin-4-ylmethoxy)-propyl]-oxazolidin-2-one;

(R)-3-(2,3-dihydro-benzo[1,4]dioxin-6-yl)-5-[3-(6-methoxy-quinazolin-4-yloxy)-propyl]-oxazolidin-2-one;

(S)-3-(2,3-dihydro-benzo[1,4]dioxin-6-yl)-5-[3-(6-methoxy-quinazolin-4-yloxy)-propyl]-oxazolidin-2-one;

6-{(R)-5-[(R)-3-hydroxy-5-(6-methoxy-[1,5]naphthyridin-4-yl)-pentyl]-2-oxo-oxazolidin-3-yl}-4H-benzo[1,4]thiazin-3-one;

6-{(R)-5-[(S)-3-hydroxy-5-(6-methoxy-[1,5]naphthyridin-4-yl)-pentyl]-2-oxo-oxazolidin-3-yl}-4H-benzo[1,4]thiazin-3-one;

6-{(S)-5-[(R)-3-hydroxy-5-(6-methoxy-[1,5]naphthyridin-4-yl)-pentyl]-2-oxo-oxazolidin-3-yl}-4H-benzo[1,4]thiazin-3-one;

6-{(S)-5-[(S)-3-hydroxy-5-(6-methoxy-[1,5]naphthyridin-4-yl)-pentyl]-2-oxo-oxazolidin-3-yl}-4H-benzo[1,4]thiazin-3-one;

(R)-3-(2,3-dihydro-benzo[1,4]dioxin-6-yl)-5-[(R)-2-hydroxy-5-(6-methoxy-[1,5]naphthyridin-4-yl)-pentyl]-oxazolidin-2-one;

(R)-3-(2,3-dihydro-benzo[1,4]dioxin-6-yl)-5-[(S)-2-hydroxy-5-(6-methoxy-[1,5]naphthyridin-4-yl)-pentyl]-oxazolidin-2-one;

(S)-3-(2,3-dihydro-benzo[1,4]dioxin-6-yl)-5-[(R)-2-hydroxy-5-(6-methoxy-[1,5]naphthyridin-4-yl)-pentyl]-oxazolidin-2-one;

(S)-3-(2,3-dihydro-benzo[1,4]dioxin-6-yl)-5-[(S)-2-hydroxy-5-(6-methoxy-[1,5]naphthyridin-4-yl)-pentyl]-oxazolidin-2-one;

(R)-3-(2,3-dihydro-benzo[1,4]dioxin-6-yl)-5-[5-(6-methoxy-[1,5]naphthyridin-4-yl)-pentyl]-oxazolidin-2-one;

(S)-3-(2,3-dihydro-benzo[1,4]dioxin-6-yl)-5-[5-(6-methoxy-[1,5]naphthyridin-5-yl)-pentyl]-oxazolidin-2-one;

6-{(R)-5-[5-(6-methoxy-[1,5]naphthyridin-4-yl)-pentyl]-2-oxo-oxazolidin-3-yl}-4H-benzo[1,4]thiazin-3-one;

(R)-6-(5-{2-[2-(6-methoxy-[1,5]naphthyridin-4-yl)-ethylamino]-ethyl}-2-oxo-oxazolidin-3-yl)-4H-benzo[1,4]oxazin-3-one;

(S)-6-(5-{2-[2-(6-methoxy-[1,5]naphthyridin-4-yl)-ethylamino]-ethyl}-2-oxo-oxazolidin-3-yl)-4H-benzo[1,4]oxazin-3-one;

6-[(R)-5-(2-{((R)-2,3-dihydroxy-propyl)-[2-(6-methoxy-[1,5]naphthyridin-4-yl)-ethyl]-amino}-ethyl)-2-oxo-oxazolidin-3-yl]-4H-benzo[1,4]oxazin-3-one;

6-[(S)-5-(2-{((R)-2,3-dihydroxy-propyl)-[2-(6-methoxy-[1,5]naphthyridin-4-yl)-ethyl]-amino}-ethyl)-2-oxo-oxazolidin-3-yl]-4H-benzo[1,4]oxazin-3-one;

(R)-{{2-[3-(2,3-dihydro-benzo[1,4]dioxin-6-yl)-2-oxo-oxazolidin-5-yl]-ethyl}-[2-(6-methoxy-[1,5]naphthyridin-4-yl)-ethyl]-amino}-acetic acid tert-butyl ester;

(S)-{{2-[3-(2,3-dihydro-benzo[1,4]dioxin-6-yl)-2-oxo-oxazolidin-5-yl]-ethyl}-[2-(6-methoxy-[1,5]naphthyridin-4-yl)-ethyl]-amino}-acetic acid tert-butyl ester;

(R)-3-{{2-[3-(2,3-dihydro-benzo[1,4]dioxin-6-yl)-2-oxo-oxazolidin-5-yl]-ethyl}-[2-(6-methoxy-[1,5]naphthyridin-4-yl)-ethyl]-amino}-propionic acid methyl ester;

(S)-3-{{2-[3-(2,3-dihydro-benzo[1,4]dioxin-6-yl)-2-oxo-oxazolidin-5-yl]-ethyl}-[2-(6-methoxy-[1,5]naphthyridin-4-yl)-ethyl]-amino}-propionic acid methyl ester;

(R)-4-{{2-[3-(2,3-dihydro-benzo[1,4]dioxin-6-yl)-2-oxo-oxazolidin-5-yl]-ethyl}-[2-(6-methoxy-[1,5]naphthyridin-4-yl)-ethyl]-amino}-butyric acid ethyl ester;

(S)-4-{{2-[3-(2,3-dihydro-benzo[1,4]dioxin-6-yl)-2-oxo-oxazolidin-5-yl]-ethyl}-[2-(6-methoxy-[1,5]naphthyridin-4-yl)-ethyl]-amino}-butyric acid ethyl ester;

6-((R)-5-{[3-(6-methoxy-[1,5]naphthyridin-4-yl)-propylamino]-methyl}-2-oxo-oxazolidin-3-yl)-4H-benzo[1,4]oxazin-3-one;

6-((R)-5-{[3-(3-fluoro-6-methoxy-[1,5]naphthyridin-4-yl)-propylamino]-methyl}-2-oxo-oxazolidin-3-yl)-4H-benzo[1,4]oxazin-3-one;

6-((R)-5-{[3-(3-fluoro-6-methoxy-[1,5]naphthyridin-4-yl)-propylamino]-methyl}-2-oxo-oxazolidin-3-yl)-4H-benzo[1,4]thiazin-3-one;

(R)-3-(2,3-dihydro-benzo[1,4]dioxin-6-yl)-5-{[3-(3-fluoro-6-methoxy-[1,5]naphthyridin-4-yl)-propylamino]-methyl}-oxazolidin-2-one;

(R)-3-(2,3-dihydro-benzo[1,4]dioxin-6-yl)-5-({((S)-2,3-dihydroxy-propyl)-[3-(3-fluoro-6-methoxy-[1,5]naphthyridin-4-yl)-propyl]-amino}-methyl)-oxazolidin-2-one;

6-[(R)-5-({((S)-2,3-dihydroxy-propyl)-[3-(3-fluoro-6-methoxy-[1,5]naphthyridin-4-yl)-propyl]-amino}-methyl)-2-oxo-oxazolidin-3-yl]-4H-benzo[1,4]thiazin-3-one;

6-[(R)-5-({((R)-2,3-dihydroxy-propyl)-[3-(3-fluoro-6-methoxy-[1,5]naphthyridin-4-yl)-propyl]-amino}-methyl)-2-oxo-oxazolidin-3-yl]-4H-benzo[1,4]oxazin-3-one;

6-[(R)-5-({((R)-2,3-dihydroxy-propyl)-[3-(6-methoxy-[1,5]naphthyridin-4-yl)-propyl]-amino}-methyl)-2-oxo-oxazolidin-3-yl]-4H-benzo[1,4]oxazin-3-one;

{[(R)-3-(2,3-dihydro-benzo[1,4]dioxin-6-yl)-2-oxo-oxazolidin-5-ylmethyl]-[3-(6-methoxy-[1,5]naphthyridin-4-yl)-propyl]-amino}-acetic acid tert-butyl ester;

3-{[(R)-3-(2,3-dihydro-benzo[1,4]dioxin-6-yl)-2-oxo-oxazolidin-5-ylmethyl]-[3-(6-methoxy-[1,5]naphthyridin-4-yl)-propyl]-amino}-propionic acid methyl ester;

4-{[(R)-3-(2,3-dihydro-benzo[1,4]dioxin-6-yl)-2-oxo-oxazolidin-5-ylmethyl]-[3-(6-methoxy-[1,5]naphthyridin-4-yl)-propyl]-amino}-butyric acid ethyl ester;

4-{[(R)-3-(2,3-dihydro-benzo[1,4]dioxin-6-yl)-2-oxo-oxazolidin-5-ylmethyl]-[3-(6-methoxy-[1,5]naphthyridin-4-yl)-propyl]-amino}-butyric acid ethyl ester;

3-{[(R)-3-(2,3-dihydro-benzo[1,4]dioxin-6-yl)-2-oxo-oxazolidin-5-ylmethyl]-[3-(6-methoxy-[1,5]naphthyridin-4-yl)-propyl]-amino}-propionic acid;

(R)-6-(5-{3-[(6-methoxy-[1,5]naphthyridin-4-ylmethyl)-amino]-propyl}-2-oxo-oxazolidin-3-yl)-4H-benzo[1,4]oxazin-3-one;

(S)-6-(5-{3-[(6-methoxy-[1,5]naphthyridin-4-ylmethyl)-amino]-propyl}-2-oxo-oxazolidin-3-yl)-4H-benzo[1,4]oxazin-3-one;

(R)-6-(5-{3-[(3-methoxy-quinoxalin-5-ylmethyl)-amino]-propyl}-2-oxo-oxazolidin-3-yl)-4H-benzo[1,4]oxazin-3-one;

(S)-6-(5-{3-[(3-methoxy-quinoxalin-5-ylmethyl)-amino]-propyl}-2-oxo-oxazolidin-3-yl)-4H-benzo[1,4]oxazin-3-one;

(R)-6-(5-{3-[(6-methoxy-quinolin-4-ylmethyl)-amino]-propyl}-2-oxo-oxazolidin-3-yl)-4H-benzo[1,4]oxazin-3-one;

(S)-6-(5-{3-[(6-methoxy-quinolin-4-ylmethyl)-amino]-propyl}-2-oxo-oxazolidin-3-yl)-4H-benzo[1,4]oxazin-3-one;

(R)-2-methoxy-8-({3-[2-oxo-3-(3-oxo-3,4-dihydro-2H-benzo[1,4]oxazin-6-yl)-oxazolidin-5-yl]-propylamino}-methyl)-quinoline-5-carboxylic acid methyl ester;

(S)-2-methoxy-8-({3-[2-oxo-3-(3-oxo-3,4-dihydro-2H-benzo[1,4]oxazin-6-yl)-oxazolidin-5-yl]-propylamino}-methyl)-quinoline-5-carboxylic acid methyl ester;

(R)-6-(5-{3-[(3-fluoro-6-methoxy-quinolin-4-ylmethyl)-amino]-propyl}-2-oxo-oxazolidin-3-yl)-4H-benzo[1,4]oxazin-3-one;

(S)-6-(5-{3-[(3-fluoro-6-methoxy-quinolin-4-ylmethyl)-amino]-propyl}-2-oxo-oxazolidin-3-yl)-4H-benzo[1,4]oxazin-3-one;

(R)-6-(5-{3-[(3-fluoro-6-methoxy-[1,5]naphthyridin-4-ylmethyl)-amino]-propyl}-2-oxo-oxazolidin-3-yl)-4H-benzo[1,4]oxazin-3-one;
(S)-6-(5-{3-[(3-fluoro-6-methoxy-[1,5]naphthyridin-4-ylmethyl)-amino]-propyl}-2-oxo-oxazolidin-3-yl)-4H-benzo[1,4]oxazin-3-one;
(R)-6-(5-{3-[(7-fluoro-2-methoxy-quinolin-8-ylmethyl)-amino]-propyl}-2-oxo-oxazolidin-3-yl)-4H-benzo[1,4]oxazin-3-one;
(S)-6-(5-{3-[(7-fluoro-2-methoxy-quinolin-8-ylmethyl)-amino]-propyl}-2-oxo-oxazolidin-3-yl)-4H-benzo[1,4]oxazin-3-one;
6-((R)-5-{3-[((R)-2,3-dihydroxy-propyl)-(3-fluoro-6-methoxy-[1,5]naphthyridin-4-ylmethyl)-amino]-propyl}-2-oxo-oxazolidin-3-yl)-4H-benzo[1,4]thiazin-3-one;
6-((S)-5-{3-[((R)-2,3-dihydroxy-propyl)-(3-fluoro-6-methoxy-[1,5]naphthyridin-4-ylmethyl)-amino]-propyl}-2-oxo-oxazolidin-3-yl)-4H-benzo[1,4]thiazin-3-one;
6-((R)-5-{3-[((R)-3-chloro-2-hydroxy-propyl)-(3-fluoro-6-methoxy-[1,5]naphthyridin-4-ylmethyl)-amino]-propyl}-2-oxo-oxazolidin-3-yl)-4H-benzo[1,4]thiazin-3-one;
6-((S)-5-{3-[((R)-3-chloro-2-hydroxy-propyl)-(3-fluoro-6-methoxy-[1,5]naphthyridin-4-ylmethyl)-amino]-propyl}-2-oxo-oxazolidin-3-yl)-4H-benzo[1,4]thiazin-3-one;
6-((R)-5-{3-[((S)-3-dimethylamino-2-hydroxy-propyl)-(3-fluoro-6-methoxy-[1,5]naphthyridin-4-ylmethyl)-amino]-propyl}-2-oxo-oxazolidin-3-yl)-4H-benzo[1,4]thiazin-3-one;
6-((S)-5-{3-[((S)-3-dimethylamino-2-hydroxy-propyl)-(3-fluoro-6-methoxy-[1,5]naphthyridin-4-ylmethyl)-amino]-propyl}-2-oxo-oxazolidin-3-yl)-4H-benzo[1,4]thiazin-3-one;
(R)-6-(2-oxo-5-{3-[(quinolin-4-ylmethyl)-amino]-propyl}-oxazolidin-3-yl)-4H-benzo[1,4]thiazin-3-one;
(S)-6-(2-oxo-5-{3-[(quinolin-4-ylmethyl)-amino]-propyl}-oxazolidin-3-yl)-4H-benzo[1,4]thiazin-3-one;
(R)-6-(5-{3-[(naphthalen-1-ylmethyl)-amino]-propyl}-2-oxo-oxazolidin-3-yl)-4H-benzo[1,4]thiazin-3-one;
(S)-6-(5-{3-[(naphthalen-1-ylmethyl)-amino]-propyl}-2-oxo-oxazolidin-3-yl)-4H-benzo[1,4]thiazin-3-one;
(R)-2-methoxy-8-({3-[2-oxo-3-(3-oxo-3,4-dihydro-2H-benzo[1,4]thiazin-6-yl)-oxazolidin-5-yl]-propylamino}-methyl)-quinoline-5-carboxylic acid methyl ester;
(S)-2-methoxy-8-({3-[2-oxo-3-(3-oxo-3,4-dihydro-2H-benzo[1,4]thiazin-6-yl)-oxazolidin-5-yl]-propylamino}-methyl)-quinoline-5-carboxylic acid methyl ester;
(R)-6-[5-(3-{[3-methoxy-8-(2-methoxy-ethoxy)-quinoxalin-5-ylmethyl]-amino}-propyl)-2-oxo-oxazolidin-3-yl]-4H-benzo[1,4]thiazin-3-one;
(S)-6-[5-(3-{[3-methoxy-8-(2-methoxy-ethoxy)-quinoxalin-5-ylmethyl]-amino}-propyl)-2-oxo-oxazolidin-3-yl]-4H-benzo[1,4]thiazin-3-one;
(R)-6-(5-{3-[(6-fluoro-quinolin-4-ylmethyl)-amino]-propyl}-2-oxo-oxazolidin-3-yl)-4H-benzo[1,4]thiazin-3-one;
(S)-6-(5-{3-[(6-fluoro-quinolin-4-ylmethyl)-amino]-propyl}-2-oxo-oxazolidin-3-yl)-4H-benzo[1,4]thiazin-3-one;
(R)-6-(5-{3-[(3-methoxy-quinoxalin-5-ylmethyl)-amino]-propyl}-2-oxo-oxazolidin-3-yl)-4H-benzo[1,4]thiazin-3-one;
(S)-6-(5-{3-[(3-methoxy-quinoxalin-5-ylmethyl)-amino]-propyl}-2-oxo-oxazolidin-3-yl)-4H-benzo[1,4]thiazin-3-one;
(R)-6-(5-{3-[(6-methoxy-quinolin-4-ylmethyl)-amino]-propyl}-2-oxo-oxazolidin-3-yl)-4H-benzo[1,4]thiazin-3-one;
(S)-6-(5-{3-[(6-methoxy-quinolin-4-ylmethyl)-amino]-propyl}-2-oxo-oxazolidin-3-yl)-4H-benzo[1,4]thiazin-3-one;
(R)-6-(5-{3-[(isoquinolin-5-ylmethyl)-amino]-propyl}-2-oxo-oxazolidin-3-yl)-4H-benzo[1,4]thiazin-3-one;
(S)-6-(5-{3-[(isoquinolin-5-ylmethyl)-amino]-propyl}-2-oxo-oxazolidin-3-yl)-4H-benzo[1,4]thiazin-3-one;
(R)-6-(5-{3-[(4-methoxy-naphthalen-1-ylmethyl)-amino]-propyl}-2-oxo-oxazolidin-3-yl)-4H-benzo[1,4]thiazin-3-one;
(S)-6-(5-{3-[(4-methoxy-naphthalen-1-ylmethyl)-amino]-propyl}-2-oxo-oxazolidin-3-yl)-4H-benzo[1,4]thiazin-3-one;
(R)-6-(2-oxo-5-{3-[(quinolin-5-ylmethyl)-amino]-propyl}-oxazolidin-3-yl)-4H-benzo[1,4]thiazin-3-one;
(S)-6-(2-oxo-5-{3-[(quinolin-5-ylmethyl)-amino]-propyl}-oxazolidin-3-yl)-4H-benzo[1,4]thiazin-3-one;
(R)-6-(2-oxo-5-{3-[(quinolin-8-ylmethyl)-amino]-propyl}-oxazolidin-3-yl)-4H-benzo[1,4]thiazin-3-one;
(S)-6-(2-oxo-5-{3-[(quinolin-8-ylmethyl)-amino]-propyl}-oxazolidin-3-yl)-4H-benzo[1,4]thiazin-3-one;
(R)-6-(5-{3-[(4-hydroxy-naphthalen-1-ylmethyl)-amino]-propyl}-2-oxo-oxazolidin-3-yl)-4H-benzo[1,4]thiazin-3-one;
(S)-6-(5-{3-[(4-hydroxy-naphthalen-1-ylmethyl)-amino]-propyl}-2-oxo-oxazolidin-3-yl)-4H-benzo[1,4]thiazin-3-one;
(R)-6-(5-{3-[(2-hydroxy-naphthalen-1-ylmethyl)-amino]-propyl}-2-oxo-oxazolidin-3-yl)-4H-benzo[1,4]thiazin-3-one;
(S)-6-(5-{3-[(2-hydroxy-naphthalen-1-ylmethyl)-amino]-propyl}-2-oxo-oxazolidin-3-yl)-4H-benzo[1,4]thiazin-3-one;
(R)-6-(5-{3-[(7-fluoro-2-methoxy-quinolin-8-ylmethyl)-amino]-propyl}-2-oxo-oxazolidin-3-yl)-4H-benzo[1,4]thiazin-3-one;
(S)-6-(5-{3-[(7-fluoro-2-methoxy-quinolin-8-ylmethyl)-amino]-propyl}-2-oxo-oxazolidin-3-yl)-4H-benzo[1,4]thiazin-3-one;
(R)-6-(5-{3-[(2,3-dimethoxy-naphthalen-1-ylmethyl)-amino]-propyl}-2-oxo-oxazolidin-3-yl)-4H-benzo[1,4]thiazin-3-one;
(S)-6-(5-{3-[(2,3-dimethoxy-naphthalen-1-ylmethyl)-amino]-propyl}-2-oxo-oxazolidin-3-yl)-4H-benzo[1,4]thiazin-3-one;
(R)-6-(5-{3-[(4,7-dimethoxy-naphthalen-1-ylmethyl)-amino]-propyl}-2-oxo-oxazolidin-3-yl)-4H-benzo[1,4]thiazin-3-one;
(S)-6-(5-{3-[(4,7-dimethoxy-naphthalen-1-ylmethyl)-amino]-propyl}-2-oxo-oxazolidin-3-yl)-4H-benzo[1,4]thiazin-3-one;
(R)-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-acetic acid tert-butyl ester;
(S)-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-acetic acid tert-butyl ester;
(R)-3-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-propionic acid methyl ester;
(S)-3-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-propionic acid methyl ester;

(R)-4-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-butyric acid ethyl ester;

(S)-4-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-butyric acid ethyl ester;

(R)-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-acetic acid;

(S)-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-acetic acid;

(R)-3-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-propionic acid;

(S)-3-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-propionic acid;

(R)-4-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-butyric acid;

(S)-4-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-butyric acid;

6-((R)-5-{3-[(3-fluoro-6-methoxy-[1,5]naphthyridin-4-ylmethyl)-amino]-propyl}-2-oxo-oxazolidin-3-yl)-4H-benzo[1,4]oxazin-3-one;

6-((R)-5-{3-[((S)-2,3-dihydroxy-propyl)-(3-fluoro-6-methoxy-[1,5]naphthyridin-4-ylmethyl)-amino]-propyl}-2-oxo-oxazolidin-3-yl)-4H-benzo[1,4]oxazin-3-one;

6-((R)-5-{3-[((R)-2,3-dihydroxy-propyl)-(3-fluoro-6-methoxy-[1,5]naphthyridin-4-ylmethyl)-amino]-propyl}-2-oxo-oxazolidin-3-yl)-4H-benzo[1,4]oxazin-3-one;

6-((R)-5-{3-[(3-fluoro-6-methoxy-[1,5]naphthyridin-4-ylmethyl)-(2-hydroxy-ethyl)-amino]-propyl}-2-oxo-oxazolidin-3-yl)-4H-benzo[1,4]oxazin-3-one;

(S)-3-(2,3-dihydro-benzo[1,4]dioxin-6-yl)-5-{(1R,2S)-1,2-dihydroxy-3-[(6-methoxy-[1,5]naphthyridin-4-ylmethyl)-amino]-propyl}-oxazolidin-2-one;

(S)-3-(2,3-dihydro-benzo[1,4]dioxin-6-yl)-5-{(1R,2S)-3-[(3-fluoro-6-methoxy-quinolin-4-ylmethyl)-amino]-1,2-dihydroxy-propyl}-oxazolidin-2-one;

(S)-3-(2,3-dihydro-benzo[1,4]dioxin-6-yl)-5-{(1R,2S)-1,2-dihydroxy-3-[(3-methoxy-quinoxalin-5-ylmethyl)-amino]-propyl}-oxazolidin-2-one;

(R)-3-(2,3-dihydro-benzo[1,4]dioxin-6-yl)-5-{(1R,2S)-1,2-dihydroxy-3-[(6-methoxy-[1,5]naphthyridin-4-ylmethyl)-amino]-propyl}-oxazolidin-2-one;

(R)-3-(2,3-dihydro-benzo[1,4]dioxin-6-yl)-5-{(1R,2S)-3-[(3-fluoro-6-methoxy-[1,5]naphthyridin-4-ylmethyl)-amino]-1,2-dihydroxy-propyl}-oxazolidin-2-one;

6-((S)-5-{(1R,2S)-1,2-dihydroxy-3-[(6-methoxy-[1,5]naphthyridin-4-ylmethyl)-amino]-propyl}-2-oxo-oxazolidin-3-yl)-4H-benzo[1,4]thiazin-3-one;

6-((S)-5-{(1R,2S)-3-[(3-fluoro-6-methoxy-[1,5]naphthyridin-4-ylmethyl)-amino]-1,2-dihydroxy-propyl}-2-oxo-oxazolidin-3-yl)-4H-benzo[1,4]thiazin-3-one;

6-((S)-5-{(1R,2S)-3-[(3-fluoro-6-methoxy-quinolin-4-ylmethyl)-amino]-1,2-dihydroxy-propyl}-2-oxo-oxazolidin-3-yl)-4H-benzo[1,4]thiazin-3-one;

(R)-3-(2,3-dihydro-benzo[1,4]dioxin-6-yl)-5-{(1S,2R)-1,2-dihydroxy-3-[(6-methoxy-[1,5]naphthyridin-4-ylmethyl)-amino]-propyl}-oxazolidin-2-one;

(R)-3-(2,3-dihydro-benzo[1,4]dioxin-6-yl)-5-{(1S,2R)-3-[(3-fluoro-6-methoxy-[1,5]naphthyridin-4-ylmethyl)-amino]-1,2-dihydroxy-propyl}-oxazolidin-2-one;

(S)-3-(2,3-dihydro-benzo[1,4]dioxin-6-yl)-5-{(1S,2R)-1,2-dihydroxy-3-[(6-methoxy-[1,5]naphthyridin-4-ylmethyl)-amino]-propyl}-oxazolidin-2-one;

6-((R)-5-{(1S,2R)-1,2-dihydroxy-3-[(6-methoxy-[1,5]naphthyridin-4-ylmethyl)-amino]-propyl}-2-oxo-oxazolidin-3-yl)-4H-benzo[1,4]thiazin-3-one;

6-((R)-5-{(1S,2R)-1,2-dihydroxy-3-[(3-methoxy-quinoxalin-5-ylmethyl)-amino]-propyl}-2-oxo-oxazolidin-3-yl)-4H-benzo[1,4]thiazin-3-one;

6-((R)-5-{(1S,2R)-3-[(3-fluoro-6-methoxy-[1,5]naphthyridin-4-ylmethyl)-amino]-1,2-dihydroxy-propyl}-2-oxo-oxazolidin-3-yl)-4H-benzo[1,4]thiazin-3-one;

6-((R)-5-{(1S,2R)-3-[(3-fluoro-6-methoxy-quinolin-4-ylmethyl)-amino]-1,2-dihydroxy-propyl}-2-oxo-oxazolidin-3-yl)-4H-benzo[1,4]thiazin-3-one;

6-((S)-5-{(1S,2R)-3-[(3-fluoro-6-methoxy-[1,5]naphthyridin-4-ylmethyl)-amino]-1,2-dihydroxy-propyl}-2-oxo-oxazolidin-3-yl)-4H-benzo[1,4]thiazin-3-one;

6-((R)-5-{(1S,2R)-3-[(3-fluoro-6-methoxy-[1,5]naphthyridin-4-ylmethyl)-amino]-1,2-dihydroxy-propyl}-2-oxo-oxazolidin-3-yl)-4H-benzo[1,4]oxazin-3-one;

6-((R)-5-{(1S,2R)-3-[(3-fluoro-6-methoxy-quinolin-4-ylmethyl)-amino]-1,2-dihydroxy-propyl}-2-oxo-oxazolidin-3-yl)-4H-benzo[1,4]oxazin-3-one;

6-((S)-5-{(1S,2R)-3-[(3-fluoro-6-methoxy-[1,5]naphthyridin-4-ylmethyl)-amino]-1,2-dihydroxy-propyl}-2-oxo-oxazolidin-3-yl)-4H-benzo[1,4]oxazin-3-one;

2-(6-methoxy-[1,5]naphthyridin-4-yloxy)-N-[(R)-2-oxo-3-(3-oxo-3,4-dihydro-2H-benzo[1,4]thiazin-6-yl)-oxazolidin-5-ylmethyl]-acetamide;

(R)-3-(3-fluoro-4-methyl-phenyl)-5-{2-[(R)-2-hydroxy-2-(3-methoxy-quinoxalin-5-yl)-ethylamino]-ethyl}-oxazolidin-2-one;

(R)-3-(3-fluoro-4-methyl-phenyl)-5-{2-[(S)-2-hydroxy-2-(3-methoxy-quinoxalin-5-yl)-ethylamino]-ethyl}-oxazolidin-2-one;

(S)-3-(3-fluoro-4-methyl-phenyl)-5-{2-[(R)-2-hydroxy-2-(3-methoxy-quinoxalin-5-yl)-ethylamino]-ethyl}-oxazolidin-2-one;

(S)-3-(3-fluoro-4-methyl-phenyl)-5-{2-[(S)-2-hydroxy-2-(3-methoxy-quinoxalin-5-yl)-ethylamino]-ethyl}-oxazolidin-2-one;

6-((R)-5-{[2-(6-methoxy-[1,5]naphthyridin-4-ylamino)-ethylamino]-methyl}-2-oxo-oxazolidin-3-yl)-4H-benzo[1,4]thiazin-3-one;

6-((R)-5-{[2-(6-methoxy-[1,5]naphthyridin-4-ylamino)-ethylamino]-methyl}-2-oxo-oxazolidin-3-yl)-4H-benzo[1,4]oxazin-3-one;

6-((S)-5-{3-[(3-fluoro-6-methoxy-[1,5]naphthyridin-4-ylmethyl)-amino]-propyl}-2-oxo-oxazolidin-3-yl)-4H-benzo[1,4]oxazin-3-one;

6-((R)-5-{[3-(6-methoxy-[1,5]naphthyridin-4-yl)-propylamino]-methyl}-2-oxo-oxazolidin-3-yl)-4H-pyrido[3,2-b][1,4]oxazin-3-one;

(3R)-3-(2,3-dihydro-benzo[1,4]dioxin-6-yl)-5-{(3R)-[(3-fluoro-6-methoxy-[1,5]naphthyridin-4-ylmethyl)-amino]-2-hydroxy-propyl}-oxazolidin-2-one;

(3R)-3-(2,3-dihydro-benzo[1,4]dioxin-6-yl)-5-{(3S)-[(3-fluoro-6-methoxy-[1,5]naphthyridin-4-ylmethyl)-amino]-2-hydroxy-propyl}-oxazolidin-2-one;

(3S)-3-(2,3-dihydro-benzo[1,4]dioxin-6-yl)-5-{(3R)-[(3-fluoro-6-methoxy-[1,5]naphthyridin-4-ylmethyl)-amino]-2-hydroxy-propyl}-oxazolidin-2-one;

(3S)-3-(2,3-dihydro-benzo[1,4]dioxin-6-yl)-5-{(3S)-[(3-fluoro-6-methoxy-[1,5]naphthyridin-4-ylmethyl)-amino]-2-hydroxy-propyl}-oxazolidin-2-one;

6-((R)-5-{3-[(3-amino-propyl)-(3-fluoro-6-methoxy-[1,5]
naphthyridin-4-ylmethyl)-amino]-propyl}-2-oxo-oxazo-
lidin-3-yl)-4H-benzo[1,4]oxazin-3-one;
6-((R)-5-{3-[(3-fluoro-6-methoxy-[1,5]naphthyridin-4-ylm-
ethyl)-(3-hydroxy-propyl)-amino]-propyl}-2-oxo-oxazo-
lidin-3-yl)-4H-benzo[1,4]oxazin-3-one;
6-((R)-5-{(R)-3-[(3-fluoro-6-methoxy-[1,5]naphthyridin-4-
ylmethyl)-amino]-1-hydroxy-propyl}-2-oxo-oxazolidin-
3-yl)-4H-benzo[1,4]oxazin-3-one;
6-((S)-5-{(S)-3-[(3-fluoro-6-methoxy-[1,5]naphthyridin-4-
ylmethyl)-amino]-1-hydroxy-propyl}-2-oxo-oxazolidin-
3-yl)-4H-benzo[1,4]oxazin-3-one;
(R)-5-{(R)-1-amino-3-[(3-fluoro-6-methoxy-[1,5]naphthy-
ridin-4-ylmethyl)-amino]-propyl}-3-(2,3-dihydro-benzo
[1,4]dioxin-6-yl)-oxazolidin-2-one;
(S)-5-{(S)-1-amino-3-[(3-fluoro-6-methoxy-[1,5]naphthyri-
din-4-ylmethyl)-amino]-propyl}-3-(2,3-dihydro-benzo[1,
4]dioxin-6-yl)-oxazolidin-2-one;
6-((5R)-5-{(2R)-3-[(3-fluoro-6-methoxy-[1,5]naphthyridin-
4-ylmethyl)-amino]-2-hydroxy-propyl}-2-oxo-oxazoli-
din-3-yl)-4H-benzo[1,4]thiazin-3-one;
6-((5S)-5-{(2R)-3-[(3-fluoro-6-methoxy-[1,5]naphthyridin-
4-ylmethyl)-amino]-2-hydroxy-propyl}-2-oxo-oxazoli-
din-3-yl)-4H-benzo[1,4]thiazin-3-one;
6-((5R)-5-{(2S)-3-[(3-fluoro-6-methoxy-[1,5]naphthyridin-
4-ylmethyl)-amino]-2-hydroxy-propyl}-2-oxo-oxazoli-
din-3-yl)-4H-benzo[1,4]thiazin-3-one;
6-(5S)-5-{(2S)-3-[(3-fluoro-6-methoxy-[1,5]naphthyridin-
4-ylmethyl)-amino]-2-hydroxy-propyl}-2-oxo-oxazoli-
din-3-yl)-4H-benzo[1,4]thiazin-3-one;
6-((5R)-5-{(2R)-3-[(3-fluoro-6-methoxy-quinolin-4-ylm-
ethyl)-amino]-2-hydroxy-propyl}-2-oxo-oxazolidin-3-
yl)-4H-benzo[1,4]thiazin-3-one;
6-((5R)-5-{(2S)-3-[(3-fluoro-6-methoxy-quinolin-4-ylm-
ethyl)-amino]-2-hydroxy-propyl}-2-oxo-oxazolidin-3-
yl)-4H-benzo[1,4]thiazin-3-one;
6-(5S)-5-{(2R)-3-[(3-fluoro-6-methoxy-quinolin-4-ylm-
ethyl)-amino]-2-hydroxy-propyl}-2-oxo-oxazolidin-3-
yl)-4H-benzo[1,4]thiazin-3-one;
6-(5S)-5-{(2S)-3-[(3-fluoro-6-methoxy-quinolin-4-ylm-
ethyl)-amino]-2-hydroxy-propyl}-2-oxo-oxazolidin-3-
yl)-4H-benzo[1,4]thiazin-3-one;
6-((5R)-5-{(2R)-3-[(3-fluoro-6-methoxy-[1,5]naphthyridin-
4-ylmethyl)-amino]-2-hydroxy-propyl}-2-oxo-oxazoli-
din-3-yl)-4H-benzo[1,4]oxazin-3-one;
6-((5R)-5-{(2S)-3-[(3-fluoro-6-methoxy-[1,5]naphthyridin-
4-ylmethyl)-amino]-2-hydroxy-propyl}-2-oxo-oxazoli-
din-3-yl)-4H-benzo[1,4]oxazin-3-one;
6-(5S)-5-{(2R)-3-[(3-fluoro-6-methoxy-[1,5]naphthyridin-
4-ylmethyl)-amino]-2-hydroxy-propyl}-2-oxo-oxazoli-
din-3-yl)-4H-benzo[1,4]oxazin-3-one;
6-(5S)-5-{(2S)-3-[(3-fluoro-6-methoxy-[1,5]naphthyridin-
4-ylmethyl)-amino]-2-hydroxy-propyl}-2-oxo-oxazoli-
din-3-yl)-4H-benzo[1,4]oxazin-3-one;
6-((5R)-5-{(2R)-3-[(3-fluoro-6-methoxy-quinolin-4-ylm-
ethyl)-amino]-2-hydroxy-propyl}-2-oxo-oxazolidin-3-
yl)-4H-benzo[1,4]oxazin-3-one;
6-((5R)-5-{(2S)-3-[(3-fluoro-6-methoxy-quinolin-4-ylm-
ethyl)-amino]-2-hydroxy-propyl}-2-oxo-oxazolidin-3-
yl)-4H-benzo[1,4]oxazin-3-one;
6-((5S)-5-{(2R)-3-[(3-fluoro-6-methoxy-quinolin-4-ylm-
ethyl)-amino]-2-hydroxy-propyl}-2-oxo-oxazolidin-3-
yl)-4H-benzo[1,4]oxazin-3-one;
6-((5S)-5-{(2S)-3-[(3-fluoro-6-methoxy-quinolin-4-ylm-
ethyl)-amino]-2-hydroxy-propyl}-2-oxo-oxazolidin-3-
yl)-4H-benzo[1,4]oxazin-3-one;
6-((5R)-5-{(2R)-3-[(7-fluoro-2-methoxy-quinolin-8-ylm-
ethyl)-amino]-2-hydroxy-propyl}-2-oxo-oxazolidin-3-
yl)-4H-benzo[1,4]oxazin-3-one;
6-((5R)-5-{(2S)-3-[(7-fluoro-2-methoxy-quinolin-8-ylm-
ethyl)-amino]-2-hydroxy-propyl}-2-oxo-oxazolidin-3-
yl)-4H-benzo[1,4]oxazin-3-one;
6-((5S)-5-{(2R)-3-[(7-fluoro-2-methoxy-quinolin-8-ylm-
ethyl)-amino]-2-hydroxy-propyl}-2-oxo-oxazolidin-3-
yl)-4H-benzo[1,4]oxazin-3-one;
6-((5S)-5-{(2S)-3-[(7-fluoro-2-methoxy-quinolin-8-ylm-
ethyl)-amino]-2-hydroxy-propyl}-2-oxo-oxazolidin-3-
yl)-4H-benzo[1,4]oxazin-3-one;

and salts (in particular pharmaceutically acceptable salts) thereof, whereby the first 128 compounds in the list above (counted from the top of the list) and their salts (in particular their pharmaceutically acceptable salts) constitute a particular sub-embodiment and the first 318 compounds in the list above (counted from the top of the list) and their salts (in particular their pharmaceutically acceptable salts) constitute another particular sub-embodiment.

The compounds of formula I according to embodiments i) to lxiii) are suitable for the use as chemotherapeutic active compounds in human and veterinary medicine and as substances for preserving inorganic and organic materials in particular all types of organic materials for example polymers, lubricants, paints, fibres, leather, paper and wood.

These compounds according to the invention are particularly active against bacteria and bacteria-like organisms. They are therefore particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casseliflavus, S. epidermidis, S. haemolyticus*, or *Peptostreptococcus* spp.; pharyngitis, rheumatic fever, and glomerulonephritis related to infection by *Streptococcus pyogenes*, Groups C and G streptococci, *Corynebacterium diphtheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. haemolyticus*, etc.), *Streptococcus pyogenes, Streptococcus agalactiae*, Streptococcal groups C-F (minute colony streptococci), viridans streptococci, *Corynebacterium minutissimum, Clostridium* spp., or *Bartonella henselae*; uncomplicated acute urinary tract infections related to infection by *Staphylococcus aureus*, coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; infections caused by *Mycobacterium tuberculosis, M. leprae, M. paratuberculosis, M. kansasii*, or *M. chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae*.

The compounds of formula I according to the present invention are further useful for the preparation of a medicament for the treatment of infections that are mediated by bacteria such as *E. coli, Klebsiella pneumoniae* and other Enterobacteriaceae, *Acinetobacter* spp., *Stenothrophomonas maltophilia, Neisseria meningitidis, Bacillus cereus, Bacillus anthracis, Corynebacterium* spp., *Propionibacterium acnes* and bacteroide spp.

The compounds of formula I according to the present invention are further useful to treat protozoal infections caused by *Plasmodium malaria, Plasmodium falciparum, Toxoplasma gondii, Pneumocystis carinii, Trypanosoma brucei* and *Leishmania* spp.

The present list of pathogens is to be interpreted merely as examples and in no way as limiting.

One aspect of this invention therefore relates to the use of a compound of formula I according to this invention, or of a pharmaceutically acceptable salt thereof, for the manufacture of a medicament for the prevention or treatment of a bacterial infection.

As well as in humans, bacterial infections can also be treated using compounds of formula I (or pharmaceutically acceptable salts thereof) in other species like pigs, ruminants, horses, dogs, cats and poultry.

The present invention also relates to pharmacologically acceptable salts and to compositions and formulations of compounds of formula I.

Any reference to a compound of formula I is to be understood as referring also to the salts (and especially the pharmaceutically acceptable salts) of such compounds, as appropriate and expedient.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

A pharmaceutical composition according to the present invention contains at least one compound of formula I (or a pharmaceutically acceptable salt thereof) as the active agent and optionally carriers and/or diluents and/or adjuvants, and may also contain additional known antibiotics.

The compounds of formula I and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment of a bacterial infection in a patient comprising the administration to said patient of a pharmaceutically active amount of a derivative according to formula I or a pharmaceutically acceptable salt thereof.

Besides, any preferences indicated for the compounds of formula I (whether for the compounds themselves, salts thereof, compositions containing the compounds or salts thereof, uses of the compounds or salts thereof, etc.) apply mutatis mutandis to compounds of formula $I_{CE}$.

Moreover, the compounds of formula I may also be used for cleaning purposes, e.g. to remove pathogenic microbes and bacteria from surgical instruments or to make a room or an area aseptic. For such purposes, the compounds of formula I could be contained in a solution or in a spray formulation.

The compounds of formula I can be manufactured in accordance with the present invention using the procedures described hereafter.

Preparation of Compounds of Formula I

Abbreviations

The following abbreviations are used throughout the specification and the examples:

Ac acetyl
AcOH acetic acid
AD-mix α 1,4-bis(dihydroquinine)phthalazine, $K_3Fe(CN)_6$, $K_2CO_3$ and $K_2OsO_4.2H_2O$
AD-mix β 1,4-bis(dihydroquinidine)phthalazine, $K_3Fe(CN)_6$, $K_2CO_3$ and $K_2OsO_4.2H_2O$
Alloc allyloxycarbonyl
aq. aqueous
9-BBN 9-borabicyclo[3.3.1]nonane
BINAP 2,2'-bis-(diphenylphosphino)-1,1'-binaphthalene
br. broad
Boc tert-butoxycarbonyl
n-BuLi n-butyllithium
t-Bu tert-butyl
Cbz benzyloxycarbonyl
CDI 1,1'-carbonyldiimidazole
conc. concentrated
dba dibenzylidene acetone
DBU 1,8-diazabicyclo(5.4.0)undec-7-ene
DCC N,N'-dicyclohexylcarbodiimide
1,2-DCE 1,2-dichloroethane
DCM dichloromethane
DHQD dihydroquinidine
DIBAH diisobutylaluminium hydride
DIPA N,N-diisopropylamine
DIPEA N,N-diisopropylethylamine
DMA N,N-dimethylacetamide
DMAP 4-dimethylaminopyridine
DMF N,N-dimethylformamide
DMSO dimethylsulfoxide
DPPA diphenyl phosphoryl azide
EA ethyl acetate
EDC 1-(3-dimethylaminopropyl)-3-ethylcarbodiimide hydrochloride
ee enantiomeric excess
ESI Electron Spray Ionisation
eq. equivalent ether diethyl ether
Et ethyl
EtOH ethanol
FC flash column chromatography on $SiO_2$
FMOC 9-fluorenylmethoxycarbonyl
HATU O-(7-azabenzotriazol-1-yl)-N,N,N',N'-tetramethyluronium hexafluorophosphate
Hex hexane
Hept heptane
HOBT 1-hydroxybenzotriazole hydrate
HV high vacuum conditions
KHMDS potassium hexamethyldisilazide
LC Liquid Chromatography
LDA lithium diisopropylamide
LiHMDS lithium hexamethyldisilazide
MCPBA meta-chloroperbenzoic acid
Me methyl
MeCN acetonitrile
MeOH methanol
MS Mass Spectroscopy
Ms methanesulfonyl
NMO N-methyl-morpholine N-oxide
org. organic
Pd/C palladium on carbon
Ph phenyl
PHAL phtalazine
prep. TLC preparative thin layer chromatography
Pyr pyridine
i-Pr iso-propyl
quant. quantitative
rac. racemic
rt room temperature
sat. saturated
$SiO_2$ silica gel
TBAF tetrabutylammonium fluoride
TBDMS tert-butyldimethylsilyl
TBDPS tert-butyldiphenylsilyl
TEA triethylamine
TEMPO 2,2,6,6-tetramethyl-1-piperidinyloxy
Tf triflyl (=trifluoromethanesulfonyl)
TFA trifluoroacetic acid
THF tetrahydrofuran
Tol tolyl
p-TsCl para-toluenesulfonyl chloride
General Reaction Techniques:
Reaction Technique 1 (Amine Protection):
Amines are usually protected as carbamates such as Alloc, Cbz, Boc or FMOC. They are obtained by reacting the amine with allyl or benzyl chloroformate, di tert-butyl dicarbonate or FMOC chloride in presence of a base such as NaOH, TEA, DMAP or imidazole.

They can also be protected as N-benzyl derivatives by reaction with benzyl bromide or chloride in presence of a base such as $Na_2CO_3$ or TEA. Alternatively, N-benzyl derivatives can be obtained through reductive amination in presence of benzaldehyde (see reaction technique 4).

Amines can furthermore be protected as sulphonamides by their reaction with 2-nitro- or 4-nitro-phenylsulphonyl chloride in a solvent such as DCM or THF in presence of a base such as TEA or aq. NaOH between −10° C. and 40° C.

Further strategies to introduce other amine protecting groups have been described in Protecting Groups in Organic Synthesis, 3rd Ed (1999), 494-653; T. W. Greene, P. G. M. Wuts; (Publisher: John Wiley and Sons, Inc., New York, N.Y.).

Reaction Technique 2 (Oxazolidinone Formation):
The 1,2-aminoalcohol derivative is reacted with phosgene, diphosgene or triphosgene. This reaction is preferably carried out in a dry aprotic solvent such as DCM or THF in presence of an organic base such as TEA or Pyr and at a temperature between −30° and +40° C. Alternatively the 1,2-aminoalcohol derivative is reacted with carbonyldiimidazole or N,N'-disuccinimidyl carbonate in a dry aprotic solvent such as DCM or THF in presence of an organic base such as TEA or Pyr and at a temperature between −30° and +80° C.

Reaction Technique 3 (Amino Deprotection):
The benzyl carbamates are deprotected by hydrogenolysis over a noble metal catalyst (e.g. Pd/C or $Pd(OH)_2$/C). The Boc group is removed under acidic conditions such as HCl in an organic solvent such as MeOH or dioxane, or TFA neat or diluted in a solvent such DCM. The Alloc group is removed in presence of tetrakis(triphenylphosphine)palladium(0) in presence of an allyl cation scavenger such as morpholine, dimedone or tributyltin hydride between 0° C. and 50° C. in a solvent such as THF.

The N-benzyl protected amines are deprotected by hydrogenolysis over a noble catalyst (e.g. $Pd(OH)_2$).

The N-acetyl protecting group is removed under basic conditions such as $Na_2CO_3$, LiOH or NaOH in aq. MeOH or THF, or under acidic conditions such as aq. HCl in THF.

The 2- or 4-nitro-phenylsulphonamides can be deprotected by using either thioglycolic acid or thiophenol in DMF in presence of a base such as LiOH, $K_2CO_3$ or DBU (see *Tetrahedron Lett.* (1995), 36, 6373).

Further general methods to remove amine protecting groups have been described in *Protecting Groups in Organic Synthesis*, $3^{rd}$ Ed (1999), 494-653; T. W. Greene, P. G. M. Wuts; (Publisher: John Wiley and Sons, Inc., New York, N.Y.).

Reaction Technique 4 (Reductive Amination):
The reaction between the amine and the aldehyde or ketone is performed in a solvent system allowing the removal of the formed water through physical or chemical means (e.g. distillation of the solvent-water azeotrope or presence of drying agents such as molecular sieves, $MgSO_4$ or $Na_2SO_4$). Such solvent is typically toluene, Hex, THF, DCM or DCE or mixture of solvents such as MeOH-DCE. The reaction can be catalyzed by traces of acid (usually AcOH). The intermediate imine is reduced with a suitable reducing agent (e.g. $NaBH_4$, $NaBH_3CN$, or $NaBH(OAc)_3$ or through hydrogenation over a noble catalyst such as Pd/C. The reaction is carried out between −10° C. and 110° C., preferably between 0° C. and 60° C. The reaction can also be carried out in one pot. It can also be performed in protic solvents such as MeOH or water in presence of a picoline-borane complex (*Tetrahedron* (2004), 60, 7899-7906).

Reaction Technique 5 (Amide Reduction with $BHA_3$):
The amide derivatives are treated with diborane, $BH_3$.THF or $BH_3$.$Me_2$S complexes in a dry solvent such as THF between −10° C. and 60° C. The reaction is further treated with diluted HCl between 0° C. and 50° C.

Reaction Technique 6 (Substitution):
The alcohol is reacted with MsCl, TfCl or TsCl in presence of a base such as TEA in a dry aprotic solvent such as Pyr, THF or DCM between −30° C. and 50° C. In the case of the triflate or mesylate, $Tf_2O$ or $Ms_2O$ can also be used. These sulfonates can be reacted with sodium iodide in MeCN or DMF between 40° C. and 120° C. delivering the corresponding iodide derivatives. Once activated (either as a sulphonate or a iodide derivative), the alcohol reacts either with an alcoholate generated from an alcohol with an inorganic base such as NaH or $K_2CO_3$ or with an organic base such as LiHMDS between −20° C. and 60° C., or with an amine in presence of an organic base such as TEA.

Reaction Technique 7 (Acylation):

The amine is reacted with an activated form of a carboxylic acid such as a carbonyl chloride derivative (e.g. acetyl or butyl chloride) in presence of an organic base such as TEA between −20° C. and 40° C. or a carboxylic anhydride such as acetic acid anhydride between 20 and 100° C. The amine can also be reacted with the required carboxylic acid in presence of an activating agent (see reaction technique 9).

Reaction Technique 8 (Alkylation):

The amine derivative is reacted with an alkyl halide such as MeI in presence of an inorganic base such as $K_2CO_3$ or an organic base such as TEA in a solvent such as THF between 0° C. and 80° C. In the particular case wherein a methyl group is introduced, dimethyl sulphate can also be used. Further details can be found in Comprehensive Organic Transformations. A guide to Functional Group Preparations; $2^{nd}$ Edition, R. C. Larock, Wiley-VC; New York, Chichester, Weinheim, Brisbane, Singapore, Toronto, 1999. Section Amines p. 779.

Reaction Technique 9 (Amide Coupling):

The carboxylic acid is reacted with the amine in presence of an activating agent such as DCC, EDC, HOBT, n-propylphosphonic cyclic anhydride, HATU or di-(N-succinimidyl)-carbonate, in a dry aprotic solvent such as DCM, MeCN or DMF between −20° C. and 60° C. (see G. Benz in Comprehensive Organic Synthesis, B. M. Trost, I. Fleming, Eds; Pergamon Press: New York (1991), vol. 6, p. 381). Alternatively, the carboxylic acid can be activated by conversion into its corresponding acid chloride by reaction with oxalyl chloride or thionyl chloride neat or in a solvent like DCM between −20° and 60° C. Further activating agents can be found in Comprehensive Organic Transformations. A guide to Functional Group Preparations; $2^{nd}$ Edition, R. C. Larock, Wiley-VC; New York, Chichester, Weinheim, Brisbane, Singapore, Toronto, 1999. Section nitriles, carboxylic acids and derivatives p. 1941-1949.

Reaction Technique 10 (Oxazolidine Ring Formation Via Glycydyl Esters):

The aniline carbamate is reacted in a dry solvent such as THF with a strong organic base such as n-BuLi between −100° C. and −30° C. or with t-BuOLi, t-BuOK or KHMDS between −100° C. and −30° C. The anion is reacted at these temperatures with the required epoxide and allowed to reach rt.

Reaction Technique 11 (Mitsunobu):

The alcohol is reacted with different nucleophiles such as phenols, phthalimide or hydrazoic acid (generated from $NaN_3$ in acidic medium) in presence of $PPh_3$ and DEAD or DIAD in a solvent such as THF, DMF, DCM or DME between −20° C. and 60° C. as reviewed by O. Mitsunobu, in Synthesis (1981), 1. In the particular case of basic amines, the reaction is performed with the corresponding 2- or 4-nitro-phenylsulfonamides; the free amine is subsequently liberated as described in reaction technique 3. The reaction might also be performed using a polymer-supported $PPh_3$.

Reaction Technique 12 (Wittig):

The required phosphonium salt is treated in a solvent such as water with an inorganic base such as NaOH. The corresponding phosphorane is collected by filtration and dried in vacuo. It is reacted with the required aldehyde in an aprotic solvent such as THF, DCM or toluene between 0° C. and 90° C. Alternatively the Wittig-Horner variant of the reaction can be used wherein the phosphono ester (generated from the corresponding bromide and triethylphosphite) is reacted with the adehyde in presence of a base such as NaH or NaOMe in a solvent such as ether or THF between 0° C. and 50° C.

Reaction Technique 13 (Acetonide Conversion into Diol):

The acetonide is converted into its corresponding diol under acidic conditions such as diluted aq. HCl in MeOH or by using an acidic resin such as Amberlite IR120H or DOWEX 50W8 in a water-solvent mixture such as MeOH/water or THF/water.

Reaction Technique 14 (Cis Dihydroxylation):

The diol is obtained by dihydroxylation of the corresponding ethylenic derivative using a catalytic amount of osmium tetroxide in the presence a co-oxidant such as NMO in aq. solvent such as an acetone-water or DCM-water mixture (see Cha, J. K. Chem. Rev. (1995), 95, 1761-1795). The chiral cis-diols are obtained by using AD-mix α or AD-mix β in presence of methanesulfonamide in a water/2-methyl-2 propanol mixture as described in Chem. Rev. (1994), 94, 2483. The sense of induction relies on the chiral ligand contained in the AD mixture, either a dihydroquinine-based ligand in AD-mix α or a dihydroquinidine-based ligand in AD-mix β.

Reaction Technique 15 (Heck):

The unsaturated halide or triflate is reacted with an alkene and a strong base such as triethylamine, potassium carbonate, cesium carbonate or sodium acetate and an organopalladium catalyst such as tetrakis(triphenylphosphine)palladium(0), palladium chloride or palladium(II) acetate in a solvent such as DMF. The ligand is triphenylphosphine, $P(o-tolyl)_3$ or BINAP. Further details can be obtained in R. F. Heck, Org. React. (1982), 27, 345-390 or A. de Meijere, F. E. Meyer, Jr., Angew. Chem. Int. Ed. Engl. (1994), 33(23-24), 2379-2411.

Reaction Technique 16 (Hydroboration):

The vinyl derivatives were hydroborated with $BH_3.THF$, $BH_3.Me_2S$, $BH_2Cl.dioxane$ complexes or 9-BBN in solvents such as THF or dioxane between 0° C. and 90° C. (for a review, see Smith, K.; Pelter, A. G. Comprehensive Organic Synthesis, B. M. Trost, I. Fleming, Eds; Pergamon Press: New York (1991), vol. 8, p. 703-731) followed by oxidative workup with aq. NaOH and 30% $H_2O_2$ between 40° C. and 90° C. (see also Pelter, A.; Smith, K. G. Comprehensive Organic Synthesis, B. M. Trost, I. Fleming, Eds; Pergamon Press: New York (1991), vol. 7, p. 593-611). The preparation and use of dioxane-monochloroborane complex is described in J. Org. Chem., 66, 5359-5365; 2001.

Reaction Technique 17 (Hydroxy Deprotection):

The silyl ether groups are removed either using fluoride anion sources such as TBAF in THF between 0° C. and 40° C. or HF in MeCN between 0° C. and 40° C. or using acidic conditions such as AcOH in THF/MeOH or HCl in MeOH. Further methods to remove the TBDMS and TBDPS groups are given in Protecting Groups in Organic Synthesis $3^{rd}$ Ed; 1999, 133-139 and 142-143 respectively; T. W. Greene, P. G. M. Wuts; (Publisher: John Wiley and Sons, Inc., New York, N.Y.). Further general methods to remove alcohol protecting groups are described in Protecting Groups in Organic Synthesis $3^{rd}$ Ed; 1999, 23-147; T. W. Greene, P. G. M. Wuts; (Publisher: John Wiley and Sons, Inc., New York, N.Y.).

Reaction Technique 18 (Formation of Aldehydes):

The alcohols can be transformed into their corresponding aldehydes through oxidation under Swern (see D. Swern et al., J. Org. Chem. (1978), 43, 2480-2482) or Dess Martin (see D. B. Dess and J. C. Martin, J. Org. Chem. (1983), 48, 4155) conditions, respectively Alternatively the esters can be transformed into their corresponding aldehydes by controlled reduction with a bulky hydride reagent such as DIBAH.

Reaction Technique 19 (Oxidation of Alcohols/Aldehydes into Acids):

Aldehydes can be oxidized into their corresponding acids by a variety of methods as described in *Comprehensive Organic Transformations. A guide to Functional Group Preparations;* 2nd Edition, R. C. Larock, Wiley-VC; New York, Chichester, Weinheim, Brisbane, Singapore, Toronto, 1999. Section nitriles, carboxylic acids and derivatives p. 1653-1655. Among them, potassium permanganate in an acetone-water mixture (see *Synthesis* (1987), 85) or sodium chlorite in 2-methyl-2-propanol in presence of 2-methyl-2-butene (see *Tetrahedron* (1981), 37, 2091-2096) are frequently used.

Alcohols can be directly oxidized into their corresponding acids by a variety of methods as described in *Comprehensive Organic Transformations. A guide to Functional Group Preparations;* 2nd Edition, R. C. Larock, Wiley-VC; New York, Chichester, Weinheim, Brisbane, Singapore, Toronto, 1999. Section nitriles, carboxylic acids and derivatives p. 1646-1648. Among them, the Jones reagents ($CrO_3/H_2SO_4$), $NaIO_4$ in presence of $RuCl_3$, $KMnO_4$ or $Pyr.H_2Cr_2O_7$ are frequently used.

Reaction Technique 20 (Reduction of Azides into Amines):

The azides are hydrogenated over a noble metal catalyst such as Pd/C in solvent such as MeOH or EA. In case the molecule is containing an unsaturated double or triple bond, the reduction can be performed using $PPh_3$ in presence of water as described in *J. Med. Chem.* (1993), 36, 2558-68.

Reaction Technique 21 (Hydrolysis of Esters into Carboxylic Acids):

When the ester side chain is a linear alkyl, the hydrolysis is usually performed by treatment with an alkali hydroxide such as LiOH, KOH or NaOH in a water-dioxan or water-THF mixture between 0° C. and 80° C. When the ester side chain is tert-butyl, the hydrolysis can also be performed in neat TFA or diluted TFA or HCl in an organic solvent such as ether or THF. When the ester side chain is the allyl group, the reaction is performed in presence of tetrakis(triphenylphosphine)palladium(0) in presence of an allyl cation scavenger such as morpholine, dimedone or tributyltin hydride between 0° C. and 50° C. in a solvent such as THF. When the ester side chain is benzyl, the reaction is performed under hydrogen in presence of a noble metal catalyst such as Pd/C in a solvent such as MeOH, THF or EA. Further strategies to introduce other acid protecting groups and general methods to remove them have been described in *Protecting Groups in Organic Synthesis* 3rd Ed; 1999, 369-441; T. W. Greene, P. G. M. Wuts; (Publisher: John Wiley and Sons, Inc., New York, N.Y.).

Reaction Technique 22 (Reduction of Carboxylates into Alcohols):

The ester is reduced with a boron or aluminium hydride reducing agent such as $LiBH_4$ or $LiAlH_4$ in a solvent such as THF between −20° C. and 40° C. Alternatively, the ester function is hydrolyzed into its corresponding acid using an alkali hydroxide such as NaOH, KOH or LiOH in water or in a mixture of water with polar protic or aprotic organic solvent such as THF or MeOH between −10° C. and 50° C. The resulting carboxylic acid is further reduced into the corresponding alcohol using a borane derivative such as a $BH_3.THF$ complex in a solvent such as THF between −10° C. and 40° C.

Reaction Technique 23 (Protection of Alcohols):

The alcohols are protected as silyl ether (usually TBDMS or TBDPS). The alcohol is reacted with the required silyl chloride reagent (TBDMSCl or TBDPSCl) in presence of a base such as imidazole or TEA in a solvent such as DCM or DMF between 10° C. and 40° C.

Further strategies to introduce other alcohol protecting groups have been described in Protecting Groups in Organic Synthesis 3rd Ed; 1999, 23-147; T. W. Greene, P. G. M. Wuts; (Publisher: John Wiley and Sons, Inc., New York, N.Y.).

General Preparation Methods:

Preparation of Compounds of Formula I:

Sections a) to au) hereafter describe general methods for preparing the compounds of formula I. In these sections, the symbols $R^1$, U, V, W, X, $Y^1$, $Y^2$, A, B, D and E have the same meanings as in formula I unless mentioned otherwise.

a) The compounds of formula I can be obtained by reacting a compound of formula II

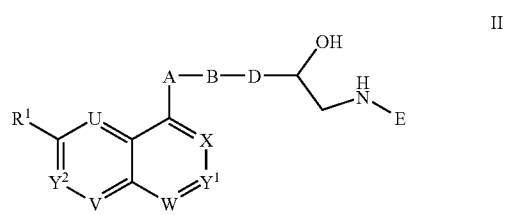

with a carbonic acid derivative of formula III

wherein $L^0$ and $L^{00}$ are both halogen, $OCCl_3$, imidazolyl or succinimidyloxy, or $L^0$ is halogen and $L^{00}$ is $OCCl_3$. This reaction is preferably carried out in a dry aprotic solvent such as DCM or THF in presence of an organic base such as TEA or Pyr and at a temperature between −30° and +40° C. In case there is one or two free amino or alcohol functions in the chain A-B-D, these functional groups are protected prior to the reaction and removed thereafter.

b) The compounds of formula I can be obtained by reacting a compound of formula IV

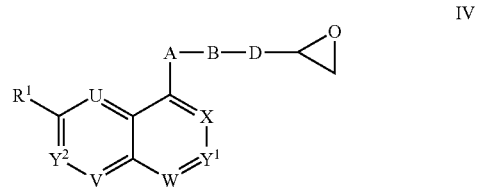

with the anion of compound of formula V

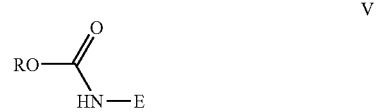

wherein R represents alkyl or benzyl. This reaction can be performed following reaction technique 10.

c) The compounds of formula I wherein A is $CH_2CH_2$, B is $NHCH_2$ and D is $CH_2$ can be prepared by one of the ways summarised in Scheme 1 hereafter.

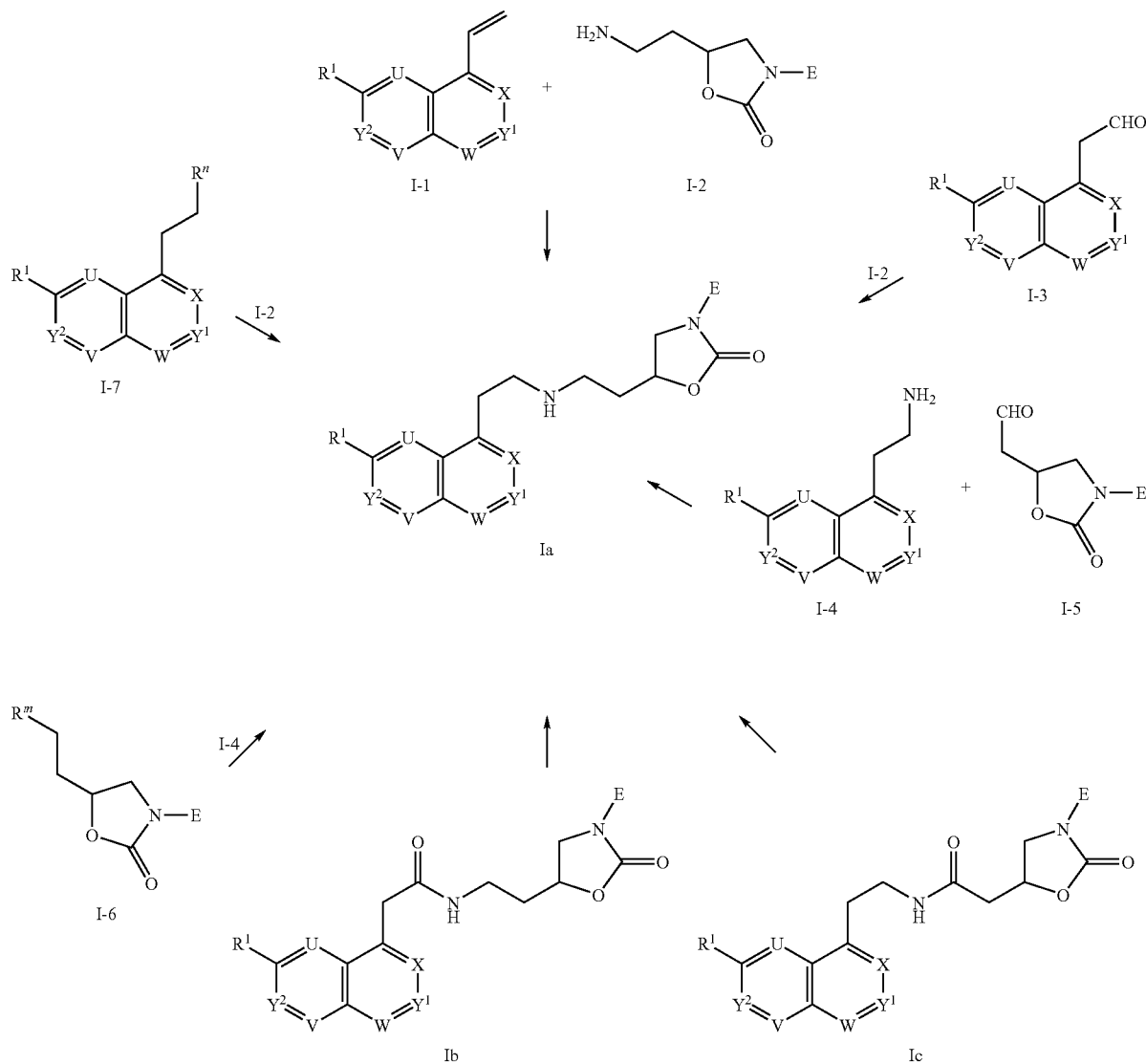

Scheme 1

In Scheme 1, $R^m$ and $R^n$ represent OH, halogen, MsO, TsO, TfO or $N_3$.

The compounds of formula Ia can be obtained by reacting the vinyl derivatives of formula I-1 with the amines of formula I-2 in a solvent such as methanol between 40° C. and 120° C. in analogy to *Aust. J. Chem.* (2004), 57, 29. Compounds of formula Ia can also be obtained by reacting the aldehydes of formula I-3 or I-5 with the amines of formula I-2 or I-4 under reductive amination conditions (reaction technique 4). The compounds of formula Ia can also be obtained by reducing the amides of formula Ib or Ic with a borohydride reagent such as diborane (reaction technique 5). The compounds of formula Ia can further be obtained by reacting the compounds of formula I-6 or I-7 wherein $R^m$ or $R^n$ represents halogen, mesyloxy, tosyloxy or triflyloxy with the amines of formula I-4 or I-2 (reaction technique 6). Alternatively the amine derivatives of formula I-2 or I-4 can be transformed into their corresponding sulphonamides after reaction with 2- or 4-nitrophenylsulfonyl chloride in presence of an organic base and subsequent reaction with the alcohol derivatives of formula I-7 or I-6 wherein $R^n$ and $R^m$ represent OH under Mitsunobu conditions [reaction technique 11]. The amines of formula Ia are obtained after further hydrolysis in presence of $K_2CO_3$ [reaction technique 3].

The compounds of formula I wherein A is $CH_2CH_2$, B is $NR^{4a}CH_2$ and D is $CH_2$ can then be obtained from the compounds of formula Ia. Hence, the central amino group of the compounds of formula Ia can be further transformed by alkylation with compounds of formula $Hal-(CH_2)_q COOR^{4a'}$ wherein Hal represents halogen, q represents the integer 1 to 4 and $R^{4a'}$ represents alkyl, in presence of DIPEA and NaI The resulting esters can be transformed into the corresponding acid ($R^{4a'}$=H) by acidic hydrolysis in presence of aq. HCl. The central amino group of compound Ia can also be reacted with glycidol or the appropriate alkyl halide or hydroxy- or dihydroxy-alkyl halide, thus affording the corresponding compounds of formula I wherein A is $CH_2CH_2$, B is $NR^{4a}CH_2$, D is $CH_2$ and $R^{4a}$ is alkyl which may be substituted once or twice by hydroxy groups.

d) The compounds of formula I wherein A is $CH_2CH_2$, B is $CH_2NH$ and D is $CH_2$ can be prepared by one of the ways summarised in Scheme 2 hereafter.

Scheme 2
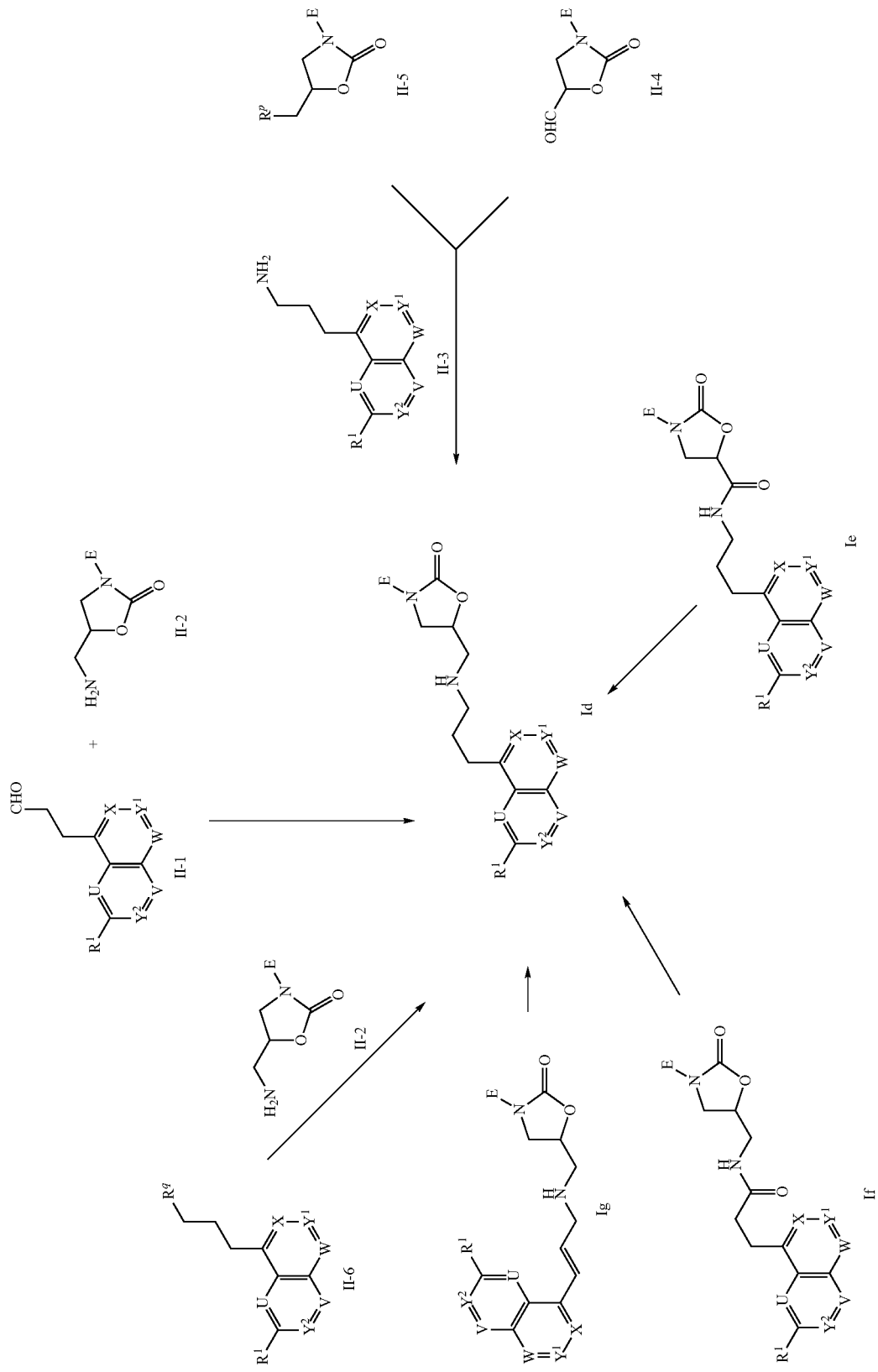

In Scheme 2, $R^p$ and $R^q$ represent OH, halogen, MsO, TsO, TfO or $N_3$.

The compounds of formula Id can be obtained by reacting the aldehydes of formula II-1 with the amines of formula II-2 under reductive amination conditions [ref 4 reductive amination]. The compounds of formula Id can also be obtained by reacting the aldehydes of formula II-4 with the amines of formula II-3 under reductive amination conditions (reaction technique 4). The compounds of formula Id can further be obtained by reducing the amide function of compounds of formula Ie or If with a borohydride reagent such as diborane (reaction technique 5). The compounds of formula Id can furthermore be obtained by reacting the compounds of formula II-5 wherein $R^p$ represents halogen, mesyloxy, tosyloxy or triflyloxy with a compound of formula II-3 (reaction technique 6). The compounds of formula Id can besides be obtained by reacting the compounds of formula II-6 wherein $R^q$ represents halogen, mesyloxy, tosyloxy or triflyloxy with the compounds of formula II-2 (reaction technique 6). Alternatively the compounds of formula Id can also be obtained after transformation of the amines of formula II-2 or II-3 into their corresponding 2- or 4-nitrophenylsulfonamides and subsequent reaction with the alcohols of formula II-6 ($R^q$=OH) or II-5 ($R^p$=OH) respectively under Mitsunobu conditions and deprotection as described above. The compounds of formula Id can also be obtained by hydrogenation of compounds of formula Ig over a noble metal catalyst such as Pd/C.

e) The compounds of formula I wherein A is $CH_2CH_2$, B is $CH_2NR^3$, D is $CH_2$ and $R^3$ is alkyl, aminoethyl, arylalkyl or alkylcarbonyl can be prepared according to one of the methods hereafter.

The compounds of formula Id wherein $R^3$ is alkylcarbonyl can be acylated with an activated form of a carboxylic acid (reaction technique 7). In the particular case of carboxyethylcarbonyl, the reaction can be performed by reacting the compounds of formula Id wherein $R^3$ is H with succinic anhydride or with a succinic acid monoester (e.g. methyl, ethyl or benzyl ester) followed by ester deprotection. Compounds of formula Id wherein $R^3$ is alkyl, aminoethyl or arylalkyl are obtained by alkylation with alkyl halogenides, Boc- or Cbz-aminoethyl halogenides or arylalkyl halogenides (reaction technique 8). They can also be obtained through reductive amination with the corresponding alkanals or benzaldehyde (reaction technique 4). Alternatively, in the cases wherein $R^3$ is alkyl, aminoethyl or arylalkyl, the strategies used for obtaining compounds of formula Id can be applied starting from the corresponding compounds wherein the NH of the amide of formula If and Ie or one hydrogen on the primary amine of compounds of formula II-2 or II-3 are replaced by alkyl, Boc- or Cbz-aminoethyl or arylalkyl. In the particular case wherein $R^3$ is aminoethyl, an additional deprotection step is required to remove the Cbz or Boc protecting group on the terminal amino group.

f) The compounds of formula I wherein A is $CH_2CH_2$, B is NHCO and D is $CH_2$ can be prepared as summarised in Scheme 3 hereafter.

Scheme 3

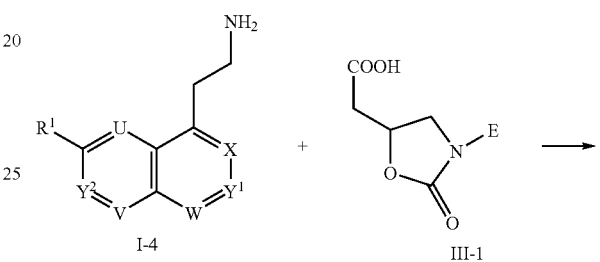

I-4     III-1

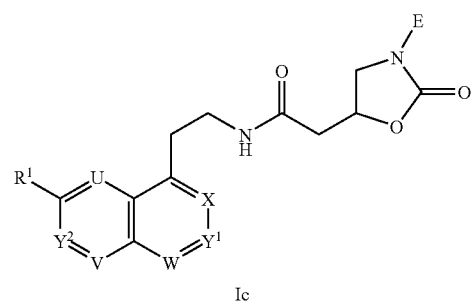

Ic

The compounds of formula Ic can thus be obtained by reacting an activated form of a carboxylic acid of formula III-1 with the amines of formula I-4 (reaction technique 9).

g) The compounds of formula I wherein A is $CH_2CH_2$, B is CONH and D is $CH_2$ can be prepared by one of the ways summarised in Scheme 4 hereafter.

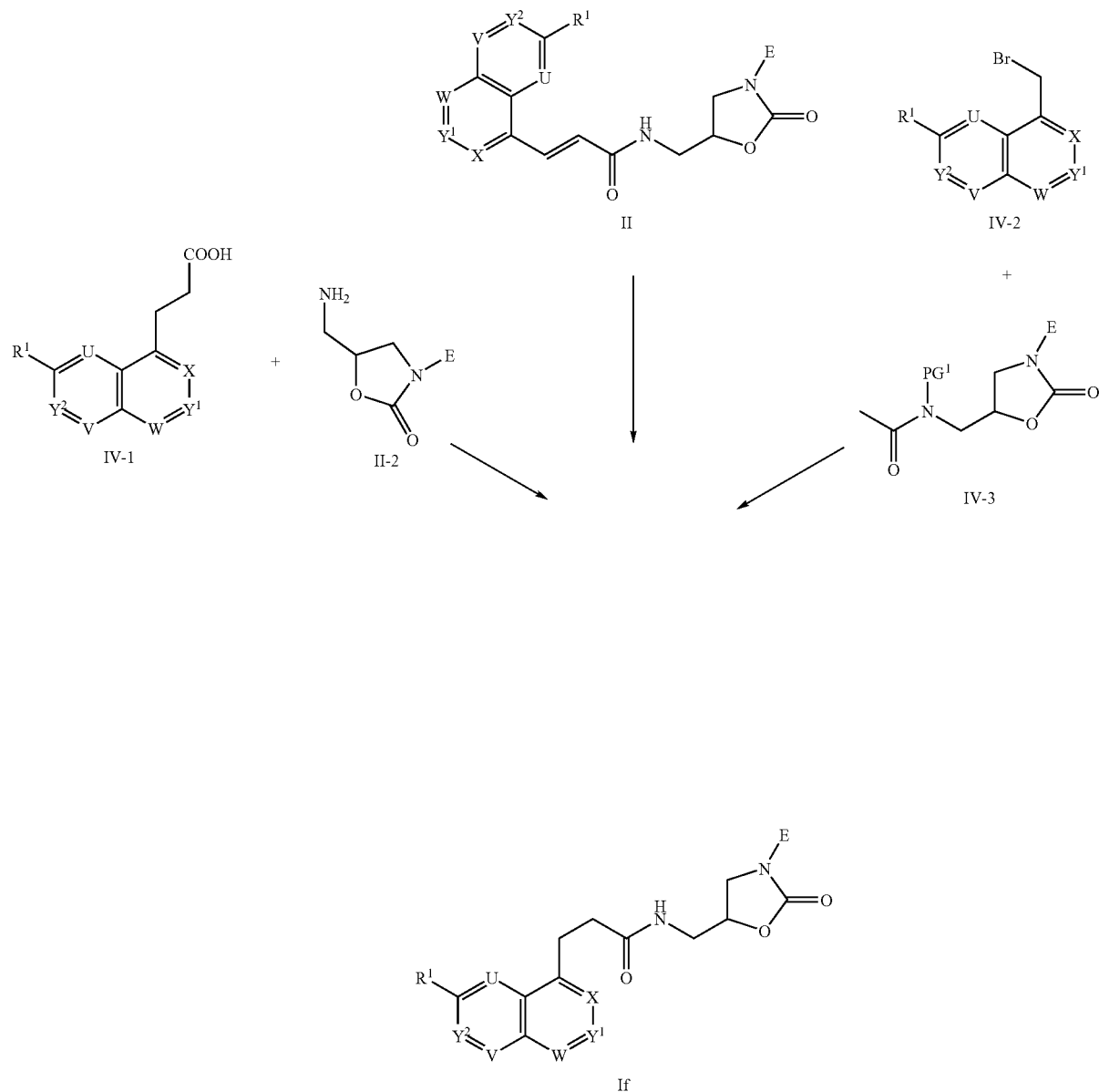

Scheme 4

In Scheme 4, $PG^1$ represents an amino protecting group such as benzyl and $R^6$ is hydrogen or alkyl.

The compounds of formula If (wherein $R^4$ is H or alkyl) can be obtained by reacting an activated form of a carboxylic acid of formula IV-1 with the amines of formula II-2 (reaction technique 9). The compounds of formula If can also be obtained by hydrogenation of a compound of formula Ii (the preparation of which is described in section 1)) over a noble metal catalyst such as Pd/C. The compounds of formula If wherein $R^4$=H can also be obtained by quenching the anion generated by the reaction of the acetamides of formula IV-3 and n-BuLi, with the halogenides of formula IV-2, followed by removal of the amino protecting group.

The compounds of formula If wherein the nitrogen atom of the amide function is substituted (i.e. the compounds of formula I wherein A is $CH_2CH_2$, B is $CONR^4$ and D is $CH_2$, $R^4$ being alkyl) can be prepared using the strategies used for obtaining compounds of formula If, starting however from the corresponding compounds wherein one hydrogen of the primary amine of compounds of formula II-2 is replaced by $R^4$.

h) The compounds of formula I wherein A is $CH_2CH_2$, B is $CH_2NH$ and D is CO can be prepared by one of the ways summarised in Scheme 5 hereafter.

Scheme 5

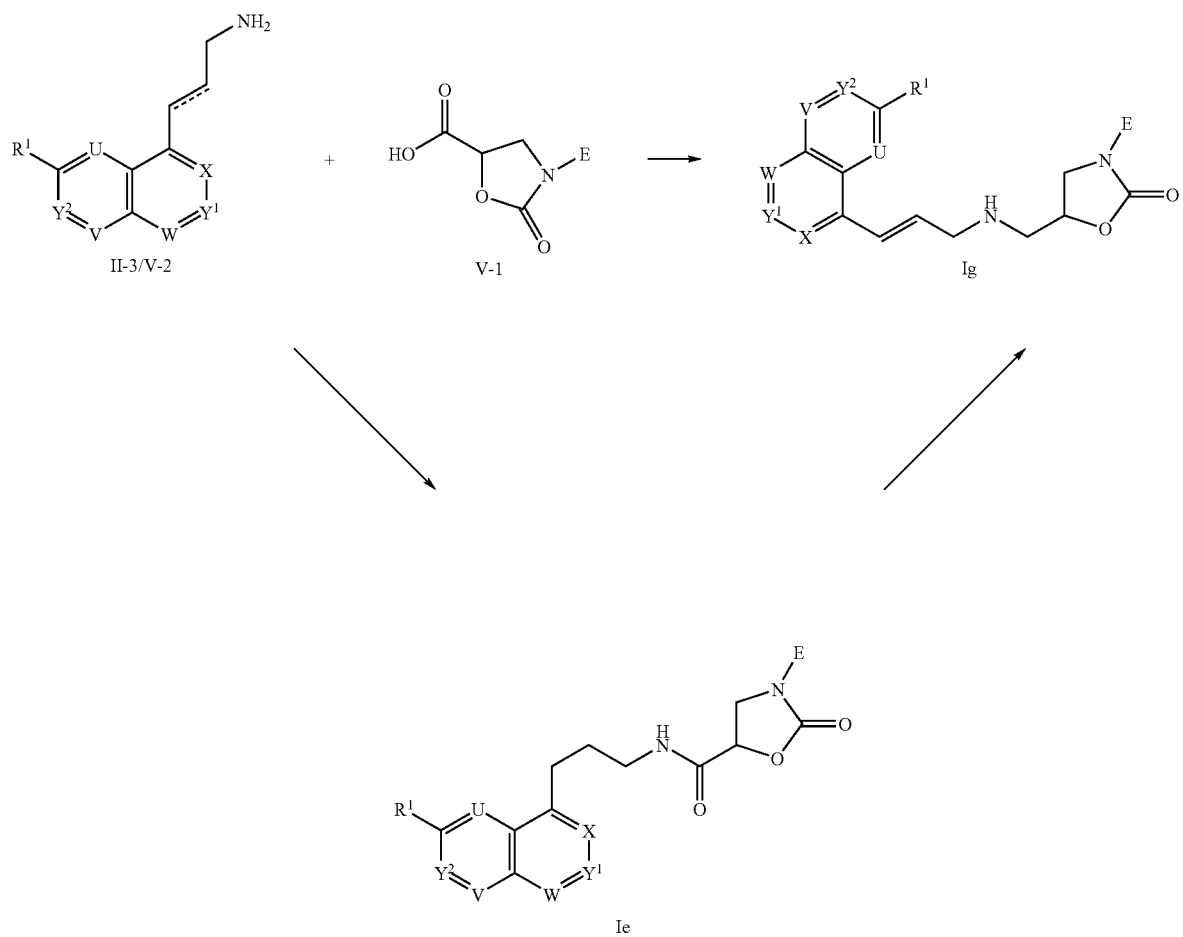

In Scheme 5, the dotted line indicates the optional presence of a double bond.

The compounds of formula Ie and Ig can be obtained by reacting an activated form of a carboxylic acid of formula V-1 with the amines of formula II-3 or V-2 respectively (reaction technique 9). The compounds of formula Ie can also be obtained by hydrogenation of a compound of formula Ig over a noble metal catalyst such as Pd/C.

i) The compounds of formula I wherein A is $CH_2CO$, B is $NHCH_2$ and D is $CH_2$ can be prepared as shown in Scheme 6 hereafter.

Scheme 6

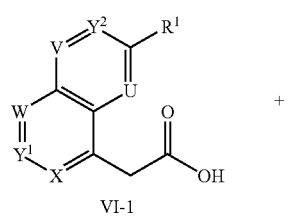

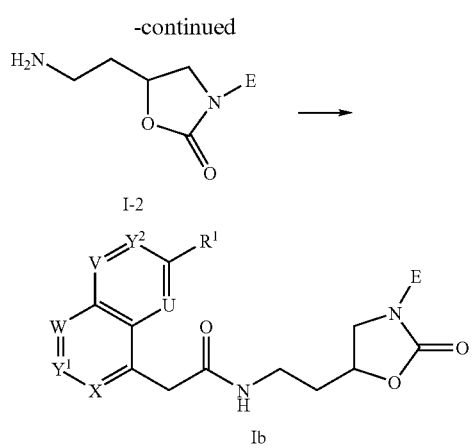

The compounds of formula Ib can be obtained by reacting the carboxylic acid derivatives of formula VI-1 with the amine derivatives of formula I-2 (reaction technique 9).

j) The compounds of formula I wherein A is CH=CH, B is $CH_2NH$ and D is $CH_2$ can be prepared by one of the ways summarised in Scheme 7 hereafter.

Scheme 7

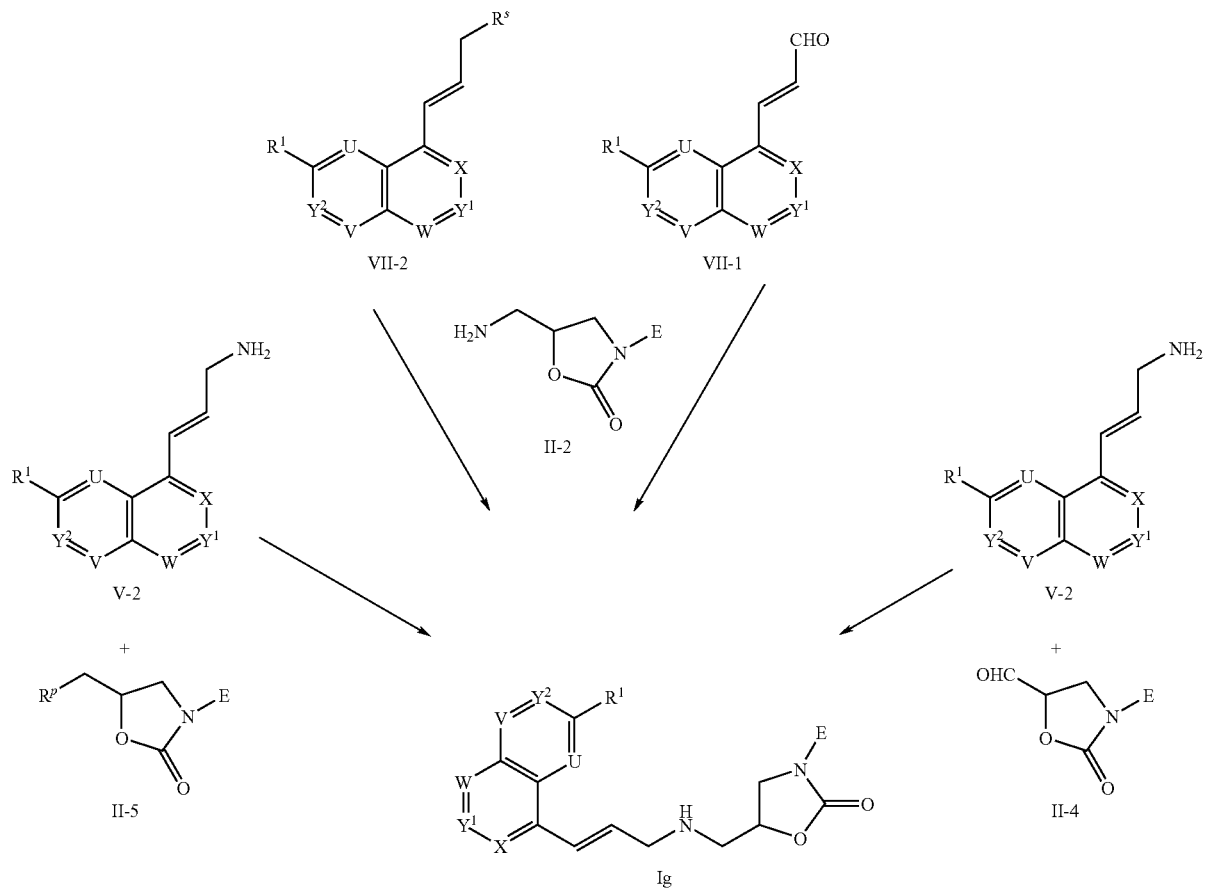

In Scheme 7, $R^p$ and $R^s$ each represent OH, halogen, MsO, TsO, TfO or $N_3$.

The compounds of formula Ig can be obtained by reacting the aldehydes of formula VII-1 with the amines of formula II-2 under reductive amination conditions (reaction technique 4). The compounds of formula Ig can also be obtained by reacting the aldehydes of formula II-4 with the amines of formula V-2 under reductive amination conditions (reaction technique 4). The compounds of formula Ig can also be obtained by reacting the compounds of formula II-5 wherein $R^q$ represents halogen, mesyloxy, tosyloxy or triflyloxy with compounds of formula V-2 (reaction technique 6). The compounds of formula Ig can also be obtained by reacting the compounds of formula VII-2 wherein $R^s$ represents halogen, mesyloxy, tosyloxy or triflyloxy with compounds of formula II-2 (reaction technique 6). Alternatively, the amines of formula II-2 or V-2 can be converted into their corresponding 2- or 4-nitrophenylsulfonamides (reaction technique 1) and subsequently be reacted with the alcohols of formula VII-2 ($R^s$=OH) or II-5 ($R^q$=OH) under Mitsunobu conditions (reaction technique 11), the resulting intermediates being then deprotected (reaction technique 3) to afford the compounds of formula Ig.

k) The compounds of formula I wherein A is CH=CH, B is $CH_2NR^5$, D is $CH_2$ and $R^5$ is alkyl or acyl can be prepared using the methods described hereafter.

The compounds of formula Ig can be acylated with an activated form of a carboxylic acid (reaction technique 7) or alkylated with an alkylhalogenide or arylalkyl halogenide (reaction technique 8). The compounds of formula Ig wherein $R^5$ is alkyl can also be obtained through reductive amination of compounds of formula Ig wherein $R^5$ is H with the corresponding alkanals. Alternatively in the case wherein $R^5$ is alkyl, the strategies used for obtaining compounds of formula Ig wherein $R^5$ is H can be applied starting from the corresponding compounds wherein one hydrogen on the primary amine of compounds of formula II-2 or V-2 is replaced by alkyl. These derivatives are obtained by reductive amination between amines of formula II-2 or V-2 and alkanals.

l) The compounds of formula I wherein A is CH=CH, B is CONH and D is $CH_2$ can be prepared by one of the ways summarised in Scheme 8 hereafter.

Scheme 8

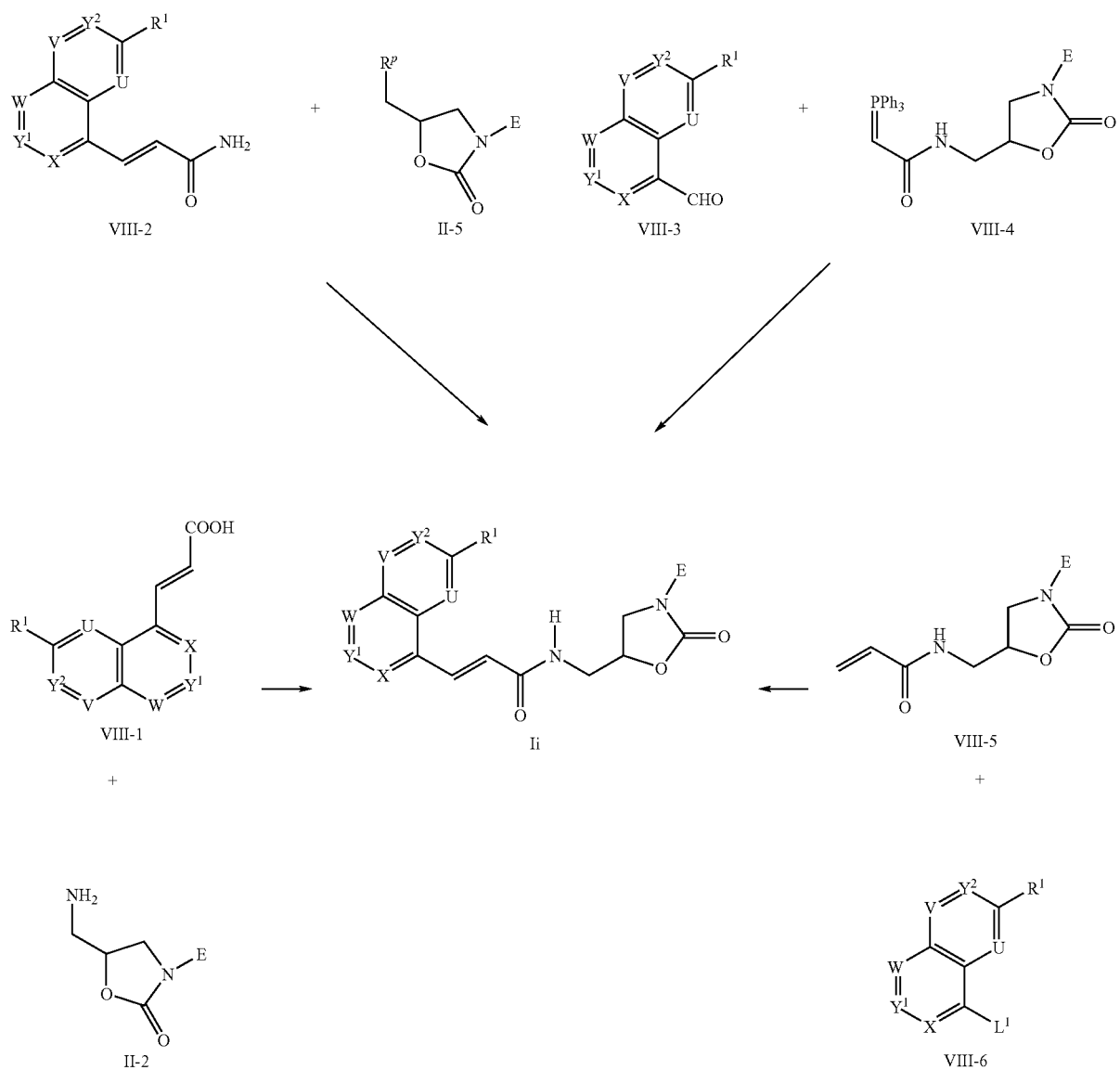

In Scheme 8, $L^1$ represents OTf or halogen such as bromine.

The compounds of formula Ii can also be obtained by reacting an activated form of a carboxylic acid of formula VIII-1 with the amines of formula II-2 (reaction technique 9). The compounds of formula Ii can also be obtained by reacting the amides of formula VIII-2 with the halogenides of formula II-5 ($R^p$=halogen). The compounds of formula Ii can also be obtained by reacting the aldehydes of formula VIII-3 with a phosphorane derivative of formula VIII-4 (reaction technique 12). The compounds of formula Ii can also be obtained by reacting the halogenides or triflates of formula VIII-6 with the acrylates of formula VIII-5 under Heck conditions (reaction technique 15).

m) The compounds of formula I wherein A is CH=CH, B is $CONR^6$, D is $CH_2$ and $R^6$ is alkyl or phenylalkyl can be prepared using the strategies used for obtaining compounds of formula Ii, starting however from the corresponding compounds wherein one hydrogen of the primary amine of compounds of formula II-2 is replaced by alkyl or phenylalkyl. These derivatives are obtained by reductive amination between amines of formula II-2 and an alkanal or arylalkyl aldehyde.

n) The compounds of formula I wherein A is CH(OH)CH(OH), B is CONH and D is $CH_2$ can be prepared by one of the ways summarised in Scheme 9 hereafter.

Scheme 9

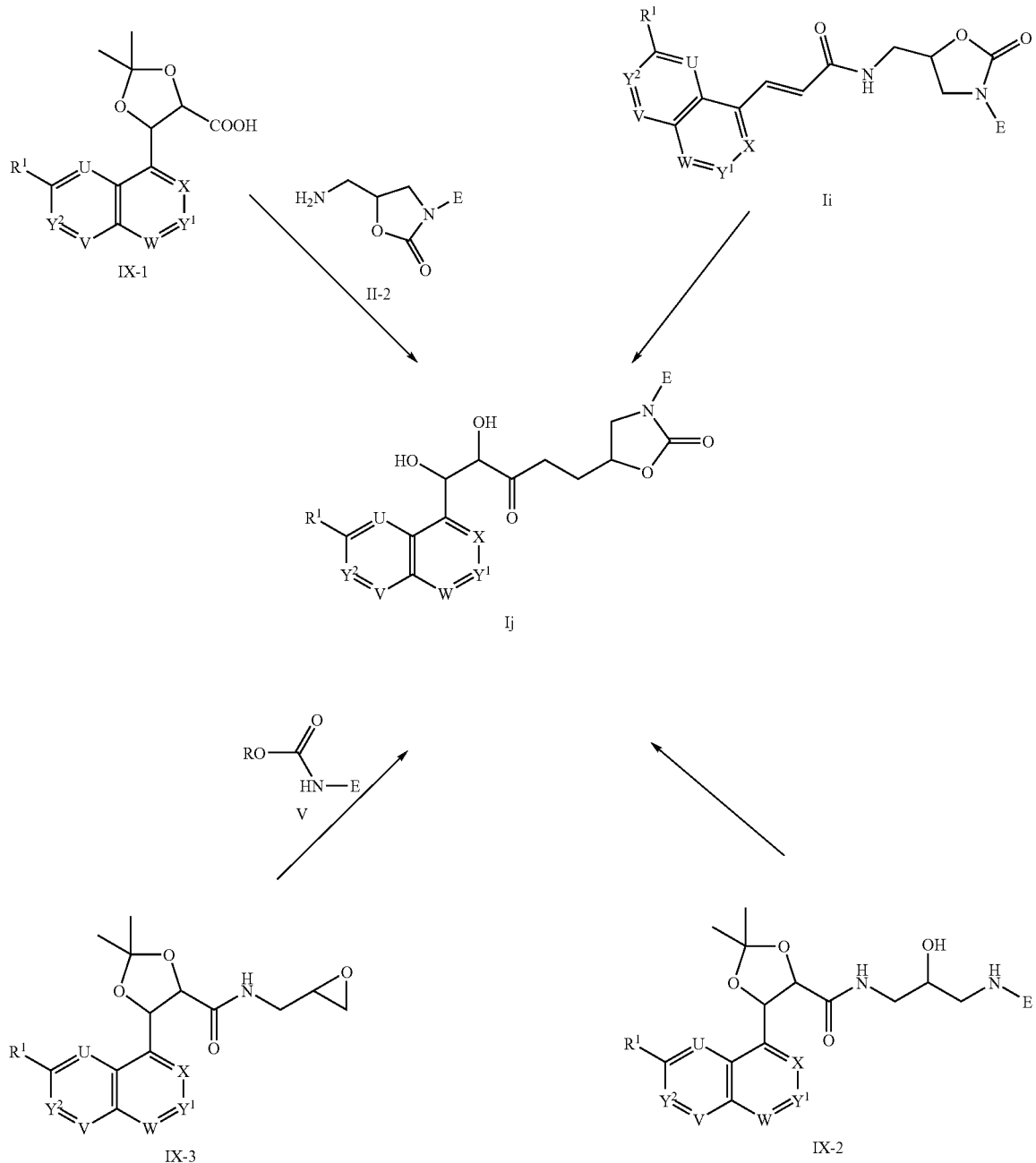

The compounds of formula Ij can be obtained by reacting the aminoalcohol derivatives of formula IX-2 with carbonic acid derivatives (reaction technique 2) followed by conversion of the acetonides into the corresponding diols (reaction technique 13). The compounds of formula Ij can also be obtained by reacting activated forms of the carboxylic acids of formula IX-1 with the amines of formula II-2 (reaction technique 9) followed by conversion of the acetonides into the corresponding diols (reaction technique 13). The compounds of formula Ij can besides be obtained by reacting the epoxides of formula IX-3 with the anion of the carbamates of formula V (reaction technique 10) followed by conversion of the acetonides into the corresponding diols (reaction technique 13). The compounds of formula Ij can furthermore be obtained by converting the acrylamide derivatives of formula Ii into the corresponding diol derivatives (reaction technique 14).

o) The compounds of formula I wherein A is CH(OH)CH (OH), B is $CH_2NH$ and D is $CH_2$ can be prepared by one of the ways summarised in Scheme 10 hereafter.

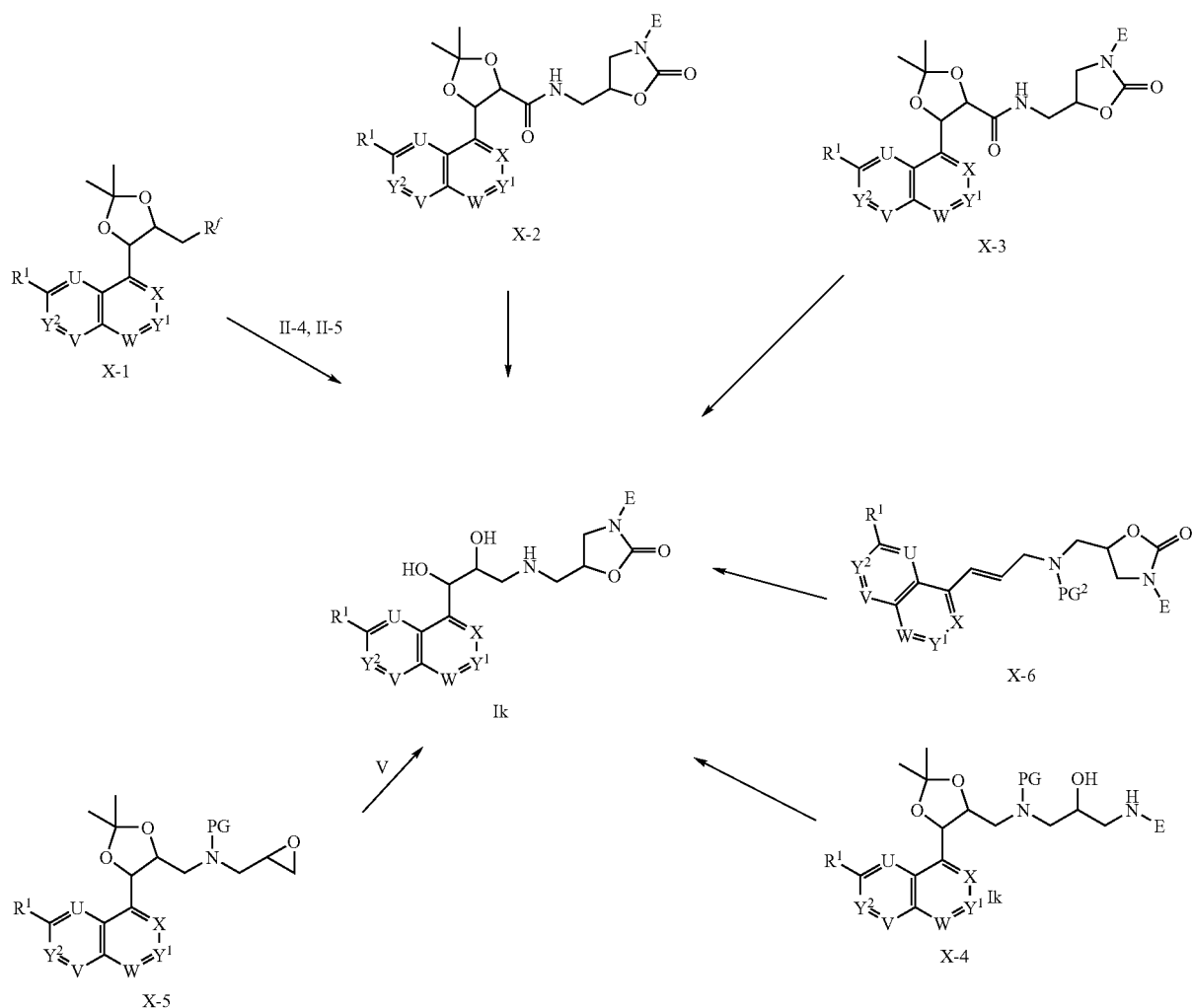

Scheme 10

In Scheme 10, $PG^2$ represents Boc or Cbz and $R^f$ represents OH, halogen such as bromine, MsO, TsO, TfO, $N_3$ or $NH_2$.

The compounds of formula Ik can be obtained by reacting the aminoalcohol derivatives of formula X-4 with carbonic acid derivatives (reaction technique 2) followed by conversion of the acetonides into the corresponding diols (reaction technique 13) and removal of the amino protecting group (reaction technique 3). The compounds of formula Ik can also be obtained by reacting halogenide, mesyloxy, tosyloxy or triflyloxy derivatives of formula X-1 ($R^f$=OMs, OTf, OTs, halogen such as bromine) with the amines of formula II-2 (reaction technique 6) followed by conversion of the acetonides into the corresponding diols (reaction technique 13). The compounds of formula Ik can also be obtained by reacting an amino derivatives of formula X-1 ($R^f$=$NH_2$) with a halogenide or a mesyloxy, tosyloxy or triflyloxy derivative of formula II-5 (reaction technique 6) or with the aldehydes of formula II-4 under reductive amination condition, followed by conversion of the acetonide into the corresponding diol (reaction technique 13). The compounds of formula Ik can also be obtained by reacting the epoxide of formula X-5 with the anion of the carbamates of formula V (reaction technique 10) followed by conversion of the acetonide into the corresponding diol (reaction technique 13) and removal of the amino protecting group (reaction technique 3). The compounds of formula Ik can also be obtained by converting the vinyl derivatives of formula X-6 into the corresponding diol derivatives (reaction technique 14) followed by removal of the amino protecting group $PG^2$. The compounds of formula Ik can also be obtained by reduction of the amide function of compounds of formula X-2 or X-3 using a borohydride reagent such as diborane (reaction technique 5) followed by removal of the acetonide protecting group (reaction technique 13).

p) The compounds of formula I wherein A is $CH(OH)CH_2$, B is CONH and D is $CH_2$ can be prepared by one of the ways summarised in Scheme 11 hereafter.

Scheme 11

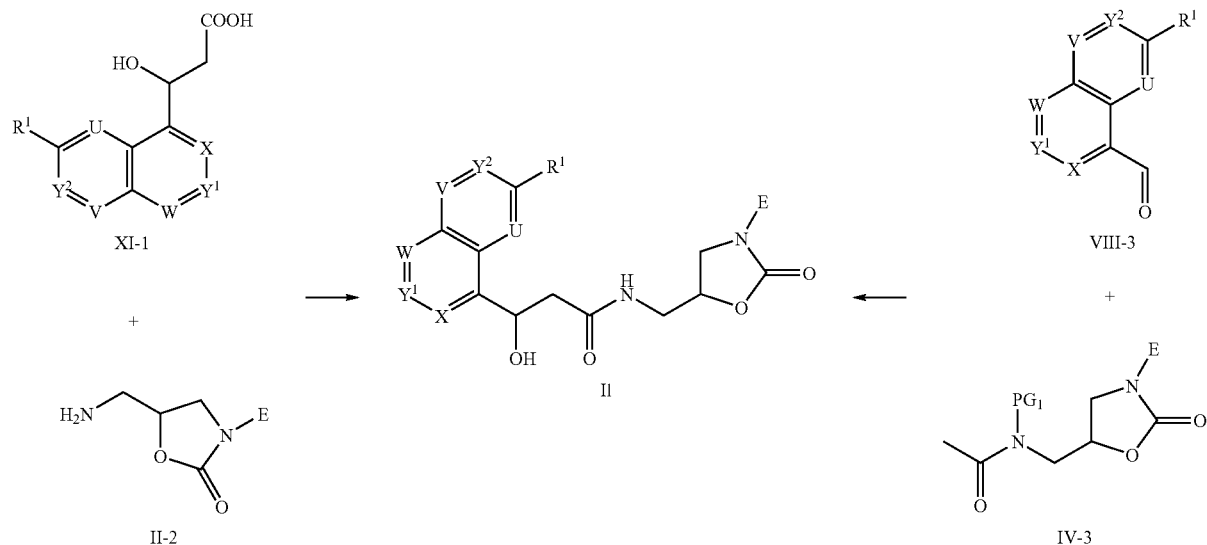

The compounds of formula II can also be obtained by reacting a carboxylic acid derivatives of formula XI-1 with the amine derivatives of formula II-2 (reaction technique 9). The compounds of formula II can also be obtained by hydroboration of the unsaturated amides of formula Ii (reaction technique 16). The compounds of formula II can furthermore be obtained by reacting the anion generated from the acetamides of formula IV-3 on the aldehydes of formula VIII-3, followed by removal of the amino protecting group as described earlier.

q) The compounds of formula I wherein A is CH(OH)CH$_2$, B is CH$_2$NH and D is CH$_2$ can be prepared by one of the ways summarised in Scheme 12 hereafter.

Scheme 12

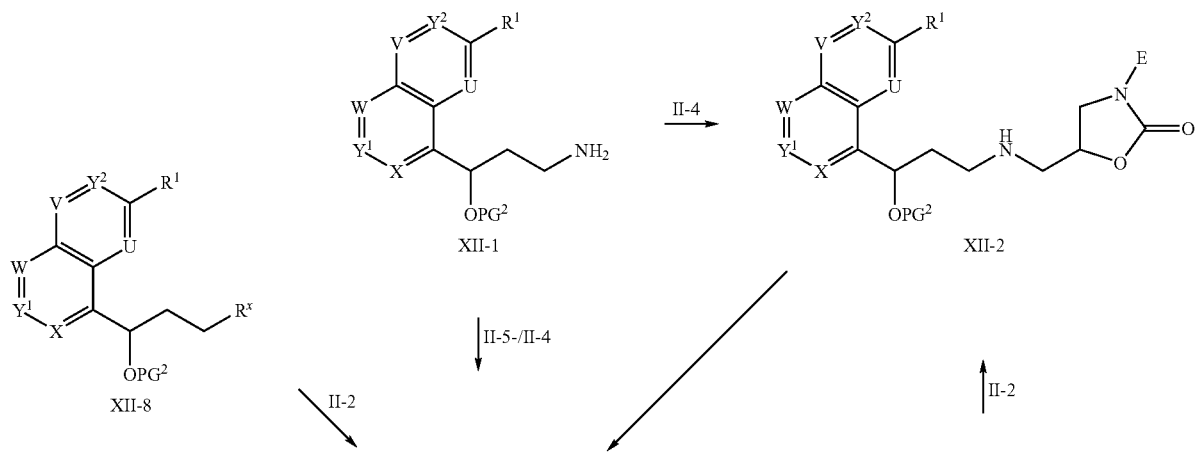

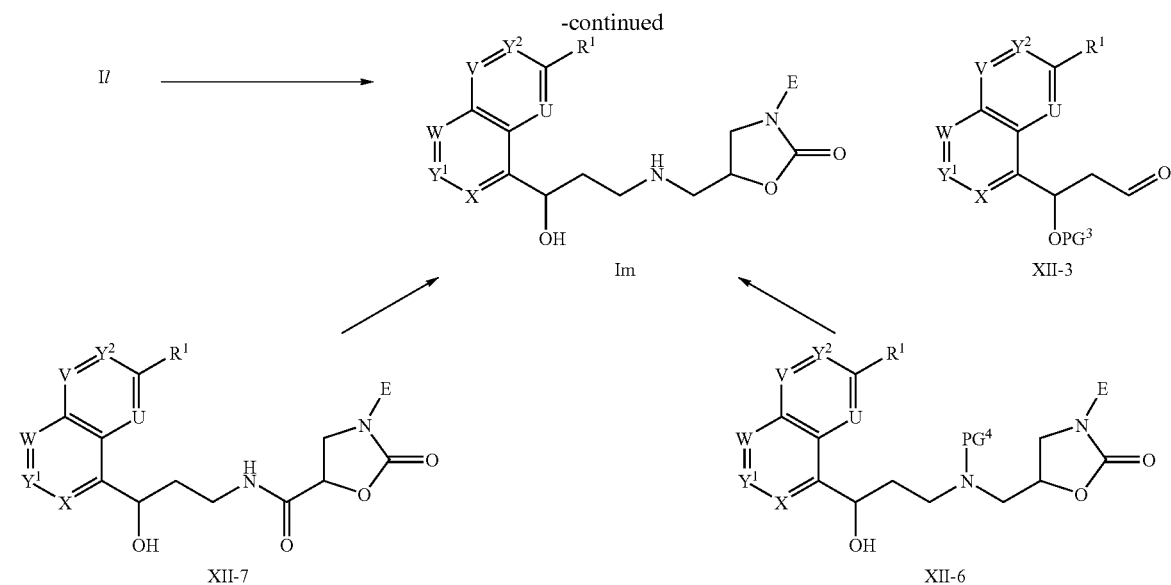

In Scheme 12, PG$^3$ represents a hydroxy protecting group such as TBDMS or TBDPS, PG$^4$ represents an amino protecting group such as Cbz, Boc or Alloc and R$^x$ represents OH, OMs, OTf, OTs or halogen such as bromine.

The compounds of formula Im can be obtained by deprotection of compounds of formula XII-2 or XII-6 (reaction technique 17 or reaction technique 3). The compounds of formula Im can also be obtained by reduction of the amide function of compounds of formula Il or XII7 (reaction technique 5). The compounds of formula Im can furthermore be obtained by reductive amination of the amines of formula XII-1 or II-2 with the aldehydes of formula II-4 or XII-3 respectively (reaction technique 4) followed by removal of the alcohol protecting group (reaction technique 17). Alternatively the compounds of formula Im can also be obtained by alkylation of the amines of formula II-2 or XII-1 with halogenide, mesyloxy, tosyloxy or triflyloxy derivatives of compounds of formula XII-8 or II-5 respectively (reaction technique 6) followed by removal of the alcohol protecting group (reaction technique 17).

r) The compounds of formula I wherein A is CH$_2$CH(OH), B is CONH and D is CH$_2$ can be prepared by one of the ways summarised in Scheme 13 hereafter.

Scheme 13

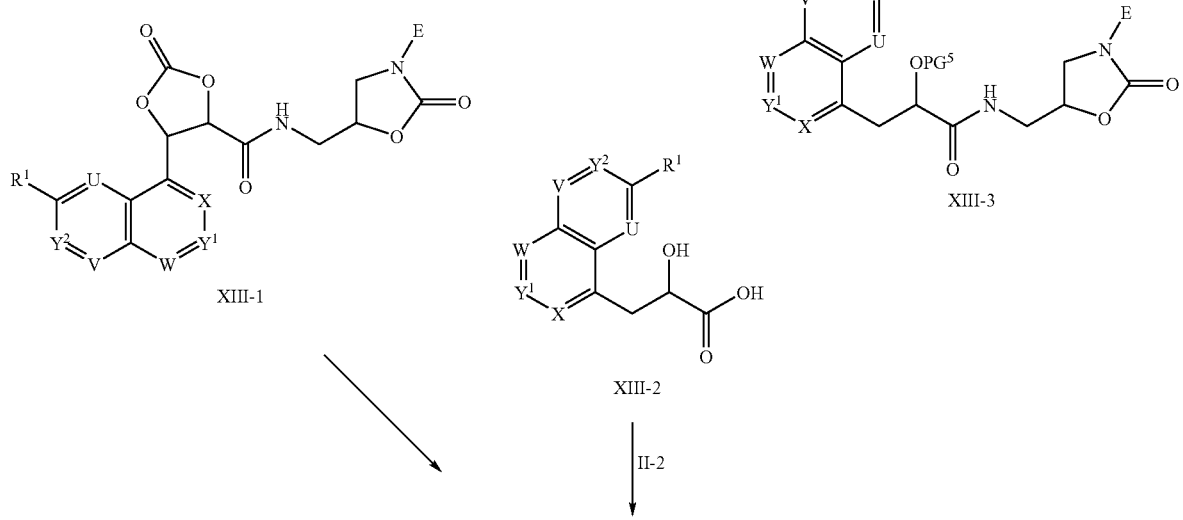

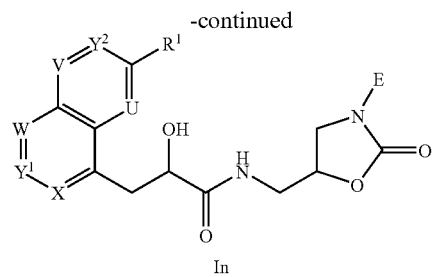
In

In Scheme 13, $PG^5$ represents a hydroxy protecting group such as TBDMS or TBDPS.

The compounds of formula In can be obtained by deprotection of compounds of formula XIII-3. The compounds of formula In can be obtained by hydrogenolysis of the carbonate function of compounds of formula XIII-1 over a noble metal catalyst such as palladium on charcoal. The compounds of formula In can also be obtained by reacting the carboxylic acid derivatives of formula XIII-2 with the amine derivatives of formula II-2 (reaction technique 9).

s) The compounds of formula I wherein A is CH=CH, B is $CH_2NH$ and D is CO can be prepared as summarised in Scheme 14 hereafter.

Scheme 14

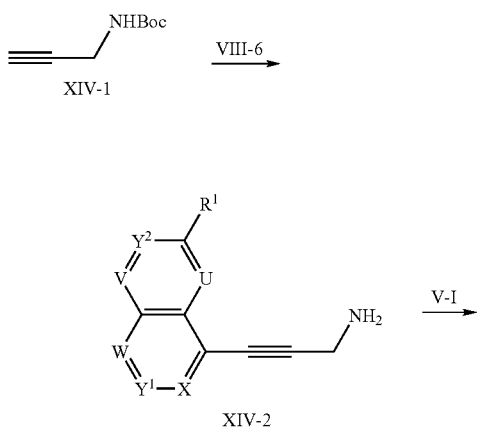

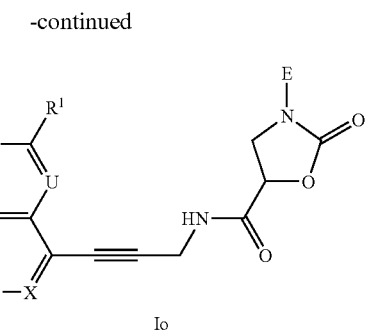
Io

The commercially available N-Boc-propargylamine can be reacted with the derivatives of formula VIII-6 wherein $L^1$ is OTf or Br under Sonogashira conditions, using a catalytic amount of a palladium salt, an organic base such as TEA and a catalytic amount of a copper derivative (usually copper iodide) in a solvent such a DMF between 20° C. to 100° C. (see Sonogashira, K. in *Metal-Catalyzed Reactions*, Diedrich, F., Stang, P. J., Eds; Wiley-VCH: New York 1998), after which Boc deprotection conditions (reaction technique 3) afford the amines of formula XIV-2. These amines can be reacted with the acids of formula V-1 to afford the compounds of formula Io.

t) The compounds of formula I wherein A is $CH_2CH(NH_2)$, B is $CH_2NH$ and D is $CH_2$ can be prepared by one of the ways summarised in Scheme 15 hereafter.

Scheme 15

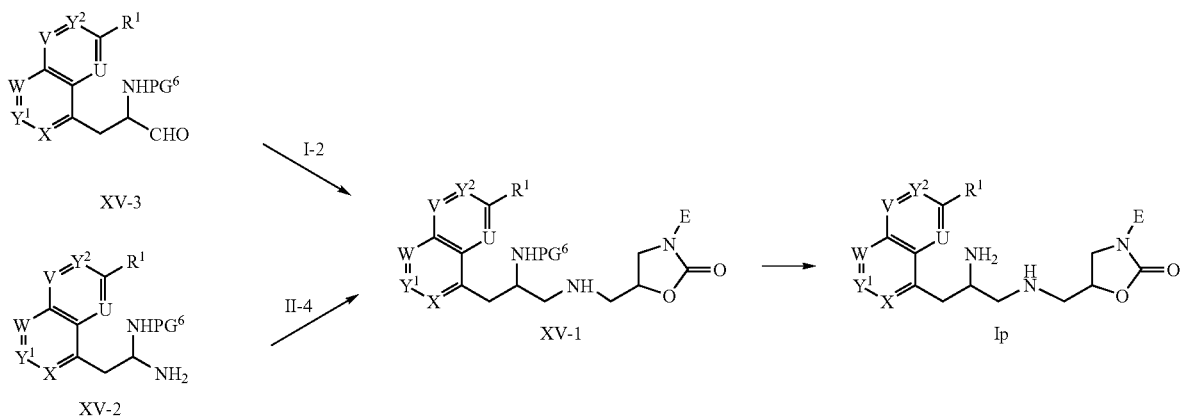

In Scheme 15, $PG^6$ represents an amino protecting group such as Cbz, Boc or Alloc.

The compounds of formula Ip can be obtained by deprotection of compounds of formula XV-1 (reaction technique 3). The compounds of formula XV-1 can be obtained by reductive amination of the amines of formula XV-2 or I-2 with the aldehydes of formula II-4 or XV-3 respectively (reaction technique 4).

u) The compounds of formula I wherein A is CH(OH)CH(NH$_2$), B is CONH and D is CH$_2$ can be prepared by one of the ways summarised in Scheme 16 hereafter.

removal of the alcohol and amino protecting groups (reaction technique 17 and reaction technique 3). The compounds of formula Iq can also be obtained by reacting the epoxides of formula XVI-2 with the anion of the carbamates of formula V (reaction technique 10) followed by the removal of the alcohol and amino protecting groups. The compounds of formula Iq can also be obtained by reacting the carboxylic acid derivatives of formula XVI-3 or XVI-4 with the amine derivatives of formula II-2 (reaction technique 9) followed by removal of the amino protecting group (reaction technique 3). In the case Scheme 16

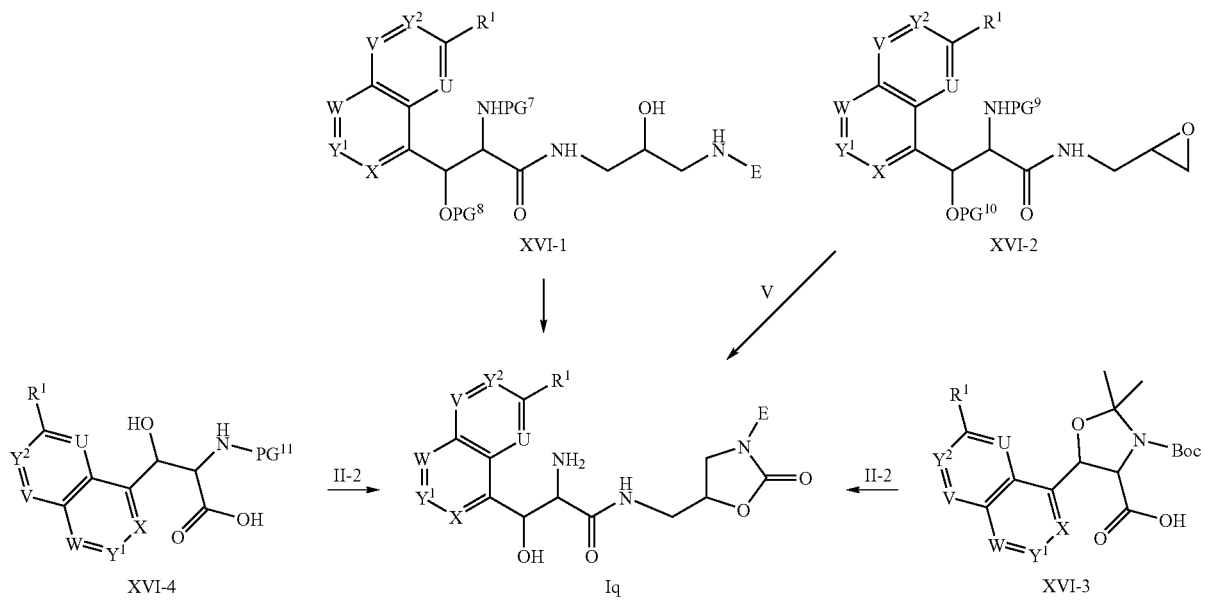

In Scheme 16, $PG^7$, $PG^9$ and $PG^{11}$ each represent an amino protecting group such as Cbz, Boc or Alloc, and $PG^8$ and $PG^{10}$ each represent a hydroxy protecting group such as TBDMS or TBDPS.

The compounds of formula Iq can be obtained by reacting the aminoalcohol derivatives of formula XVI-1 with a carbonic acid derivative (reaction technique 2) followed by the wherein compounds of formula XVI-3 are used, the protecting group is removed by an acidic treatment such as HCl in THF.

v) The compounds of formula I wherein A is NHCH$_2$, B is CH$_2$NH and D is CH$_2$ can be prepared by one of the ways summarised in Scheme 17 hereafter.

Scheme 17

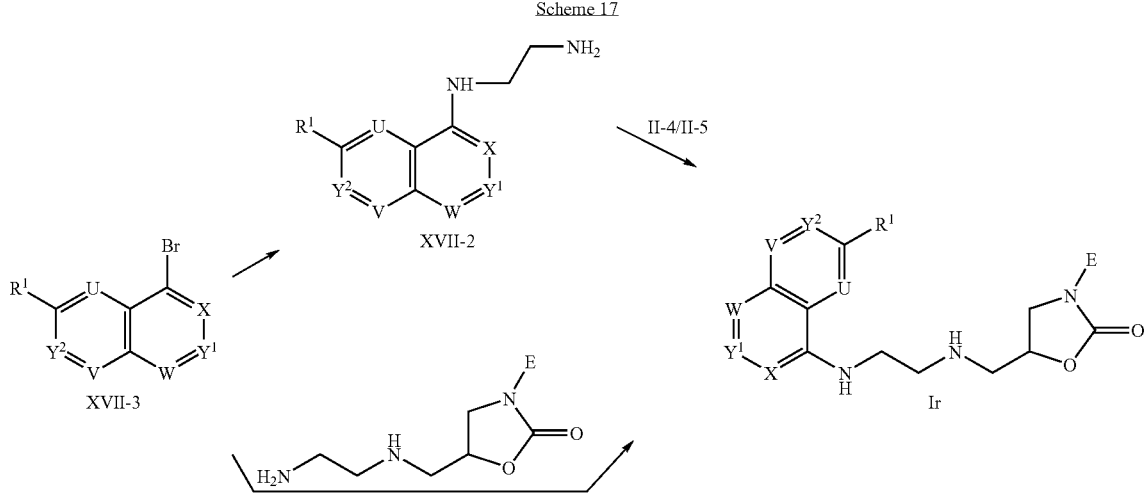

The compounds of formula Ir can be obtained by reacting halogenides of formula XVII-3 (e.g. bromides) with the amines of formula XVII-1. Alternatively the halogenides of formula XVII-3 can be reacted with ethylene diamine followed by substitution with compounds of formula II-5 following reaction technique 6. The compounds of formula Ir can also be obtained through reductive amination of the amines of formula XVII-2 or XVII-1 with the aldehydes of formula II-4 or VIII-3 respectively.

w) The compounds of formula I wherein A is $CH_2CH(NH_2)$, B is CONH and D is $CH_2$ can be prepared by one of the ways summarised in Scheme 18 hereafter.

Scheme 18

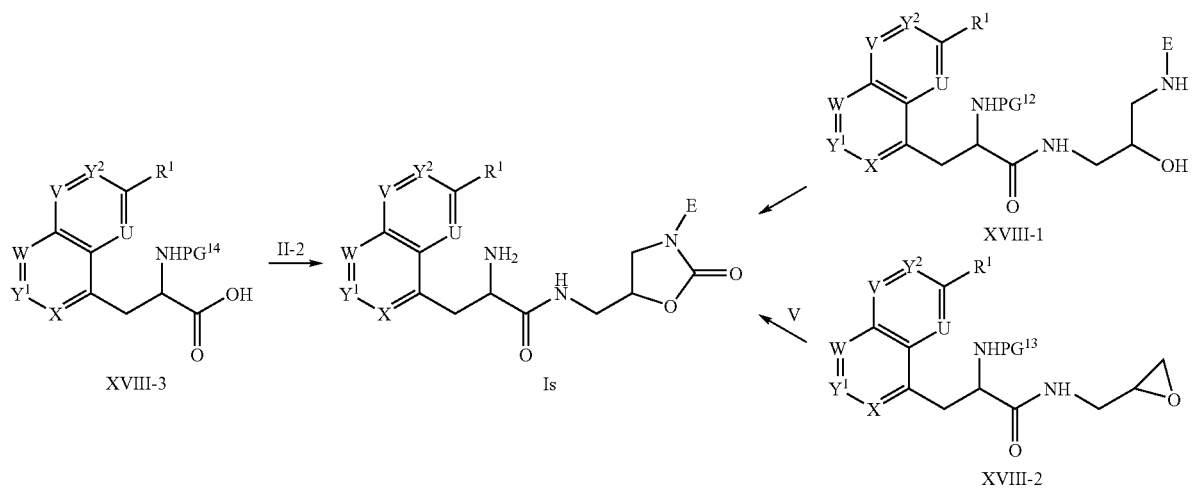

Scheme 19

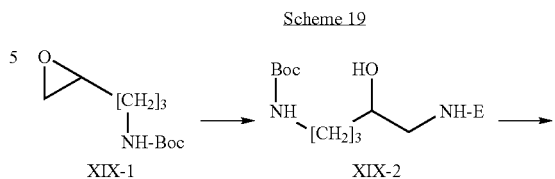

In Scheme 18, $PG^{12}$, $PG^{13}$ and $PG^{14}$ each represent an amino protecting group such as Cbz, Boc or Alloc.

The compounds of formula Is can be obtained by reacting the aminoalcohol derivatives of formula XVIII-1 with a carbonic acid derivative (reaction technique 2) followed by the removal of the amino protecting group (reaction technique 3). The compounds of formula Is can also be obtained by reacting the epoxides of formula XVIII-2 with the anions of the carbamates of formula V (reaction technique 10) followed by the removal of the amino protecting group (reaction technique 3). The compounds of formula Is can furthermore be obtained by reacting the carboxylic acid derivatives of formula XVIII-3 with the amine derivatives of formula II-2 (reaction technique 9) followed by removal of the amino protecting group (reaction technique 3).

x) The compounds of formula I wherein A is $COCH_2$, B is CONH and D is $CH_2$ can be prepared by oxidation of compounds of formula II using an oxidizing agent such as $MnO_2$ in a solvent such as THF or THF-DCM at rt. Other oxidation methods such as Swern or Dess Martin oxidation protocols can also be used.

y) The compounds of formula I wherein A is $CH(NH_2)CH_2$, B is CONH and D is $CH_2$ can be prepared by transforming the alcohol function in compounds of formula II into its corresponding mesylate, azide and amine.

z) The compounds of formula I wherein A is $CH_2NH$ or CONH, B is $CH_2CH_2$ and D is $CH_2$ can be prepared as summarised in Scheme 19 hereafter.

-continued

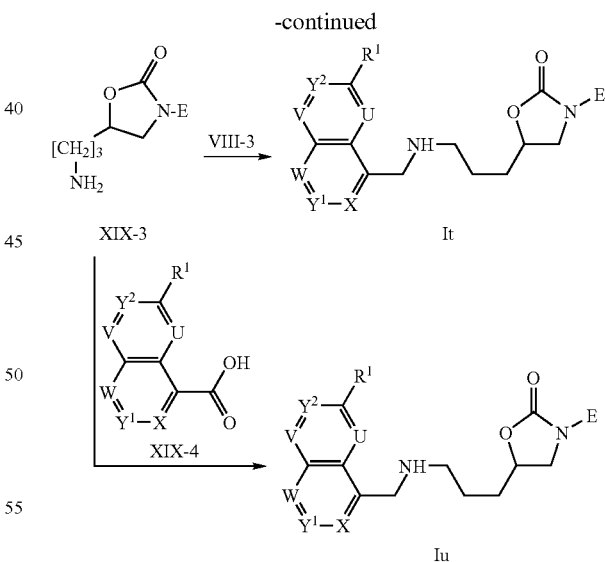

The compounds of formula It (A=$CH_2NH$, B=$CH_2CH_2$ and D=$CH_2$) can be prepared from the commercially available (3-oxiranylpropyl)carbamic acid tert-butyl ester of formula XIX-1 after transformation into the oxazolidinone derivatives of formula XIX-3 by epoxide opening with the amines E-$NH_2$, oxazolidinone formation (reaction technique 2) and removal of the Boc protecting group (reaction technique 3). The amines of formula XIX-3 can then be reacted with the aldehydes of formula VIII-3 under reductive amination conditions to give the compounds of formula It.

The compounds of formula Iu (A=CONH, B=CH$_2$CH$_2$ and D=CH$_2$) can be prepared by reacting the amines of formula XIX-3 with the acids of formula XIX-4 (reaction technique 9).

aa) The compounds of formula I wherein A is NHCH$_2$, B is CH$_2$NH and D is CO can be prepared by one of the ways summarised in Scheme 20 hereafter.

-continued

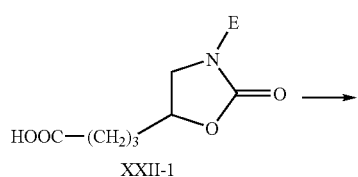

XXII-1

Scheme 20

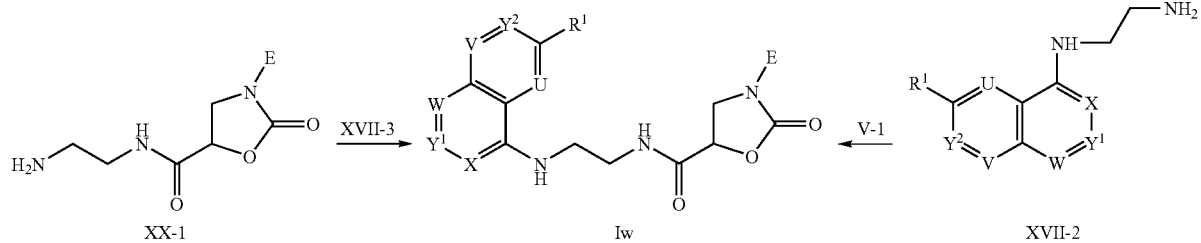

The compounds of formula Iw can be obtained by reacting the amines of formula XVII-2 with the carboxylic acids of formula V-1 (reaction technique 9). They can also be obtained by reacting the halogenides of formula XVII-3 with the amines of formula XX-1.

ab) The compounds of formula I wherein A is NHCH$_2$, B is CH$_2$CH$_2$ and D is CH$_2$ can be prepared by one of the ways summarised in Scheme 21 hereafter.

Scheme 21

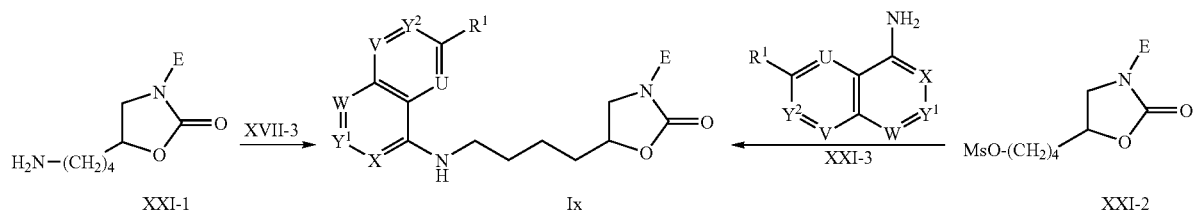

The compounds of formula Ix can be obtained by reacting the halogenides of formula XVII-3 with the amines of formula XXI-1. They can also be obtained by substitution of the mesylates of formula XXI-2 with the amino derivatives of formula XXI-3.

ac) The compounds of formula I wherein A is NHCO, B is CH$_2$CH$_2$ and D is CH$_2$ can be prepared as summarised in Scheme 22 hereafter.

Scheme 22

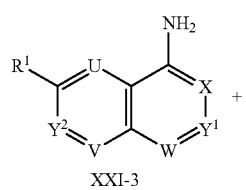

XXI-3

+

-continued

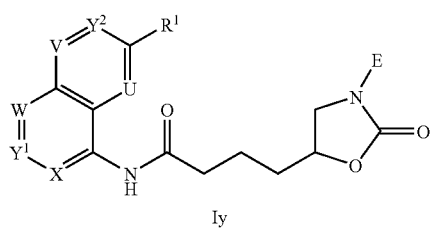

Iy

The compounds of formula Iy can be obtained by reacting the carboxylic acids of formula XXII-1 with the amines of formula XXI-3 (reaction technique 9).

ac) The compounds of formula I wherein A is NHCO, B is CH(R$^8$)NH and D is CH$_2$ can be prepared as summarised in Scheme 23 hereafter.

Scheme 23

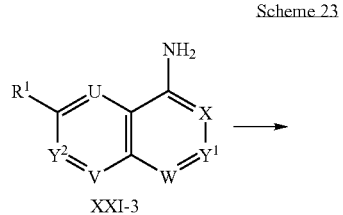

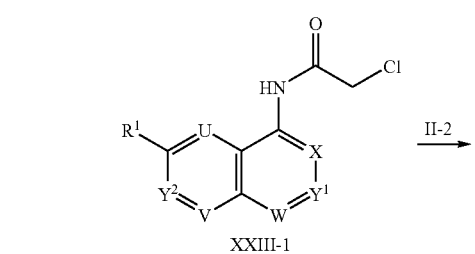

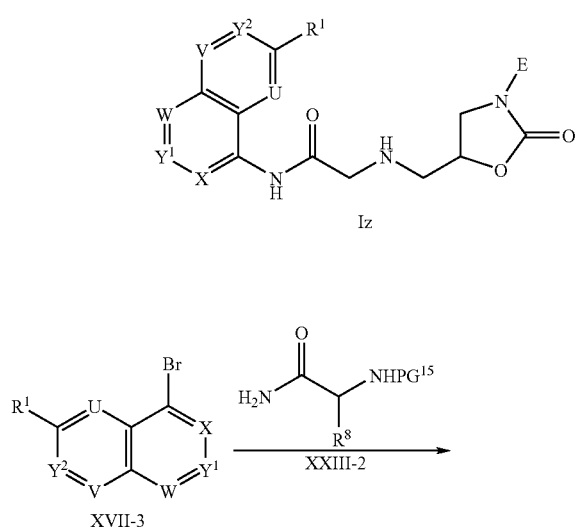

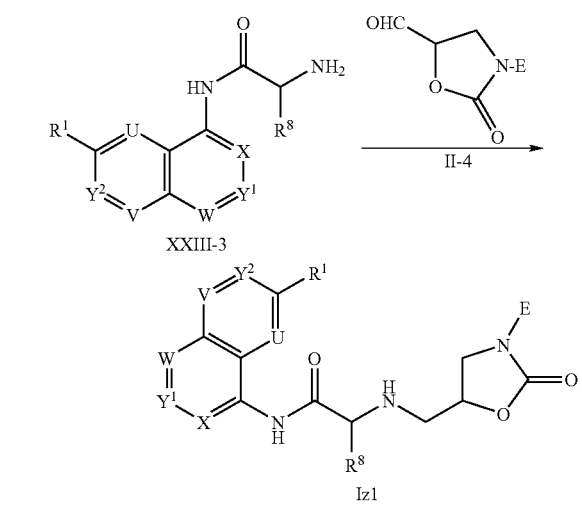

In Scheme 23, $PG^{15}$ represents an amino protecting group such as Cbz or Boc.

The compounds of formula Iz ($R^8$=H) can be obtained by reacting the amine derivatives of formula XXI-3 with chloroacetyl chloride followed by reaction with the amine derivatives of formula II-2.

The compounds of formula Iz1 ($R^8$=alkyl) can be obtained by reacting the bromo derivatives of formula XVII-3 with the N-protected amino acid derived amides of formula XXIII-2 under Buchwald Hartwig conditions. After deprotection (reaction technique 3), the amines of formula XXIII-3 are obtained, which can be subjected to a reductive amination with the aldehydes of formula II-4 (reaction technique 4) to afford the compounds of formula Iz1.

ad) The compounds of formula I wherein A is CH(OH) $CH_2$, $COCH_2$ or $CH(NH_2)CH_2$, B is $CH_2CH_2$ and D is $CH_2$ can be prepared as summarised in Scheme 24 hereafter.

Scheme 24

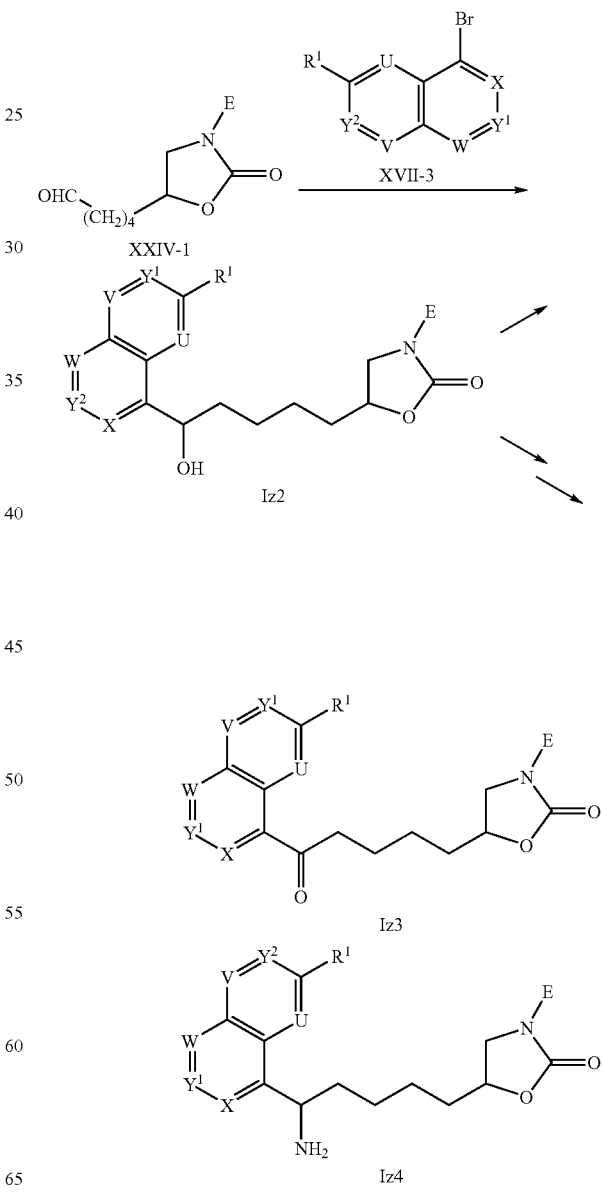

The compounds of formula Iz2 (A=CH(OH)CH$_2$) can be obtained by reacting the aldehydes of formula XXIV-1 with the anions generated by reaction of n-BuLi with the bromo derivatives of formula XVII-3. The compounds of formula Iz3 (A=COCH$_2$) can be obtained by oxidation of derivatives of formula Iz2 with MnO$_2$ or an oxidative method (reaction technique 18). The compounds of formula Iz4 (A=CH(NH$_2$)CH$_2$) can be obtained by conversion of the compounds of formula Iz2 into their corresponding mesylates, azides and amines as described above.

ae) The compounds of formula I wherein A is CH(OH)CH$_2$ or CH(NH$_2$)CH$_2$, B is N(R$^2$)CO and D is CH$_2$ can be prepared as summarised in Scheme 25 hereafter.

Scheme 25

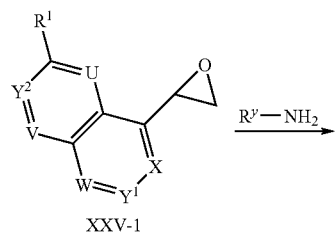

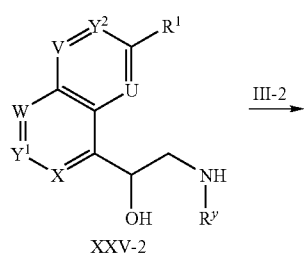

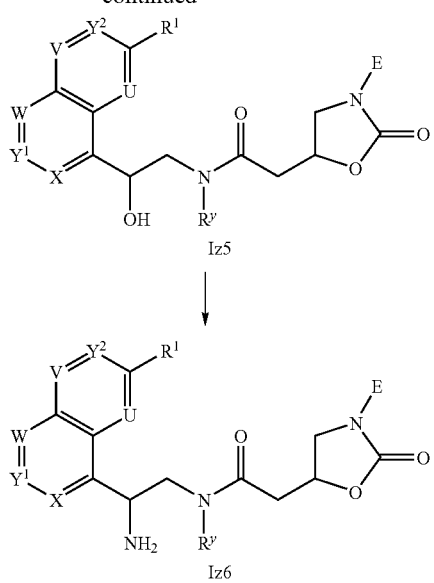

In Scheme 25, R$^y$ represents (depending on the case) hydrogen, alkyl or a nitrogen protecting group such as p-methoxybenzyl or diphenylmethyl.

To obtain compounds wherein A is CH(OH)CH$_2$, the epoxides of formula XXV-1 can be reacted with the amines R$^y$—NH$_2$ to afford the intermediates of formula XXV-2. In cases wherein R$^y$ is a transient protecting group such as p-methoxybenzyl, it can be removed and the resulting amines can be acylated with the carboxylic acids of formula III-2, affording compounds of formula Iz5 wherein R$^y$ is hydrogen. If R$^y$ is alkyl, the resulting amines can be directly acylated with the carboxylic acids of formula III-2 to obtain the compounds of formula Iz5.

If compounds wherein A is CH(NH$_2$)CH$_2$ are desired, the compounds of formula Iz5 are converted into compounds of formula Iz6 (transformation of the alcohol function into its corresponding mesylate, azide and amine using reaction technique 6).

af) The compounds of formula I wherein A is CH(OH)CH(NH$_2$), B is CH$_2$CH$_2$ or CH$_2$NH and D is CH$_2$ can be prepared as summarised in Scheme 26 hereafter.

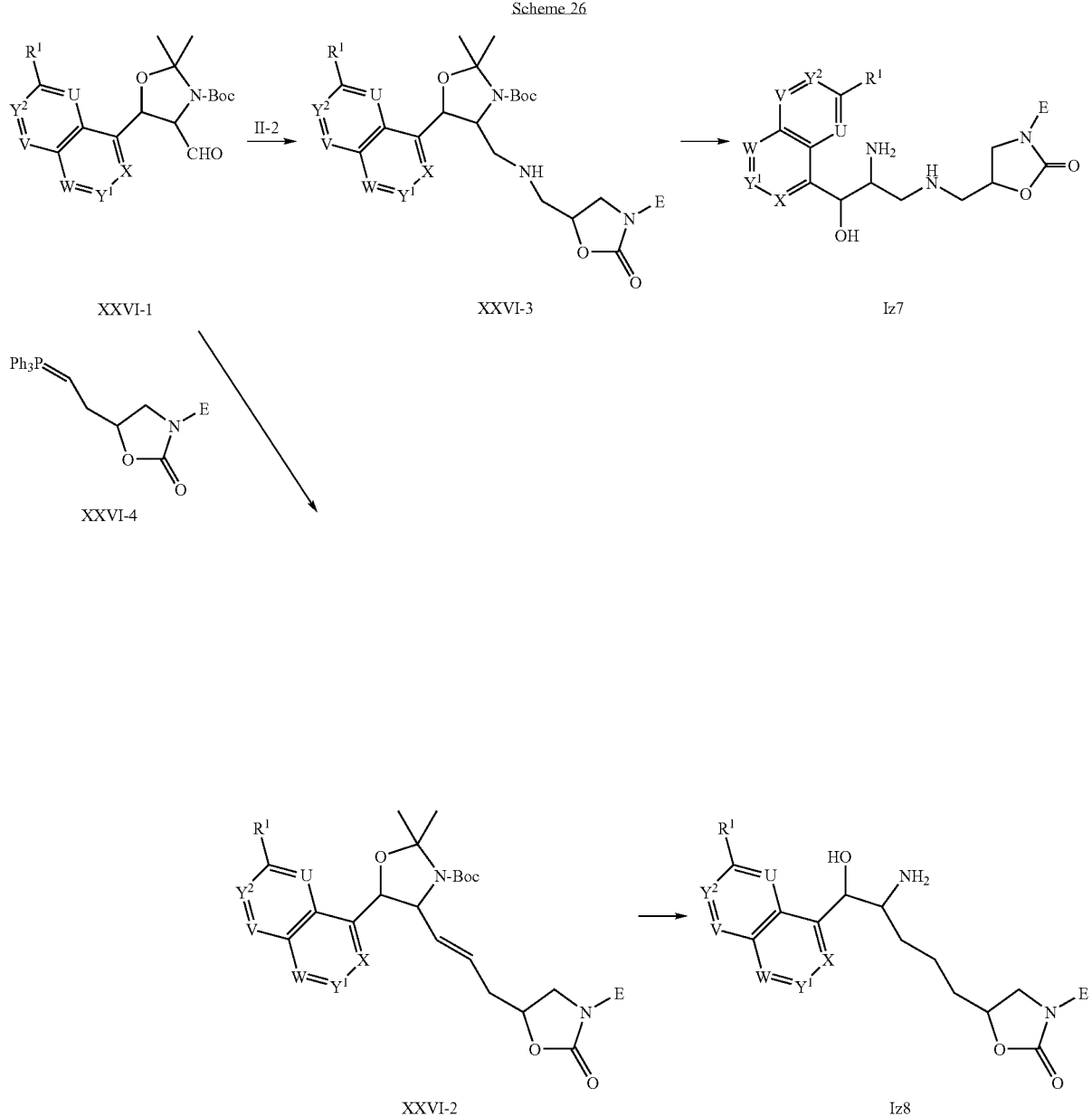

Scheme 26

The aldehydes of formula XXVI-1 can be reacted with the amines of formula II-2 under reductive amination conditions (reaction technique 4). After removal of the protecting groups, the intermediates of formula XXVI-3 yields the compounds of formula Iz7.

The aldehydes of formula XXVI-1 can be reacted with the phosphoranes of formula XXVI-4 under Wittig conditions (reaction technique 12). The resulting ethylenic compounds of formula XXVI-2 are further hydrogenated over a noble metal catalyst and the protecting groups are removed under acidic conditions affording compounds of formula Iz8.

ag) The compounds of formula I wherein A is CH(NH$_2$)CH$_2$, B is CH$_2$NH and D is CH$_2$ can be prepared by transformation of the alcohol function of compounds of formula Im (see Scheme 12) into its corresponding mesylate, azide and amine.

ah) The compounds of formula I wherein A is COCH$_2$, B is CONH and D is CH$_2$ can be prepared by oxidation of the alcohol function of compounds of formula It (see Scheme 11) into its corresponding ketone using an oxidation agent such as MnO$_2$.

ai) The compounds of formula I wherein A is CH$_2$NH, B is CH$_2$CH$_2$ or COCH$_2$ and D is CH$_2$ can be prepared as summarised in Scheme 27 hereafter.

Scheme 27

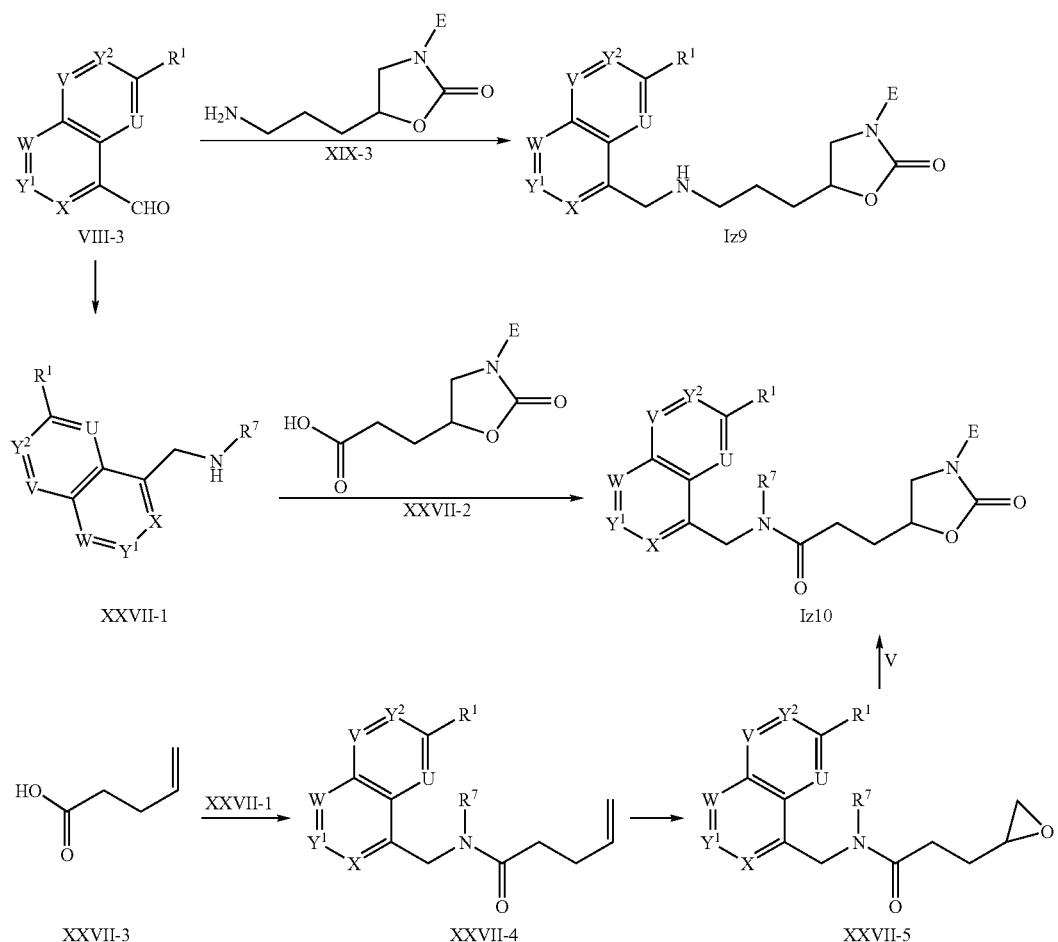

If compounds of formula I wherein A is CH$_2$NH, B is CH$_2$CH$_2$ and D is CH$_2$ are sought, the aldehydes of formula VIII-3 can be reacted with the amines of formula XXVII-1 under reductive amination conditions, affording compounds of formula Iz9. The central amino group of the compounds of formula Iz9 can be further transformed by alkylation with a compound of formula Hal[CH$_2$]$_r$COOR$^{7'}$ wherein Hal represents halogen, r represents the integer 1 to 4 and R$^{7'}$ represents alkyl, in presence of DIPEA and NaI. The resulting ester can be transformed into the corresponding acid by acidic hydrolysis in presence of aq. HCl. The central amino group of compound Iz9 can also be reacted with glydidol affording the corresponding N-2,3-dihydroxypropyl derivative or with the epichlorhydrin affording the corresponding N-3-chloro-2-hydroxypropyl derivative which can in turn be further transformed by reaction with an amine of formula NH(R$^w$)$_2$ wherein R$^w$ represents alkyl, to afford the corresponding N-3-dialkylamino-2-hydroxypropyl derivative. These reaction sequences allow to convert compounds of formula Iz9 into compounds of formula I wherein A is CH$_2$N(R$^7$), B is CH$_2$CH$_2$ and D is CH$_2$.

If compounds of formula I wherein A is CH$_2$N(R$^7$), B is COCH$_2$ and D is CH$_2$ are sought, the aldehydes of formula VIII-3 can be reacted with NH$_4$OAc or amines of formula R$^7$NH$_2$ under reductive amination conditions (reaction technique 4), affording compounds of formula XXVII-1 which can be reacted with the acids of formula XXVII-2 under amide formation conditions (reaction technique 9), affording the compounds of formula Iz10. The compounds of formula Iz10 can also be obtained by reacting the carboxylic acid of formula XXVII-3 with the amines of formula XXVII-1 and transforming the compounds of formula XXVII-4 into their corresponding epoxides by sequential cis-dihydroxylation following reaction technique 14, mesylation of the primary alcohol function using general technique 6 and ring closure in presence of a base such as K$_2$CO$_3$ or TEA. The epoxides of formula XXVII-5 can then be reacted with the anions generated from the carbamates of formula V as described in section b) to give the compounds of formula Iz10.

aj) The compounds of formula I wherein A is NHCH$_2$, B is CONH and D is CH$_2$ can be prepared as summarised in Scheme 28 hereafter.

Scheme 28

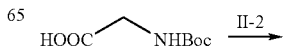

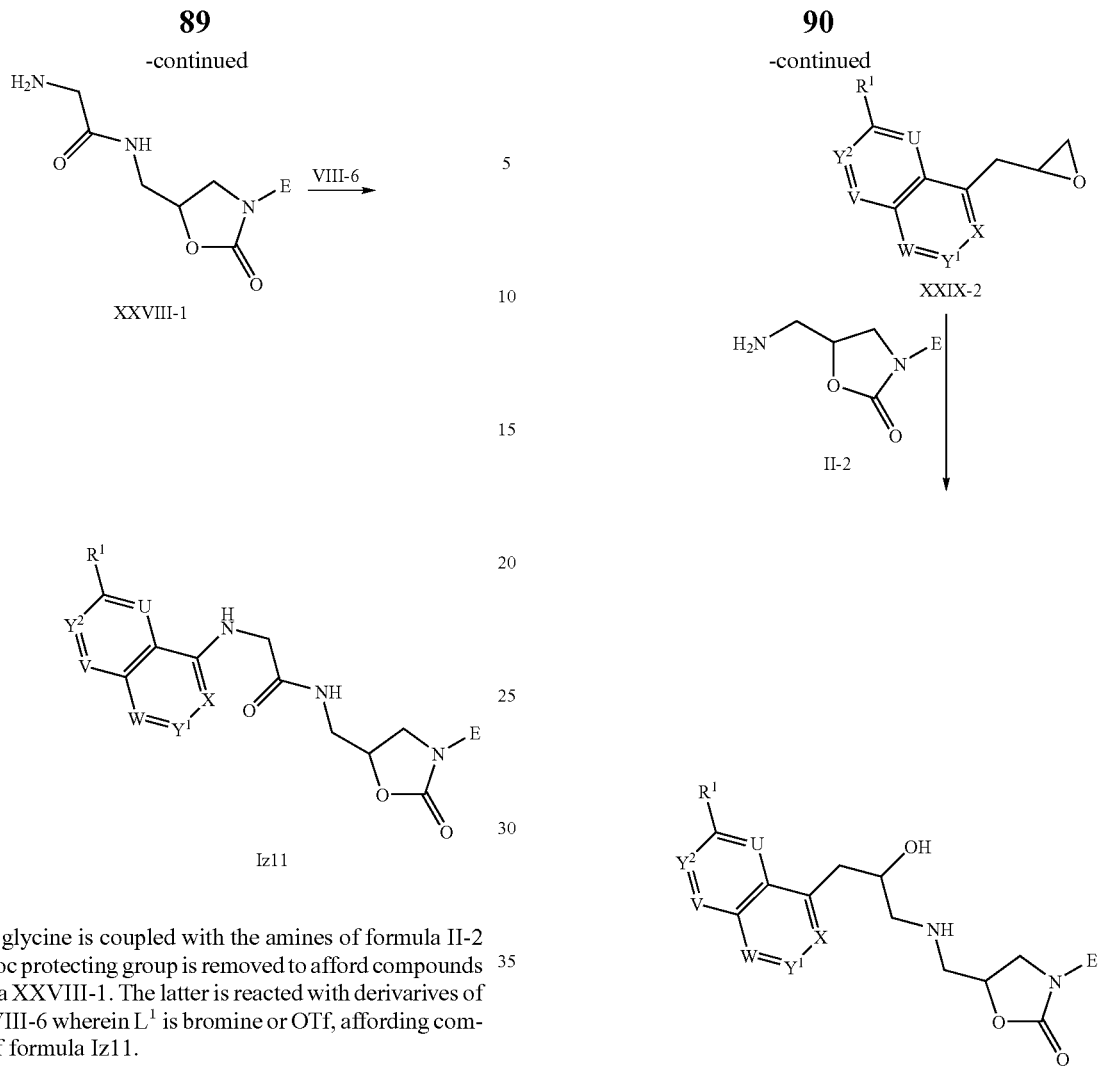

N-Boc glycine is coupled with the amines of formula II-2 and the Boc protecting group is removed to afford compounds of formula XXVIII-1. The latter is reacted with derivarives of formula VIII-6 wherein $L^1$ is bromine or OTf, affording compounds of formula Iz11.

ak) The compounds of formula I wherein A is $CH_2CH(OH)$, B is $CH_2NH$ and D is $CH_2$ can be prepared as summarised in Scheme 29 hereafter.

Scheme 29

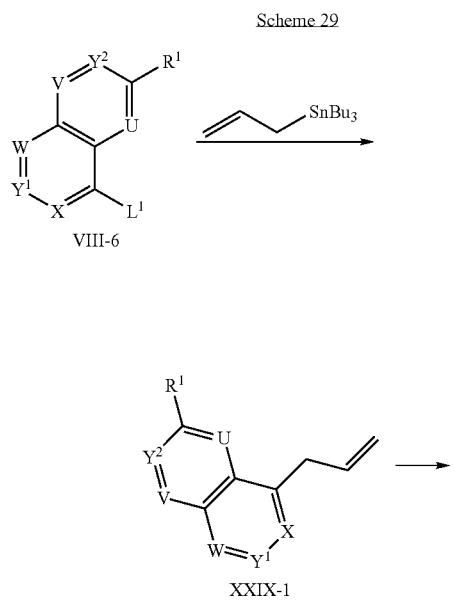

Derivatives of formula VIII-6 wherein $L^1$ represents OTf are reacted with an organotin reagent under Stille coupling conditions (as described in *J. Am. Chem. Soc.* (1987), 109, 5478); typical reaction conditions involve a palladium(0) source such as tetrakis(triphenylphosphine) palladium or dichloro bis(triphenylphophine)palladium, LiCl and a radical scavenger such as 2,6-dimethyl-4-methylphenol in a solvent such as DMF or dioxane at a temperature ranging between 0° C. and 100° C., more preferably at a temperature ranging between 20° C. and 80° C. The resulting allyl derivatives of formula XXIX-1 are transformed into their corresponding epoxides of formula XXIX-2 either by using MCPBA or via cis dihydroxylation using $OsO_4$ followed by monomesylation and ring closure. The intermediate epoxide derivative is reacted with the amine of formula II-2 affording compounds of formula Iz12.

al) The compounds of formula I wherein A is $CH_2CH(OH)$ or $CH_2CH(NH_2)$ B is $CH_2CH_2$ and D is $CH_2$ can be prepared as summarised in Scheme 30 hereafter.

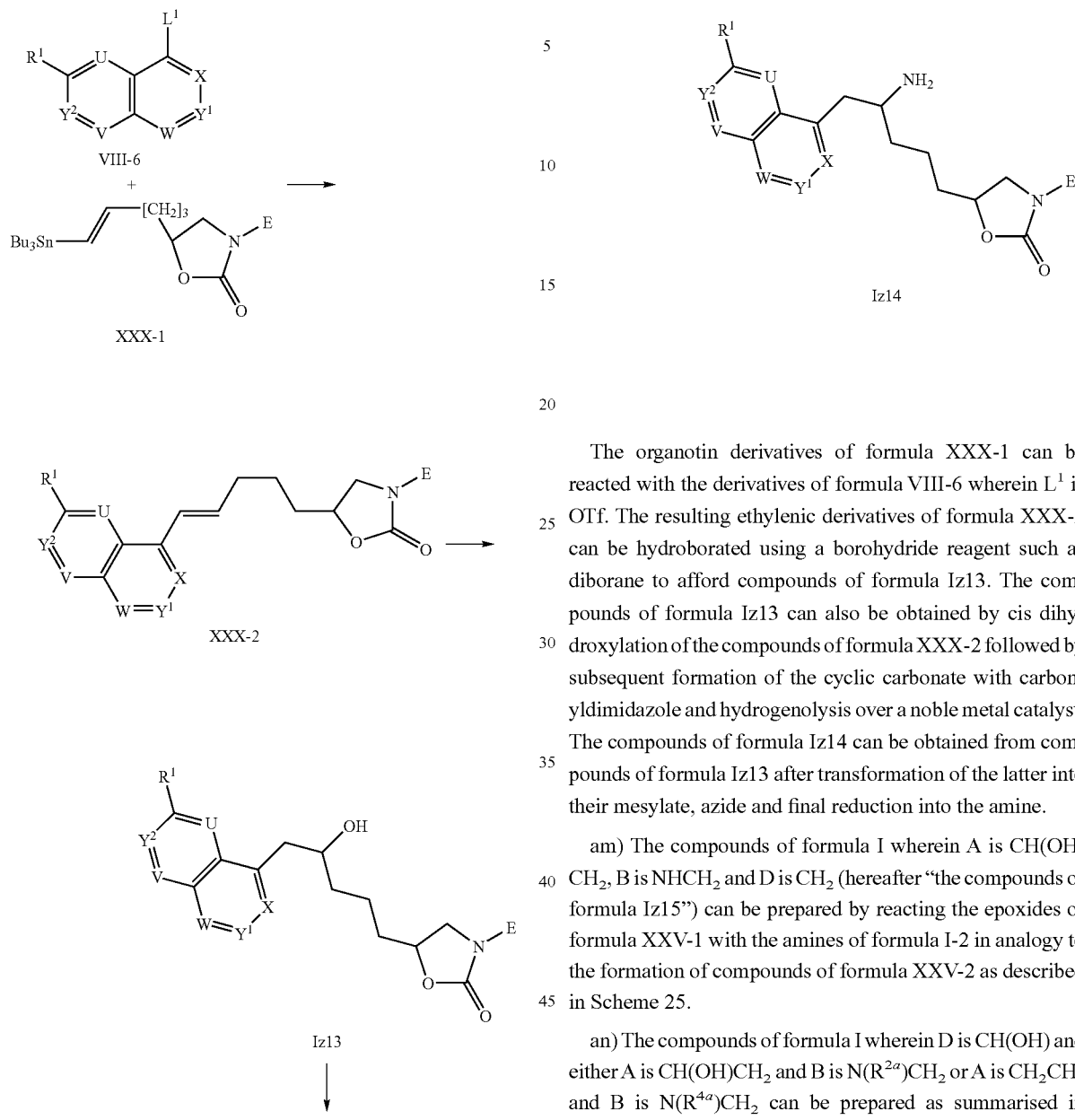

The organotin derivatives of formula XXX-1 can be reacted with the derivatives of formula VIII-6 wherein $L^1$ is OTf. The resulting ethylenic derivatives of formula XXX-2 can be hydroborated using a borohydride reagent such as diborane to afford compounds of formula Iz13. The compounds of formula Iz13 can also be obtained by cis dihydroxylation of the compounds of formula XXX-2 followed by subsequent formation of the cyclic carbonate with carbonyldimidazole and hydrogenolysis over a noble metal catalyst. The compounds of formula Iz14 can be obtained from compounds of formula Iz13 after transformation of the latter into their mesylate, azide and final reduction into the amine.

am) The compounds of formula I wherein A is CH(OH)CH$_2$, B is NHCH$_2$ and D is CH$_2$ (hereafter "the compounds of formula Iz15") can be prepared by reacting the epoxides of formula XXV-1 with the amines of formula I-2 in analogy to the formation of compounds of formula XXV-2 as described in Scheme 25.

an) The compounds of formula I wherein D is CH(OH) and either A is CH(OH)CH$_2$ and B is N(R$^{2a}$)CH$_2$ or A is CH$_2$CH$_2$ and B is N(R$^{4a}$)CH$_2$ can be prepared as summarised in Scheme 30a hereafter.

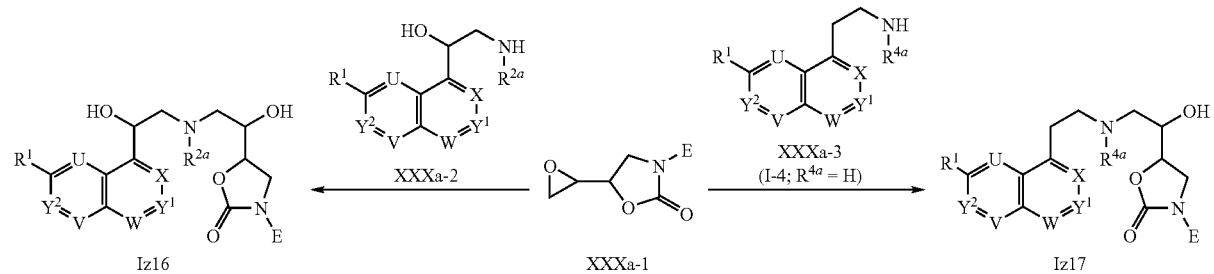

In Scheme 30a, $R^{2a}$ represents hydrogen or alkyl and $R^{4a}$ represents hydrogen or alkyl.

The epoxide group of the compounds of formula XXXa-1 can be opened using the amines of formula XXXa-2, yielding the compounds of formula Iz16 (i.e. the compounds of formula I wherein A is $CH(OH)CH_2$, B is $N(R^{2a})CH_2$ and D is $CH(OH)$). The epoxide group of the compounds of formula XXXa-1 can also be opened using the amines of formula XXXa-3, yielding the compounds of formula Iz17 (i.e. the compounds of formula I wherein A is $CH_2CH_2$, B is $N(R^{4a})CH_2$ and D is $CH(OH)$).

ao) The compounds of formula I wherein A is $CH_2CH_2$ and B is $CH_2CH_2NH$ and D is $CH_2$ or wherein A is $CH_2N(R^7)$, B is $CH_2CH_2$ and D is $CH(OH)$ can be prepared as summarised in Scheme 30b hereafter.

Scheme 30b

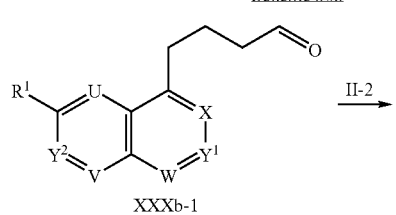

XXXb-1

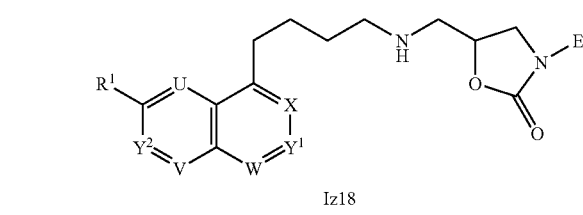

Iz18

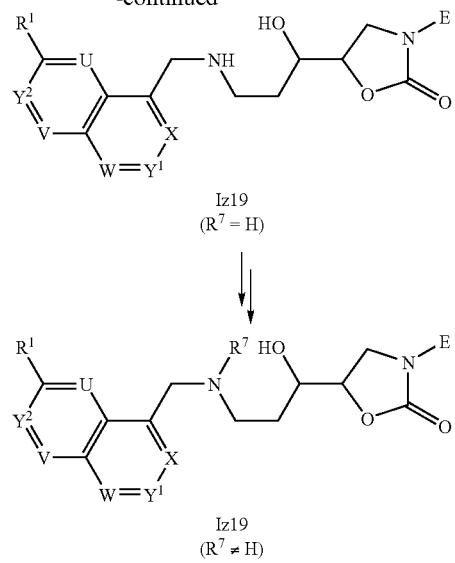

The aldehydes of formula XXXb-1 can be coupled by reductive amination (see reaction technique 4) with the amines of formula II-2 to yield the compounds of formula Iz18 (i.e. the compounds of formula I wherein A is $CH_2CH_2$ and B is $CH_2CH_2NH$ and D is $CH_2$).

Similarly, the amines of formula XXXb-1 can be coupled with the aldehydes of formula VIII-3 (see reaction technique 4) to yield the compounds of formula Iz19 wherein $R^7$ is H (i.e. the compounds of formula I wherein A is $CH_2N(R^7)$ and B is $CH_2CH_2$ and D is $CH(OH)$). To obtain compounds of formula Iz19 wherein $R^7$ is not H, the compounds of formula Iz19 wherein $R^7$ is H can be submitted to the appropriate reaction sequence involving optionally the protection of the hydroxy group (reaction technique 23) or the amino group (reaction technique 1), alkylation or acylation with the appropriate reagent (reaction technique 7 or 8), possibly a further transformation of the side chain if needed and the removal of the hydroxy protecting group(s) (reaction technique 17) or the amino protecting group (reaction technique 3) if required.

Compounds of formula Iz19 with the inversed configuration at the carbon bearing the hydroxy group can be obtained according to the following reaction sequence: protection of the amine with a Boc group, Mitsunobu reaction with 4-nitro benzoate (reaction technique 11), basic hydrolysis of the benzoate with NaOH and removal of the Boc group (reaction technique 3).

ap) The compounds of formula I wherein A is $CH_2NH$, B is $CH_2CH_2$ and D is $CH(NH_2)$ are obtained by reaction of the compounds of formula Iz19 (see section ao) above) with di-tert-butyl imidodicarbonate (reaction technique 11) followed by removal of the Boc protecting group (reaction technique 3).

aq) The compounds of formula I wherein A is $CH_2CH_2$, B is $CH_2CH(OH)$, $CH(NHR^{3a})CH_2$, $COCH_2$ or $CH_2CH_2$ and D is $CH_2$ or wherein A is $CH_2CH_2$, B is $CH_2CH_2$ and D is $CH(OH)$ can be prepared as summarised in Scheme 30c hereafter.

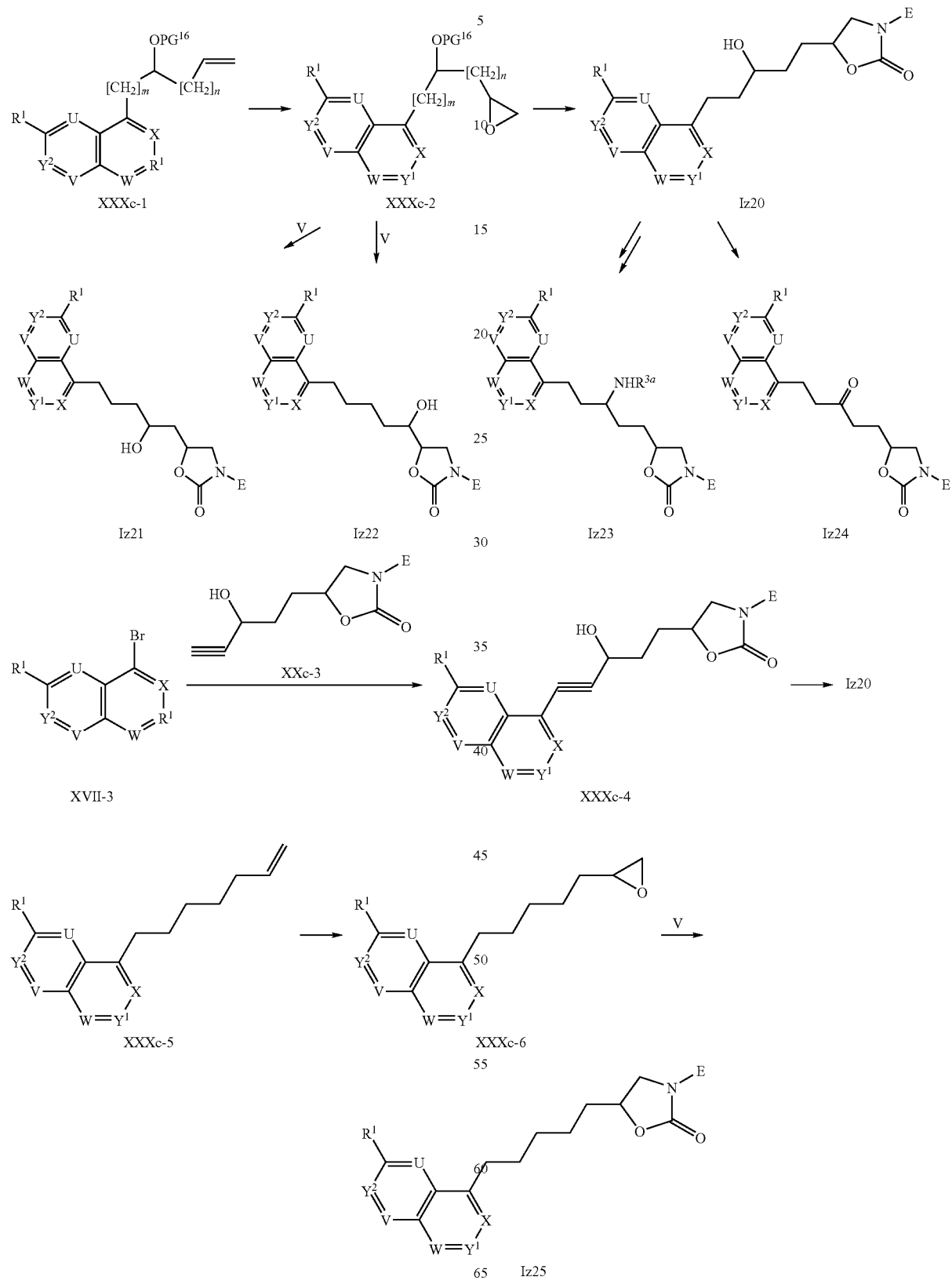

In Scheme 30c, $PG^{16}$ represents a hydroxy protecting group such as TBDMS or TBDPS and n and m are integers such as n+m=4.

The compounds of formula XXXc-1 can be cis-dihydroxylated using reaction technique 14 and the resulting diols can be transformed into the corresponding epoxides of formula XXXc-2 after sequential activation of the primary alcohol function as a mesylate (reaction technique 6) and reaction with a base such $K_2CO_3$ or TEA. The epoxides of formula XXXc-2 can be converted into the corresponding oxazolidinones of formulae Iz20, Iz21 and Iz22 by reaction with the anion generated from the carbamates of formula V as described in section b) above followed by removal of the alcohol protecting group (reaction technique 17). The compounds of formula Iz20 can also be obtained by reacting the bromo derivatives of formula XVII-3 with the acetylene derivatives of formula) XXXc-3 under Sonogashira conditions as described in *Tetrahedron Lett.* (1975), 50, 4467, followed by hydrogenation of the triple bond over a noble metal catalyst.

The compounds of formula Iz23 and Iz24 can be obtained (Scheme 30c) respectively by transforming the compounds of formula Iz20 into the corresponding azides (reaction technique 11) and subsequently hydrogenating (reaction technique 20) to give the corresponding primary amines of formula Iz23 ($R^{3a}$=H), and by oxidation of the alcohol function of the compounds of formula Iz20 to give the corresponding ketones of formula Iz24 (reaction technique 18). The amino group of the compounds of formula Iz23 wherein $R^{3a}$ is H can be further transformed either through reaction with a compound of formula HalCOR wherein R represents alkyl and Hal represents halogen, thus affording the corresponding amide derivatives, or by reaction with a compound of formula $HalSO_2R$ wherein R represents alkyl and Hal represents halogen, thus affording the corresponding sulfonamide derivatives.

The compounds of formula Iz25 can be made in analogy to the compounds of formula Iz20, starting from the vinyl derivatives of formula XXXc-5.

ar) The compounds of formula I wherein A is $CH_2CH_2$ or CH=CH, B is $CH_2O$ and D is $CH_2$ can be prepared as summarised in Scheme 30d hereafter.

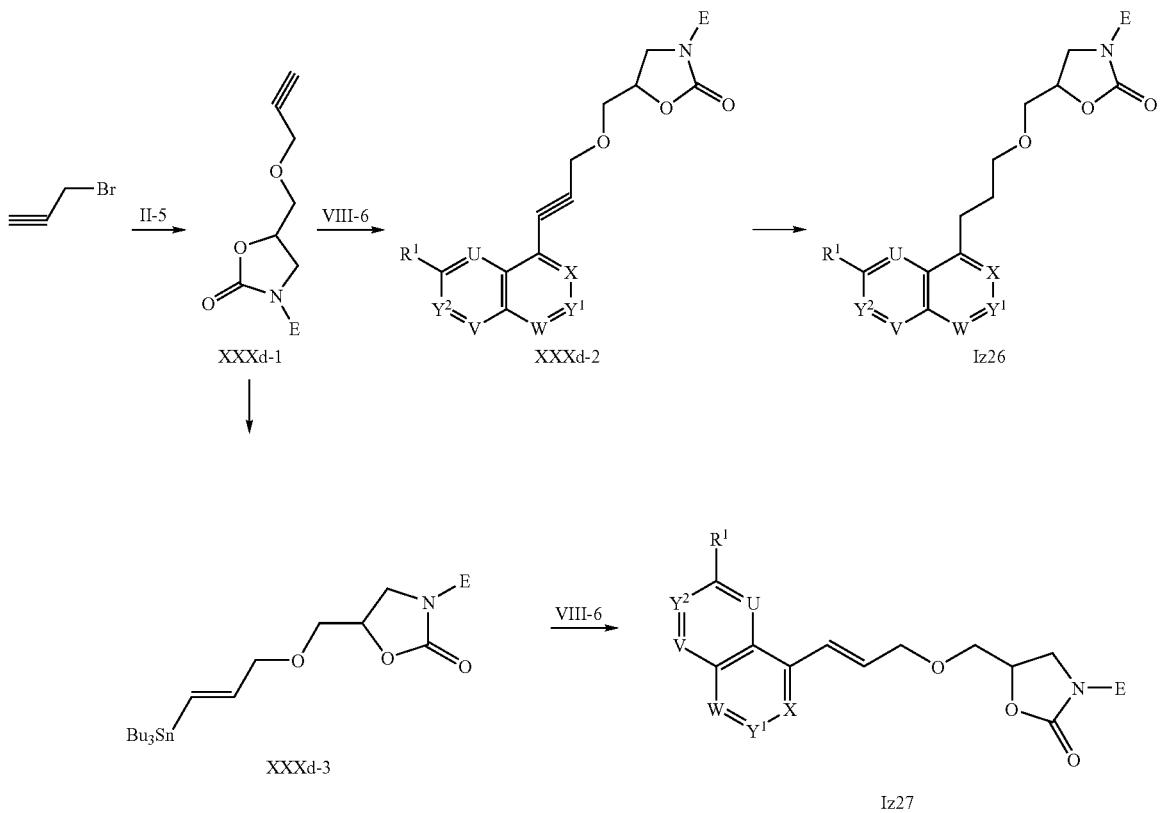

Scheme 30d

The oxazolidinones of formula II-5 can be reacted with propargyl bromide, affording the ethers of formula XXXd-1, which can then be reacted with the bromo derivatives of formula VIII-6 wherein $L^1$ is OTf or Br, affording the intermediates of formula XXXd-2. The compounds of formula Iz26 can then be obtained by hydrogenation of the triple bond of said intermediates over a noble metal catalyst. The compounds of formula Iz27 can be obtained by hydrostannation of intermediate XXXd-1 followed by reaction with the derivatives of formula VIII-6.

as) The compounds of formula I wherein A is $CH_2O$, B is $CH_2CH_2$ and D is $CH_2$ can be obtained by reacting the bromomethyl derivatives of formula IV-2 with the alcohols of formula XXXVI-2 (see Scheme 36) in presence of a base such as NaH.

at) The compounds of formula I wherein A is $OCH_2$, B is $CH_2$, $CH_2CH_2$, CH=CH or CONH and D is $CH_2$ can be prepared as summarised in Scheme 30e hereafter.

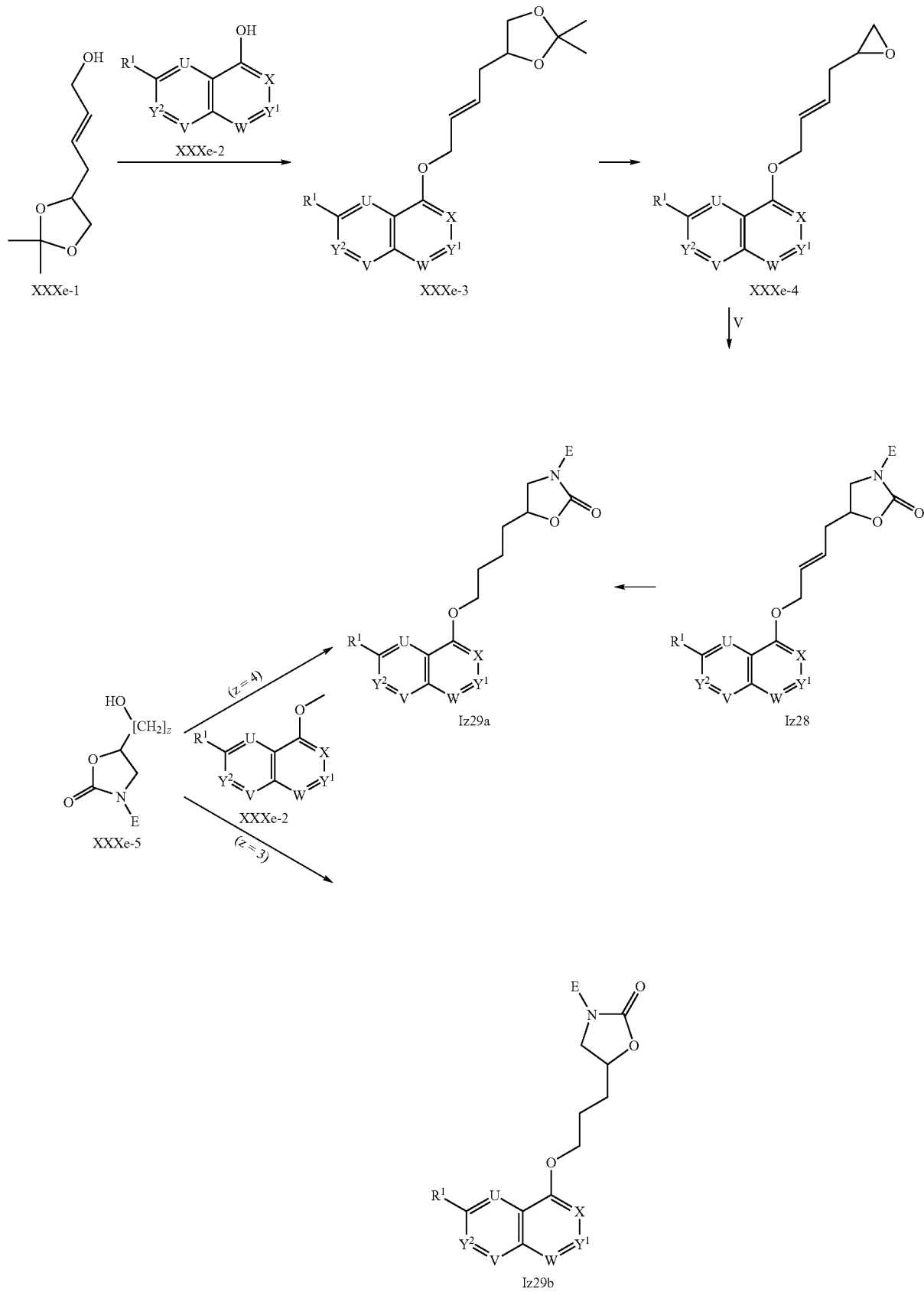
Scheme 30e

-continued

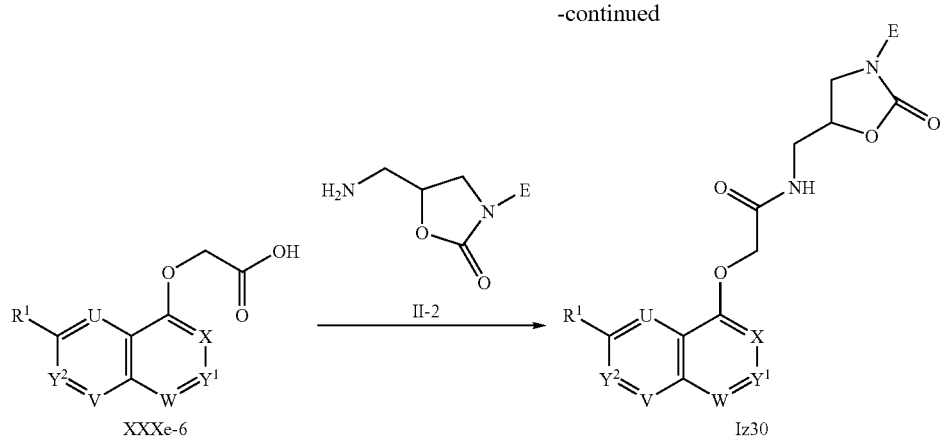

In Scheme 30e, z is the integer 3 or 4.

The compounds of formula Iz28 can be obtained (Scheme 30e) by reacting the phenols of formula XXXe-2 with the allylic alcohols of formula XXXe-1 (reaction technique 11), removing the acetonides in the resulting compounds of formula XXXe-3 (reaction technique 13), transforming the diol into the corresponding epoxides of formula XXXe-4 after sequential activation of the primary alcohol function as a mesylate (reaction technique 6) and reaction with a base such $K_2CO_3$ or TEA and finally converting the epoxides of formula XXXe-4 into the corresponding oxazolidinones of formula Iz28 by reaction with the anions generated from the carbamates of formula V as described in section b) above. The compounds of formula Iz29a or Iz29b can be obtained by reacting the phenols of formula XXXe-2 with the alcohols of formula XXXe-5 following reaction technique 11. The compounds of formula Iz29a can moreover be obtained by reduction of the compounds of formula Iz28 over a noble metal catalyst. The compounds of formula Iz30 can be obtained from the amines of formula II-2 and the acids of formula XXXe-6 using reaction technique 9. The compounds of formula XXXe-6 can be obtained from the phenols of formula XXXe-2 and bromoacetic acid ethyl ester in the presence of a base such as NaH, followed by ester hydrolysis using reaction technique 21.

au) The compounds of formula I wherein A is $CH_2N(R^7)$, B is $CH_2CH(OH)$ and D is $CH(OH)$ can be prepared as summarised in Scheme 30f hereafter.

Scheme 30f

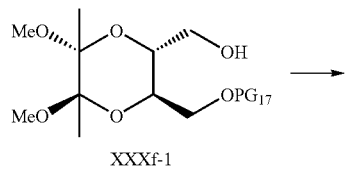

XXXf-1

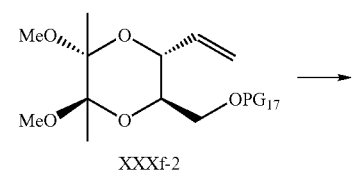

XXXf-2

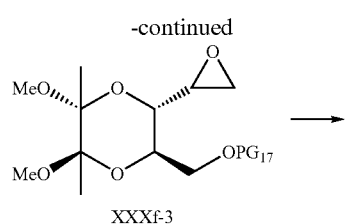

XXXf-3

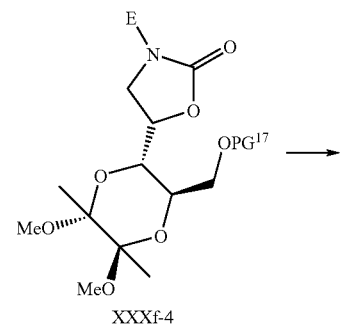

XXXf-4

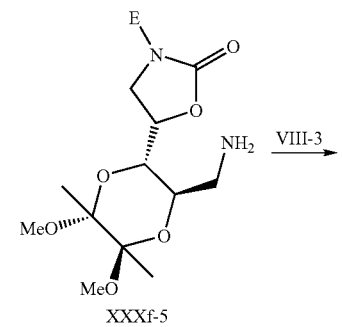

XXXf-5

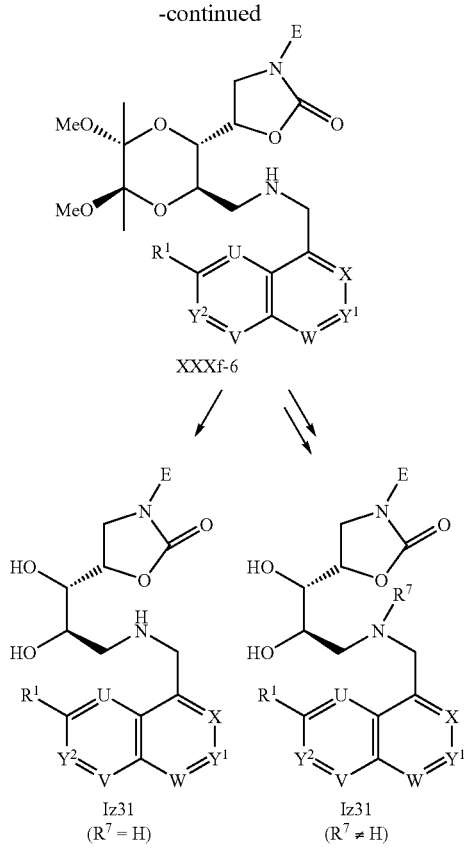

In Scheme 30f, $PG^{17}$ represents an alcohol protecting group such as TBDMS or TBDPS.

The compounds of formula Iz31 can be obtained starting from the intermediates of formula XXXf-1 (*J. Chem. Soc., Perkin Trans.*1: *Organic and Bio-Organic Chemistry* (1999), 12, 1627-1630). The latter can be oxidized into the corresponding aldehydes using general technique 18 and transformed into the compounds of formula XXXf-2 using general technique 12. The epoxides of formula XXXf-3 can then be obtained by reaction with MCPBA. This epoxides can be transformed into the corresponding oxazolidinones by reaction with the anion generated from the carbamates of formula V as described in section b) above. The alcohol protecting group in the compounds of formula XXXf-4 can be removed following general technique 17 and the intermediate alcohols can then be transformed into the corresponding amines of formula XXXf-5 by sequential activation of the alcohols as mesylates using general technique 6, reaction with sodium azide and reduction into the corresponding amines using general technique 20. The compounds of formula XXXf-6 can be obtained by reaction with the aldehydes of formula VIII-3 using general technique 4. The diols of formula Iz31 wherein $R^7$ is H can then be obtained by treatment with an acid such as TFA. The diols of formula Iz31 wherein $R^7$ is other than H can be obtained from the compounds of formula XXXf-6 using the appropriate reaction sequence involving the alkylation or acylation of the amino group with the appropriate reagent (reaction technique 7 or 8), possibly a further transformation of the side chain if needed and finally a treatment with an acid such as TFA to obtain the desired diols.

Whenever the compounds of formula I are obtained in the form of mixtures of enantiomers, the enantiomers can be separated using methods known to one skilled in the art, e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as triethylamine, diethylamine) and eluent B (hexane), at a flow rate of 0.8 to 150 mL/min.

The compounds of formula I thus obtained may, if desired, be converted into their salts, and notably into their pharmaceutically acceptable salts.

Preparation of Compounds of Formula II:

The compounds of formula II can be obtained through opening of the epoxide derivatives of formula IV with amines of formula $E-NH_2$, wherein E has the same meaning as in formula I.

Preparation of Compounds of Formula IV:

Compounds of formula IV are obtained either through epoxidation of the corresponding ethylenic derivatives of formula VI

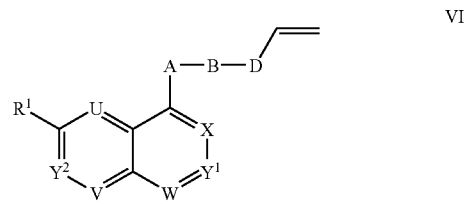

either with a peracid such as MCPBA or $H_2O_2$ in the presence of an inorganic base such as NaOH or urea, or through cis-dihydroxylation of the same ethylenic derivatives of formula VI with $OsO_4$/NMO as described in *Tetrahedron Lett.* (1976), 23, 1973-76, followed by conversion into the corresponding epoxides after mesylation and ring closure under basic conditions such as TEA.

In case chiral epoxides are required, they can be obtained by hydrolytic kinetic resolution (HKR) catalyzed by chiral (salen)-Co(III) complex (e.g. [(R,R)-N,N'-bis(3,5-di-tert-butylsalicylidene)-1,2-cyclohexanediaminato(2-)]cobalt(III) of the racemic mixture of epoxides as described by Jacobsen et al. in *J. Am. Chem. Soc.* (2002), 124, 1307-1315 and *Science* (1997), 277, 936-938. Alternatively the chiral epoxides can also be obtained from the ethylenic derivatives of formula VI through either Shi chiral epoxidation using a chiral ketone as described *Acc. Chem Res.* (2004), 37, 488-496 or through chiral cis-dihydroxylation using AD mixtures in presence of methanesulfonamide in a water/2-methyl-2-propanol mixture as described in *Chem. Rev.* (1994), 94, 2483. The sense of induction relies on the chiral ligand contained in the mixture, either a dihydroquinine-based ligand in AD-mix α or a dihydroquinidine-based ligand in AD-mix β.

In the particular case wherein BD represents $CH_2N(R^9)$ $CH_2$ ($R^9$ being H, $R^3$, $R^5$ or $R^7$), the chiral epoxides can also be obtained by reacting the amines of formula VII

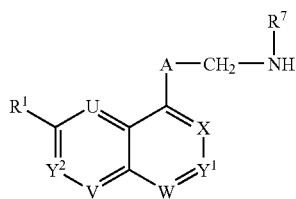

VII wherein $R^9$ is H, $R^3$, $R^5$ or $R^7$ with the two chiral epichlorhydrines followed by optional (when $R^9$ is H) protection of the amine function and reaction with the carbamates of formula V.

The compounds of formula VI can be obtained by reacting reactant 1 with reactant 2 as summarised in Table 1 hereafter.

Preparation of Other Synthetic Intermediates Present in Schemes 1 to 31:

The compounds of formula IX-3 (Scheme 9) can be obtained either as described in Table 1 or by reaction of the carboxylic acids of formula IX-1 with 2,3-epoxypropylamine (prepared according to *J. Org. Chem* (1995), 60, 3692-3699). The compounds of formula IX-2 can be obtained by reaction of the compounds of formula IX-3 with the amines of formula E-NH$_2$.

Compounds of formula X-2 (Scheme 10) can be obtained by reaction of the carboxylic acid of formula IX-1 with the amines of formula II-2. Compounds of formula X-3 can be obtained by reaction of the carboxylic acid of formula V-1 with the amines of formula X-1 ($R^f$=NH$_2$). Compounds of formula X-5 can be obtained by reaction of the amines of formula X-1 ($R^f$=NH$_2$) with epichlorhydrine followed by

TABLE 1

| Group -ABD-CH=CH$_2$ in formula VI | Reactant 1 | Reactant 2 | Reaction type |
|---|---|---|---|
| —CH$_2$CH$_2$NHCH$_2$CH$_2$CH=CH$_2$ | I-3 | NH$_2$CH$_2$CH$_2$CH=CH$_2$ | RA |
| —CH$_2$CH$_2$CH$_2$NHCH$_2$CH=CH$_2$ | II-1 | NH$_2$CH$_2$CH=CH$_2$ | RA |
| —CH$_2$CH$_2$NHCOCH$_2$CH=CH$_2$ | I-4 | ClCOCH$_2$CH=CH$_2$ | AF |
| —CH$_2$CH$_2$CONHCH$_2$CH=CH$_2$ | IV-1 | NH$_2$CH$_2$CH=CH$_2$ | AF |
| —CH$_2$CH$_2$CH$_2$NHCOCH=CH$_2$ | II-3 | ClCOCH=CH$_2$ | AF |
| —CH$_2$CONHCH$_2$CH$_2$CH=CH$_2$ | VI-1 | NH$_2$CH$_2$CH$_2$CH=CH$_2$ | AF |
| —CH=CHCH$_2$NHCH$_2$CH=CH$_2$ | V-2 | CHOCH$_2$CH=CH$_2$ | RA |
| —CH=CHCONHCH$_2$CH=CH$_2$ | VIII-1 | NH$_2$CH$_2$CH=CH$_2$ | AF |
| —CH(OH)CH(OH)CONHCH$_2$CH=CH$_2$ | IX-1 | NH$_2$CH$_2$CH=CH$_2$ | AF, AD |
| —CH(OH)CH(OH)CH$_2$NHCH$_2$CH=CH$_2$ | X-1 ($R^f$ = NH$_2$) | CH(O)CH$_2$CH=CH$_2$ | RA, AD |
| —CH(OH)CH$_2$CONHCH$_2$CH=CH$_2$ | XI-1 | NH$_2$CH$_2$CH=CH$_2$ | AF |
| —CH(OH)CH$_2$CH$_2$NHCH$_2$CH=CH$_2$ | XII-3 | NH$_2$CH$_2$CH=CH$_2$ | RA, DP |
| —CH$_2$CH(OH)CONHCH$_2$CH=CH$_2$ | XIII-2 | NH$_2$CH$_2$CH=CH$_2$ | AF |
| —CH$_2$CH(NHPG$^6$)CH$_2$NHCH$_2$CH=CH$_2$ | XV-3 | NH$_2$CH$_2$CH=CH$_2$ | RA |
| —CH(OH)CH(NHPG$^{11}$)CONHCH$_2$CH=CH$_2$ | XVI-4 | NH$_2$CH$_2$CH=CH$_2$ | AF |
| —NHCH$_2$CH$_2$NHCH$_2$CH=CH$_2$ | XVII-3 | NH$_2$(CH$_2$)$_2$NHCH$_2$CH=CH$_2$ | S |
| —NHCH$_2$CH$_2$NHCOCH=CH$_2$ | XVII-2 | HOOCCH=CH$_2$ | AF |
| —CH$_2$CH(NHPG$^{14}$)CONHCH$_2$CH=CH$_2$ | XVIII-3 | NH$_2$CH$_2$CH=CH$_2$ | AF |
| —C≡CCH$_2$NHCOCH=CH$_2$ | XIV-2 | HOOCCH=CH$_2$ | AF |
| —NH(CH$_2$)$_4$CH=CH$_2$ | XXI-3 | NH$_2$(CH$_2$)$_4$CH=CH$_2$ | S |
| —CH$_2$NH(CH$_2$)$_3$CH=CH$_2$ | VIII-3 | NH$_2$(CH$_2$)$_3$CH=CH$_2$ | RA |
| —CONH(CH$_2$)$_3$CH=CH$_2$ | XIX-4 | NH$_2$(CH$_2$)$_3$CH=CH$_2$ | AF |
| —NHCO(CH$_2$)$_3$CH=CH$_2$ | XXI-3 | HOOC(CH$_2$)$_3$CH=CH$_2$ | AF |
| —NHCOCH$_2$NHCH$_2$CH=CH$_2$ | XXIII-1 | NH$_2$CH$_2$CH=CH$_2$ | S |
| —NHCOCH(R$^6$)NHCH$_2$CH=CH$_2$ | XXIII-2 | BrCH$_2$CH=CH$_2$ | AL |
| —CH(OH)(CH$_2$)$_4$CH=CH$_2$ | XVII-3 | CH(O)(CH$_2$)$_4$CH=CH$_2$ | BL |
| —C(=O)(CH$_2$)$_4$CH=CH$_2$ | Oxidation of the compound of formula VI wherein -ABD-CH=CH$_2$ is —CH(OH)(CH$_2$)$_4$CH=CH$_2$ | | |
| —CH(NH$_2$)(CH$_2$)$_4$CH=CH$_2$ | Mesylation/azide/reduction of the compound of formula VI wherein -ABD-CH=CH$_2$ is —CH(OH)(CH$_2$)$_4$CH=CH$_2$ | | |
| —CH(OH)CH$_2$NHCOCH$_2$CH=CH$_2$ | XXV-2 | HOOC(CH$_2$)$_3$CH=CH$_2$ | AF |
| —CH(NH$_2$)CH$_2$NHCOCH$_2$CH=CH$_2$ | Mesylation/azide/reduction of the compound of formula VI wherein -ABD-CH=CH$_2$ is —CH(OH)CH$_2$NHCOCH$_2$CH=CH$_2$ | | |
| —CH(OH)CH(NH$_2$)CH$_2$NH CH$_2$CH=CH$_2$ | XXVI-1 | NH$_2$CH$_2$CH=CH$_2$ | AF, DP |
| —CH$_2$N(R)CO(CH$_2$)$_2$CH=CH$_2$ | XXVII-3 | HOOC(CH$_2$)$_2$CH=CH$_2$ | AF |
| —NHCH$_2$CONHCH$_2$CH=CH$_2$ | XVII-3 | NH$_2$CH$_2$CONHCH$_2$CH=CH$_2$ | S |
| —CH$_2$CH(OH)CH$_2$NHCH$_2$CH=CH$_2$ | XXIX-2 | NH$_2$CH$_2$CH=CH$_2$ | EP |
| —CH$_2$CH(OH)(CH$_2$)$_3$CH=CH$_2$ | XXXIII-31 | CHO(CH$_2$)$_3$CH=CH$_2$ | BL$^1$ |

In Table 1:

AF = amide bond formation; RA = reductive amination; AL = alkylation; AD = acetonide deprotection; GR = Grignard reaction; AP = alcohol protection; DP = deprotection of the alcohol; S = Substitution; BL = Bromine/lithium exchange with n-BuLi followed by reaction with the corresponding aldehyde; EP = epoxide opening.
$^1$Hexenal prepared according to WO 92/07866

PG$^8$, PG$^{11}$, and PG$^{14}$ are each an amino protecting group such as Cbz or Boc. $R^7$ and $R^8$ have the same meanings as in formula I.

protection of the central amine function. Compounds of formula X-4 can be obtained from compounds of formula X-5 after reaction with the amines of formula E-NH$_2$. Compounds of formula X-6 are obtained by protection of the free amine of compounds of formula Ih (reaction technique 1).

The compounds of formula XII-6 can be obtained by hydroboration of the compounds of formula X-6. The compounds of formula XII-7 can be obtained through reaction of compounds of formula XII-1 with compounds of formula V-1 (reaction technique 9).

The compounds of formula XIII-1 (Scheme 13) are obtained from compounds of formula Ii after cis-dihydroxylation of the central double bond and reaction with phosgene, diphosgene or triphosgene in presence of an organic base such as TEA or Pyr or CDI in an inert solvent such as DCM or THF at a temperature ranging between −78° C. and 50° C., and preferably at a temperature ranging between 0° C. and 20° C. The compounds of formula XIII-3 are prepared by transformation of the corresponding allyl amides as described above. The required allyl amides are obtained as described in Table 1.

The compounds of formula XVI-2 (Scheme 16) can be obtained by reaction of the acids of formula XVI-4, the hydroxy group of which has been previously protected (reaction technique 23), with allylamine (reaction technique 9) followed by epoxidation of the terminal double bond as described above. The compounds of formula XVI-1 can be obtained from compounds of formula XVI-2 after reaction with the amines of formula E-NH$_2$.

Preparation of Certain Starting Compounds Present in Schemes 1 to 31:

A possible preparation route for the aldehydes of formula I-3, the amines of formula I-4, the compounds of formula I-7 and the acids of formula VI-1 is summarised in Scheme 31 hereafter.

In Scheme 31, R$^1$, U, V, W, X, Y$^1$ and Y$^2$ are as defined in formula I, R$^z$ is mesyloxy, triflyloxy, tosyloxy or halogen such as bromine.

The known vinyl derivatives of formula I-1 (for U=N, V=W=X=CH and R$^1$=OMe, or W=N, U=V=X=CH and R$^1$=OMe, see WO 2006/002047; for U=W=N, V=X=CH and R$^1$=OMe, see WO 02/08224; for V=N, U=W=X=CH and R$^1$=OMe, see WO 2006/021448; for U=W=N, V=CH, X=CF and R$^1$=OMe, or W=N, U=V=CH, X=CF and R$^1$=OMe, see WO 2004/058144; for W=N, U=V=X=CH, R$^1$=CN, see WO 2004/002490) can be hydroborated (reaction technique 16). The resulting alcohols of formula I-7 (R$^n$=OH) can be either oxidized into the corresponding aldehydes of formula I-3 (reaction technique 18) or the carboxylic acids of formula VI-1 (reaction technique 18) or transformed into the corresponding amines of formula I-4 after activation of the alcohols into mesylate, triflate, tosylate or halogenide derivatives and subsequent reaction with sodium azide and reduction into amines (reaction technique 20).

The aldehydes of formula II-1 can be obtained by oxidation of the alcohol of formula I-7 (R$^n$=OH).

A possible preparation route for the bromo derivatives of formula IV-2 and an alternative route for the acids of formula VI-1 is summarised in Scheme 32 hereafter.

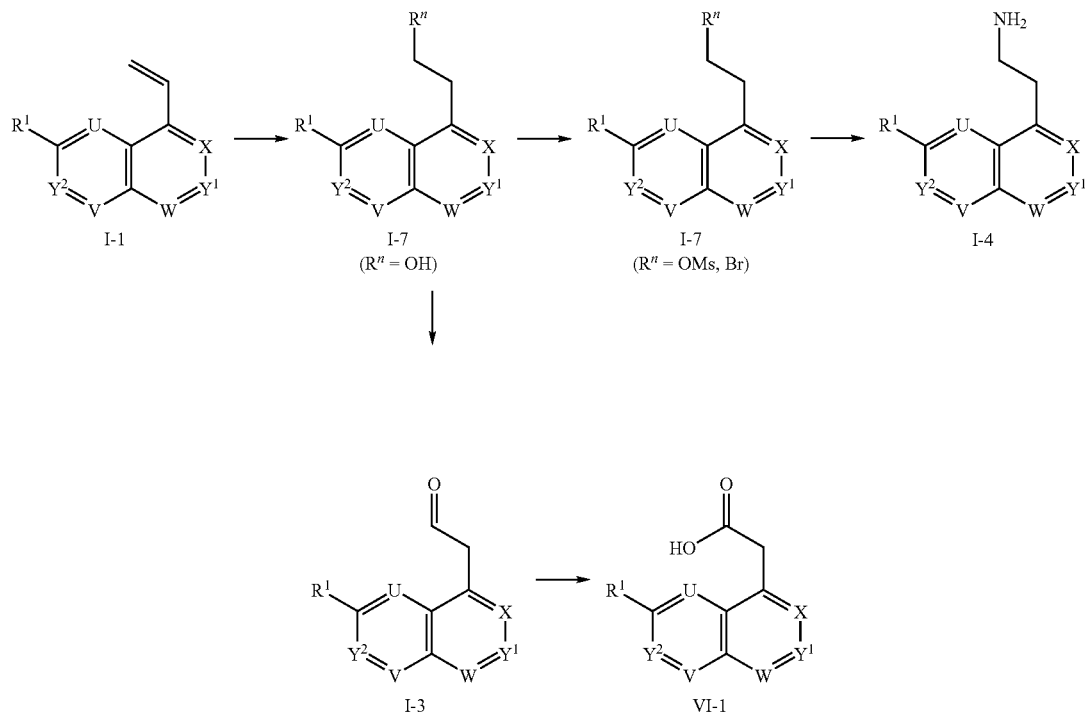

Scheme 32

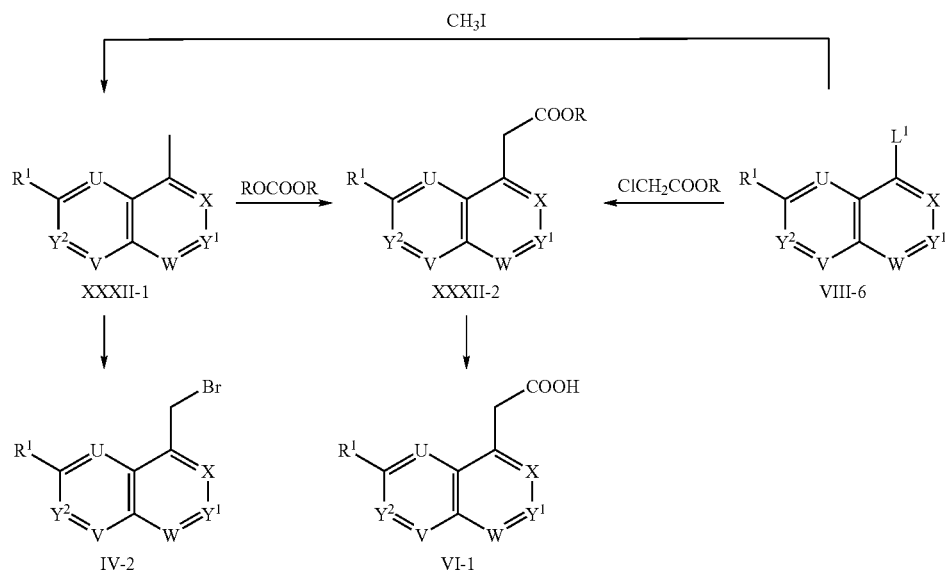

In Scheme 32, $R^1$, U, V, W, X, $Y^1$ and $Y^2$ are as defined in formula I, R is alkyl or arylalkyl and $L^1$ is ZnCl or $Cu_{0.5}Li_{0.5}$.

According to the route shown in Scheme 32, the bromo derivatives of formula IV-2 can be obtained by bromination of the methyl derivatives of formula XXXII-1 (which can be prepared for example by reaction of the organometallic derivatives of formula VIII-6 with methyl iodide) with either NBS or bromine. The anions generated by the reaction of the methyl derivatives of formula XXXII-1 with a strong organic base such as n-BuLi can be reacted with a dialkylcarbonate to give the esters of formula XXXII-2 which were hydrolyzed to give the acids of formula VI-1. Alternatively, the esters of formula XXXII-2 can be obtained by reacting the derivatives of formula VIII-5 wherein $L^1$ is ZnCl or $Cu_{0.5}Li_{0.5}$ with ethyl bromoacetate as described in EP 1 484 304 and *Bioorg. & Med. Chem.* (2004), 12, 5785-5791.

A possible preparation route for the acids of formula XI-1, the amines of formula XII-1, the aldehydes of formula XV-2 and the amines of formula XV-3 is summarised in Scheme 33 hereafter.

Scheme 33

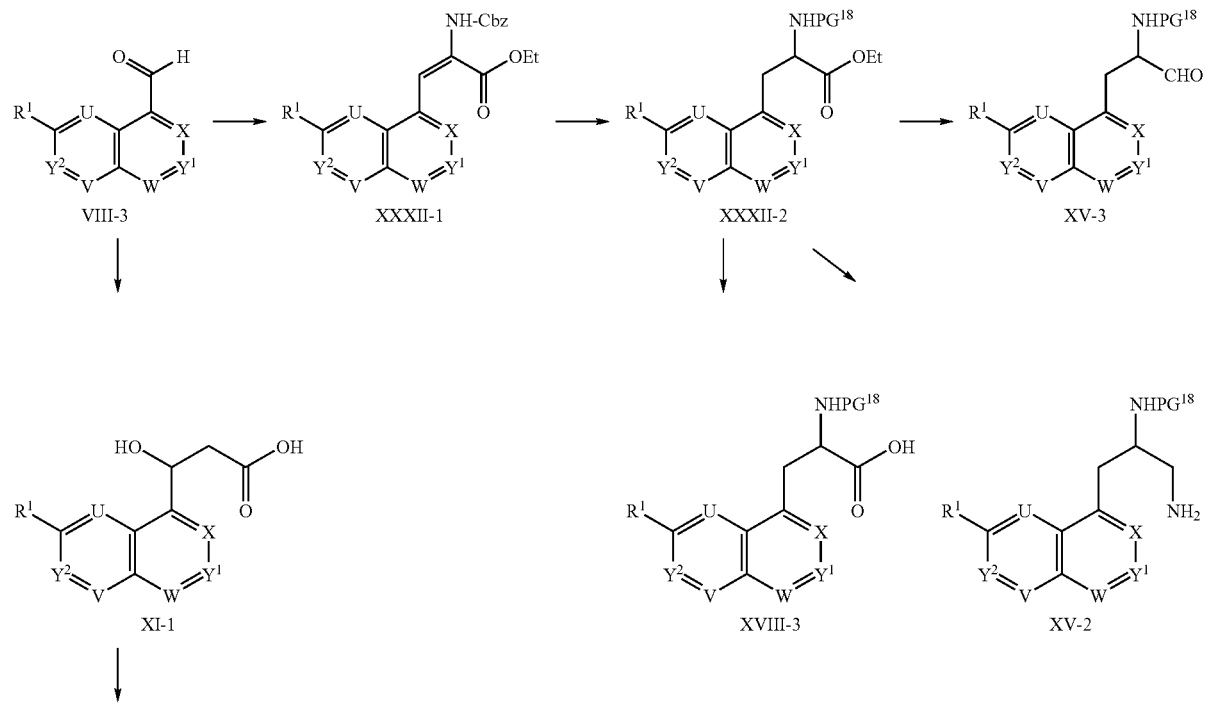

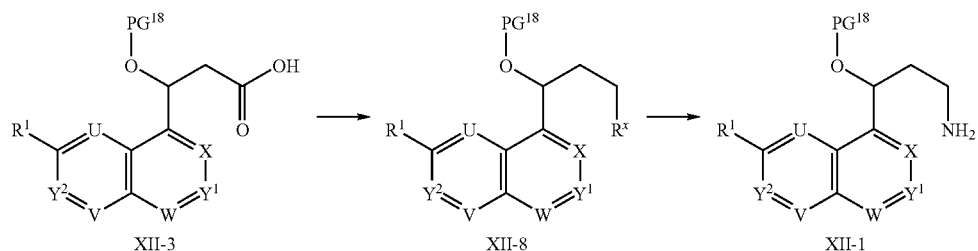

In Scheme 33, $R^1$, U, V, W, X, $Y^1$ and $Y^2$ are as defined in formula I, $PG^{18}$ is an amino protecting group such as Cbz or Boc, $PG^{19}$ is an alcohol protecting group such as TBDMS or TBDPS and $R^x$ is OH, halogen, MsO, TsO, TfO or $N_3$.

The acids of formula XI-1 can be obtained (Scheme 33) after addition of the anion of tert-butyl acetate generated by the action of a strong base such as n-BuLi or LDA between −80° C. and −40° C. in a solvent such as THF, on the aldehydes of formula VIII-3, followed by cleavage of the ester. The compounds of formula XII-8 ($R^x$=OH) can be obtained from compounds of formula XI-1 after transformation of the acids into their corresponding ethyl or methyl esters, protection of the secondary alcohol function (e.g. as a TBDMS ether; see reaction technique 23) and reduction into the alcohols of formula XII-8 via the aldehydes of formula XII-3 (see Scheme 33). Compounds of formula XII-1 are obtained by subsequent transformation of compounds of formula XII-8 ($R^x$=OH) into their corresponding mesylates and azides (XII-8; $R^x$=OMs, $N_3$ respectively) followed by reduction into the corresponding amines (reaction technique 20). Compounds of formula XII-3 can also be obtained by oxidation of the corresponding alcohol (XII-8; $R^x$=OH) (reaction technique 18).

A possible preparation route for the alcohols of formula I-7, the acids of formula IV-1, the compounds of formula V-2 or VII-2, the aldehydes of formula VII-1, the acids of formula VIII-1, the unsaturated esters of formula VIII-2, the alcohols or amines of formula X-1, the aldehydes of formula XV-2 and the amines of formula XV-3 is summarised in Scheme 34 hereafter.

Scheme 34

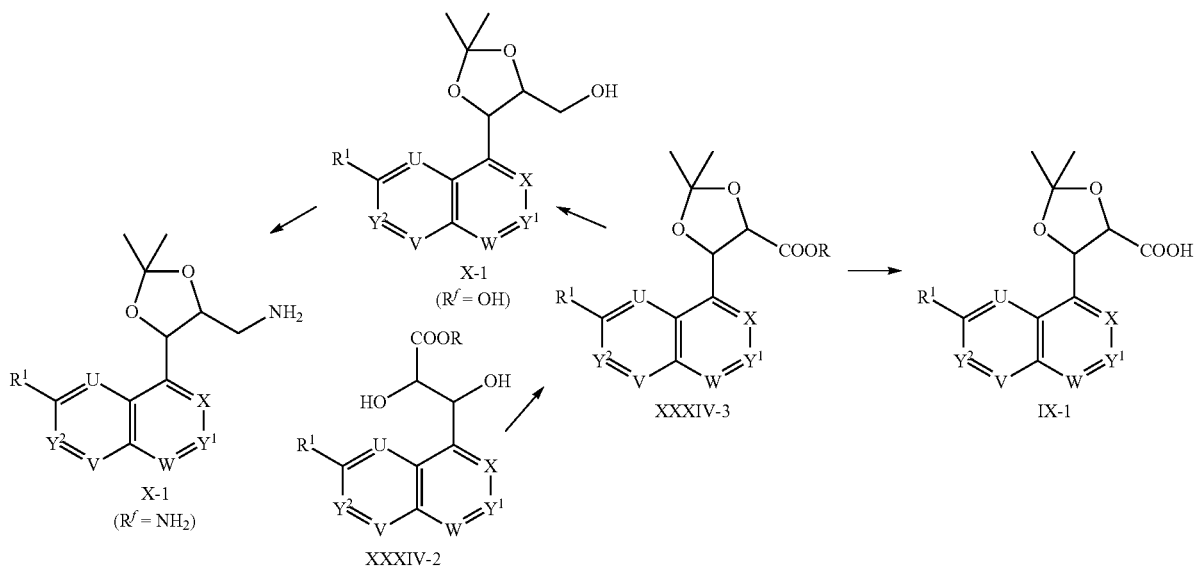

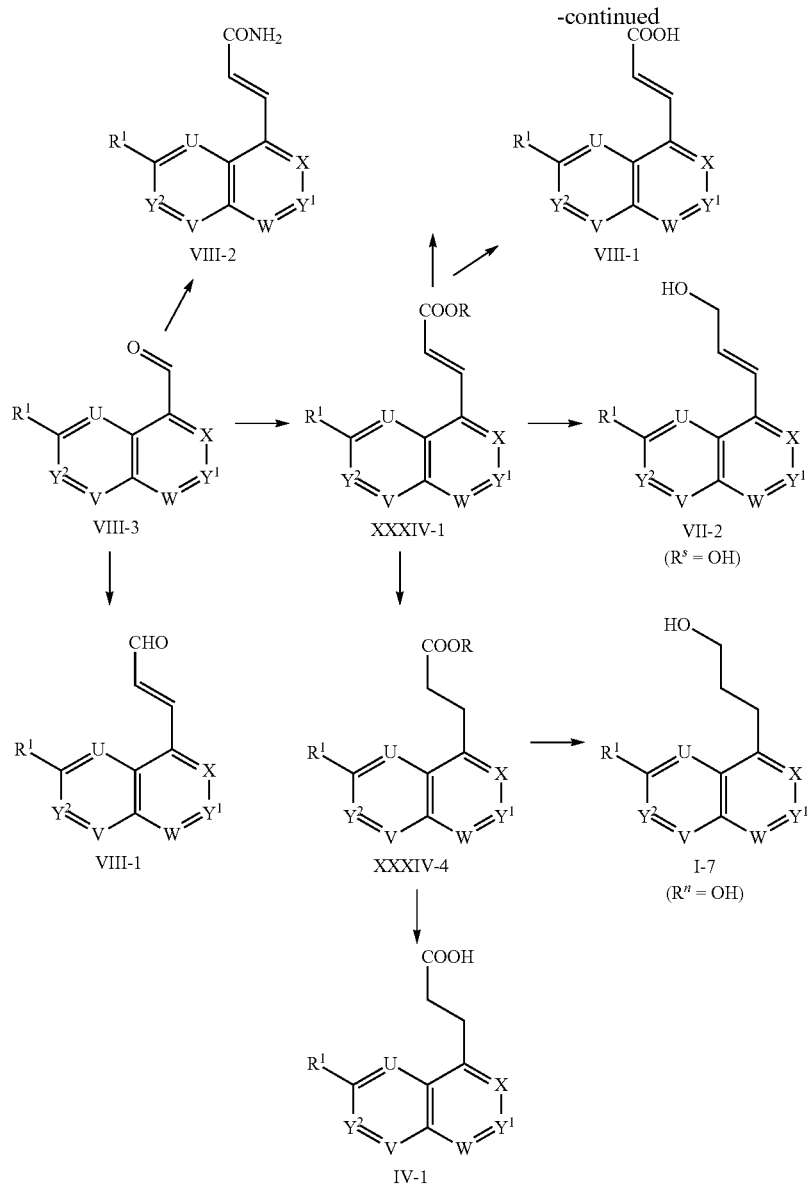
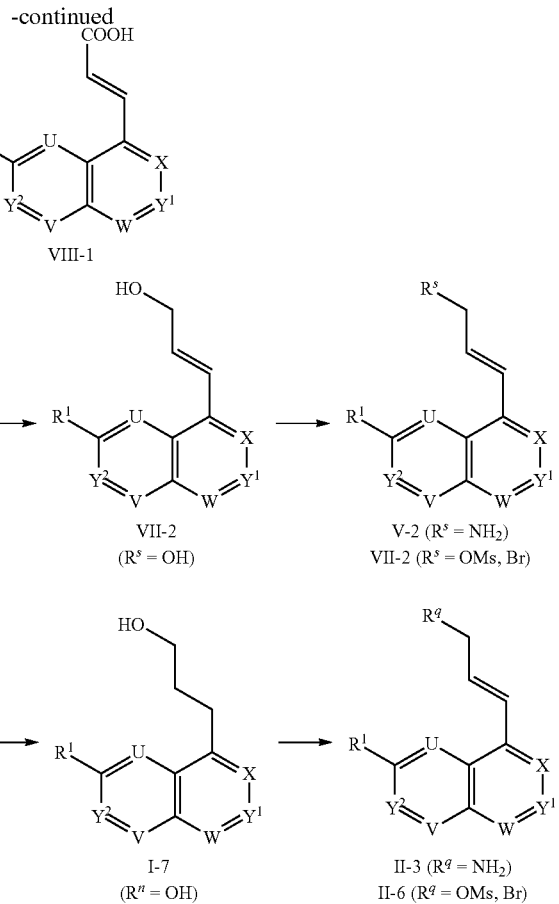

In Scheme 34, $R^1$, U, V, W, X, $Y^1$ and $Y^2$ are as defined in formula I, $R^q$ and $R^s$ are each mesyloxy, trifyloxy, tosyloxy, halogen such as bromine or amino and R is alkyl or arylalkyl.

The aldehydes of formula VII-1 can be obtained from the known aldehydes of formula VIII-3 through reaction with the commercially available (formylmethylene)triphenylphosphorane (see Scheme 34). Said aldehydes of formula VIII-3 can be transformed using the same type of reaction into the corresponding unsaturated amides of formula VIII-2 or esters of formula XXXIV-1. The unsaturated esters of formula XXXIV-1 can be reduced into the saturated esters of formula XXXIV-4 through hydrogenation over a noble metal catalyst. Both esters of formulae XXXIV-1 and XXXIV-4 can either be hydrolyzed into their corresponding acids of formulae VIII-1 and IV-1 or reduced into their corresponding alcohols of formula VII-3 ($R^s$=OH) and I-7 ($R^n$=OH) through reaction with a borohydride reagent such as $NaBH_4$. These two alcohols are further sequentially transformed into their corresponding sulfonate esters and halogenides of formula VII-2 ($R^s$=OMs, OTs, OTf, halogen) and II-6 ($R^q$=OMs, OTs, OTf, halogen), and finally into their corresponding amines of formula V-2 ($R^s$=$NH_2$) and II-3 ($R^q$=$NH_2$) after reaction with sodium azide and reduction with triphenyl phosphine/water.

The unsaturated ester of formula XXXIV-1 (Scheme 34) can further be cis dihydroxylated using an ADMIX mixture and the resulting diol of formula XXXIV-2 can be protected as an acetonide ester of formula XXXIV-3. This ester can either be hydrolyzed into the corresponding free acid of formula IX-1 or reduced into the corresponding alcohol of formula X-1 ($R^f$=OH). This alcohol can further be transformed into the corresponding amine of formula X-1 ($R^f$=$NH_2$) after sequential transformation into a mesylate, halogenide and azide and final reduction into an amine as described above.

The compounds of formula XIII-2 (Scheme 13) can be obtained through hydrolysis of the corresponding esters, the latter being obtained by reaction of the aldehydes of formula VIII-3 with ethyl bromoacetate under Darzens conditions followed by hydrogenolysis of the intermediate epoxides over a noble metal catalyst such as palladium on charcoal.

The compounds of formula XV-3 can be obtained by reduction of the esters of formula XXXIII-2 (Scheme 33) with DIBAH. The compounds of formula XV-2 can be obtained by reduction of the esters XXXIII-2 (Scheme 33) into their corresponding alcohols and further transformation into their mesylates, substitution with sodium azide and reduction into the corresponding amines by using $PPh_3/H_2O$.

A possible preparation route for the compounds of formulae XVI-3 and XVI-4 is summarised in Scheme 35 hereafter.

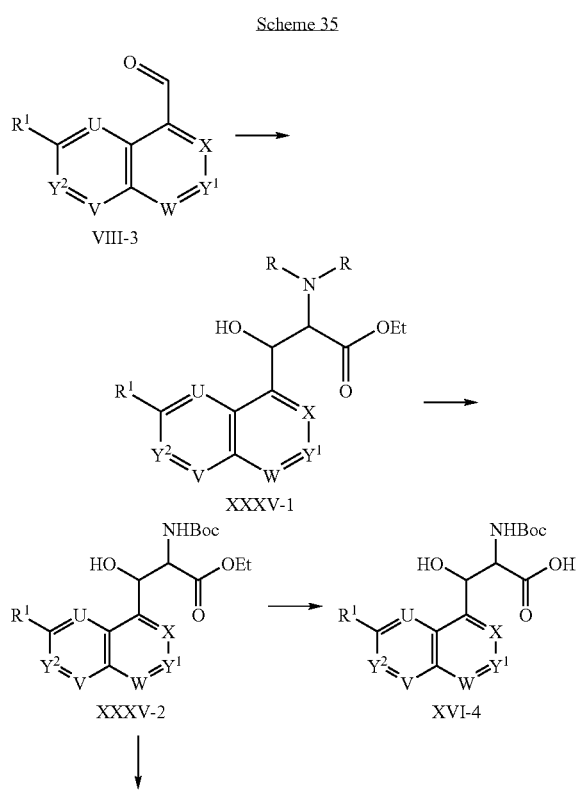

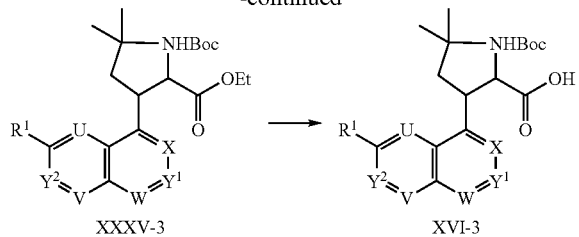

In Scheme 35, $R^1$, U, V, W, X, $Y^1$ and $Y^2$ are as defined in formula I and R represents benzyl.

The compounds of formula XVI-3 can be obtained (Scheme 35) by hydrolysis of the esters of formula XXXV-3 which are obtained by treatment of the hydroxyl esters of formula XXXV-2 with acetone dimethylacetal in presence of a Lewis acid catalyst such as $BF_3$ etherate. The compounds of formula XVI-4 can be obtained by reacting the anion generated by the reaction of a strong organic base such as DBU or n-BuLi on N,N-dibenzylglycine ethyl ester, on the aldehydes of formula VIII-3, followed removal of the benzyl protecting groups by hydrogenolysis, reprotection as a Boc carbamate and basic hydrolysis of the ethyl ester group.

The compounds of formula XVII-2 can be obtained by reacting the halogenides of formula XVII-3 with ethylene diamine.

The compounds of formula XVIII-3 are obtained by hydrolysis of compounds of formula XXXII-2 (Scheme 33), the latter being obtained by reaction of the aldehydes of formula VIII-3 with the commercially available benzyloxycarbonylamino(dimethoxyphosphoryl)acetic acid methyl ester in a Wittig Horner type reaction, followed by sequential hydrogenation over a noble metal catalyst such as Pd/C and reinstallation of an amine protecting group.

The compounds of formula XXVI-1 (Scheme 26) can be obtained by reduction of the esters of formula XXXV-3 (Scheme 35) with DIBAH.

Besides, the amine derivatives of formula I-2, II-2, XIX-3 or XXI-1 can be obtained by one of the ways summarised in Scheme 36 hereafter.

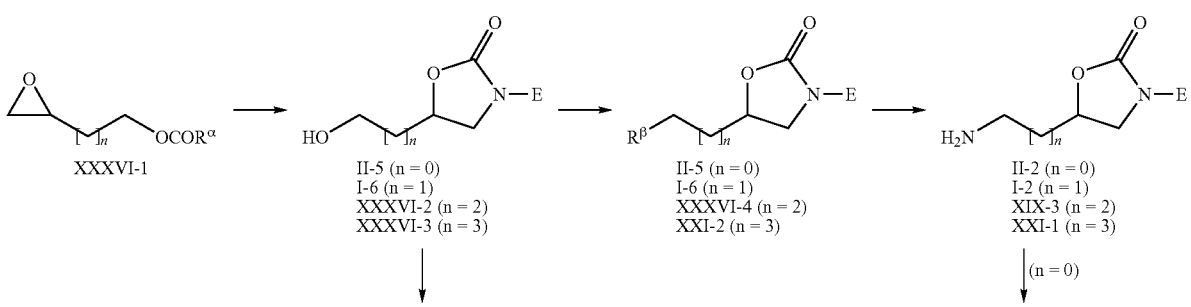

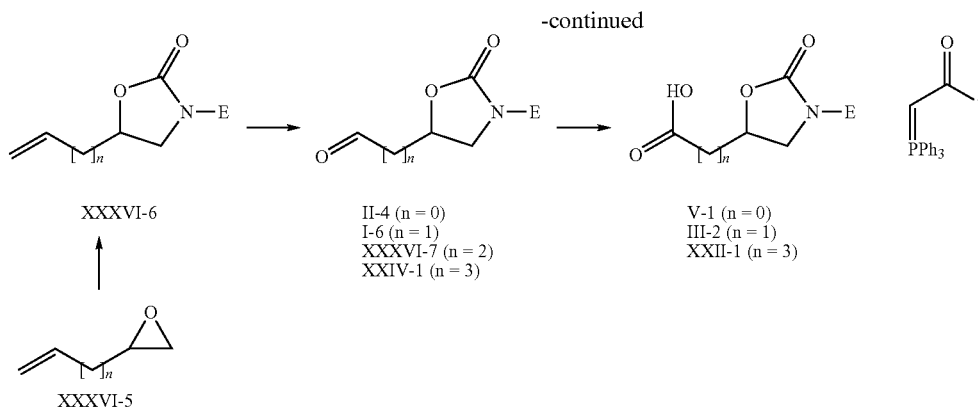

In Scheme 36, E is as defined in formula I, $R^\alpha$ is alkyl or arylalkyl, $R^\beta$ is mesyloxy, triflyloxy, tosyloxy or halogen such as bromine and n is an integer from 0 to 4.

Thus, the amine derivatives of formula I-2, II-2, XIX-3 or XXI-1 can be obtained (Scheme 36) from the corresponding epoxy derivatives of formula XXXVI-1 (which are either commercially available (n=0) or prepared according to WO 2004/106493 (n=1), WO 98/33786 (n=2) or WO 2006/032882 (n=3)). The epoxy derivatives can be reacted with the anion of the carbamates of formula V (reaction technique 2). The resulting alcohols of formula I-6, II-5, XXXVI-2 or XXXVI-3 can then sequentially be transformed into their corresponding sulfonates, halogenides, azides and finally reduced to give the amines of formula I-2, II-2, XIX-3 or XXI-1.

The compounds of formula XXXc-3 can be obtained as summarised in Scheme 37 hereafter.

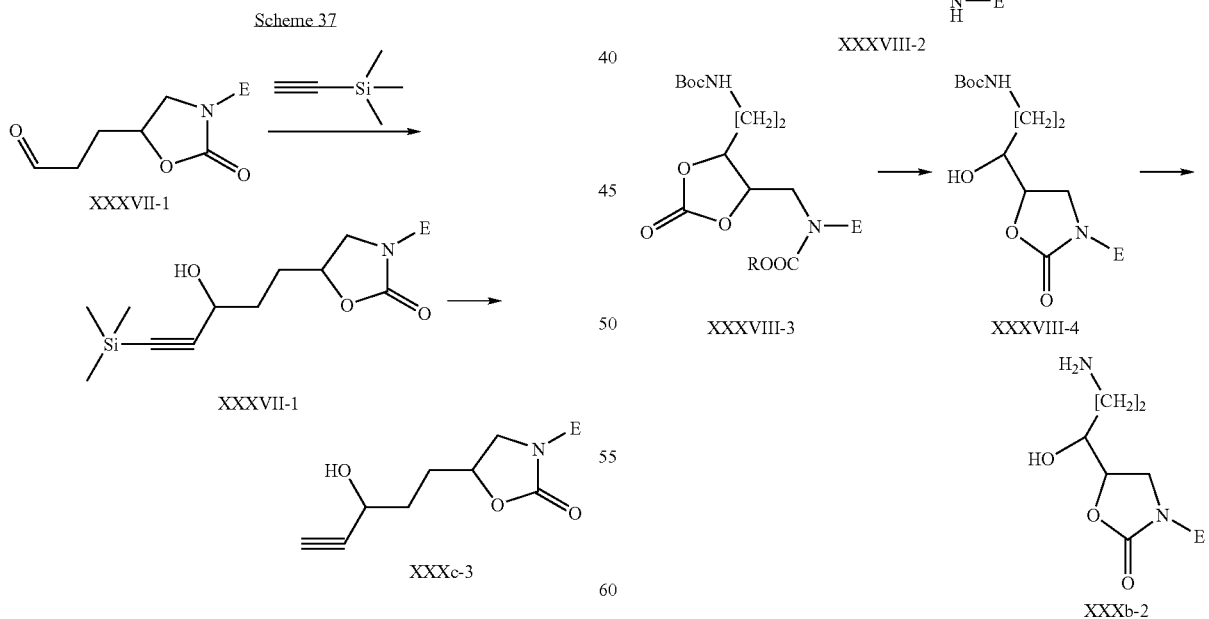

Thus, the compounds of formula XXXc-3 can be obtained (Scheme 37) by reaction of the aldehydes of formula XXXVII-1 with the anion generated from trimethylsilylacetylene. The intermediate silyl derivatives of formula XXXVII-2 can then converted into the compounds of formula XXXc-3 by treatment with $K_2CO_3$ in MeOH.

A possible preparation route for the compounds of formulae XXXa-1, XXX-2 and XXXe-5 is summarised in Scheme 38 hereafter.

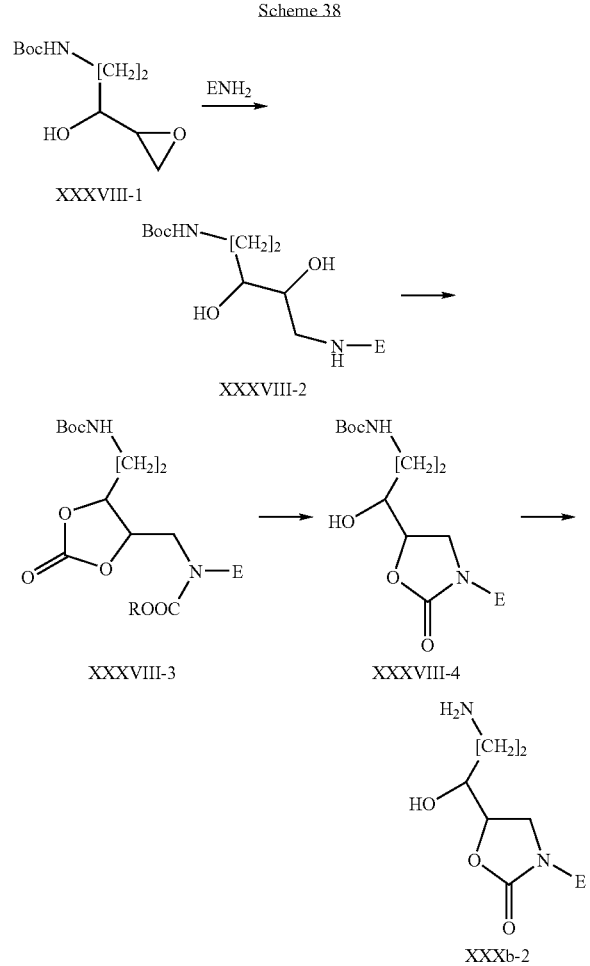

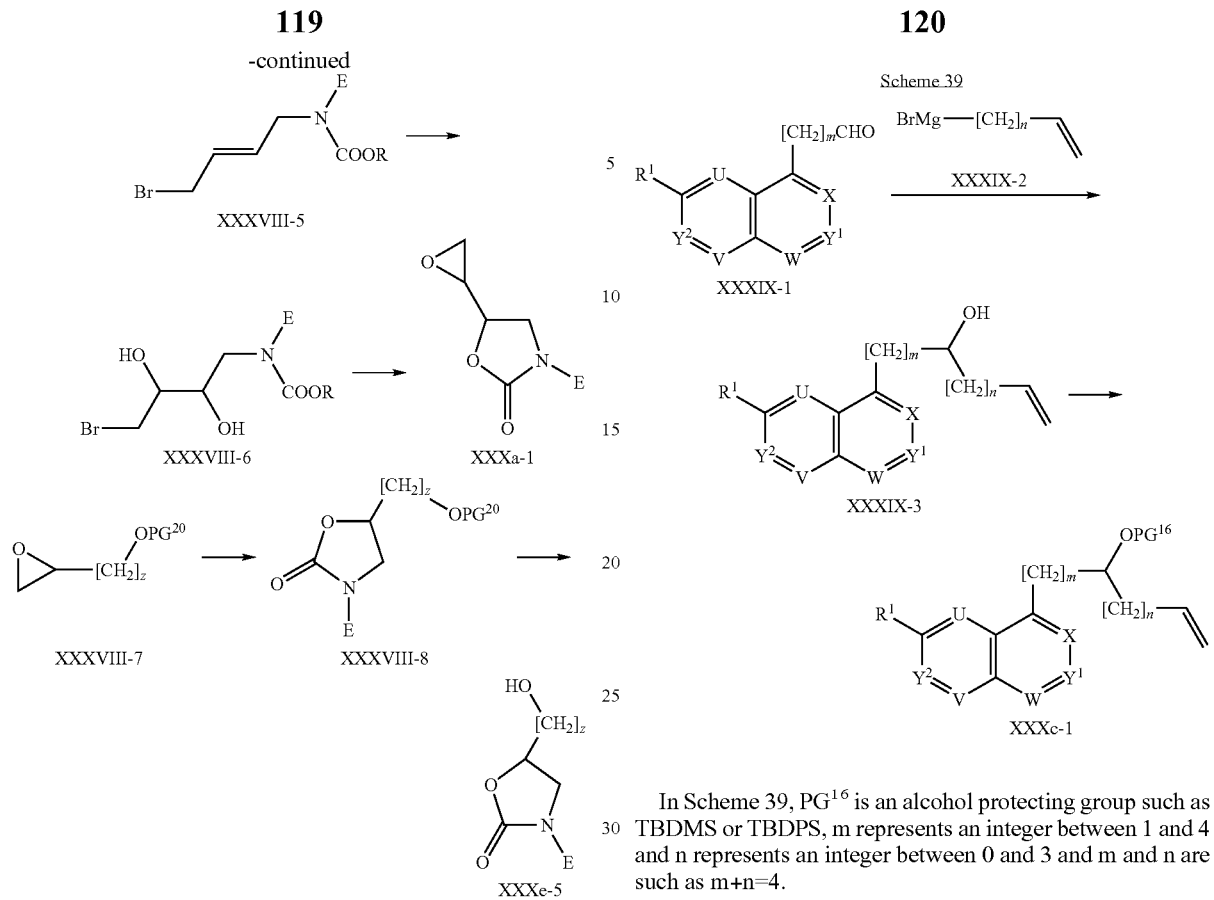

In Scheme 38, R represents alkyl or benzyl, z is the integer 3 or 4 and $PG^{20}$ is an alcohol protecting group such as TBDMS or TBDPS.

The epoxides of formula XXXVIII-1 can be reacted with the amines of formula $ENH_2$ and the resulting diols of formula XXXVIII-2 can then be transformed into cyclic carbonates by reaction with CDI. Their amine function can then be protected as a carbamate using reaction technique 1. The resulting carbonates of formula XXVIII-3 can be treated with a base such as $K_2CO_3$ in a solvent such MeOH, affording the corresponding oxazolidinones of formula XXVIII-4. Removal of the Boc protecting group using reaction technique 3 gives the amines of formula XXXb-2.

The compounds of formula XXXa-1 can be obtained starting from (E)-1,4-dibromobut-2-ene. The latter can be reacted with the anions generated from the carbamates of formula V as described in section b) above. The resulting intermediates of formula XXXVIII-5 can be cis-hydroxylated using reaction technique 14. The diols of formula XXXVIII-6 can then be treated with NaOMe, affording the epoxides of formula XXXa-1.

The compounds of formula XXXe-5 can be prepared by starting from the epoxides of formula XXXVIII-7 (prepared according to *Angew. Chem. Int. Ed.* (2007), 46(31), 5896-5900). The latter can be reacted with the anion generated from the carbamates of formula V as described in section b) above. The protecting group in the intermediates of formula XXXVIII-8 can then be removed using reaction technique 17.

The compounds of formula XXXc-1 can be obtained as summarised in Scheme 39 hereafter.

In Scheme 39, $PG^{16}$ is an alcohol protecting group such as TBDMS or TBDPS, m represents an integer between 1 and 4 and n represents an integer between 0 and 3 and m and n are such as m+n=4.

The aldehydes of formula XXXIX-1 were reacted with the Grignard reagents of formula XXXIX-2 in an anhydrous solvent such as ether and the resulting alcohols of formula XXXIX-3 were protected using reaction technique 23.

The aldehydes of formula XXXIX-1 wherein m is 0, 2 and 3 have been described earlier respectively as compounds of formulae VIII-3, II-1 and XXXb-1. The aldehydes of formula XXXIX-1 wherein m is 3 or 4 can be prepared as described in Scheme 40.

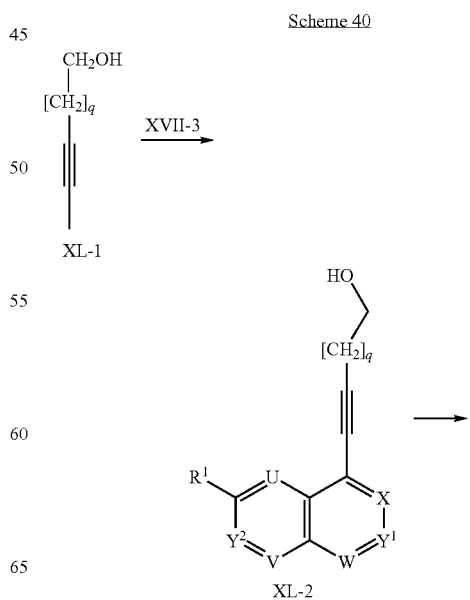

-continued

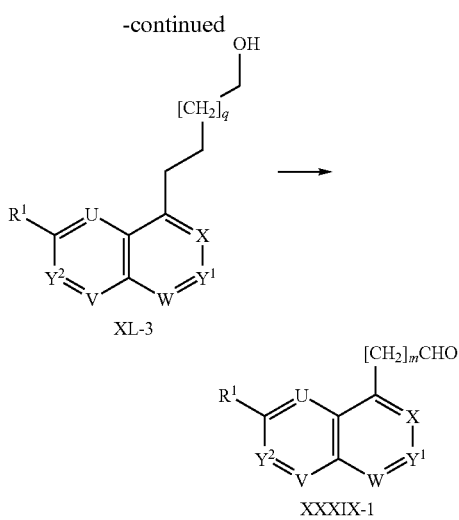

In Scheme 40, q represents 1, 2 or 3 and m represents 3 or 4.

The bromo derivatives of formula XVII-3 can be reacted (Scheme 40) with the acetylenic alcohol derivatives of formula XL-1 under Sonogashira conditions (as described in *Chem. Rev.* (2007); 107(3) 874-922) and the resulting intermediates of formula XL-2 can be hydrogenated over a noble metal catalyst. The resulting alcohol of formula XL-3 can be oxidized using reaction technique 18 to give the compounds of formula XXXIX-1.

The compounds of formula XXXc-5 can be obtained by Wittig olefination of the homologue of the aldehyde of formula XXXIX-1 (wherein m would be 5; obtainable in analogy to the route of Scheme 40) with methylenetriphenylphosphorane following reaction technique 12.

The compounds of formula IV-3 wherein $PG^1$ is benzyl are obtained by reductive amination of the amine of formula II-2 with benzaldehyde followed by acetylation with acetic acid anhydride or acetyl chloride.

The compounds of formula VIII-4 are obtained from the compounds of formula II-2 after subsequent reaction with bromacetylchloride and triphenylphosphine followed by the liberation of the phosphorane with an inorganic base such as $K_2CO_3$.

The acrylamides of formula VIII-5 are obtained by reaction of acrylic acid with the amines of formula II-2 (reaction technique 9).

The amides of formula XX-1 are obtained by reaction of an activated form of the acids of formula V-1 with the commercially available tert-butoxycarbonyl-1,2-ethanediamine with the carboxylic acids V-1 (reaction technique 9) followed by removal of the Boc protecting group.

The compounds of formula XVII-1 are obtained by reductive amination of the commercially available mono-Boc-ethylenediamine with the aldehydes of formula II-4 followed by removal of the Boc protecting group.

The phosphoranes of formula XXVI-4 are obtained by reaction the bromides of formula I-6 ($R^b$=Br) with $PPh_3$ followed by treatment with a base such as NaOH.

The compounds of formula XXX-1 are obtained by hydrostannation of the corresponding acetylenic compounds, the latter being obtained from the aldehydes XXXVI-7 and tetrachloromethane in presence of $PPh_3$ followed by treatment with n-BuLi (Corey Fuchs protocol; *Tetrahedron Letters* (1972), 3769).

The vinyl derivatives of formula I-1 can be prepared as described in WO 2006/002047, WO 02/08224, WO 2006/021448, WO 2004/058144 or WO 2004/02490.

The aldehydes of formula VIII-3 can be prepared as described in WO 2006/021448, WO 2006/046552, WO 2006/032466 or WO 01/00615.

The compounds of formula VIII-6 wherein $L^1$ is OTf can be prepared as described in WO 00/40554, WO 02/08224, WO 2004/002490 or WO2004/02992.

The compounds of formula XVII-3 can be prepared as described in WO 03/087098, WO 2006/105289, WO 2006/002047, WO 2006/021448 or WO 2004/058144.

The aldehydes of formula XIX-4 can be prepared by oxidation of the corresponding aldehydes of formula VIII-3.

The amine derivatives of formula XXI-3 can be obtained as described in WO 2006/046552, *J. Am. Chem. Soc.* (1949), 1901-1905, *J. Am. Chem. Soc.* (1946), 1553-1556, WO 99/58533, WO 96/33195 or WO 02/08224.

The epoxides of formula XXV-1 can be obtained as described in WO 00/78748, WO 2006/021448, WO 2004/002490, WO 2006/046552, WO 2006/021448 or WO 2006/046552.

Moreover, the alcohol of formula XXXe-1 can be prepared according to *J. Org. Chem.* (1989), 54(21), 5153-61.

Particular embodiments of the invention are described in the following Examples, which serve to illustrate the invention in more detail without limiting its scope in any way.

EXAMPLES

General Methods

Method A: Epoxide Opening:
A solution of epoxide (1 mmol) and aniline (1 mmol) in $EtOH/H_2O$ (9:1, 1 mL) is heated at 80° C. for 12 h. The volatiles are removed under reduced pressure and the residue purified by chromatography on $SiO_2$.

Method B: Oxazolidinone Formation with CDI:
A solution of amino alcohol (1 mmol) and CDI (1-2 eq.) in THF (2 mL) is heated at 50° C. until completion of the reaction. The mixture is partitioned between EA (20 mL) and water (20 mL), the organic phase washed with brine (20 mL), dried over $MgSO_4$ and concentrated.

Method C: Cbz-Protection of Anilines:
A mixture of aniline (1 mmol), sat. aq. $NaHCO_3$ (2 mL) and acetone (2 mL) is treated dropwise with Cbz-Cl (1 05 eq). After $CO_2$ evolvement ceased, the mixture is partitioned between EA and aq. bicarbonate, the organic layer dried over $MgSO_4$ and concentrated.

Method D: Oxazolidinones:
A solution of chlorohydrin (0.5 mmol) and Cbz-protected aniline (0.5 mmol, prepared according to Method C) in DMF (2 mL) is treated with t-BuOLi (0.68 mL of a 2.2M solution in THF, 3 eq). The mixture is stirred at rt until completion of reaction, diluted with EA and washed with water. The organic layer is concentrated. Purification by chromatography on $SiO_2$ (EA/MeOH 9:1+1% $NH_4OH$) gives the corresponding oxazolidinone.

Method E: Boc Deprotection:
The Boc-protected amine (1 mmol) is dissolved in DCM (5 mL) and treated with TFA (2 mL). The mixture is stirred at rt for 1 h, concentrated in vacuo and taken up in $DCM/NH_4OH$. The org. layer is washed with water, dried over $MgSO_4$ and concentrated.

Method F: Ester Saponification:
LiOH monohydrate (1.5 eq) is added to a solution of ester (1 mmol) in THF/MeOH/water (2:2:1, 3 mL). The mixture is stirred at rt until completion of reaction. The pH of the mixture is adjusted to 3 and the product either isolated by filtration or by extraction with EA.

Method G: Heck Coupling:

A solution of aromatic halide (1 mmol) and acrylic ester or amide (1 eq.; in case of ethyl acrylate, a 5-fold excess is used) in DMF (3 mL) was degassed and treated with TEA (3 eq.), Pd(OAc)$_2$ (0.033 eq.) and P(o-Tol)$_3$ (0.1 eq.). The mixture was heated at 100° C. until completion of reaction. The product was isolated after aqueous workup.

Method H: Amide Coupling Using Propylphosphonic Anhydride:

A solution of acid (1 mmol) and amine (1 mmol) in DMF (5 mL) at 0° C. is treated sequentially with TEA (3 eq.) and a 50% solution of propylphosphonic anhydride in EA (1.05 eq.). The mixture is stirred at rt until completion of reaction. The product is isolated after aqueous workup (EA/water).

Method I: Amide Coupling Using HOBT/EDC:

EDC (1.1 eq.) is added to a solution of acid (1 eq.), amine (1 eq.), DIPEA (2 eq.) and HOBT (1.1 eq.) in DMF (15 mL/mmol) at rt. The mixture is stirred until complete conversion. Aqueous workup (EA/water) followed by crystallization yielded the coupling product.

Method J: Reductive Amination I:

A solution of the amine (1 mmol) and the aldehyde or ketone (1 mmol) in 1,2-DCE/MeOH 1:1 (10 mL) is stirred at rt overnight. NaBH$_4$ (2-5 eq.) is added and the reaction allowed to proceed for another hour. The reaction is diluted with DCM and aq. NH$_4$OH. The org. phase is washed with water, dried over MgSO$_4$ and concentrated.

Method K: Reductive Amination II:

A solution of the amine (1 mmol) and the aldehyde or ketone (1 mmol) in DCE/MeOH 1:1 (10 mL) is treated with NaBH(OAc)$_3$ (2 eq). The mixture is stirred at rt until complete conversion. The reaction is diluted with DCM and aq. NH$_4$OH. The org. phase is washed with water, dried over MgSO$_4$ and concentrated.

Method L: Asymmetric Dihydroxylation (Sharpless, AD-Mix β):

To a solution of the olefin (1 eq) in t-BuOH (4 mL/mmol) and water (4 mL/mmol) is added sequentially methanesulfonamide (1.1 eq.), K$_2$CO$_3$ (3 eq.), K$_3$Fe(CN)$_6$ (3 eq.), (DHQD)$_2$PHAL (0.002 eq.) and K$_2$OsO$_4$ (0.001 eq.). The mixture is vigorously stirred at rt until complete conversion. The reaction is then quenched by the careful, portion wise addition of sodium bisulfite (1 g/mmol) and the phases are separated. The aqueous phase is extracted with EA and the combined org. layers washed with water and brine, dried over MgSO$_4$ and concentrated.

Example 1

(E)-[(S)-3-(2,3-dihydro-benzo[1,4]dioxin-6-yl)-2-oxo-oxazolidin-5-ylmethyl]-3-(6-methoxy-[1,5]naphthyridin-4-yl)-acrylamide 1.i. (R)-3-(2,3-dihydro-benzo[1,4]dioxin-6-yl)-5-hydroxymethyl-oxazolidin-2-one A solution of (2,3-dihydro-benzo[1,4]dioxin-6-yl)-carbamic acid benzyl ester (3.0 g, 10.5 mmol, prepared according to method C) in THF (60 mL) was cooled to −78° C. before the dropwise addition of n-BuLi (5.1 mL of a 2.5M solution in hexanes, 1.2 eq.). The mixture was stirred at −78° C. for 1 h and then warmed to −15° C. At this temperature (R)-glycidyl butyrate (1.98 g, 1.2 eq.) was added dropwise. The mixture was stirred at rt overnight. Cs$_2$CO$_3$ (tip of a spatula) was added and the mixture heated at 40° C. until complete conversion. The mixture was diluted with EA and washed with sat. NH$_4$Cl solution and water. The org. layer was dried over MgSO$_4$ and concentrated. Chromatography on SiO$_2$ (Hex/EA 2:1, 1:1) gave the desired intermediate as a beige solid (1.09 g, 41% yield).

$^1$H NMR (DMSO d6) δ: 7.13 (d, J=2.5 Hz, 1H), 6.96 (dd, J=2.5, 8.9 Hz, 1H), 6.86 (d, J=8.9 Hz, 1H), 5.16 (t, J=5.8 Hz, 1H), 4.70-4.50 (m, 1H), 4.30-4.10 (m, 4H), 4.10-3.90 (m, 1H), 4.80-4.70 (m, 1H), 4.70-4.60 (m, 1H), 4.60-4.50 (m, 1H).

1.ii. Methanesulfonic acid (R)-3-(2,3-dihydro-benzo[1,4]dioxin-6-yl)-2-oxo-oxazolidin-5-ylmethyl ester A solution of intermediate 1.i (1 g, 4 mmol) in DCM (20 mL) was cooled to 0° C. DIPEA (0.62 g, 1.2 eq.) and MsCl (0.502 g, 1.1 eq) were added and the mixture stirred at 0° C. for 1 h. The mixture was diluted with DCM and washed with water. The org. phase was dried over MgSO$_4$ and concentrated to give the title mesylate as a colourless solid (1.26 g, 97% yield) which was used in the next step without further purification.

MS (ESI, m/z): 329.8 [M+H$^+$].

1.iii. (R)-5-azidomethyl-3-(2,3-dihydro-benzo[1,4]dioxin-6-yl)-oxazolidin-2-one

A solution of intermediate 1.ii (1.26 g, 3.8 mmol) in DMF (20 mL) was treated with NaN$_3$ (0.3 g, 1.2 eq.) and the mixture heated at 80° C. overnight. The mixture was cooled and partitioned between ether and water. The org. phase was washed with water and brine, dried over MgSO$_4$ and concentrated to give the desired azide as a colourless solid (0.95 g, 90% yield).

MS (ESI, m/z): 277.1 [M+H$^+$].

1.iv. (S)-5-aminomethyl-3-(2,3-dihydro-benzo[1,4]dioxin-6-yl)-oxazolidin-2-one

A solution of intermediate 1.iii (0.95 g, 3.4 mmol) in EtOH/THF (1:1, 40 mL) was hydrogenated over Pd(OH)$_2$ (0.18 g, 0.1 eq.) under 1 bar of H$_2$ for 3 h. The catalyst was filtered off and the filtrate concentrated in vacuo to give the desired amine as a colourless solid (0.62 g, 72% yield).

$^1$H NMR (DMSO d6) δ: 7.12 (d, J=2.5 Hz, 1H), 6.98 (dd, J=2.5, 8.9 Hz, 1H), 6.86 (d, J=8.9 Hz, 1H), 4.60-4.50 (m, 1H), 4.30-4.10 (m, 4H), 3.99 (t, J=8.8 Hz, 1H), 3.79 (dd, J=6.5, 8.8 Hz, 1H), 3.90-3.75 (m, 2H).

MS (ESI, m/z): 251.0 [M+H$^+$].

1.v. (E)-3-(6-methoxy-[1,5]naphthyridin-4-yl)-acrylic acid ethyl ester

Triethylphosphonoacetate (7.3 g, 32.6 mmol) was added to a suspension of a NaH dispersion (1.4 g, 32.5 mmol, 55% in paraffin) in THF (40 mL) at 0° C. The mixture was stirred at 0° C. for 20 min before the dropwise addition of 6-methoxy-[1,5]naphthyridine-4-carbaldehyde (4.0 g, 21.3 mmol; prepared as in WO 2006/032466) in THF. The mixture was stirred at rt for 5 h, diluted with water and EA. The phases were separated and the aq. phase extracted with EA (2 times 50 mL). The combined org. phases were washed with brine, dried over MgSO$_4$ and concentrated. The residue was purified by chromatography on SiO$_2$ (Hex/EA 1:1) to give the desired alkene as a colourless solid (3.0 g, 56% yield).

MS (ESI, m/z): 258.9 [M+H$^+$].

1.vi. (E)-3-(6-methoxy-[1,5]naphthyridin-4-yl)-acrylic acid

Intermediate 1.v (0.75 g, 2.9 mmol) was hydrolysed according to method F to give the desired acid as a colourless solid (0.56 g, 85% yield).

$^1$H NMR (DMSO d6) δ: 12.8 (br, 1H), 8.83 (d, J=4.4 Hz, 1H), 8.50 (d, J=16.3 Hz, 1H), 8.31 (d, J=9.1 Hz, 1H), 8.06 (d, J=4.4 Hz, 1H), 7.33 (d, J=9.1 Hz, 1H), 7.12 (d, J=16.3 Hz, 1H), 4.07 (s, 3H).

MS (ESI, m/z): 231.2 [M+H$^+$].

1.vii. (E)-[(S)-3-(2,3-dihydro-benzo[1,4]dioxin-6-yl)-2-oxo-oxazolidin-5-ylmethyl]-3-(6-methoxy-[1,5]naphthyridin-4-yl)-acrylamide Intermediates 1.vi (0.57 g, 2.5 mmol) and 1.iv (0.62 g, 2.5 mmol) were coupled according to method H. After workup, the residue was crystallised from ether/MeOH (9:1), filtered and dried at HV to give the title compound as a colourless solid (0.66 g, 57% yield).

MS (ESI, m/z): 462.9 [M+H$^+$].

Example 2

(E)-[(S)-3-(2,3-dihydro-benzo[1,4]dioxin-6-yl)-2-oxo-oxazolidin-5-ylmethyl]-3-(6-methoxy-quinolin-4-yl)-acrylamide

2.i. (E)-3-(6-methoxy-quinolin-4-yl)-acrylic acid ethyl ester

This compound was synthesised from 4-bromo-6-methoxy-quinoline (1.73 g, 7.2 mmol; prepared as in WO 03/087098) and ethyl acrylate (5 eq.) according to method G. The product was isolated after chromatography on SiO$_2$ (Hex/EA 2:1) as a colourless solid (1.6 g, 87% yield).

$^1$H NMR (DMSO d6) δ: 8.76 (d, J=4.6 Hz, 1H), 8.39 (d, J=15.8 Hz, 1H), 7.99 (d, J=9.9 Hz, 1H), 7.83 (d, J=4.6 Hz, 1H), 7.50-7.40 (m, 2H), 6.89 (d, J=15.8 Hz, 1H), 4.27 (q, J=7.1 Hz, 2H), 3.97 (s, 3H), 1.31 (t, J=7.1 Hz, 3H).

2.ii. (E)-3-(6-methoxy-quinolin-4-yl)-acrylic acid

Intermediate 2.i (1.63 g, 6.3 mmol) was hydrolysed according to method F to give the desired acid as a yellowish solid (1.33 g, 92% yield).

MS (ESI, m/z): 230.1 [M+H$^+$].

2.iii. (E)-[(S)-3-(2,3-dihydro-benzo[1,4]dioxin-6-yl)-2-oxo-oxazolidin-5-ylmethyl]-3-(6-methoxy-quinolin-4-yl)-acrylamide This compound was obtained according to method H starting from intermediate 2.ii (0.31 g, 1.35 mmol) and intermediate 1.iv (0.34 g, 1.25 mmol). The product was isolated after crystallization from ether/MeOH (9:1) and obtained as a beige solid (0.29 g, 46% yield).

$^1$H NMR (DMSO d6) δ: 8.80-8.70 (m, 2H), 8.15 (d, J=15.7 Hz, 1H), 7.98 (d, J=9.4 Hz, 1H), 7.62 (d, J=4.5 Hz, 1H), 7.50-7.40 (m, 2H), 7.11 (d, J=2.5 Hz, 1H), 6.95-6.80 (m, 3H), 4.60-4.50 (m, 1H), 4.30-4.00 (m, 5H), 3.96 (s, 3H), 3.77 (dd, J=6.4, 9.1 Hz, 1H), 3.65-3.55 (m, 2H).

MS (ESI, m/z): 462.1 [M+H$^+$].

Example 3

(E)-[(R)-3-(2,3-dihydro-benzo[1,4]dioxin-6-yl)-2-oxo-oxazolidin-5-ylmethyl]-3-(6-methoxy-[1,5]naphthyridin-4-yl)-acrylamide

3.i. (R)-5-aminomethyl-3-(2,3-dihydro-benzo[1,4]dioxin-6-yl)-oxazolidin-2-one This amine was prepared starting from (2,3-dihydro-benzo[1,4]dioxin-6-yl)-carbamic acid benzyl ester (5.0 g, 17.5 mmol) and (S)-glycidyl butyrate (3.02 g, 1.1 eq) and using the procedure of Example 1, steps 1.i to 1.iv. The title amine was isolated as a beige solid (0.66 g).

$^1$H NMR (DMSO d6) δ: 7.12 (d, J=2.5 Hz, 1H), 6.98 (dd, J=2.5, 8.9 Hz, 1H), 6.86 (d, J=8.9 Hz, 1H), 4.60-4.50 (m, 1H), 4.30-4.10 (m, 4H), 3.99 (t, J=8.8 Hz, 1H), 3.79 (dd, J=6.5, 8.8 Hz, 1H), 3.90-3.75 (m, 2H).

MS (ESI, m/z): 251.0 [M+H$^+$].

3.ii. (E)-[(R)-3-(2,3-dihydro-benzo[1,4]dioxin-6-yl)-2-oxo-oxazolidin-5-ylmethyl]-3-(6-methoxy-[1,5]naphthyridin-4-yl)-acrylamide The title compound was obtained according to method H starting from intermediate 3.i (0.35 g, 1.4 mmol) and intermediate 1.vi (0.33 g, 1.14 mmol). The product was isolated after crystallization from ether/MeOH (9:1) and obtained as a beige solid (0.2 g, 31% yield).

MS (ESI, m/z): 462.8 [M+H$^+$].

Example 4

(E)-3-(6-methoxy-[1,5]naphthyridin-4-yl)-N-[(R)-2-oxo-3-(3-oxo-3,4-dihydro-2H-benzo[1,4]thiazin-6-yl)-oxazolidin-5-ylmethyl]-acrylamide

4.i. (R)-3-chloro-2-hydroxy-propyl)-carbamic acid tert-butyl ester

This intermediate (25.6 g, 45% yield) was prepared according to the literature (Org. Process Research and Development (2003), 7, 533-546) starting from (R)-epichlorohydrin (25 g, 270 mmol).

$^1$H NMR (CDCl$_3$) δ: 4.95 (br, 1H), 4.00-3.80 (m, 1H), 3.60-3.50 (m, 2H), 3.50-3.35 (m, 2H), 3.30-3.20 (m, 1H), 1.42 (s, 9H).

4.ii. (R)-1-oxiranylmethyl-carbamic acid tert-butyl ester

NaOMe (1.9 g, 34.9 mmol) was added to a solution of intermediate 4.i (3.66 g, 17.4 mmol) in MeOH. The mixture was stirred at rt 6 h, concentrated in vacuo and partitioned between water and ether. The org. layer was washed with sat. NH$_4$Cl solution, dried over MgSO$_4$ and concentrated to give the title epoxide as a colourless oil (1.38 g, 45% yield).

$^1$H NMR (DMSO d6) δ: 4.71 (br, 1H), 3.52 (m, 1H), 3.21 (m, 1H), 3.08 (m, 1H), 2.77 (m, 1H), 1.42 (s, 9H).

4.iii. [(S)-2-hydroxy-3-(3-oxo-3,4-dihydro-2H-benzo[1,4]thiazin-6-ylamino)-propyl]-carbamic acid tert-butyl ester This amino alcohol is synthesized according to method A starting from intermediate 4.ii (0.78 g, 4.5 mmol) and 6-amino-4H-benzo[1,4]thiazin-3-one (0.68 g, 4.5 mmol). The compound was isolated after chromatography on SiO$_2$ (Hex/EA 2:1, 1:1, 1:2) as a beige foam (1.08 g, 68% yield).
MS (ESI, m/z): 354.2 [M+H$^+$].

4.iv. [(R)-2-oxo-3-(3-oxo-3,4-dihydro-2H-benzo[1,4]thiazin-6-yl)-oxazolidin-5-ylmethyl]-carbamic acid tert-butyl ester A solution of intermediate 4.iii. (1.5 g, 4.2 mmol) and CDI (0.78 g, 1.1 eq.) in THF was stirred at rt for 3 h. The mixture was then heated at 50° C. for 2 h. 1 eq. of NaH was added and the mixture stirred at rt overnight. The mixture was concentrated in vacuo, partitioned between EA and water, the org. layer was washed with brine, dried over MgSO$_4$ and concentrated. Chromatography on SiO$_2$ (hex/EA 1:2) gave the title oxazolidinone (0.68 g, 38% yield) as a pink foam.
$^1$H NMR (DMSO d6) δ: 10.56 (s, 1H), 7.30 (m, 2H), 7.18 (m, 1H), 7.08 (dd, J=8.5, 2.3 Hz, 1H), 4.66 (m, 1H), 4.02 (m, 1H), 3.73 (dd, J=8.8, 6.2 Hz, 1H), 3.40 (s, 2H), 3.30-3.20 (m, 2H), 1.34 (s, 9H).
MS (ESI, m/z): 278.2 [M−H$^+$].

4.v. 6-((R)-5-aminomethyl-2-oxo-oxazolidin-3-yl)-4H-benzo[1,4]thiazin-3-one

The Boc group of intermediate 4.iv (0.6 g, 1.58 mmol) was removed according to method E. The title amine was isolated as a beige foam (0.37 g, 85% yield).
MS (ESI, m/z): 280.2 [M+H$^+$].

4.vi. (E)-3-(6-methoxy-[1,5]naphthyridin-4-yl)-N-[(R)-2-oxo-3-(3-oxo-3,4-dihydro-2H-benzo[1,4]thiazin-6-yl)-oxazolidin-5-ylmethyl]-acrylamide This compound is obtained starting from intermediate 4.v (0.2 g, 0.72 mmol) and intermediate 1.vi. (0.164 g, 0.72 mmol) and using method H. The product was isolated after crystallization from ether/MeOH (9:1) and obtained as a colourless solid (0.167 g, 47% yield).
$^1$H NMR (DMSO d6) δ: 10.54 (s, 1H), 8.80 (d, J=4.7 Hz, 1H), 8.71 (m, 1H), 8.31 (m, 2H), 7.84 (d, J=4.7 Hz, 1H), 7.05-7.25 (m, 5H), 4.80-4.90 (m, 1H), 4.20-4.00 (m, 4H), 3.76 (m, 1H), 3.61 (m, 2H), 3.40 (s, 2H).

Example 5

(E)-N-[(R)-3-(2,3-dihydro-benzo[1,4]dioxin-6-yl)-2-oxo-oxazolidin-5-ylmethyl]-3-(3-methoxy-quinoxalin-5-yl)-acrylamide 5.i. (E)-3-(3-methoxy-quinoxalin-5-yl)-acrylic acid The title acid was obtained starting from 3-methoxy-quinoxaline-5-carbaldehyde (4 g, 21.2 mmol; prepared as in WO 2006/021448) and using the procedure of Example 1, steps 1.v to 1.vi. It was isolated as a beige solid (2.9 g).
$^1$H NMR (DMSO d6) δ: 12.49 (s, 1H), 8.67 (s, 1H), 8.53 (d, J=16.3 Hz, 1H), 8.24 (d, J=7.5 Hz, 1H), 8.07 (d, J=8.3 Hz, 1H), 7.68 (t, J=7.8 Hz, 1H), 6.92 (d, J=16.3 Hz, 1H), 4.10 (s, 3H).

5.ii. (E)-N-[(R)-3-(2,3-dihydro-benzo[1,4]dioxin-6-yl)-2-oxo-oxazolidin-5-ylmethyl]-3-(3-methoxy-quinoxalin-5-yl)-acrylamide Following the general method I and starting from intermediate 5.i (0.082 g, 0.36 mmol) and intermediate 3.i (0.1 g, 0.36 mmol), the title compound was isolated as a beige solid (0.058 g, 51% yield).
$^1$H NMR (DMSO d6) δ: 8.65 (s, 1H), 8.59 (m, 1H), 8.36 (d, J=15.8 Hz, 1H), 8.02 (m, 2H), 7.67 (t, J=7.9 Hz, 1H), 7.06 (m, 2H), 6.94 (dd, J=8.8, 2.3 Hz, 1H), 6.83 (m, 1H), 4.78 (m, 1H), 4.25-4.00 (m, 8H), 3.73 (m, 1H), 3.57 (t, J=5.6 Hz, 3H).
MS (ESI, m/z): 463.2 [M+H$^+$].

Example 6

(E)-N-[(R)-3-(2,3-dihydro-benzo[1,4]dioxin-6-yl)-2-oxo-oxazolidin-5-ylmethyl]-3-(3-methoxy-quinolin-5-yl)-acrylamide 6.i. (E)-3-(3-methoxy-quinolin-5-yl)-acrylic acid The desired intermediate was synthesised from 5-bromo-3-methoxy-quinoline (5.0 g, 21 mmol; prepared as in DE 10316081) and ethyl acrylate (5 eq.) according to general method G. The hydrolysis was carried out according to method F. The product was isolated as a colourless solid (0.83 g).
$^1$H NMR (DMSO d6) δ: 8.69 (d, J=2.9 Hz, 1H), 8.35 (d, J=15.8 Hz, 1H), 8.01 (m, 2H), 7.84 (d, J=2.9 Hz, 1H), 7.60 (m, 1H), 6.62 (d, J=15.8 Hz, 1H), 4.02 (s, 3H).

6.ii. (E)-N-[(R)-3-(2,3-dihydro-benzo[1,4]dioxin-6-yl)-2-oxo-oxazolidin-5-ylmethyl]-3-(3-methoxy-quinolin-5-yl)-acrylamide The title compound is obtained according to method H starting from intermediate 6.i (0.092 g, 0.4 mmol) and intermediate 3.i (0.1 g, 0.4 mmol). The product was isolated after chromatography on SiO$_2$ (EA) and obtained as a colourless solid (0.038 g, 21% yield).
$^1$H NMR (DMSO d6) δ: 8.68 (d, J=2.6 Hz, 1H), 8.61 (m, 1H), 8.17 (d, J=15.8 Hz, 1H), 7.98 (d, J=8.2 Hz, 1H), 7.81 (m, 2H), 7.61 (m, 1H), 7.09 (d, J=2.6 Hz, 1H), 6.94 (m, 1H), 6.82 (m, 2H), 4.78 (m, 1H), 4.19 (m, 4H), 4.10 (t, J=9.1 Hz, 1H), 4.00 (m, 3H), 3.74 (m, 1H), 3.59 (t, J=5.6 Hz, 2H).
MS (ESI, m/z): 462.1 [M+H$^+$].

Example 7

(E)-N-[(R)-3-(2,3-dihydro-benzo[1,4]dioxin-6-yl)-2-oxo-oxazolidin-5-ylmethyl]-N-ethyl-3-(6-methoxy-[1,5]naphthyridin-4-yl)-acrylamide 7.i. (R)-3-(2,3-dihydro-benzo[1,4]dioxin-6-yl)-5-ethylaminomethyl-oxazolidin-2-one Intermediate 3.i (0.25 g, 1 mmol) was reacted according to method J with acetaldehyde. The target intermediate was obtained after chromatography on SiO$_2$ (EA, EA/MeOH 9:1+1% NH$_4$OH) as a colourless oil (0.17 g, 62% yield).
$^1$H NMR (DMSO d6) δ: 7.10 (d, J=2.6 Hz, 1H), 6.95 (m, 1H), 6.83 (m, 1H), 4.63 (m, 1H), 4.21 (m, 4H), 4.00 (m, 1H), 3.72 (dd, J=8.8, 6.7 Hz, 1H), 2.77 (d, J=5.6 Hz, 2H), 2.56 (q, J=7.0 Hz, 2H), 0.98 (t, J=7.0 Hz, 3H).

7.ii. (E)-N-[(R)-3-(2,3-dihydro-benzo[1,4]dioxin-6-yl)-2-oxo-oxazolidin-5-ylmethyl]-N-ethyl-3-(6-methoxy-[1,5]naphthyridin-4-yl)-acrylamide The title compound is obtained according to method H starting from intermediate 7.i (0.085 g, 0.3 mmol) and intermediate 1.vi (0.07 g, 0.3 mmol). The product was isolated after chromatography on SiO$_2$ (EA, EA/MeOH 9:1+1% NH$_4$OH) and obtained as a colourless foam (0.095 g, 63% yield).
MS (ESI, m/z): 490.9 [M+H$^+$].

Example 8

(E)-N-benzyl-N-[(RS)-3-(2,3-dihydro-benzo[1,4] dioxin-6-yl)-2-oxo-oxazolidin-5-ylmethyl]-3-(6-methoxy-[1,5]naphthyridin-4-yl)-acrylamide

8.i. (R)-5-(benzylamino-methyl)-3-(2,3-dihydro-benzo[1,4]dioxin-6-yl)-oxazolidin-2-one Intermediate 3.i (0.25 g, 1 mmol) was reacted according to method J with benzaldehyde. The target intermediate was obtained after chromatography on SiO$_2$ (EA, EA/MeOH 9:1+1% NH$_4$OH) as a colourless oil (0.33 g, 97% yield)
$^1$H NMR (DMSO d6) δ: 7.26 (m, 5H), 7.09 (d, J=2.6 Hz, 1H), 6.94 (m, 1H), 6.83 (m, 1H), 4.67 (m, 1H), 4.20 (m, 4H), 4.00 (m, 1H), 3.73 (m, 3H), 2.75 (d, J=5.3 Hz, 2H), 2.38 (s, 1H).

8.ii. (E)-N-benzyl-N-[(RS)-3-(2,3-dihydro-benzo[1,4]dioxin-6-yl)-2-oxo-oxazolidin-5-ylmethyl]-3-(6-methoxy-[1,5]naphthyridin-4-yl)-acrylamide This compound was obtained according to method H starting from above intermediate 8.i (0.1 g, 0.3 mmol) and intermediate 1.vi (0.07 g, 0.3 mmol). The product was isolated after chromatography on SiO$_2$ (EA) and obtained as a colourless foam (0.071 g, 43% yield).
MS (ESI, m/z): 553.3 [M+H$^+$].

Example 9

(E)-3-(3-methoxy-quinoxalin-5-yl)-N-[(R)-2-oxo-3-(3-oxo-3,4-dihydro-2H-benzo[1,4]thiazin-6-yl)-oxazolidin-5-ylmethyl]-acrylamide The title compound was obtained according to method H starting from intermediate 5.i (0.07 g, 0.3 mmol) and intermediate 4.v (0.085 g, 0.3 mmol). The product was isolated after crystallization from ether/MeOH (0.088 g, 59% yield).
$^1$H NMR (DMSO d6) δ: 10.54 (s, 1H), 8.65 (d, J=0.9 Hz, 1H), 8.59 (m, 1H), 8.36 (d, J=16.1 Hz, 1H), 8.02 (d, J=7.9 Hz, 2H), 7.66 (m, 1H), 7.29 (m, 2H), 7.08 (m, 2H), 4.82 (m, 1H), 4.07 (m, 4H), 3.76 (dd, J=9.1, 6.4 Hz, 1H), 3.60 (t, J=5.0 Hz, 2H), 3.38 (s, 2H).

Example 10

(E)-3-(3-methoxy-quinolin-5-yl)-N-[(R)-2-oxo-3-(3-oxo-3,4-dihydro-2H-benzo[1,4]thiazin-6-yl)-oxazolidin-5-ylmethyl]-acrylamide The title compound was obtained according to method H starting from intermediate 6.i (0.07 g, 0.3 mmol) and intermediate 4.v (0.085 g, 0.3 mmol). The product was isolated after crystallization from ether/MeOH (0.05 g, 33% yield).
$^1$H NMR (DMSO d6) δ: 10.55 (s, 1H), 8.68 (s, 1H), 8.61 (m, 1H), 8.17 (d, J=16.1 Hz, 1H), 7.98 (d, J=8.5 Hz, 1H), 7.81 (m, 2H), 7.60 (m, 1H), 7.30 (m, 2H), 7.10 (m, 1H), 6.77 (d, J=15.5 Hz, 1H), 4.83 (m, 1H), 4.2-4.0 (m, 1H), 4.0 (s, 3H), 3.77 (m, 1H), 3.62 (m, 2H), 3.60 (s, 2H).

Example 11

(E)-3-(6-methoxy-[1,5]naphthyridin-4-yl)-N-methyl-N-[(R)-2-oxo-3-(3-oxo-3,4-dihydro-2H-benzo[1,4]thiazin-6-yl)-oxazolidin-5-ylmethyl]-acrylamide

11.i. ((R)-3-chloro-2-hydroxy-propyl)-methyl-carbamic acid tert-butyl ester A 2M solution of methylamine in THF (32 mL, 65 mmol) was added to a solution of (R)-epichlorohydrin (5 g, 54 mmol) in EtOH (15 mL). The flask was sealed and heated at 40° C. overnight. The mixture was concentrated under reduced pressure, taken up in EA (100 mL) and Boc$_2$O (14.1 g, 65 mmol) and TEA (9 mL, 65 mmol) were added. The mixture was stirred at rt for 2 h, diluted with EA (100 mL) and washed with 1M HCl (100 mL) and brine, dried over MgSO$_4$ and concentrated. The residue was purified by chromatography on SiO$_2$ (Hept/EA 9:1, 2:1) to give the desired chlorohydrin (3.44 g, 28% yield) as a colourless liquid.
$^1$H NMR (CDCl$_3$) δ: 4.15 (br, 1H), 3.99 (m, 1H), 3.52 (m, 2H), 3.44 (m, 2H), 2.95 (s, 3H), 1.46 (s, 9H).

11.ii. Methyl-[(R)-2-oxo-3-(3-oxo-3,4-dihydro-2H-benzo[1,4]thiazin-6-yl)-oxazolidin-5-ylmethyl]-carbamic acid tert-butyl ester Starting from intermediate 11.i (0.448 g, 2 mmol) and (3-oxo-3,4-dihydro-2H-benzo[1,4]thiazin-6-yl)-carbamic acid benzyl ester (0.629 g, 2 mmol, prepared according to method C), the title oxazolidinone was prepared according to general method D and isolated after chromatography on SiO$_2$ (Hex/EA 1:1, EA) as a yellowish foam (0.35 g, 45% yield).
MS (ESI, m/z): 394.1 [M+H$^+$].

11.iii. 6-((R)-5-methylaminomethyl-2-oxo-oxazolidin-3-yl)-4H-benzo[1,4]thiazin-3-one The Boc group of intermediate 11.ii (0.35 g, 0.89 mmol) was removed according to method E. The title amine was isolated as a beige foam (0.24 g, 92% yield).
MS (ESI, m/z): 294.2 [M+H$^+$].

11.iv. (E)-3-(6-methoxy-[1,5]naphthyridin-4-yl)-N-methyl-N-[(R)-2-oxo-3-(3-oxo-3,4-dihydro-2H-benzo[1,4]thiazin-6-yl)-oxazolidin-5-ylmethyl]-acrylamide The title compound was obtained according to method H starting from intermediate 11.iii (0.12 g, 0.4 mmol) and intermediate 1.vi (0.094 g, 0.4 mmol). The product was isolated after chromatography on SiO$_2$ (EA/MeOH 9:1+1% NH$_4$OH) followed by crystallization from ether/MeOH (0.084 g, 41% yield).
MS (ESI, m/z): 506.2 [M+H$^+$].

Example 12

(E)-N-[(R)-3-(3-fluoro-4-methyl-phenyl)-2-oxo-oxazolidin-5-ylmethyl]-3-(6-methoxy-[1,5]naphthyridin-4-yl)-acrylamide

12.i. (R)-5-aminomethyl-3-(3-fluoro-4-methyl-phenyl)-oxazolidin-2-one

The intermediate amine (0.8 g, yellowish solid) was obtained starting from (3-fluoro-4-methyl-phenyl)-carbamic acid benzyl ester (1.3 g, 5 mmol) and intermediate 4.i (1.57 g, 7.5 mmol) following sequentially methods C, D and E.
$^1$H NMR (CDCl$_3$) δ: 7.32 (m, 1H), 7.14 (m, 2H), 4.66 (m, 1H), 4.01 (t, J=8.8 Hz, 1H), 3.81 (dd, J=8.8, 6.7 Hz, 1H), 3.10 (m, 1H), 2.97 (m, 1H), 2.24 (d, J=1.8 Hz, 4H).

12.ii. (E)-N-[(R)-3-(3-fluoro-4-methyl-phenyl)-2-oxo-oxazolidin-5-ylmethyl]-3-(6-methoxy-[1,5]naphthyridin-4-yl)-acrylamide The title compound was obtained according to method H starting from intermediate 12.i (0.091 g, 0.4 mmol) and intermediate 1.vi (0.094 g, 0.4 mmol). The product was isolated after chromatography on SiO$_2$ (EA/MeOH 9:1+1% NH$_4$OH) as a yellowish solid (0.099 g, 55% yield).
MS (ESI, m/z): 437.1 [M+H$^+$].

Example 13

(E)-N-[(R)-3-(3-fluoro-4-methyl-phenyl)-2-oxo-oxazolidin-5-ylmethyl]-3-(6-methoxy-[1,5]naphthyridin-4-yl)-N-methyl-acrylamide 13.i. (R)-3-(3-fluoro-4-methyl-phenyl)-5-methylaminomethyl-oxazolidin-2-one This amine (0.85 g, yellowish solid) was obtained starting from (3-fluoro-4-methyl-phenyl)-carbamic acid benzyl ester (1.3 g, 5 mmol) and intermediate 11.i (1.1 g, 5 mmol) following sequentially methods C, D and E.
$^1$H NMR (CDCl$_3$) δ: 7.36 (m, 1H), 7.13 (m, 2H), 4.73 (m, 1H), 4.01 (t, J=8.5 Hz, 1H), 3.82 (m, 1H), 2.88 (m, 1H), 2.49 (s, 3H), 2.23 (d, J=1.8 Hz, 2H).

13.ii. (E)-N-[(R)-3-(3-fluoro-4-methyl-phenyl)-2-oxo-oxazolidin-5-ylmethyl]-3-(6-methoxy-[1,5]naphthyridin-4-yl)-N-methyl-acrylamide The title compound was obtained according to method H starting from intermediate 13.i (0.097 g, 0.4 mmol) and intermediate 1.vi (0.094 g, 0.4 mmol). The product was isolated after crystallization from ether/MeOH as a colourless solid (0.133 g, 72% yield).
MS (ESI, m/z): 451.2 [M+H$^+$].

Example 14

(E)-N-[(R)-3-(4-ethyl-phenyl)-2-oxo-oxazolidin-5-ylmethyl]-3-(6-methoxy-[1,5]naphthyridin-4-yl)-N-methyl-acrylamide 14.i. (R)-3-(4-ethyl-phenyl)-5-methylaminomethyl-oxazolidin-2-one This amine (0.32 g, brownish solid) was obtained starting from (4-ethyl-phenyl)-carbamic acid benzyl ester (0.383 g, 1.5 mmol) and intermediate 11.i (0.336 g, 1.5 mmol) following sequentially methods C, D and E.
MS (ESI, m/z): 235.2 [M+H$^+$].

14.ii. (E)-N-[(R)-3-(4-ethyl-phenyl)-2-oxo-oxazolidin-5-ylmethyl]-3-(6-methoxy-[1,5]naphthyridin-4-yl)-N-methyl-acrylamide The title compound was obtained according to method I starting from intermediate 14.i (0.1 g, 0.43 mmol) and intermediate 1.vi (0.098 g, 0.43 mmol). The product was isolated after chromatography on SiO$_2$ (EA, EA/MeOH 9:1) as a yellowish oil (0.056 g, 29% yield).
MS (ESI, m/z): 447.0 [M+H$^+$].

Example 15

(E)-3-(6-methoxy-[1,5]naphthyridin-4-yl)-N-methyl-N-[(R)-2-oxo-3-(4-propyl-phenyl)-oxazolidin-5-ylmethyl]-acrylamide 15.i. (R)-5-methylaminomethyl-3-(4-propyl-phenyl)-oxazolidin-2-one This amine (0.27 g, yellowish solid) was obtained starting from (4-propyl-phenyl)-carbamic acid benzyl ester (0.404 g, 1.5 mmol) and intermediate 11.i. (0.336 g, 1.5 mmol) following sequentially methods C, D and E.
MS (ESI, m/z): 249.3 [M+H$^+$].

15.ii. (E)-3-(6-methoxy-[1,5]naphthyridin-4-yl)-N-methyl-N-[(R)-2-oxo-3-(4-propyl-phenyl)-oxazolidin-5-ylmethyl]-acrylamide The title compound was obtained according to method I starting from intermediate 15.i (0.1 g, 0.4 mmol) and intermediate 1.vi (0.093 g, 0.4 mmol). The product was isolated after chromatography on SiO$_2$ (EA, EA/MeOH 9:1) as a yellowish oil (0.056 g, 29% yield).
$^1$H NMR (DMSO d6) δ: 8.79 (d, J=4.7 Hz, 1H), 8.48 (d, J=15.5 Hz, 1H), 8.23 (d, J=8.8 Hz, 1H), 7.67 (m, 2H), 7.44 (m, 2H), 7.17 (m, 3H), 4.97 (m, 1H), 4.12 (m, 5H), 3.85 (dd, J=9.1, 7.0 Hz, 1H), 3.68 (dd, J=14.4, 6.7 Hz, 1H), 2.55 (m, 2H), 3.42 (s, 3H), 1.59 (m, 4H), 0.91 (t, J=7.3 Hz, 3H).
MS (ESI, m/z): 461.2 [M+H$^+$].

Example 16

(E)-3-(2-cyano-quinolin-8-yl)-N-[(R)-3-(2,3-dihydro-benzo[1,4]dioxin-6-yl)-2-oxo-oxazolidin-5-ylmethyl]-acrylamide 16.i. N-[(R)-3-(2,3-dihydro-benzo[1,4]dioxin-6-yl)-2-oxo-oxazolidin-5-ylmethyl]-acrylamide A solution of intermediate 3.i (1.0 g, 4 mmol) in DCM (20 mL) was cooled to 0° C. and TEA (0.44 g, 1.1 eq.) was added. A solution of acryloyl chloride (0.361 g, 1 eq.) in DCM (1 mL) was then added dropwise. The mixture was stirred at 0° C. for 1 h and at rt over night. The clear solution was diluted with DCM (50 mL) and washed with 0.1M HCl (2*50 mL), dried over MgSO$_4$ and concentrated. Chromatography on SiO$_2$ (EA, EA/MeOH 9:1+1% NH$_4$OH) gave the desired acrylamide (1.03 g, 85% yield) as a colourless foam.
$^1$H NMR (DMSO d6) δ: 8.45 (m, 1H), 7.07 (d, J=2.6 Hz, 1H), 6.92 (m, 1H), 6.83 (m, 1H), 6.25 (m, 1H), 6.09 (m, 1H), 5.60 (dd, J=10.0, 2.3 Hz, 1H), 4.70 (m, 1H), 4.21 (m, 4H), 4.05 (t, J=9.1 Hz, 1H), 3.67 (dd, J=9.1, 6.2 Hz, 1H), 3.48 (t, J=5.6 Hz, 2H).
MS (ESI, m/z): 305.3 [M+H$^+$].

16.ii. (E)-3-(2-cyano-quinolin-8-yl)-N-[(R)-3-(2,3-dihydro-benzo[1,4]dioxin-6-yl)-2-oxo-oxazolidin-5-ylmethyl]-acrylamide The title product was obtained according to method G starting from intermediate 16.i (0.2 g, 0.66 mmol) and trifluoro-methanesulfonic acid 2-cyano-quinolin-8-yl ester (0.2 g, 0.66 mmol, prepared as in WO 2004/002992). The product was isolated as a brownish solid (0.12 g, 40% yield) after crystallization from EA.

$^1$H NMR (DMSO d6) δ: 8.70 (d, J=8.5 Hz, 1H), 8.65 (m, 1H), 8.52 (d, J=16.1 Hz, 1H), 8.14 (m, 3H), 7.85 (m, 1H), 7.01 (m, 3H), 6.83 (m, 1H), 4.77 (m, 1H), 4.18 (m, 4H), 4.10 (t, J=9.1 Hz, 1H), 3.74 (dd, J=9.1, 6.2 Hz, 1H), 3.59 (t, J=5.3 Hz, 2H).

MS (ESI, m/z): 457.3 [M+H$^+$].

Example 17

(E)-N-[(R)-3-(2,3-dihydro-benzo[1,4]dioxin-6-yl)-2-oxo-oxazolidin-5-ylmethyl]-3-(6-fluoro-quinolin-4-yl)-acrylamide 17.i. Trifluoro-methanesulfonic acid 6-fluoro-quinolin-4-yl ester A mixture of 6-fluoro-quinolin-4-ol (2 g, 12.3 mmol), 2,6-lutidine (2.0 g. 18.4 mmol) and DMAP (0.15 g, 1.2 mmol) in DCM (50 mL) was cooled to 0° C. At this temperature, trifluoromethane sulfonic anhydride (3.9 g, 13.5 mmol) was added dropwise and the mixture stirred at 0° C. for 3 h. A sat. NH$_4$Cl solution was added and the phases separated. The org. layer was washed with water, dried over MgSO$_4$ and concentrated. Chromatography on SiO$_2$ (DCM) gave the desired triflate (1.8 g, 50% yield) as a brownish solid.

$^1$H NMR (CDCl$_3$) δ: 8.95 (d, J=5.0 Hz, 1H), 8.22 (dd, J=9.4, 5.3 Hz, 1H), 7.64 (m, 2H), 7.46 (d, J=5.0 Hz, 1H).

MS (ESI, m/z): 296.0 [M+H$^+$].

17.ii. (E)-N-[(R)-3-(2,3-dihydro-benzo[1,4]dioxin-6-yl)-2-oxo-oxazolidin-5-ylmethyl]-3-(6-fluoro-quinolin-4-yl)-acrylamide The title product was obtained according to method G starting from intermediate 16.i (0.2 g, 0.66 mmol) and intermediate 17.i (0.193 g, 0.66 mmol). The product was isolated as a yellow solid (0.013 g, 5% yield) after chromatography on SiO$_2$ (EA, EA/MeOH 19:1, 9:1+1% NH$_4$OH) and crystallization from ether.

MS (ESI, m/z): 450.2 [M+H$^+$].

Example 18

(E)-N-[(R)-3-(2,3-dihydro-benzo[1,4]dioxin-6-yl)-2-oxo-oxazolidin-5-ylmethyl]-3-(2-methoxy-quinolin-8-yl)-acrylamide This compound was obtained according to method G starting from intermediate 16.i (0.2 g, 0.66 mmol) and trifluoro-methanesulfonic acid 2-methoxy-quinolin-8-yl ester (0.2 g, 0.66 mmol, prepared as in WO 2004/002490). The product was isolated as a colourless solid (0.022 g, 7% yield) after chromatography on SiO$_2$ (EA, EA/MeOH 19:1, 9:1+1% NH$_4$OH) and crystallization from ether.

MS (ESI, m/z): 461.8 [M+H$^+$].

Example 19

(E)-3-(6-methoxy-[1,5]naphthyridin-4-yl)-N-methyl-N-[(R)-3-(4-methyl-3-trifluoromethyl-phenyl)-2-oxo-oxazolidin-5-ylmethyl]-acrylamide The title compound was obtained in analogy to Example 13. The product was isolated after chromatography on SiO$_2$ (EA/MeOH 9:1) as a colourless solid (0.1 g, 56% yield).

MS (ESI, m/z): 501.1 [M+H$^+$].

The following compounds have been obtained in analogy to Example 13:

| Example | Name | Yield | ESI (M + H$^+$) |
|---|---|---|---|
| 20 | (E)-N-[(R)-3-(3-bromo-4-methyl-phenyl)-2-oxo-oxazolidin-5-ylmethyl]-3-(6-methoxy-[1,5]naphthyridin-4-yl)-N-methyl-acrylamide | 64% | 511.1 |
| 21 | (E)-N-[(R)-3-(4-bromo-3-methyl-phenyl)-2-oxo-oxazolidin-5-ylmethyl]-3-(6-methoxy-[1,5]naphthyridin-4-yl)-N-methyl-acrylamide | 53% | 513.1 |
| 22 | (E)-N-[(R)-3-(4-bromo-3-fluoro-phenyl)-2-oxo-oxazolidin-5-ylmethyl]-3-(6-methoxy-[1,5]naphthyridin-4-yl)-N-methyl-acrylamide | 59% | 515.1 |
| 23 | (E)-N-[(S)-3-(3-fluoro-4-methyl-phenyl)-2-oxo-oxazolidin-5-ylmethyl]-3-(6-methoxy-[1,5]naphthyridin-4-yl)-N-methyl-acrylamide | 53% | 451.2 |
| 24 | (E)-3-(6-methoxy-[1,5]naphthyridin-4-yl)-N-methyl-N-[(S)-2-oxo-3-(3-oxo-3,4-dihydro-2H-benzo[1,4]thiazin-6-yl)-oxazolidin-5-ylmethyl]-acrylamide | 8% | 506.2 |
| 25 | (E)-N-[(S)-3-(2,3-dihydro-benzo[1,4]dioxin-6-yl)-2-oxo-oxazolidin-5-ylmethyl]-3-(6-methoxy-[1,5]naphthyridin-4-yl)-N-methyl-acrylamide | 32% | 451.2 |
| 26 | (E)-N-[(S)-3-(4-ethyl-phenyl)-2-oxo-oxazolidin-5-ylmethyl]-3-(3-methoxy-quinoxalin-5-yl)-N-methyl-acrylamide | 52% | 447.3 |

Example 27

N-[(R)-3-(2,3-dihydro-benzo[1,4]dioxin-6-yl)-2-oxo-oxazolidin-5-ylmethyl]-3-(6-methoxy-[1,5]naphthyridin-4-yl)-propionamide A solution of the compound of Example 3 (0.11 g, 0.24 mmol) in EA/MeOH/THF (1:1:1, 30 mL) was hydrogenated over Pd/C (10%, 25 mg) at 1 bar of H$_2$ for 1 h. The catalyst was filtered off over Celite and the filtrate concentrated and dried at HV to give the title compound (0.11 g, 99% yield) as a colourless foam.

MS (ESI, m/z): 465.2 [M+H$^+$].

Example 28

3-(3-methoxy-quinolin-5-yl)-N-[(R)-2-oxo-3-(3-oxo-3,4-dihydro-2H-benzo[1,4]thiazin-6-yl)-oxazolidin-5-ylmethyl]-propionamide

28.i. 3-(3-methoxy-quinolin-5-yl)-propionic acid

This compound was synthesised from 5-bromo-3-methoxy-quinoline (5.0 g, 21 mmol; prepared as in DE 10316081) and ethyl acrylate (5 eq.) according to method G followed by hydrogenation over Pd/C in THF/MeOH 4:1. The hydrolysis was carried out according to method F. The product was isolated as a colourless solid (0.1 g).
MS (ESI, m/z): 232.3 [M+H$^+$].

28.ii. 3-(3-methoxy-quinolin-5-yl)-N-[(R)-2-oxo-3-(3-oxo-3,4-dihydro-2H-benzo[1,4]thiazin-6-yl)-oxazolidin-5-ylmethyl]-propionamide The title compound was obtained according to method H starting from intermediate 28.i (0.093 g, 0.4 mmol) and intermediate 4.v (0.111 g, 0.4 mmol). The product was isolated after chromatography on SiO$_2$ (EA, EA/MeOH 9:1) as a colourless solid (0.066 g, 33% yield).
MS (ESI, m/z): 493.1 [M+H$^+$].

Example 29

(R)-3-(2,3-dihydro-benzo[1,4]dioxin-6-yl)-5-{[(E)-3-(6-methoxy-[1,5]naphthyridin-4-yl)-allylamino]-methyl}-oxazolidin-2-one

29.i. 3-(6-methoxy-[1,5]naphthyridin-4-yl)-prop-2-yn-1-ol

A solution of 8-bromo-2-methoxy-[1,5]naphthyridine (4.0 g, 16.7 mmol, prepared as in WO 2006/032466) and propargylalcohol (1.9 g, 33.5 mmol) in DMF (50 mL) and TEA (10.16 g, 100 mmol) was degassed by bubbling N$_2$ through for 10 min. CuI (0.318 g, 1.6 mmol) and Pd(PPh$_3$)$_2$Cl$_2$ (0.588 g, 0.84 mmol) were added and the brown solution was stirred at rt overnight. The mixture was partitioned between water and EtOAc and the org. layer was washed several times with water and a sat. NH$_4$Cl solution, dried over MgSO$_4$ and concentrated. Chromatography on SiO$_2$ (Hex/EA 1:1, EA) followed by crystallization from ether gave the coupling product as a beige solid (1.95 g, 54% yield).
$^1$H NMR (DMSO d6) δ: 8.75 (d, J=4.5 Hz, 1H), 8.29 (d, J=9.0 Hz, 1H), 7.73 (d, J=4.5 Hz, 1H), 7.31 (d, J=9.0 Hz, 1H), 5.49 (t, J=6.0 Hz, 1H), 4.46 (d, J=6.0 Hz, 1H), 4.07 (s, 3H).
MS (ESI, m/z): 215.3 [M+H$^+$].

29.ii. (E)-3-(6-methoxy-[1,5]naphthyridin-4-yl)-prop-2-en-1-ol

A solution of intermediate 29.i (1.5 g, 7.1 mmol) in toluene/THF 1:1 (100 mL) was cooled to −78° C. and a solution of sodium dihydrido-bis(2-methoxyethoxy)aluminate (Red-Al, 65% in toluene, 2 eq.) was added dropwise at this temperature. The reaction was monitored by LCMS. After quenching with MeOH (2 mL) and a sat. solution of Rochelles salt (30 mL) at −78° C., the mixture was diluted with EA, washed with water and brine, dried over MgSO$_4$ and concentrated. Chromatography on SiO$_2$ (EA/Hex 2:1, EA) gave the title alcohol (0.99 g, 64% yield) as a colourless solid.
$^1$H NMR (DMSO d6) δ: 8.71 (d, J=4.5 Hz, 1H), 8.25 (d, J=9.0 Hz, 1H), 7.84 (d, J=4.5 Hz, 1H), 7.60 (dt, J=1.9, 16.2 Hz, 1H), 7.26 (d, J=9.0 Hz, 1H), 7.01 (dt, J=4.7, 16.2 Hz, 1H), 5.06 (t, J=5.5 Hz, 1H), 4.23 (m, 2H), 4.07 (s, 3H).

29.iii. (E)-3-(6-methoxy-[1,5]naphthyridin-4-yl)-propenal

MnO$_2$ (1.9 g, 21.6 mmol) was added to a solution of intermediate 29.ii (0.22 g, 1 mmol) in DCM/THF 1:1 (20 mL). The mixture was stirred at rt for 30 min, filtered over Celite and MgSO$_4$ and the volatiles were removed under reduced pressure. The compound was isolated as a colourless solid (0.16 g, 74% yield)
$^1$H NMR (DMSO d6) δ: 9.91 (d, J=7.7 Hz, 1H), 8.88 (d, J=4.5 Hz, 1H), 8.63 (d, J=16.0 Hz, 1H), 8.35 (d, J=9.0 Hz, 1H), 8.13 (d, J=4.5 Hz, 1H), 7.40 (m, 2H), 7.26 (d, J=9.0 Hz, 1H), 4.11 (s, 3H).

29.iv. (R)-3-(2,3-dihydro-benzo[1,4]dioxin-6-yl)-5-{[(E)-3-(6-methoxy-[1,5]naphthyridin-4-yl)-allylamino]-methyl}-oxazolidin-2-one Intermediate 3.i (0.2 g, 0.8 mmol) and intermediate 29.iii (0.16 g, 0.8 mmol) were coupled according to method J. The title compound was isolated as a yellowish foam (0.035 g, 10% yield) after aqueous workup and chromatography on SiO$_2$ (EA, EA/MeOH 9:1).
MS (ESI, m/z): 450.9 [M+H$^+$].

Example 30

(R)-3-(2,3-dihydro-benzo[1,4]dioxin-6-yl)-5-{[3-(6-methoxy-[1,5]naphthyridin-4-yl)-propylamino]-methyl}-oxazolidin-2-one Intermediate 3.i (0.2 g, 0.8 mmol) and intermediate 29.iii (0.16 g, 0.8 mmol) were coupled according to method J. The title compound was isolated as a colourless foam (0.018 g, 5% yield) after aqueous workup and chromatography on SiO$_2$ (EA, EA/MeOH 9:1).
MS (ESI, m/z): 451.1 [M+H$^+$].

Example 31

N-[(R)-3-(2,3-dihydro-benzo[1,4]dioxin-6-yl)-2-oxo-oxazolidin-5-ylmethyl]-N-[(E)-3-(6-methoxy-[1,5]naphthyridin-4-yl)-allyl]-acetamide A solution of the compound of Example 29 (0.041 g, 0.09 mmol) in THF (2 mL) was treated with acetic anhydride (0.1 mL). The mixture was stirred at rt overnight. NaOH (1M, 2 mL) was added and the phases separated. The org. phase was concentrated in vacuo and the residue purified by chromatography on SiO$_2$ (EA/MeOH 9:1) to give the title compound (0.03 g, 67% yield) as a colourless foam.
MS (ESI, m/z): 490.9 [M+H$^+$].

Example 32

6-((R)-5-{[(E)-3-(6-methoxy-[1,5]naphthyridin-4-yl)-allylamino]-methyl}-2-oxo-oxazolidin-3-yl)-4H-benzo[1,4]thiazin-3-one Intermediate 5 v. (0.125 g, 0.45 mmol) and intermediate 29 iii. (0.096 g, 0.45 mmol) were coupled according to method J.

The compound was isolated after aqueous workup and chromatography on SiO$_2$ (EA, EA/MeOH 9:1) as a colourless foam (0.05 g, 23% yield).
MS (ESI, m/z): 477.7 [M+H$^+$].

Example 33

6-((R)-5-{[3-(6-methoxy-[1,5]naphthyridin-4-yl)-propylamino]-methyl}-2-oxo-oxazolidin-3-yl)-4H-benzo[1,4]thiazin-3-one

33.i. 3-(6-methoxy-[1,5]naphthyridin-4-yl)-propan-1-ol

A solution of intermediate 29.i (3.11 g, 14.5 mmol) in THF/MeOH 1:1 (200 mL) was hydrogenated over Pd/C (10%, 1.5 g) under 1 bar of H$_2$ for 3 h. The catalyst was filtered over Celite and the filtrate concentrated in vacuo to give the desired alcohol (2.78 g, 88% yield) as a colourless solid.
$^1$H NMR (DMSO d6) δ: 8.65 (d, J=4.4 Hz, 1H), 8.21 (d, J=9.1 Hz, 1H), 7.51 (d, J=4.4 Hz, 1H), 7.22 (d, J=9.1 Hz, 1H), 4.48 (t, J=5.3 Hz, 1H), 3.46 (td, J=6.4, 5.3 Hz, 2H), 1.87 (m, 2H), 3.13 (m, 2H).
MS (ESI, m/z): 219.3 [M+H$^+$].

33.ii. 3-(6-methoxy-[1,5]naphthyridin-4-yl)-propionaldehyde

A solution of intermediate 33.i (1.0 g, 4.6 mmol) in DCM (20 mL) was cooled to 0° C. DIPEA (1.8 g, 13.8 mmol) was added followed by a solution of pyridine sulfurtrioxide complex (0.766 g, 4.8 mmol) in DMSO (5.5 mL). The mixture was stirred at 0° C. for 1 h. Water was added and the aq. layer extracted with DCM (3 times 20 mL). The combined org. layers were washed with water (2 times 20 mL), dried over MgSO$_4$ and concentrated. The compound was purified by chromatography on SiO$_2$ (Hex/EA 1:1, EA, EA/MeOH 9:1) to give the desired aldehyde as a colourless oil (0.46 g, 46% yield).
$^1$H NMR (CDCl$_3$) δ: 9.88 (t, J=1.5 Hz, 1H), 8.66 (d, J=4.4 Hz, 1H), 8.19 (d, J=9.1 Hz, 1H), 7.40 (d, J=4.4 Hz, 1H), 7.12 (d, J=9.1 Hz, 1H), 4.05 (s, 4H), 3.47 (t, J=7.6 Hz, 3H), 2.99 (td, J=7.3, 1.2 Hz, 2H).

33.iii. 6-((R)-5-{[3-(6-methoxy-[1,5]naphthyridin-4-yl)-propylamino]-methyl}-2-oxo-oxazolidin-3-yl)-4H-benzo[1,4]thiazin-3-one Intermediate 5.v (0.594 g, 2.1 mmol) and aldehyde 33.ii (0.46 g, 2.1 mmol) were coupled according to method J. The compound was isolated after aqueous workup and chromatography on SiO$_2$ (EA, EA/MeOH 9:1) as a colourless foam (0.28 g, 28% yield).
MS (ESI, m/z): 480.3 [M+H$^+$].

Example 34

6-((RS)-5-{[3-(6-methoxy-[1,5]naphthyridin-4-yl)-propylamino]-methyl}-2-oxo-oxazolidin-3-yl)-4H-benzo[1,4]oxazin-3-one

34.i. 6-((RS)-5-aminomethyl-2-oxo-oxazolidin-3-yl)-4H-benzo[1,4]oxazin-3-one The desired amine was prepared using the protocol of Example 4, steps 4.iii-4.v starting from 6-amino-4H-benzo[1,4]oxazin-3-one (0.5 g, 2.9 mmol). The compound was isolated as beige solid (0.135 g, 18% yield over 3 steps).
MS (ESI, m/z): 264.3 [M+H$^+$].

34.ii. 6-((RS)-5-{[3-(6-methoxy-[1,5]naphthyridin-4-yl)-propylamino]-methyl}-2-oxo-oxazolidin-3-yl)-4H-benzo[1,4]oxazin-3-one A solution of aldehyde 33.ii (0.11 g, 0.5 mmol) and intermediate 34.i (0.13 g, 0.5 mmol) in THF/MeOH (1:1, 16 mL) was stirred at rt for 8 h. NaBH(OAc)$_3$ (0.32 g, 3 eq.) was added and stirring continued overnight. The mixture was partitioned between EA and NaHCO$_3$ solution. The org. phase was dried over MgSO$_4$ and concentrated. Chromatography on SiO$_2$ (EA/MeOH 9:1+1% NH$_4$OH) yielded the title compound (0.122 g, 53% yield) as a colourless foam.
$^1$H NMR (DMSO d6) δ: 10.69 (s, 1H), 8.64 (d, J=4.7 Hz, 1H), 8.21 (d, J=9.1 Hz, 1H), 7.51 (d, J=4.4 Hz, 1H), 7.31 (t, J=1.2 Hz, 1H), 7.22 (d, J=8.8 Hz, 1H), 6.92 (d, J=1.2 Hz, 2H), 6.92 (d, J=1.2 Hz, 2H), 4.66 (m, 1H), 4.51 (s, 2H), 4.00 (m, 5H), 3.74 (dd, J=8.8, 6.7 Hz, 1H), 3.13 (m, 3H), 2.81 (d, J=5.3 Hz, 2H), 2.63 (t, J=7.0 Hz, 3H), 1.86 (m, 2H).
MS (ESI, m/z): 464.4 [M+H$^+$].

Example 35

6-((R)-5-{[3-(3-methoxy-quinolin-5-yl)-propylamino]-methyl}-2-oxo-oxazolidin-3-yl)-4H-benzo[1,4]thiazin-3-one

35.i. 3-(3-methoxy-quinolin-5-yl)-propionaldehyde

This aldehyde was prepared using sequentially the protocols of Example 29, step 29.i and Example 33, steps 33.i to 33.ii and starting from 5-bromo-3-methoxy-quinoline (4 g, 16.7 mmol; prepared as in DE 10316081). After chromatography on SiO$_2$ (Hex/EA 1:1, EA), the compound was obtained as a yellowish solid (0.95 g, 30% yield over 3 steps).

35.ii. 6-((R)-5-{[3-(3-methoxy-quinolin-5-yl)-propylamino]-methyl}-2-oxo-oxazolidin-3-yl)-4H-benzo[1,4]thiazin-3-one Intermediate 5.v (0.092 g, 0.33 mmol) and intermediate 35.i (0.071 g, 0.33 mmol) were coupled according to method J. The compound was isolated after aqueous workup and chromatography on SiO$_2$ (EA, EA/MeOH 9:1) as a yellowish foam (0.041 g, 26% yield).
MS (ESI, m/z): 479.1 [M+H$^+$].

Example 36

N-[(R)-3-(2,3-dihydro-benzo[1,4]dioxin-6-yl)-2-oxo-oxazolidin-5-ylmethyl]-N-[3-(6-methoxy-[1,5]naphthyridin-4-yl)-propyl]-acetamide This compound was prepared starting from the compound of Example 30 (0.059 g, 0.13 mmol) and following the protocol of Example 31. The product was isolated after chromatography on SiO$_2$ (EA/MeOH 9:1) as a colourless foam (0.05 g, 77% yield).
MS (ESI, m/z): 492.5 [M+H$^+$].

Example 37

N-[3-(6-methoxy-[1,5]naphthyridin-4-yl)-propyl]-N-[(R)-2-oxo-3-(3-oxo-3,4-dihydro-2H-benzo[1,4]thiazin-6-yl)-oxazolidin-5-ylmethyl]-succinamic acid A solution of the compound of Example 33 (0.06 g, 0.125 mmol) in DCM (3 mL) was treated with succinic anhydride (0.025 g, 2 eq.). The mixture was stirred in a sealed flask at 50° C. overnight, concentrated in vacuo and purified by chromatography on $SiO_2$ (DCM/MeOH 9:1) followed by crystallization from ether. The product was obtained as a colourless solid (0.036 g, 50% yield).

In NMR at rt rotamers are observed, at 100° C. a single compound.

$^1$H NMR (DMSO d6, 100° C.) δ: 10.27 (dd, J=2.3, 1.5 Hz, 1H), 8.65 (d, J=4.4 Hz, 1H), 8.20 (d, J=9.1 Hz, 1H), 7.54 (d, J=4.4 Hz, 1H), 7.27 (m, 2H), 7.19 (d, J=8.8 Hz, 1H), 7.08 (dd, J=8.5, 2.3 Hz, 1H), 4.84 (dd, J=1.8, 0.6 Hz, 1H), 4.05 (s, 3H), 4.05 (m, 1H), 3.70 (m, 3H), 3.52 (m, 2H), 3.40 (s, 2H), 2.96 (m, 2H), 2.55 (m, 2H), 2.40 (m, 2H), 2.07 (m, 2H).

MS (ESI, m/z): 580.3 [M+H$^+$].

Example 38

N-[3-(6-methoxy-[1,5]naphthyridin-4-yl)-propyl]-N-[(R)-2-oxo-3-(3-oxo-3,4-dihydro-2H-benzo[1,4]thiazin-6-yl)-oxazolidin-5-ylmethyl]-propionamide Propionyl chloride (0.018 g, 1.5 eq.) was added to a solution of the compound of Example 33 (0.06 g, 0.125 mmol) and TEA (0.02 g, 1.5 eq) in DCM (3 mL). The mixture was stirred at rt overnight, concentrated in vacuo and purified by chromatography on $SiO_2$ (DCM/MeOH 9:1). The title compound was isolated as a colourless foam (0.04 g, 63% yield).

MS (ESI, m/z): 534.5 [M−H$^+$].

Example 39

(R)-3-(2,3-dihydro-benzo[1,4]dioxin-6-yl)-5-({ethyl-[3-(6-methoxy-[1,5]naphthyridin-4-yl)-propyl]-amino}-methyl)-oxazolidin-2-one Intermediate 7.i (0.085 g, 0.31 mmol) and intermediate 33.ii (0.066 g, 0.31 mmol) were coupled according to method K. The compound was isolated after aq. workup and chromatography on $SiO_2$ (EA, EA/MeOH 9:1) as a yellowish foam (0.015 g, 10% yield).

MS (ESI, m/z): 479.3 [M+H$^+$].

Example 40

(RS)-5-({benzyl-[3-(6-methoxy-[1,5]naphthyridin-4-yl)-propyl]-amino}-methyl)-3-(2,3-dihydro-benzo[1,4]dioxin-6-yl)-oxazolidin-2-one Intermediate 8.i (0.1 g, 0.3 mmol) and intermediate 33.ii (0.063 g, 0.3 mmol) were coupled according to method K. The compound was isolated after aq. workup and chromatography on $SiO_2$ (EA, EA/MeOH 9:1) as a yellowish foam (0.022 g, 14% yield).

MS (ESI, m/z): 541.3 [M+H$^+$].

Example 41

(R)-5-({2-amino-ethyl)-[3-(6-methoxy-[1,5]naphthyridin-4-yl)-propyl]-amino}-methyl)-3-(2,3-dihydro-benzo[1,4]dioxin-6-yl)-oxazolidin-2-one

41.i. (2-{[(R)-3-(2,3-dihydro-benzo[1,4]dioxin-6-yl)-2-oxo-oxazolidin-5-ylmethyl]-amino}-ethyl)-carbamic acid tert-butyl ester Intermediate 3.i (0.47 g, 1.88 mmol) was reacted according to method J with (2-oxo-ethyl)-carbamic acid tert-butyl ester (0.3 g, 1.9 mmol). The target intermediate was obtained after chromatography on $SiO_2$ (EA) as a colourless oil (0.33 g, 45% yield).

MS (ESI, m/z): 394.2 [M+H$^+$]

41.ii. (2-{[(R)-3-(2,3-dihydro-benzo[1,4]dioxin-6-yl)-2-oxo-oxazolidin-5-ylmethyl]-[3-(6-methoxy-[1,5]naphthyridin-4-yl)-propyl]-amino}-ethyl)-carbamic acid tert-butyl ester Intermediate 41.i (0.16 g, 0.4 mmol) and intermediate 33.ii (0.086 g, 0.4 mmol) were coupled according to method K. The compound was isolated after aq. workup and chromatography on $SiO_2$ (EA) as a yellowish foam (0.196 g, 82% yield).

$^1$H NMR (DMSO d6) δ: 8.63 (d, J=4.7 Hz, 1H), 8.21 (d, J=9.1 Hz, 1H), 7.51 (d, J=4.4 Hz, 1H), 7.21 (d, J=8.8 Hz, 1H), 7.08 (d, J=2.6 Hz, 1H), 6.91 (d, J=2.6 Hz, 1H), 6.80 (m, 1H), 4.19 (m, 4H), 4.00 (m, 4H), 3.70 (m, 1H), 3.09 (m, 2H), 2.97 (m, 2H), 2.76 (t, J=5.0 Hz, 2H), 2.58 (m, 4H), 1.85 (m, 2H), 1.30 (s, 9H).

MS (ESI, m/z): 594.3 [M+H$^+$].

41.iii. (R)-5-({(2-amino-ethyl)-[3-(6-methoxy-[1,5]naphthyridin-4-yl)-propyl]-amino}-methyl)-3-(2,3-dihydro-benzo[1,4]dioxin-6-yl)-oxazolidin-2-one The Boc group of above intermediate 41.ii (0.19 g, 0.32 mmol) was removed according to method E. The title compound was isolated after chromatography on $SiO_2$ (EA/MeOH 9:1, 4:1+1% $NH_4OH$) as a colourless foam (0.154 g, 97% yield).

MS (ESI, m/z): 494.2 [M+H$^+$].

The following compounds have been obtained in analogy to Example 41:

| Example | Name | Yield | ESI (M + H$^+$) |
|---|---|---|---|
| 42 | 6-[(R)-5-({[3-(3-methoxy-quinolin-5-yl)-propyl]-methyl-amino}-methyl)-2-oxo-oxazolidin-3-yl]-4H-benzo[1,4]thiazin-3-one | 71% | 493.0 |

| Example | Name | Yield | ESI (M + H⁺) |
|---|---|---|---|
| 43 | (R)-3-(3-fluoro-4-methyl-phenyl)-5-({[3-(3-methoxy-quinolin-5-yl)-propyl]-methyl-amino}-methyl)-oxazolidin-2-one | 67% | 438.4 |
| 44 | (R)-5-({[3-(3-methoxy-quinolin-5-yl)-propyl]-methyl-amino}-methyl)-3-(4-methyl-3-trifluoromethyl-phenyl)-oxazolidin-2-one | 59% | 488.5 |
| 45 | (R)-3-(4-ethyl-phenyl)-5-({[3-(3-methoxy-quinolin-5-yl)-propyl]-methyl-amino}-methyl)-oxazolidin-2-one | 21% | 434.3 |
| 46 | (R)-5-({[3-(3-methoxy-quinolin-5-yl)-propyl]-methyl-amino}-methyl)-3-(4-propyl-phenyl)-oxazolidin-2-one | 34% | 448.5 |
| 47 | (R)-3-(3-bromo-4-methyl-phenyl)-5-({[3-(3-methoxy-quinolin-5-yl)-propyl]-methyl-amino}-methyl)-oxazolidin-2-one | 41% | 498.2 |
| 48 | (R)-3-(4-bromo-3-methyl-phenyl)-5-({[3-(3-methoxy-quinolin-5-yl)-propyl]-methyl-amino}-methyl)-oxazolidin-2-one | 23% | 498.2 |
| 49 | (R)-3-(4-bromo-3-fluoro-phenyl)-5-({[3-(3-methoxy-quinolin-5-yl)-propyl]-methyl-amino}-methyl)-oxazolidin-2-one | 31% | 502.4 |
| 50 | (S)-3-(3-fluoro-4-methyl-phenyl)-5-({[3-(3-methoxy-quinolin-5-yl)-propyl]-methyl-amino}-methyl)-oxazolidin-2-one | 73% | 438.3 |

Example 51

(S)-3-(2,3-dihydro-benzo[1,4]dioxin-6-yl)-2-oxo-oxazolidine-5-carboxylic acid [3-(6-methoxy-[1,5]naphthyridin-4-yl)-propyl]amide

51.i. [3-(6-methoxy-[1,5]naphthyridin-4-yl)-prop-2-ynyl]-carbamic acid tert-butyl ester To a solution of N-Boc propargyl amine (3.25 g, 20.9 mmol) and 8-bromo-2-methoxy-[1,5]naphthyridine (5.00 g, 20.9 mmol; prepared as in WO 2006/032466) and TEA (17.5 mL, 6 eq.) in DMF (120 mL) were added Pd(PPh₃)₂Cl₂ (755 mg, 1.08 mmol) and CuI (432 mg, 2.27 mmol). The mixture was degassed with a stream of N₂ for 15 min and then stirred at rt for 5 h. The mixture was partitioned between water and EA, the org. layer was washed several times with water and a sat. NH₄Cl solution, dried over MgSO₄ and concentrated. Chromatography on SiO₂ (Hex/EA 1:1, EA) gave the coupling product as a beige solid (2.90 g, 44% yield).

51.ii. [3-(6-methoxy-[1,5]naphthyridin-4-yl)-propyl]-carbamic acid tert-butyl ester A solution of intermediate 51.i (105 mg, 0.334 mmol) in MeOH (5 mL) was hydrogenated over Pd/C (10%, 4 mg) under 1 bar of H₂ for 4 h. The catalyst was filtered off over Celite and the filtrate concentrated in vacuo to afford the title product as a brown oil (78 mg, 74% yield).
MS (ESI, m/z): 318.3 [M+H⁺].

51.iii. 3-(6-methoxy-[1,5]naphthyridin-4-yl)-propylamine

The Boc group of intermediate 51.ii (78 mg, 0.246 mmol) was removed according to method E. The title amine was isolated without further purification as a yellow oil (46 mg, 87% yield).

51.iv. (S)-3-(2,3-dihydro-benzo[1,4]dioxin-6-yl)-2-oxo-oxazolidine-5-carboxylic acid To a solution of intermediate 1.i (985 mg, 3.92 mmol) in 1:1 water/MeCN (20 mL) cooled to 0° C. was added diacetoxyiodobenzene (2.83 g, 8.62 mmol)) and TEMPO (122 mg, 0.78 mmol). The mixture was stirred at 0° C. for 30 min and at rt overnight. EA and sat. Na₂CO₃ were added and the phases separated. The aq. layer was washed once more with EA and then carefully (!) acidified with 1M HCl. The water phase was then extracted twice with EA. The combined org. layers were washed with brine and dried over MgSO₄ and concentrated to afford the title acid as a white solid (847 mg, 81% yield).

MS (ESI, m/z): 266.3 [M+H⁺].

51.v. (S)-3-(2,3-dihydro-benzo[1,4]dioxin-6-yl)-2-oxo-oxazolidine-5-carboxylic acid [3-(6-methoxy-[1,5]naphthyridin-4-yl)-propyl]-amide To a solution of intermediate 51.iii (42 mg, 0.191 mmol), intermediate 51.iv (51 mg, 0.191 mmol) and DIPEA (0.126 mL, 4 eq.) in DMF (2 mL) was added HATU (145 mg, 2 eq.). The resulting orange solution was stirred at rt for 4 h. EA and water were added and the phases were separated. The aq. phase was extracted with EA and the combined org. extracts were washed with brine/water (3 times), dried over MgSO₄, concentrated under reduced pressure. The residue was chromatographed on SiO₂ (DCM/MeOH/NH₄OH 1000/12.5/1) to afford the title compound as a pale beige solid (53 mg, 60% yield).

¹H NMR (DMSO d6) δ: 8.65 (d, J=4.4 Hz, 1H), 8.47 (t, J=5.6 Hz, 1H), 8.22 (d, J=9.1 Hz, 1H), 7.54 (d, J=4.4 Hz, 1H), 7.22 (d, J=9.1 Hz, 1H), 7.10 (d, J=2.6 Hz, 1H), 6.95 (dd, J=8.8, 2.6 Hz, 1H), 6.83 (m, 1H), 4.99 (dd, J=9.4, 5.9 Hz, 1H), 4.20 (m, 5H), 4.00 (s, 3H), 3.89 (dd, J=9.1, 6.2 Hz, 1H), 3.15 (m, 4H), 1.93 (m, 2H), 1.16 (m, 2H).

MS (ESI, m/z): 465.5 [M+H⁺].

Example 52

6-((RS)-5-{[(2R,3R)-2,3-dihydroxy-3-(6-methoxy-[1,5]naphthyridin-4-yl)-propylamino]-methyl}-2-oxo-oxazolidin-3-yl)-4H-benzo[1,4]thiazin-3-one and 6-((RS)-5-{[(2S,3S)-2,3-dihydroxy-3-(6-methoxy-[1,5]naphthyridin-4-yl)-propylamino]-methyl}-2-oxo-oxazolidin-3-yl)-4H-benzo[1,4]thiazin-3-one

52.i. [3-(6-methoxy-[1,5]naphthyridin-4-yl)-allyl]-[2-oxo-3-(3-oxo-3,4-dihydro-2H-benzo[1,4]thiazin-6-yl)-oxazolidin-5-ylmethyl]-carbamic acid tert-butyl ester A solution of the compound of Example 32 (0.24 g, 0.5 mmol) in DCM (2 mL) was treated with an excess of Boc$_2$O. The mixture was stirred at rt overnight, concentrated in vacuo and purified by chromatography on SiO$_2$ (Hex/EA 1:1, EA, EA/MeOH 9:1) to give the title intermediate as a colourless oil (0.25 g, 86% yield).

MS (ESI, m/z): 578.4 [M+H$^+$].

52.ii. [(2R,3R)-2,3-dihydroxy-3-(6-methoxy-[1,5]naphthyridin-4-yl)-propyl]-[(RS)-2-oxo-3-(3-oxo-3,4-dihydro-2H-benzo[1,4]thiazin-6-yl)-oxazolidin-5-ylmethyl]-carbamic acid tert-butyl ester and [(2S,3S)-2,3-dihydroxy-3-(6-methoxy-[1,5]naphthyridin-4-yl)-propyl]-[(RS)-2-oxo-3-(3-oxo-3,4-dihydro-2H-benzo[1,4]thiazin-6-yl)-oxazolidin-5-ylmethyl]-carbamic acid tert-butyl ester To a solution of intermediate 52.i (0.25 g, 0.43 mmol) in t-BuOH/H$_2$O (1:1, 10 mL) was added methane sulfonamide (0.045 g, 1.1 eq) and AD-mix β (1.0 g). The mixture was vigorously stirred at rt overnight, carefully quenched by addition of sodium bisulfite (1 g). The mixture was diluted with EA, the phases separated and the organic phase dried over MgSO$_4$ and concentrated. The residue was purified by chromatography on SiO$_2$ (EA, EA/MeOH 9:1) to give the title diol as a colourless solid (0.054 g, 20% yield).

MS (ESI, m/z): 612.2 [M+H$^+$].

52.iii. 6-((RS)-5-{[(2R,3R)-2,3-dihydroxy-3-(6-methoxy-[1,5]naphthyridin-4-yl)-propylamino]-methyl}-2-oxo-oxazolidin-3-yl)-4H-benzo[1,4]thiazin-3-one and 6-((RS)-5-{[(2S,3S)-2,3-dihydroxy-3-(6-methoxy-[1,5]naphthyridin-4-yl)-propylamino]-methyl}-2-oxo-oxazolidin-3-yl)-4H-benzo[1,4]thiazin-3-one The Boc group of intermediate 52.ii (0.054 g, 0.088 mmol) was removed using method E. After chromatography on SiO$_2$ (EA/MeOH 4:1+1% NH$_4$OH) followed by trituration with ether/MeOH, the title compound were isolated as a colourless solid (0.013 g, 29% yield).

MS (ESI, m/z): 512.3 [M+H$^+$].

Example 53

(2S,3R)-N-[(S)-3-(2,3-dihydro-benzo[1,4]dioxin-6-yl)-2-oxo-oxazolidin-5-ylmethyl]-2,3-dihydroxy-3-(6-methoxy-[1,5]naphthyridin-4-yl)-propionamide A mixture of the compound of Example 1 (0.2 g, 0.4 mmol), methanesulfonamide (0.05 g) and AD-mix β (0.8 g) in t-BuOH/H$_2$O/EA (6 mL/2 mL/6 mL) was vigorously stirred at rt overnight. Potassium hexacyanoferrate (0.38 g), K$_2$CO$_3$ (0.16 g), (DHQD)$_2$PHAL (17 mg) and K$_2$OsO$_4$ (8 mg) were added and stirring continued for 2 h. The reaction was carefully quenched by the portionwise addition of sodium bisulfite (1 g). The phases were separated and the aq. phase extracted with EA. The combined org. layers were dried over MgSO$_4$ and concentrated. Crystallization from ether gave the desired product as a colourless solid (0.2 g, 98% yield).

MS (ESI, m/z): 497.0 [M+H$^+$].

Example 54

(2R,3S)-2,3-dihydroxy-3-(6-methoxy-[1,5]naphthyridin-4-yl)-N-[(R)-2-oxo-3-(3-oxo-3,4-dihydro-2H-benzo[1,4]thiazin-6-yl)-oxazolidin-5-ylmethyl]-propionamide A mixture of the compound of Example 4 (0.08 g, 0.16 mmol), methanesulfonamide (0.017 g) and AD-mix α (0.7 g) in t-BuOH/H$_2$O (5 mL/5 mL) was vigorously stirred at rt overnight. DMA (0.5 mL) added and stirring continued for 5 h. The reaction was carefully quenched by the portionwise addition of sodium bisulfite (1 g). The phases were separated and the aq. phase extracted with EA. The combined org. layers were dried over MgSO$_4$ and concentrated. Chromatography on SiO$_2$ (EA/MeOH 9:1, 4:1, +1% NH$_4$OH) followed by trituration with ether/MeOH gave the desired product as a colourless solid (0.022 g, 26% yield).

$^1$H NMR (DMSO d6) δ: 10.55 (s, 1H), 8.76 (d, J=4.7 Hz, 1H), 8.26 (d, J=9.1 Hz, 1H), 7.96 (m, 1H), 7.75 (dd, J=4.4, 0.6 Hz, 1H), 7.31 (dd, J=5.6, 3.2 Hz, 2H), 7.25 (d, J=9.1 Hz, 1H), 7.09 (dd, J=8.5, 2.3 Hz, 1H), 6.01 (m, 1H), 5.47 (d, J=6.7 Hz, 1H), 5.39 (d, J=7.3 Hz, 1H), 4.79 (m, 1H), 4.54 (dd, J=7.0, 1.8 Hz, 1H), 4.01 (m, 4H), 3.83 (m, 1H), 3.51 (m, 2H), 3.42 (s, 2H).

MS (ESI, m/z): 526.2 [M+H$^+$].

Example 55

(2S,3R)-2,3-dihydroxy-3-(6-methoxy-[1,5]naphthyridin-4-yl)-N—[(R)-2-oxo-3-(3-oxo-3,4-dihydro-2H-benzo[1,4]thiazin-6-yl)-oxazolidin-5-ylmethyl]-propionamide A mixture of the compound of Example 4 (0.08 g, 0.16 mmol), methanesulfonamide (0.017 g) and AD-mix β (0.7 g) in t-BuOH/H$_2$O (5 mL/5 mL) was vigorously stirred at rt overnight. DMA (0.5 mL) was added and stirring continued for 5 h. The reaction was carefully quenched by the portionwise addition of sodium bisulfite (1 g). The phases were separated and the aq. phase extracted with EA. The combined org. layers were dried over MgSO$_4$ and concentrated. Chromatography on SiO$_2$ (EA/MeOH 9:1, 4:1, +1% NH$_4$OH) followed by trituration with ether/MeOH gave the desired product as a colourless solid (0.030 g, 35% yield).

$^1$H NMR (DMSO d6) δ: 10.54 (s, 1H), 8.77 (d, J=4.4 Hz, 1H), 8.25 (d, J=9.1 Hz, 1H), 7.97 (m, 1H), 7.77 (m, 1H), 7.27 (m, 3H), 7.06 (dd, J=8.8, 2.3 Hz, 1H), 6.01 (dd, J=6.2, 0.9 Hz, 1H), 5.49 (d, J=6.4 Hz, 1H), 5.37 (d, J=7.3 Hz, 1H), 4.77 (m, 1H), 4.52 (dd, J=7.3, 1.8 Hz, 1H), 4.01 (m, 4H), 3.80 (dd, J=8.8, 5.6 Hz, 1H), 3.51 (m, 2H), 3.42 (m, 2H).

MS (ESI, m/z): 526.2 [M+H$^+$].

Example 56

N-[(R)-3-(2,3-dihydro-benzo[1,4]dioxin-6-yl)-2-oxo-oxazolidin-5-ylmethyl]-(3RS)-3-hydroxy-3-(6-methoxy-[1,5]naphthyridin-4-yl)-propionamide

56.i. (RS)-3-hydroxy-3-(6-methoxy-[1,5]naphthyridin-4-yl)-propionic acid tert-butyl ester The aldol reaction between 6-methoxy-[1,5]naphthyridine-4-carbaldehyde (1.9 g, 10 mmol, WO 2006/032466) and tert-butyl acetate (1.2 g, 10.5 mmol) was carried out as described in the literature (*J. Org. Chem.* (1990), 55, 4744-4750). The title compound was isolated after chromatography on $SiO_2$ (Hex/EA 1:1) as a beige solid (2.33 g, 77% yield).

$^1$H NMR (DMSO d6) δ: 8.78 (d, J=4.5 Hz, 1H), 8.27 (d, J=9.1 Hz, 1H), 7.77 (d, J=4.5 Hz, 1H), 7.26 (d, J=9.1 Hz, 1H), 5.94 (m, 1H), 5.69 (d, J=5.0 Hz, 1H), 4.05 (s, 3H), 2.92 (dd, J=2.7, 14.4 Hz, 1H), 2.43 (dd, J=9.0, 14.4 Hz, 1H), 1.36 (s, 9H).

MS (ESI, m/z): 305.1 [M+H$^+$].

56.ii. (RS)-3-hydroxy-3-(6-methoxy-[1,5]naphthyridin-4-yl)-propionic acid

A solution of intermediate 56.i (2.33 g, 7.6 mmol) in DCM (6 mL) was treated with TFA (2 mL). The mixture was stirred at rt for 1 h, concentrated in vacuo and taken up in aq. $NH_4OH$. The aq. phase was extracted once with DCM and then concentrated in vacuo to half of the volume. The pH was adjusted to 3 by addition of 1M HCl. The precipitate that formed was filtered off, washed with water and dried at HV to give the title acid as a colourless solid (1.12 g, 59% yield).

$^1$H NMR (DMSO d6) δ: 8.78 (d, J=4.5 Hz, 1H), 8.27 (d, J=9.1 Hz, 1H), 7.77 (d, J=4.5 Hz, 1H), 7.26 (d, J=9.1 Hz, 1H), 5.94 (m, 1H), 5.69 (br, 1H), 4.01 (s, 3H), 2.92 (dd, J=2.7, 14.4 Hz, 1H), 2.43 (dd, J=9.0, 14.4 Hz, 1H).

MS (ESI, m/z): 249.1 [M+H$^+$].

56.iii. N-[(R)-3-(2,3-dihydro-benzo[1,4]dioxin-6-yl)-2-oxo-oxazolidin-5-ylmethyl]-(3RS)-3-hydroxy-3-(6-methoxy-[1,5]naphthyridin-4-yl)-propionamide This compound was obtained according to method I starting from intermediate 56.ii (0.149 g, 0.6 mmol) and intermediate 3.i (0.15 g, 0.6 mmol). The product was isolated after chromatography on $SiO_2$ (DCM/MeOH 19:1) as a colourless foam (0.056 g, 29% yield).

MS (ESI, m/z): 481.0 [M+H$^+$].

Example 57

(R)-N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-propionamide

57.i. (R)-3-hydroxy-3-(6-methoxy-[1,5]naphthyridin-4-yl)-propionic acid methyl ester The Mukaiyama aldol reaction between 6-methoxy-[1,5]naphthyridine-4-carbaldehyde (0.38 g, 2 mmol; prepared as in WO 2006/032466) and the silylenol ether of methyl acetate was carried out as described in the literature (*J. Am. Chem. Soc.* (2005), 127, 3774) using the (R,R) chiral bis-phosphoramide catalyst. The title intermediate was isolated after chromatography on $SiO_2$ (Hex/EA 1:1) as a beige solid (0.14 g, 67% yield).

$^1$H NMR (CDCl$_3$) δ: 8.77 (d, J=4.4 Hz, 1H), 8.27 (d, J=9.4 Hz, 1H), 7.61 (d, J=4.7 Hz, 1H), 7.16 (d, J=9.1 Hz, 1H), 5.78 (m, 1H), 4.94 (d, J=6.7 Hz, 1H), 4.05 (s, 3H), 3.70 (s, 3H), 3.14 (dd, J=15.8, 4.4 Hz, 1H), 2.95 (m, 1H).

MS (ESI, m/z): 263.4 [M+H$^+$].

57.ii. (R)-3-hydroxy-3-(6-methoxy-[1,5]naphthyridin-4-yl)-propionic acid

LiOH hydrate (0.035 g, 1 eq.) was added to a solution of intermediate 57.i (0.22 g, 0.84 mmol) in THF/H$_2$O (5:1, 10 mL). The mixture was stirred at rt overnight. The pH was adjusted to 3 by addition of 1M HCl and the aq. phase was extracted several times with EA. The combined org. layers were dried over MgSO$_4$ and concentrated to give the title acid as a yellowish solid (0.14 g, 67% yield).

MS (ESI, m/z): 249.4 [M+H$^+$].

57.iii. (R)-N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-propionamide This compound was obtained according to method I starting from intermediate 57.ii (0.05 g, 0.2 mmol) and intermediate 3.i (0.05 g, 0.2 mmol). The product was isolated after chromatography on $SiO_2$ (DCM/MeOH 19:1) as a colourless foam (0.056 g, 48% yield).

MS (ESI, m/z): 481.0 [M+H$^+$].

Example 58

(S)-N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-propionamide The title compound was prepared in analogy to Example 57 but using the (S,S) chiral bis-phosphoramide catalyst. The product was isolated after chromatography on $SiO_2$ (DCM/MeOH 19:1) as a colourless foam (0.022 g, 21% yield).

MS (ESI, m/z): 481.0 [M+H$^+$].

Example 59

(Z)-N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-acrylamide A solution of the compound of Example 57 (0.1 g, 0.2 mmol) in DCM was treated with MnO$_2$ (0.5 g, 27 eq.). The mixture was stirred at rt for 2 h. MnO$_2$ (0.25 g) was added and stirring continued for 1 h. The suspension was filtered over Celite and the volatiles were removed under reduced pressure. Chromatography on $SiO_2$ (DCM/MeOH 19:1) gave the title compound (0305 g, 50% yield) as a yellowish foam.

MS (ESI, m/z): 478.8 [M+H$^+$].

Example 60

(R)-3-(2,3-dihydro-benzo[1,4]dioxin-6-yl)-5-{[(3RS)-3-hydroxy-3-(6-methoxy-[1,5]naphthyridin-4-yl)-propylamino]-methyl}-oxazolidin-2-one (mixture of diastereomers)

A solution of the compound of Example 57 (0.04 g, 0.08 mmol) in THF (2 mL) was treated with a 1M solution of BH$_3$ in THF (0.16 mL). The mixture was stirred at 50° C. overnight. More BH$_3$ solution (0.5 mL) was added and stirring continued. When LC/MS indicated complete conversion, the reaction was quenched by addition of 1M HCl (1 mL) and the mixture was partitioned between DCM and NH$_4$OH. The org. layer was dried over MgSO$_4$ and concentrated. Chromatography on SiO$_2$ (EA, EA/MeOH 9:1) gave the title compound (0.013 g, 34% yield) as a colourless oil.

MS (ESI, m/z): 467.2 [M+H$^+$].

Example 61

3-(2,3-dihydro-benzo[1,4]dioxin-6-yl)-5-[5-hydroxy-5-(6-methoxy-[1,5]naphthyridin-4-yl)-pentyl]oxazolidin-2-one (mixture of diastereomers)

61.i. rac-3-(2,3-dihydro-benzo[1,4]dioxin-6-yl)-5-hex-5-enyl-oxazolidin-2-one

Starting from rac-1,2-epoxy-octene (6.3 g, 50 mmol) and 2,3-dihydro-benzo[1,4]dioxin-6-ylamine (7.6 g, 50 mmol) and following sequentially methods A and B, the title compound was isolated after chromatography on SiO$_2$ (Hept/EA1:1) as a yellowish oil (7.5 g, 50% yield over 2 steps).

$^1$H NMR (CDCl$_3$) δ: 7.02 (m, 2H), 6.84 (m, 1H), 5.79 (m, 1H), 4.99 (m, 2H), 4.59 (m, 1H), 4.24 (s, 4H), 4.00 (m, 1H), 3.57 (t, J=7.9 Hz, 1H), 2.08 (m, 2H), 1.84 (m, 1H), 1.71 (m, 1H), 1.49 (m, 4H).

61.ii. rac-5-[(S)-3-(2,3-dihydro-benzo[1,4]dioxin-6-yl)-2-oxo-oxazolidin-5-yl]-pentanal Intermediate 61.i (7.4 g, 25 mmol) was dihydroxylated according to method L. The resulting crude diol was dissolved in acetone (100 mL) and a solution of NaIO$_4$ (1.2 eq.) in water was added. A precipitate formed immediately. After 20 min complete conversion was observed. The precipitate was filtered off and the filtrate concentrated in vacuo. The residue was dissolved in EA and washed with water and brine. The org. phase was dried over MgSO$_4$ and concentrated. Chromatography on SiO$_2$ (Hept/EA 1:1, EA) gave the title aldehyde as a yellow oil (7.6 g, 100% yield).

$^1$H NMR (DMSO d6) δ: 9.78 (t, J=1.5 Hz, 1H), 7.06 (d, J=2.6 Hz, 1H), 6.97 (m, 1H), 6.84 (m, 1H), 4.59 (m, 1H), 4.23 (m, 5H), 4.01 (t, J=8.5 Hz, 1H), 3.57 (dd, J=8.8, 7.0 Hz, 1H), 2.48 (td, J=7.0, 1.5 Hz, 2H), 1.90-1.40 (m, 6H).

61.iii. 3-(2,3-dihydro-benzo[1,4]dioxin-6-yl)-5-[5-hydroxy-5-(6-methoxy-[1,5]naphthyridin-4-yl)-pentyl]-oxazolidin-2-one (mixture of diastereomers)

A solution of 8-bromo-2-methoxy-[1,5]naphthyridine (0.24 g, 1 mmol) in THF (5 mL) was cooled to −78° C. At this temperature n-BuLi (1.1 eq., 2.5M solution in hexanes) was added dropwise and the mixture stirred at −78° C. for 15 min. A solution of intermediate 61.ii (0.305 g, 1 mmol) in THF (3 mL) was added dropwise and the mixture stirred at −78° C. for 1 h and then slowly warmed to rt. The mixture was poured on a sat. NH$_4$Cl solution and was extracted with EA. The org. layer was dried over MgSO$_4$ and concentrated. The residue was purified by chromatography on SiO$_2$ (Hept/EA 1:1, EA, EA/MeOH 9:1) to give the title compound as a colourless foam (0.125 g, 27% yield).

MS (ESI, m/z): 466.0 [M+H$^+$].

Example 62

3-(2,3-dihydro-benzo[1,4]dioxin-6-yl)-5-[5-(3-fluoro-6-methoxy-[1,5]naphthyridin-4-yl)-5-hydroxy-pentyl]-oxazolidin-2-one (mixture of diastereomers)

The title compound was prepared in analogy to Example 61, starting from 8-bromo-7-fluoro-2-methoxy-[1,5]naphthyridine (0.257 g, 1 mmol) and intermediate 61.ii (0.305 g, 1 mmol). The compound was isolated after chromatography on SiO$_2$ (Hex/EA 2:1, 1:1, EA) as a colourless foam (0.15 g, 31% yield).

$^1$H NMR (DMSO d6) δ: 8.75 (d, J=1.2 Hz, 1H), 8.27 (m, 1H), 7.23 (d, J=9.1 Hz, 1H), 7.06 (m, 1H), 6.93 (m, 1H), 6.82 (m, 1H), 5.74 (m, 1H), 5.46 (d, J=5.9 Hz, 1H), 4.56 (m, 1H), 4.20 (d, J=1.8 Hz, 4H), 4.00 (m, 4H), 3.57 (td, J=7.9, 0.6 Hz, 1H), 1.93 (m, 2H), 1.65 (m, 2H), 1.40 (m, 4H).

MS (ESI, m/z): 484.2 [M+H$^+$].

Example 63 rac-3-(2,3-dihydro-benzo[1,4]dioxin-6-yl)-5-[5-(6-methoxy-[1,5]naphthyridin-4-yl)-5-oxo-pentyl]-oxazolidin-2-one A solution of the compound of Example 61 (0.55 g, 0.12 mmol) in DCM (5 mL) was treated with MnO$_2$ (0.5 g, 50 eq.). The mixture was stirred at rt for 1 h, filtered over MgSO$_4$ and concentrated. Chromatography on SiO$_2$ (EA) gave the title compound as a colourless oil (0.025 g, 46% yield).

$^1$H NMR (CDCl$_3$) δ: 8.85 (d, J=4.4 Hz, 1H), 8.26 (d, J=9.1 Hz, 1H), 7.62 (d, J=4.7 Hz, 1H), 7.18 (d, J=9.1 Hz, 1H), 7.05 (d, J=2.3 Hz, 1H), 6.98 (dd, J=8.8, 2.6 Hz, 1H), 6.84 (m, 1H), 4.62 (m, 1H), 4.23 (m, 4H), 4.06 (m, 4H), 3.58 (m, 1H), 3.42 (t, J=7.3 Hz, 2H), 1.73 (m, 6H).

MS (ESI, m/z): 464.2 [M+H$^+$].

Example 64

5-[5-amino-5-(6-methoxy-[1,5]naphthyridin-4-yl)-pentyl]-3-(2,3-dihydro-benzo[1,4]dioxin-6-yl)-oxazolidin-2-one (mixture of diastereomers)

64.i. Methanesulfonic acid 5-[3-(2,3-dihydro-benzo[1,4]dioxin-6-yl)-2-oxo-oxazolidin-5-yl]-1-(6-methoxy-[1,5]naphthyridin-4-yl)-pentyl ester A solution of the compound of Example 61 (0.62 g, 1.33 mmol) in DCM (6.5 mL) at 0° C. was sequentially treated with DIPEA (0.206 g, 1.2 eq.) and MsCl (0.17 g, 1.1 eq). The mixture was stirred at this temperature for 5 h, diluted with DCM (50 mL) and washed with water (50 mL), dried over MgSO$_4$ and concentrated to give the crude mesylate as a yellow foam (0.75 g, 100% yield) which was used without purification in the next step.

MS (ESI, m/z): 544.2 [M+H$^+$].

64.ii. 5-[5-azido-5-(6-methoxy-[1,5]naphthyridin-4-yl)-pentyl]-3-(2,3-dihydro-benzo[1,4]dioxin-6-yl)-oxazolidin-2-one A solution of intermediate 64.i (0.74 g, 1.36 mmol) in DMF (7 mL) was treated with NaN$_3$ (0.106 g, 1.2 eq.). The mixture was heated at 80° C. overnight. The mixture was partitioned between water and EA (40 mL each), the org. layer was washed with water and brine, dried over MgSO$_4$ and concentrated to give the azide as a orange oil (0.64 g, 96% yield) which was used without purification in the next step.

64.iii. 5-[(5-amino-5-(6-methoxy-[1,5]naphthyridin-4-yl)-pentyl]-3-(2,3-dihydro-benzo[1,4]dioxin-6-yl)-oxazolidin-2-one (mixture of diastereomers)

A solution of intermediate 64.ii (0.64 g, 1.3 mmol) in MeOH/THF 1:1 (10 mL) was hydrogenated over Pd/C (10%, 0.138 g) under 1 bar of H$_2$ for 7 h. The catalyst was filtered off over Celite and the filtrate concentrated in vacuo. Chromatography on SiO$_2$ (EA, EA/MeOH 9:1, 4:1+1% NH$_4$OH) gave the title compound as a yellowish foam (0.31 g, 51% yield).

$^1$H NMR (DMSO d6) δ: 8.72 (d, J=4.4 Hz, 1H), 8.23 (d, J=9.1 Hz, 1H), 7.72 (d, J=4.4 Hz, 1H), 7.22 (d, J=9.1 Hz, 1H), 7.07 (d, J=2.6 Hz, 1H), 6.93 (dd, J=9.1, 2.6 Hz, 1H), 6.82 (m, 1H), 4.80 (m, 1H), 4.56 (dd, J=7.3, 6.2 Hz, 1H), 4.19 (m, 4H), 4.00 (m, 4H), 3.58 (dd, J=8.8, 7.3 Hz, 1H), 2.16 (br, 2H), 1.57 (m, 8H).

Example 65

(RS)-3-(2,3-dihydro-benzo[1,4]dioxin-6-yl)-5-[4-(6-methoxy-quinazolin-4-ylamino)-butyl]-oxazolidin-2-one 65.i. Tert-butyl-hex-5-enyloxy-dimethyl-silane To a solution of 5-hexen-1-ol (5 g, 50 mmol) in THF (80 mL) were sequentially added TBDMSCl (8.4 g, 55 mmol) and imidazole (4.01 g, 60 mmol). The mixture was stirred at rt overnight. Water was added and the two phases separated. The aq. phase was extracted with ether and the combined org. layers were dried over MgSO$_4$ and concentrated to give the title intermediate as a colourless liquid (11.2 g, 100% yield).

$^1$H NMR (CDCl$_3$) δ: 5.81 (m, 1H), 4.98 (m, 2H), 3.61 (t, J=6.2 Hz, 2H), 2.06 (q, J=7.3 Hz, 2H), 1.48 (m, 4H), 0.90 (m, 9H), 0.07 (m, 6H).

65.ii. Rac-tert-butyl-dimethyl-(4-oxiranyl-butoxy)-silane

MCPBA (12.8 g, 1.1 eq) was added to a solution of intermediate 65.i (10.1 g, 47.5 mmol) in DCM (90 mL). The mixture was stirred at rt for 22 h. After filtration, the filtrate was diluted with DCM and washed with 1M NaOH (30 mL). The org. layer was dried over MgSO$_4$ and concentrated. Chromatography on SiO$_2$ (Hex, Hex/EA 19:1, 9:1) gave the title epoxide as a colourless liquid (10.2 g, 93% yield).

$^1$H NMR (CDCl$_3$) δ: 3.62 (m, 2H), 2.91 (m, 1H), 2.74 (dd, J=5.0, 4.1 Hz, 1H), 2.46 (dd, J=5.0, 2.6 Hz, 1H), 1.56 (m, 6H), 0.89 (m, 9H), 0.05 (m, 6H).

65.iii. Rac-5-[4-(tert-butyl-dimethyl-silanyloxy)-butyl]-3-(2,3-dihydro-benzo[1,4]dioxin-6-yl)-oxazolidin-2-one The title intermediate was prepared using sequentially methods A and B, starting from intermediate 65.ii (2.5 g, 11 mmol). After chromatography on SiO$_2$ (Hex/EA 2:1), a yellowish solid (2.2 g, 49% yield over 2 steps) was obtained.

$^1$H NMR (DMSO d6) δ: 7.08 (d, J=2.6 Hz, 1H), 6.94 (m, 1H), 6.83 (m, 1H), 4.60 (m, 1H), 4.20 (m, 4H), 4.05 (t, J=8.8 Hz, 1H), 3.59 (m, 4H), 1.68 (m, 2H), 1.45 (m, 4H), 0.83 (m, 9H), 0.01 (s, 6H).

65.iv. (rac)-3-(2,3-dihydro-benzo[1,4]dioxin-6-yl)-5-(4-hydroxy-butyl)-oxazolidin-2-one A solution of intermediate 65.iii (2.2 g, 5.4 mmol) in THF (10 mL) was treated with a 1M solution of TBAF in THF (5.5 mL). The mixture was stirred at rt overnight and then partitioned between water and EA. The org. phase was washed with brine, dried over MgSO$_4$ and concentrated. The residue was purified by chromatography on SiO$_2$ (EA) to give the title alcohol as a colourless oil (1.45 g, 91% yield).

$^1$H NMR (CDCl$_3$) δ: 7.06 (d, J=2.6 Hz, 1H), 6.98 (m, 1H), 6.84 (m, 1H), 4.60 (m, 1H), 4.24 (m, 4H), 4.01 (t, J=8.5 Hz, 1H), 3.67 (m, 2H), 3.59 (dd, J=8.8, 7.0 Hz, 1H), 1.70 (m, 8H).

65.v. (rac)-5-(4-amino-butyl)-3-(2,3-dihydro-benzo[1,4]dioxin-6-yl)-oxazolidin-2-one A solution of intermediate 65.iv (0.85 g, 2.9 mmol) and DIPEA (0.45 g, 1.2 eq.) in DCM (12 mL) was cooled to 0° C. and MsCl (0.365 g, 1.1 eq.) was added dropwise. The mixture was stirred at 0° C. for 5 h, diluted with DCM and washed with water. The org. phase was dried over MgSO$_4$ and concentrated. The mesylate was dissolved in DMF (15 ml) and NaN$_3$ (0.22 g, 1.2 eq) was added. The mixture was heated at 80° C. overnight before being partitioned between water and EA. The org. phase was washed with water and brine, dried over MgSO$_4$ and concentrated. The azide, dissolved in EtOH/THF (5:3, 16 mL), was hydrogenated over Pd(OH)$_2$ (0.21 g, 0.1 eq) under 1 bar of H$_2$ for 4 h. The catalyst was filtered off and the filtrate concentrated to give the title amine as a yellowish oil (0.86 g, 95% yield).

$^1$H NMR (CDCl$_3$) δ: 7.06 (d, J=2.6 Hz, 1H), 6.97 (d, J=2.6 Hz, 1H), 6.84 (m, 1H), 4.24 (s, 5H), 4.01 (s, 1H), 2.73 (s, 2H), 1.52 (m, 8H).

65.vi. (RS)-3-(2,3-dihydro-benzo[1,4]dioxin-6-yl)-5-[4-(6-methoxy-quinazolin-4-ylamino)-butyl]-oxazolidin-2-one A solution of intermediate 65.v (0.15 g, 0.5 mmol) and 4-chloro-6-methoxy-quinazoline (0.1 g, 0.5 mmol) in DMF (5 mL) was cooled to 0° C. A NaH dispersion (55% in paraffin, 0.05 g, 2 eq.) was added and the mixture stirred at rt for 5 h. The mixture was diluted with EA and water (30 mL each) and the phases were separated. The aq. phase was extracted twice more with EA and the combined org. layers were washed with water and brine, dried over MgSO$_4$ and concentrated. The residue was purified by chromatography on SiO$_2$ (EA/MeOH 19:1, 9:1+1% NH$_4$OH).

$^1$H NMR (CDCl$_3$) δ: 8.57 (s, 1H), 7.77 (d, J=9.1 Hz, 1H), 7.68 (m, 1H), 7.38 (dt, J=8.8, 2.9 Hz, 1H), 7.03 (dd, J=7.3, 2.6 Hz, 1H), 6.94 (m, 1H), 6.82 (m, 1H), 5.89 (m, 1H), 4.61 (m, 1H), 4.23 (s, 4H), 4.01 (t, J=8.5 Hz, 1H), 3.90 (m, 4H), 3.68 (m, 1H), 3.58 (dd, J=8.8, 7.3 Hz, 1H), 1.73 (m, 6H).

MS (ESI, m/z): 451.3 [M+H$^+$].

Example 66

N-[(R)-3-(2,3-dihydro-benzo[1,4]dioxin-6-yl)-2-oxo-oxazolidin-5-ylmethyl]-(2RS)-2-hydroxy-3-(6-methoxy-[1,5]naphthyridin-4-yl)-propionamide 66.i. 3-(6-methoxy-[1,5]naphthyridin-4-yl)-oxirane-2-carboxylic acid tert-butyl ester t-BuOK (0.637 g, 5.55 mmol) was dissolved in t-BuOH (7 mL) and added dropwise to a suspension of 6-methoxy-[1,5]

naphthyridine-4-carbaldehyde (0.94 g, 5 mmol) and tert-butyl bromoacetate (0.98 g, 5 mmol) in t-BuOH (5 mL). The mixture was stirred at rt for 2 h, filtered through Celite and concentrated to give the desired epoxide as a mixture of diastereomers (1.5 g, 99% yield), which was used as such in next step.

MS (ESI, m/z): 303.1 [M+H$^+$].

66.ii. (rac)-2-hydroxy-3-(6-methoxy-[1,5]naphthyridin-4-yl)-propionic acid tert-butyl ester A solution of intermediate 66.i (1.5 g, 4.95 mmol) in EA (15 mL) was hydrogenated over Pd/C (10%, 0.26 g) and 1 bar of H$_2$ for 22 h. The reaction was not complete. The catalyst was filtered off over Celite and the filtrate concentrated in vacuo. Chromatography on SiO$_2$ (Hex/EA 4:1, 2:1, 1:1) gave the desired alcohol as a yellow solid (0.58 g, 38% yield), along with unreacted cis-epoxide (0.54 g, 36% yield).

$^1$H NMR (CDCl$_3$) δ: 8.69 (d, J=4.4 Hz, 1H), 8.22 (d, J=9.1 Hz, 1H), 7.45 (d, J=4.7 Hz, 1H), 7.13 (d, J=9.1 Hz, 1H), 4.62 (m, 1H), 4.21 (d, J=6.4 Hz, 1H), 3.76 (dd, J=13.5, 4.1 Hz, 1H), 3.34 (dd, J=13.5, 8.2 Hz, 1H), 1.35 (s, 9H).

MS (ESI, m/z): 305.4 [M+H$^+$].

66.iii. (rac)-2-hydroxy-3-(6-methoxy-[1,5]naphthyridin-4-yl)-propionic acid

The ester of intermediate 66.ii (0.578 g, 1.9 mmol) was hydrolyzed according to method F. The desired acid was isolated as a beige solid (0.34 g, 72% yield).

$^1$H NMR (DMSO d6) δ: 8.66 (d, J=4.4 Hz, 1H), 8.23 (d, J=9.1 Hz, 1H), 7.55 (d, J=4.4 Hz, 1H), 7.24 (d, J=9.1 Hz, 1H), 4.51 (dd, J=8.8, 4.4 Hz, 1H), 4.02 (s, 3H), 3.66 (dd, J=13.2, 4.4 Hz, 1H), 3.18 (dd, J=13.5, 9.1 Hz, 1H).

66.iv. N-[(R)-3-(2,3-dihydro-benzo[1,4]dioxin-6-yl)-2-oxo-oxazolidin-5-ylmethyl]-(2RS)-2-hydroxy-3-(6-methoxy-[1,5]naphthyridin-4-yl)-propionamide The title compound was obtained according to method I, starting from intermediate 66.iii (0.1 g, 0.4 mmol) and intermediate 3.i (0.1 g, 0.4 mmol). The product was isolated after chromatography on SiO$_2$ (EA, EA/MeOH 19:1, 9:1+1% NH$_4$OH) as a colourless solid (0.15 g, 78% yield, diastereomeric mixture).

MS (ESI, m/z): 481.3 [M+H$^+$].

Example 67

(2RS)-2-hydroxy-3-(6-methoxy-[1,5]naphthyridin-4-yl)-N-[(R)-2-oxo-3-(3-oxo-3,4-dihydro-2H-benzo[1,4]thiazin-6-yl)-oxazolidin-5-ylmethyl]-propionamide The title compound was obtained according to method I starting from intermediate 66.iii (0.1 g, 0.4 mmol) and intermediate 4.v (0.112 g, 0.4 mmol). The product was isolated after chromatography on SiO$_2$ (EA, EA/MeOH 19:1, 9:1+1% NH$_4$OH) as a colourless solid (0.126 g, 61% yield, diastereomeric mixture).

MS (ESI, m/z): 509.9 [M+H$^+$].

Example 68

(2RS,3RS)-2-amino-N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-propionamide

68.i. 2-(benzhydryl-amino)-3-hydroxy-3-(6-methoxy-[1,5]naphthyridin-4-yl)-propionic acid methyl ester (mixture of diastereomers)

A mixture of Zn(OTf)$_2$ (0.064 g, 0.17 mmol) and 6-methoxy-[1,5]naphthyridine-4-carbaldehyde (0.5 g, 2.6 mmol) and molecular sieves (4 Å, 0.66 g) in toluene (13 mL) at 0° C. was treated with (benzhydrylidene-amino)-acetic acid methyl ester (0.44 g, 1.7 mmol) and diallylamine (0.25 g, 1.7 mmol). The mixture was left at 4° C. over the weekend. The reaction was quenched by careful addition of Na$_2$CO$_3$ and filtered. The filtrate was diluted with EA and water and the 2 phases separated. The org. phase was dried over MgSO$_4$ and concentrated. The residue was dissolved in MeOH (10 mL) and AcOH (0.175 g, 3 mmol) and NaCNBH$_3$ (0.166 g, 2.6 mmol) was added. The mixture was stirred at rt overnight and partitioned between a NaHCO$_3$ solution and EA. The org. phase was dried over MgSO$_4$ and concentrated. Chromatography on SiO$_2$ (Hex/EA 1:1) gave the title intermediate as a yellow oil (0.5 g, 64% yield).

MS (ESI, m/z): 444.3 [M+H$^+$].

68.ii. 2-(benzhydryl-amino)-3-hydroxy-3-(6-methoxy-[1,5]naphthyridin-4-yl)-propionic acid (mixture of diastereomers)

The methyl ester of intermediate 68.i (0.5 g, 1.13 mmol) was hydrolyzed according to method F. The acid was isolated as a colourless solid (0.44 g, 91% yield) after chromatography on SiO$_2$ (EA, EA/MeOH 9:1).

$^1$H NMR (DMSO d6) δ: 8.88 (d, J=4.7 Hz, 1H), 8.26 (d, J=9.1 Hz, 1H), 7.84 (d, J=4.7 Hz, 1H), 7.14 (m, 7H), 6.78 (m, 1H), 6.53 (t, J=7.9 Hz, 2H), 6.40 (d, J=7.0 Hz, 2H), 5.83 (d, J=1.8 Hz, 1H), 4.62 (s, 1H), 3.58 (s, 3H), 3.30 (m, 1H).

68.iii. 2-(benzhydryl-amino)-N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-propionamide Intermediate 68.ii (0.2 g, 0.47 mmol) and intermediate 3.i (0.12 g, 0.47 mmol) were coupled according to method I. The product was isolated after chromatography on SiO$_2$ (EA) as a colourless oil (0.15 g, 48% yield).

MS (ESI, m/z): 662.4 [M+H$^+$].

68.iv. (2RS,3RS)-2-amino-N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-propionamide A solution of intermediate 68.iii (0.15 g, 0.23 mmol) in MeOH/AcOH (1:1, 10 mL) was hydrogenated over Pd(OH)$_2$ (0.012 g, 0.1 eq) under 1 bar of H$_2$ for 4 h at rt and 4 h at 60° C. The catalyst was filtered off and the filtrate concentrated in vacuo. The residue was purified by chromatography on SiO$_2$ (EA/MeOH 4:1+1% NH$_4$OH) followed by trituration with ether to give the title compound (0.037 g, 33% yield).

MS (ESI, m/z): 496.3 [M+H$^+$].

Example 69

(2RS)-2-amino-N-[(R)-3-(2,3-dihydro-benzo[1,4]dioxin-6-yl)-2-oxo-oxazolidin-5-ylmethyl]-3-(6-methoxy-[1,5]naphthyridin-4-yl)-propionamide

69.i. (Z)-2-benzyloxycarbonylamino-3-(6-methoxy-[1,5]naphthyridin-4-yl)-acrylic acid methyl ester A solution of benzyloxycarbonylamino-(dimethoxy-phosphoryl)-acetic acid methyl ester (2.07 g, 6.25 mmol) in DCM (10 mL) was cooled to 0° C. and DBU (0.95 g, 6.25 mmol) was added dropwise. The mixture was stirred at 0° C. for 15 min and then added via syringe dropwise to a suspension of 6-methoxy-[1,5]naphthyridine-4-carbaldehyde (0.94 g, 5 mmol) in DCM (15 mL) at 0° C. The mixture was stirred at 0° C. for 1 h, diluted with DCM, washed with water, dried over MgSO$_4$ and concentrated. Chromatography on SiO$_2$ (Hex/EA 1:1) gave the product (25:1 Z/E mixture) as a colourless foam (1.92 g, 98% yield).

MS (ESI, m/z): 394.2 [M+H$^+$].

69.ii. (rac)-2-amino-3-(6-methoxy-[1,5]naphthyridin-4-yl)-propionic acid methyl ester A mixture of intermediate 69.i (0.68 g, 1.7 mmol), ammonium formate (1.09 g, 10 eq.) and Pd/C (10%, 0.05 g) in MeOH (12 mL) in a sealed flask was heated at 60° C. for 4 h. The catalyst was filtered off and the mixture partitioned between DCM and NH$_4$OH. The org. layer was dried over MgSO$_4$ and concentrated. Chromatography on SiO$_2$ (EA, EA/MeOH 9:1) gave the title amine as a colourless oil (0.37 g, 82% yield).

$^1$H NMR (DMSO d6) δ: 8.66 (d, J=4.4 Hz, 1H), 8.23 (d, J=9.1 Hz, 1H), 7.52 (d, J=4.4 Hz, 1H), 7.23 (d, J=9.1 Hz, 1H), 4.02 (s, 3H), 3.88 (dd, J=7.9, 5.9 Hz, 1H), 3.50 (m, 4H), 3.18 (dd, J=12.9, 8.2 Hz, 1H), 3.29 (s, 1H), 1.84 (s, 2H).

MS (ESI, m/z): 262.4 [M+H$^+$].

69.iii. (rac)-2-tert-butoxycarbonylamino-3-(6-methoxy-[1,5]naphthyridin-4-yl)-propionic acid methyl ester A solution of above amine (0.372 g, 1.4 mmol) in DCM (5 ml) was treated with TEA (0.29 g, 2 eq.) and Boc$_2$O (0.62 g, 2.8 mmol). The mixture was stirred at rt overnight, concentrated in vacuo and purified by chromatography on SiO$_2$ (Hex/EA 1:1, EA) to give the title intermediate as a yellowish solid (0.46 g, 90% yield).

MS (ESI, m/z): 362.2 [M+H$^+$].

69.iv. (rac)-2-tert-butoxycarbonylamino-3-(6-methoxy-[1,5]naphthyridin-4-yl)-propionic acid The ester of intermediate 69.iii (0.45 g, 1.25 mmol) was hydrolysed according to method F. The product was isolated as a colourless solid (0.32 g, 74% yield).

$^1$H NMR (DMSO d6) δ: 12.57 (m, 1H), 8.66 (d, J=4.4 Hz, 1H), 8.24 (d, J=9.1 Hz, 1H), 7.53 (d, J=4.4 Hz, 1H), 7.25 (d, J=9.1 Hz, 1H), 7.16 (m, 1H), 4.04 (s, 3H), 4.51 (m, 1H), 3.76 (dd, J=13.5, 5.0 Hz, 1H), 3.15 (dd, J=12.9, 10.3 Hz, 1H), 1.24 (s, 7H).

MS (ESI, m/z): 348.2 [M+H$^+$].

69.v. [(RS)-1-{[(R)-3-(2,3-dihydro-benzo[1,4]dioxin-6-yl)-2-oxo-oxazolidin-5-ylmethyl]-carbamoyl}-2-(6-methoxy-[1,5]naphthyridin-4-yl)-ethyl]-carbamic acid tert-butyl ester Intermediate 69.iv (0.1 g, 0.3 mmol) and intermediate 3.i (0.076 g, 0.3 mmol) were coupled according to method H. The product was isolated after chromatography on SiO$_2$ (EA) as a colourless oil (0.14 g, 79% yield).

MS (ESI, m/z): 580.3 [M+H$^+$].

69.vi. (2RS)-2-amino-N-[(R)-3-(2,3-dihydro-benzo[1,4]dioxin-6-yl)-2-oxo-oxazolidin-5-ylmethyl]-3-(6-methoxy-[1,5]naphthyridin-4-yl)-propionamide The Boc group of intermediate 69.v (0.11 g, 0.19 mmol) was removed according to method E. The product was isolated after chromatography on SiO$_2$ (EA, EA/MeOH 9:1, 4:1) as a colourless foam (0.08 g, 88% yield).

MS (ESI, m/z): 480.3 [M+H$^+$].

Example 70

(5R)-5-{[(2RS)-2-amino-3-(6-methoxy-[1,5]naphthyridin-4-yl)-propylamino]-methyl}-3-(2,3-dihydro-benzo[1,4]dioxin-6-yl)-oxazolidin-2-one

70.i. [(rac)-1-formyl-2-(6-methoxy-[1,5]naphthyridin-4-yl)-ethyl]-carbamic acid tert-butyl ester DIBAH (1.47 ml, 2.5 mmol, 1.7M solution in toluene) was slowly added to a solution of intermediate 69.iii (0.36 g, 1 mmol) in toluene (15 mL) at −78° C. The mixture was stirred at −78° C. for 2 h and quenched by dropwise addition of sat. Rochelles salt solution (1 mL). The mixture was allowed to warm to rt, diluted with EA, dried over MgSO$_4$ and concentrated. Chromatography on SiO$_2$ (Hex/EA 1:1, EA) gave the desired aldehyde as a colourless foam (0.11 g, 33% yield).

MS (ESI, m/z): 332.2 [M+H$^+$].

70.ii. [(RS)-2-{[(R)-3-(2,3-dihydro-benzo[1,4]dioxin-6-yl)-2-oxo-oxazolidin-5-ylmethyl]-amino}-1-(6-methoxy-[1,5]naphthyridin-4-ylmethyl)-ethyl]-carbamic acid tert-butyl ester Intermediate 70.i (0.1 g, 0.3 mmol) and intermediate 3.i (0.09 g, 0.3 mmol) were coupled according to method K. The compound was isolated after chromatography on SiO$_2$ (EA, EA/MeOH 9:1) as a yellowish oil (0.11 g, 64% yield).

MS (ESI, m/z): 566.3 [M+H$^+$].

70.iii. (5R)-5-{[(2RS)-2-amino-3-(6-methoxy-[1,5]naphthyridin-4-yl)-propylamino]-methyl}-3-(2,3-dihydro-benzo[1,4]dioxin-6-yl)-oxazolidin-2-one The Boc group of intermediate 70.ii (0.11 g, 0.19 mmol) was removed according to method E. The product was isolated after chromatography on SiO$_2$ (EA, EA/MeOH 9:1, 4:1) as a colourless foam (0.04 g, 40% yield).

MS (ESI, m/z): 466.2 [M+H$^+$].

Example 71

(S)-3-(2,3-dihydro-benzo[1,4]dioxin-6-yl)-2-oxo-oxazolidine-5-carboxylic acid [3-(6-methoxy-[1,5]naphthyridin-4-yl)-prop-2-ynyl]-amide

71.i. (S)-3-(2,3-dihydro-benzo[1,4]dioxin-6-yl)-2-oxo-oxazolidine-5-carboxylic acid prop-2-ynylamide To a solution of intermediate 51.iv (385 mg, 1.45 mmol), propargylamine (0.093 mL, 1.45 mmol) and DIPEA (0.96 mL, 4 eq.) in DMF (3 mL) was added HATU (1.10 g, 2 eq.). The resulting solution was stirred at rt for 48 h. EA and water were added and the phases were separated. The aq. phase was extracted with EA and the combined org. extracts were washed with brine/water (3 times), dried over MgSO$_4$, concentrated under reduced pressure. The residue was triturated with ether to afford the title amide as an off-white solid (394 mg, 90% yield).

MS (ESI, m/z): 303.2 [M+H$^+$].

71.ii. (S)-3-(2,3-dihydro-benzo[1,4]dioxin-6-yl)-2-oxo-oxazolidine-5-carboxylic acid [3-(6-methoxy-[1,5]naphthyridin-4-yl)-prop-2-ynyl]-amide To a solution of trifluoro-methanesulfonic acid 6-methoxy-[1,5]naphthyridin-4-yl ester (383 mg, 1.24 mmol; prepared as in WO 02/08224), intermediate 71.i (375 mg, 1.24 mmol) and TEA (1.04 mL, 6 eq.) in DMF (4 mL) were added Pd(PPh$_3$)$_2$Cl$_2$ (44 mg, 0.05 eq.) and CuI (24 mg, 0.1 eq.). The mixture was degassed with a stream of N$_2$ for 15 min and then stirred at rt for 20 h. The mixture was partitioned between a sat. NH$_4$Cl solution and EA, the org. layer was washed several times with water and a sat. NH$_4$Cl solution, dried over MgSO$_4$ and concentrated. The residue was chromatographed on SiO$_2$ (DCM/MeOH/NH$_4$OH: 1000/50/4) to afford the title compound as a colourless solid (51 mg, 9% yield).

$^1$H NMR (DMSO d6) δ: 9.08 (m, 1H), 8.72 (d, J=4.7 Hz, 1H), 8.26 (d, J=9.1 Hz, 1H), 7.70 (d, J=4.4 Hz, 1H), 7.28 (d, J=9.1 Hz, 1H), 7.11 (d, J=2.3 Hz, 1H), 6.97 (dd, J=8.8, 2.6 Hz, 1H), 6.84 (m, 1H), 5.09 (dd, J=9.4, 5.9 Hz, 1H), 4.34 (d, J=5.6 Hz, 2H), 4.21 (m, 5H), 4.01 (s, 3H), 3.95 (dd, J=9.4, 6.2 Hz, 1H).

MS (ESI, m/z): 461.1 [M+H$^+$].

Example 72

(rac)-3-(2,3-dihydro-benzo[1,4]dioxin-6-yl)-5-{2-[2-(6-methoxy-[1,5]naphthyridin-4-yl)-ethylamino]-ethyl}-oxazolidin-2-one

72.i. [(rac)-3,4-dihydroxy-butyl]-carbamic acid benzyl ester

The title diol was obtained according to method L starting from but-3-enyl-carbamic acid benzyl ester (8.0 g, 39 mmol; see *Heterocycles* (2006), 67(2), 549-554). The product was isolated without further purification as a yellow oil (9.49 g, 100% yield).

72.ii. Toluene-4-sulfonic acid (rac)-4-benzyloxycarbonylamino-2-hydroxy-butyl ester A solution of p-TsCl (7.94 g, 41.6 mmol) in DCM (50 mL) was added dropwise to a solution of intermediate 72.i (9.49 g, 41.6 mmol) in DCM (170 mL) and Pyr (23 mL) at 5° C. The mixture was stirred at rt for 3 h, poured in 1M HCl and extracted with DCM. The org. layer was dried over MgSO$_4$ and concentrated. Chromatography on SiO$_2$ (Hex/EA 4:1, EA) afforded the title tosylate as a colourless oil (8.94 g, 57% yield).

MS (ESI, m/z): 394.3 [M+H$^+$].

72.iii. [(rac)-2-oxiranyl-ethyl]-carbamic acid benzyl ester

NaOH 2M (12 mL) was added to a solution of intermediate 72.ii (8.93 g, 22.7 mmol) in THF (90 mL). The mixture was vigorously stirred at rt for 1 h, partitioned between water and EA. The org. layer washed with brine, dried over MgSO$_4$ and concentrated to afford the title epoxide (4.59 g, 99% yield).

$^1$H NMR (DMSO d6) δ: 7.35 (m, 5H), 5.10 (s, 2H), 5.00 (m, 1H), 3.38 (q, J=6.4 Hz, 2H), 2.98 (m, 1H), 2.76 (t, J=4.4 Hz, 1H), 2.50 (dd, J=5.0, 2.6 Hz, 1H), 1.94 (m, 1H), 1.60 (m, 1H).

72.iv. [(rac)-4-(2,3-dihydro-benzo[1,4]dioxin-6-ylamino)-3-hydroxy-butyl]-carbamic acid benzyl ester A solution of intermediate 72.iii (1.97 g, 8.9 mmol) and 2,3-dihydro-benzo[1,4]dioxin-6-ylamine (1.35 g, 8.9 mmol) in EtOH/water 9:1 (50 mL) was heated at 80° C. overnight. The mixture was concentrated and chromatographed on SiO$_2$ (Hept/EA 1:1, EA) to afford the title intermediate as a beige solid (2.06 g, 62% yield).

MS (ESI, m/z): 373.4 [M+H$^+$].

72.v. {2-[(rac)-3-(2,3-dihydro-benzo[1,4]dioxin-6-yl)-2-oxo-oxazolidin-5-yl]-ethyl}-carbamic acid benzyl ester Triphosgene (598 mg, 2.04 mmol) was added to a solution of intermediate 72.iv (1.90 g, 5.09 mmol) and Pyr (2.05 mL, 5 eq.) in DCM (30 mL). The mixture was stirred at rt for 4 h. The mixture was concentrated, partitioned between EA and water. The org. phase was washed with sat. CuSO$_4$, dried over MgSO$_4$ and concentrated. The residue was chromatographed on SiO$_2$ (Hept/EA 1:1, EA) to afford the title intermediate as a colourless foam (1.28 g, 63% yield).

MS (ESI, m/z): 399.2 [M+H$^+$].

72.vi. (rac)-5-(2-amino-ethyl)-3-(2,3-dihydro-benzo[1,4]dioxin-6-yl)-oxazolidin-2-one A solution of intermediate 72.v (1.28 g, 3.21 mmol) in MeOH (25 mL) was hydrogenated over Pd(OH)$_2$ for 2 h. Catalyst filtered off and filtrate concentrated to afford the title intermediate as a colourless foam (0.73 g, 86% yield).

MS (ESI, m/z): 265.3 [M+H$^+$].

72.vii. (rac)-3-(2,3-dihydro-benzo[1,4]dioxin-6-yl)-5-{2-[2-(6-methoxy-[1,5]naphthyridin-4-yl)-ethylamino]-ethyl}-oxazolidin-2-one Glacial AcOH (0.031 mL, 0.537 mmol) was added dropwise to an ice-chilled solution of intermediate 72.vi (142 mg, 0.537 mmol) in MeOH (2 mL). The solution was warmed to rt and 2-methoxy-8-vinyl-[1,5]naphthyridine (100 mg, 0.537 mmol; see WO 2007/016610) was added. The resulting mixture was heated in a sealed tube at 70° C. for 4 h. The mixture was concentrated and made strongly basic by adding NH₄OH. The mixture was extracted with DCM-MeOH 9:1 (3 times) and the combined org. layers were concentrated and the residue was chromatographed on SiO₂ (DCM/MeOH/NH₄OH: 1000:50:4) to afford the title compound as a colourless foam (12 mg, 5% yield).

$^1$H NMR (CDCl₃) δ: 8.66 (d, J=4.4 Hz, 1H), 8.18 (d, J=9.1 Hz, 1H), 7.39 (d, J=4.4 Hz, 1H), 7.10 (d, J=9.1 Hz, 1H), 7.04 (d, J=2.6 Hz, 1H), 6.94 (dd, J=9.1 Hz, 1H), 6.83 (d, J=9.1, 2.3 Hz, 1H), 4.69 (m, 1H), 4.21 (m, 4H), 4.05 (s, 3H), 3.97 (t, J=8.5 Hz, 1H), 3.59 (dd, J=8.5, 7.3 Hz, 1H), 3.35 (t, J=6.7 Hz, 2H), 3.09 (t, J=7.0 Hz, 2H), 2.87 (m, 2H), 1.91 (m, 2H).

MS (ESI, m/z): 451.2 [M+H⁺].

Example 73

6-((rac)-5-{2-[2-(6-methoxy-[1,5]naphthyridin-4-yl)-ethylamino]-ethyl}-2-oxo-oxazolidin-3-yl)-4H-benzo[1,4]thiazin-3-one 73.i. [(rac)-3-hydroxy-4-(3-oxo-3,4-dihydro-2H-benzo[1,4]thiazin-6-ylamino)-butyl]-carbamic acid benzyl ester This compound was prepared starting from intermediate 72.iii (1.97 g, 8.9 mmol) and 6-amino-4H-benzo[1,4]thiazin-3-one (1.60 g, 8.9 mmol) and using the protocol of Example 72, step 72.iv. Chromatography on SiO₂ (DCM/MeOH/NH₄OH: 1000:50:4) afforded the expected compound as a beige solid (2.34 g, 65% yield).

MS (ESI, m/z): 402.3 [M+H⁺].

73.ii. {2-[(rac)-2-oxo-3-(3-oxo-3,4-dihydro-2H-benzo[1,4]thiazin-6-yl)-oxazolidin-5-yl]-ethyl}-carbamic acid benzyl ester The title intermediate was prepared starting from intermediate 73.i (2.01 g, 5.0 mmol) and using the protocol of Example 72, step 72.v. Chromatography on SiO₂ (DCM/MeOH/NH₄OH: 1000:50:4) afforded the title intermediate as a colourless foam (0.71 g, 33% yield).

MS (ESI, m/z): 428.1 [M+H⁺].

73.iii. 6-[(rac)-5-(2-amino-ethyl)-2-oxo-oxazolidin-3-yl]-4H-benzo[1,4]thiazin-3-one A mixture of intermediate 73.ii (700 mg, 1.64 mmol) and Et₃SiH (200 mg, 1.05 eq.) was dissolved in TFA (5 mL) and stirred at rt for 48 h. The mixture was concentrated in vacuo, partitioned between DCM and NH₄OH. Aqueous phase extracted once more with DCM. The combined org. layers were washed with water, dried over MgSO₄ and concentrated. The residue was chromatographed on SiO₂ (1000:200:16 DCM/MeOH/NH₄OH) to afford the title intermediate as a colorless foam (285 mg, 59% yield).

MS (ESI, m/z): 294.3 [M+H⁺].

73.iv. 6-((rac)-5-{2-[2-(6-methoxy-[1,5]naphthyridin-4-yl)-ethylamino]-ethyl}-2-oxo-oxazolidin-3-yl)-4H-benzo[1,4]thiazin-3-one The title compound was prepared starting from intermediate 73.iii (222 mg, 0.76 mmol) and 2-methoxy-8-vinyl-[1,5]naphthyridine (141 mg, 0.76 mmol; see WO 2007/016610) and using the protocol of Example 72, step 72.vii. Chromatography on SiO₂ (DCM/MeOH/NH₄OH: 1000:100:8) afforded the title compound as a colourless foam (80 mg, 22% yield).

$^1$H NMR (CDCl₃) δ: 9.28 (br. s, 1H), 8.67 (d, J=4.4 Hz, 1H), 8.20 (d, J=9.1 Hz, 1H), 7.41 (d, J=4.7 Hz, 1H), 7.24 (d, J=10.2 Hz, 1H), 7.10 (d, J=9.1 Hz, 1H), 7.03 (dd, J=8.8, 2.3 Hz, 1H), 6.95 (d, J=2.3 Hz, 1H), 4.63 (m, 1H), 4.06 (s, 3H), 3.75 (t, J=8.5 Hz, 1H), 3.47 (s, 2H), 3.40 (m, 3H), 3.11 (t, J=7.0 Hz, 2H), 2.90 (m, 1H), 2.80 (m, 1H), 2.00 (m, 1H), 1.81 (m, 1H).

MS (ESI, m/z): 480.3 [M+H⁺].

Example 74

6-((rac)-5-{2-[2-(3-fluoro-6-methoxy-[1,5]naphthyridin-4-yl)-ethylamino]-ethyl}-2-oxo-oxazolidin-3-yl)-4H-benzo[1,4]thiazin-3-one The title compound was prepared starting from intermediate 73.iii (66 mg, 0.225 mmol) and 7-fluoro-2-methoxy-8-vinyl-[1,5]naphthyridine (51 mg, 0.225 eq.; see WO 2007/016610) and using the protocol of Example 72, step 72.vii. Chromatography on SiO₂ (DCM/MeOH/NH₄OH: 1000:100:8) afforded the title compound as a pale yellow solid (24 mg, 21% yield).

$^1$H NMR (CDCl₃) δ: 9.14 (br. s, 1H), 8.62 (s, 1H), 8.18 (d, J=9.1 Hz, 1H), 7.24 (d, J=10.2 Hz, 1H), 7.04 (m, 3H), 4.63 (m, 1H), 4.07 (s, 3H), 3.80 (t, J=8.8 Hz, 1H), 3.48 (dd, J=8.5, 7.6 Hz, 1H), 3.40 (m, 4H), 3.07 (t, J=7.0 Hz, 2H), 2.92 (m, 1H), 2.80 (m, 1H), 2.01 (m, 1H), 1.82 (m, 1H).

MS (ESI, m/z): 498.3 [M+H⁺].

Example 75

N-{2-[(rac)-3-(2,3-dihydro-benzo[1,4]dioxin-6-yl)-2-oxo-oxazolidin-5-yl]-ethyl}-2-(3-methoxy-quinoxalin-5-yl)-acetamide 75.i. (3-methoxy-quinoxalin-5-yl)-methanol To a stirred suspension of 3-methoxy-quinoxaline-5-carbaldehyde (4.05 g, 21.5 mmol; see WO 2006/032466) in EtOH (150 mL) cooled at 0° C., NaBH₄ (814 mg, 21.5 mmol) was added in one portion. The reaction mixture was warmed to rt and stirred for 1 h. The mixture was quenched at 0° C. by addition of 1M HCl until H₂ evolvement ceased, then concentrated under reduced pressure. The phases were separated between EA and sat. aq. NaHCO₃, the org. layer was dried over MgSO₄ and concentrated under reduced pressure. The residue was chromatographed on SiO₂ (DCM-MeOH—NH₄OH: 1000:50:4) to afford the title alcohol as a dark yellow solid (2.92 g, 71% yield).

MS (ESI, m/z): 191.1 [M+H⁺].

75.ii. 8-bromomethyl-2-methoxy-quinoxaline

To a stirred solution of intermediate 75.i (2.91 g, 15.3 mmol) in DMF (25 mL), PBr₃ (1.58 mL, 1.1 eq.) was added dropwise at rt. After stirring for 30 min water was added and the mixture was extracted with EA. The org. layer was washed several times with water and then with brine, dried over MgSO₄ and concentrated. The residue was chromatographed on SiO₂ with Hept/EA (2:1) to afford the title bromide as a pale yellow solid (2.64 g, 68% yield).

$^1$H NMR (CDCl₃) δ: 8.51 (s, 1H), 8.00 (dd, J=8.2, 1.2 Hz, 1H), 7.78 (dd, J=7.3, 1.5 Hz, 1H), 7.53 (dd, J=8.2, 7.3 Hz, 1H), 5.09 (s, 2H), 4.15 (s, 3H).

75.iii. (3-methoxy-quinoxalin-5-yl)-acetonitrile

NaCN (633 mg, 12.9 mmol) was added to a suspension of intermediate 75.ii (2.18 g, 8.61 mmol) in 4:1 i-PrOH/water (80 mL) and the mixture was heated to reflux for 1 h. After being cooled to rt water (100 mL) was added and the mixture was extracted with EA. The org. layer was washed with brine, dried over MgSO$_4$ and concentrated. The residue was chromatographed on SiO$_2$ with Hept/EA (2:1) to afford the title nitrile as a pale yellow solid (1.70 g, 100% yield).
MS (ESI, m/z): 200.3 [M+H$^+$].

75.iv. (3-methoxy-quinoxalin-5-yl)-acetic acid

A solution of intermediate 75.iii (400 mg, 2.0 mmol) in conc. HCl was heated to 80° C. for 2 h. After cooling to rt the pH was adjusted to 3 using NH$_4$OH. The mixture was extracted with EA. Some material crystallized out of the solution, which was filtered (corresponding phenol via hydrolysis of MeO-group). The filtrate was concentrated and the resulting product (0.176 g, 40% yield) was used as such in the following step.
MS (ESI, m/z): 219.3 [M+H$^+$].

75.v. N-{2-[(rac)-3-(2,3-dihydro-benzo[1,4]dioxin-6-yl)-2-oxo-oxazolidin-5-yl]-ethyl}-2-(3-methoxy-quinoxalin-5-yl)-acetamide This compound was obtained according to method I starting from intermediate 75.iv (140 mg, 0.642 mmol) and intermediate 72.vi (188.4 mg, 1 eq.). Purification by chromatography on SiO$_2$ (DCM-MeOH—NH$_4$OH: 1000:25:2) afforded the title compound as a colourless solid (78 mg, 26% yield).
MS (ESI, m/z): 465.2 [M+H$^+$].

Example 76

6-methoxy-quinoline-4-carboxylic acid {3-[(rac)-2-oxo-3-(3-oxo-3,4-dihydro-2H-benzo[1,4]thiazin-6-yl)-oxazolidin-5-yl]-propyl}-amide 76.i. [(rac)-4-hydroxy-5-(3-oxo-3,4-dihydro-2H-benzo[1,4]thiazin-6-ylamino)-pentyl]-carbamic acid tert-butyl ester A solution of ((rac)-3-oxiranyl-propyl)-carbamic acid tert-butyl ester (1.08 g, 5.34 mmol) and 6-amino-4H-benzo[1,4]thiazin-3-one (1.01 g, 5.61 mmol) in 9:1 EtOH/H$_2$O (20 mL) was heated at 70° C. overnight. After cooling the mixture was concentrated in vacuo and chromatographed on SiO$_2$ (DCM-MeOH—NH$_4$OH: 1000:50:4) to afford the title intermediate as beige foam (767 mg, 38% yield).
MS (ESI, m/z): 382.1 [M+H$^+$].

76.ii. {3-[(rac)-2-oxo-3-(3-oxo-3,4-dihydro-2H-benzo[1,4]thiazin-6-yl)-oxazolidin-5-yl]-propyl}-carbamic acid tert-butyl ester A solution of intermediate 76.i (519 mg, 1.36 mmol) and CDI (455 mg, 2 eq.) in anhydrous THF (5.5 mL) was heated at 50° C. for 3 h. After cooling the mixture was concentrated in vacuo and partitioned between EA and water. The org. layer was washed with brine, dried over MgSO$_4$ and concentrated in vacuo. The residue was chromatographed on SiO$_2$ (DCM-MeOH—NH$_4$OH: 1000:50:4) to afford the title intermediate as an off-white foam (412 mg, 74% yield).
MS (ESI, m/z): 408.5 [M+H$^+$].

76.iii. 6-[(rac)-5-(3-amino-propyl)-2-oxo-oxazolidin-3-yl]-4H-benzo[1,4]thiazin-3-one A solution of intermediate 76.ii (402 mg, 0.987 mmol) and Et$_3$SiH (126 mg, 1.1 eq.) in DCM (4 mL) was dissolved in TFA (4 mL) and stirred at rt for 30 min. The mixture was concentrated in vacuo and partitioned between DCM and NH$_4$OH. The aq. phase was extracted once more with DCM. The combined org. layers were washed with water, dried over MgSO$_4$ and concentrated to afford the title intermediate as a yellow solid (290 mg, 96% yield).
MS (ESI, m/z): 308.2 [M+H$^+$].

76.iv. 6-methoxy-quinoline-4-carboxylic acid {3-[(rac)-2-oxo-3-(3-oxo-3,4-dihydro-2H-benzo[1,4]thiazin-6-yl)-oxazolidin-5-yl]-propyl}-amide This compound was obtained according to method I starting from 6-methoxy-4-quinolinecarboxylic acid (39 mg, 0.192 mmol) and intermediate 76.iii (59 mg, 0.192 mmol). The residue was triturated with DCM to afford the title compound as a colourless solid (68 mg, 72% yield).
MS (ESI, m/z): 493.1 [M+H$^+$].

Example 77

6-((rac)-5-{3-[(6-methoxy-[1,5]naphthyridin-4-ylmethyl)-amino]-propyl}-2-oxo-oxazolidin-3-yl)-4H-benzo[1,4]thiazin-3-one A suspension of intermediate 76.iii (63 mg, 0.204 mmol), 6-methoxy-[1,5]naphthyridine-4-carbaldehyde (38 mg, 0.204 mmol; see WO 2006/032466) and 3 Å molecular sieves (400 mg) in DCE/MeOH 3:1 (2 mL) was stirred at 50° C. overnight. NaBH$_4$ was added, at 0° C., and stirring was continued at 0° C. for 30 min and then at rt for 35 min. The mixture was filtered and the filtrate was partitioned between DCM/MeOH 9/1 and NH$_4$OH. The org. layer was dried over Na$_2$SO$_4$ and concentrated. The residue was chromatographed on SiO$_2$ (DCM-MeOH—NH4OH: 1000:50:4) to afford the title compound as a colourless foam (74 mg, 75% yield).
MS (ESI, m/z): 480.3 [M+H$^+$].

Example 78

6-((rac)-5-{3-[(3-fluoro-6-methoxy-[1,5]naphthyridin-4-ylmethyl)-amino]-propyl}-2-oxo-oxazolidin-3-yl)-4H-benzo[1,4]thiazin-3-one A suspension of intermediate 76.iii (61 mg, 0.20 mmol), 6-methoxy-[1,5]naphthyridine-4-carbaldehyde (41 mg, 0.20 mmol; see WO 2006/032466) and 3 Å molecular sieves (400 mg) in DCE/MeOH 3:1 (2 mL) was stirred at 50° C. overnight. NaBH$_4$ was added, at 0° C., and stirring was continued at 0° C. for 30 min and then at rt for 35 min. The mixture was filtered and the filtrate was partitioned between DCM/MeOH 9/1 and NH$_4$OH. The organic layer was dried over Na$_2$SO$_4$ and concentrated. The residue was chromatographed on SiO$_2$ (DCM-MeOH—NH$_4$OH: 1000:50:4) to afford the title compound as a colourless foam (89 mg, 90% yield).
MS (ESI, m/z): 498.2 [M+H$^+$].

Example 79

6-((rac)-5-{3-[(3-fluoro-6-methoxy-quinolin-4-ylmethyl)-amino]-propyl}-2-oxo-oxazolidin-3-yl)-4H-benzo[1,4]thiazin-3-one 79.i. 3-fluoro-6-methoxy-quinoline-4-carbaldehyde To a solution of DIPA (15.5 mL) in THF (300 mL), cooled to −78° C., was added n-BuLi (2.35N in hexanes, 44 mL). The reaction mixture was stirred 5 min at this temperature before warming to 0° C. The reaction mixture was stirred 15 min before cooling to −78° C. 3-fluoro-6-methoxy-quinoline (15 g, 84.7 mmol; see WO 2006/058700) in THF (50 mL+10 mL rinse) was added and the mixture was stirred 3 h at −78° C. DMF (3 mL, 1.2 eq.) was added quickly (within one min). After 45 min, the reaction mixture was quenched by adding 1-propanol (8 mL). The mixture was warmed to rt and extracted twice with EA. The combined org. layers were washed with brine, dried over $Na_2SO_4$, filtered and concentrated to dryness. The residue triturated in Hept to give the title intermediate as an orange solid (9.0 g, 52% yield).

79.ii. 6-((rac)-5-{3-[(3-fluoro-6-methoxy-quinolin-4-ylmethyl)-amino]-propyl}-2-oxo-oxazolidin-3-yl)-4H-benzo[1,4]thiazin-3-one A suspension of intermediate 76.iii (25 mg, 0.081 mmol), intermediate 79.i (18 mg, 0.089 mmol) and 3 Å molecular sieves (200 mg) in DCE/MeOH 3:1 (2 mL) was stirred at 50° C. overnight. $NaBH_4$ was added, at 0° C., and stirring was continued at 0° C. for 30 min and then at rt for 35 min. The mixture was filtered and the filtrate was partitioned between DCM/MeOH 9/1 and $NH_4OH$. The org. layer was dried over $Na_2SO_4$ and concentrated. The residue was chromatographed on $SiO_2$ (DCM-MeOH—$NH_4OH$: 1000:50:4) to afford the title compound as a colourless foam (12 mg, 30% yield).
$^1$H NMR (CDCl$_3$) δ: 8.62 (m, 2H), 7.99 (d, J=9.1 Hz, 1H), 7.30 (m, 4H), 6.90 (dd, J=8.8, 2.3 Hz, 1H), 4.61 (m, 1H), 4.23 (d, J=1.8 Hz, 2H), 3.95 (m, 4H), 3.52 (dd, J=8.5, 7.0 Hz, 1H), 3.39 (s, 2H), 2.75 (t, J=6.7 Hz, 2H), 1.71 (m, 4H).
MS (ESI, m/z): 497.2 [M+H$^+$].

Example 80

N-(6-methoxy-[1,5]naphthyridin-4-yl)-4-[(RS)-2-oxo-3-(3-oxo-3,4-dihydro-2H-benzo[1,4]thiazin-6-yl)-oxazolidin-5-yl]-butyramide 80.i. Hex-5-enoic acid (6-methoxy-[1,5]naphthyridin-4-yl)-amide To a suspension of 6-methoxy-[1,5]naphthyridin-4-ylamine (1.5 g, 8.56 mmol) and TEA (1.55 mL, 1.3 eq.) in DCM (8.5 mL) was added 5-hexenoyl chloride (1.36 g, 1.2 eq.) in DCM (1.5 mL) at rt. The resulting suspension was vigorously stirred at rt for 20 h. The mixture was then washed with water. The org. layer was dried over $Na_2SO_4$ and concentrated. The residue was chromatographed on $SiO_2$ (DCM-MeOH—$NH_4OH$: 1000:50:4) to afford the title intermediate as a yellow solid (1.66 g, 71% yield).
MS (ESI, m/z): 272.2 [M+H$^+$].

80.ii. (rac)-5,6-dihydroxy-hexanoic acid (6-methoxy-[1,5]naphthyridin-4-yl)-amide The title diol was obtained according to method L starting from intermediate 80.i (1.61 g, 5.94 mmol). The product was crystallized from DCM to give the desired intermediate as a colourless solid (1.45 g, 80% yield).
MS (ESI, m/z): 306.2 [M+H$^+$].

80.iii. Toluene-4-sulfonic acid (rac)-2-hydroxy-5-(6-methoxy-[1,5]naphthyridin-4-ylcarbamoyl)-pentyl ester A solution of p-TsCl (918 mg, 4.81 mmol) in DCM (3 mL) was added dropwise to a solution of intermediate 80.ii (1.40, 4.59 mmol) in DCM (30 mL) and Pyr (2.8 mL) at 5° C. The mixture was stirred at rt for 16 h, poured in 1M HCl and extracted with DCM. The org. layer was dried over $MgSO_4$ and concentrated. The residue was chromatographed on $SiO_2$ (DCM-MeOH—$NH_4OH$: 1000:50:4) to afford the title intermediate as a colourless foam (1.35 g, 64% yield).
MS (ESI, m/z): 459.8 [M+H$^+$].

80.iv. N-(6-methoxy-[1,5]naphthyridin-4-yl)-4-(rac)-oxiranyl-butyramide

2M NaOH (2 mL) was added to a solution of intermediate 80.iii (1.32 g, 2.88 mmol) in THF (4 mL). The mixture was vigorously stirred at rt for 1 h, partitioned between water and EA. The org. layer washed with brine, dried over $MgSO_4$ and concentrated. The residue was chromatographed on $SiO_2$ (DCM-MeOH—$NH_4OH$: 1000:50:4) to afford the title intermediate as a colourless solid (514 mg, 62% yield).
MS (ESI, m/z): 288.3 [M+H$^+$].

80.v. (rac)-5-hydroxy-6-(3-oxo-3,4-dihydro-2H-benzo[1,4]thiazin-6-ylamino)-hexanoic acid (6-methoxy-[1,5]naphthyridin-4-yl)-amide A solution of intermediate 80.iv (484 mg, 1.69 mmol) and 6-amino-4H-benzo[1,4]thiazin-3-one (304 mg, 1.69 mmol) in EtOH/water 9:1 (10 mL) was heated at 80° C. overnight. The mixture was concentrated and chromatographed on $SiO_2$ (EA/MeOH 9:1) to afford the title intermediate as a yellow foam (250 mg, 32% yield).
MS (ESI, m/z): 468.2 [M+H$^+$].

80.vi. N-(6-methoxy-[1,5]naphthyridin-4-yl)-4-[(RS)-2-oxo-3-(3-oxo-3,4-dihydro-2H-benzo[1,4]thiazin-6-yl)-oxazolidin-5-yl]-butyramide A solution of intermediate 80.v (242 mg, 0.52 mmol) and CDI (173 mg, 2 eq.) in anhydr. THF (20 mL) was heated at 50° C. for 5 h. After cooling, the mixture was concentrated in vacuo, partitioned between DCM and water. The org. layer was washed with brine, dried over $MgSO_4$ and concentrated in vacuo. The residue was chromatographed on $SiO_2$ (DCM-MeOH—$NH_4OH$: 1000:50:4) to afford the title intermediate as a colourless solid (75 mg, 29% yield).
$^1$H NMR (DMSO d6) δ: 10.54 (s, 1H), 9.74 (s, 1H), 8.65 (d, J=5.0 Hz, 1H), 8.40 (d, J=5.3 Hz, 1H), 8.24 (d, J=9.1 Hz, 1H), 7.31 (m, 3H), 7.07 (dd, J=8.5, 2.3 Hz, 1H), 4.73 (m, 1H), 4.11 (m, 4H), 3.67 (m, 1H), 3.42 (s, 2H), 2.72 (m, 2H), 1.80 (m, 4H).
MS (ESI, m/z): 494.1 [M+H$^+$].

Example 81

(S)-3-(2,3-dihydro-benzo[1,4]dioxin-6-yl)-5-{[2-(6-methoxy-[1,5]naphthyridin-4-ylamino)-ethylamino]-methyl}-oxazolidin-2-one 81.i. N$^1$-(6-methoxy-[1,5]naphthyridin-4-yl)-ethane-1,2-diamine A mixture of 8-chloro-2-methoxy-1,5-naphthyridine (1.71 g, 8.81 mmol) and ethylenediamine (1.18 mL, 2 eq.) was heated slowly to 80° C. over 1 h and subsequently up to 100° C. for 2 h. After cooling to rt, the yellow solution was taken in DCM and successively washed with $NaHCO_3$. The aq. layer was back extracted with DCM (3 times) and the combined org. layers were concentrated to afford the title intermediate as a pale yellow oil (0.98 g, 51% yield).
MS (ESI, m/z): 219.4 [M+H$^+$].

81.ii. (S)-3-(2,3-dihydro-benzo[1,4]dioxin-6-yl)-5-{[2-(6-methoxy-[1,5]naphthyridin-4-ylamino)-ethylamino]-methyl}-oxazolidin-2-one A solution of intermediate 1.ii (80 mg, 0.243 mmol) and intermediate 81.i (133 mg, 2.5 eq.) in dry DMSO (2.5 mL) was heated at 70° C. for 3 days. After cooling to rt, water was added and the mixture was extracted with EA. The combined org. layers were washed with brine, dried over MgSO$_4$ and concentrated and the residue was chromatographed with (DCM-MeOH—NH$_4$OH 1000-50-4-1000-100-8) to afford the title compound as a colourless foam (57 mg, 52% yield).
MS (ESI, m/z): 452.1 [M+H$^+$].

Example 82

(S)-3-(2,3-dihydro-benzo[1,4]dioxin-6-yl)-2-oxo-oxazolidine-5-carboxylic acid [2-(6-methoxy-[1,5]naphthyridin-4-ylamino)-ethyl]-amide

82.i. (S)-3-(2,3-dihydro-benzo[1,4]dioxin-6-yl)-2-oxo-oxazolidine-5-carboxylic acid To a solution of (S)-3-(2,3-dihydro-benzo[1,4]dioxin-6-yl)-5-hydroxymethyl-oxazolidin-2-one (985 mg, 3.92 mmol) in 1:1 water/MeCN (20 mL) cooled to 0° C. was added diacetoxyiodobenzene (2.83 g, 2.2 eq.) and TEMPO (122 mg, 0.2 eq). The mixture was stirred at 0° C. for 30 min and at rt overnight. EA and sat. Na$_2$CO$_3$ were added and the phases were separated. The aq. layer was washed once more with EA and then carefully acidified with 1M HCl. The water phase was then extracted twice with EA. The combined org. layers were washed with brine and dried over MgSO$_4$ and concentrated to afford the title intermediate as a colourless solid (847 mg, 81% yield).
MS (ESI, m/z): 266.3 [M+H$^+$].

82.ii. (S)-3-(2,3-dihydro-benzo[1,4]dioxin-6-yl)-2-oxo-oxazolidine-5-carboxylic acid [2-(6-methoxy-[1,5]naphthyridin-4-ylamino)-ethyl]-amide To a solution of intermediate 81.i (52 mg, 0.24 mmol), intermediate 82.i (64 mg, 0.24 mmol) and DIPEA (0.159 mL, 4 eq.) in DMF (2 mL) was added HATU (183 mg, 2 eq.). The resulting solution was stirred at rt for 48 h. EA and water were added and the phases were separated. The aq. phase was extracted with EA and the combined org. extracts were washed with brine/water (3 times), dried over MgSO$_4$ and concentrated under reduced pressure. The residue was chromatographed on SiO$_2$ (DCM/MeOH/NH$_4$OH 1000/50/4) to afford the title compound as a pale beige solid (41 mg, 37% yield).
MS (ESI, m/z): 466.1 [M+H$^+$].

Example 83

(S)-2-{[(R)-3-(2,3-dihydro-benzo[1,4]dioxin-6-yl)-2-oxo-oxazolidin-5-ylmethyl]-amino}-N-(6-methoxy-[1,5]naphthyridin-4-yl)-propionamide

83.i. (S)-3-(2,3-dihydro-benzo[1,4]dioxin-6-yl)-2-oxo-oxazolidine-5-carbaldehyde A solution of oxalyl chloride (0.229 mL, 2.71 mmol) in DCM (5 mL) was cooled to −78° C. and DMSO (0.395 mL, 5.572 mmol) was added dropwise. The mixture was stirred for 10 min at that temperature and a suspension of (S)-3-(2,3-dihydro-benzo[1,4]dioxin-6-yl)-5-hydroxymethyl-oxazolidin-2-one (400 mg, 1.59 mmol) in DCM (6 mL) was then added dropwise within 1 min. Stirring was continued for 20 min. TEA (0.665 mL, 4.78 mmol) was added and the mixture was stirred for 5 min, and then allowed to warm to 0° C. The mixture was filtered through Celite and concentrated with a bath temperature below 30° C. The residue was partitioned between water and EA and the org. layer was washed with brine, dried over Na$_2$SO$_4$ and concentrated with a bath temperature below 30° C. The highly unstable intermediate was used immediately in the next step.

83.ii. [(S)-1-(6-methoxy-[1,5]naphthyridin-4-ylcarbamoyl)-ethyl]-carbamic acid benzyl ester A mixture of N-benzyloxycarbonylalanine amide (800 mg, 3.60 mmol), Cs$_2$CO$_3$ (1.44 g), rac-BINAP (162 mg) and Pd$_2$(dba)$_3$ (65 mg) in dioxane (50 mL) was sonicated for 10 min (ligand exchange; mixture turns from purple to orange). 8-bromo-2-methoxy-[1,5]naphthyridine (861 mg, 1 eq.; see WO 2006/032466) was added and the mixture heated at 100° C. overnight. The reaction mixture was then poured on water and extracted with EA. The org. extracts were washed with NH$_4$Cl and concentrated. The residue was chromatographed on SiO$_2$ (Hex/EA 1:1) to afford the title intermediate as a yellow solid (1.27 g, 93% yield).
MS (ESI, m/z): 380.8 [M+H$^+$].

83.iii. (S)-2-amino-N-(6-methoxy-[1,5]naphthyridin-4-yl)-propionamide

A solution of intermediate 83.ii (1.02 g, 2.68 mmol) in MeOH (25 mL) was hydrogenated over Pd(OH)$_2$ (142 mg) for 2 h. The catalyst was filtered off, the filtrate concentrated and residue chromatographed on SiO$_2$ (1000:50:4 DCM/MeOH/NH$_4$OH) to afford the title intermediate as a colourless solid (0.564 g, 85% yield).
MS (ESI, m/z): 246.9 [M+H$^+$].

83.iv. (S)-2-{[(R)-3-(2,3-dihydro-benzo[1,4]dioxin-6-yl)-2-oxo-oxazolidin-5-ylmethyl]-amino}-N-(6-methoxy-[1,5]naphthyridin-4-yl)-propionamide The title compound was obtained as a colourless solid (9 mg, 6% yield) using method K and starting from intermediate 83.iii (80 mg) and intermediate 83.i (81 mg).
MS (ESI, m/z): 480.0 [M+H$^+$].

Example 84

2-{[(R)-3-(2,3-dihydro-benzo[1,4]dioxin-6-yl)-2-oxo-oxazolidin-5-ylmethyl]-amino}-N-(6-methoxy-[1,5]naphthyridin-4-yl)-acetamide

84.i. 2-chloro-N-(6-methoxy-[1,5]naphthyridin-4-yl)-acetamide

To a solution of 6-methoxy-[1,5]naphthyridin-4-ylamine (553 mg, 3.16 mmol) in THF (45 mL) was added potassium tert-butoxide (390 mg, 1.1 eq.) at 0° C. The resulting brown suspension was stirred at rt for 1.5 h and then added dropwise to a solution of ethyl chloroacetate (387 mg, 1 eq.) in THF (30 mL) at −5° C. The mixture was allowed to warm to rt and was further stirred for 3 h. Water was added and the mixture was concentrated under reduced pressure. The resulting precipitate was filtered and further dried at HV to afford the title intermediate as a beige solid (357 mg, 45% yield).
MS (ESI, m/z): 252.1 [M+H⁺].

84.ii. 2-{[(R)-3-(2,3-dihydro-benzo[1,4]dioxin-6-yl)-2-oxo-oxazolidin-5-ylmethyl]-amino}-N-(6-methoxy-[1,5]naphthyridin-4-yl)-acetamide A solution of intermediate 84.i (157 mg, 0.624 mmol) and intermediate 3.i (312 mg, 2 eq.) in THF (3 mL) was heated at 50° C. for 16 h, then at 60° C. for 48 h, then at 70° C. for 48 h. The mixture was concentrated and the residue was crystallized from MeOH/Et₂O (3/1) to afford the title compound as an off-white solid (220 mg, 76% yield).
MS (ESI, m/z): 466.2 [M+H⁺].

Example 85

2-[(R)-3-(2,3-dihydro-benzo[1,4]dioxin-6-yl)-2-oxo-oxazolidin-5-yl]-N-[2-(6-methoxy-quinolin-4-yl)-ethyl]-acetamide

85.i. 3-(6-methoxy-quinolin-4-yl)-propionic acid ethyl ester

A solution of intermediate 2.i (1.0 g, 3.9 mmol) in EtOH/AcOH 9:1 (50 mL) was hydrogenated over Pd/C (10%, 0.1 eq.) under 1 bar of H₂ for 4 h. The catalyst was filtered off over Celite and the filtrate concentrated in vacuo. The residue was partitioned between 1M NaOH and EA. The org. layer was dried over MgSO₄ and concentrated to give the desired intermediate as a beige solid (1.1 g, quant.).
¹H NMR (DMSO d6) δ: 8.61 (d, J=4.4 Hz, 1H), 7.91 (d, J=8.8 Hz, 1H), 7.35 (m, 3H), 4.04 (q, J=7.0 Hz, 2H), 3.92 (s, 3H), 3.31 (m, 2H), 2.77 (t, J=7.3 Hz, 2H), 1.13 (t, J=7.0 Hz, 3H).

85.ii. 3-(6-methoxy-quinolin-4-yl)-propionic acid

A solution of intermediate 85.i (1.1 g, 3.9 mmol) was hydrolysed according to method F. The desired acid was isolated as a beige solid (0.7 g, 72% yield).
¹H NMR (DMSO d6) δ: 12.28 (s, 1H), 8.61 (d, J=4.4 Hz, 1H), 7.91 (m, 1H), 7.35 (m, 3H), 3.92 (s, 3H), 3.28 (t, J=7.6 Hz, 2H), 2.69 (t, J=7.6 Hz, 2H).
MS (ESI, m/z):232.3 [M+H].

85.iii. 2-(6-methoxy-quinolin-4-yl)-ethylamine

A suspension of intermediate 85.ii (0.7 g, 3 mmol) in benzene (30 mL) was treated sequentially with TEA (0.367 g, 3.6 mmol) and DPPA (0.916 g, 3.3 mmol). The resulting solution was heated at reflux for 1 h, cooled to rt and diluted with EA. The org. phase was washed with water, dried over MgSO₄ and concentrated. The intermediate isocyanate was dissolved in THF (30 mL) and 1M NaOH (15 mL). The mixture was vigorously stirred at rt for 45 min, diluted with water and extracted with EA (2 times 20 mL) and chloroform (2 times 20 mL). The combined org. phases were dried over MgSO₄ and concentrated to give the desired amine as a yellow oil (0.66 g, 100% yield).
¹H NMR (DMSO d6) δ: 8.60 (d, J=4.4 Hz, 1H), 7.90 (dd, J=8.8, 0.6 Hz, 1H), 3.92 (m, 4H), 7.35 (m, 3H), 3.29 (br, 2H), 3.10 (t, J=7.0 Hz, 3H), 2.90 (t, J=7.0 Hz, 3H).
MS (ESI, m/z): 203.2 [M+H⁺].

85.iv. [(R)-3-(2,3-dihydro-benzo[1,4]dioxin-6-yl)-2-oxo-oxazolidin-5-yl]-acetic acid ethyl ester A solution of ethyl (R)-4-chloro-3-hydroxybutyrate (5.0 g, 30 mmol) and 2,3-dihydro-1,4-benzodioxin-6-yl isocyanate (5.3 g, 30 mmol) in benzene (150 ml) was stirred at 80° C. for 48 h. The reaction mixture was concentrated in vacuo, taken up in EA and washed twice with brine. The org. layer was dried over MgSO₄ and concentrated. The residue was purified by chromatography on SiO₂ (hept/EA 9:1 to 1:1) to give the desired carbamate (8.3 g, 81% yield) as a yellow oil. This intermediate was dissolved in DMF (40 ml) and treated with K₂CO₃ (3.3 g, 24 mmol). The heterogeneous mixture was stirred at rt for 20 h, water was added and the mixture extracted with EA. The org. layers were washed with water and brine, dried over MgSO₄ and concentrated. The residue was purified by chromatography on SiO₂ (Hept/EA 2:1, 1:1) to give the desired oxazolidinone (0.96 g, 13% yield) as an orange solid.
¹H NMR (CDCl₃) δ: 7.07 (d, J=2.6 Hz, 1H), 6.98 (m, 1H), 6.84 (m, 1H), 4.97 (m, 1H), 4.18 (m, 7H), 3.72 (dd, J=9.1, 6.4 Hz, 1H), 2.96 (m, 1H), 2.76 (dd, J=16.4, 7.9 Hz, 1H), 1.27 (m, 3H).
MS (ESI, m/z):308.3 [M+H⁻].

85.v. [(R)-3-(2,3-dihydro-benzo[1,4]dioxin-6-yl)-2-oxo-oxazolidin-5-yl]-acetic acid A suspension of intermediate 85.v (0.097 g, 0.3 mmol) in 4N HCl (1.2 mL) was heated at 50° C. for 1 h and at 60° C. for 90 min. Dioxane (0.4 mL) was added and the mixture heated at 70° C. for 90 min. Water was added and the aq. phase was extracted with DCM/MeOH 9:1. The org. phase was dried over MgSO₄ and concentrated to give the desired acid (0.08 g, 89% yield) as a brown foam.
¹H NMR (DMSO d6) δ: 7.08 (d, J=2.6 Hz, 1H), 6.92 (m, 1H), 6.83 (m, 1H), 4.89 (m, 1H), 4.20 (m, 4H), 4.10 (t, J=9.1 Hz, 1H), 2.78 (m, 2H).
MS (ESI, m/z):280.3 [M+H⁻].

85.vi. 2-[(R)-3-(2,3-dihydro-benzo[1,4]dioxin-6-yl)-2-oxo-oxazolidin-5-yl]-N-[2-(6-methoxy-quinolin-4-yl)-ethyl]-acetamide Intermediate 85.iii (0.036 g, 0.18 mmol) and intermediate 85.v (0.05 g, 0.18 mmol) were coupled according to method I. The title compound was isolated after chromatography on SiO₂ (EA/MeOH 9:1) as a beige foam (0.04 g, 48% yield)
¹H NMR (DMSO d6) δ: 8.61 (d, J=4.4 Hz, 1H), 8.28 (m, 1H), 7.91 (d, J=9.1 Hz, 1H), 7.55 (d, J=2.1 Hz, 1H), 7.35 (m, 2H), 7.08 (d, J=2.1 Hz, 1H), 6.92 (m, 1H), 6.84 (m, 1H), 4.92 (m, 1H), 4.21 (m, 4H), 4.08 (t, J=8.5 Hz, 1H), 3.92 (s, 3H), 3.72 (m, 1H), 3.43 (m, 2H), 3.17 (m, 2H), 2.60 (m, 2H).
MS (ESI, m/z):464.4 [M+H⁻].

Example 86

(S)-3-(2,3-dihydro-benzo[1,4]dioxin-6-yl)-5-({[3-(3-methoxy-quinolin-5-yl)-propyl]methyl-amino}-methyl)-oxazolidin-2-one

86.i. (S)-3-(2,3-dihydro-benzo[1,4]dioxin-6-yl)-5-methylaminomethyl-oxazolidin-2-one This compound (0.34 g, yellowish oil) was obtained starting from (2,3-dihydro-benzo[1,4]dioxin-6-yl)-carbamic acid benzyl ester (0.383 g, 1.5 mmol) and ((S)-3-chloro-2-hydroxy-propyl)-methyl-carbamic acid tert-butyl ester (prepared from (S)-epichlorohydrin in analogy to Example 11, step 11.i; 0.336 g, 1.5 mmol) following sequentially methods C, D and E.

$^1$H NMR (CDCl$_3$) δ: 7.26 (s, 1H), 7.08 (d, J=2.6 Hz, 1H), 6.99 (dd, J=8.8, 2.6 Hz, 1H), 6.84 (d, J=8.8 Hz, 1H), 4.73 (m, 1H), 4.24 (m, 4H), 3.99 (t, J=8.5 Hz, 1H), 3.78 (dd, J=8.8, 7.0 Hz, 1H), 2.90 (m, 2H), 2.50 (s, 3H).

86.ii. (S)-3-(2,3-dihydro-benzo[1,4]dioxin-6-yl)-5-({[3-(3-methoxy-quinolin-5-yl)-propyl]-methyl-amino}-methyl)-oxazolidin-2-one This compound was obtained according to method I starting from intermediate 86.i (0.1 g, 0.38 mmol) and intermediate 35.i (0.085 g, 0.38 mmol). The product was isolated after chromatography on SiO$_2$ (EA/MeOH 9:1) as a yellowish oil (0.082 g, 46% yield).

$^1$H NMR (CDCl$_3$) δ: 8.66 (d, J=2.6 Hz, 1H), 7.90 (d, J=8.5 Hz, 1H), 7.52 (d, J=2.6 Hz, 1H), 7.45 (m, 1H), 7.33 (m, 1H), 7.05 (d, J=2.6 Hz, 1H), 6.94 (dd, J=8.8, 2.6 Hz, 1H), 6.80 (m, 1H), 4.67 (m, 1H), 4.20 (s, 4H), 3.94 (m, 5H), 3.71 (dd, J=8.8, 7.0 Hz, 1H), 3.02 (m, 2H), 2.71 (m, 2H), 2.55 (t, J=7.0 Hz, 2H), 2.34 (s, 3H), 1.89 (m, 2H).

MS (ESI, m/z): 464.4 [M+H$^+$].

Example 87

N-[(R)-3-(3-fluoro-4-methyl-phenyl)-2-oxo-oxazolidin-5-ylmethyl]-3-(3-methoxy-quinolin-5-yl)-N-methyl-propionamide The title compound was obtained according to method H starting from intermediate 13.i (0.050 g, 0.2 mmol) and intermediate 28.i (0.049 g, 0.2 mmol). The product was isolated after chromatography on SiO$_2$ (EA, EA/MeOH 19:1+1% NH$_4$OH) followed by crystallization from ether/MeOH as a colourless solid (0.072 g, 75% yield).

MS (ESI, m/z): 452.3 [M+H$^+$].

Example 88

2-[(R)-3-(2,3-dihydro-benzo[1,4]dioxin-6-yl)-2-oxo-oxazolidin-5-yl]-N-[(R)-2-hydroxy-2-(3-methoxy-quinoxalin-5-yl)-ethyl]-N-methyl-acetamide

88.i. (1RS)-(3-methoxy-quinoxalin-5-yl)-2-methylamino-ethanol

A solution of (rac)-2-methoxy-8-oxiranyl-quinoxaline (see WO 2006/021448; 0.505 g, 2.5 mmol) and methylamine (33% solution in MeOH, 1 mL) in EtOH/H$_2$O (9:1, 5 mL) was heated at 80° C. for 5 h. The mixture was concentrated in vacuo and purified by chromatography on SiO$_2$ (EA/MeOH 9:1, 4:1+1% NH$_4$OH) to give the title amino alcohol (0.24 g, 41%) as a beige solid.

$^1$H NMR (DMSO d6) δ: 8.58 (s, 1H), 7.94 (dd, J=8.2, 1.5 Hz, 1H), 7.79 (m, 1H), 7.57 (dd, J=8.2, 7.6 Hz, 1H), 5.59 (dd, J=8.5, 4.1 Hz, 1H), 4.08 (s, 3H), 3.09 (dd, J=12.3, 4.1 Hz, 1H), 2.94 (dd, J=12.3, 8.5 Hz, 1H), 2.52 (s, 3H).

MS (ESI, m/z): 234.1 [M+H$^+$].

88.ii. 2-[(R)-3-(2,3-dihydro-benzo[1,4]dioxin-6-yl)-2-oxo-oxazolidin-5-yl]-N-[(R)-2-hydroxy-2-(3-methoxy-quinoxalin-5-yl)-ethyl]-N-methyl-acetamide Intermediate 88.i (0.117 g, 0.5 mmol) and intermediate 85.v (0.14 g, 0.5 mmol) were coupled according to method H.

The title compound was isolated after chromatography on SiO$_2$ (EA, EA/MeOH 9:1) as a beige foam (0.187 g, 76% yield).

MS (ESI, m/z):495.2 [M+H$^-$].

Example 89

6-((R)-5-{[(2RS)-2-amino-3-(6-methoxy-[1,5]naphthyridin-4-yl)-propylamino]-methyl}-2-oxo-oxazolidin-3-yl)-4H-benzo[1,4]thiazin-3-one

89.i. (1-(6-methoxy-[1,5]naphthyridin-4-ylmethyl)-(2RS)-{[2-oxo-3-(3-oxo-3,4-dihydro-2H-benzo[1,4]thiazin-6-yl)-oxazolidin-5-ylmethyl]-amino}-ethyl)-carbamic acid tert-butyl ester Intermediate 70.i (0.2 g, 0.6 mmol) and intermediate 5.v (0.17 g, 0.6 mmol) were coupled according to method K. The compound was isolated after chromatography on SiO$_2$ (DCM/MeOH 19:1, 9:1+0.5% NH$_4$OH) as a yellowish oil (0.1 g, 28% yield).

MS (ESI, m/z): 595.3 [M+H$^+$].

89.ii. 6-((R)-5-{[(2RS)-amino-3-(6-methoxy-[1,5]naphthyridin-4-yl)-propylamino]-methyl}-2-oxo-oxazolidin-3-yl)-4H-benzo[1,4]thiazin-3-one The Boc group of intermediate 89.i (0.1 g, 0.17 mmol) was removed according to method E. The product was isolated after chromatography on SiO$_2$ (DCM/MeOH 19:1, 9:1+0.5% NH$_4$OH) as a yellowish foam (0.034 g, 41% yield).

$^1$H NMR (DMSO d6) δ: 10.55 (br, 1H), 8.65 (dd, J=4.4, 1.5 Hz, 1H), 8.22 (d, J=9.1 Hz, 1H), 7.53 (d, J=4.4 Hz, 1H), 7.26 (m, 3H), 7.08 (dd, J=8.5, 2.3 Hz, 1H), 4.69 (m, 1H), 4.00 (m, 4H), 3.75 (m, 1H), 3.41 (s, 2H), 2.94 (d, J=5.0 Hz, 1H), 2.80 (m, 2H), 2.59 (m, 2H).

MS (ESI, m/z): 495.2 [M+H$^+$].

Example 90

6-((RS)-5-{3-[(6-fluoro-quinolin-5-ylmethyl)-amino]-propyl}-2-oxo-oxazolidin-3-yl)-4H-benzo[1,4]thiazin-3-one

90.i. 6-fluoro-quinoline-5-carbaldehyde

To a solution of DIPA (1.1 mL, 7.75 mmol)) in THF (820 mL) cooled to −78° C., was added n-BuLi (2.5N in hexanes, 3 mL). The mixture was stirred 5 minutes at this temperature and was warmed in an ice-bath. After 10 min, the mixture was cooled down to −78° C. and a solution of 3-fluoro-6-methoxy-quinoline (see WO 2005/054232; 0.95 g, 6.46 mmol) in THF (8+2 mL rinse) was added. The reaction proceeded for 4 h. DMF (0.75 mL, 9.68 mmol) was added. The mixture was stirred 30 min at −78° C. The mixture was warmed to rt, stirred further 30 min and water (20 mL) was added. The two layers were decanted. The aq. layer was extracted with EA (2×50 mL). The combined org. layers were washed with brine, dried over Na$_2$SO$_4$, filtered and concentrated to dryness. The residue was chromatographed (Hept-EA 1-1) to afford first the starting material and then the expected aldehyde (0.17 g) as a 2-1 mixture with its regioisomer.

$^1$H NMR (CDCl3) δ: 10.76 (s, 2/3H), 10.48 (s, 1/3H), 9.59 (m, 2/3H), 8.94 (m, 1H), 8.65 (d, J=6.7 Hz, 1/3H), 8.37 (ddd, J=9.1, 5.3, 0.6 Hz, 2/3H), 8.13 (m, 2/3H), 7.50 (m, 5/3H).

90.ii. 6-((RS)-5-{3-[(6-fluoro-quinolin-5-ylmethyl)-amino]-propyl}-2-oxo-oxazolidin-3-yl)-4H-benzo[1,4]thiazin-3-one This compound was obtained according to method of J by coupling intermediate 90.i (18 mg, 0.089 mmol) with intermediate 76.iii (25 mg, 0.081 mmol) as a colourless solid (5 mg, 13% yield).

$^1$H NMR (CDCl$_3$) δ: 8.89 (dd, J=4.1, 1.5 Hz, 1H), 8.52 (dt, J=8.5, 0.9 Hz, 1H), 8.33 (br. s, 1H), 8.05 (dd, J=9.4, 5.6 Hz, 1H), 7.47 (m, 2H), 7.28 (m, 2H), 6.91 (dd, J=8.5, 2.3 Hz, 1H), 4.62 (m, 1H), 4.24 (d, J=2.1 Hz, 2H), 3.96 (t, J=8.5 Hz, 1H), 3.51 (dd, J=8.5, 7.3 Hz, 1H), 3.40 (s, 2H), 2.78 (m, 2H), 1.70 (m, 4H).

MS (ESI, m/z): 467.2 [M+H$^+$].

Example 91

N-(6-methoxy-[1,5]naphthyridin-4-yl)-2-{[(R)-2-oxo-3-(3-oxo-3,4-dihydro-2H-benzo[1,4]thiazin-6-yl)-oxazolidin-5-ylmethyl]-amino}-acetamide

91.i. 2-chloro-N-(6-methoxy-[1,5]naphthyridin-4-yl)-acetamide

To a solution of 6-methoxy-1,5-naphthyridin-4-amine (553 mg, 3.116 mmol) in THF (45 mL) was added t-BuOK (390 mg, 1.1 eq) at 0° C. The resulting brown suspension was stirred at rt for 1.5 h and then added dropwise to a solution of ethyl chloroacetate (0.337 mL, 1 eq) in THF (30 mL) at −5° C. The mixture was allowed to warm to rt and was further stirred for 3 h. Water was added and the solvent was removed under reduced pressure. The resulting precipitate was filtered and further dried at HV to afford the title intermediate as a beige solid (357 mg, 45% yield).

MS (ESI, m/z): 252.1 [M+H$^+$].

91.ii. N-(6-methoxy-[1,5]naphthyridin-4-yl)-2-{[(R)-2-oxo-3-(3-oxo-3,4-dihydro-2H-benzo[1,4]thiazin-6-yl)-oxazolidin-5-ylmethyl]-amino}-acetamide A solution of intermediate 91.i (54 mg, 0.215 mmol) and intermediate 4 v. (1 eq.) in THF (1 mL) was heated at 70° C. for 4 days. More amine (1 eq.) and MeCN (1 mL) were added and the mixture was further stirred at 70° C. for 5 days. The mixture was concentrated and the residue was chromatographed on SiO$_2$ (DCM/MeOH/NH4OH: 1000/25/2-1000/100/8) to afford the title compound as a pale pink solid (33 mg, 31% yield).

MS (ESI, m/z): 495.2 [M+H$^+$].

Example 92

(R*)-3-(2,3-dihydro-benzo[1,4]dioxin-6-yl)-5-{2-[(R*)-2-hydroxy-2-(3-methoxy-quinoxalin-5-yl)-ethylamino]-ethyl}-oxazolidin-2-one A solution of intermediate 72.vi (262 mg, 1 mmol) and rac-2-methoxy-8-oxiranyl-quinoxaline (prepared as in WO 2004/002490; 200 mg, 1 mmol) were coupled according to method A. The title compound was isolated after FC (EA/MeOH 9:1+1% NH$_4$OH) as a yellowish oil (180 mg, 39% yield).

MS (ESI, m/z): 467.3 [M+H$^+$].

Example 93

N-[(R)-2-hydroxy-2-(6-methoxy-[1,5]naphthyridin-4-yl)-ethyl]-N-methyl-2-[(R)-2-oxo-3-(3-oxo-3,4-dihydro-2H-benzo[1,4]thiazin-6-yl)-oxazolidin-5-yl]-acetamide

93.i. (R)-1-(6-methoxy-[1,5]naphthyridin-4-yl)-2-methylamino-ethanol

A solution of (R)-2-methoxy-8-oxiranyl-[1,5]naphthyridine (prepared as in WO 02/08224, 0.1 g, 0.49 mmol) in EtOH/H$_2$O (9:1, 3 mL) was treated with methylamine (33% solution in EtOH, 0.5 mL) and heated in a sealed flask at 80° C. for 3 h. The volatiles were removed under reduced pressure and the residue purified by FC (EA/MeOH 9:1, 4:1, 2:1, +1% NH$_4$OH) to give the desired aminoalcohol as a yellow oil (0.077 g, 67% yield).

$^1$H NMR (DMSO d6) δ: 8.74 (d, J=4.7 Hz, 1H) 8.24 (d, J=9.1 Hz, 1H), 7.24 (d, J=8.8 Hz, 1H), 7.24 (d, J=8.8 Hz, 1H), 5.72 (dd, J=7.9, 2.6 Hz, 1H), 4.00 (s, 3H), 2.93 (dd, J=12.6, 3.2 Hz, 1H), 2.63 (dd, J=12.3, 8.2 Hz, 1H), 2.37 (s, 3H).

MS (ESI, m/z): 234.2 [M+H$^+$].

93.ii. (3R)-hydroxy-4-(3-oxo-3,4-dihydro-2H-benzo[1,4]thiazin-6-ylamino)-butyric acid tert-butyl ester (R)-oxiranyl-acetic acid tert-butyl ester (prepared as in *J. Am. Chem. Soc.* (2000), 122, 11090; 0.5 g, 3.2 mmol) and 6-amino-4H-benzo[1,4]thiazin-3-one (0.577 g, 3.2 mmol) were coupled according to method A. The title intermediate was isolated after FC (Hept/EA 1:2, EA) as a light brown solid (0.6 g, 57% yield).

MS (ESI, m/z): 339.3 [M+H$^+$].

93.iii. (R)-[2-oxo-3-(3-oxo-3,4-dihydro-2H-benzo[1,4]thiazin-6-yl)-oxazolidin-5-yl]-acetic acid tert-butyl ester Starting from intermediate 93.ii (0.6 g, 1.8 mmol) and following method B, the desired oxazolidinone was isolated after FC (Hept/EA 1:1, EA) as a beige solid (0.248 g, 38% yield).

$^1$H NMR (DMSO d6) δ: 10.54 (s, 1H), 7.29 (m, 2H), 7.11 (dd, J=8.5, 2.6 Hz, 1H), 4.92 (m, 1H), 4.11 (t, J=8.8 Hz, 1H), 3.73 (dd, J=8.8, 7.0 Hz, 1H), 2.80 (m, 2H), 3.42 (s, 2H), 1.39 (s, 9H).

MS (ESI, m/z): 365.2 [M+H$^+$].

93.iv. (R)-[2-oxo-3-(3-oxo-3,4-dihydro-2H-benzo[1,4]thiazin-6-yl)-oxazolidin-5-yl]-acetic acid A solution of intermediate 93.iii (0.248 g, 0.68 mmol) in DCM (1.5 mL) was treated with Et$_3$SiH (0.12 mL, 0.75 mmol) and TFA (1.5 mL). The mixture was stirred at rt for 4 h, concentrated in vacuo and partitioned between DCM and water (15 mL each). The aq. phase was once more extracted with DCM and the combined org. layers washed with water, dried over MgSO$_4$ and concentrated to give the title acid as a off-white solid (0.178 g, 85% yield).

$^1$H NMR (DMSO d6) δ: 12.55 (m, 1H), 10.53 (s, 1H), 7.29 (m, 2H), 7.11 (dd, J=8.5, 2.3 Hz, 1H), 4.93 (m, 1H), 4.12 (t, J=9.1 Hz, 1H), 3.74 (m, 1H), 3.42 (s, 2H), 2.82 (m, 2H).

MS (ESI, m/z): 309.2 [M+H$^+$].

93.v. N-[(R)-2-hydroxy-2-(6-methoxy-[1,5]naphthy-ridin-4-yl)-ethyl]-N-methyl-2-[(R)-2-oxo-3-(3-oxo-3,4-dihydro-2H-benzo[1,4]thiazin-6-yl)-oxazolidin-5-yl]-acetamide The title compound was obtained starting from intermediate 93.iv (0.055 g, 0.178 mmol) and intermediate 93.i (0.041 g, 0.178 mmol) following method H. The compound was isolated after FC (EA/MeOH 9:1+1% NH$_4$OH) as a colourless solid (0.073 g, 79% yield).
MS (ESI, m/z): 524.1 [M+H$^+$].

Example 94

(S)-3-(2,3-dihydro-benzo[1,4]dioxin-6-yl)-5-[3-(6-methoxy-[1,5]naphthyridin-4-yl)-propoxymethyl]-oxazolidin-2-one

94.i. (3S)-(2,3-dihydro-benzo[1,4]dioxin-6-yl)-5-prop-2-ynyloxymethyl-oxazolidin-2-one A solution of (3S)-(2,3-dihydro-benzo[1,4]dioxin-6-yl)-5-hydroxymethyl-oxazolidin-2-one (prepared in analogy to Example 1, step 1.i (0.502 g, 2 mmol) and propargyl bromide (80% solution in toluene, 0.237 mmol, 1.1 eq.) in DMF (10 mL) was cooled to 0° C. and NaH dispersion (55% in mineral oil, 100 mg, 1.2 eq.) was added. The mixture was stirred at 0° C. for 30 min and at rt for 4 h and partitioned between ether and water. The org. phase was washed with water, dried over MgSO$_4$ and concentrated. The product was purified by FC (Hept/EA 2:1, 1:1) to give a colourless oil (0.565 g, 97% yield) which was used in the next step without characterization.

94.ii. (3S)-(2,3-dihydro-benzo[1,4]dioxin-6-yl)-5-[3-(6-methoxy-[1,5]naphthyridin-4-yl)-prop-2-yny-loxymethyl]-oxazolidin-2-one A solution of intermediate 94.i (0.565 g, 1.95 mmol) and 8-bromo-2-methoxy-[1,5]naphthyridine (0.454 g, 1.9 mmol) in DMF (10 mL) and TEA (1.6 mL) was purged with N$_2$ for 15 min. CuI (0.04 g) and Pd(PPh$_3$)$_2$Cl$_2$ (0.066 g) were added and the mixture stirred at rt for 5 h and at 50° C. for 1 h. The mixture was diluted with water and extracted several times with EA. The combined org. layers were washed with water and brine, dried over MgSO$_4$ and concentrated. The product was purified by FC (Hept/EA 1:1, EA) and isolated as a colourless solid (0.3 g, 35% yield).
$^1$H NMR (DMSO d6) δ: 8.74 (d, J=4.4 Hz, 1H), 8.28 (d, J=9.1 Hz, 1H), 7.75 (d, J=4.7 Hz, 1H), 7.30 (d, J=9.1 Hz, 1H), 7.09 (d, J=2.6 Hz, 1H), 6.94 (dd, J=8.8, 2.6 Hz, 1H), 6.81 (m, 1H), 4.86 (m, 1H), 4.65 (s, 2H), 4.20 (m, 5H), 4.08 (t, J=9.1 Hz, 1H), 4.01 (s, 3H), 3.85 (m, 3H).
MS (ESI, m/z): 448.5 [M+H$^+$].

94.iii. (S)-3-(2,3-dihydro-benzo[1,4]dioxin-6-yl)-5-[3-(6-methoxy-[1,5]naphthyridin-4-yl)-propoxym-ethyl]-oxazolidin-2-one A solution of intermediate 94.ii (0.1 g, 0.223 mmol) in MeOH/THF (1:1, 20 mL) was hydrogenated at 1 bar of H$_2$ over Pd/C (10%, 24 mg) for 3 h. The catalyst was filtered off over Celite and the filtrate concentrated. The product was purified by FC (EA, EA/MeOH 9:1) to give a colourless oil (0.075 g, 74% yield).
$^1$H NMR (CDCl$_3$) δ: 8.64 (d, J=4.4 Hz, 1H), 8.17 (d, J=9.1 Hz, 1H), 7.35 (d, J=4.4 Hz, 1H), 7.09 (m, 2H), 7.00 (dd, J=8.8, 2.6 Hz, 1H), 6.84 (m, 1H), 4.71 (m, 1H), 4.23 (m, 4H), 4.04 (s, 3H), 3.98 (t, J=8.5 Hz, 2H), 3.83 (dd, J=8.8, 6.2 Hz, 1H), 3.67 (d, J=4.4 Hz, 2H), 3.60 (t, J=6.2 Hz, 3H), 3.21 (m, 2H), 2.09 (m, 3H).
MS (ESI, m/z): 452.2 [M+H$^+$].

Example 95 rac-3-(2,3-dihydro-benzo[1,4]dioxin-6-yl)-5-[(E)-3-(6-methoxy-[1,5]naphthyridin-4-yl)-allyloxym-ethyl]-oxazolidin-2-one

95.i. 5-[3-(dibutyl-pentyl-stannanyl)-allyloxym-ethyl]-3-(2,3-dihydro-benzo[1,4]dioxin-6-yl)-oxazo-lidin-2-one A solution of rac-3-(2,3-dihydro-benzo[1,4]dioxin-6-yl)-5-hydroxymethyl-oxazolidin-2-one (prepared in analogy to Example 1, step 1.i; 0.852 g, 3.4 mmol) and tributyl-(3-chloro-propenyl)-stannane (prepared according to *J. Org. Chem.* (2000), 65, 7070; 1.2 g, 3.4 mmol) in DMF (20 mL) was cooled to 0° C. and a NaH dispersion (50% in mineral oil, 325 mg, 2 eq.) was added. The mixture was stirred at 0° C. for 30 min and at rt overnight. The volatiles were removed under reduced pressure and the residue partitioned between EA and water. The org. phase was washed with water, dried over MgSO$_4$ and concentrated. The product was purified by FC (Hept/EA 2:1) to give a yellow oil (1.06 g, 53% yield).
$^1$H NMR (CDCl$_3$) δ: 7.09 (d, J=2.9 Hz, 1H), 7.01 (dd, J=8.8, 2.6 Hz, 1H), 6.84 (m, 1H), 6.22 (m, 1H), 6.01 (m, 1H), 4.72 (m, 1H), 4.22 (m, 6H), 4.03 (m, 5H), 3.86 (dd, J=8.8, 6.4 Hz, 1H), 3.66 (m, 3H), 1.49 (m, 6H), 1.30 (m, 6H), 0.89 (m, 15H).

95.ii. rac-3-(2,3-dihydro-benzo[1,4]dioxin-6-yl)-5 [(E)-3-(6-methoxy-[1,5]naphthyridin-4-yl)-ally-loxymethyl]-oxazolidin-2-one A solution of intermediate 95.i (1 g, 1.68 mmol) and 8-bromo-2-methoxy-[1,5]naphthyridine (403 mg, 1.68 mmol, 1 eq.) in DMF (7 mL) was degassed by bubbling N$_2$ through for 30 min. Pd(PPh$_3$)$_2$Cl$_2$ (60 mg, 0.05 eq) was added and the mixture heated at 80° C. for 4.5 h. The solution was cooled to rt and partitioned between EA (100 mL) and water (100 mL). The aq. layer was washed twice more with EA (2×80 mL) and the org. layers were washed with water (4×80 mL) and with brine (80 mL). The combined org. layers were dried over MgSO$_4$, filtered and concentrated. The crude product was purified by FC (Hept/EA 1:1, EA, EA/MeOH 9:1) to give the title compound as a yellow foam (0.49 g, 65% yield).
$^1$H NMR (DMSO d6) δ: 8.70 (d, J=4.7 Hz, 1H), 8.23 (d, J=9.1 Hz, 1H), 7.82 (d, J=4.7 Hz, 1H), 7.59 (m, 2H), 7.25 (d, J=9.1 Hz, 1H), 7.09 (d, J=2.6 Hz, 1H), 6.96 (m, 2H), 6.81 (m, 1H), 4.90 (br., 1H), 4.35 (dd, J=5.3, 1.8 Hz, 2H), 4.19 (m, 4H), 4.07 (m, 1H), 3.97 (s, 3H), 3.78 (m, 3H).
MS (ESI, m/z): 450.3 [M+H$^+$].

Example 96

N-[2-(6-methoxy-[1,5]naphthyridin-4-yl)-ethyl]-2-[(R)-2-oxo-3-(3-oxo-3,4-dihydro-2H-benzo[1,4] thiazin-6-yl)-oxazolidin-5-yl]-acetamide

96.i. 3-(6-methoxy-[1,5]naphthyridin-4-yl)-propionic acid ethyl ester

A solution of intermediate 1.v (2.58 g, 10 mmol) in MeOH (250 mL) was treated with Pd/C (10%, 1 g) and hydrogenated (1 bar of H$_2$) for 2.5 h. The catalyst was filtered off and the filtrate concentrated in vacuo to give the title intermediate as a brownish oil (2.6 g, 100% yield).
MS (ESI, m/z): 261.2 [M+H$^+$].

96.ii.
3-(6-methoxy-[1,5]naphthyridin-4-yl)-propionic acid

The title compound (1.8 g, 78% yield) was obtained starting from intermediate 96.i (2.6 g, 10 mmol) and following method F.
$^1$H NMR (DMSO d6) δ: 8.66 (d, J=4.4 Hz, 1H), 8.23 (d, J=9.1 Hz, 1H), 7.53 (d, J=4.7 Hz, 1H), 7.24 (d, J=8.8 Hz, 1H), 4.01 (s, 3H), 3.34 (t, J=7.6 Hz, 2H), 2.74 (t, J=7.9 Hz, 2H).

96.iii.
2-(6-methoxy-[1,5]naphthyridin-4-yl)-ethylamine

A suspension of intermediate 96.ii (1.8 g, 7.7 mmol) in benzene (80 mL) was treated sequentially with TEA (1.3 mL, 9.3 mmol) and DPPA (1.85 mL, 8.5 mmol). The resulting solution was heated at reflux for 1.5 h, cooled to rt and diluted with EA. The org. phase was washed with water and brine, dried over MgSO$_4$ and concentrated. The residue was dissolved in THF (80 mL), NaOH (1M, 40 mL) was added and the mixture vigorously stirred at rt for 1 h. The mixture was diluted with water and extracted with EA (2×40 mL) and chloroform (2×40 mL). The combined org. layers were dried over MgSO$_4$ and concentrated. The residue was purified by FC (EA/MeOH 9:1, 4:1+1% NH$_4$OH) to give the title intermediate as a yellowish oil (0.8 g, 51% yield).
$^1$H NMR (DMSO d6) δ: 8.65 (d, J=4.4 Hz, 1H), 8.22 (d, J=8.8 Hz, 1H), 7.52 (d, J=4.4 Hz, 1H), 7.22 (d, J=8.8 Hz, 1H), 4.01 (s, 3H), 3.20 (t, J=7.0 Hz, 3H), 2.98 (m, 2H).

96.iv. N-[2-(6-methoxy-[1,5]naphthyridin-4-yl)-ethyl]-2-[(R)-2-oxo-3-(3-oxo-3,4-dihydro-2H-benzo[1,4]thiazin-6-yl)-oxazolidin-5-yl]-acetamide Intermediate 96.iii (0.07 g, 0.35 mmol) and intermediate 93.iv (0.055 g, 0.178 mmol) were coupled according to method H. The title compound was isolated as a yellowish solid (0.07 g, 79% yield).
$^1$H NMR (DMSO d6) δ: 10.54 (s, 1H), 8.67 (d, J=4.7 Hz, 1H), 8.23 (d, J=8.8 Hz, 1H), 8.13 (m, 1H), 7.51 (d, J=4.4 Hz, 1H), 7.27 (m, 3H), 7.08 (dd, J=8.8, 2.3 Hz, 1H), 5.9 (m, 1H), 4.09 (t, J=8.8 Hz, 1H), 4.03 (s, 3H), 3.71 (dd, J=8.8, 6.4 Hz, 1H), 3.53 (m, 2H), 3.42 (s, 2H), 3.27 (m, 2H), 2.59 (dd, J=6.7, 2.3 Hz, 2H).
MS (ESI, m/z): 494.1 [M+H$^+$].

Example 97

(R*)-3-(2,3-dihydro-benzo[1,4]dioxin-6-yl)-5-{(R*)-1-hydroxy-2-[2-(6-methoxy-[1,5]naphthyridin-4-yl)-ethylamino]-ethyl}-oxazolidin-2-one 97.i. (4-bromo-but-2-enyl)-(2,3-dihydro-benzo[1,4]dioxin-6-yl)-carbamic acid benzyl ester A solution of (2,3-dihydro-benzo[1,4]dioxin-6-yl)-carbamic acid benzyl ester (5 g, 17.5 mmol) in dry THF (85 mL) was cooled to −78° C. At this temperature n-BuLi (2.5M solution in hexanes, 14 mL) was added dropwise and the clear solution stirred at −78° C. for 20 min. A solution of E-1,4-dibromobut-2-ene (4.9 g, 23 mmol) in THF (42 mL) was added dropwise and the mixture slowly allowed to warm to rt. The mixture was poured on water and extracted with EA. The combined org. extracts were dried over MgSO$_4$ and concentrated. The product was purified by FC (Hept/EA 9:1, 4:1) and obtained as a greenish oil (2.88 g, 38% yield) which was used as such in the next step despite some contaminations with starting material.
MS (ESI, m/z): 418.1 [M+H$^+$].

97.ii. Rac-(4-bromo-2,3-dihydroxy-butyl)-(2,3-dihydro-benzo[1,4]dioxin-6-yl)-carbamic acid benzyl ester A solution of intermediate 97.i (2.88 g, 6.9 mmol) in DCM (22 mL) and water (6 mL) was treated with NMO hydrate (917 mg, 1.1 eq.) and K$_2$OsO$_4$.dihydrate (12 mg). The mixture was vigorously stirred at rt overnight. The phases were separated and the aq. phase extracted with DCM. The combined org. extracts were dried over MgSO$_4$ and concentrated. The product was purified by FC (Hept/EA 2:1, EA) to give the title diol as a brownish oil (0.72 g, 23% yield).
MS (ESI, m/z): 454.1 [M+H$^+$].

97.iii. 3-(2,3-dihydro-benzo[1,4]dioxin-6-yl)-5-oxiranyl-oxazolidin-2-one

A solution of intermediate 97.ii (0.72 g, 1.6 mmol) in MeOH (5.5 mL) was treated with NaOMe (86 mg, 1 eq.). The mixture was stirred at rt for 2 days. The solvent was removed under reduced pressure and the residue was taken up in EA and water. The org. phase was washed with brine, dried over MgSO$_4$ and concentrated. The product was crystallized from EA and ether to give the title epoxide as a brownish solid (0.26 g, 63% yield).
$^1$H NMR (DMSO d6) δ: 7.10 (d, J=2.6 Hz, 1H), 6.96 (dd, J=9.1, 2.6 Hz, 1H), 6.85 (m, 1H), 4.51 (m, 1H), 4.21 (d, J=2.1 Hz, 4H), 4.11 (t, J=9.1 Hz, 1H), 3.88 (dd, J=9.1, 6.4 Hz, 1H), 3.32 (m, 1H), 2.83 (t, J=4.7 Hz, 1H), 2.73 (dd, J=5.0, 2.6 Hz, 1H).
MS (ESI, m/z): 264.5 [M+H$^+$].

97.iv. (R*)-3-(2,3-dihydro-benzo[1,4]dioxin-6-yl)-5-{(R*)-1-hydroxy-2-[2-(6-methoxy-[1,5]naphthyridin-4-yl)-ethylamino]-ethyl}-oxazolidin-2-one A solution of intermediate 97.iii (0.1 g, 0.38 mmol) and intermediate 96.iii (0.077 g, 0.38 mmol) in EtOH/H$_2$O (9:1, 3 mL) was heated at reflux overnight. The volatiles were removed under reduced pressure and the residue purified by FC (EA/MeOH 9:1+1% NH$_4$OH) to give the title compound as a dark oil (0.055 g, 31% yield).
$^1$H NMR (CDCl$_3$) δ: 8.67 (d, J=4.4 Hz, 1H), 8.19 (d, J=9.1 Hz, 1H), 7.39 (d, J=4.4 Hz, 1H), 7.10 (m, 2H), 6.98 (dd, J=8.8, 2.6 Hz, 1H), 6.84 (m, 1H), 4.57 (m, 1H), 4.24 (m, 4H), 4.08 (s, 3H), 3.96 (m, 2H), 3.72 (m, 1H), 3.37 (t, J=7.0 Hz, 2H), 3.13 (m, 2H), 2.93 (m, 2H).
MS (ESI, m/z): 476.2 [M+H$^+$].

Example 98

(R*)-3-(2,3-dihydro-benzo[1,4]dioxin-6-yl)-5-{(R*)-1-hydroxy-2-[2-(6-methoxy-quinolin-4-yl)-ethylamino]-ethyl}-oxazolidin-2-one The title compound was obtained starting from intermediate 97.iii (0.08 g, 0.3 mmol) and 2-(6-methoxy-quinolin-4-yl)-ethylamine (prepared according to J. Chem. Soc. (1947), 1684; 0.061 g, 0.3 mmol) and following the procedure of Example 97, step 97.iv. The product was isolated as a brown solid (0.015 g, 10% yield).

$^1$H NMR (DMSO d6) δ: 8.61 (d, J=4.4 Hz, 1H), 7.90 (d, J=8.8 Hz, 1H), 7.37 (m, 3H), 7.11 (d, J=2.6 Hz, 1H), 6.94 (dd, J=8.8, 2.6 Hz, 1H), 6.83 (m, 1H), 5.18 (d, J=5.3 Hz, 1H), 4.62 (m, 1H), 4.21 (m, 4H), 3.98 (m, 1H), 3.92 (s, 3H), 3.79 (dd, J=8.8, 6.4 Hz, 1H), 3.59 (m, 1H), 3.18 (t, J=7.3 Hz, 2H), 2.92 (t, J=7.3 Hz, 2H), 2.70 (d, J=6.4 Hz, 2H).

MS (ESI, m/z): 466.1 [M+H$^+$].

Example 99

(R*)-3-(2,3-dihydro-benzo[1,4]dioxin-6-yl)-5-((R*)-1-hydroxy-2-{[2-(6-methoxy-[1,5]naphthyridin-4-yl)-ethyl]-methyl-amino}-ethyl)-oxazolidin-2-one

99.i. [2-(6-methoxy-[1,5]naphthyridin-4-yl)-ethyl]-methyl-amine

A solution of 2-methoxy-8-vinyl-[1,5]naphthyridine (prepared as in WO 02/08224; 0.28 g, 1.5 mmol) in MeOH (6 mL) was treated with methyl amine hydrochloride (0.1 g, 1 eq.) and heated in a sealed flask at reflux for 5 h. AcOH (0.9 mL) was added and the mixture heated at reflux overnight. The mixture was concentrated in vacuo, taken up in aq. ammonia and extracted with DCM/MeOH (9:1). The combined org. extracts were dried over MgSO$_4$ and concentrated. The residue was purified by FC (DCM/MeOH 9:1+1% NH$_4$OH) to give the title amine as a brown oil (0.06 g, 19% yield).

$^1$H NMR (DMSO d6) δ: 8.58 (d, J=4.1 Hz, 1H), 8.19 (d, J=9.1 Hz, 1H), 7.47 (d, J=4.4 Hz, 1H), 7.19 (d, J=8.8 Hz, 1H), 3.90 (s, 3H), 3.25 (m, 2H), 2.84 (m, 2H), 2.49 (s, 3H).

99.ii. (R*)-3-(2,3-dihydro-benzo[1,4]dioxin-6-yl)-5-((R*)-1-hydroxy-2-{[2-(6 methoxy-[1,5]naphthyridin-4-yl)-ethyl]-methyl-amino}-ethyl)-oxazolidin-2-one The title compound was obtained starting from intermediate 97.iii (0.074 g, 0.28 mmol) and intermediate 99.i (0.061 g, 0.28 mmol) and following the procedure of Example 97, step 97.iv. The product was isolated as a brown solid (0.023 g, 17% yield).

$^1$H NMR (DMSO d6) δ: 8.65 (d, J=4.4 Hz, 1H), 8.22 (d, J=9.1 Hz, 1H), 7.58 (d, J=4.4 Hz, 1H), 7.23 (d, J=9.1 Hz, 1H), 7.09 (d, J=2.3 Hz, 1H), 6.92 (m, 1H), 6.83 (m, 1H), 5.03 (d, J=5.6 Hz, 1H), 4.52 (m, 1H), 4.21 (m, 4H), 4.03 (s, 3H), 3.89 (m, 1H), 3.75 (dd, J=8.8, 6.4 Hz, 1H), 3.60 (m, 1H), 3.28 (m, 2H), 2.81 (m, 2H), 2.64 (m, 2H), 2.35 (s, 3H).

MS (ESI, m/z): 481.3 [M+H$^+$].

Example 100

(R*)-3-(2,3-dihydro-benzo[1,4]dioxin-6-yl)-(R*)-5-(1-hydroxy-2-{[(RS)-2-hydroxy-2-(3-methoxy-quinoxalin-5-yl)-ethyl]-methyl-amino}-ethyl)-oxazolidin-2-one The title product was obtained as a colourless foam (0.12 g, 80% yield) starting from intermediate 97.iii (0.08 g, 0.3 mmol) and intermediate 93.i (0.071 g, 0.3 mmol) and following the procedure of Example 97, step 97.iv.

MS (ESI, m/z): 497.4 [M+H$^+$].

Example 101

6-((S)-5-{(S)-1-hydroxy-2-[2-(6-methoxy-[1,5]naphthyridin-4-yl)-ethylamino]-ethyl}-2-oxo-oxazolidin-3-yl)-4H-benzo[1,4]thiazin-3-one

101.i. [(2S,3S)-2,3-dihydroxy-4-(3-oxo-3,4-dihydro-2H-benzo[1,4]thiazin-6-ylamino)-butyl]-carbamic acid tert-butyl ester ((S)-2-hydroxy-2-(S)-oxiranyl-ethyl)-carbamic acid tert-butyl ester (prepared according to *Tetrahedron Lett.* (1993), 34, 5545; 1.4 g, 6.9 mmol) and 6-amino-4H-benzo[1,4]thiazin-3-one (1.49 g, 1.2 eq.) were coupled according to method A. The title intermediate was isolated after FC (Hept/EA 1:2, EA) as a beige foam (1.59 g, 59% yield).

$^1$H NMR (DMSO d6) δ: 10.21 (s, 1H), 6.93 (d, J=7.9 Hz, 1H), 6.55 (m, 1H), 6.24 (m, 3H), 5.56 (m, 1H), 4.51 (m, 2H), 4.01 (q, J=7.0 Hz, 1H), 3.49 (m, 2H), 3.08 (m, 2H), 2.92 (m, 2H), 1.35 (m, 10H).

MS (ESI, m/z): 264.4 [M+H$^+$].

101.ii. {(4S,5S)-2-oxo-5-[(3-oxo-3,4-dihydro-2H-benzo[1,4]thiazin-6-ylamino)-methyl]-[1,3]dioxolan-4-ylmethyl}-carbamic acid tert-butyl ester A solution of intermediate 101.i (1.57 g, 4.1 mmol) in THF (100 mL) was treated with CDI (0.797 g, 1.2 eq.). The mixture was stirred at rt overnight, diluted with EA and washed with water and brine. The org. phase was dried over MgSO$_4$ and concentrated. The residue was purified by FC (EA) to give the title carbonate as a beige foam (1.26 g, 75% yield).

$^1$H NMR (CDCl$_3$) δ: 8.44 (s, 1H), 7.10 (d, J=8.5 Hz, 1H), 6.34 (dd, J=8.5, 2.6 Hz, 1H), 6.22 (d, J=2.3 Hz, 1H), 5.08 (m, 1H), 4.65 (m, 1H), 4.51 (m, 1H), 4.15 (m, 1H), 3.55 (m, 4H), 3.37 (s, 2H), 1.45 (m, 9H).

MS (ESI, m/z): 410.1 [M+H$^+$].

101.iii. {(S)-2-hydroxy-2-[(S)-2-oxo-3-(3-oxo-3,4-dihydro-2H-benzo[1,4]thiazin-6-yl)-oxazolidin-5-yl]-ethyl}-carbamic acid tert-butyl ester A solution of intermediate 101.ii (1.26 g, 3 mmol) in DCM (100 mL) was treated with DIPEA (2.6 mL, 5 eq.) and methyl chloroformate (0.6 mL, 2.5 eq.). The mixture was stirred at rt overnight, washed with water, dried over MgSO$_4$ and concentrated. The crude was dissolved in MeOH (50 mL) and K$_2$CO$_3$ (0.212 g, 0.5 eq.) was added. The mixture was stirred at rt for 2 h, concentrated in vacuo and purified by crystallization from EA. The title oxazolidinone was isolated as a colourless solid (0.69 g, 55% yield).

$^1$H NMR (DMSO d6) δ: 10.54 (s, 1H), 7.31 (m, 2H), 7.09 (dd, J=8.8, 2.6 Hz, 1H), 6.85 (m, 1H), 5.35 (d, J=5.9 Hz, 1H), 4.62 (m, 1H), 4.03 (m, 1H), 3.76 (dd, J=8.5, 6.2 Hz, 1H), 3.57 (dd, J=5.9, 1.5 Hz, 1H), 3.41 (s, 2H), 3.07 (m, 2H), 1.37 (s, 9H).

MS (ESI, m/z): 410.1 [M+H$^+$].

101.iv. 6-[(S)-5-((S)-2-amino-1-hydroxy-ethyl)-2-oxo-oxazolidin-3-yl]-4H-benzo[1,4]thiazin-3-one The Boc group of intermediate 101.iii (0.69 g, 1.69 mmol) was removed according to method E. The desired intermediate was isolated as a colourless solid (0.13 g, 25% yield).

MS (ESI, m/z): 310.3 [M+H$^+$].

101.v. 6((S)-5-{(S)-1-hydroxy-2-[2-(6-methoxy-[1,5]naphthyridin-4-yl)-ethylamino]-ethyl}-2-oxo-oxazolidin-3-yl)-4H-benzo[1,4]thiazin-3-one AcOH (0.023 μL, 0.4 mmol) was added to a solution of intermediate 101.iv (0.123 g, 0.4 mmol) and 2-methoxy-8-vinyl-[1,5]naphthyridine (0.074 g, 0.4 mmol) in MeOH (3 mL). The mixture was stirred at 70° C. overnight, diluted with DCM and washed with NH$_4$OH. The org. phase was washed with water, dried over MgSO$_4$ and concentrated. The residue was purified by FC (DCM/MeOH 19:1+0.5% NH$_4$OH) to give the title compound as a colourless solid (0.035 g, 18% yield).

$^1$H NMR (DMSO d6) δ: 10.54 (s, 1H), 8.66 (d, J=4.4 Hz, 1H), 8.22 (d, J=9.1 Hz, 1H), 7.55 (d, J=4.4 Hz, 1H), 7.28 (m, 3H), 7.08 (dd, J=8.5, 2.1 Hz, 1H), 5.20 (m, 1H), 4.66 (m, 1H), 4.00 (m, 4H), 3.79 (m, 1H), 3.61 (m, 1H), 3.41 (s, 2H), 2.98 (t, J=6.7 Hz, 2H), 2.72 (m, 2H).

MS (ESI, m/z): 496.4 [M+H$^+$].

Example 102

(S)-3-(2,3-dihydro-benzo[1,4]dioxin-6-yl)-5-{(S)-1-hydroxy-2-[(RS)-2-hydroxy-2-(3-methoxy-quinoxalin-5-yl)-ethylamino]-ethyl}-oxazolidin-2-one

102.i. (S)-5-((S)-2-amino-1-hydroxy-ethyl)-3-(2,3-dihydro-benzo[1,4]dioxin-6-yl)-oxazolidin-2-one The title compound was prepared starting from ((S)-2-hydroxy-2-(S)-oxiranyl-ethyl)-carbamic acid tert-butyl ester (prepared according to *Tetrahedron Lett*. (1993), 34, 5545; 1.29 g, 6.3 mmol) and 2,3-dihydro-benzo[1,4]dioxin-6-ylamine following the procedures of Example 101, steps 101.i to 101.iv. The desired amine was isolated as a colourless solid (0.28 g).

$^1$H NMR (CDCl$_3$) δ: 7.09 (d, J=2.6 Hz, 1H), 7.00 (dd, J=9.1, 2.6 Hz, 1H), 6.85 (m, 1H), 4.62 (m, 1H), 4.24 (m, 4H), 3.97 (m, 2H), 3.67 (m, 2H), 2.98 (dd, J=3.5, 2.3 Hz, 2H).

102.ii. (S)-3-(2,3-dihydro-benzo[1,4]dioxin-6-yl)-5-{(S)-1-hydroxy-2-[(RS)-2-hydroxy-2-(3-methoxy-quinoxalin-5-yl)-ethylamino]-ethyl}-oxazolidin-2-one A solution of intermediate 102.i (0.14 g, 0.5 mmol) and 2-methoxy-8-oxiranyl-quinoxaline (0.1 g, 0.5 mmol) in EtOH/H$_2$O (9:1, 3 mL) was heated at reflux overnight. The volatiles were removed under reduced pressure and the residue was purified by FC (EA/MeOH 9:1+1% NH$_4$OH) to give the title compound as a beige foam (0.02 g, 8% yield).

MS (ESI, m/z): 483.3 [M+H$^+$].

Example 103

6-((R*)-5-{(R*)-1-hydroxy-3-[(6-methoxy-[1,5]naphthyridin-4-ylmethyl)-amino]-propyl}-2-oxo-oxazolidin-3-yl)-4H-benzo[1,4]thiazin-3-one

103.i. ((E)-5-bromo-pent-3-enyl)-carbamic acid tert-butyl ester

A solution of ((E)-5-hydroxy-pent-3-enyl)-carbamic acid tert-butyl ester (27.5 g, 137 mmol) and PPh$_3$ (39.4 g, 1.1 eq.) in DCM (1 L) at −40° C. was treated with NBS (27 g, 1.1 eq.). The mixture was stirred at −40° C. for 30 min until complete dissolution of NBS. The mixture was quenched by addition of a sat. NaHCO$_3$ solution (1 L) and warmed to rt. The phases were separated and the org. phase dried over MgSO$_4$ and concentrated. The residue was purified by FC (Hept/EA 2:1) to give the title bromide as an orange oil (15.4 g, 43% yield).

$^1$H NMR (CDCl$_3$) δ: 5.73 (m, 1H), 4.52 (br., 1H), 3.93 (m, 1H), 3.18 (m, 1H), 2.25 (q, J=6.2 Hz, 1H), 1.46 (m, 6H).

103.ii. ((R*)-3-hydroxy-3-(R*)-oxiranyl-propyl)-carbamic acid tert-butyl ester Intermediate 103.i (2.8 g, 10.6 mmol) was dihydroxylated according to method L. The title epoxide (cyclisation product of intermediate diol) was isolated after FC (Hept/EA 4:1→1:2) as a colourless oil (1.17 g, 51% yield).

$^1$H NMR (CDCl$_3$) δ: 4.85 (m, 1H), 3.48 (m, 2H), 3.20 (m, 1H), 3.00 (m, 1H), 2.88 (m, 1H), 2.80 (m, 1H), 2.71 (dd, J=5.0, 2.9 Hz, 1H), 1.75 (m, 2H), 1.42 (s, 11H).

103.iii. [(3R*,4R*)-3,4-dihydroxy-5-(3-oxo-3,4-dihydro-2H-benzo[1,4]thiazin-6-ylamino)-pentyl]-carbamic acid tert-butyl ester Intermediate 103.ii (0.94 g, 4.3 mmol) and 6-amino-4H-benzo[1,4]thiazin-3-one (0.93 g, 1.2 eq.) were coupled according to method A. The title amino alcohol was isolated after FC (EA) as a beige oil (0.95 g, 55% yield).

MS (ESI, m/z): 398.2 [M+H$^+$].

103.iv. {(R*)-3-hydroxy-3-[(R*)-2-oxo-3-(3-oxo-3,4-dihydro-2H-benzo[1,4]thiazin-6-yl)-oxazolidin-5-yl]-propyl}-carbamic acid tert-butyl ester The title intermediate was obtained as a beige solid (0.42 g, 48% yield) starting from intermediate 103.iii (0.95 g, 2.4 mmol) and following the procedure from Example 101, steps 101.ii and 101.iii.

$^1$H NMR (DMSO d6) δ: 10.54 (s, 1H), 7.31 (m, 2H), 7.10 (dd, J=8.5, 2.3 Hz, 1H), 6.75 (td, J=2.3, 1.2 Hz, 1H), 5.15 (d, J=6.2 Hz, 1H), 4.55 (m, 1H), 4.02 (m, 1H), 3.77 (dd, J=8.5, 6.4 Hz, 1H), 3.56 (m, 1H), 3.41 (s, 2H), 1.58 (m, 2H), 1.37 (m, 9H).

103.v. 6-[(R*)-5-((R*)-3-amino-1-hydroxy-propyl)-2-oxo-oxazolidin-3-yl]-4H-benzo[1,4]thiazin-3-one The Boc group of intermediate 103.iv (0.43 g, 1 mmol) was removed using method E. The title amino alcohol was isolated as a colourless solid (0.14 g, 43% yield).

$^1$H NMR (DMSO d6) δ: 10.55 (s, 1H), 7.30 (m, 2H), 7.10 (dd, J=8.5, 2.1 Hz, 1H), 5.47 (dd, J=5.0, 0.6 Hz, 1H), 4.59 (s, 1H), 4.02 (m, 1H), 3.78 (dd, J=8.5, 5.9 Hz, 1H), 3.67 (d, J=0.6 Hz, 1H), 3.41 (s, 2H), 2.90 (ddd, J=7.3, 1.2, 0.6 Hz, 2H), 1.74 (dd, J=7.3, 1.8 Hz, 2H).

MS (ESI, m/z): 324.2 [M+H$^+$].

103.vi. 6-((R*)-5-{(R*)-1-hydroxy-3-[(6-methoxyl-[1,5]naphthyridin-4-ylmethyl)-amino]-propyl}-2-oxo-oxazolidin-3-yl)-4H-benzo[1,4]thiazin-3-one Intermediate 103.v (40 mg, 0.124 mmol) and 6-methoxy-[1,5]naphthyridine-4-carbaldehyde (23 mg, 0.124 mmol) were coupled according to method K. The title compound was isolated after FC (EA/MeOH 9:1+1% NH$_4$OH) as a colourless solid (0.05 g, 82% yield).

$^1$H NMR (DMSO d6) δ: 10.53 (s, 1H), 8.72 (d, J=4.4 Hz, 1H), 8.24 (d, J=9.1 Hz, 1H), 7.68 (d, J=4.4 Hz, 1H), 7.28 (m,

3H), 7.09 (m, 1H), 4.56 (d, J=3.2 Hz, 1H), 4.24 (s, 2H), 4.00 (s, 4H), 3.75 (m, 2H), 3.40 (s, 2H), 2.74 (m, 2H), 1.67 (m, 2H).

MS (ESI, m/z): 496.4 [M+H$^+$].

Example 104

6-((R*)-5-{(R*)-3-[(3-fluoro-6-methoxy-[1,5]naphthyridin-4-ylmethyl)-amino]-1-hydroxy-propyl}-2-oxo-oxazolidin-3-yl)-4H-benzo[1,4]thiazin-3-one Intermediate 103.v (100 mg, 0.31 mmol) and 3-fluoro-6-methoxy-[1,5]naphthyridine-4-carbaldehyde (64 mg, 0.31 mmol) were coupled according to method K. The title compound was isolated after FC (EA/MeOH 9:1+1% NH$_4$OH) as a colourless solid (0.073 g, 46% yield).

$^1$H NMR (DMSO d6) δ: 10.52 (s, 1H), 8.79 (s, 1H), 8.27 (d, J=9.1 Hz, 1H), 7.27 (m, 3H), 7.07 (dd, J=8.5, 2.3 Hz, 1H), 4.51 (m, 1H), 4.21 (s, 2H), 3.98 (m, 4H), 3.73 (dd, J=8.8, 6.2 Hz, 1H), 3.62 (m, 1H), 3.40 (s, 2H), 2.64 (m, 2H), 1.59 (m, 2H).

MS (ESI, m/z): 514.2 [M+H$^+$].

Example 105

(R*)-3-(2,3-dihydro-benzo[1,4]dioxin-6-yl)-5-{(R*)-3-[(3-fluoro-6-methoxy-[1,5]naphthyridin-4-ylmethyl)-amino]-1-hydroxy-propyl}-oxazolidin-2-one 105.i. (R*)-5-((R*)-3-amino-1-hydroxy-propyl)-3-(2,3-dihydro-benzo[1,4]dioxin-6-yl)-oxazolidin-2-one The title amino alcohol was obtained starting from intermediate 103.ii (3.9 g, 18 mmol) and 2,3-dihydro-benzo[1,4]dioxin-6-ylamine (3.3 g, 21.8 mmol) and following the procedures of Example 103, steps 103.iii to 103.v. The compound was isolated as a beige solid (0.93 g, 17% yield over all steps).

$^1$H NMR (DMSO d6) δ: 7.11 (d, J=2.6 Hz, 1H), 6.96 (m, 1H), 6.83 (m, 1H), 4.50 (m, 1H), 4.20 (m, 4H), 3.97 (t, J=8.8 Hz, 1H), 3.76 (dd, J=8.8, 6.7 Hz, 1H), 3.67 (m, 1H), 3.50 (m, 1H), 2.70 (m, 2H), 1.51 (m, 2H).

MS (ESI, m/z): 295.5 [M+H$^+$].

105.ii. (R*)-3-(2,3-dihydro-benzo[1,4]dioxin-6-yl)-5-{(R*)-3-[(3-fluoro-6-methoxy-[1,5]naphthyridin-4-ylmethyl)-amino]-hydroxy-propyl}-oxazolidin-2-one Intermediate 105.i (923 mg, 3.1 mmol) and 3-fluoro-6-methoxy-[1,5]naphthyridine-4-carbaldehyde (647 mg, 3.1 mmol) were coupled according to method K. The title compound was isolated after FC (EA/MeOH 9:1+1% NH$_4$OH) as a off-white solid (0.947 g, 62% yield).

$^1$H NMR (DMSO d6) δ: 8.79 (s, 1H), 8.28 (d, J=9.1 Hz, 1H), 7.23 (d, J=9.1 Hz, 1H), 7.09 (d, J=2.6 Hz, 1H), 6.93 (m, 1H), 6.82 (m, 1H), 4.47 (m, 1H), 4.19 (m, 6H), 4.04 (s, 3H), 3.95 (m, 1H), 3.72 (dd, J=8.5, 6.4 Hz, 1H), 3.61 (m, 1H), 2.65 (m, 2H), 1.59 (m, 2H).

MS (ESI, m/z): 485.0 [M+H$^+$].

Example 106

(S*)-3-(2,3-dihydro-benzo[1,4]dioxin-6-yl)-5-{(R*)-3-[(3-fluoro-6-methoxy-[1,5]naphthyridin-4-ylmethyl)-amino]-1-hydroxy-propyl}-oxazolidin-2-one 106.i. {(R*)-3-[(R*)-3-(2,3-dihydro-benzo[1,4]dioxin-6-yl)-2-oxo-oxazolidin-5-yl]-3-hydroxy-propyl}-(3-fluoro-6-methoxy-[1,5]naphthyridin-4-ylmethyl)-carbamic acid tert-butyl ester A solution of the compound of Example 105 (0.923 g, 1.9 mmol) in DCM (15 mL) was treated with TEA (0.32 mL, 1.2 eq.) and Boc$_2$O (0.5 g, 1.2 eq.). The mixture was stirred at rt for 4 h, concentrated in vacuo and purified by FC (EA). The desired intermediate was isolated as a yellowish foam (0.1 g, 100% yield).

$^1$H NMR (DMSO d6) δ: 8.79 (s, 1H), 8.28 (d, J=9.1 Hz, 1H), 7.23 (d, J=9.1 Hz, 1H), 7.09 (d, J=2.6 Hz, 1H), 6.93 (m, 1H), 6.83 (m, 1H), 5.10 (m, 1H), 5.01 (s, 2H), 4.48 (m, 1H), 4.20 (m, 4H), 4.05 (s, 3H), 3.94 (t, J=9.1 Hz, 1H), 3.70 (m, 1H), 3.38 (m, 2H), 1.68 (m, 2H), 1.29 (m, 9H).

MS (ESI, m/z): 585.2 [M+H$^+$].

106.ii. 4-nitro-benzoic acid (R*)-3-[tert-butoxycarbonyl-(3-fluoro-6-methoxy-[1,5]naphthyridin-4-ylmethyl)-amino]-1-[(S*)-3-(2,3-dihydro-benzo[1,4]dioxin-6-yl)-2-oxo-oxazolidin-5-yl]-propyl ester A solution of intermediate 106.i (0.205 g, 0.35 mmol), PPh$_3$ (0.1 g, 1.1 eq.) and 4-nitrobenzoic acid (0.072 g, 1.2 eq.) in THF (2 mL) was treated dropwise with DIAD (0.09 mL, 1.2 eq.). The mixture was stirred at rt for one day, concentrated in vacuo and purified by FC (Hept/EA 2:1, 1:1, 1:2) to give the title intermediate as a yellowish foam (0.24 g, 93% yield).

MS (ESI, m/z): 734.0 [M+H$^+$].

106.iii. {(R*)-3-[(S*)-3-(2,3-dihydro-benzo[1,4]dioxin-6-yl)-2-oxo-oxazolidin-5-yl]-3-hydroxy-propyl}-(3-fluoro-6-methoxy-[1,5]naphthyridin-4-ylmethyl)-carbamic acid tert-butyl ester A solution of intermediate 106.ii (0.23 g, 0.3 mmol) in THF/MeOH/H$_2$O (2:2:1, 2 mL) was treated with LiOH hydrate (0.018 g, 1.3 eq.). The mixture was stirred at rt overnight and concentrated in vacuo. The residue was partitioned between EA and water, the org. phase dried over MgSO$_4$ and concentrated. The residue was purified by FC (EA) to give the title intermediate as a colourless foam (0.2 g, 100% yield).

MS (ESI, m/z): 585.2 [M+H$^+$].

106.iv. (S*)-3-(2,3-dihydro-benzo[1,4]dioxin-6-yl)-5-{(R*)-3-[(3-fluoro-6-methoxy-[1,5]naphthyridin-4-ylmethyl)-amino]-1-hydroxy-propyl}-oxazolidin-2-one The Boc protecting group of intermediate 106.iii (0.2 g, 0.34 mmol) was removed according to method E. The title compound was isolated after FC (EA/MeOH 9:1+1% NH$_4$OH) as a colourless foam (0.088 g, 53% yield).

$^1$H NMR (DMSO d6) δ: 8.81 (s, 1H), 8.29 (d, J=9.1 Hz, 1H), 7.24 (d, J=9.1 Hz, 1H), 7.10 (d, J=2.6 Hz, 1H), 6.93 (m,

1H), 6.82 (m, 1H), 4.43 (m, 1H), 4.26 (s, 2H), 4.20 (dd, J=3.5, 1.2 Hz, 5H), 4.04 (s, 3H), 3.92 (t, J=8.8 Hz, 1H), 3.75 (m, 2H), 2.71 (m, 2H), 1.54 (m, 2H).
MS (ESI, m/z): 485.0 [M+H$^+$].

Example 107

(S*)-5-{(R*)-1-amino-3-[(3-fluoro-6-methoxy-[1,5] naphthyridin-4-ylmethyl)-amino]-propyl}-3-(2,3-dihydro-benzo[1,4]dioxin-6-yl)-oxazolidin-2-one A solution of intermediate 106.i (0.2 g, 0.35 mmol) in THF (2 mL) was treated with di-tert. butyl iminodicarboxylate (0.114 g, 1.5 eq.), PPh$_3$ (0.102 g, 1.1 eq.) and DIAD (0.09 mL, 1.2 eq.). The mixture was stirred at rt for one day, concentrated in vacuo and purified by FC (Hept/EA 2:1, 1:1, 2:1). This intermediate was dissolved in DCM (1 mL) and TFA (0.5 mL) was added. The mixture was stirred at rt for 2 h, concentrated in vacuo and partitioned between DCM and NH$_4$OH. The aq. phase was extracted several times with DCM/MeOH 9:1 and the combined org. phases washed with brine, dried over MgSO$_4$ and concentrated. The product was isolated after FC (EA/MeOH 9:1, 4:1+1% NH$_4$OH) as a colourless foam (0.038 g, 23% yield).
$^1$H NMR (DMSO d6) δ: 8.79 (s, 1H), 8.28 (d, J=9.1 Hz, 1H), 7.23 (d, J=9.1 Hz, 1H), 7.08 (d, J=2.3 Hz, 1H), 6.94 (m, 1H), 6.82 (m, 1H), 4.34 (m, 1H), 4.19 (m, 6H), 4.03 (s, 3H), 3.86 (m, 2H), 2.89 (m, 1H), 2.64 (m, 2H), 1.59 (s, 1H), 1.31 (m, 1H).
MS (ESI, m/z): 484.1 [M+H$^+$].

Example 108

(R)-3-(2,3-dihydro-benzo[1,4]dioxin-6-yl)-5-[(E)-4-(6-methoxy-quinolin-4-yloxy)-but-2-enyl]-oxazolidin-2-one 108.i. 4-[4-((R)-2,2-dimethyl-[1,3]dioxolan-4-yl)-but-2-enyloxy]-6-methoxy-quinoline A solution of 6-methoxy-quinolin-4-ol (0.54 g, 3 mmol) and (E)-4-((R)-2,2-dimethyl-[1,3]dioxolan-4-yl)-but-2-en-1-ol (prepared according to *J. Am. Chem. Soc.* (2001), 123, 9525; 0.53 g, 3 mmol) in THF was treated with PPh$_3$ (977 mg, 1.2 eq.) and dropwise with DIAD (0.77 mL, 1.2 eq.). The mixture was stirred at rt for 3 days, concentrated in vacuo and purified by FC (EA) to give the product as a yellowish oil (0.73 g, 72% yield).
$^1$H NMR (DMSO d6) δ: 8.54 (d, J=5.0 Hz, 1H), 7.84 (m, 1H), 7.57 (m, 10H), 7.36 (m, 2H), 6.97 (d, J=5.3 Hz, 1H), 5.92 (m, 2H), 4.79 (d, J=4.4 Hz, 2H), 4.11 (m, 1H), 3.99 (m, 2H), 3.87 (s, 4H), 3.48 (dd, J=7.9, 6.7 Hz, 1H), 3.28 (m, 2H), 2.33 (m, 6H), 1.29 (s, 3H), 1.24 (s, 3H).

108.ii. (E)-(R)-6-(6-methoxy-quinolin-4-yloxy)-hex-4-ene-1,2-diol

A mixture of intermediate 108.i (0.73 g, 2.2 mmol) in THF/MeOH/AcOH (1:1:1, 20 mL) was heated at 70° C. for 2 days. The mixture was cooled to rt, TFA (2 mL) was added and stirring continued for 2 h at rt. The volatiles were removed under reduced pressure and the residue partitioned between DCM and NH$_4$OH. The org. layer was washed with water, dried over MgSO$_4$ and concentrated to give the title diol as a colourless solid (0.25 g, 38% yield).
MS (ESI, m/z): 290.2 [M+H$^+$].

108.iii. 6-methoxy-4-((E)-(R)-4-oxiranyl-but-2-enyloxy)-quinoline

A solution of TsCl (0.171 g, 1.05 eq.) in DCM (2 mL) was added dropwise to a solution of intermediate 108.ii (0.25 g, 0.86 mmol) in Pyr (6 mL). The mixture was stirred at rt for 3 h, diluted with EA and washed with 3M HCl (60 mL). Org. layers washed with brine, dried over MgSO$_4$ and concentrated. The residue was dissolved in THF and cooled to 0° C. NaH dispersion (50% in mineral oil, 41 mg, 1 eq.) was added and the mixture left at 4° C. overnight (fridge). The mixture was partitioned between EA and water, the org. phase dried over MgSO$_4$ and concentrated. The product was purified by FC (Hex/EA 1:1, EA, EA/MeOH 9:1) to give the title epoxide as a colourless oil (0.11 g, 50% yield).
$^1$H NMR (DMSO d6) δ: 8.60 (d, J=5.3 Hz, 1H), 7.93 (d, J=9.1 Hz, 1H), 7.47 (d, J=2.9 Hz, 1H), 7.34 (dd, J=9.4, 2.9 Hz, 1H), 6.71 (d, J=5.3 Hz, 1H), 5.96 (m, 2H), 4.75 (dd, J=2.9, 1.2 Hz, 2H), 3.95 (s, 3H), 3.04 (m, 1H), 2.79 (m, 1H), 2.54 (dd, J=4.7, 2.6 Hz, 1H), 2.42 (m, 2H).

108.iv. (E)-(R)-1-(2,3-dihydro-benzo[1,4]dioxin-6-ylamino)-6-(6-methoxy-quinolin-4-yloxy)-hex-4-en-2-ol The title amino alcohol was obtained starting from intermediate 108.iii (0.115 g, 0.424 mmol) and 2,3-dihydro-benzo[1,4]dioxin-6-ylamine (0.064 g, 1 eq.) and following method A. The compound was isolated as a colourless oil (0.088 g, 49% yield).
MS (ESI, m/z): 423.3 [M+H$^+$].

108.v. (R)-3-(2,3-dihydro-benzo[1,4]dioxin-6-yl)-5-[(E)-4-(6-methoxy-quinolin-4-yloxy)-but-2-enyl]-oxazolidin-2-one The title compound was obtained starting from intermediate 108.iv (0.088 g, 0.2 mmol) and following method B. The compound was isolated after purification on prep. TLC (EA/MeOH 19:1) as a beige foam (0.03 g, 32% yield).
$^1$H NMR (CDCl$_3$) δ: 8.59 (m, 1H), 7.93 (d, J=9.1 Hz, 1H), 7.45 (d, J=2.9 Hz, 1H), 7.34 (dd, J=9.1, 2.9 Hz, 1H), 7.04 (d, J=2.6 Hz, 1H), 6.96 (m, 1H), 6.82 (m, 1H), 6.69 (m, 1H), 5.99 (m, 2H), 4.73 (m, 3H), 4.23 (s, 4H), 4.02 (t, J=8.5 Hz, 1H), 3.93 (m, 3H), 3.65 (dd, J=8.8, 6.4 Hz, 1H), 2.64 (t, J=5.9 Hz, 2H).
MS (ESI, m/z): 449.2 [M+H$^+$].

Example 109 rac-3-(2,3-dihydro-benzo[1,4]dioxin-6-yl)-5-[4-(6-methoxy-quinolin-4-yloxy)-butyl]-oxazolidin-2-one 109.i. Rac-5-[4-(tert-butyl-dimethyl-silanyloxy)-butyl]-3-(2,3-dihydro-benzo[1,4]dioxin-6-yl)-oxazolidin-2-one A solution of (2,3-dihydro-benzo[1,4]dioxin-6-yl)-carbamic acid benzyl ester (0.75 g, 2.6 mmol) and rac-tert-butyl-dimethyl-(4-oxiranyl-butoxy)-silane (prepared according to *Angew. Chem.* (2007), 46, 5896; 0.91 g, 1.5 eq.) in DMF (8 mL) at 0° C. was treated with a 2.2M solution of t-BuOLi in THF (3.6 mL, 3 eq.). The mixture was stirred at rt for 22 h. HCl 1M (5.3 mL) was added and the mixture partitioned between EA and water. The org. phase was washed with water and brine, dried over MgSO$_4$ and concentrated. The product was purified by FC (Hex/EA 1:1, 1:2) to give the title intermediate as a yellowish oil (0.87 g, 81% yield).
MS (ESI, m/z): 408.7 [M+H$^+$].

109.ii. rac-3-(2,3-dihydro-benzo[1,4]dioxin-6-yl)-5-(4-hydroxy-butyl)-oxazolidin-2-one A solution of intermediate 109.i (0.87 g, 2.1 mmol) in THF (4 mL) was treated with a 1M solution of TBAF in THF (2.1 mL). The mixture was stirred at rt for 5 h, partitioned between water and EA, The org. phase was washed with water and brine, dried over MgSO$_4$ and concentrated. The residue was purified by FC (Hex/EA 1:1, EA) to give the title alcohol as a colourless oil (0.29 g, 46%).
$^1$H NMR (CDCl$_3$) δ: 7.06 (d, J=2.6 Hz, 1H), 6.99 (m, 1H), 6.84 (m, 1H), 4.61 (m, 1H), 4.24 (m, 4H), 4.01 (t, J=8.5 Hz, 1H), 3.67 (m, 2H), 3.59 (dd, J=8.8, 7.3 Hz, 1H), 1.69 (m, 6H).

109.iii. Rac-3-(2,3-dihydro-benzo[1,4]dioxin-6-yl)-5-[4-(6-methoxy-quinolin-4-yloxy)-butyl]-oxazolidin-2-one A solution of intermediate 109.ii (0.29 g, 0.98 mmol) and 6-methoxy-quinolin-4-ol (0.216 g, 1 eq.) in THF (4 mL) was treated with PPh$_3$ (313 mg, 1.2 eq.) and dropwise with DIAD (0.25 mL, 1.2 eq.). The mixture was stirred at rt for 3 days, concentrated in vacuo and purified by FC (EA, EA/MeOH 9:1+1% NH$_4$OH) to give the product as a yellowish foam (0.3 g, 70% yield).
$^1$H NMR (CDCl$_3$) δ: 8.61 (d, J=5.3 Hz, 1H), 7.94 (d, J=9.4 Hz, 1H), 7.44 (d, J=2.9 Hz, 1H), 7.35 (dd, J=9.4, 2.9 Hz, 1H), 7.06 (s, 1H), 6.98 (m, 1H), 6.84 (m, 1H), 6.70 (d, J=5.3 Hz, 1H), 4.24 (m, 6H), 4.04 (t, J=8.5 Hz, 1H), 3.94 (s, 3H), 3.61 (dd, J=8.8, 7.0 Hz, 1H), 2.05 (m, 6H).
MS (ESI, m/z): 451.3 [M+H$^+$].

Example 110 rac-3-[3-(2,3-dihydro-benzo[1,4]dioxin-6-yl)-2-oxo-oxazolidin-5-yl]-N-(3-methoxy-quinoxalin-5-ylmethyl)-N-methyl-propionamide

110.i. (3-methoxy-quinoxalin-5-ylmethyl)-methyl-amine

Methylamine (2M in THF, 5 mL) and 3-methoxy-quinoxaline-5-carbaldehyde (0.94 g, 5 mmol, prepared according to WO 2006/021448) were coupled according to method K. The title amine was isolated as a yellowish solid (0.52 g, 51% yield).
$^1$H NMR (CDCl$_3$) δ: 8.49 (d, J=0.6 Hz, 1H), 7.93 (d, J=8.2 Hz, 1H), 7.63 (m, 1H), 7.51 (m, 1H), 4.24 (s, 2H), 4.10 (s, 3H), 2.46 (d, J=0.9 Hz, 3H).
MS (ESI, m/z): 204.3 [M+H$^+$].

110.ii. Pent-4-enoic acid (3-methoxy-quinoxalin-5-ylmethyl)-methyl-amide

Intermediate 110.i (0.867 g, 4.2 mmol) and 4-pentenoic acid (0.427 g, 1 eq.) were coupled according to method H. The title amide was isolated as an orange oil (1.18 g, 97% yield).
$^1$H NMR (CDCl$_3$) δ: 8.51 (d, J=10.8 Hz, 1H), 7.96 (m, 1H), 7.56 (m, 2H), 5.87 (m, 1H), 5.03 (m, 4H), 4.11 (m, 3H), 3.04 (s, 3H), 2.48 (m, 4H) (rotamers).

110.iii. Rac-4,5-dihydroxy-pentanoic acid (3-methoxy-quinoxalin-5-ylmethyl)-methyl-amide Intermediate 110.ii (1.18 g, 4.1 mmol) was dihydroxylated according to method L. The title diol was isolated after FC (EA/MeOH 9:1) as a colourless oil (1.17 g, 89% yield).
$^1$H NMR (CDCl$_3$) δ: 8.52 (d, J=10.8 Hz, 1H), 7.97 (m, 1H), 7.56 (m, 2H), 7.42 (dd, J=7.0, 0.9 Hz, 1H), 5.15 (m, 3H), 4.11 (m, 3H), 3.59 (m, 3H), 3.06 (m, 3H), 2.65 (m, 2H), 1.89 (m, 2H) (rotamers).

110.iv. Rac-toluene-4-sulfonic acid 2-hydroxy-4-[(3-methoxy-quinoxalin-5-ylmethyl)-methyl-carbamoyl]-butyl ester A solution of intermediate 110.iii (1.17 g, 3.7 mmol) in DCM (10 mL) was cooled to 0° C. and Pyr (0.59 mL, 2 eq.) was added. A solution of TsCl (0.733 g, 1.05 eq.) in DCM was then added dropwise and the mixture stirred at 0° C. for 1 h and at rt for 24 h. The mixture was diluted with DCM and washed with water. The org. phase was dried over MgSO$_4$ and concentrated. The product was isolated after FC (Hex/EA 1:1, EA, EA/MeOH 9:1) as a colourless oil (0.5 g, 29% yield).
MS (ESI, m/z): 474.0 [M+H$^+$].

110.v. Rac-3-[3-(2,3-dihydro-benzo[1,4]dioxin-6-yl)-2-oxo-oxazolidin-5-yl]-N-(3-methoxy-quinoxalin-5-ylmethyl)-N-methyl-propionamide A solution of intermediate 110.iv (0.24 g, 0.5 mmol) and (2,3-dihydro-benzo[1,4]dioxin-6-yl)-carbamic acid benzyl ester (0.143 g, 1 eq.) in DMF (3 mL) was treated with a 2.2M solution of t-BuOLi in THF (0.68 mL, 3 eq.). The mixture was stirred at rt for 30 h, then partitioned between EA and water. The org. phase was washed with water and brine, dried over MgSO$_4$ and concentrated. The residue was purified by FC (Hept/EA 1:1, EA) to give the title compound as a colourless foam (0.1 g, 42% yield).
MS (ESI, m/z): 479.0 [M+H$^+$].

Example 111

(R*)-3-(2,3-dihydro-benzo[1,4]dioxin-6-yl)-5-[(R*)-1-hydroxy-5-(6-methoxy-[1,5]naphthyridin-4-yl)-pentyl]-oxazolidin-2-one

111.i. 5-(6-methoxy-[1,5]naphthyridin-4-yl)-pentanal

This intermediate was prepared starting from 8-bromo-2-methoxy-[1,5]naphthyridine (2 g, 8.3 mmol) and 4-pentyn-1-ol (1 mL, 1.3 eq.) and following the procedures of Example 29 step 29.i and Example 33, steps 33.i and 33.ii. The title aldehyde was isolated as a yellow oil (1.1 g, 50% yield over 3 steps).
$^1$H NMR (CDCl$_3$) δ: 9.77 (t, J=1.5 Hz, 1H), 8.66 (d, J=4.4 Hz, 1H), 8.18 (d, J=9.1 Hz, 1H), 7.36 (d, J=4.7 Hz, 1H), 7.11 (d, J=8.8 Hz, 1H), 4.07 (s, 3H), 3.18 (d, J=7.6 Hz, 2H), 2.52 (dd, J=7.3, 1.8 Hz, 2H), 1.8 (m, 4H).

111.ii. Rac-7-(6-methoxy-[1,5]naphthyridin-4-yl)-hept-1-en-3-ol

A solution of intermediate 111.i (1.1 g, 4.5 mmol) in dry THF (50 mL) was cooled to −78° C. and vinylmagnesium chloride solution (1.7M in THF, 3.17 mL, 1.2 eq.) was added dropwise. The mixture was allowed to warm to rt and stirred at this temperature overnight. Water and EA was added and the phases separated. The org. phase was washed with water and a NH$_4$Cl solution, dried over MgSO$_4$ and concentrated. The residue was purified by FC (Hex/EA 1:1, EA) to give the title allylic alcohol as a colourless oil (0.22 g, 18% yield).

$^1$H NMR (CDCl$_3$) δ: 8.65 (d, J=4.4 Hz, 1H), 8.18 (m, 1H), 7.36 (d, J=4.4 Hz, 1H), 7.10 (d, J=8.8 Hz, 1H), 5.86 (m, 1H), 5.21 (m, 1H), 5.10 (dt, J=11.1, 1.8 Hz, 1H), 4.09 (m, 4H), 3.18 (m, 2H), 1.83 (m, 3H), 1.57 (m, 4H).

111.iii. (2S*,3R*)-7-(6-methoxy-[1,5]naphthyridin-4-yl)-heptane-1,2,3-triol

Intermediate 111.ii (0.43 g, 1.58 mmol) was dihydroxylated according to method L and the desired triol was isolated as a colourless oil (0.29 g, 60% yield) after FC (Hept/EA 1:1, EA/MeOH 9:1).

MS (ESI, m/z): 307.4 [M+H$^+$].

111.iv. Toluene-4-sulfonic acid (2S*,3R*)-2,3-dihydroxy-7-(6-methoxy-[1,5]naphthyridin-4-yl)-heptyl ester Intermediate 111.iii (0.29 g, 0.95 mmol) was transformed into the desired tosylate using a procedure analog to that of Example 110, step 110.iv. The product was isolated as a colourless oil (0.24 g, 55% yield).

MS (ESI, m/z): 461.1 [M+H$^+$].

111.v. (R*)-5-(6-methoxy-[1,5]naphthyridin-4-yl)-1-(S*)-oxiranyl-pentan-1-ol

A solution of intermediate 111.iv (0.24 g, 0.52 mmol) in THF (5 mL) was treated with aq. NaOH solution (2N, 0.5 mL). The mixture was vigorously stirred at rt for 2.5 h, diluted with EA and water and the phases separated. The org. phase was dried over MgSO$_4$ and concentrated. The title epoxide was isolated as a yellowish oil (0.08 g, 53% yield).

$^1$H NMR (CDCl$_3$) δ: 8.65 (d, J=4.7 Hz, 1H), 8.18 (d, J=9.1 Hz, 1H), 7.37 (dd, J=4.4, 0.6 Hz, 1H), 7.10 (d, J=9.1 Hz, 1H), 4.07 (s, 3H), 3.19 (t, J=7.3 Hz, 2H), 2.98 (m, 1H), 2.80 (m, 1H), 2.71 (m, 1H), 1.82 (m, 3H), 1.62 (m, 3H).

111.vi. (R*)-3-(2,3-dihydro-benzo[1,4]dioxin-6-yl)-5-[(R*)-1-hydroxy-5-(6-methoxy-[1,5]naphthyridin-4-yl)-pentyl]-oxazolidin-2-one A solution of intermediate 111.v (0.08 g, 0.28 mmol) and (2,3-dihydro-benzo[1,4]dioxin-6-yl)-carbamic acid benzyl ester (0.08 g, 1 eq.) in DMF (1 mL) was treated with a 2.2M solution of t-BuOLi in THF (0.47 mL, 3 eq.). The mixture was stirred at rt for 30 h, partitioned between EA and water. The org. phase was washed with water and brine, dried over MgSO$_4$ and concentrated. The residue was purified by FC (Hept/EA 1:1, EA/MeOH 9:1) to give the title compound as a colourless foam (0.027 g, 21% yield).

$^1$H NMR (CDCl$_3$) δ: 8.66 (d, J=4.4 Hz, 1H), 8.20 (d, J=9.1 Hz, 1H), 7.37 (d, J=4.4 Hz, 1H), 7.11 (d, J=9.1 Hz, 1H), 7.07 (m, 2H), 6.98 (m, 1H), 6.84 (m, 1H), 4.48 (m, 1H), 4.23 (m, 4H), 4.07 (m, 3H), 3.96 (m, 1H), 3.87 (m, 1H), 3.20 (t, J=7.3 Hz, 2H), 1.86 (m, 2H), 1.61 (m, 4H).

MS (ESI, m/z): 466.2 [M+H$^+$].

Example 112

(R)-3-(2,3-dihydro-benzo[1,4]dioxin-6-yl)-5-{[4-(6-methoxy-[1,5]naphthyridin-4-yl)-butylamino]-methyl}-oxazolidin-2-one Intermediate 111.i (0.1 g, 0.434 mmol) and intermediate 3.i (0.11 g, 1 eq.) were coupled according to method J. The title compound was isolated after FC (EA/MeOH 9:1+1% NH$_4$OH) as a colourless foam (0.08 g, 40% yield).

$^1$H NMR (DMSO d6) δ: 8.65 (d, J=4.4 Hz, 1H), 8.18 (d, J=9.1 Hz, 1H), 7.35 (d, J=4.4 Hz, 1H), 7.09 (m, 2H), 6.99 (dd, J=8.8, 2.6 Hz, 1H), 6.83 (d, J=8.8 Hz, 1H), 4.70 (d, J=2.1 Hz, 1H), 4.23 (m, 5H), 4.05 (m, 4H), 3.77 (dd, J=8.8, 7.0 Hz, 1H), 3.18 (t, J=7.3 Hz, 3H), 2.90 (m, 2H), 2.71 (m, 2H), 1.84 (m, 2H), 1.59 (m, 2H).

MS (ESI, m/z): 465.3 [M+H$^+$].

Example 113

6-((R)-5-{[4-(6-methoxy-[1,5]naphthyridin-4-yl)-butylamino]-methyl}-2-oxo-oxazolidin-3-yl)-4H-benzo[1,4]thiazin-3-one Intermediate 111.i (0.08 g, 0.35 mmol) and intermediate 4.v (0.097 g, 1 eq.) were coupled according to method J. The title compound was isolated after FC (EA/MeOH 9:1+1% NH$_4$OH) and crystallization from EA/ether as a colourless solid (0.022 g, 13% yield).

MS (ESI, m/z): 494.2 [M+H$^+$].

Example 114

(RS)-3-(2,3-dihydro-benzo[1,4]dioxin-6-yl)-5-[(RS)-3-hydroxy-5-(6-methoxy-[1,5]naphthyridin-4-yl)-pentyl]-oxazolidin-2-one 114.i. 5-(tert-butyl-dimethyl-silanyloxy)-1-(2,3-dihydro-benzo[1,4]dioxin-6-ylamino)-pentan-2-ol Tert-butyl-dimethyl-(3-oxiranyl-propoxy)-silane (prepared according to Org. Lett. (2005), 7, 4427; 1.6 g, 7.4 mmol) and 2,3-dihydro-benzo[1,4]dioxin-6-ylamine (1.35 g, 8.87 mmol) were coupled according to method A. The title amino alcohol was isolated after FC (Hex/EA 4:1) as a yellow oil (2.1 g, 79% yield).

$^1$H NMR (DMSO d6) δ: 6.54 (d, J=8.8 Hz, 1H), 6.07 (m, 2H), 4.95 (m, 1H), 4.56 (d, J=5.0 Hz, 1H), 4.10 (m, 4H), 3.56 (m, 3H), 2.83 (m, 2H), 1.51 (m, 4H), 1.26 (m, 4H), 0.84 (s, 9H), 0.00 (s, 6H).

114.ii. Rac-5-[3-(tert-butyl-dimethyl-silanyloxy)-propyl]-3-(2,3-dihydro-benzo[1,4]dioxin-6-yl)-oxazolidin-2-one Starting from intermediate 114.i (2.16 g, 5.87 mmol) and following method B, the title intermediate was obtained after FC (Hex/EA 2:1) as a yellowish solid (1.77 g, 77% yield).

$^1$H NMR (CDCl$_3$) δ: 7.07 (d, J=2.6 Hz, 1H), 6.99 (m, 1H), 6.84 (m, 1H), 4.65 (m, 1H), 4.24 (m, 4H), 4.02 (t, J=8.5 Hz, 1H), 3.64 (m, 3H), 1.77 (m, 4H), 0.89 (m, 9H), 0.06 (m, 6H).

114.iii. Rac-3-(2,3-dihydro-benzo[1,4]dioxin-6-yl)-5-(3-hydroxy-propyl)-oxazolidin-2-one A solution of intermediate 114.ii (1.77 g, 4.5 mmol) in THF was treated with a 1M solution of TBAF in THF (5.4 mL, 1.2 eq.). The mixture was stirred at rt for 2 h, diluted with EA and washed with water and brine. The org. layer was dried over MgSO₄ and concentrated. The title intermediate was obtained after FC (Hex/EA 4:1, EA) as a colourless oil (0.98 g, 78% yield).

¹H NMR (CDCl₃) δ: 7.06 (d, J=2.6 Hz, 1H), 6.98 (m, 1H), 6.84 (m, 1H), 4.67 (m, 1H), 4.24 (m, 4H), 4.03 (t, J=8.5 Hz, 1H), 3.74 (m, 2H), 3.60 (dd, J=8.5, 7.0 Hz, 1H), 1.82 (m, 4H).

114.iv. Rac-3-[3-(2,3-dihydro-benzo[1,4]dioxin-6-yl)-2-oxo-oxazolidin-5-yl]-propionaldehyde A solution of intermediate 114.iii (0.98 g, 3.5 mmol) in DCM at 0° C. was treated sequentially with DIPEA (3.6 mL, 21 mmol) and a solution of Pyr.SO₃ complex (1.1 g, 2 eq.) in DMSO (4.2 mL). The mixture was stirred at 0° C. for 2 h. Water was added and the mixture extracted with DCM. The combined org. phases were washed with water and brine, dried over MgSO₄ and concentrated. The title intermediate was isolated after FC (Hex/EA 1:1) as a colourless oil (0.89 g, 92% yield).

¹H NMR (CDCl₃) δ: 9.84 (s, 1H), 7.06 (d, J=2.6 Hz, 1H), 6.97 (m, 1H), 6.85 (m, 1H), 4.66 (m, 1H), 4.25 (m, 4H), 4.06 (m, 1H), 3.60 (dd, J=8.8, 6.7 Hz, 1H), 2.77 (m, 2H), 2.15 (m, 1H), 2.02 (m, 1H).

114.v. (RS)-3-(2,3-dihydro-benzo[1,4]dioxin-6-yl)-5-((RS)-3-hydroxy-5-trimethylsilanyl-pent-4-ynyl)-oxazolidin-2-one In a flame-dried 2-necked flask (25 mL) a solution of TMS acetylene (0.56 mL, 3.8 mmol) in dry THF (10 mL) was cooled to −78° C. At this temperature n-BuLi (2.5M in hexanes, 1.4 mL) was added dropwise. The mixture was stirred at −78° C. for 15 min before the dropwise addition of a solution of intermediate 114.iv (0.89 g, 3.2 mmol) in THF (5 mL). The mixture was stirred at −78° C. for 1 h, quenched by addition of a sat. NH₄Cl solution and partitioned between water and EA. The org. phase was washed with brine, dried over MgSO₄ and concentrated. The title intermediate was isolated after FC (Hept/EA 1:1, EA) as a colourless oil (0.76 g, 63% yield).

¹H NMR (CDCl₃) δ: 7.07 (dd, J=2.6, 0.9 Hz, 1H), 6.99 (m, 1H), 6.85 (m, 1H), 4.67 (m, 1H), 4.47 (m, 1H), 4.24 (m, 4H), 4.04 (t, J=8.8 Hz, 1H), 3.61 (ddd, J=9.7, 7.0, 2.6 Hz, 1H), 1.93 (m, 4H), 0.16 (m, 9H).

114.vi. (RS)-3-(2,3-dihydro-benzo[1,4]dioxin-6-yl)-5-((RS)-3-hydroxy-pent-4-ynyl)-oxazolidin-2-one K₂CO₃ (0.28 g, 1 eq.) was added to a solution of intermediate 114.v (0.76 g, 2.02 mmol) in MeOH (20 mL) at rt. The mixture was stirred for 30 min and then concentrated in vacuo. The residue was taken up in EA and washed with water and brine, dried over MgSO₄ and concentrated. The intermediate was isolated as a colourless oil (0.59 g, 97% yield) which was used as such in the next step.

¹H NMR (CDCl₃) δ:7.06 (d, J=2.6 Hz, 1H), 6.99 (m, 1H), 6.85 (m, 1H), 4.67 (m, 1H), 4.50 (m, 1H), 4.24 (m, 4H), 4.05 (m, 1H), 3.62 (m, 1H), 2.50 (d, J=1.2 Hz, 1H), 1.95 (m, 4H).

114.vii. (RS)-3-(2,3-dihydro-benzo[1,4]dioxin-6-yl)-5-[(RS)-3-hydroxy-5-(6-methoxy-[1,5]naphthyridin-4-yl)-pent-4-ynyl]-oxazolidin-2-one Intermediate 114.vi (0.59 g, 1.9 mmol) was coupled with 8-bromo-2-methoxy-[1,5]naphthyridine (0.51 g, 2.1 mmol) following the procedure of Example 29, step 29.i. The title intermediate was isolated after FC (Hept/EA 1:1, EA, EA/MeOH 9:1) as a beige foam (0.67 g, 75% yield).

¹H NMR (DMSO d6) δ: 8.73 (d, J=4.4 Hz, 1H) 8.26 (d, J=9.1 Hz, 1H), 7.71 (d, J=4.7 Hz, 1H), 7.29 (d, J=9.1 Hz, 1H), 7.09 (m, 1H), 6.96 (m, 1H), 6.83 (m, 1H), 5.73 (m, 1H), 4.70 (m, 2H), 4.20 (m, 4H), 4.08 (m, 1H), 4.00 (s, 3H), 3.67 (dd, J=9.4, 7.3 Hz, 1H), 1.95 (m, 4H).

MS (ESI, m/z): 462.0 [M+H⁺].

114.viii. (RS)-3-(2,3-dihydro-benzo[1,4]dioxin-6-yl)-5-[(RS)-3-hydroxy-5-(6-methoxy-[1,5]naphthyridin-4-yl)-pentyl]-oxazolidin-2-one The title compound was obtained starting from intermediate 114.vii (0.65 g, 1.4 mmol) following the procedure of Example 33, step 33.i and isolated after FC (EA, EA/MeOH 9:1) as a colourless foam (0.54 g, 82% yield).

¹H NMR (DMSO d6) δ: 8.65 (d, J=4.7 Hz, 1H), 8.22 (d, J=9.1 Hz, 1H), 7.53 (d, J=4.4 Hz, 1H), 7.22 (d, J=9.1 Hz, 1H), 7.09 (d, J=2.6 Hz, 1H), 6.95 (dd, J=8.8, 2.6 Hz, 1H), 6.83 (m, 1H), 4.62 (dd, J=5.3, 2.1 Hz, 2H), 4.21 (m, 4H), 4.03 (m, 5H), 3.58 (m, 2H), 3.19 (m, 2H), 1.65 (m, 4H).

MS (ESI, m/z): 329.8 [M+H⁺].

Example 115 rac-3-(2,3-dihydro-benzo[1,4]dioxin-6-yl)-5-[5-(6-methoxy-[1,5]naphthyridin-4-yl)-3-oxo-pentyl]-oxazolidin-2-one A solution of the compound of Example 114 (0.07 g, 0.15 mmol) in DCM (2 mL) was treated with a 15% solution of Dess Martin periodinane (0.4 mL, 1 eq.). The mixture was stirred at rt for 2 h, diluted with DCM and washed with a sat. NaHCO₃ solution. The org. phase was concentrated and purified by FC (EA, EA/MeOH 9:1) to give the title compound as a yellowish glue (0.061 g, 88% yield).

¹H NMR (DMSO d6) δ: 8.65 (d, J=4.1 Hz, 1H), 8.23 (m, 1H), 7.52 (d, J=4.1 Hz, 2H), 7.23 (m, 1H), 7.07 (d, J=2.3 Hz, 1H), 6.94 (m, 1H), 6.83 (m, 1H), 4.59 (m, 1H), 4.19 (m, 4H), 4.02 (m, 4H), 3.63 (m, 1H), 3.31 (m, 1H), 2.99 (m, 2H), 2.64 (m, 2H), 1.90 (m, 2H).

MS (ESI, m/z): 464.2 [M+H⁺].

Example 116

(RS)-5-[(RS)-3-amino-5-(6-methoxy-[1,5]naphthyridin-4-yl)-pentyl]-3-(2,3-dihydro-benzo[1,4]dioxin-6-yl)-oxazolidin-2-one 116.i. (RS)-5-[(RS)-3-azido-5-(6-methoxy-[1,5]naphthyridin-4-yl)-pentyl]-3-(2,3-dihydro-benzo[1,4]dioxin-6-yl)-oxazolidin-2-one A solution of the compound of Example 114 (0.5 g, 1.07 mmol) and PPh₃ (0.338 g, 1.2 eq.) in THF at −10° C. (10 mL) was treated with DPPA (0.279 mL, 1.2 eq.) and DIAD (0.277 mL, 1.3 eq) and the temperature slowly raised to rt over 2 h. The mixture was partitioned between EA and a sat. NaHCO₃ solution. The org. phase was washed with water and brine, dried over MgSO₄ and concentrated. The residue was purified by FC (Hex/EA 1:1, EA, EA/MeOH) to give the desired azide (0.628 g, contaminated with PPh₃O) which was used in the next step without further purification.

MS (ESI, m/z): 491.1 [M+H⁺].

116.ii. (RS)-5-[(RS)-3-amino-5-(6-methoxy-[1,5]naphthyridin-4-yl)-pentyl]-3-(2,3-dihydro-benzo[1,4]dioxin-6-yl)-oxazolidin-2-one A solution of intermediate 116.i (0.62 g, 0.6 mmol) in THF/MeOH 1:1 (20 mL) was hydrogenated over Pd/C (10%, 0.1 g) and 1 bar of $H_2$ for 2 h. The catalyst was filtered off over Celite and the filtrate concentrated in vacuo. The residue was purified by FC (EA, EA/MeOH 9:1+1% $NH_4OH$) to give the title compound as a colourless foam (0.22 g, 75%).

$^1$H NMR (CDCl$_3$) δ: 8.67 (d, J=4.4 Hz, 1H), 8.19 (d, J=9.1 Hz, 1H), 7.39 (d, J=4.7 Hz, 1H), 7.12 (d, J=9.1 Hz, 1H), 7.04 (d, J=2.6 Hz, 1H), 6.97 (m, 1H), 6.84 (m, 1H), 4.61 (d, J=7.3 Hz, 1H), 4.24 (m, 4H), 4.07 (s, 3H), 4.00 (t, J=8.8 Hz, 1H), 3.58 (m, 1H), 3.26 (m, 2H), 2.78 (d, J=2.9 Hz, 1H), 1.86 (m, 6H).

MS (ESI, m/z): 465.4 [M+H$^+$].

Example 117

(RS)-N-[(RS)-1-{2-[3-(2,3-dihydro-benzo[1,4]dioxin-6-yl)-2-oxo-oxazolidin-5-yl]-ethyl}-3-(6-methoxy-[1,5]naphthyridin-4-yl)-propyl]-methanesulfonamide A solution of the compound of Example 116 (0.05 g, 0.1 mmol) in DCM (2 mL) at rt was treated sequentially with TEA (0.03 mL, 2 eq.) and MsCl (0.013 mL, 1.5 eq.). The mixture was stirred at rt for 2 h, washed with water and purified by FC (EA, EA/MeOH 9:1) to give the title compound as a colourless foam (0.052 g, 89% yield).

$^1$H NMR (DMSO d6) δ: 8.66 (d, J=4.4 Hz, 1H), 8.22 (d, J=9.1 Hz, 1H), 7.55 (d, J=4.4 Hz, 1H), 7.23 (d, J=9.1 Hz, 1H), 7.16 (d, J=7.9 Hz, 1H), 7.09 (d, J=2.6 Hz, 1H), 6.96 (m, 1H), 6.84 (m, 1H), 4.65 (m, 1H), 4.21 (m, 4H), 4.03 (m, 4H), 3.65 (dd, J=9.1, 7.0 Hz, 1H), 3.39 (m, 1H), 3.18 (m, 2H), 2.92 (s, 3H), 1.86 (m, 6H).

MS (ESI, m/z): 543.3 [M+H$^+$].

Example 118

N-[(RS)-1-{2-[(RS)-3-(2,3-dihydro-benzo[1,4]dioxin-6-yl)-2-oxo-oxazolidin-5-yl]ethyl}-3-(6-methoxy-[1,5]naphthyridin-4-yl)-propyl]-acetamide A solution of the compound of Example 116 (0.05 g, 0.1 mmol) in DCM (1 mL) at rt was treated sequentially with TEA (0.03 mL, 2 eq.) and AcCl (1.5 eq.). The mixture was stirred at rt for 1 h, washed with water (2 mL) and purified by FC (EA, EA/MeOH 9:1) to give the title compound as a colourless foam (0.048 g, 88% yield).

$^1$H NMR (DMSO d6) δ: 8.64 (dd, J=4.4, 0.6 Hz, 1H), 8.22 (dd, J=9.1, 0.6 Hz, 1H), 7.72 (m, 1H), 7.52 (dd, J=4.4, 1.2 Hz, 1H), 7.22 (dd, J=8.8, 0.6 Hz, 1H), 7.08 (d, J=2.3 Hz, 1H), 6.95 (dd, J=8.8, 2.6 Hz, 1H), 6.83 (m, 1H), 4.60 (m, 1H), 4.20 (m, 4H), 4.02 (m, 4H), 3.83 (m, 1H), 3.61 (m, 1H), 3.09 (m, 2H), 1.81 (s, 3H), 1.86 (m, 6H).

MS (ESI, m/z): 507.2 [M+H$^+$].

Example 119 rac-3-(2,3-dihydro-benzo[1,4]dioxin-6-yl)-5-[3-(7-fluoro-2-methoxy-quinolin-8-ylmethoxy)-propyl]-oxazolidin-2-one A solution of intermediate 114.iii (0.135 g, 0.5 mmol) and 8-bromomethyl-7-fluoro-2-methoxy-quinoline (prepared according to WO 2007/081597; 0.14 g, 0.5 mmol) in DMF (3 mL) was treated with NaH dispersion (55% in mineral oil, 24 mg, 1.1 eq.). The mixture was stirred at rt for 2 h, partitioned between water and EA. Org. phase washed with water and brine, dried over MgSO$_4$ and concentrated. The residue was purified by FC (hept/EA 2:1, 1:1) to give the title compound as a yellowish oil (0.115 g, 49% yield).

$^1$H NMR (DMSO d6) δ:8.25 (d, J=9.1 Hz, 1H), 7.93 (dd, J=9.1, 6.7 Hz, 1H), 7.33 (t, J=9.1 Hz, 1H), 7.05 (d, J=2.6 Hz, 1H), 6.99 (d, J=8.8 Hz, 1H), 6.90 (m, 1H), 6.81 (m, 1H), 5.01 (d, J=1.8 Hz, 2H), 4.59 (m, 1H), 4.19 (m, 4H), 3.98 (m, 4H), 3.57 (m, 3H), 1.66 (m, 4H).

MS (ESI, m/z): 468.9 [M+H$^+$].

Example 120 rac-3-(2,3-dihydro-benzo[1,4]dioxin-6-yl)-5-[3-(6-methoxy-quinolin-4-ylmethoxy)-propyl]-oxazolidin-2-one A solution of intermediate 114.iii (0.135 g, 0.5 mmol) and 4-bromomethyl-6-methoxyquinoline (prepared according to WO 2006/093253; 0.14 g, 0.5 mmol) in DMF (3 mL) was treated with a NaH dispersion (55%, 24 mg, 1.1 eq.). The mixture was stirred at rt for 2 h, partitioned between water and EA. The org. phase was washed with water and brine, dried over MgSO$_4$ and concentrated. The residue was purified by FC (Hept/EA 2:1, 1:1) to give the title compound as a yellowish oil (0.051 g, 23% yield).

$^1$H NMR (DMSO d6) δ: 8.69 (m, 1H), 7.93 (d, J=9.4 Hz, 1H), 7.47 (d, J=4.4 Hz, 1H), 7.39 (dd, J=9.4, 2.9 Hz, 1H), 7.30 (d, J=2.6 Hz, 1H), 7.08 (d, J=2.6 Hz, 1H), 6.94 (m, 1H), 6.83 (m, 1H), 4.95 (s, 2H), 4.66 (m, 1H), 4.20 (m, 4H), 4.02 (m, 1H), 3.89 (s, 3H), 3.63 (m, 3H), 1.76 (m, 4H).

MS (ESI, m/z): 451.2 [M+H$^+$].

Example 121 rac-3-(2,3-dihydro-benzo[1,4]dioxin-6-yl)-5-[3-(6-methoxy-quinazolin-4-yloxy)-propyl]-oxazolidin-2-one A solution of intermediate 114.iii (0.135 g, 0.5 mmol) and 4-chloro-6-methoxy-quinazoline (0.097 g, 0.5 mmol) in DMF (3 mL) was treated with a NaH dispersion (55%, 24 mg, 1.1 eq.). The mixture was stirred at rt for 2 h, partitioned between water and EA. The org. phase was washed with water and brine, dried over MgSO$_4$ and concentrated. The residue was purified by FC (Hept/EA 2:1, 1:1) to give the title compound as a yellowish oil (0.14 g, 64% yield).

$^1$H NMR (DMSO d6) δ: 8.65 (s, 1H), 7.83 (d, J=9.1 Hz, 1H), 7.56 (dd, J=9.1, 2.6 Hz, 1H), 7.40 (d, J=2.9 Hz, 1H), 7.09 (d, J=2.6 Hz, 1H), 6.95 (m, 1H), 6.83 (m, 1H), 4.74 (m, 1H), 4.60 (m, 2H), 4.20 (m, 4H), 4.09 (t, J=8.8 Hz, 1H), 3.89 (m, 3H), 3.69 (dd, J=9.1, 7.0 Hz, 1H), 1.95 (m, 4H).

MS (ESI, m/z): 438.2 [M+H$^+$].

Example 122

6-{(RS)-5-[(RS)-3-hydroxy-5-(6-methoxy-[1,5]naphthyridin-4-yl)-pentyl]-2-oxo-oxazolidin-3-yl}-4H-benzo[1,4]thiazin-3-one

122.i. Rac-1-(6-methoxy-[1,5]naphthyridin-4-yl)-hept-6-en-3-ol

A solution of intermediate 33.ii (1.55 g, 7.17 mmol) in dry THF (60 mL) was cooled to −75° C. and a solution of 3-butenylmagnesium bromide (0.5M in THF, 14.3 mL, 1 eq.) was added dropwise. The mixture was stirred at −75° C. for 3 h and quenched by addition of water. The mixture was extracted with EA and the org. extracts washed with brine, dried over MgSO$_4$ and concentrated. The residue was purified by FC (Hex/EA 1:1, EA) to give the desired product (1.3 g) in a mixture with starting aldehyde.

122.ii. Rac-8-[3-(tert-butyl-dimethyl-silanyloxy)-hept-6-enyl]-2-methoxy-[1,5]naphthyridine A solution of intermediate 122.i (1 g, 3.67 mmol) in THF (20 mL) was treated with imidazole (0.575 g, 2.3 eq.) and TBDMSCl (1.1 g, 2 eq). The mixture was stirred at rt overnight. More imidazole (0.575 g) and TBDMSCl (1.1 g) were added and stirring continued for another 3 h. The precipitate was filtered off and the filtrate concentrated in vacuo. The residue was partitioned between EA and water. The org. phase was dried over MgSO$_4$ and concentrated. The residue was purified by FC (Hex/EA 1:1, EA) to give the desired product as a yellowish oil (1.6 g, 100% yield).
$^1$H NMR (CDCl$_3$) δ: 8.65 (d, J=4.7 Hz, 1H), 8.18 (d, J=9.1 Hz, 1H), 7.37 (d, J=4.7 Hz, 1H), 7.11 (d, J=9.1 Hz, 1H), 5.83 (m, 1H), 4.99 (m, 2H), 4.07 (s, 3H), 3.83 (t, J=5.6 Hz, 1H), 3.29 (m, 1H), 3.12 (m, 1H), 2.14 (m, 2H), 1.92 (m, 2H), 1.67 (m, 2H), 0.90 (s, 9H), 0.06 (s, 6H).

122.iii. (2RS,5RS)-5-(tert-butyl-dimethyl-silanyloxy)-7-(6-methoxy-[1,5]naphthyridin-4-yl)-heptane-1,2-diol (mixture of diastereomers)

Intermediate 122.ii was dihydroxylated according to method L. The title diol was isolated after FC (Hex/EA 1:1, EA) as a colourless oil (0.93 g, 61% yield).
$^1$H NMR (CDCl$_3$) δ: 8.66 (m, 1H), 8.19 (d, J=8.8 Hz, 1H), 7.36 (d, J=4.4 Hz, 1H), 7.11 (d, J=9.1 Hz, 1H), 4.07 (s, 3H), 3.89 (m, 1H), 3.66 (m, 2H), 3.45 (m, 1H), 3.26 (m, 1H), 3.11 (m, 2H), 1.96 (m, 2H), 1.75 (m, 2H), 1.57 (m, 6H), 0.91 (m, 9H), 0.08 (m, 6H).

122.iv. Toluene-4-sulfonic acid (2RS,5RS)-5-(tert-butyl-dimethyl-silanyloxy)-2-hydroxy-7-(6-methoxy-[1,5]naphthyridin-4-yl)-heptyl ester A solution of intermediate 122.iii (0.93 g, 2.2 mmol) was reacted with TsCl in analogy to the procedure of Example 110, step 110.iv. The title tosylate was isolated after FC (Hex/EA 2.1, 1:1) as a colourless oil (0.92 g, 72% yield).
MS (ESI, m/z): 575.3 [M+H$^+$].

122.v. 8-[(RS)-3-(tert-butyl-dimethyl-silanyloxy)-5-(RS)-oxiranyl-pentyl]-2-methoxy-[1,5]naphthyridine Intermediate 122.iv (0.92 g, 2.46 mmol) was transformed into the title epoxide following the procedure of Example 111, step 111.v. The desired intermediate was isolated after FC (Hex/EA 2:1, 1:1) as a colourless oil (0.42 g, 42% yield).
$^1$H NMR (CDCl$_3$) δ: 8.66 (d, J=4.4 Hz, 1H), 8.18 (d, J=9.1 Hz, 1H), 7.36 (d, J=4.7 Hz, 1H), 7.11 (d, J=9.1 Hz, 1H), 4.07 (s, 3H), 3.86 (m, 1H), 3.29 (m, 1H), 3.11 (m, 1H), 2.93 (m, 1H), 2.75 (dd, J=5.0, 4.1 Hz, 1H), 2.46 (dd, J=5.0, 2.6 Hz, 1H), 1.78 (m, 6H), 0.91 (m, 9H), 0.06 (s, 6H).

122.vi. 6-{(RS)-5-[(RS)-3-(tert-butyl-dimethyl-silanyloxy)-5-(6-methoxy-[1,5]naphthyridin-4-yl)-pentyl]-2-oxo-oxazolidin-3-yl}-4H-benzo[1,4]thiazin-3-one The title oxazolidinone (yellow oil; 0.1 g, 31% yield) was obtained starting from intermediate 122.v and (3-oxo-3,4-dihydro-2H-benzo[1,4]thiazin-6-yl)-carbamic acid benzyl ester (prepared according to method C; 0.163 g, 1 eq.) following the procedure of Example 110, step 110.v.
MS (ESI, m/z): 609.2 [M+H$^+$].

122.vii. 6-{(RS)-5-[(RS)-3-hydroxy-5-(6-methoxy-[1,5]naphthyridin-4-yl)-pentyl]-2-oxo-oxazolidin-3-yl}-4H-benzo[1,4]thiazin-3-one A solution of intermediate 122.vi (0.1 g, 0.16 mmol) in THF (1 mL) was treated with a 1M solution of TBAF in THF (0.2 mL, 1.2 eq.). The mixture was stirred at rt overnight. The mixture was partitioned between EA and water and the org. phase was washed with water and brine, dried over MgSO$_4$ and concentrated. The residue was purified by FC (DCM/MeOH 19:1) to give the title compound as a yellowish foam (0.044 g, 57% yield).
MS (ESI, m/z): 495.3 [M+H$^+$].

Example 123

(RS)-3-(2,3-dihydro-benzo[1,4]dioxin-6-yl)-5-[(RS)-2-hydroxy-5-(6-methoxy-[1,5]naphthyridin-4-yl)-pentyl]oxazolidin-2-one The title compound was obtained as a brownish oil (0.016 g) starting from intermediate 111.i (0.54 g, 2.34 mmol) and allyl magnesium bromide following the procedures of Example 122, steps 122.i to 122.vii.
MS (ESI, m/z): 466.2 [M+H$^+$].

Example 124 rac-3-(2,3-dihydro-benzo[1,4]dioxin-6-yl)-5-[5-(6-methoxy-[1,5]naphthyridin-4-yl)-pentyl]-oxazolidin-2-one

124.i. 6-(6-methoxy-[1,5]naphthyridin-4-yl)-hexanal

The title intermediate was obtained starting from 8-bromo-2-methoxy-[1,5]naphthyridine (4 g, 16.7 mmol) and hex-5-yn-1-ol (2.7 g, 1.65 eq.) and following the procedures of Example 29, step 29.i and Example 33, steps 33.i and 33.ii. The title aldehyde was isolated as a yellowish liquid (1.2 g, 42% yield over 3 steps).
$^1$H NMR (DMSO d6) δ: 9.63 (t, J=1.8 Hz, 1H), 8.65 (d, J=4.4 Hz, 1H), 8.21 (d, J=9.1 Hz, 1H), 7.51 (d, J=4.4 Hz, 1H), 7.22 (d, J=9.1 Hz, 1H), 4.00 (s, 3H), 3.10 (m, 2H), 2.41 (td, J=7.3, 1.8 Hz, 2H), 1.73 (m, 2H), 1.58 (m, 2H), 1.35 (m, 2H).
MS (ESI, m/z): 259.3 [M+H$^+$].

124.ii. 8-hept-6-enyl-2-methoxy-[1,5]naphthyridine

Methyltriphenylphosphoniumbromide (1.19 g, 3.3 mmol, 1.25 eq.) was suspended in THF (8 mL). t-BuOK (373 mg, 3.3 mmol, 1.25 eq.) was added in one portion and the yellow suspension was stirred at rt for 1 h. The mixture was cooled to 0° C. and a solution of intermediate 124.i (685 mg, 2.6 mmol) in THF (8 mL) was added dropwise. The ice bath was removed and the mixture stirred at rt for 4 h. Ether (25 mL) was added and the mixture washed with water (40 mL) and sat. NH$_4$Cl (40 mL). The aq. phase was washed once again with ether (30 mL). The org. phases were combined, dried over MgSO$_4$ and concentrated. The residue was purified by FC (Hept/EA 4:1, 2:1, 1:1) to give the title intermediate as a yellowish liquid (0.39 g, 57% yield). 0.15 g (22%) of starting aldehyde was also recovered.

¹H NMR (CDCl₃) δ: 8.65 (d, J=4.4 Hz, 1H), 8.18 (d, J=9.1 Hz, 1H), 7.36 (d, J=4.4 Hz, 1H), 7.10 (d, J=9.1 Hz, 1H), 5.79 (m, 1H), 4.96 (m, 2H), 4.07 (m, 3H), 3.16 (m, 2H), 2.06 (m, 2H), 1.78 (m, 2H), 1.47 (m, 4H).

MS (ESI, m/z): 257.3 [M+H⁺].

124.iii. Rac-7-(6-methoxy-[1,5]naphthyridin-4-yl)-heptane-1,2-diol

Intermediate 124.ii (0.39 g, 1.5 mmol) was dihydroxylated according to method L. The title intermediate was isolated as a yellowish oil (0.46 g, 100% yield).

¹H NMR (CDCl₃) δ: 8.64 (d, J=4.7 Hz, 1H), 8.18 (d, J=9.1 Hz, 1H), 7.35 (d, J=4.7 Hz, 1H), 7.10 (d, J=9.1 Hz, 1H), 4.06 (m, 3H), 3.65 (m, 2H), 3.44 (m, 1H), 3.16 (m, 2H), 2.05 (br., 1H), 1.80 (s, 3H), 1.45 (m, 6H).

MS (ESI, m/z): 291.5 [M+H⁺].

124.iv. Rac-2-methoxy-8-(5-oxiranyl-pentyl)-[1,5]naphthyridine

The title epoxide was obtained starting from intermediate 124.iii (0.47 g, 1.6 mmol) and following the procedures of Example 110, step 110.iv and Example 111, step 111.v. The compound was isolated as a yellowish oil (0.28 g, 64% yield over 2 steps).

MS (ESI, m/z): 273.5 [M+H⁺].

124.v. Rac-3-(2,3-dihydro-benzo[1,4]dioxin-6-yl)-5-[5-(6-methoxy-[1,5]naphthyridin-4-yl)-pentyl]-oxazolidin-2-one The title compound was obtained starting from intermediate 124.iv (0.14 g, 0.5 mmol) and 2,3-dihydro-benzo[1,4]dioxin-6-ylamine (1.7 eq) following methods A and B. The compound was isolated as a colourless solid (0.063 g, 25% yield over 2 steps) after FC (hept/EA 1:1, 1:2) and crystallization from ether.

¹NMR (DMSO d6) δ: 8.65 (d, J=4.4 Hz, 1H), 8.22 (d, J=9.1 Hz, 1H), 7.53 (d, J=4.4 Hz, 1H), 7.22 (d, J=9.1 Hz, 1H), 7.08 (d, J=2.6 Hz, 1H), 6.94 (m, 1H), 6.83 (m, 1H), 4.60 (m, 1H), 4.20 (m, 4H), 4.03 (m, 4H), 3.60 (dd, J=8.8, 7.0 Hz, 1H), 3.12 (m, 2H), 1.72 (m, 4H), 1.42 (m, 4H).

MS (ESI, m/z): 450.4 [M+H⁺].

Example 125

6-{(R)-5-[5-(6-methoxy-[1,5]naphthyridin-4-yl)-pentyl]-2-oxo-oxazolidin-3-yl}-4H-benzo[1,4]thiazin-3-one The title compound was obtained starting from intermediate 124.iv (0.14 g, 0.5 mmol) and 6-amino-4H-benzo[1,4]thiazin-3-one (1.7 eq.) following methods A and B. The compound was isolated as an off-white solid (0.015 g, 12% yield over 2 steps) after FC (Hept/EA 1:1) and crystallization from ether.

¹H NMR (DMSO d6) δ: 10.54 (s, 1H), 8.65 (d, J=4.4 Hz, 1H), 8.22 (d, J=9.1 Hz, 1H), 7.53 (d, J=4.4 Hz, 1H), 7.27 (m, 3H), 7.06 (dd, J=8.8, 2.6 Hz, 1H), 4.64 (m, 1H), 4.06 (t, J=8.8 Hz, 1H), 4.00 (s, 3H), 3.61 (dd, J=8.8, 7.3 Hz, 1H), 3.41 (m, 2H), 3.35 (m, 1H), 3.13 (m, 2H), 1.74 (m, 4H), 1.44 (m, 4H).

MS (ESI, m/z): 479.2 [M+H⁺].

Example 126 rac-6-(5-{2-[2-(6-methoxy-[1,5]naphthyridin-4-yl)-ethylamino]-ethyl}-2-oxo-oxazolidin-3-yl)-4H-benzo[1,4]oxazin-3-one

126.i. Rac-(2-oxiranyl-ethyl)-carbamic acid tert-butyl ester

A solution of but-3-enyl-carbamic acid tert-butyl ester (23.97 g, 140 mmol) in DCM (500 mL) was treated with MCPBA (75%, 32.2 g, 1 eq.). The mixture was stirred at rt for 7 h, diluted with DCM and washed with NaOH 1N. The org. phase was dried over MgSO₄ and concentrated. The residue was purified by FC (Hex/EA 9:1, EA) to give the title epoxide as a colourless oil (14 g, 53% yield).

¹H NMR (CDCl₃) δ: 4.77 (br., 1H), 3.29 (q, J=6.2 Hz, 2H), 2.97 (m, 1H), 2.76 (dd, J=5.0, 4.1 Hz, 1H), 2.51 (dd, J=5.0, 2.9 Hz, 1H), 1.88 (m, 1H), 1.61 (m, 1H), 1.44 (s, 9H).

126.ii. Rac-6-[5-(2-amino-ethyl)-2-oxo-oxazolidin-3-yl]-4H-benzo[1,4]oxazin-3-one The title amine was obtained starting from intermediate 126.i (3.7 g, 20 mmol) and following sequentially methods A, B and E. The compound was isolated as a colourless solid (1.1 g, 27% yield over 3 steps).

¹H NMR (DMSO d6) δ: 10.76 (s, 1H), 7.31 (d, J=1.8 Hz, 1H), 6.92 (m, 2H), 4.77 (m, 1H), 4.51 (s, 2H), 4.11 (t, J=8.8 Hz, 1H), 3.70 (dd, J=8.8, 6.7 Hz, 1H), 2.90 (m, 2H), 2.05 (m, 2H).

126.iii. Rac-6-(5-{2-[2-(6-methoxy-[1,5]naphthyridin-4-yl)-ethylamino]-ethyl}-2-oxo-oxazolidin-3-yl)-4H-benzo[1,4]oxazin-3-one The title compound was obtained starting from intermediate 126.ii (0.37 g, 2 mmol) and 2-methoxy-8-vinyl-[1,5]naphthyridine following the procedure of Example 72, step 72.vii. The compound was isolated after FC (DCM/MeOH 9:1+0.5% NH₄OH) as a colourless foam (0.12 g, 13% yield).

¹H NMR (DMSO d6) δ: 8.65 (d, J=4.4 Hz, 1H), 8.22 (d, J=9.1 Hz, 1H), 7.55 (d, J=4.4 Hz, 1H), 7.30 (d, J=2.6 Hz, 1H), 7.23 (d, J=9.1 Hz, 1H), 6.93 (m, 1H), 6.86 (m, 1H), 4.70 (s, 1H), 4.51 (s, 2H), 4.02 (m, 4H), 3.65 (dd, J=8.8, 7.0 Hz, 1H), 3.27 (m, 2H), 2.98 (t, J=7.3 Hz, 2H), 2.74 (m, 2H), 1.85 (m, 2H).

MS (ESI, m/z): 464.3 [M+H⁺].

Example 127

6-[(RS)-5-(2-{((R)-2,3-dihydroxy-propyl)-[2-(6-methoxy-[1,5]naphthyridin-4-yl)-ethyl]-amino}-ethyl)-2-oxo-oxazolidin-3-yl]-4H-benzo[1,4]oxazin-3-one hydrochloride A solution of the compound of Example 126 (0.088 g, 0.19 mmol) in THF/MeOH (1:1, 2 mL) was treated with (S)-glycidol (0.063 mL, 5 eq.). The mixture was heated at 70° C. overnight, concentrated in vacuo and purified by FC (DCM/MeOH 9:1+1% NH₄OH) to give 65 mg of a brownish foam (66% yield) which was transformed into its hydrochloride salt (0.04 g, 37% yield).

MS (ESI, m/z): 538.3 [M+H⁺].

Example 128 rac-{{2-[3-(2,3-dihydro-benzo[1,4]dioxin-6-yl)-2-oxo-oxazolidin-5-yl]-ethyl}-[2-(6-methoxy-[1,5]naphthyridin-4-yl)-ethyl]-amino}-acetic acid tert-butyl ester A solution of the compound of Example 72 (0.2 g, 0.44 mmol) in THF (3 mL) was treated with DIPEA (0.147 mL, 2 eq.), tert-butyl bromoacetate (0.129 g, 1.5 eq.) and NaI (0.067 g, 1 eq.). The mixture was heated at 80° C. for 2 h, partitioned between EA and water. The org. phase was dried over MgSO$_4$ and concentrated. The residue was purified by FC (EA) to give the title compound as a yellowish oil (0.17 g, 67% yield).
MS (ESI, m/z): 565.4 [M+H$^+$].

Example 129 rac-3-{{2-[3-(2,3-dihydro-benzo[1,4]dioxin-6-yl)-2-oxo-oxazolidin-5-yl]-ethyl}-[2-(6-methoxy-[1,5]naphthyridin-4-yl)-ethyl]-amino}-propionic acid methyl ester A solution of the compound of Example 72 (0.2 g, 0.44 mmol) in THF (3 mL) was treated with DIPEA (0.147 mL, 2 eq.), methyl 3-bromopropionate (0.074 g, 1 eq.) and NaI (0.067 g, 1 eq.). The mixture was heated at 80° C. for 2 h, partitioned between EA and water. The org. phase was dried over MgSO$_4$ and concentrated. The residue was purified by FC (EA) to give the title compound as a yellowish oil (0.1 g, 42% yield).
$^1$H NMR (DMSO d6) δ: 8.64 (d, J=4.4 Hz, 1H), 8.22 (d, J=9.1 Hz, 1H), 7.57 (d, J=4.4 Hz, 1H), 7.23 (d, J=9.1 Hz, 1H), 7.07 (d, J=2.3 Hz, 1H), 6.93 (m, 1H), 6.83 (m, 1H), 4.56 (d, J=0.6 Hz, 1H), 4.21 (m, 4H), 4.01 (m, 4H), 3.95 (m, 1H), 3.63 (m, 1H), 3.54 (s, 3H), 3.29 (m, 2H), 2.82 (m, 4H), 2.63 (m, 2H), 2.47 (m, 2H), 1.80 (m, 2H).

Example 130 rac-4-{{2-[3-(2,3-dihydro-benzo[1,4]dioxin-6-yl)-2-oxo-oxazolidin-5-yl]-ethyl}-[2-(6-methoxy-[1,5]naphthyridin-4-yl)-ethyl]-amino}-butyric acid ethyl ester A solution of the compound of Example 72 (0.2 g, 0.44 mmol) in THF (3 mL) was treated with DIPEA (0.147 mL, 2 eq.), ethyl 4-bromobutyrate (0.087 g, 1 eq.) and NaI (0.067 g, 1 eq.). The mixture was heated at 80° C. for 2 h, then partitioned between EA and water. The org. phase was dried over MgSO$_4$ and concentrated. The residue was purified by FC (EA) to give the title compound as a yellowish oil (0.17 g, 68% yield).
$^1$H NMR (DMSO d6) δ: 8.64 (d, J=4.4 Hz, 1H), 8.21 (d, J=9.1 Hz, 1H), 7.57 (d, J=4.4 Hz, 1H), 7.22 (d, J=9.1 Hz, 1H), 7.07 (d, J=2.3 Hz, 1H), 6.93 (m, 1H), 6.83 (m, 1H), 4.60 (m, 1H), 4.20 (m, 4H), 3.99 (m, 7H), 3.64 (m, 1H), 3.24 (m, 2H), 2.81 (m, 2H), 2.63 (m, 2H), 2.22 (t, J=7.3 Hz, 3H), 1.81 (m, 2H), 1.63 (t, J=7.0 Hz, 2H), 1.15 (m, 3H).

Example 131

6-((R)-5-{[3-(6-methoxy-[1,5]naphthyridin-4-yl)-propylamino]-methyl}-2-oxo-oxazolidin-3-yl)-4H-benzo[1,4]oxazin-3-one 131.i. (R)-[2-oxo-3-(3-oxo-3,4-dihydro-2H-benzo[1,4]oxazin-6-yl)-oxazolidin-5-ylmethyl]-carbamic acid tert-butyl ester A solution of (3-oxo-3,4-dihydro-2H-benzo[1,4]oxazin-6-yl)-carbamic acid benzyl ester (prepared according to method C, 1.4 g, 4.7 mmol) and intermediate 4.i (0.984 g, 4.7 mmol) in DMF (15 mL) at 0° C. was treated dropwise with a 2.2M solution of t-BuOLi in THF (6.4 mL, 3 eq.). The mixture was stirred at 0° C. for 1 h and at rt overnight. 1M HCl (9.4 mL) was added and the mixture partitioned between EA and water. The aq. phase was extracted once more with EA and the combined org. phases were washed several times with water and brine, dried over MgSO$_4$ and concentrated. The residue was purified by FC (Hept/EA 1:2, EA) to give the title intermediate as a colourless solid (0.5 g, 29% yield).
MS (ESI, m/z): 362.2 [M−H$^+$].

131.ii. 6-((R)-5-aminomethyl-2-oxo-oxazolidin-3-yl)-4H-benzo[1,4]oxazin-3-one

Intermediate 131.i (0.5 g, 1.3 mmol) was deprotected following method E. The title amine was isolated after FC (DCM/MeOH 9:1+1% NH$_4$OH) as a colourless solid (0.2 g, 58% yield).
$^1$H NMR (DMSO d6) δ: 10.76 (s, 1H), 7.27 (m, 1H), 6.94 (m, 2H), 4.85 (m, 1H), 4.53 (s, 2H), 4.11 (m, 1H), 3.75 (m, 1H), 3.25 (m, 2H).
MS (ESI, m/z): 264.5 [M+H$^+$].

131.iii. 6-((R)-5-{[3-(6-methoxy-[1,5]naphthyridin-4-yl)-propylamino]-methyl}-2-oxo-oxazolidin-3-yl)-4H-benzo[1,4]oxazin-3-one Intermediate 131.ii (0.15 g, 0.57 mmol) and intermediate 33.ii (0.123 g, 0.57 mmol) were coupled according to method K. The title compound was isolated after FC (EA, EA/MeOH 9:1) as a colourless foam (0.094 g, 36% yield).
MS (ESI, m/z): 464.3 [M+H$^+$].

Example 132

6-((R)-5-{[3-(3-fluoro-6-methoxy-[1,5]naphthyridin-4-yl)-propylamino]-methyl}-2-oxo-oxazolidin-3-yl)-4H-benzo[1,4]oxazin-3-one 132.i. (E)-3-(3-fluoro-6-methoxy-[1,5]naphthyridin-4-yl)-acrylic acid ethyl ester A NaH dispersion in mineral oil (55%, 0.13 g, 3 mmol) was added to a solution of triethylphosphonoacetate (0.62 g, 2.75 mmol) and 3-fluoro-6-methoxy-[1,5]naphthyridine-4-carbaldehyde (prepared according to WO 2006/032466; 0.51 g, 2.5 mmol) in THF (10 mL) at 0° C. The mixture was stirred at 0° C. for 1 h and at rt for another hour. The mixture was partitioned between EA and water. The org. phase was washed with water and brine, dried over MgSO$_4$ and concentrated. The title intermediate was isolated after FC (Hept/EA 2:1) as a yellowish solid (0.59 g, 86% yield).
$^1$H NMR (CDCl$_3$) δ: 8.71 (d, J=2.3 Hz, 1H), 8.50 (d, J=16.7 Hz, 1H), 8.20 (d, J=9.1 Hz, 1H), 7.35 (s, 1H), 7.12 (d, J=8.8 Hz, 1H), 4.32 (q, J=7.0 Hz, 2H), 4.14 (s, 3H), 1.37 (t, J=7.0 Hz, 3H).
MS (ESI, m/z): 277.2 [M+H$^+$].

132.ii. 3-(3-fluoro-6-methoxy-[1,5]naphthyridin-4-yl)-propionic acid ethyl ester Intermediate 132.i (0.59 g, 2.1 mmol) was reduced in analogy to the procedure of Example 33, step 33.i to yield the title intermediate as a colourless oil (0.53 g, 90% yield).

¹H NMR (CDCl₃) δ: 8.62 (d, J=0.6 Hz, 1H), 8.17 (d, J=9.1 Hz, 1H), 7.07 (d, J=9.1 Hz, 1H), 4.12 (m, 5H), 3.50 (td, J=7.9, 1.5 Hz, 2H), 2.80 (t, J=7.9 Hz, 2H), 1.20 (m, 3H).
MS (ESI, m/z): 279.4 [M+H⁺].

132.iii. 3-(3-fluoro-6-methoxy-[1,5]naphthyridin-4-yl)-propan-1-ol

A solution of intermediate 132.ii (0.53 g, 1.9 mmol) in EtOH (5 mL) was treated with NaBH₄ (0.144 g, 2 eq.). The mixture was stirred at rt overnight. Excess NaBH₄ was quenched by addition of 1M HCl. The mixture was partitioned between EA and a sat. NaHCO₃ solution. The org. phase was washed with water and brine, dried over MgSO₄ and concentrated. The residue was purified by FC (Hept/EA 1:1, EA) to give the title intermediate as a yellowish solid (0.38 g, 85% yield).
¹H NMR (CDCl₃) δ: 8.64 (s, 1H), 8.21 (d, J=9.1 Hz, 1H), 7.10 (d, J=9.1 Hz, 1H), 4.10 (s, 3H), 3.50 (m, 2H), 3.34 (td, J=7.0, 1.8 Hz, 2H), 2.91 (m, 1H), 2.03 (m, 2H).
MS (ESI, m/z): 237.1 [M+H⁺].

132.iv. 3-(3-fluoro-6-methoxy-[1,5]naphthyridin-4-yl)-propionaldehyde

The title aldehyde was obtained starting from intermediate 132.iii (0.38 g, 1.6 mmol) and following the procedure of Example 33, step 33.ii. The compound was isolated after FC (EA) as a beige solid (0.31 g, 81% yield).
¹H NMR (CDCl₃) δ: 9.87 (s, 1H), 8.63 (s, 1H), 8.18 (d, J=9.1 Hz, 1H), 7.08 (d, J=9.1 Hz, 1H), 4.06 (s, 3H), 3.50 (td, J=7.6, 1.5 Hz, 2H), 2.92 (td, J=7.9, 1.5 Hz, 2H).
MS (ESI, m/z): 235.2 [M+H⁺].

132.v. 6-((R)-5-{[3-(3-fluoro-6-methoxy-[1,5]naphthyridin-4-yl)-propylamino]-methyl}-2-oxo-oxazolidin-3-yl)-4H-benzo[1,4]oxazin-3-one Intermediate 132.iv (0.125 g, 0.53 mmol) and intermediate 131.ii (0.14 g, 0.53 mmol) were coupled according to method K. The title compound was isolated as a colourless foam (0.09 g, 36% yield) after FC (EA, EA/MeOH 9:1).
¹H NMR (CDCl₃) δ: 8.60 (d, J=0.9 Hz, 1H), 8.17 (d, J=9.1 Hz, 1H), 7.39 (d, J=2.6 Hz, 1H), 7.06 (d, J=9.1 Hz, 1H), 6.93 (m, 1H), 6.80 (dd, J=8.8, 2.3 Hz, 1H), 4.74 (s, 1H), 4.57 (s, 2H), 4.07 (s, 3H), 3.97 (t, J=8.5 Hz, 1H), 3.82 (dd, J=8.5, 7.0 Hz, 1H), 3.25 (td, J=7.9, 1.8 Hz, 2H), 2.97 (d, J=4.1 Hz, 1H), 2.92 (d, J=5.6 Hz, 1H), 2.75 (m, 2H), 1.97 (m, 2H).
MS (ESI, m/z): 482.2 [M+H⁺].

Example 133

6-((R)-5-{[3-(3-fluoro-6-methoxy-[1,5]naphthyridin-4-yl)-propylamino]-methyl}-2-oxo-oxazolidin-3-yl)-4H-benzo[1,4]thiazin-3-one Intermediate 132.iv (0.046 g, 0.2 mmol) and intermediate 4.v (0.065 g, 0.2 mmol) were coupled according to method K. The title compound was isolated after FC (EA, EA/MeOH 9:1) as a colourless foam (0.06 g, 60% yield).
¹H NMR (DMSO d6) δ: 10.53 (s, 1H), 8.74 (d, J=0.6 Hz, 1H), 8.25 (d, J=8.8 Hz, 1H), 7.29 (m, 2H), 7.21 (d, J=9.1 Hz, 1H), 7.08 (dd, J=8.5, 2.3 Hz, 1H), 4.67 (m, 1H), 4.00 (m, 4H), 3.74 (dd, J=8.5, 6.7 Hz, 1H), 3.41 (s, 2H), 3.15 (m, 2H), 2.80 (d, J=5.3 Hz, 2H), 2.63 (t, J=6.7 Hz, 2H), 1.81 (m, 2H).
MS (ESI, m/z): 498.1 [M+H⁺].

Example 134

(R)-3-(2,3-dihydro-benzo[1,4]dioxin-6-yl)-5-{[3-(3-fluoro-6-methoxy-[1,5]naphthyridin-4-yl)-propylamino]-methyl}-oxazolidin-2-one Intermediate 132.iv (0.117 g, 0.5 mmol) and intermediate 3.i (0.138 g, 0.5 mmol) were coupled according to method K. The title compound was isolated after FC (EA, EA/MeOH 9:1) as a colourless foam (0.12 g, 51% yield).
¹H NMR (DMSO d6) δ: 8.74 (s, 1H), 8.25 (d, J=9.1 Hz, 1H), 7.21 (d, J=9.1 Hz, 1H), 7.08 (d, J=2.6 Hz, 1H), 6.93 (m, 1H), 6.82 (m, 1H), 4.63 (m, 1H), 4.18 (m, 4H), 3.96 (m, 4H), 3.75 (m, 2H), 3.14 (m, 2H), 2.77 (m, 2H), 2.62 (t, J=6.7 Hz, 2H), 1.80 (m, 2H).
MS (ESI, m/z): 469.0 [M+H⁺].

Example 135

(R)-3-(2,3-dihydro-benzo[1,4]dioxin-6-yl)-5-({((S)-2,3-dihydroxy-propyl)-[3-(3-fluoro-6-methoxy-[1,5]naphthyridin-4-yl)-propyl]-amino}-methyl)-oxazolidin-2-one A solution of the compound of Example 134 (0.05 g, 0.1 mmol) in THF/MeOH (1:1, 1 mL) was treated with (R)-glycidol (0.02 mL, 5 eq.). The mixture was heated at 70° C. overnight, concentrated in vacuo and purified by FC (DCM/MeOH 9:1+1% NH₄OH) to give the title compound as a colourless foam (20 mg, 35% yield).
MS (ESI, m/z): 543.3 [M+H⁺].

Example 136

6-[(R)-5-({((S)-2,3-dihydroxy-propyl)-[3-(3-fluoro-6-methoxy-[1,5]naphthyridin-4-yl)-propyl]-amino}-methyl)-2-oxo-oxazolidin-3-yl]-4H-benzo[1,4]thiazin-3-one A solution of the compound of Example 133 (0.03 g, 0.06 mmol) in THF/MeOH (1:1, 0.5 mL) was treated with (R)-glycidol (0.02 mL, 5 eq.). The mixture was heated at 70° C. overnight, concentrated in vacuo and purified by FC (DCM/MeOH 9:1+1% NH₄OH) to give the title compound as a yellowish foam (14 mg, 40% yield).
MS (ESI, m/z): 572.1 [M+H⁺].

Example 137

6-[(R)-5-({((R)-2,3-dihydroxy-propyl)-[3-(3-fluoro-6-methoxy-[1,5]naphthyridin-4-yl)-propyl]-amino}-methyl)-2-oxo-oxazolidin-3-yl]-4H-benzo[1,4]oxazin-3-one A solution of the compound of Example 132 (0.086 g, 0.18 mmol) in THF/MeOH (1:1, 0.5 mL) was treated with (S)-glycidol (0.06 mL, 5 eq.). The mixture was heated at 70° C. for 3 h, concentrated in vacuo and purified by FC (DCM/MeOH 9:1+1% NH₄OH) to give the title compound as a colourless solid (15 mg).
MS (ESI, m/z): 556.2 [M+H⁺].

Example 138

6-[(R)-5-({((R)-2,3-dihydroxy-propyl)-[3-(6-methoxy-[1,5]naphthyridin-4-yl)-propyl]-amino}-methyl)-2-oxo-oxazolidin-3-yl]-4H-benzo[1,4]oxazin-3-one A solution of the compound of Example 131 (0.088 g, 0.19 mmol) in THF/MeOH (1:1, 0.5 mL) was treated with (S)-glycidol (0.06 mL, 5 eq.). The mixture was heated at 70° C. for 3 h, concentrated in vacuo and purified by FC (DCM/MeOH 9:1+1% NH$_4$OH) to give the title compound as a colourless solid (20 mg).
MS (ESI, m/z): 538.2 [M+H$^+$].

Example 139

{[(R)-3-(2,3-dihydro-benzo[1,4]dioxin-6-yl)-2-oxo-oxazolidin-5-ylmethyl]-[3-(6-methoxy-[1,5]naphthyridin-4-yl)-propyl]-amino}-acetic acid tert-butyl ester The compound of Example 30 (0.2 g, 0.44 mmol) was reacted with tert-butyl bromoacetate (0.065 mL, 1 eq.) following the procedure of Example 128. The compound was isolated after FC (Hept/EA 2:1, EA) as a brownish oil (0.08 g, 32% yield).
$^1$H NMR (CDCl$_3$) δ: 8.65 (d, J=4.4 Hz, 1H), 8.18 (d, J=9.1 Hz, 1H), 7.36 (d, J=4.4 Hz, 1H), 7.09 (m, 2H), 6.98 (dd, J=8.8, 2.6 Hz, 1H), 6.82 (d, J=8.8 Hz, 1H), 4.67 (m, 1H), 4.23 (m, 4H), 4.06 (s, 3H), 3.96 (t, J=8.5 Hz, 1H), 3.83 (dd, J=8.8, 7.0 Hz, 1H), 3.38 (s, 2H), 3.17 (m, 2H), 3.01 (qd, J=14.1, 5.6 Hz, 2H), 2.84 (td, J=7.0, 1.5 Hz, 2H), 1.95 (m, 2H), 1.45 (m, 9H).
MS (ESI, m/z): 565.4 [M+H$^+$].

Example 140

3-{[(R)-3-(2,3-dihydro-benzo[1,4]dioxin-6-yl)-2-oxo-oxazolidin-5-ylmethyl]-[3-(6-methoxy-[1,5]naphthyridin-4-yl)-propyl]-amino}-propionic acid methyl ester The compound of Example 30 (0.15 g, 0.33 mmol) was reacted with methyl 3-bromopropionate (0.055 mL, 1 eq.) following the procedure of Example 129. The compound was isolated after FC (EA) as a yellowish oil (0.03 g, 17% yield).
$^1$H NMR (CDCl$_3$) δ: 8.64 (d, J=4.7 Hz, 1H), 8.17 (d, J=8.8 Hz, 1H), 7.36 (d, J=4.7 Hz, 1H), 7.10 (d, J=9.1 Hz, 1H), 7.05 (d, J=2.6 Hz, 1H), 6.97 (m, 1H), 6.82 (m, 1H), 4.65 (m, 1H), 4.23 (m, 4H), 4.05 (s, 3H), 3.92 (t, J=8.8 Hz, 1H), 3.73 (dd, J=8.8, 6.4 Hz, 1H), 3.64 (s, 3H), 3.13 (t, J=7.9 Hz, 2H), 2.80 (m, 6H), 2.44 (t, J=6.4 Hz, 2H), 1.95 (m, 2H).
MS (ESI, m/z): 537.3 [M+H$^+$].

Example 141

4-{[(R)-3-(2,3-dihydro-benzo[1,4]dioxin-6-yl)-2-oxo-oxazolidin-5-ylmethyl]-[3-(6-methoxy-[1,5]naphthyridin-4-yl)-propyl]-amino}-butyric acid ethyl ester The compound of Example 30 (0.2 g, 0.44 mmol) was reacted with ethyl 4-bromobutyrate (0.123 mL, 1.5 eq.) following the procedure of Example 130. The title compound was isolated after FC (EA) as a colourless oil (0.09 g, 36% yield).

$^1$H NMR (CDCl$_3$) δ: 8.66 (d, J=4.7 Hz, 1H), 8.18 (d, J=9.1 Hz, 1H), 7.37 (d, J=4.4 Hz, 1H), 7.11 (d, J=9.1 Hz, 1H), 7.06 (d, J=2.6 Hz, 1H), 6.97 (dd, J=9.1, 2.9 Hz, 1H), 6.82 (m, 1H), 4.64 (dd, J=1.8, 0.9 Hz, 1H), 4.24 (s, 4H), 4.10 (q, J=7 Hz, 2H), 4.06 (m, 3H), 3.95 (t, J=8.5 Hz, 1H), 3.72 (dd, J=8.8, 6.7 Hz, 1H), 3.16 (t, J=7.9 Hz, 2H), 2.69 (m, 6H), 2.33 (t, J=7.3 Hz, 2H), 1.94 (dd, J=2.9, 1.8 Hz, 2H), 1.76 (m, 2H), 1.23 (m, 3H).
MS (ESI, m/z): 565.4 [M+H$^+$].

Example 142

{[(R)-3-(2,3-dihydro-benzo[1,4]dioxin-6-yl)-2-oxo-oxazolidin-5-ylmethyl]-[3-(6-methoxy-[1,5]naphthyridin-4-yl)-propyl]-amino}-acetic acid hydrochloride The compound of Example 139 (0.07 g, 0.124 mmol) was dissolved in dioxane (5 mL) and conc. HCl (37%, 0.5 mL) was added. The mixture was stirred at rt overnight, concentrated in vacuo and crystallized from MeOH/ether to give the title hydrochloride salt (beige solid; 0.04 g, 59% yield).
MS (ESI, m/z): 509.1 [M+H$^+$].

Example 143

3-{[(R)-3-(2,3-dihydro-benzo[1,4]dioxin-6-yl)-2-oxo-oxazolidin-5-ylmethyl]-[3-(6-methoxy-[1,5]naphthyridin-4-yl)-propyl]-amino}-propionate lithium salt The compound of Example 140 (0.009 g, 0.016 mmol) was dissolved in THF/H$_2$O (5:1, 1 mL). LiOH hydrate (2 eq.) was added and the mixture stirred at rt overnight. The mixture was concentrated in vacuo and crystallized from MeOH/ether to give the title lithium salt (8 mg, 100% yield).
MS (ESI, m/z): 523.2 [M+H$^+$].

Example 144 rac-6-(5-{3-[(6-methoxy-[1,5]naphthyridin-4-ylmethyl)-amino]-propyl}-2-oxo-oxazolidin-3-yl)-4H-benzo[1,4]oxazin-3-one

144.i. Rac-6-[5-(3-amino-propyl)-2-oxo-oxazolidin-3-yl]-4H-benzo[1,4]oxazin-3-one The title intermediate was obtained starting from 6-amino-4H-benzo[1,4]oxazin-3-one (3.6 g, 17.9 mmol) and following the procedures of Example 76, steps 76.i to 76.iii. The compound was isolated as a beige foam (1 g, 19% yield over 3 steps).
$^1$H NMR (CDCl$_3$) δ: 7.43 (d, J=2.6 Hz, 1H), 6.93 (m, 1H), 6.79 (m, 1H), 4.75 (m, 1H), 4.57 (s, 2H), 4.05 (s, 1H), 2.79 (t, J=6.7 Hz, 2H), 2.0-1.6 (m, 4H).

144.ii. Rac-6-(5-{3-[(6-methoxy-[1,5]naphthyridin-4-ylmethyl)-amino]-propyl}-2-oxo-oxazolidin-3-yl)-4H-benzo[1,4]oxazin-3-one The title compound was obtained starting from intermediate 144.i (0.1 g, 0.34 mmol) and 6-methoxy-[1,5]naphthyridine-4-carbaldehyde (0.064 g, 1 eq.) and following method K. The compound was isolated after FC (EA/MeOH 9:1+1% NH$_4$OH) as a colourless solid (0.12 g, 74% yield).

¹H NMR (DMSO d6) δ: 10.70 (m, 1H), 8.72 (d, J=4.4 Hz, 1H), 8.24 (d, J=9.1 Hz, 1H), 7.69 (d, J=4.4 Hz, 1H), 7.32 (d, J=2.1 Hz, 1H), 7.23 (d, J=9.1 Hz, 1H), 6.91 (m, 2H), 4.66 (m, 1H), 4.51 (s, 2H), 4.23 (s, 2H), 4.03 (m, 4H), 3.62 (dd, J=9.1, 7.3 Hz, 1H), 2.61 (t, J=6.7 Hz, 2H), 1.77 (m, 2H), 1.58 (m, 2H).
MS (ESI, m/z): 464.4 [M+H⁺].

Example 145 rac-6-(5-{3-[(3-methoxy-quinoxalin-5-ylmethyl)-amino]-propyl}-2-oxo-oxazolidin-3-yl)-4H-benzo[1,4]oxazin-3-one The title compound was obtained starting from intermediate 144.i (0.1 g, 0.34 mmol) and 3-methoxy-quinoxaline-5-carbaldehyde (0.065 g, 1 eq.) and following method K. The compound was isolated after FC (EA/MeOH 9:1+1% NH₄OH) as a colourless solid (0.127 g, 80% yield).
¹H NMR (DMSO d6) δ: 10.70 (m, 1H), 8.58 (s, 1H), 7.87 (dd, J=8.2, 1.5 Hz, 1H), 7.76 (dd, J=7.0, 1.2 Hz, 1H), 7.57 (dd, J=8.2, 7.3 Hz, 1H), 7.31 (d, J=2.3 Hz, 1H), 6.90 (m, 3H), 4.64 (m, 1H), 4.52 (m, 3H), 4.18 (m, 2H), 4.03 (m, 4H), 3.61 (dd, J=9.1, 7.0 Hz, 1H), 2.59 (t, J=6.7 Hz, 2H), 1.76 (m, 2H), 1.57 (m, 2H).
MS (ESI, m/z): 464.4 [M+H⁺].

Example 146 rac-6-(5-{3-[(6-methoxy-quinolin-4-ylmethyl)-amino]-propyl}-2-oxo-oxazolidin-3-yl)-4H-benzo[1,4]oxazin-3-one The title compound was obtained starting from intermediate 144.i (0.1 g, 0.34 mmol) and 6-methoxy-quinoline-4-carbaldehyde (0.064 g, 1 eq) and following method K. The compound was isolated after FC (EA/MeOH 9:1+1% NH₄OH) as a colourless foam (0.055 g, 35% yield).
MS (ESI, m/z): 463.1 [M+H⁺].

Example 147 rac-2-methoxy-8-({3-[2-oxo-3-(3-oxo-3,4-dihydro-2H-benzo[1,4]oxazin-6-yl)-oxazolidin-5-yl]-propylamino}-methyl)-quinoline-5-carboxylic acid methyl ester The title compound was obtained starting from intermediate 144.i (0.1 g, 0.34 mmol) and 8-formyl-2-methoxy-quinoline-5-carboxylic acid methyl ester (prepared according to WO 2006/046552; 0.084 g, 1 eq.) and following method K. The compound was isolated after FC (EA/MeOH 9:1+1% NH₄OH) as a colourless foam (0.055 g, 35% yield).
MS (ESI, m/z): 521.4 [M+H⁺].

Example 148 rac-6-(5-{3-[(3-fluoro-6-methoxy-quinolin-4-ylmethyl)-amino]-propyl}-2-oxo-oxazolidin-3-yl)-4H-benzo[1,4]oxazin-3-one The title compound was obtained starting from intermediate 144.i (0.1 g, 0.34 mmol) and 3-fluoro-6-methoxy-quinoline-4-carbaldehyde (prepared according to WO 2007/086016; 0.07 g, 1 eq.) and following method K. The compound was isolated after FC (EA/MeOH 9:1+1% NH₄OH) as a colourless foam (0.021 g, 13% yield).
MS (ESI, m/z): 481.4 [M+H⁺].

Example 149 rac-6-(5-{3-[(3-fluoro-6-methoxy-[1,5]naphthyridin-4-ylmethyl)-amino]-propyl}-2-oxo-oxazolidin-3-yl)-4H-benzo[1,4]oxazin-3-one The title compound was obtained starting from intermediate 144.i (0.1 g, 0.34 mmol) and 3-fluoro-6-methoxy-[1,5]naphthyridine-4-carbaldehyde (prepared according to WO 2006/032466; 0.07 g, 1 eq.) and following method K. The compound was isolated after FC (EA/MeOH 9:1+1% NH₄OH) as a colourless foam (0.13 g, 79% yield).
MS (ESI, m/z): 482.2 [M+H⁺].

Example 150 rac-6-(5-{3-[(7-fluoro-2-methoxy-quinolin-8-ylmethyl)-amino]-propyl}-2-oxo-oxazolidin-3-yl)-4H-benzo[1,4]oxazin-3-one 150.i. (7-fluoro-2-methoxy-quinolin-8-yl)-methanol A suspension of 8-bromomethyl-7-fluoro-2-methoxy-quinoline (32.03 g, 118.59 mmol) in acetone (460 mL) and water (585 mL) was treated with NaHCO₃ (16.32 g, 194.28 mmol). The mixture was heated at reflux for 6 h. The volatiles were removed under reduced pressure and the aq. phase was extracted with EA (2×250 mL). The combined org. layers were washed with brine, dried over MgSO₄ and concentrated to afford the title alcohol as a yellow oil (24 g, 97% yield).
¹H NMR (DMSO d6) δ: 8.24 (d, J=8.8 Hz, 1H), 7.88 (dd, J=9.1, 6.4 Hz, 1H), 7.31 (m, 1H), 6.98 (d, J=9.1 Hz, 1H), 5.01 (dd, J=5.9, 1.8 Hz, 2H), 4.86 (dd, J=6.2, 5.3 Hz, 1H), 4.02 (m, 3H).

150.ii. 7-fluoro-2-methoxy-quinoline-8-carbaldehyde

To a solution of oxalyl chloride (29.42 mL, 347.63 mmol) in DCM (510 mL), cooled to −78° C., was added dropwise a solution of DMSO (29.58 mL, 417.16 mmol, 3.6 eq.) in DCM (210 mL) over 55 min such that the internal temperature stayed below −70° C. The mixture was stirred 15 min before a solution of intermediate 150.i (24.01 g, 115.88 mmol) in DCM (550 mL) was added dropwise over 1 h 45. The mixture was further stirred 1 h at this temperature then a solution of TEA (121.13 mL, 869.07 mmol, 7.5 eq.) in DCM (140 mL) was added dropwise over 1 h 15. The mixture was stirred 40 min before warming gradually to rt. The reaction was quenched adding a sat. NaHCO₃ solution (600 mL). The two layers were separated and the org layer was dried over Na₂SO₄, filtered and concentrated. The title aldehyde was isolated after FC (EA) as a yellowish solid (24 g, 100% yield).
¹H NMR (CDCl₃) δ: 11.28 (dd, J=1.5, 0.6 Hz, 1H), 8.00 (d, J=9.1 Hz, 1H), 7.92 (dd, J=9.1, 5.9 Hz, 1H), 7.20 (ddd, J=10.3, 9.1, 0.6 Hz, 1H), 6.96 (d, J=8.8 Hz, 1H), 4.09 (s, 3H).

150.iii. rac-6-(5-{3-[(7-fluoro-2-methoxy-quinolin-8-ylmethyl)-amino]-propyl}-2-oxo-oxazolidin-3-yl)-4H-benzo[1,4]oxazin-3-one The title compound was obtained starting from intermediate 144.i (0.1 g, 0.34 mmol) and intermediate 150.ii (0.07 g, 1 eq.) and following method K. The compound was isolated after FC (EA/MeOH 9:1+1% NH₄OH) as a colourless foam (0.1 g, 61% yield).
MS (ESI, m/z): 479.1 [M+H⁺].

Example 151

6-((RS)-5-{3-[((R)-2,3-dihydroxy-propyl)-(3-fluoro-6-methoxy-[1,5]naphthyridin-4-ylmethyl)-amino]-propyl}-2-oxo-oxazolidin-3-yl)-4H-benzo[1,4]thiazin-3-one A solution of the compound of Example 78 (0.05 g, 0.1 mmol) in THF/MeOH (1:1, 0.5 mL) was treated with (S)-glycidol (0.06 mL, 5 eq.). The mixture was heated at 70° C. for 3 h, concentrated in vacuo and purified by FC (EA/MeOH 19:1+1% NH$_4$OH) to give the title compound as a colourless solid (0.03 g, 52% yield).
MS (ESI, m/z): 572.1 [M+H$^+$].

Example 152

6-((RS)-5-{3-[((R)-3-chloro-2-hydroxy-propyl)-(3-fluoro-6-methoxy-[1,5]naphthyridin-4-ylmethyl)-amino]-propyl}-2-oxo-oxazolidin-3-yl)-4H-benzo[1,4]thiazin-3-one A solution of the compound of Example 78 (0.135 g, 0.27 mmol) in THF/MeOH (1:1, 2 mL) was treated with (R)-epichlorohydrin (0.032 mL, 1.5 eq.). The mixture was heated at 70° C. overnight, concentrated in vacuo and purified by FC (EA/MeOH 19:1+1% NH$_4$OH) to give the title compound as a colourless foam (0.1 g, 52% yield).
MS (ESI, m/z): 589.9 [M+H$^+$].

Example 153

6-((RS)-5-{3-[((S)-3-dimethylamino-2-hydroxy-propyl)-(3-fluoro-6-methoxy-[1,5]naphthyridin-4-ylmethyl)-amino]-propyl}-2-oxo-oxazolidin-3-yl)-4H-1-benzo[1,4]thiazin-3-one A solution of the compound of Example 152 (0.04 g, 0.07 mmol) in a 30% solution of dimethylamine in EtOH (1 mL) was heated at 70° C. in a sealed flask overnight. The mixture was partitioned between DCM and water, the org. phase was dried over MgSO$_4$ and concentrated. The title compound was isolated after FC (EA/MeOH 9:1+1% NH$_4$OH) as a yellowish foam (0.028 g, 69% yield).
MS (ESI, m/z): 599.4 [M+H$^+$].

The following compounds have been obtained in analogy to Example 78 starting from intermediate 76.iii:

| Example | Name | Yield | ESI (M + H$^+$) |
|---|---|---|---|
| 154 | rac-6-(2-oxo-5-{3-[(quinolin-4-ylmethyl)-amino]-propyl}-oxazolidin-3-yl)-4H-benzo[1,4]thiazin-3-one | 9 | 449.3 |
| 155 | rac-6-(5-{3-[(naphthalen-1-ylmethyl)-amino]-propyl}-2-oxo-oxazolidin-3-yl)-4H-benzo[1,4]thiazin-3-one | 53 | 448.4 |
| 156 | rac-2-methoxy-8-({3-[2-oxo-3-(3-oxo-3,4-dihydro-2H-benzo[1,4]thiazin-6-yl)-oxazolidin-5-yl]-propylamino}-methyl)-quinoline-5-carboxylic acid methyl ester | 44 | 537.3 |
| 157 | rac-6-[5-(3-{[3-methoxy-8-(2-methoxy-ethoxy)-quinoxalin-5-ylmethyl]-amino}-propyl)-2-oxo-oxazolidin-3-yl]-4H-benzo[1,4]thiazin-3-one | 48 | 554.3 |
| 158 | rac-6-(5-{3-[(6-fluoro-quinolin-4-ylmethyl)-amino]-propyl}-2-oxo-oxazolidin-3-yl)-4H-benzo[1,4]thiazin-3-one | 56 | 467.03 |
| 159 | rac-6-(5-{3-[(3-methoxy-quinoxalin-5-ylmethyl)-amino]-propyl}-2-oxo-oxazolidin-3-yl)-4H-benzo[1,4]thiazin-3-one | 22 | 480.17 |
| 160 | rac-6-(5-{3-[(6-methoxy-quinolin-4-ylmethyl)-amino]-propyl}-2-oxo-oxazolidin-3-yl)-4H-benzo[1,4]thiazin-3-one | 36 | 479.16 |
| 161 | rac-6-(5-{3-[(isoquinolin-5-ylmethyl)-amino]-propyl}-2-oxo-oxazolidin-3-yl)-4H-benzo[1,4]thiazin-3-one | 8 | 449.15 |
| 162 | rac-6-(5-{3-[(4-methoxy-naphthalen-1-ylmethyl)-amino]-propyl}-2-oxo-oxazolidin-3-yl)-4H-benzo[1,4]thiazin-3-one | 4 | 478.16 |
| 163 | rac-6-(2-oxo-5-{3-[(quinolin-5-ylmethyl)-amino]-propyl}-oxazolidin-3-yl)-4H-benzo[1,4]thiazin-3-one | 16 | 449.14 |
| 164 | rac-6-(2-oxo-5-{3-[(quinolin-8-ylmethyl)-amino]-propyl}-oxazolidin-3-yl)-4H-benzo[1,4]thiazin-3-one | 39 | 449.14 |
| 165 | rac-6-(5-{3-[(4-hydroxy-naphthalen-1-ylmethyl)-amino]-propyl}-2-oxo-oxazolidin-3-yl)-4H-benzo[1,4]thiazin-3-one | 3 | 464.15 |
| 166 | rac-6-(5-{3-[(2-hydroxy-naphthalen-1-ylmethyl)-amino]-propyl}-2-oxo-oxazolidin-3-yl)-4H-benzo[1,4]thiazin-3-one | 47 | 464.4 |
| 167 | rac-6-(5-{3-[(7-flouro-2-methoxy-quinolin-8-ylmethyl)-amino]-propyl}-2-oxo-oxazolidin-3-yl)-4H-benzo[1,4]thiazin-3-one | 59 | 497.4 |
| 168 | rac-6-(5-{3-[(2,3-dimethoxy-naphthalen-1-ylmethyl)-amino]-propyl}-2-oxo-oxazolidin-3-yl)-4H-benzo[1,4]thiazin-3-one | 69 | 508.1 |
| 169 | rac-6-(5-{3-[(4,7-dimethoxy-naphthalen-1-ylmethyl)-amino]-propyl}-2-oxo-oxazolidin-3-yl)-4H-benzo[1,4]thiazin-3-one | 62 | 508.1 |

Example 170 rac-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-acetic acid tert-butyl ester The title compound was obtained starting from the compound of Example 77 (0.09 g, 0.19 mmol) and tert-butyl bromoacetate following the procedure of Example 128. The compound was isolated after FC (EA) as a colourless foam (0.064 g, 57% yield).
MS (ESI, m/z): 594.3 [M+H$^+$].

Example 171 rac-3-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-propionic acid methyl ester The title compound was obtained starting from the compound of Example 77 (0.09 g, 0.19 mmol) and methyl 3-bromopropionate following the procedure of Example 129. The compound was isolated after FC (EA) as a colourless foam (0.027 g, 25% yield).
MS (ESI, m/z): 566.4 [M+H$^+$].

Example 172 rac-4-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-butyric acid ethyl ester The title compound was obtained starting from compound of Example 77 (0.09 g, 0.19 mmol) and ethyl 4-bromobutyrate following the procedure of Example 130. The compound was isolated after FC (EA) as a colourless foam (0.079 g, 71% yield).
MS (ESI, m/z): 594.2 [M+H$^+$].

Example 173 rac-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-acetic acid hydrochloride The compound of Example 170 (0.06 g, 0.1 mmol) was dissolved in dioxane (4 mL) and conc. HCl (37%, 0.4 mL) was added. The mixture was stirred at rt for 48 h, concentrated in vacuo and crystallized from MeOH/ether to give the hydrochloride salt (beige solid; 0.052 g, 90% yield).
MS (ESI, m/z): 538.2 [M+H$^+$].

Example 174 rac-3-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-propionic acid hydrochloride The compound of Example 171 (0.022 g, 0.04 mmol) was dissolved in dioxane (4 mL) and conc. HCl (37%, 0.15 mL) was added. The mixture was stirred at 50° C. for 5 days, concentrated in vacuo and crystallized from MeOH/ether to give the title hydrochloride salt (beige solid; 0.008 g, 35% yield).
MS (ESI, m/z): 552.5 [M+H$^+$].

Example 175 rac-4-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-butyric acid hydrochloride The compound of Example 172 (0.075 g, 0.126 mmol) was dissolved in dioxane (5 mL) and conc. HCl (37%, 0.5 mL) was added. The mixture was stirred at rt for 48 h, concentrated in vacuo and crystallized from MeOH/ether to give the title hydrochloride salt (beige solid; 0.068 g, 95% yield).
MS (ESI, m/z): 566.4 [M+H$^+$].

Example 176

6-((R)-5-{3-[(3-fluoro-6-methoxy-[1,5]naphthyridin-4-ylmethyl)-amino]-propyl}-2-oxo-oxazolidin-3-yl)-4H-benzo[1,4]oxazin-3-one 176.i. (R)-6-[5-(3-amino-propyl)-2-oxo-oxazolidin-3-yl]-4H-benzo[1,4]oxazin-3-one The title intermediate was obtained starting from (R)-(3-oxiranyl-propyl)-carbamic acid tert-butyl ester (prepared as in WO 2007/069555; 1.0 g, 5 mmol) and 6-amino-4H-benzo[1,4]oxazin-3-one (0.815 g, 5 mmol) and following the procedures of Example 76, steps 76.i to 76.iii. The compound was isolated as a beige foam (0.5 g, 35% yield over 3 steps).
$^1$H NMR (CDCl$_3$) δ: 7.43 (d, J=2.6 Hz, 1H), 6.93 (m, 1H), 6.79 (m, 1H), 4.75 (m, 1H), 4.57 (s, 2H), 4.05 (s, 1H), 2.79 (t, J=6.7 Hz, 2H), 2.0-1.6 (m, 4H).

176.ii. 6-((R)-5-{3-[(3-fluoro-6-methoxy-[1,5]naphthyridin-4-ylmethyl)-amino]-propyl}-2-oxo-oxazolidin-3-yl)-4H-benzo[1,4]oxazin-3-one The title compound was obtained starting from intermediate 176.i (0.25 g, 0.86 mmol) and 3-fluoro-6-methoxy-[1,5]naphthyridine-4-carbaldehyde (0.177 g, 1 eq.) and following method K. The compound was isolated after FC (EA/MeOH 19:1, 9:1+1% NH$_4$OH) as a colourless foam (0.29 g, 70% yield).
MS (ESI, m/z): 482.2 [M+H$^+$].

Example 177

6-((R)-5-{3-[((S)-2,3-dihydroxy-propyl)-(3-fluoro-6-methoxy-[1,5]naphthyridin-4-ylmethyl)-amino]-propyl}-2-oxo-oxazolidin-3-yl)-4H-benzo[1,4]oxazin-3-one A solution of the compound of Example 176 (0.07 g, 0.145 mmol) in THF/MeOH (1:1, 1 mL) was treated with (R)-glycidol (0.046 mL, 5 eq.). The mixture was heated at 70° C. for 6 h, concentrated in vacuo and purified by FC (EA/MeOH 19:1+1% NH$_4$OH) to give the title compound as a colourless solid (0.08 g, 99% yield).
MS (ESI, m/z): 556.2 [M+H$^+$].

Example 178

6-((R)-5-{3-[((R)-2,3-dihydroxy-propyl)-(3-fluoro-6-methoxy-[1,5]naphthyridin-4-ylmethyl)-amino]-propyl}-2-oxo-oxazolidin-3-yl)-4H-1-benzo[1,4]oxazin-3-one A solution of the compound of Example 176 (0.07 g, 0.145 mmol) in THF/MeOH (1:1, 1 mL) was treated with (S)-glycidol (0.046 mL, 5 eq.). The mixture was heated at 70° C. for 6 h, concentrated in vacuo and purified by FC (EA/MeOH 19:1+1% $NH_4OH$) to give the title compound as a colourless solid (0.07 g, 87% yield).
MS (ESI, m/z): 556.2 [M+H$^+$].

Example 179

6-((R)-5-{3-[(3-fluoro-6-methoxy-[1,5]naphthyridin-4-ylmethyl)-(2-hydroxy-ethyl)-amino]-propyl}-2-oxo-oxazolidin-3-yl)-4H-benzo[1,4]oxazin-3-one

179.i. 6-((R)-5-{3-[[2-(tert-butyl-dimethyl-silanyloxy)-ethyl]-(3-fluoro-6-methoxy-[1,5]naphthyridin-4-ylmethyl)-amino]propyl}-2-oxo-oxazolidin-3-yl)-4H-benzo[1,4]oxazin-3-one The compound of Example 176 (0.11 g, 0.228 mmol) and (tert-butyl-dimethyl-silanyloxy)-acetaldehyde (0.44 mL, 1 eq.) were coupled according to method K. The title intermediate was isolated after FC (EA, EA/MeOH 9:1) as a yellowish oil (0.14 g, 96% yield).
MS (ESI, m/z): 640.4 [M+H$^+$].

179.ii. 6-((R)-5-{3-[(3-fluoro-6-methoxy-[1,5]naphthyridin-4-ylmethyl)-(2-hydroxy-ethyl)-amino]-propyl}-2-oxo-oxazolidin-3-yl)-4H-benzo[1,4]oxazin-3-one A solution of intermediate 179.i (0.14 g, 0.22 mmol) in THF was treated with TBAF (1M in THF, 1 eq.). The mixture was stirred at rt for 3 h, partitioned between water and EA. The org. phase was washed with brine, dried over $MgSO_4$ and concentrated. The residue was purified by FC (EA/MeOH 9:1+1% $NH_4OH$) to give the title compound as a colourless foam (0.09 g, 78% yield).
$^1$H NMR (DMSO d6) δ 10.69 (s, 1H), 8.80 (d, J=0.6 Hz, 1H), 8.27 (d, J=9.1 Hz, 1H), 7.30 (d, J=2.3 Hz, 1H), 7.22 (d, J=9.1 Hz, 1H), 6.93 (m, 1H), 6.88 (d, J=2.3 Hz, 1H), 4.53 (m, 3H), 4.23 (m, 3H), 4.02 (m, 4H), 3.50 (m, 3H), 2.58 (m, 4H), 1.59 (m, 4H).
MS (ESI, m/z): 526.1 [M+H$^+$].

Example 180

(S)-3-(2,3-dihydro-benzo[1,4]dioxin-6-yl)-5-{(1R,2S)-1,2-dihydroxy-3-[(6-methoxy-[1,5]naphthyridin-4-ylmethyl)-amino]-propyl}-oxazolidin-2-one

180.i. (2R,3S,5R,6R)-3-(tert-butyl-diphenyl-silanyloxymethyl)-5,6-dimethoxy-5,6-dimethyl-[1,4]dioxane-2-carbaldehyde

[(2S,3S,5R,6R)-3-(tert-butyl-diphenyl-silanyloxymethyl)-5,6-dimethoxy-5,6-dimethyl-[1,4]dioxan-2-yl]-methanol (prepared from dimethyl L-tartrate according to *J. Chem. Soc. Perkin* 1 (1999), 1635; 9.2 g, 19.4 mmol) was dissolved in DCM (100 mL) and cooled to 0° C. DIPEA (19.9 mL, 6 eq.) was added and a solution of Pyr.SO$_3$ complex (6.17 g, 2 eq.) in DMSO (27.5 mL, 20 eq.) was added dropwise over 20 min. The mixture was stirred at 0° C. for 4 h, diluted with DCM (200 mL) and washed several times with water. The org. phase was dried over $MgSO_4$ and concentrated. The title aldehyde was isolated after FC (Hept/EA 2:1) as a colourless oil (8.6 g, 94% yield).
$^1$H NMR (CDCl$_3$) δ: 9.70 (d, J=1.5 Hz, 1H), 7.70 (m, 4H), 7.40 (m, 6H), 4.30 (m, 1H), 3.86 (m, 3H), 3.27 (s, 3H), 3.21 (s, 3H), 1.58 (s, 3H), 1.37 (s, 3H), 1.27 (m, 9H).

180.ii. Tert-butyl-((2S,3S,5R,6R)-5,6-dimethoxy-5,6-dimethyl-3-vinyl-[1,4]dioxan-2-ylmethoxy)-diphenyl-silane A suspension of methyl triphenylphosphonium bromide (8.1 g, 22.8 mmol) in THF (70 mL) was treated with t-BuOK (2.56 g, 22.8 mmol). The mixture was stirred at rt for 1 h, cooled to 0° C. and a solution of intermediate 180.i (8.6 g, 18.2 mmol) in THF (70 mL) was added dropwise. The ice bath was removed and the mixture stirred at rt for 1 h. Ether was added and the org. phase washed with water and $NH_4Cl$ solution, dried over $MgSO_4$ and concentrated. The title compound was isolated after FC (Hept/EA 4:1) as a yellowish oil (7.5 g, 87% yield).
$^1$H NMR (CDCl$_3$) δ: 7.71 (m, 4H), 7.37 (m, 6H), 5.81 (m, 1H), 5.37 (m, 1H), 5.21 (ddd, J=10.3, 1.8, 0.6 Hz, 1H), 4.21 (m, 1H), 3.69 (m, 3H), 3.25 (m, 6H), 1.33 (s, 3H), 1.31 (s, 3H), 1.04 (m, 9H).

180.iii. Tert-butyl-((2S,3S,5R,6R)-5,6-dimethoxy-5,6-dimethyl-3-(RS)-oxiranyl-[1,4]dioxan-2-ylmethoxy)-diphenyl-silane To a solution of intermediate 180.ii (1.37 g, 2.9 mmol) in DCM (30 mL) was added MCPBA (70%; 0.858 g, 1.2 eq.). The mixture was stirred at rt for 24 h, diluted with DCM (20 mL) and washed with 1M NaOH (20 mL) and water, dried over $MgSO_4$ and concentrated. The crude product was purified by FC (Hept/EA 4:1) to give the title epoxides (1.03 g, 73% yield) as a inseparable 3:2 mixture of diastereoisomers (according to NMR). The mixture was used as such in the next step.

180.iv. (S)-1-[(2S,3S,5R,6R)-3-(tert-butyl-diphenyl-silanyloxymethyl)-5,6-dimethoxy-5,6-dimethyl-[1,4]dioxan-2-yl]-2-(2,3-dihydro-benzo[1,4]dioxin-6-ylamino)-ethanol and (R)-1-[(2S,3S,5R,6R)-3-(tert-butyl-diphenyl-silanyloxymethyl)-5,6-dimethoxy-5,6-dimethyl-[1,4]dioxan-2-yl]-2-(2,3-dihydro-benzo[1,4]dioxin-6-ylamino)-ethanol Intermediate 180.iii (2.3 g, 4.8 mmol) and 1,4-benzodioxan-6-amine (0.91 g, 1.25 eq.) were coupled according to method A. The two diastereomers were separated by FC (Hex/EA 3:1).
Major isomer (1.55 g, 50% yield, elutes first): (S)-1-[(2S,3S,5R,6R)-3-(tert-butyl-diphenyl-silanyloxymethyl)-5,6-dimethoxy-5,6-dimethyl-[1,4]dioxan-2-yl]-dihydro-benzo[1,4]dioxin-6-ylamino)-ethanol
$^1$H NMR (CDCl$_3$) δ: 7.67 (m, 4H), 7.40 (m, 6H), 6.69 (dd, J=8.2, 0.6 Hz, 1H), 6.21 (m, 2H), 4.59 (d, J=4.7 Hz, 1H), 4.20 (m, 4H), 4.02 (m, 2H), 3.93 (m, 1H), 3.74 (m, 4H), 3.46 (m, 1H), 3.22 (m, 5H), 3.01 (s, 3H), 1.28 (m, 3H), 1.17 (s, 3H), 1.02 (m, 9H).
Minor isomer (0.95 g, 31% yield, more polar): (R)-1-[(2S,3S,5R,6R)-3-(tert-butyl-diphenyl-silanyloxymethyl)-5,6- dimethoxy-5,6-dimethyl-[1,4]dioxan-2-yl]-2-(2,3-dihydro-benzo[1,4]dioxin-6-ylamino)-ethanol ¹H NMR (CDCl₃) δ: 7.69 (m, 4H), 7.38 (m, 6H), 6.68 (m, 1H), 6.21 (m, 2H), 4.20 (m, 4H), 3.99 (m, 2H), 3.91 (m, 1H), 3.78 (m, 2H), 3.43 (m, 2H), 3.23 (s, 3H), 3.16 (s, 3H), 1.30 (s, 3H), 1.26 (s, 3H), 1.02 (m, 9H).

180.v. (S)-5-[(2S,3S,5R,6R)-3-(tert-butyl-diphenyl-silanyloxymethyl)-5,6-dimethoxy-5,6-dimethyl-[1,4]dioxan-2-yl]-3-(2,3-dihydro-benzo[1,4]dioxin-6-yl)-oxazolidin-2-one Intermediate 180.iv (major isomer; 1.5 g, 2.4 mmol) was transformed into the desired oxazolidinone following method B. The title intermediate was isolated after FC (Hept/EA 2:1) as a colourless foam (1.25 g, 77% yield).

180.vi. (S)-3-(2,3-dihydro-benzo[1,4]dioxin-6-yl)-5-((2S,3S,5R,6R)-3-hydroxymethyl-5,6-dimethoxy-5,6-dimethyl-[1,4]dioxan-2-yl)-oxazolidin-2-one A solution of intermediate 180.v (1.2 g, 1.8 mmol) in THF (20 mL) was treated with a 1M solution of TBAF in THF (2 mL, 1.1 eq.). The mixture was stirred at rt for 1 h, partitioned between EA and water. The org. phase was washed with brine, dried over MgSO₄ and concentrated. The title intermediate was isolated after FC (Hept/EA 1:1, EA) as a colourless solid (0.63 g, 82% yield).

¹H NMR (CDCl₃) δ: 7.03 (m, 2H), 6.85 (d, J=8.5 Hz, 1H), 4.62 (dt, J=8.5, 6.7 Hz, 1H), 4.25 (m, 4H), 3.98 (m, 3H), 3.77 (m, 4H), 3.28 (s, 3H), 3.26 (s, 3H), 2.11 (t, J=0.6 Hz, 1H), 1.32 (s, 3H), 1.29 (s, 3H).

180.vii. Methanesulfonic acid (2S,3S,5R,6R)-3-[(S)-3-(2,3-dihydro-benzo[1,4]dioxin-6-yl)-2-oxo-oxazolidin-5-yl]-5,6-dimethoxy-5,6-dimethyl-[1,4]dioxan-2-ylmethyl ester MsCl (0.23 mL, 2 eq) was added dropwise to a solution of intermediate 180.vi (0.63 g, 1.49 mmol) and TEA (0.62 mL, 3 eq.) in DCM (12 mL) at 0° C. The mixture was stirred at 0° C. for 1 h, partitioned between DCM and water. The org. phase was dried over MgSO₄ and concentrated to give the title intermediate as a colourless foam (0.58 g, 77% yield).

¹H NMR (CDCl₃) δ: 7.02 (m, 2H), 6.86 (m, 1H), 4.56 (m, 2H), 4.37 (m, 1H), 4.25 (m, 4H), 3.99 (m, 2H), 3.91 (m, 2H), 3.28 (s, 3H), 3.25 (s, 3H), 3.10 (s, 3H), 1.31 (s, 3H), 1.31 (s, 3H).

180.viii. (S)-5-((2R,3S,5R,6R)-3-azidomethyl-5,6-dimethoxy-5,6-dimethyl-[1,4]dioxan-2-yl)-3-(2,3-dihydro-benzo[1,4]dioxin-6-yl)-oxazolidin-2-one A solution of intermediate 180.vii (0.58 g, 1.15 mmol) in DMF (5 mL) was treated with NaN₃ (0.09 g, 1.2 eq.). The mixture was heated at 80° C. overnight, partitioned between EA and water. The org. phase was washed with water and brine, dried over MgSO₄ and concentrated. The title azide was obtained after FC (Hex/EA 2:1, 1:1) as a colourless oil (0.48 g, 93% yield).

¹H NMR (CDCl₃) δ: 7.02 (m, 2H), 6.86 (d, J=8.8 Hz, 1H), 4.53 (m, 1H), 4.25 (m, 4H), 3.99 (m, 2H), 3.85 (m, 2H), 3.50 (d, J=5.0 Hz, 2H), 3.32 (s, 3H), 3.27 (s, 3H), 1.28 (m, 6H).

180.ix. (S)-5-((2R,3S,5R,6R)-3-aminomethyl-5,6-dimethoxy-5,6-dimethyl-[1,4]dioxan-2-yl)-3-(2,3-dihydro-benzo[1,4]dioxin-6-yl)-oxazolidin-2-one Intermediate 180.viii (0.48 g, 1 mmol) was hydrogenated over Pd/C in analogy to Example 33, step 33.i. The title amine was isolated as a greyish foam (0.4 g, 88% yield).

¹H NMR (CDCl₃) δ 7.01 (m, 2H), 6.85 (d, J=8.8 Hz, 1H), 4.60 (m, 1H), 4.24 (m, 4H), 3.99 (m, 2H), 3.86 (dd, J=9.7, 6.2 Hz, 1H), 3.74 (m, 1H), 3.63 (m, 1H), 3.28 (s, 3H), 3.26 (s, 3H), 2.95 (m, 2H), 1.31 (s, 3H), 1.28 (s, 3H).

180.x. (S)-3-(2,3-dihydro-benzo[1,4]dioxin-6-yl)-5-{(1R,2S)-1,2-dihydroxy-3-[(6)-methoxy-[1,5]naphthyridin-4-ylmethyl)-amino]-propyl}-oxazolidin-2-one Intermediate 180.ix (0.045 g, 0.1 mmol) and 6-methoxy-[1,5]naphthyridine-4-carbaldehyde (0.02 g, 1 eq.) were coupled according to method K. The coupling product was isolated after FC (EA/MeOH 9:1). This intermediate was dissolved in TFA/H₂O 3:1 and heated at 80° C. for 3 h. The volatiles were removed under reduced pressure and the residue partitioned between DCM and NH₄OH. The org. phase was washed with water, dried over MgSO₄ and concentrated. The residue was purified by FC (EA/MeOH 9:1+1% NH₄OH) to give the title compound as a colourless foam (0.034 g, 66% yield).

¹H NMR (CDCl₃) δ: 8.70 (d, J=4.4 Hz, 1H), 8.20 (d, J=9.1 Hz, 1H), 7.46 (d, J=4.4 Hz, 1H), 7.12 (d, J=9.1 Hz, 1H), 7.05 (d, J=2.6 Hz, 1H), 6.92 (dd, J=8.8, 2.6 Hz, 1H), 6.81 (m, 1H), 4.62 (m, 1H), 4.37 (s, 2H), 4.22 (s, 4H), 4.02 (m, 10H), 3.70 (dd, J=7.6, 1.2 Hz, 1H), 3.05 (m, 1H), 2.93 (m, 1H).

MS (ESI, m/z): 483.3 [M+H⁺].

Example 181

(S)-3-(2,3-dihydro-benzo[1,4]dioxin-6-yl)-5-{(1R,2S)-3-[(3-fluoro-6-methoxy-quinolin-4-ylmethyl)-amino]-1,2-dihydroxy-propyl}-oxazolidin-2-one The title compound was obtained as a beige solid (0.03 g) starting from intermediate 180.ix (0.13 g, 0.3 mmol) and 3-fluoro-6-methoxy-quinoline-4-carbaldehyde (0.059 g, 1 eq.) and following the procedure of Example 180, step 180.x.

¹H NMR (CDCl₃) δ: 8.63 (s, 1H), 8.01 (d, J=9.1 Hz, 1H), 7.33 (dd, J=9.1, 2.3 Hz, 1H), 7.27 (m, 3H), 7.07 (d, J=2.6 Hz, 1H), 6.97 (dd, J=9.1, 2.6 Hz, 1H), 6.83 (m, 1H), 4.61 (m, 1H), 4.25 (m, 6H), 3.98 (m, 7H), 3.68 (m, 1H), 3.08 (m, 1H), 2.92 (dd, J=12.3, 6.2 Hz, 1H).

MS (ESI, m/z): 500.2 [M+H⁺].

Example 182

(S)-3-(2,3-dihydro-benzo[1,4]dioxin-6-yl)-5-{(1R,2S)-1,2-dihydroxy-3-[(3-methoxy-quinoxalin-5-ylmethyl)-amino]-propyl}-oxazolidin-2-one The title compound was obtained as a beige solid (0.016 g) starting from intermediate 180.ix (0.13 g, 0.3 mmol) and 3-methoxy-quinoxaline-5-carbaldehyde (0.059 g, 1 eq.) and following the procedure of Example 180, step 180.x.

MS (ESI, m/z): 483.3 [M+H⁺].

Example 183

(R)-3-(2,3-dihydro-benzo[1,4]dioxin-6-yl)-5-{(1R, 2S)-1,2-dihydroxy-3-[(6-methoxy-[1,5]naphthyridin-4-ylmethyl)-amino]propyl}-oxazolidin-2-one

183.i. (R)-5-((2R,3S,5R,6R)-3-aminomethyl-5,6-dimethoxy-5,6-dimethyl-[1,4]dioxan-2-yl)-3-(2,3-dihydro-benzo[1,4]dioxin-6-yl)-oxazolidin-2-one The title intermediate was obtained as a greyish solid (0.2 g, 0.44 mmol) starting from intermediate 180.iv (minor isomer, 0.95 g, 1.5 mmol) and following the procedures of Example 180, steps 180.v to 180.ix.

$^1$H NMR (CDCl$_3$) δ: 7.02 (m, 2H), 6.85 (m, 1H), 4.77 (s, 1H), 4.25 (m, 4H), 4.04 (m, 2H), 3.92 (m, 1H), 3.82 (dd, J=9.7, 2.3 Hz, 1H), 3.24 (m, 3H), 3.22 (s, 3H), 2.97 (d, J=3.5 Hz, 1H), 2.84 (dd, J=13.2, 6.7 Hz, 1H), 1.43 (s, 3H), 1.29 (s, 3H).

183.ii. (R)-3-(2,3-dihydro-benzo[1,4]dioxin-6-yl)-5-{(1R,2S)-1,2-dihydroxy-3-[(6-methoxyl-[1,5]naphthyridin-4-ylmethyl)-amino]-propyl}-oxazolidin-2-one The title compound was obtained as a beige solid (0.032 g) starting from intermediate 183.i (0.1 g, 0.23 mmol) and 6-methoxy-[1,5]naphthyridine-4-carbaldehyde (0.044 g, 1 eq.) and following the procedure of Example 180, step 180.x.

MS (ESI, m/z): 483.3 [M+H$^+$].

Example 184

(R)-3-(2,3-dihydro-benzo[1,4]dioxin-6-yl)-5-{(1R, 2S)-3-[(3-fluoro-6-methoxy-[1,5]naphthyridin-4-ylmethyl)-amino]-1,2-dihydroxy-propyl}-oxazolidin-2-one The title compound was obtained as a beige solid (0.015 g) starting from intermediate 183.i (0.1 g, 0.23 mmol) and 3-fluoro-6-methoxy-[1,5]naphthyridine-4-carbaldehyde (0.049 g, 1 eq.) and following the procedure of Example 180, step 180.x.

MS (ESI, m/z): 501.3 [M+H$^+$].

Example 185

6-((S)-5-{(1R,2S)-1,2-dihydroxy-3-[(6-methoxy-[1,5]naphthyridin-4-ylmethyl)-amino]propyl}-2-oxo-oxazolidin-3-yl)-4H-1-benzo[1,4]thiazin-3-one

185.i. 6-{(S)-2-[(2S,3S,5R,6R)-3-(tert-butyl-diphenyl-silanyloxymethyl)-5,6-dimethoxy-5,6-dimethyl-[1,4]dioxan-2-yl]-2-hydroxy-ethylamino}-4H-benzo[1,4]thiazin-3-one This intermediate was obtained starting from intermediate 180.iii (5 g, 10.3 mmol) and 6-amino-4H-benzo[1,4]thiazin-3-one (2.3 g, 1.25 eq.) following method A. The major (less polar) diastereoisomer was isolated after FC (Hex/EA 4:1, 2:1) as a colourless foam (1.37 g, 20% yield).

$^1$H NMR (CDCl$_3$) δ: 7.96 (s, 1H), 7.66 (m, 4H), 7.40 (m, 6H), 7.07 (d, J=8.5 Hz, 1H), 6.35 (dd, J=8.5, 2.3 Hz, 1H), 6.12 (d, J=2.3 Hz, 1H), 4.42 (m, 1H), 4.76 (d, J=4.1 Hz, 1H), 4.03 (m, 1H), 3.93 (m, 1H), 3.74 (m, 3H), 3.49 (m, 1H), 3.38 (s, 2H), 3.28 (m, 1H), 3.19 (s, 3H), 3.00 (s, 3H), 1.27 (s, 3H), 1.17 (s, 3H), 1.05 (m, 9H).

185.ii. 6-[(S)-5-((2R,3S,5R,6R)-3-aminomethyl-5,6-dimethoxy-5,6-dimethyl-[1,4]dioxan-2-yl)-2-oxo-oxazolidin-3-yl]-4H-benzo[1,4]thiazin-3-one The title intermediate was obtained as a colourless foam (0.4 g) starting from intermediate 185.i (1.35 g, 2.02 mmol) and following the procedures of Example 180, steps 180.v to 180.ix.

$^1$H NMR (CDCl$_3$) δ: 7.42 (d, J=2.3 Hz, 1H), 7.27 (m, 1H), 6.93 (dd, J=8.5, 2.3 Hz, 1H), 4.65 (m, 1H), 4.01 (m, 2H), 3.89 (dd, J=10.0, 5.9 Hz, 1H), 3.63 (m, 1H), 3.39 (s, 2H), 3.27 (s, 3H), 3.25 (s, 3H), 2.94 (m, 2H), 1.30 (s, 3H), 1.26 (m, 3H).

185.iii. 6-((S)-5-{(1R,2S)-1,2-dihydroxy-3-[(6-methoxy-[1,5]naphthyridin-4-ylmethyl)-amino]propyl}-2-oxo-oxazolidin-3-yl)-4H-benzo[1,4]thiazin-3-one The title compound was obtained as a beige solid (0.052 g) starting from intermediate 185.ii (0.132 g, 0.29 mmol) and 6-methoxy-[1,5]naphthyridine-4-carbaldehyde (0.055 g, 1 eq.) and following the procedure of Example 180, step 180.x.

MS (ESI, m/z): 512.4 [M+H$^+$].

Example 186

6-((S)-5-{(1R,2S)-3-[(3-fluoro-6-methoxy-[1,5]naphthyridin-4-ylmethyl)-amino]-1,2-dihydroxy-propyl}-2-oxo-oxazolidin-3-yl)-4H-benzo[1,4]thiazin-3-one The title compound was obtained as a beige solid (0.053 g) starting from intermediate 185.ii (0.133 g, 0.29 mmol) and 3-fluoro-6-methoxy-[1,5]naphthyridine-4-carbaldehyde (0.06 g, 1 eq.) and following the procedure of Example 180, step 180.x.

MS (ESI, m/z): 530.2 [M+H$^+$].

Example 187

6-((S)-5-{(1R,2S)-3-[(3-fluoro-6-methoxy-quinolin-4-ylmethyl)-amino]-1,2-dihydroxy-propyl}-2-oxo-oxazolidin-3-yl)-4H-benzo[1,4]thiazin-3-one The title compound was obtained as a beige solid (0.033 g) starting from intermediate 185.ii (0.133 g, 0.29 mmol) and 3-fluoro-6-methoxy-quinoline-4-carbaldehyde (0.06 g, 1 eq.) and following the procedure of Example 180, step 180.x.

MS (ESI, m/z): 529.3 [M+H$^+$].

Example 188

(R)-3-(2,3-dihydro-benzo[1,4]dioxin-6-yl)-5-{(1S, 2R)-1,2-dihydroxy-3-[(6-methoxy-[1,5]naphthyridin-4-ylmethyl)-amino]-propyl}-oxazolidin-2-one

188.i. Tert-butyl-((2R,3R,5S,6S)-5,6-dimethoxy-5,6-dimethyl-3-(RS)-oxiranyl-[1,4]dioxan-2-ylmethoxy)-diphenyl-silane This intermediate was prepared starting from [(2R,3R,5S,6S)-3-(tert-butyl-diphenyl-silanyloxymethyl)-5,6-dimethoxy-5,6-dimethyl-[1,4]dioxan-2-yl]-methanol (prepared from dimethyl D-tartrate according to J. Chem. Soc. Perkin 1 (1999), 1635; 11 g, 23 mmol) and following the procedure of Example 180, steps 180.i to 180.iii. The compound was isolated as a colourless oil (4.7 g) as a 3:2 mixture of diastereomers.

188.ii. (R)-1-[(2R,3R,5S,6S)-3-(tert-butyl-diphenyl-silanyloxymethyl)-5,6-dimethoxy-5,6-dimethyl-[1,4]dioxan-2-yl]-2-(2,3-dihydro-benzo[1,4]dioxin-6-ylamino)-ethanol and (S)-1-[(2R,3R,5S,6S)-3-(tert-Butyl-diphenyl-silanyloxymethyl)-5,6-dimethoxy-5,6-dimethyl-[1,4]dioxan-2-yl]-2-(2,3-dihydro-benzo[1,4]dioxin-6-ylamino)-ethanol Intermediate 1881 (3.0 g, 6.1 mmol) and 1,4-benzodioxan-6-amine (1.02 g, 1 eq.) were coupled according to method A. The two diastereomers were separated by FC (Hex/EA 3:1).

Major isomer (1.94 g, 49% yield, elutes first): (R)-1-[(2R,3R,5S,6S)-3-(tert-butyl-diphenyl-silanyloxymethyl)-5,6-dimethoxy-5,6-dimethyl-[1,4]dioxan-2-yl]-2-(2,3-dihydro-benzo[1,4]dioxin-6-ylamino)-ethanol $^1$H NMR (CDCl$_3$) δ 7.67 (m, 4H), 7.40 (m, 6H), 6.69 (dd, J=8.2, 0.6 Hz, 1H), 6.21 (m, 2H), 4.59 (d, J=4.7 Hz, 1H), 4.20 (m, 4H), 4.02 (m, 2H), 3.93 (m, 1H), 3.74 (m, 4H), 3.46 (m, 1H), 3.22 (m, 5H), 3.01 (s, 3H), 1.28 (m, 3H), 1.17 (s, 3H), 1.02 (m, 9H).

Minor isomer (1.5 g, 39% yield, more polar): (S)-1-[(2R,3R,5S,6S)-3-(tert-butyl-diphenyl-silanyloxymethyl)-5,6-dimethoxy-5,6-dimethyl-[1,4]dioxan-2-yl]-2-(2,3-dihydro-benzo[1,4]dioxin-6-ylamino)-ethanol $^1$H NMR (CDCl$_3$) δ: 7.69 (m, 4H), 7.38 (m, 6H), 6.68 (m, 1H), 6.21 (m, 2H), 4.20 (m, 4H), 3.99 (m, 2H), 3.91 (m, 1H), 3.78 (m, 2H), 3.43 (m, 2H), 3.23 (s, 3H), 3.16 (s, 3H), 1.30 (s, 3H), 1.26 (s, 3H), 1.02 (m, 9H).

188.iii. (R)-5-((2S,3R,5S,6S)-3-aminomethyl-5,6-dimethoxy-5,6-dimethyl-[1,4]dioxan-2-yl)-3-(2,3-dihydro-benzo[1,4]dioxin-6-yl)-oxazolidin-2-one The title intermediate was obtained as a colourless foam (0.37 g) starting from intermediate 188.ii (major isomer; 1.94 g, 3.04 mmol) and following the procedures of Example 180, steps 180.v to 180.ix.

$^1$H NMR (CDCl$_3$) δ: 7.02 (m, 2H), 6.85 (m, 1H), 4.60 (m, 1H), 4.24 (m, 4H), 3.99 (m, 2H), 3.85 (dd, J=10.0, 6.4 Hz, 1H), 3.63 (m, 1H), 3.28 (s, 3H), 3.25 (s, 3H), 2.94 (m, 2H), 1.31 (s, 3H), 1.28 (s, 3H).

188.iv. (R)-3-(2,3-dihydro-benzo[1,4]dioxin-6-yl)-5-{(1S,2R)-1,2-dihydroxy-3-[(6-methoxy-[1,5]naphthyridin-4-ylmethyl)-amino]propyl}-oxazolidin-2-one The title compound was obtained as a beige solid (0.12 g) starting from intermediate 188.iii (0.185 g, 0.43 mmol) and 6-methoxy-[1,5]naphthyridine-4-carbaldehyde (0.082 g, 1 eq.) and following the procedure of Example 180, step 180.x.

$^1$H NMR (CDCl$_3$) δ: 8.73 (d, J=4.4 Hz, 1H), 8.23 (d, J=9.1 Hz, 1H), 7.45 (d, J=4.4 Hz, 1H), 7.15 (d, J=9.1 Hz, 1H), 7.08 (d, J=2.6 Hz, 1H), 6.98 (m, 1H), 6.84 (m, 1H), 4.63 (m, 1H), 4.33 (s, 2H), 4.24 (s, 4H), 4.08 (m, 3H), 4.02 (m, 3H), 3.69 (dd, J=8.2, 1.5 Hz, 1H), 2.99 (d, J=3.8 Hz, 1H), 2.87 (m, 1H).
MS (ESI, m/z): 483.3 [M+H$^+$].

Example 189

(R)-3-(2,3-dihydro-benzo[1,4]dioxin-6-yl)-5-{(1S,2R)-3-[(3-fluoro-6-methoxy-[1,5]naphthyridin-4-ylmethyl)-amino]-1,2-dihydroxy-propyl}-oxazolidin-2-one The title compound was obtained as a beige solid (0.07 g) starting from intermediate 188.iii (0.185 g, 0.43 mmol) and 3-fluoro-6-methoxy-[1,5]naphthyridine-4-carbaldehyde (0.09 g, 1 eq.) and following the procedure of Example 180, step x).
MS (ESI, m/z): 501.3 [M+H$^+$].

Example 190

(S)-3-(2,3-dihydro-benzo[1,4]dioxin-6-yl)-5-{(1S,2R)-1,2-dihydroxy-3-[(6-methoxy-[1,5]naphthyridin-4-ylmethyl)-amino]-propyl}-oxazolidin-2-one 190.i. (S)-5-((2S,3R,5S,6S)-3-aminomethyl-5,6-dimethoxy-5,6-dimethyl-[1,4]dioxan-2-yl)-3-(2,3-dihydro-benzo[1,4]dioxin-6-yl)-oxazolidin-2-one The title intermediate was obtained as a colourless foam (0.37 g) starting from intermediate 188.ii (minor isomer; 1.5 g, 2.4 mmol) and following the procedures of Example 180, steps 180.v to 180.ix.

$^1$H NMR (CDCl$_3$) δ: 7.03 (m, 2H), 6.86 (m, 1H), 4.76 (m, 1H), 4.24 (m, 4H), 4.04 (m, 2H), 3.92 (m, 1H), 3.82 (dd, J=9.7, 2.1 Hz, 1H), 3.24 (s, 3H), 3.22 (s, 3H), 2.99 (m, 1H), 2.84 (dd, J=13.2, 6.7 Hz, 1H), 1.29 (s, 3H), 1.27 (m, 3H).

190.ii. (S)-3-(2,3-dihydro-benzo[1,4]dioxin-6-yl)-5-{(1S,2R)-1,2-dihydroxy-3-[(6-methoxy-[1,5]naphthyridin-4-ylmethyl)-amino]-propyl}-oxazolidin-2-one The title compound was obtained as a beige solid (0.12 g) starting from intermediate 190.i (0.21 g, 0.49 mmol) and 6-methoxy-[1,5]naphthyridine-4-carbaldehyde (0.093 g, 1 eq.) and following the procedure of Example 180, step 180.x.
MS (ESI, m/z): 483.3 [M+H$^+$].

Example 191

6-((R)-5-{(1S,2R)-1,2-dihydroxy-3-[(6-methoxy-[1,5]naphthyridin-4-ylmethyl)-amino]-propyl}-2-oxo-oxazolidin-3-yl)-4H-benzo[1,4]thiazin-3-one 191.i. 6-{(R)-2-[(2R,3R,5S,6S)-3-(tert-butyl-diphenyl-silanyloxymethyl)-5,6-dimethoxy-5,6-dimethyl-[1,4]dioxan-2-yl]-2-hydroxy-ethylamino}-4H-benzo[1,4]thiazin-3-one and 6-{(S)-2-[(2R,3R,5S,6S)-3-(tert-butyl-diphenyl-silanyloxymethyl)-5,6-dimethoxy-5,6-dimethyl-[1,4]dioxan-2-yl]-2-hydroxy-ethylamino}-4H-benzo[1,4]thiazin-3-one Intermediate 188.i (3.1 g, 6.4 mmol) and 6-amino-4H-benzo[1,4]thiazin-3-one (1.15 g, 1 eq.) were coupled according to method A. The two diastereomers were separated by FC (Hex/EA 4:1, 1:1).

Major isomer (1.49 g, 35% yield, elutes first): (R)-enantiomer:
$^1$H NMR (CDCl$_3$) δ: 7.72 (s, 1H), 7.66 (m, 4H), 7.40 (m, 6H), 7.07 (d, J=8.5 Hz, 1H), 6.34 (dd, J=8.5, 2.6 Hz, 1H), 6.10 (d, J=2.3 Hz, 1H), 4.75 (d, J=4.1 Hz, 1H), 4.02 (m, 1H), 3.91 (m, 1H), 3.73 (m, 3H), 3.46 (d, J=3.2 Hz, 1H), 3.37 (s, 2H), 3.25 (m, 1H), 3.19 (s, 3H), 3.00 (s, 3H), 1.26 (m, 6H), 1.05 (s, 9H).

Minor isomer (0.59 g, 14% yield, more polar): (S)-enantiomer:
$^1$H NMR (CDCl$_3$) δ: 7.66 (m, 4H), 7.37 (m, 6H), 7.06 (d, J=8.5 Hz, 1H), 6.30 (dd, J=8.2, 2.1 Hz, 1H), 6.03 (d, J=2.3 Hz, 1H), 4.27 (m, 1H), 3.98 (m, 3H), 3.78 (d, J=3.5 Hz, 2H), 3.35

(s, 2H), 3.28 (m, 2H), 3.24 (s, 3H), 3.14 (s, 3H), 2.81 (d, J=9.4 Hz, 1H), 1.27 (m, 6H), 1.03 (s, 9H).

191.ii. 6-[(R)-5-((2S,3R,5S,6S)-3-aminomethyl-5,6-dimethoxy-5,6-dimethyl-[1,4]dioxan-2-yl)-2-oxo-oxazolidin-3-yl]-4H-benzo[1,4]thiazin-3-one The title intermediate was obtained as a colourless foam (1.36 g) starting from intermediate 191.i (major isomer; 3.29 g, 4.9 mmol) and following the procedures of Example 180, steps 180.v to 180.ix.
MS (ESI, m/z): 454.2 [M+H$^+$].

191.iii. 6-((R)-5-{(1S,2R)-1,2-dihydroxy-3-[(6-methoxy-[1,5]naphthyridin-4-ylmethyl)-amino]-propyl}-2-oxo-oxazolidin-3-yl)-4H-benzo[1,4]thiazin-3-one The title compound was obtained as a beige solid (0.03 g) starting from intermediate 191.ii (0.15 g, 0.33 mmol) and 6-methoxy-[1,5]naphthyridine-4-carbaldehyde (0.062 g, 1 eq.) and following the procedure of Example 180, step 180.x.
MS (ESI, m/z): 512.3 [M+H$^+$].

Example 192

6-((R)-5-{(1S,2R)-1,2-dihydroxy-3-[(3-methoxy-quinoxalin-5-ylmethyl)-amino]-propyl}-2-oxo-oxazolidin-3-yl)-4H-benzo[1,4]thiazin-3-one The title compound was obtained as a beige solid (0.03 g) starting from intermediate 191.ii (0.15 g, 0.33 mmol) and 3-methoxy-quinoxaline-5-carbaldehyde (0.062 g, 1 eq.) and following the procedure of Example 180, step 180.x.
MS (ESI, m/z): 512.3 [M+H$^+$].

Example 193

6-((R)-5-{(1S,2R)-3-[(3-fluoro-6-methoxy-[1,5]naphthyridin-4-ylmethyl)-amino]-1,2-dihydroxy-propyl}-2-oxo-oxazolidin-3-yl)-4H-benzo[1,4]thiazin-3-one The title compound was obtained as a beige solid (0.045 g) starting from intermediate 191.ii (0.15 g, 0.33 mmol) and 3-fluoro-6-methoxy-[1,5]naphthyridine-4-carbaldehyde (0.069 g, 1 eq.) and following the procedure of Example 180, step 180.x.
MS (ESI, m/z): 530.2 [M+H$^+$].

Example 194

6-((R)-5-{(1S,2R)-3-[(3-fluoro-6-methoxy-quinolin-4-ylmethyl)-amino]-1,2-dihydroxy-propyl}-2-oxo-oxazolidin-3-yl)-4H-benzo[1,4]thiazin-3-one The title compound was obtained as a beige solid (0.01 g) starting from intermediate 191.ii (0.15 g, 0.33 mmol) and 3-fluoro-6-methoxy-quinoline-4-carbaldehyde (0.069 g, 1 eq.) and following the procedure of Example 180, step 180.x.
MS (ESI, m/z): 529.2 [M+H$^+$].

Example 195

6-((S)-5-{(1S,2R)-3-[(3-fluoro-6-methoxy-[1,5]naphthyridin-4-ylmethyl)-amino]-1,2-dihydroxy-propyl}-2-oxo-oxazolidin-3-yl)-4H-benzo[1,4]thiazin-3-one

195.i. 6-[(S)-5-((2S,3R,5S,6S)-3-aminomethyl-5,6-dimethoxy-5,6-dimethyl-[1,4]dioxan-2-yl)-2-oxo-oxazolidin-3-yl]-4H-benzo[1,4]thiazin-3-one The title intermediate was obtained as a colourless foam (0.23 g) starting from intermediate 191.i (minor isomer; 0.91 g, 1.36 mmol) and following the procedures of Example 180, steps 180.v to 180.ix.
MS (ESI, m/z): 454.2 [M+H$^+$].

195.ii. 6-((S)-5-{(1S,2R)-3-[(3-fluoro-6-methoxy-[1,5]naphthyridin-4-ylmethyl)-amino]-1,2-dihydroxy-propyl}-2-oxo-oxazolidin-3-yl)-4H-benzo[1,4]thiazin-3-one The title compound was obtained as a beige solid (0.01 g). starting from intermediate 195.i (0.116 g, 0.26 mmol) and 3-fluoro-6-methoxy-[1,5]naphthyridine-4-carbaldehyde (0.052 g, 1 eq.) and following the procedure of Example 180, step 180.x.
MS (ESI, m/z): 530.2 [M+H$^+$].

Example 196

6-((R)-5-{(1S,2R)-3-[(3-fluoro-6-methoxy-[1,5]naphthyridin-4-ylmethyl)-amino]-1,2-dihydroxy-propyl}-2-oxo-oxazolidin-3-yl)-4H-benzo[1,4]oxazin-3-one

196.i. 6-{(R)-2-[(2R,3R,5S,6S)-3-(tert-butyl-diphenyl-silanyloxymethyl)-5,6-dimethoxy-5,6-dimethyl-[1,4]dioxan-2-yl]-2-hydroxy-ethylamino}-4H-benzo[1,4]oxazin-3-one and 6-{(S)-2-[(2R,3R,5S,6S)-3-(tert-butyl-diphenyl-silanyloxymethyl)-5,6-dimethoxy-5,6-dimethyl-[1,4]dioxan-2-yl]-2-hydroxy-ethylamino}-4H-benzo[1,4]oxazin-3-one Intermediate 188.i (5.1 g, 10.5 mmol) and 6-amino-4H-benzo[1,4]oxazin-3-one (1.72 g, 1 eq.) were coupled according to method A. The two diastereomers were separated by FC (Hex/EA 4:1, 1:1).
Major isomer (2.2 g, 32% yield, elutes first): 6-{(R)-2-[(2R,3R,5S,6S)-3-(tert-butyl-diphenyl-silanyloxymethyl)-5,6-dimethoxy-5,6-dimethyl-[1,4]dioxan-2-yl]-2-hydroxy-ethylamino}-4H-benzo[1,4]oxazin-3-one
MS (ESI, m/z): 651.1 [M+H$^+$].
Minor isomer (0.72 g, 10% yield, more polar): 6-{(S)-2-[(2R,3R,5S,6S)-3-(tert-butyl-diphenyl-silanyloxymethyl)-5,6-dimethoxy-5,6-dimethyl-[1,4]dioxan-2-yl]-2-hydroxy-ethylamino}-4H-benzo[1,4]oxazin-3-one
MS (ESI, m/z): 651.1 [M+H$^+$].

196.ii. 6-[(R)-5-((2S,3R,5S,6S)-3-aminomethyl-5,6-dimethoxy-5,6-dimethyl-[1,4]dioxan-2-yl)-2-oxo-oxazolidin-3-yl]-4H-benzo[1,4]oxazin-3-one The title intermediate was obtained as a colourless foam (0.95 g) starting from intermediate 196.i (major isomer; 2.2 g, 3.4 mmol) and following the procedures of Example 180, steps 180.v to 180.ix.
MS (ESI, m/z): 438.2 [M+H$^+$].

196.iii. 6-((R)-5-{(1S,2R)-1,2-dihydroxy-3-[(6-methoxy-[1,5]naphthyridin-4-ylmethyl)-amino]-propyl}-2-oxo-oxazolidin-3-yl)-4H-benzo[1,4]oxazin-3-one The title compound was obtained as a beige solid (0.015 g) starting from intermediate 196.ii (0.5 g, 1.14 mmol) and 3-fluoro-6-methoxy-[1,5]naphthyridine-4-carbaldehyde (0.235 g, 1 eq.) and following the procedure of Example 180, step 180.x.
MS (ESI, m/z): 514.2 [M+H$^+$].

Example 197

6-((R)-5-{(1S,2R)-3-[(3-fluoro-6-methoxy-quinolin-4-ylmethyl)-amino]-1,2-dihydroxy-propyl}-2-oxo-oxazolidin-3-yl)-4H-benzo[1,4]oxazin-3-one The title compound was obtained as a beige solid (0.011 g) starting from intermediate 196.ii (0.225 g, 0.514 mmol) and 3-fluoro-6-methoxy-quinoline-4-carbaldehyde (0.105 g, 1 eq.) and following the procedure of Example 180, step 180.x.
MS (ESI, m/z): 512.17 [M+H$^+$].

Example 198

6-((S)-5-{(1S,2R)-3-[(3-fluoro-6-methoxy-[1,5]naphthyridin-4-ylmethyl)-amino]-1,2-dihydroxy-propyl}-2-oxo-oxazolidin-3-yl)-4H-benzo[1,4]oxazin-3-one 198.i. 6-[(S)-5-((2S,3R,5S,6S)-3-aminomethyl-5,6-dimethoxy-5,6-dimethyl-[1,4]dioxan-2-yl)-2-oxo-oxazolidin-3-yl]-4H-benzo[1,4]oxazin-3-one The title intermediate was obtained as a colourless foam (0.27 g) starting from intermediate 196.i (minor isomer; 0.72 g, 1.1 mmol) and following the procedures of Example 180, steps 180.v to 180.ix.
MS (ESI, m/z): 438.3 [M+H$^+$].

198.ii. 6-((S)-5-{(1S,2R)-3-[(3-fluoro-6-methoxy-[1,5]naphthyridin-4-ylmethyl)-amino]-1,2-dihydroxy-propyl}-2-oxo-oxazolidin-3-yl)-4H-benzo[1,4]oxazin-3-one The title compound was obtained as a beige solid (0.032 g) starting from intermediate 198.i (0.27 g, 0.62 mmol) and 3-fluoro-6-methoxy-[1,5]naphthyridine-4-carbaldehyde (0.127 g, 1 eq.) and following the procedure of Example 180, step 180.x.
MS (ESI, m/z): 514.28 [M+H$^+$].

Example 199

2-(6-methoxy-[1,5]naphthyridin-4-yloxy)-N-[(R)-2-oxo-3-(3-oxo-3,4-dihydro-2H-1-benzo[1,4]thiazin-6-yl)-oxazolidin-5-ylmethyl]-acetamide 199.i. (6-methoxy-[1,5]naphthyridin-4-yloxy)-acetic acid K$_2$CO$_3$ (785 mg, 1 eq.) was added to a suspension of 6-methoxy-[1,5]naphthyridin-4-ol (1 g, 5.7 mmol, WO 02/08224) in DMSO (7 mL). The mixture was vigorously stirred for 2.5 h after which ethyl bromoacetate was added dropwise. The resulting mixture was heated at 50° C. for 4 h. 2N NaOH (5 mL) was then added at 50° C. and stirring was continued at rt overnight. The mixture was quenched with water. AcOH was added and the mixture was extracted with DCM/MeOH 9:1. The org. layer was washed with water, dried over MgSO$_4$ and concentrated to afford the title intermediate as a pale yellow solid (693 mg, 52% yield).
MS (ESI, m/z): 235.2 [M+H$^+$].

199.ii. 2-(6-methoxy-[1,5]naphthyridin-4-yloxy)-N-[(R)-2-oxo-3-(3-oxo-3,4-dihydro-2H-benzo[1,4]thiazin-6-yl)-oxazolidin-5-ylmethyl]-acetamide Starting from intermediate 199.i (127 mg, 0.54 mmol) and intermediate 4.v (227 mg, 1.5 eq.) and using method I, the title compound was obtained as a yellow solid (21 mg, 8% yield).
MS (ESI, m/z): 496.1 [M+H$^+$].

Example 200

(RS)-3-(3-fluoro-4-methyl-phenyl)-5-{2-[(RS)-2-hydroxy-2-(3-methoxy-quinoxalin-5-yl)-ethylamino]-ethyl}-oxazolidin-2-one 200.i. (RS)-(2-oxiranyl-ethyl)-carbamic acid benzyl ester To a solution of but-3-enyl-carbamic acid benzyl ester (prepared according to *Heterocycles* (2006), 67(2), 549-554; 21.5 g, 105 mmol) in chloroform (380 mL) was added, dropwise over a period of 1 h, a solution of MCPBA (28.3 g, 1.1 eq.) in chloroform (270 mL) at 10° C. Stirring was continued for 20 h at rt. The reaction mixture was filtered and 10% sodium sulfite solution was added to the filtrate (until starch-iodide paper test was negative). The mixture was washed with 5% Na$_2$CO$_3$ and brine. The org. layer was dried over MgSO$_4$ and concentrated to afford the title intermediate as a colourless liquid (21.6 g, 93% yield).
MS (ESI, m/z): 222.1 [M+H$^+$].

200.ii. (RS)-[4-(3-fluoro-4-methyl-phenylamino)-3-hydroxy-butyl]-carbamic acid benzyl ester Starting from intermediate 200.i (8.84 g, 40.0 mmol) and 3-fluoro-4-methyl-phenylamine (commercial; 5.0 g, 1 eq.) and using method A, the title compound was obtained as a brown oil (5.1 g, 37% yield).
MS (ESI, m/z): 347.1 [M+H$^+$].

200.iii. (RS)-{2-[3-(3-fluoro-4-methyl-phenyl)-2-oxo-oxazolidin-5-yl]ethyl}-carbamic acid benzyl ester Starting from intermediate 200.ii (3.0 g, 8.66 mmol) and using method B, the title compound was obtained as a beige solid (1.7 g, 53% yield).
MS (ESI, m/z): 373.2 [M+H$^+$].

200.iv. (RS)-5-(2-amino-ethyl)-3-(3-fluoro-4-methyl-phenyl)-oxazolidin-2-one

A solution of intermediate 200.iii (1.65 g, 4.43 mmol) in MeOH (30 mL) was hydrogenated over Pd(OH)$_2$ (20% on charcoal, 235 mg) for 3 h. The catalyst was filtered off and the filtrate was concentrated to afford the title intermediate as a beige solid (690 mg, 65% yield).
MS (ESI, m/z): 239.0 [M+H$^+$].

200.v. (RS)-3-(3-fluoro-4-methyl-phenyl)-5-{2-[(RS)-2-hydroxy-2-(3-methoxy-quinoxalin-5-yl)-ethylamino]-ethyl}-oxazolidin-2-one Starting from intermediate 200.iv (118 mg, 0.50 mmol) and rac-2-methoxy-8-oxiranyl-quinoxaline (prepared as in WO 2004/002490; 100 mg, 0.50 mmol) and using method A, the title compound was obtained as an off-white solid (2.2 mg, 1% yield).

$^1$H NMR (CDCl$_3$) δ: 8.50 (s, 1H), 7.95 (dd, J=8.5, 1.5 Hz, 1H), 7.76 (m, 1H), 7.56 (m, 1H), 7.33 (dd, J=12.0, 2.1 Hz, 1H), 7.13 (m, 2H), 5.54 (m, 1H), 5.54 (m, 1H), 4.78 (m, 1H), 4.06 (s, 3H), 3.63 (m, 2H), 3.13 (m, 1H), 2.95 (m, 3H), 2.24 (d, J=1.8 Hz, 3H), 1.99 (m, 2H).

MS (ESI, m/z): 239.0 [M+H$^+$].

Example 201

6-((R)-5-{[2-(6-methoxy-[1,5]naphthyridin-4-ylamino)-ethylamino]-methyl}-2-oxo-oxazolidin-3-yl)-4H-benzo[1,4]thiazin-3-one 201.i. N$^1$-(6-methoxy-[1,5]naphthyridin-4-yl)-ethane-1,2-diamine A mixture of 8-chloro-2-methoxy-[1,5]naphthyridine (commercial; 1.7 g, 8.80 mmol) and ethane-1,2-diamine (1.2 mL, 2 eq.) was heated slowly to 80° C. over 1 h and subsequently up to 100° C. for 2 h. After cooling to rt, the yellow solution was taken up in DCM and successively washed with sat. aq. NaHCO$_3$. The org. layer was concentrated under reduced pressure to afford the title intermediate as a pale yellow oil (981 mg, 51% yield).

MS (ESI, m/z): 219.4 [M+H$^+$].

201.ii. 6-[(S)-3-(tert-butyl-dimethyl-silanyloxy)-2-hydroxy-propylamino]-4H-benzo[1,4]thiazin-3-one To a solution of tert-butyl-dimethyl-((S)-1-oxiranylmethoxy)-silane (13.0 g, 69 mmol) in acetonitrile (220 mL) was added LiClO$_4$ (22 g, 207 mmol). 6-amino-4H-benzo[1,4]thiazin-3-one (11.4 g, 64 mmol) was added and the mixture was stirred at 50° C. for 6 h. The solvent was removed in vacuo and the residue was chromatographed (DCM/MeOH/NH$_4$OH 1000:25:2→1000:100:2) to afford the title compound as a pale brown foam (11.16 g, 44% yield).

MS (ESI, m/z): 369.3 [M+H$^+$].

201.iii. 6-[(S)-5-(tert-butyl-dimethyl-silanyloxymethyl)-2-oxo-oxazolidin-3-yl]-4H-benzo[1,4]thiazin-3-one A solution of intermediate 201.ii (11.60 g, 30 mmol) and CDI (5.57 g, 33 mmol) in THF (130 mL) was heated at 50° C. for 2 h, the mixture was concentrated in vacuo and partitioned between EA and water. Some crystallized product was filtered and washed with H$_2$O and EA to give 5.21 g of product. The org. layer was washed with brine, dried over MgSO$_4$ and concentrated. The residue was chromatographed (DCM/MeOH 1000:50:4) to give additional 2.28 g (overall 7.49 g of an off-white solid, 63% yield).

MS (ESI, m/z): 395.1 [M+H$^+$].

201.iv. 6-((S)-5-hydroxymethyl-2-oxo-oxazolidin-3-yl)-4H-benzo[1,4]thiazin-3-one A suspension of intermediate 201.iii (11.49 g, 29.1 mmol) in THF (29 mL) was treated with TBAF (1M in THF, 29.1 mL). The yellow solution was stirred at 0° C. for 3 h and then partitioned between water and EA. Some crystallized product was filtered and washed with H$_2$O and EA to give 6.49 g of product. The aq. phase was extracted with EA (3×). The combined org. layers were washed with brine, dried over MgSO$_4$, filtered and concentrated. The crude product was triturated with EA to give further 1.23 g (overall 7.72 g of an off-white solid, 95% yield).

MS (ESI, m/z): 281.3 [M+H$^+$].

201.v. Methanesulfonic acid (S)-2-oxo-3-(3-oxo-3,4-dihydro-2H-benzo[1,4]thiazin-6-yl)-oxazolidin-5-ylmethyl ester A solution of intermediate 201.iv (2.77 g, 9.88 mmol) in anhydrous DCM (100 mL) and DIPEA (4.7 mL, 28.2 mmol) was cooled to 0° C. and MsCl (1.07 mL, 13.8 mmol) was added dropwise. The resulting mixture was stirred at 0° C. for 1 h. Water was added and the mixture was extracted with DCM and the combined org. layers were washed with water. The yellow residue was trituated with EA/DCM/ether to afford the title compound as a colourless solid (2.45 g, 6.9 mmol).

$^1$H NMR (DMSO-d6) δ: 10.57 (s, 1H), 7.31 (m, 2H), 7.10 (dd, J=8.5, 2.3 Hz, 1H), 4.98 (m, 1H), 4.48 (m, 2H), 4.13 (t, J=9.4 Hz, 1H), 3.75 (dd, J=9.4, 6.4 Hz, 1H), 3.43 (s, 2H), 3.23 (s, 3H).

MS (ESI, m/z): 359.3 [M+H$^+$].

201.vi. 6-((R)-5-{[2-(6-methoxy-[1,5]naphthyridin-4-ylamino)-ethylamino]-methyl}-2-oxo-oxazolidin-3-yl)-4H-benzo[1,4]thiazin-3-one A solution of intermediate 201.i (122 mg, 0.56 mmol) and intermediate 201.v (80 mg, 0.22 mmol) in dry DMSO (2 mL) was heated at 70° C. for 3 days. After cooling to rt, water was added and the mixture was extracted with EA (3×). The combined org. layers were washed with water and brine, dried over MgSO$_4$ and concentrated. The residue was chromatographed (EA-MeOH—NH$_4$OH 1000-100-8) to afford the title compound as a pale yellow solid (30 mg, 28% yield).

$^1$H NMR (CDCl$_3$) δ: 9.29 (s, 1H), 8.37 (d, J=5.6 Hz, 1H), 8.07 (d, J=9.1 Hz, 1H), 7.25 (m, 1H), 7.16 (d, J=9.1 Hz, 1H), 7.00 (d, J=9.1 Hz, 1H), 6.83 (dd, J=8.5, 2.3 Hz, 1H), 6.48 (m, 2H), 4.70 (m, 1H), 3.91 (s, 3H), 3.82 (m, 2H), 3.40 (m, 4H), 3.06 (m, 3H), 2.90 (dd, J=13.2, 5.3 Hz, 1H).

MS (ESI, m/z): 481.4 [M+H$^+$].

Example 202

6-((R)-5-{[2-(6-methoxy-[1,5]naphthyridin-4-ylamino)-ethylamino]-methyl}-2-oxo-oxazolidin-3-yl)-4H-benzo[1,4]oxazin-3-one 202.i. 6-[(S)-3-(tert-butyl-dimethyl-silanyloxy)-2-hydroxy-propylamino]-4H-benzo[1,4]oxazin-3-one Starting from 6-amino-4H-benzo[1,4]oxazin-3-one and tert-butyl-dimethyl-((S)-1-oxiranylmethoxy)-silane and using a procedure analogous to that of Example 201, step 201.ii, the title compound was obtained as a pale brown foam (5.2 g, 66% yield).

MS (ESI, m/z): 353.3 [M+H$^+$].

202.ii. 6-[(S)-5-(tert-butyl-dimethyl-silanyloxymethyl)-2-oxo-oxazolidin-3-yl]-4H-benzo[1,4]oxazin-3-one Starting from intermediate 202.i and using a procedure analogous to that of Example 201, step 201.iii, the title compound was obtained as a colourless solid (5.15 g, 91% yield).
MS (ESI, m/z): 379.2 [M+H$^+$].

202.iii. 6-((S)-5-hydroxymethyl-2-oxo-oxazolidin-3-yl)-4H-benzo[1,4]oxazin-3-one Starting from intermediate 202.ii and using a procedure analogous to that of Example 201, step 201.iv, the title compound was obtained as a colourless solid (3.14 g, 87% yield).
MS (ESI, m/z): 265.5 [M+H$^+$].

202.iv. Methanesulfonic acid (S)-2-oxo-3-(3-oxo-3,4-dihydro-2H-benzo[1,4]oxazin-6-yl)-oxazolidin-5-ylmethyl ester Starting from intermediate 202.iii and using a procedure analogous to that of Example 201, step 201.v, the title compound was obtained as an off-white solid (1.40 g, 44% yield).
$^1$H NMR (DMSO-d6) δ: 10.72 (s, 1H), 7.29 (dd, J=2.1, 0.6 Hz, 1H), 6.94 (m, 2H), 4.95 (m, 1H), 4.52 (s, 2H), 4.49 (m, 2H), 4.11 (t, J=9.1 Hz, 1H), 3.73 (m, 2H), 3.23 (s, 3H).
MS (ESI, m/z): 343.2 [M+H$^+$].

202.v. 6-((R)-5-{[2-(6-methoxy-[1,5]naphthyridin-4-ylamino)-ethylamino]-methyl}-2-oxo-oxazolidin-3-yl)-4H-benzo[1,4]oxazin-3-one A solution of intermediate 201.i (77 mg, 0.35 mmol) and intermediate 202.iv (100 mg, 0.29 mmol) in dry DMSO (2 mL) was heated at 70° C. for 3 days. After cooling to rt, water was added and the mixture was extracted with EA (3×). The combined org. layers were washed with water and brine, dried over MgSO$_4$ and concentrated. The residue was chromatographed (EA-MeOH—NH$_4$OH 1000:50:4) to afford the title compound as a pale yellow solid (27 mg, 20% yield).
MS (ESI, m/z): 465.3 [M+H$^+$].

Example 203

6-((S)-5-{3-[(3-fluoro-6-methoxy-[1,5]naphthyridin-4-ylmethyl)-amino]-propyl}-2-oxo-oxazolidin-3-yl)-4H-benzo[1,4]oxazin-3-one

203.i. (S)-6-[5-(3-amino-propyl)-2-oxo-oxazolidin-3-yl]-4H-benzo[1,4]oxazin-3-one The title intermediate was obtained starting from (S)-(3-oxiranyl-propyl)-carbamic acid tert-butyl ester (1.0 g, 5 mmol, 50% ee; prepared according to *J. Am. Chem. Soc.* (2000), 122, 11090-11097) and 6-amino-4H-benzo[1,4]oxazin-3-one (0.815 g, 5 mmol) and following the procedures of Example 76, steps 76.i to 76.iii. The compound was isolated as a beige foam (0.35 g, 24% yield over 3 steps).
$^1$H NMR (CDCl$_3$) δ: 7.43 (d, J=2.6 Hz, 1H), 6.93 (m, 1H), 6.79 (m, 1H), 4.75 (m, 1H), 4.57 (s, 2H), 4.05 (s, 1H), 2.79 (t, J=6.7 Hz, 2H), 2.0-1.6 (m, 4H).

203.ii. 6-((S)-5-{3-[(3-fluoro-6-methoxy-[1,5]naphthyridin-4-ylmethyl)-amino]-propyl}-2-oxo-oxazolidin-3-yl)-4H-benzo[1,4]oxazin-3-one The title compound was obtained starting from intermediate 203.i (0.25 g, 0.86 mmol) and 3-fluoro-6-methoxy-[1,5]naphthyridine-4-carbaldehyde (0.177 g, 1 eq.) and following method K. The compound was isolated after FC (EA/MeOH 19:1, 9:1+1% NH$_4$OH) as a colourless foam (0.16 g, 39% yield).
MS (ESI, m/z): 482.2 [M+H$^+$].

Example 204

6-((R)-5-{[3-(6-methoxy-[1,5]naphthyridin-4-yl)-propylamino]-methyl}-2-oxo-oxazolidin-3-yl)-4H-pyrido[3,2-b][1,4]oxazin-3-one

204.i. 6-bromo-4-(2,4-dimethoxy-benzyl)-4H-pyrido[3,2-b][1,4]oxazin-3-one

A suspension of 6-bromo-4H-pyrido[3,2-b][1,4]oxazin-3-one (0.412 g, 1.8 mmol) and 2,4-dimethoxybenzyl chloride (0.336 g, 1.8 mmol; freshly prepared according to U.S. Pat. No. 5,817,653) in DMF (5 mL) was treated with Cs$_2$CO$_3$ (1.76 g, 3 eq.). The mixture was stirred at rt for 2 h, partitioned between EA and water. The aq. phase was extracted with EA and the combined org. layers washed with water, and brine, dried over MgSO$_4$ and concentrated. The residue was purified by FC (Hept/EA 1:1) to give the title intermediate as a colourless oil (0.61 g, 90% yield).
MS (ESI, m/z): 379.0 [M+H$^+$].

204.ii. {(R)-3-[4-(2,4-dimethoxy-benzyl)-3-oxo-3,4-dihydro-2H-pyrido[3,2-b][1,4]oxazin-6-yl]-2-oxo-oxazolidin-5-ylmethyl}-carbamic acid tert-butyl ester A vial was charged with intermediate 204.i (0.237 g, 0.5 mmol), ((S)-2-oxo-oxazolidin-5-ylmethyl)-carbamic acid tert-butyl ester (0.108 g, 0.5 mmol; see *Tetrahedron: Asymmetry* (2006), 17, 2548-2557), palladium acetate (0.011 g, 0.1 eq), DPEphos (0.053 g, 0.2 eq.) and K$_3$PO$_4$ (0.212 g, 2 eq.). The vial was purged with Ar and dioxane (4 ml) was added. The mixture was heated at 100° C. overnight, cooled and partitioned between EA and water. The org. phase was washed with water and brine, dried over MgSO$_4$ and concentrated. The residue was purified by FC (Hept/EA 1:1) to give the title intermediate as a colourless foam (0.11 g, 43% yield).
MS (ESI, m/z): 515.4 [M+H$^+$].

204.iii. 6-((R)-5-aminomethyl-2-oxo-oxazolidin-3-yl)-4H-pyrido[3,2-b][1,4]oxazin-3-one Intermediate 204.ii (0.14 g, 0.27 mmol) was dissolved in TFA (2 mL) and the purple mixture heated at 70° C. for 2 h. The volatiles were removed under reduced pressure and and the residue partitioned between DCM (2 mL) and NH$_4$OH (1 mL). The org. phase was dried over MgSO$_4$ and concentrated. The residue was purified by FC (DCM/MeOH 9:1+1% NH$_4$OH) to give the title intermediate as a yellowish solid (0.055 g, 77% yield).
$^1$H NMR (DMSO-d6) δ: 7.58 (m, 1H), 7.39 (m, 1H), 4.58 (m, 3H), 4.08 (d, J=0.6 Hz, 1H), 2.79 (m, 2H).

204.iv. 6-((R)-5-{[3-(6-methoxyl-[1,5]naphthyridin-4-yl)-propylamino]-methyl}-2-oxo-oxazolidin-3-yl)-4H-pyrido[3,2-b][1,4]oxazin-3-one The title compound was obtained starting from intermediate 204.iii (0.05 g, 0.2 mmol) and intermediate 33.ii (0.042 g, 1 eq.) and following method K. The compound was isolated after FC (DCM/MeOH 19:1+0.5% NH₄OH) as a colourless solid (0.045 g, 49% yield).

¹H NMR (DMSO-d6) δ: 8.63 (d, J=4.7 Hz, 1H), 8.20 (d, J=9.1 Hz, 1H), 7.54 (m, 2H), 7.38 (d, J=8.5 Hz, 1H), 7.21 (d, J=9.1 Hz, 1H), 4.67 (m, 1H), 4.57 (m, 2H), 4.10 (m, 1H), 3.98 (s, 3H), 3.84 (m, 1H), 3.12 (m, 2H), 2.81 (m, 2H), 2.61 (m, 2H), 1.85 (m, 3H).

MS (ESI, m/z): 465.3 [M+H⁺].

Example 205

(3RS)-3-(2,3-dihydro-benzo[1,4]dioxin-6-yl)-5-{(3RS)-[(3-fluoro-6-methoxy-[1,5]naphthyridin-4-ylmethyl)-amino]-2-hydroxy-propyl}-oxazolidin-2-one 205.i. rac-[2-(tert-butyl-dimethyl-silanyloxy)-pent-4-enyl]-carbamic acid tert-butyl ester Rac-(2-hydroxy-pent-4-enyl)-carbamic acid tert-butyl ester (5 g, 24.8 mmol; prepared according to *Tetrahedron Lett.* (2006), 47, 3295) was added dropwise to a mixture of TBDMSCl (3.7 g, 1 eq.) and imidazole (1.7 g, 1 eq.) in THF (55 mL). The mixture was stirred at rt overnight, filtered and the filtrate washed with water and brine, dried over MgSO₄ and concentrated. The residue was purified by FC (Hept/EA: 1, EA) to give the title intermediate as a colourless oil (2.8 g, 36% yield).

¹H NMR (CDCl₃) δ: 5.79 (m, 1H), 5.07 (m, 2H), 4.72 (m, 1H), 3.79 (m, 1H), 3.24 (m, 1H), 3.01 (m, 1H), 2.22 (m, 2H), 1.46 (m, 9H), 0.90 (m, 9H), 0.11 (m, 6H).

205.ii. [(2RS)-(tert-butyl-dimethyl-silanyloxy)-(3RS)-oxiranyl-propyl]-carbamic acid tert-butyl ester A solution of intermediate 205.i (2.8 g, 8.87 mmol) in DCM (50 mL) was treated with MCPBA (4.4 g, 2 eq.) and stirred at rt overnight. The mixture was successively washed with a sat. NaHSO₃ solution, a 5% NaHCO₃ solution and brine, dried over MgSO₄ and concentrated. The residue was purified by FC (Hept/EA 4:1) to give the desired intermediate as a colourless oil (2.3 g, 78% yield).

¹H NMR (CDCl₃) δ: 4.76 (m, 1H), 3.98 (m, 1H), 3.13 (m, 3H), 2.78 (m, 1H), 2.48 (m, 1H), 1.73 (m, 1H), 1.42 (m, 9H), 0.88 (m, 9H), 0.09 (m, 6H).

205.iii. [(2RS)-(tert-butyl-dimethyl-silanyloxy)-5-(2,3-dihydro-benzo[1,4]dioxin-6-ylamino)-(4RS)-hydroxy-pentyl]-carbamic acid tert-butyl ester A solution of intermediate 205.ii (2.3 g, 6.9 mmol) and 2,3-dihydro-benzo[1,4]dioxin-6-ylamine (1.05 g, 1 eq.) in EtOH/H₂O (9:1, 30 mL) was heated at reflux overnight. The volatiles were removed under reduced pressure and the residue purified by FC (Hept/EA 2:1) to give the title intermediate as a mixture of diastereomers (yellowish oil; 2.07 g, 62% yield)).

¹H NMR (CDCl₃) δ: 6.69 (m, 1H), 6.19 (m, 2H), 4.20 (m, 4H), 4.05 (m, 1H), 3.25 (d, J=4.7 Hz, 2H), 2.96 (m, 1H), 1.67 (m, 2H), 1.46 (m, 9H), 1.25 (m, 2H), 0.89 (m, 9H), 0.09 (m, 6H).

205.iv. {(2RS)-(tert-butyl-dimethyl-silanyloxy)-3-[3-(2,3-dihydro-benzo[1,4]dioxin-6-yl)-2-oxo-oxazolidin-(5RS)-yl]-propyl}-carbamic acid tert-butyl ester A solution of intermediate 205.iii (1.6 g, 3.3 mmol) in THF (60 mL) was treated with CDI (0.8 g, 1.5 eq.). The mixture was stirred at rt for 72 h, diluted with EA and washed with water and brine. The org. phase was dried over MgSO₄ and concentrated. The residue was purified by FC (Hept/EA 1:1) to give the title intermediate as a yellow oil (1.3 g, 77% yield).

¹H NMR (CDCl₃) δ: 7.05 (d, J=2.6 Hz, 1H), 6.97 (m, 1H), 6.84 (m, 1H), 4.75 (m, 2H), 4.24 (m, 4H), 4.05 (m, 3H), 3.59 (m, 1H), 3.18 (m, 3H), 1.85 (m, 2H), 1.44 (m, 9H), 0.89 (m, 9H), 0.11 (m, 6H).

205.v. (5RS)-(3-amino-(2RS)-hydroxy-propyl)-3-(2,3-dihydro-benzo[1,4]dioxin-6-yl)-oxazolidin-2-one A solution of intermediate 205.iv (1.3 g, 2.6 mmol) in DCM (3 mL) was treated with TFA (6 mL). The mixture was stirred at rt for 3 h, concentrated in vacuo and partitioned between DCM and NH₄OH. The org. phase was dried over MgSO₄ and concentrated. The residue was dissolved in THF (2.5 mL) and TBAF (1M, 4.2 mL) was added. The mixture was stirred at rt for 5 h, partitioned between DCM and NH₄OH. The org. phase was dried over MgSO₄ and concentrated. The residue was purified by FC (DCM/MeOH 9:1+0.5% NH₄OH) to give the title intermediate as a yellowish foam (0.3 g, 46% yield).

MS (ESI, m/z): 295.5 [M+H⁺].

205.vi. (3RS)-3-(2,3-dihydro-benzo[1,4]dioxin-6-yl)-5-{(3RS)-[(3-fluoro-6-methoxy-[1,5]naphthyridin-4-ylmethyl)-amino]-2-hydroxy-propyl}-oxazolidin-2-one Intermediate 205.v (0.07 g, 0.23 mmol) and 3-fluoro-6-methoxy-[1,5]naphthyridine-4-carbaldehyde (0.05 g, 1 eq.) were coupled according to method K. The compound was isolated after FC (EA/MeOH 19:1, 9:1+1% NH₄OH) as a beige foam (0.08 g, 69% yield).

¹H NMR (CDCl₃) δ: 8.66 (s, 1H), 8.21 (d, J=9.1 Hz, 1H), 7.08 (m, 2H), 6.97 (m, 1H), 6.84 (m, 1H), 4.85 (m, 1H), 4.36 (d, J=1.5 Hz, 2H), 4.24 (m, 5H), 4.09 (m, 3H), 3.89 (m, 1H), 3.96 (dd, J=8.8, 7.3 Hz, 1H), 2.71 (m, 1H), 2.57 (m, 1H), 1.93 (m, 3H).

Example 206

6-((R)-5-{3-[(3-amino-propyl)-(3-fluoro-6-methoxy-[1,5]naphthyridin-4-ylmethyl)-amino]-propyl}-2-oxo-oxazolidin-3-yl)-4H-benzo[1,4]oxazin-3-one 206.i. [3-((3-fluoro-6-methoxy-[1,5]naphthyridin-4-ylmethyl)-{3-[(R)-2-oxo-3-(3,4-dihydro-2H-benzo[1,4]oxazin-6-yl)-oxazolidin-5-yl]-propyl}-amino)-propyl]-carbamic acid tert-butyl ester The compound of Example 176 (0.08 g, 0.17 mmol) and (3-oxo-propyl)-carbamic acid tert-butyl ester (0.029 g, 1 eq.) were coupled according to method K. The title intermediate was isolated as a yellowish oil (0.05 g, 47% yield).

MS (ESI, m/z): 639.3 [M+H⁺].

206.ii. 6-((R)-5-{3-[(3-amino-propyl)-(3-fluoro-6-methoxyl-[1,5]naphthyridin-4-ylmethyl)-amino]-propyl}-2-oxo-oxazolidin-3-yl)-4H-benzo[1,4]oxazin-3-one The Boc group of intermediate 206.i (0.05 g, 0.08 mmol) was removed according to method E. The title compound was isolated after FC (DCM/MeOH (9:1+1% NH₄OH) as a colourless foam (0.03 g, 71% yield.

MS (ESI, m/z): 539.2 [M+H⁺].

Example 207

6-((R)-5-{3-[(3-fluoro-6-methoxy-[1,5]naphthyridin-4-ylmethyl)-(3-hydroxy-propyl)-amino]-propyl}-2-oxo-oxazolidin-3-yl)-4H-benzo[1,4]oxazin-3-one

207.i. 6-((R)-5-{3-[[3-(tert-butyl-dimethyl-silanyloxy)-propyl]-(3-fluoro-6-methoxy-[1,5]naphthyridin-4-ylmethyl)-amino]-propyl}-2-oxo-oxazolidin-3-yl)-4H-benzo[1,4]oxazin-3-one The compound of Example 176 (0.08 g, 0.17 mmol) and 3-(tert-butyl-dimethyl-silanyloxy)-propionaldehyde (0.031 g, 1 eq.) were coupled according to method K. The title intermediate was isolated as a yellowish oil (0.08 g, 74% yield).
MS (ESI, m/z): 654.1 [M+H$^+$].

207.ii. 6-((R)-5-{3-[(3-fluoro-6-methoxy-[1,5]naphthyridin-4-ylmethyl)-(3-hydroxy-propyl)-amino]-propyl}-2-oxo-oxazolidin-3-yl)-4H-benzo[1,4]oxazin-3 one The TBS group of intermediate 207.i (0.08 g, 0.122 mmol) was removed in analogy to Example 179, step 179.ii. The title compound was isolated after FC (EA, EA/MeOH 9:1) and isolated as a colourless foam (0.05 g, 76% yield).
MS (ESI, m/z): 539.2 [M+H$^+$].

Example 208

6-((S*)-5-{(S*)-3-[(3-fluoro-6-methoxy-[1,5]naphthyridin-4-ylmethyl)-amino]-1-hydroxy-propyl}-2-oxo-oxazolidin-3-yl)-4H-benzo[1,4]oxazin-3-one The title compound was obtained starting from intermediate 103.ii (3.4 g, 15.6 mmol) and 6-amino-4H-benzo[1,4]oxazin-3-one (3.08 g, 18.8 mmol) and following the procedures of Example 103, steps 103.iii to 103.v and 104. The compound was isolated as a colourless solid (0.033 g).
MS (ESI, m/z): 498.2 [M+H$^+$].

Example 209

(S*)-5-{(S*)-1-amino-3-[(3-fluoro-6-methoxy-[1,5]naphthyridin-4-ylmethyl)-amino]-propyl}-3-(2,3-dihydro-benzo[1,4]dioxin-6-yl)-oxazolidin-2-one The title compound was obtained starting from intermediate 106.i. (0.32 g, 0.55 mmol) and following the procedure of Example 107. The desired compound was isolated as a yellow foam (0.004 g, 1.5% yield).
MS (ESI, m/z): 484.0 [M+H$^+$].

Example 210

6-((5RS)-5-{(2RS)-3-[(3-fluoro-6-methoxy-[1,5]naphthyridin-4-ylmethyl)-amino]-2-hydroxy-propyl}-2-oxo-oxazolidin-3-yl)-4H-benzo[1,4]thiazin-3-one

210.i. (2RS,5RS)-6-{5-[3-amino-2-(tert-butyl-dimethyl-silanyloxy)-propyl]-2-oxo-oxazolidin-3-yl}-4H-benzo[1,4]thiazin-3-one The title intermediate was obtained starting from intermediate 205.ii (3.5 g, 10.6 mmol) and 6-amino-4H-benzo[1,4]thiazin-3-one (1.9 g, 1 eq.) and following sequentially methods A, B and E. The desired intermediate was obtained as a beige foam (0.65 g, 14% yield over 3 steps).
MS (ESI, m/z): 438.2 [M+H$^+$].

210.ii. 6-((5RS)-5-{(2RS)-3-[(3-fluoro-6-methoxy-[1,5]naphthyridin-4-ylmethyl)-amino]-2-hydroxy-propyl}-2-oxo-oxazolidin-3-yl)-4H-benzo[1,4]thiazin-3-one Starting from intermediate 210.i (0.325 g, 0.74 mmol) and 3-fluoro-6-methoxy-[1,5]naphthyridine-4-carbaldehyde (0.153 g, 1 eq) and using method K before removing the TBDMS group in analogy to Example 109, step 109.ii, the title compound was obtained as a beige solid (0.2 g, 52% yield over 2 steps).
MS (ESI, m/z): 514.2 [M+H$^+$].

Example 211

6-((5RS)-5-{(2RS)-3-[(3-fluoro-6-methoxy-quinolin-4-ylmethyl)-amino]-2-hydroxy-propyl}-2-oxo-oxazolidin-3-yl)-4H-benzo[1,4]thiazin-3-one Starting from intermediate 210.i (0.325 g, 0.74 mmol) and 3-fluoro-6-methoxy-quinoline-4-carbaldehyde (0.153 g, 1 eq.) and using method K before removing the TBDMS group in analogy to Example 109, step 109.ii, the title compound was obtained as a beige foam (0.02 g, 5% yield over 2 steps)
MS (ESI, m/z): 513.2 [M+H$^+$].

Example 212

6-((5RS)-5-{(2RS)-3-[(3-fluoro-6-methoxy-[1,5]naphthyridin-4-ylmethyl)-amino]-2-hydroxy-propyl}-2-oxo-oxazolidin-3-yl)-4H-benzo[1,4]oxazin-3-one

212.i. (2RS,5RS)-6-{5-[3-amino-2-(tert-butyl-dimethyl-silanyloxy)-propyl]-2-oxo-oxazolidin-3-yl}-4H-benzo[1,4]oxazin-3-one The title intermediate was obtained starting from intermediate 205.ii (3.5 g, 10.6 mmol) and 6-amino-4H-benzo[1,4]oxazin-3-one (1.73 g, 1 eq.) and following sequentially methods A, B and E. The desired intermediate was obtained as a beige foam (0.88 g, 19.7% yield over 3 steps).
MS (ESI, m/z): 422.2 [M+H$^+$].

212.ii. 6-((5RS)-5-{(2RS)-3-[(3-fluoro-6-methoxy-[1,5]naphthyridin-4-ylmethyl)-amino]-2-hydroxy-propyl}-2-oxo-oxazolidin-3-yl)-4H-benzo[1,4]oxazin-3-one Starting from intermediate 212.i (0.290 g, 0.67 mmol) and 3-fluoro-6-methoxy-[1,5]naphthyridine-4-carbaldehyde (0.14 g, 1 eq.) and using method K before removing the TBDMS group in analogy to Example 109, step 109.ii, the title compound was obtained as a beige solid (0.12 g, 35% yield over 2 steps).
MS (ESI, m/z): 498.2 [M+H$^+$].

Example 213

6-((5RS)-5-{(2RS)-3-[(3-fluoro-6-methoxy-quinolin-4-ylmethyl)-amino]-2-hydroxy-propyl}-2-oxo-oxazolidin-3-yl)-4H-benzo[1,4]oxazin-3-one Starting from intermediate 212.i (0.290 g, 0.67 mmol) and 3-fluoro-6-methoxy-quinoline-4-carbaldehyde (0.14 g, 1 eq.)

and using method K before removing the TBDMS group in analogy to Example 109, step 109.ii, the title compound was obtained as a beige foam (0.018 g, 5% over 2 steps).

MS (ESI, m/z): 497.3 [M+H$^+$].

Example 214

6-((5RS)-5-{(2RS)-3-[(7-fluoro-2-methoxy-quinolin-8-ylmethyl)-amino]-2-hydroxy-propyl}-2-oxo-oxazolidin-3-yl)-4H-benzo[1,4]oxazin-3-one Starting from intermediate 212.i (0.290 g, 0.67 mmol) and 7-fluoro-2-methoxy-quinoline-8-carbaldehyde (0.14 g, 1 eq.) and using method K before removing the TBDMS group in analogy to Example 109, step 109.ii, the title compound was obtained beige solid (0.055 g, 16% yield over 2 steps)

MS (ESI, m/z): 497.3 [M+H$^+$].

Pharmacological Properties of the Invention Compounds
In Vitro Assays
Experimental Methods:

These assays have been performed following the description given in "Methods for dilution Antimicrobial Susceptibility Tests for Bacteria that Grow Aerobically, 4th ed.; Approved standard: NCCLS Document M7-A4; National Committee for Clinical Laboratory Standards: Villanova, Pa., USA, 1997". Minimal inhibitory concentrations (MICs; mg/l) were determined in cation-adjusted Mueller-Hinton Broth (BBL) by a microdilution method following NCCLS guidelines (National Committee for Clinical Laboratory Standards. Methods for Dilution Antimicrobial Susceptibility). The pH of the test medium was 7.2-7.3.

Results:

All Example compounds were tested against several Gram positive and Gram negative bacteria. For calculation of the mean values mentioned below, MICs equal or below 0.063 mg/L were counted as being 0.063 mg/L.

When tested on the strain *S. aureus* 29213, the compounds of the Examples showed MICs ranging from 0.015 mg/L to 16 mg/L, with a mean value of about 0.4 mg/L. When tested on the strain *E. faecalis* 29212, the compounds of the Examples showed MICs ranging from 0.031 mg/L to 32 mg/L, with a mean value of about 2.1 mg/L. When tested on the strain *S. pneumoniae* 49619 the compounds of the Examples showed MICs ranging from 0.015 mg/L to 32 mg/L, with a mean value of about 2.2 mg/l. When tested on the strain *M. catarrhalis* A894 the compounds of the Examples showed MICs ranging from 0.015 mg/L to 32 mg/L, with a mean value of about 0.9 mg/L. When tested on the strain *E. coli* 25922 the compounds of the Examples showed MICs ranging from 0.031 mg/L to 32 mg/L, with a mean value of about 15.9 mg/l.

Typical antibacterial test results are given in the table hereafter (MIC in mg/l).

| Example No. | S. aureus 29213 |
|---|---|
| 5 | ≦0.063 |
| 14 | ≦0.063 |
| 16 | 0.125 |
| 22 | ≦0.063 |
| 28 | ≦0.063 |
| 29 | ≦0.063 |
| 35 | ≦0.063 |
| 38 | ≦0.063 |
| 43 | ≦0.063 |

-continued

| Example No. | S. aureus 29213 |
|---|---|
| 52 | 0.25 |
| 62 | ≦0.063 |
| 63 | ≦0.063 |
| 72 | ≦0.063 |
| 89 | 0.125 |
| 91 | ≦0.063 |
| 92 | 0.125 |
| 97 | ≦0.063 |
| 99 | ≦0.063 |
| 100 | ≦0.063 |
| 107 | ≦0.063 |
| 110 | ≦0.063 |
| 111 | ≦0.063 |
| 113 | ≦0.063 |
| 116 | ≦0.063 |
| 120 | 0.125 |
| 122 | ≦0.063 |
| 123 | ≦0.063 |
| 125 | ≦0.063 |
| 135 | ≦0.063 |
| 152 | ≦0.063 |
| 153 | ≦0.063 |
| 155 | ≦0.063 |
| 156 | ≦0.063 |
| 157 | 0.125 |
| 168 | ≦0.063 |
| 169 | ≦0.063 |
| 171 | ≦0.063 |
| 179 | ≦0.063 |
| 181 | ≦0.063 |
| 201 | ≦0.063 |

The invention claimed is:

1. A compound of formula I

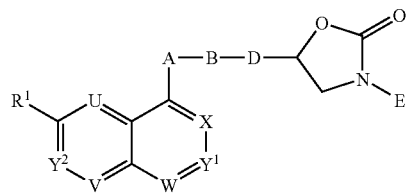

wherein $R^1$ is hydrogen, halogen, hydroxy, alkoxy or cyano;

$Y^1$ and $Y^2$ each represent CH, and one or two of U, V, W and X represent(s) N and the remaining each represent CH or, in the case of X, may also represent $CR^a$, and, in the case of W, may also represent $CR^b$, or each of U, V, W, X, $Y^1$ and $Y^2$ represents CH or each of U, V, W, X and $Y^1$ represents CH and $Y^2$ represents N, or one or, provided $R^1$ is hydrogen, two of U, V, W, X, $Y^1$ and $Y^2$ represent(s) $CR^c$ and the remaining each represent CH;

$R^a$ represents halogen;

$R^b$ represents alkoxy, alkoxycarbonyl or alkoxyalkoxy;

$R^c$, each time it occurs, independently represents hydroxy or alkoxy;

A is $CH_2CH(OH)$, $CH_2CH(NH_2)$, $CH(OH)CH(NH_2)$ or $CH(NH_2)CH_2$, B is $CH_2CH_2$, $CH_2NH$ or CONH and D is $CH_2$, or A is $CH(OH)CH_2$ and either B is $CH_2CH_2$, $CH_2NH$, $N(R^2)$CO, CONH or $N(R^2)CH_2$ and D is $CH_2$ or B is $N(R^{2a})$$CH_2$ and D is CH(OH), or A is $CH(OH)CH(OH)$, B is $CH_2NH$ or CONH and D is $CH_2$, or A is CH$_2$CH$_2$ and either B is CH$_2$CH$_2$, NR$^{4a}$CH$_2$, CH$_2$NR$^3$, NHCO, CONR$^4$, CH$_2$O, CH(OH)CH$_2$, CH$_2$CH(OH), CH(NHR$^{3a}$)CH$_2$, COCH$_2$ or CH$_2$CH$_2$NH and D is CH$_2$ or B is CH$_2$NH and D is CO, or A is CH$_2$CH$_2$, B is NR$^{4b}$CH$_2$ or CH$_2$CH$_2$ and D is CH(OH), or A is CH═CH, B is CH$_2$NR$^5$, CONR$^6$ or CH$_2$O and D is CH$_2$, or A is C≡C, B is CH$_2$NH and D is CO, or A is CH$_2$CO, B is NHCH$_2$ and D is CH$_2$, or A is COCH$_2$, B is CH$_2$CH$_2$ or CONH and D is CH$_2$, or A is CH$_2$N(R$^7$) and either B is CH$_2$CH$_2$, COCH$_2$ or CH$_2$CH(OH) and D is CH$_2$ or B is CH$_2$CH$_2$ or CH$_2$CH(OH) and D is CH(OH) or CH(NH$_2$), or A is CONH or CH$_2$O, B is CH$_2$CH$_2$ and D is CH$_2$, or A is NHCH$_2$ and either B is CH$_2$CH$_2$ or CH$_2$NH and D is CH$_2$, or B is CH$_2$NH and D is CO, or A is NHCO, B is CH(R$^8$)NH or CH$_2$CH$_2$ and D is CH$_2$, or A is OCH$_2$, B is CH$_2$, CH$_2$CH$_2$, CH═CH or CONH and D is CH$_2$;

R$^2$ is hydrogen or alkyl;

R$^{2a}$ is hydrogen or alkyl;

R$^3$ is hydrogen, phenylalkyl, CO—(CH$_2$)$_p$—COOR$^{3'}$, (CH$_2$)$_p$—COOR$^{3'}$, acyl or aminoalkyl, or R$^3$ is alkyl which may be substituted once or twice by hydroxy groups, p being an integer from 1 to 4 and R$^{3'}$ being hydrogen or alkyl;

R$^{3a}$ is hydrogen, acyl or alkylsulfonyl;

R$^4$ is hydrogen or alkyl;

R$^{4a}$ is hydrogen or (CH$_2$)$_q$—COOR$^{4a'}$, or R$^{4a}$ is alkyl which may be substituted once or twice by hydroxy groups, q being an integer from 1 to 4 and R$^{4a'}$ being hydrogen or alkyl;

R$^{4b}$ is hydrogen or alkyl;

R$^5$ is hydrogen or acyl;

R$^6$ is hydrogen, alkyl or phenylalkyl;

R$^7$ is hydrogen or (CH$_2$)$_r$—COOR$^{7'}$, or R$^7$ is alkyl which may be substituted once or twice by groups independently selected from hydroxy, halogen, amino or dimethylamino, r being an integer from 1 to 4 and R$^{7'}$ being hydrogen or alkyl;

R$^8$ is hydrogen or alkyl;

E is one of the following groups:

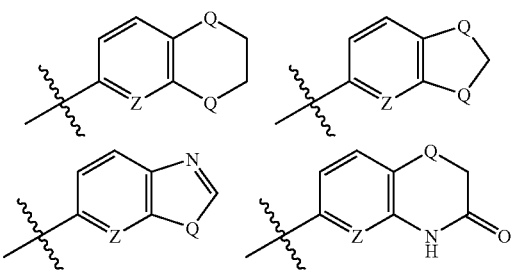

wherein Z is CH or N and Q is O or S, or

E is a phenyl group which is substituted once or twice in the meta and/or para position(s) by substituents each independently selected from halogen, (C$_1$-C$_3$)alkyl, (C$_1$-C$_3$)alkoxy, trifluoromethyl or trifluoromethoxy;

or a salt of said compound.

2. The compound of claim 1, wherein the compound is of formula I$_{CE}$

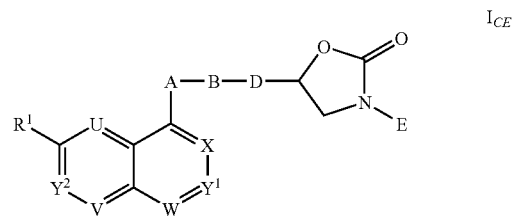

wherein

R$^1$ is hydrogen, halogen, hydroxy, alkoxy or cyano;

Y$^1$, Y$^2$ and V each represent CH, X represents CH or CR$^a$, and U and W each represent N, or Y$^1$, Y$^2$ and X each represent CH, W represents CH or CR$^b$, and U and V each represent N, or Y$^1$, Y$^2$, U and V each represent CH, and W and X each represent N, or Y$^1$, Y$^2$, U and V each represent CH, X represents CH or CR$^a$, and W represents N, or Y$^1$, Y$^2$, U, W each represent CH, X represents CH or CR$^a$ and V represents N, or Y$^1$, Y$^2$, V and W each represent CH, X represents CH or CR$^a$ and U represents N, or Y$^1$, Y$^2$, X and V each represent CH, W represents CR$^{b'}$ and U represents N, or each of U, V, W, X, Y$^1$ and Y$^2$ represents CH, or each of U, V, W, X and Y$^1$ represents CH and Y$^2$ represents N, or each of U, V, X, Y$^1$ and Y$^2$ represents CH and W represents CR$^c$, or each of U, V, W, Y$^1$ and Y$^2$ represents CH and X represents CR$^c$, or each of U, V, W and Y$^2$ represents CH and X and Y$^1$ each represent CR$^c$;

R$^a$ represents halogen;

R$^b$ represents alkoxyalkoxy;

R$^{b'}$ represents alkoxycarbonyl;

R$^c$, each time it occurs, independently represents hydroxy or alkoxy;

A is CH$_2$CH(OH), CH$_2$CH(NH$_2$), CH(OH)CH(NH$_2$) or CH(NH$_2$)CH$_2$, B is CH$_2$CH$_2$, CH$_2$NH or CONH and D is CH$_2$, or A is CH(OH)CH$_2$ and either B is CH$_2$CH$_2$, CH$_2$NH, N(R$^2$)CO, CONH or N(R$^2$)CH$_2$ and D is CH$_2$ or B is N(R$^{2a}$)CH$_2$ and D is CH(OH), or A is CH(OH)CH(OH), B is CH$_2$NH or CONH and D is CH$_2$, or A is CH$_2$CH$_2$ and either B is CH$_2$CH$_2$, NR$^{4a}$CH$_2$, CH$_2$NR$^3$, NHCO, CONR$^4$, CH$_2$O, CH(OH)CH$_2$, CH$_2$CH(OH), CH(NHR$^{3a}$)CH$_2$, COCH$_2$ or CH$_2$CH$_2$NH and D is CH$_2$ or B is CH$_2$NH and D is CO, or A is CH$_2$CH$_2$, B is NR$^{4b}$CH$_2$ or CH$_2$CH$_2$ and D is CH(OH), or A is CH═CH, B is CH$_2$NR$^5$, CONR$^6$ or CH$_2$O and D is CH$_2$, or A is C≡C, B is CH$_2$NH and D is CO, or A is CH$_2$CO, B is NHCH$_2$ and D is CH$_2$, or A is COCH$_2$, B is CH$_2$CH$_2$ or CONH and D is CH$_2$, or A is CH$_2$N(R$^7$) and either B is CH$_2$CH$_2$, COCH$_2$ or CH$_2$CH(OH) and D is CH$_2$ or B is CH$_2$CH$_2$ or CH$_2$CH(OH) and D is CH(OH) or CH(NH$_2$), or A is CONH or CH$_2$O, B is CH$_2$CH$_2$ and D is CH$_2$, or A is NHCH$_2$ and either B is CH$_2$CH$_2$ or CH$_2$NH and D is CH$_2$, or B is CH$_2$NH and D is CO, or A is NHCO, B is CH(R$^8$)NH or CH$_2$CH$_2$ and D is CH$_2$, or A is OCH$_2$, B is CH$_2$, CH$_2$CH$_2$, CH═CH or CONH and D is CH$_2$;

R$^2$ is hydrogen or alkyl;

$R^{2a}$ is hydrogen or alkyl;

$R^3$ is hydrogen, phenylalkyl, CO—$(CH_2)_p$—COOR$^{3'}$, $(CH_2)_p$—COOR$^{3'}$, acyl or aminoalkyl, or $R^3$ is alkyl which may be substituted once or twice by hydroxy groups, p being an integer from 1 to 4 and $R^{3'}$ being hydrogen or alkyl;

$R^{3a}$ is hydrogen, acyl or alkylsulfonyl;

$R^4$ is hydrogen or alkyl;

$R^{4a}$ is hydrogen or $(CH_2)_q$—COOR$^{4a'}$, or $R^{4a}$ is alkyl which may be substituted once or twice by hydroxy groups, q being an integer from 1 to 4 and $R^{4a'}$ being hydrogen or alkyl;

$R^{4b}$ is hydrogen or alkyl;

$R^5$ is hydrogen or acyl;

$R^6$ is hydrogen, alkyl or phenylalkyl;

$R^7$ is hydrogen or $(CH_2)_r$—COOR$^{7'}$, or $R^7$ is alkyl which may be substituted once or twice by groups independently selected from hydroxy, halogen, amino or dimethylamino, r being an integer from 1 to 4 and $R^{7'}$ being hydrogen or alkyl;

$R^8$ is hydrogen or alkyl;

E is one of the following groups

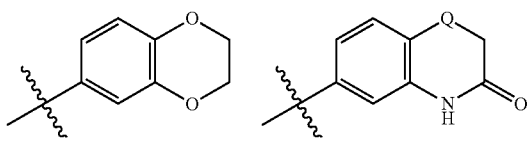

in which Q is O or S, or

E is a phenyl group which is substituted once or twice in the meta and/or para position(s) by substituents each independently selected from halogen, $(C_1-C_3)$alkyl, $(C_1-C_3)$alkoxy, trifluoromethyl or trifluoromethoxy;

or a salt of said compound.

3. The compound of claim 1, wherein when A is $CH_2N(R^7)$, then either B is $CH_2CH_2$ or $COCH_2$ and D is $CH_2$ or B is $CH_2CH_2$ or $CH_2CH(OH)$ and D is CH(OH) or $CH(NH_2)$, $R^7$ being hydrogen or $(CH_2)_r$—COOR$^{7'}$, or $R^7$ being alkyl which may be substituted once or twice by groups independently selected from hydroxy, halogen or dimethylamino, r being an integer from 1 to 4 and $R^{7'}$ being hydrogen or alkyl;

or a salt of said compound.

4. The compound of claim 1, wherein the compound is of formula $I_{P1}$

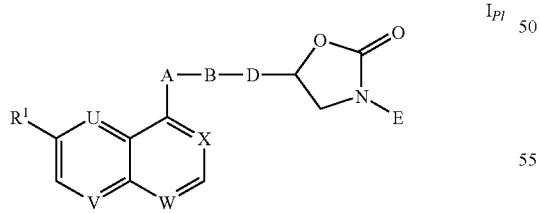

wherein $R^1$ is hydrogen, halogen, alkoxy or cyano;

one or two of U, V, W and X represent(s) N and the remaining each represent CH or, in the case of X, may also represent CR$^a$;

R$^a$ represents halogen;

A is $CH_2CH(OH)$, $CH_2CH(NH_2)$, $CH(OH)CH(NH_2)$ or $CH(NH_2)CH_2$, B is $CH_2CH_2$, $CH_2NH$ or CONH and D is $CH_2$, or A is $CH(OH)CH_2$, B is $CH_2CH_2$, $CH_2NH$, $N(R^2)CO$ or CONH and D is $CH_2$, or A is $CH(OH)CH(OH)$, B is $CH_2NH$ or CONH and D is $CH_2$, or A is $CH_2CH_2$ and either B is $NHCH_2$, $CH_2NR^3$, NHCO or CONR$^4$ and D is $CH_2$ or B is $CH_2NH$ and D is CO, or A is CH=CH, B is $CH_2NR^5$ or CONR$^6$ and D is $CH_2$, or A is C≡C, B is $CH_2NH$ and D is CO, or A is $CH_2CO$, B is $NHCH_2$ and D is $CH_2$, or A is $COCH_2$, B is $CH_2CH_2$ or CONH and D is $CH_2$, or A is $CH_2N(R^7)$, B is $CH_2CH_2$ or $COCH_2$ and D is $CH_2$, or A is CONH, B is $CH_2CH_2$ and D is $CH_2$, or A is $NHCH_2$ and either B is $CH_2CH_2$ or $CH_2NH$ and D is $CH_2$, or B is $CH_2NH$ and D is CO, or A is NHCO, B is $CH(R^8)NH$ or $CH_2CH_2$ and D is $CH_2$;

$R^2$ is hydrogen or alkyl;

$R^3$ is hydrogen, alkyl, phenylalkyl, CO—$(CH_2)_p$—COOH, acyl or aminoalkyl, p being an integer from 1 to 4;

$R^4$ is hydrogen or alkyl;

$R^5$ is hydrogen or acyl;

$R^6$ is hydrogen, alkyl or phenylalkyl;

$R^7$ is hydrogen or alkyl;

$R^8$ is hydrogen or alkyl;

E is a group of the formula

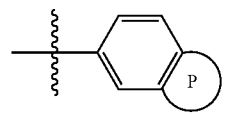

wherein P is a ring selected from one of the following rings:

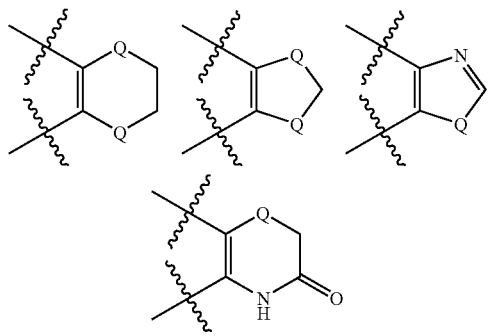

in which Q is O or S, or

E is a phenyl group which is substituted once or twice in the meta and/or para position(s) by substituents each independently selected from halogen, $(C_1-C_3)$alkyl, $(C_1-C_3)$alkoxy, trifluoromethyl or trifluoromethoxy;

or a salt of said compound.

5. The compound of claim 1, wherein $R^1$ is alkoxy;

or a salt of said compound.

6. The compound of claim 1, wherein E is one of the following groups:

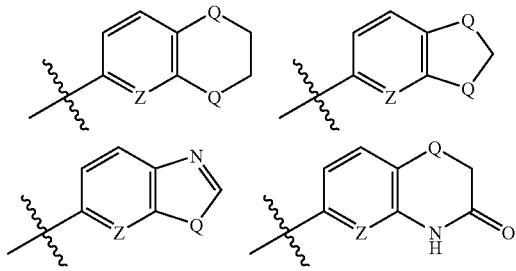

wherein Z is CH or N and Q is O or S;
or a salt of said compound.

7. The compound of claim 6, wherein E is 2,3-dihydro-benzo[1,4]dioxin-6-yl, 3-oxo-3,4-dihydro-2H-benzo[1,4]thiazine-6-yl or 3-oxo-3,4-dihydro-2H-benzo[1,4]oxazine-6-yl;
or a salt of said compound.

8. The compound of claim 1, wherein E is a phenyl group which is substituted once or twice in the meta and/or para position(s) by substituents each independently selected from halogen, (C$_1$-C$_3$)alkyl, (C$_1$-C$_3$)alkoxy, trifluoromethyl or trifluoromethoxy;
or a salt of said compound.

9. The compound of claim 1, wherein said compound is:
(E)-[(S)-3-(2,3-dihydro-benzo[1,4]dioxin-6-yl)-2-oxo-oxazolidin-5-ylmethyl]-3-(6-methoxy-[1,5]naphthyridin-4-yl)-acrylamide;
(E)-[(S)-3-(2,3-dihydro-benzo[1,4]dioxin-6-yl)-2-oxo-oxazolidin-5-ylmethyl]-3-(6-methoxy-quinolin-4-yl)-acrylamide;
(E)-[(R)-3-(2,3-dihydro-benzo[1,4]dioxin-6-yl)-2-oxo-oxazolidin-5-ylmethyl]-3-(6-methoxy-[1,5]naphthyridin-4-yl)-acrylamide;
(E)-3-(6-methoxy-[1,5]naphthyridin-4-yl)-N-[(R)-2-oxo-3-(3-oxo-3,4-dihydro-2H-benzo[1,4]thiazin-6-yl)-oxazolidin-5-ylmethyl]-acrylamide;
(E)-N-[(R)-3-(2,3-dihydro-benzo[1,4]dioxin-6-yl)-2-oxo-oxazolidin-5-ylmethyl]-3-(3-methoxy-quinoxalin-5-yl)-acrylamide;
(E)-N-[(R)-3-(2,3-dihydro-benzo[1,4]dioxin-6-yl)-2-oxo-oxazolidin-5-ylmethyl]-3-(3-methoxy-quinolin-5-yl)-acrylamide;
(E)-N-[(R)-3-(2,3-dihydro-benzo[1,4]dioxin-6-yl)-2-oxo-oxazolidin-5-ylmethyl]-N-ethyl-3-(6-methoxy-[1,5]naphthyridin-4-yl)-acrylamide;
(E)-N-benzyl-N-[3-(2,3-dihydro-benzo[1,4]dioxin-6-yl)-2-oxo-oxazolidin-5-ylmethyl]-3-(6-methoxy-[1,5]naphthyridin-4-yl)-acrylamide;
(E)-3-(3-methoxy-quinoxalin-5-yl)-N-[(R)-2-oxo-3-(3-oxo-3,4-dihydro-2H-benzo[1,4]thiazin-6-yl)-oxazolidin-5-ylmethyl]-acrylamide;
(E)-3-(3-methoxy-quinolin-5-yl)-N-[(R)-2-oxo-3-(3-oxo-3,4-dihydro-2H-benzo[1,4]thiazin-6-yl)-oxazolidin-5-ylmethyl]-acrylamide;
(E)-3-(6-methoxy-[1,5]naphthyridin-4-yl)-N-methyl-N-[(R)-2-oxo-3-(3-oxo-3,4-dihydro-2H-benzo[1,4]thiazin-6-yl)-oxazolidin-5-ylmethyl]-acrylamide;
(E)-N-[(R)-3-(3-fluoro-4-methyl-phenyl)-2-oxo-oxazolidin-5-ylmethyl]-3-(6-methoxy-[1,5]naphthyridin-4-yl)-acrylamide;
(E)-N-[(R)-3-(3-fluoro-4-methyl-phenyl)-2-oxo-oxazolidin-5-ylmethyl]-3-(6-methoxy-[1,5]naphthyridin-4-yl)-N-methyl-acrylamide;
(E)-N-[(R)-3-(4-ethyl-phenyl)-2-oxo-oxazolidin-5-ylmethyl]-3-(6-methoxy-[1,5]naphthyridin-4-yl)-N-methyl-acrylamide;
(E)-3-(6-methoxy-[1,5]naphthyridin-4-yl)-N-methyl-N-[(R)-2-oxo-3-(4-propyl-phenyl)-oxazolidin-5-ylmethyl]-acrylamide;
(E)-3-(2-cyano-quinolin-8-yl)-N-[(R)-3-(2,3-dihydro-benzo[1,4]dioxin-6-yl)-2-oxo-oxazolidin-5-ylmethyl]-acrylamide;
(E)-N-[(R)-3-(2,3-dihydro-benzo[1,4]dioxin-6-yl)-2-oxo-oxazolidin-5-ylmethyl]-3-(6-fluoro-quinolin-4-yl)-acrylamide;
(E)-N-[(R)-3-(2,3-dihydro-benzo[1,4]dioxin-6-yl)-2-oxo-oxazolidin-5-ylmethyl]-3-(2-methoxy-quinolin-8-yl)-acrylamide;
(E)-3-(6-methoxy-[1,5]naphthyridin-4-yl)-N-methyl-N-[(R)-3-(4-methyl-3-trifluoromethyl-phenyl)-2-oxo-oxazolidin-5-ylmethyl]-acrylamide;
(E)-N-[(R)-3-(3-bromo-4-methyl-phenyl)-2-oxo-oxazolidin-5-ylmethyl]-3-(6-methoxy-[1,5]naphthyridin-4-yl)-N-methyl-acrylamide;
(E)-N-[(R)-3-(4-bromo-3-methyl-phenyl)-2-oxo-oxazolidin-5-ylmethyl]-3-(6-methoxy-[1,5]naphthyridin-4-yl)-N-methyl-acrylamide;
(E)-N-[(R)-3-(4-bromo-3-fluoro-phenyl)-2-oxo-oxazolidin-5-ylmethyl]-3-(6-methoxy-[1,5]naphthyridin-4-yl)-N-methyl-acrylamide;
(E)-N-[(S)-3-(3-fluoro-4-methyl-phenyl)-2-oxo-oxazolidin-5-ylmethyl]-3-(6-methoxy-[1,5]naphthyridin-4-yl)-N-methyl-acrylamide;
(E)-3-(6-methoxy-[1,5]naphthyridin-4-yl)-N-methyl-N-[(S)-2-oxo-3-(3-oxo-3,4-dihydro-2H-benzo[1,4]thiazin-6-yl)-oxazolidin-5-ylmethyl]-acrylamide;
(E)-N-[(S)-3-(2,3-dihydro-benzo[1,4]dioxin-6-yl)-2-oxo-oxazolidin-5-ylmethyl]-3-(6-methoxy-[1,5]naphthyridin-4-yl)-N-methyl-acrylamide;
(E)-N-[(S)-3-(4-ethyl-phenyl)-2-oxo-oxazolidin-5-ylmethyl]-3-(3-methoxy-quinoxalin-5-yl)-N-methyl-acrylamide;
N-[(R)-3-(2,3-dihydro-benzo[1,4]dioxin-6-yl)-2-oxo-oxazolidin-5-ylmethyl]-3-(6-methoxy-[1,5]naphthyridin-4-yl)-propionamide;
3-(3-methoxy-quinolin-5-yl)-N-[(R)-2-oxo-3-(3-oxo-3,4-dihydro-2H-benzo[1,4]thiazin-6-yl)-oxazolidin-5-ylmethyl]-propionamide;
(R)-3-(2,3-dihydro-benzo[1,4]dioxin-6-yl)-5-{[(E)-3-(6-methoxy-[1,5]naphthyridin-4-yl)-allylamino]-methyl}-oxazolidin-2-one;
(R)-3-(2,3-dihydro-benzo[1,4]dioxin-6-yl)-5-{[3-(6-methoxy-[1,5]naphthyridin-4-yl)-propylamino]-methyl}-oxazolidin-2-one;
N-[(R)-3-(2,3-dihydro-benzo[1,4]dioxin-6-yl)-2-oxo-oxazolidin-5-ylmethyl]-N-[(E)-3-(6-methoxy-[1,5]naphthyridin-4-yl)-allyl]-acetamide;
6-((R)-5-{[(E)-3-(6-methoxy-[1,5]naphthyridin-4-yl)-allylamino]-methyl}-2-oxo-oxazolidin-3-yl)-4H-benzo[1,4]thiazin-3-one;
6-((R)-5-{[3-(6-methoxy-[1,5]naphthyridin-4-yl)-propylamino]-methyl}-2-oxo-oxazolidin-3-yl)-4H-benzo[1,4]thiazin-3-one;
6-(5-{[3-(6-methoxy-[1,5]naphthyridin-4-yl)-propylamino]-methyl}-2-oxo-oxazolidin-3-yl)-4H-benzo[1,4]oxazin-3-one;

6-((R)-5-{[3-(3-methoxy-quinolin-5-yl)-propylamino]-methyl}-2-oxo-oxazolidin-3-yl)-4H-benzo[1,4]thiazin-3-one;

N-[(R)-3-(2,3-dihydro-benzo[1,4]dioxin-6-yl)-2-oxo-oxazolidin-5-ylmethyl]-N-[3-(6-methoxy-[1,5]naphthyridin-4-yl)-propyl]-acetamide;

N-[3-(6-methoxy-[1,5]naphthyridin-4-yl)-propyl]-N-[(R)-2-oxo-3-(3-oxo-3,4-dihydro-2H-benzo[1,4]thiazin-6-yl)-oxazolidin-5-ylmethyl]-succinamic acid;

N-[3-(6-methoxy-[1,5]naphthyridin-4-yl)-propyl]-N-[(R)-2-oxo-3-(3-oxo-3,4-dihydro-2H-benzo[1,4]thiazin-6-yl)-oxazolidin-5-ylmethyl]-propionamide;

(R)-3-(2,3-dihydro-benzo[1,4]dioxin-6-yl)-5-({ethyl-[3-(6-methoxy-[1,5]naphthyridin-4-yl)-propyl]-amino}-methyl)-oxazolidin-2-one;

5-({benzyl-[3-(6-methoxy-[1,5]naphthyridin-4-yl)-propyl]-amino}-methyl)-3-(2,3-dihydro-benzo[1,4]dioxin-6-yl)-oxazolidin-2-one;

(R)-5-({(2-amino-ethyl)-[3-(6-methoxy-[1,5]naphthyridin-4-yl)-propyl]-amino}-methyl)-3-(2,3-dihydro-benzo[1,4]dioxin-6-yl)-oxazolidin-2-one;

6-[(R)-5-({[3-(3-methoxy-quinolin-5-yl)-propyl]-methyl-amino}-methyl)-2-oxo-oxazolidin-3-yl]-4H-benzo[1,4]thiazin-3-one;

(R)-3-(3-fluoro-4-methyl-phenyl)-5-({[3-(3-methoxy-quinolin-5-yl)-propyl]-methyl-amino}-methyl)-oxazolidin-2-one;

(R)-5-({[3-(3-methoxy-quinolin-5-yl)-propyl]-methyl-amino}-methyl)-3-(4-methyl-3-trifluoromethyl-phenyl)-oxazolidin-2-one;

(R)-3-(4-ethyl-phenyl)-5-({[3-(3-methoxy-quinolin-5-yl)-propyl]-methyl-amino}-methyl)-oxazolidin-2-one;

(R)-5-({[3-(3-methoxy-quinolin-5-yl)-propyl]-methyl-amino}-methyl)-3-(4-propyl-phenyl)-oxazolidin-2-one;

(R)-3-(3-bromo-4-methyl-phenyl)-5-({[3-(3-methoxy-quinolin-5-yl)-propyl]-methyl-amino}-methyl)-oxazolidin-2-one;

(R)-3-(4-bromo-3-methyl-phenyl)-5-({[3-(3-methoxy-quinolin-5-yl)-propyl]-methyl-amino}-methyl)-oxazolidin-2-one;

(R)-3-(4-bromo-3-fluoro-phenyl)-5-({[3-(3-methoxy-quinolin-5-yl)-propyl]-methyl-amino}-methyl)-oxazolidin-2-one;

(S)-3-(3-fluoro-4-methyl-phenyl)-5-({[3-(3-methoxy-quinolin-5-yl)-propyl]-methyl-amino}-methyl)-oxazolidin-2-one;

(S)-3-(2,3-dihydro-benzo[1,4]dioxin-6-yl)-2-oxo-oxazolidine-5-carboxylic acid [3-(6-methoxy-[1,5]naphthyridin-4-yl)-propyl]-amide;

6-(5-{[2,3-dihydroxy-3-(6-methoxy-[1,5]naphthyridin-4-yl)-propylamino]-methyl}-2-oxo-oxazolidin-3-yl)-4H-benzo[1,4]thiazin-3-one;

(2S,3R)-N-[(S)-3-(2,3-dihydro-benzo[1,4]dioxin-6-yl)-2-oxo-oxazolidin-5-ylmethyl]-2,3-dihydroxy-3-(6-methoxy-[1,5]naphthyridin-4-yl)-propionamide;

(2R,3S)-2,3-dihydroxy-3-(6-methoxy-[1,5]naphthyridin-4-yl)-N-[(R)-2-oxo-3-(3-oxo-3,4-dihydro-2H-benzo[1,4]thiazin-6-yl)-oxazolidin-5-ylmethyl]-propionamide;

(2S,3R)-2,3-dihydroxy-3-(6-methoxy-[1,5]naphthyridin-4-yl)-N-[(R)-2-oxo-3-(3-oxo-3,4-dihydro-2H-benzo[1,4]thiazin-6-yl)-oxazolidin-5-ylmethyl]-propionamide;

N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-propionamide;

(R)-N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-propionamide;

(S)-N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-propionamide;

(Z)-N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-acrylamide;

(R)-3-(2,3-dihydro-benzo[1,4]dioxin-6-yl)-5-{[3-hydroxy-3-(6-methoxy-[1,5]naphthyridin-4-yl)-propylamino]-methyl}-oxazolidin-2-one;

3-(2,3-dihydro-benzo[1,4]dioxin-6-yl)-5-[5-hydroxy-5-(6-methoxy-[1,5]naphthyridin-4-yl)-pentyl]-oxazolidin-2-one;

3-(2,3-dihydro-benzo[1,4]dioxin-6-yl)-5-[5-(3-fluoro-6-methoxy-[1,5]naphthyridin-4-yl)-5-hydroxy-pentyl]-oxazolidin-2-one;

(R)-3-(2,3-dihydro-benzo[1,4]dioxin-6-yl)-5-[5-(6-methoxy-[1,5]naphthyridin-4-yl)-5-oxo-pentyl]-oxazolidin-2-one;

(S)-3-(2,3-dihydro-benzo[1,4]dioxin-6-yl)-5-[5-(6-methoxy-[1,5]naphthyridin-4-yl)-5-oxo-pentyl]-oxazolidin-2-one;

5-[(5-amino-5-(6-methoxy-[1,5]naphthyridin-4-yl)-pentyl]-3-(2,3-dihydro-benzo[1,4]dioxin-6-yl)-oxazolidin-2-one;

3-(2,3-dihydro-benzo[1,4]dioxin-6-yl)-5-[4-(6-methoxy-quinazolin-4-ylamino)-butyl]-oxazolidin-2-one;

N-[(R)-3-(2,3-dihydro-benzo[1,4]dioxin-6-yl)-2-oxo-oxazolidin-5-ylmethyl]-2-hydroxy-3-(6-methoxy-[1,5]naphthyridin-4-yl)-propionamide;

2-hydroxy-3-(6-methoxy-[1,5]naphthyridin-4-yl)-N-[(R)-2-oxo-3-(3-oxo-3,4-dihydro-2H-benzo[1,4]thiazin-6-yl)-oxazolidin-5-ylmethyl]-propionamide;

2-amino-N-[(R)-3-(2,3-dihydro-benzo[1,4]dioxin-6-yl)-2-oxo-oxazolidin-5-ylmethyl]-3-hydroxy-3-(6-methoxy-[1,5]naphthyridin-4-yl)-propionamide;

2-amino-N-[(R)-3-(2,3-dihydro-benzo[1,4]dioxin-6-yl)-2-oxo-oxazolidin-5-ylmethyl]-3-(6-methoxy-[1,5]naphthyridin-4-yl)-propionamide;

(5R)-5-{[2-amino-3-(6-methoxy-[1,5]naphthyridin-4-yl)-propylamino]-methyl}-3-(2,3-dihydro-benzo[1,4]dioxin-6-yl)-oxazolidin-2-one;

(S)-3-(2,3-dihydro-benzo[1,4]dioxin-6-yl)-2-oxo-oxazolidine-5-carboxylic acid [3-(6-methoxy-[1,5]naphthyridin-4-yl)-prop-2-ynyl]-amide;

(R)-3-(2,3-dihydro-benzo[1,4]dioxin-6-yl)-5-{2-[2-(6-methoxy-[1,5]naphthyridin-4-yl)-ethylamino]-ethyl}-oxazolidin-2-one;

6-(5-{2-[2-(6-methoxy-[1,5]naphthyridin-4-yl)-ethylamino]-ethyl}-2-oxo-oxazolidin-3-yl)-4H-benzo[1,4]thiazin-3-one;

6-(5-{2-[2-(3-fluoro-6-methoxy-[1,5]naphthyridin-4-yl)-ethylamino]-ethyl}-2-oxo-oxazolidin-3-yl)-4H-benzo[1,4]thiazin-3-one;

N-{2-[3-(2,3-dihydro-benzo[1,4]dioxin-6-yl)-2-oxo-oxazolidin-5-yl]-ethyl}-2-(3-methoxy-quinoxalin-5-yl)-acetamide;

6-methoxy-quinoline-4-carboxylic acid {3-[2-oxo-3-(3-oxo-3,4-dihydro-2H-benzo[1,4]thiazin-6-yl)-oxazolidin-5-yl]-propyl}-amide;

6-(5-{3-[(6-methoxy-[1,5]naphthyridin-4-ylmethyl)-amino]-propyl}-2-oxo-oxazolidin-3-yl)-4H-benzo[1,4]thiazin-3-one;

6-(5-3-[(3-fluoro-6-methoxy-[1,5]naphthyridin-4-ylmethyl)-amino]-propyl-2-oxo-oxazolidin-3-yl)-4H-benzo[1,4]thiazin-3-one;

6-(5-{3-[(3-fluoro-6-methoxy-quinolin-4-ylmethyl)-amino]-propyl}-2-oxo-oxazolidin-3-yl)-4H-benzo[1,4]thiazin-3-one;

N-(6-methoxy-[1,5]naphthyridin-4-yl)-4-[2-oxo-3-(3-oxo-3,4-dihydro-2H-benzo[1,4]thiazin-6-yl)-oxazolidin-5-yl]-butyramide;

(S)-3-(2,3-dihydro-benzo[1,4]dioxin-6-yl)-5-{[2-(6-methoxy-[1,5]naphthyridin-4-ylamino)-ethylamino]-methyl}-oxazolidin-2-one;

(S)-3-(2,3-dihydro-benzo[1,4]dioxin-6-yl)-2-oxo-oxazolidine-5-carboxylic acid [2-(6-methoxy-[1,5]naphthyridin-4-ylamino)-ethyl]-amide;

(S)-2-{[(R)-3-(2,3-dihydro-benzo[1,4]dioxin-6-yl)-2-oxo-oxazolidin-5-ylmethyl]-amino}-N-(6-methoxy-[1,5]naphthyridin-4-yl)-propionamide;

2-{[(R)-3-(2,3-dihydro-benzo[1,4]dioxin-6-yl)-2-oxo-oxazolidin-5-ylmethyl]-amino}-N-(6-methoxy-[1,5]naphthyridin-4-yl)-acetamide;

2-[(R)-3-(2,3-dihydro-benzo[1,4]dioxin-6-yl)-2-oxo-oxazolidin-5-yl]-N-[2-(6-methoxy-quinolin-4-yl)-ethyl]-acetamide;

(S)-3-(2,3-dihydro-benzo[1,4]dioxin-6-yl)-5-({[3-(3-methoxy-quinolin-5-yl)-propyl]-methyl-amino}-methyl)-oxazolidin-2-one;

N-[(R)-3-(3-fluoro-4-methyl-phenyl)-2-oxo-oxazolidin-5-ylmethyl]-3-(3-methoxy-quinolin-5-yl)-N-methyl-propionamide;

2-[(R)-3-(2,3-dihydro-benzo[1,4]dioxin-6-yl)-2-oxo-oxazolidin-5-yl]-N-[(R)-2-hydroxy-2-(3-methoxy-quinoxalin-5-yl)-ethyl]-N-methyl-acetamide;

6-((R)-5-{[2-amino-3-(6-methoxy-[1,5]naphthyridin-4-yl)-propylamino]-methyl}-2-oxo-oxazolidin-3-yl)-4H-benzo[1,4]thiazin-3-one;

6-(5-{3-[(6-fluoro-quinolin-5-ylmethyl)-amino]-propyl}-2-oxo-oxazolidin-3-yl)-4H-benzo[1,4]thiazin-3-one;

N-(6-methoxy-[1,5]naphthyridin-4-yl)-2-{[(R)-2-oxo-3-(3-oxo-3,4-dihydro-2H-benzo[1,4]thiazin-6-yl)-oxazolidin-5-ylmethyl]-amino}-acetamide;

(R*)-3-(2,3-dihydro-benzo[1,4]dioxin-6-yl)-5-{2-[(R*)-2-hydroxy-2-(3-methoxy-quinoxalin-5-yl)-ethylamino]-ethyl}-oxazolidin-2-one;

N-[(R)-2-hydroxy-2-(6-methoxy-[1,5]naphthyridin-4-yl)-ethyl]-N-methyl-2-[(R)-2-oxo-3-(3-oxo-3,4-dihydro-2H-benzo[1,4]thiazin-6-yl)-oxazolidin-5-yl]-acetamide;

(S)-3-(2,3-dihydro-benzo[1,4]dioxin-6-yl)-5-[3-(6-methoxy-[1,5]naphthyridin-4-yl)-propoxymethyl]-oxazolidin-2-one;

3-(2,3-dihydro-benzo[1,4]dioxin-6-yl)-5-[(E)-3-(6-methoxy-[1,5]naphthyridin-4-yl)-allyloxymethyl]-oxazolidin-2-one;

N-[2-(6-methoxy-[1,5]naphthyridin-4-yl)-ethyl]-2-[(R)-2-oxo-3-(3-oxo-3,4-dihydro-2H-benzo[1,4]thiazin-6-yl)-oxazolidin-5-yl]-acetamide;

(R*)-3-(2,3-dihydro-benzo[1,4]dioxin-6-yl)-5-{(R*)-1-hydroxy-2-[2-(6-methoxy-[1,5]naphthyridin-4-yl)-ethylamino]-ethyl}-oxazolidin-2-one;

(R*)-3-(2,3-dihydro-benzo[1,4]dioxin-6-yl)-5-{(R*)-1-hydroxy-2-[2-(6-methoxy-quinolin-4-yl)-ethylamino]-ethyl}-oxazolidin-2-one;

(R*)-3-(2,3-dihydro-benzo[1,4]dioxin-6-yl)-5-((R*)-1-hydroxy-2-{[2-(6-methoxy-[1,5]naphthyridin-4-yl)-ethyl]-methyl-amino}-ethyl)-oxazolidin-2-one;

(R*)-3-(2,3-dihydro-benzo[1,4]dioxin-6-yl)-(R*)-5-(1-hydroxy-2-{[2-hydroxy-2-(3-methoxy-quinoxalin-5-yl)-ethyl]-methyl-amino}-ethyl)-oxazolidin-2-one;

6-((S)-5-{(S)-1-hydroxy-2-[2-(6-methoxy-[1,5]naphthyridin-4-yl)-ethylamino]-ethyl}-2-oxo-oxazolidin-3-yl)-4H-benzo[1,4]thiazin-3-one;

(S)-3-(2,3-dihydro-benzo[1,4]dioxin-6-yl)-5-{(S)-1-hydroxy-2-[2-hydroxy-2-(3-methoxy-quinoxalin-5-yl)-ethylamino]-ethyl}-oxazolidin-2-one;

6-((R*)-5-{(R*)-1-hydroxy-3-[(6-methoxy-[1,5]naphthyridin-4-ylmethyl)-amino]-propyl}-2-oxo-oxazolidin-3-yl)-4H-benzo[1,4]thiazin-3-one;

6-((R*)-5-{(R*)-3-[(3-fluoro-6-methoxy-[1,5]naphthyridin-4-ylmethyl)-amino]-1-hydroxy-propyl}-2-oxo-oxazolidin-3-yl)-4H-benzo[1,4]thiazin-3-one;

(R*)-3-(2,3-dihydro-benzo[1,4]dioxin-6-yl)-5-{(R*)-3-[(3-fluoro-6-methoxy-[1,5]naphthyridin-4-ylmethyl)-amino]-1-hydroxy-propyl}-oxazolidin-2-one;

(S*)-3-(2,3-dihydro-benzo[1,4]dioxin-6-yl)-5-{(R*)-3-[(3-fluoro-6-methoxy-[1,5]naphthyridin-4-ylmethyl)-amino]-1-hydroxy-propyl}-oxazolidin-2-one;

(S*)-5-{(R*)-1-amino-3-[(3-fluoro-6-methoxy-[1,5]naphthyridin-4-ylmethyl)-amino]-propyl}-3-(2,3-dihydro-benzo[1,4]dioxin-6-yl)-oxazolidin-2-one;

(R)-3-(2,3-dihydro-benzo[1,4]dioxin-6-yl)-5-[(E)-4-(6-methoxy-quinolin-4-yloxy)-but-2-enyl]-oxazolidin-2-one;

3-(2,3-dihydro-benzo[1,4]dioxin-6-yl)-5-[4-(6-methoxy-quinolin-4-yloxy)-butyl]-oxazolidin-2-one;

3-[3-(2,3-dihydro-benzo[1,4]dioxin-6-yl)-2-oxo-oxazolidin-5-yl]-N-(3-methoxy-quinoxalin-5-ylmethyl)-N-methyl-propionamide;

(R*)-3-(2,3-dihydro-benzo[1,4]dioxin-6-yl)-5-[(R*)-1-hydroxy-5-(6-methoxy-[1,5]naphthyridin-4-yl)-pentyl]-oxazolidin-2-one;

(R)-3-(2,3-dihydro-benzo[1,4]dioxin-6-yl)-5-{[4-(6-methoxy-[1,5]naphthyridin-4-yl)-butylamino]-methyl}-oxazolidin-2-one;

6-((R)-5-{[4-(6-methoxy-[1,5]naphthyridin-4-yl)-butylamino]-methyl}-2-oxo-oxazolidin-3-yl)-4H-benzo[1,4]thiazin-3-one;

3-(2,3-dihydro-benzo[1,4]dioxin-6-yl)-5-[3-hydroxy-5-(6-methoxy-[1,5]naphthyridin-4-yl)-pentyl]-oxazolidin-2-one;

3-(2,3-dihydro-benzo[1,4]dioxin-6-yl)-5-[5-(6-methoxy-[1,5]naphthyridin-4-yl)-3-oxo-pentyl]-oxazolidin-2-one;

5-[3-amino-5-(6-methoxy-[1,5]naphthyridin-4-yl)-pentyl]-3-(2,3-dihydro-benzo[1,4]dioxin-6-yl)-oxazolidin-2-one;

N-[1-{2-[3-(2,3-dihydro-benzo[1,4]dioxin-6-yl)-2-oxo-oxazolidin-5-yl]-ethyl}-3-(6-methoxy-[1,5]naphthyridin-4-yl)-propyl]-methanesulfonamide;

N-[1-{2-[3-(2,3-dihydro-benzo[1,4]dioxin-6-yl)-2-oxo-oxazolidin-5-yl]-ethyl}-3-(6-methoxy-[1,5]naphthyridin-4-yl)-propyl]-acetamide;

3-(2,3-dihydro-benzo[1,4]dioxin-6-yl)-5-[3-(7-fluoro-2-methoxy-quinolin-8-ylmethoxy)-propyl]-oxazolidin-2-one;

3-(2,3-dihydro-benzo[1,4]dioxin-6-yl)-5-[3-(6-methoxy-quinolin-4-ylmethoxy)-propyl]-oxazolidin-2-one;

3-(2,3-dihydro-benzo[1,4]dioxin-6-yl)-5-[3-(6-methoxy-quinazolin-4-yloxy)-propyl]-oxazolidin-2-one;

6-{5-[3-hydroxy-5-(6-methoxy-[1,5]naphthyridin-4-yl)-pentyl]-2-oxo-oxazolidin-3-yl}-4H-benzo[1,4]thiazin-3-one;

3-(2,3-dihydro-benzo[1,4]dioxin-6-yl)-5-[2-hydroxy-5-(6-methoxy-[1,5]naphthyridin-4-yl)-pentyl]-oxazolidin-2-one;

3-(2,3-dihydro-benzo[1,4]dioxin-6-yl)-5-[5-(6-methoxy-[1,5]naphthyridin-4-yl)-pentyl]-oxazolidin-2-one;

6-{(R)-5-[5-(6-methoxy-[1,5]naphthyridin-4-yl)-pentyl]-2-oxo-oxazolidin-3-yl}-4H-benzo[1,4]thiazin-3-one;

6-(5-{2-[2-(6-methoxy-[1,5]naphthyridin-4-yl)-ethylamino]-ethyl}-2-oxo-oxazolidin-3-yl)-4H-benzo[1,4]oxazin-3-one;

6-[5-(2-{((R)-2,3-dihydroxy-propyl)-[2-(6-methoxy-[1,5]naphthyridin-4-yl)-ethyl]-amino}-ethyl)-2-oxo-oxazolidin-3-yl]-4H-benzo[1,4]oxazin-3-one;

{{2-[3-(2,3-dihydro-benzo[1,4]dioxin-6-yl)-2-oxo-oxazolidin-5-yl]-ethyl}-[2-(6-methoxy-[1,5]naphthyridin-4-yl)-ethyl]-amino}-acetic acid tert-butyl ester;

3-{{2-[3-(2,3-dihydro-benzo[1,4]dioxin-6-yl)-2-oxo-oxazolidin-5-yl]-ethyl}-[2-(6-methoxy-[1,5]naphthyridin-4-yl)-ethyl]amino}-propionic acid methyl ester;

4-{{2-[3-(2,3-dihydro-benzo[1,4]dioxin-6-yl)-2-oxo-oxazolidin-5-yl]-ethyl}-[2-(6-methoxy-[1,5]naphthyridin-4-yl)-ethyl]-amino}-butyric acid ethyl ester;

6-((R)-5-{[3-(6-methoxy-[1,5]naphthyridin-4-yl)-propylamino]-methyl}-2-oxo-oxazolidin-3-yl)-4H-benzo[1,4]oxazin-3-one;

6-((R)-5-{[3-(3-fluoro-6-methoxy-[1,5]naphthyridin-4-yl)-propylamino]-methyl}-2-oxo-oxazolidin-3-yl)-4H-benzo[1,4]oxazin-3-one;

6-((R)-5-{[3-(3-fluoro-6-methoxy-[1,5]naphthyridin-4-yl)-propylamino]-methyl}-2-oxo-oxazolidin-3-yl)-4H-benzo[1,4]thiazin-3-one;

(R)-3-(2,3-dihydro-benzo[1,4]dioxin-6-yl)-5-{[3-(3-fluoro-6-methoxy-[1,5]naphthyridin-4-yl)-propylamino]-methyl}-oxazolidin-2-one;

(R)-3-(2,3-dihydro-benzo[1,4]dioxin-6-yl)-5-({((S)-2,3-dihydroxy-propyl)-[3-(3-fluoro-6-methoxy-[1,5]naphthyridin-4-yl)-propyl]-amino}-methyl)-oxazolidin-2-one;

6-[(R)-5-({((S)-2,3-dihydroxy-propyl)-[3-(3-fluoro-6-methoxy-[1,5]naphthyridin-4-yl)-propyl]-amino}-methyl)-2-oxo-oxazolidin-3-yl]-4H-benzo[1,4]thiazin-3-one;

6-[(R)-5-({((R)-2,3-dihydroxy-propyl)-[3-(3-fluoro-6-methoxy-[1,5]naphthyridin-4-yl)-propyl]-amino}-methyl)-2-oxo-oxazolidin-3-yl]-4H-benzo[1,4]oxazin-3-one;

6-[(R)-5-({((R)-2,3-dihydroxy-propyl)-[3-(6-methoxy-[1,5]naphthyridin-4-yl)-propyl]-amino}-methyl)-2-oxo-oxazolidin-3-yl]-4H-benzo[1,4]oxazin-3-one;

{[(R)-3-(2,3-dihydro-benzo[1,4]dioxin-6-yl)-2-oxo-oxazolidin-5-ylmethyl]-[3-(6-methoxy-[1,5]naphthyridin-4-yl)-propyl]-amino}-acetic acid tert-butyl ester;

3-{[(R)-3-(2,3-dihydro-benzo[1,4]dioxin-6-yl)-2-oxo-oxazolidin-5-ylmethyl]-[3-(6-methoxy-[1,5]naphthyridin-4-yl)-propyl]-amino}-propionic acid methyl ester;

4-{[(R)-3-(2,3-dihydro-benzo[1,4]dioxin-6-yl)-2-oxo-oxazolidin-5-ylmethyl]-[3-(6-methoxy-[1,5]naphthyridin-4-yl)-propyl]amino}-butyric acid ethyl ester;

{[(R)-3-(2,3-dihydro-benzo[1,4]dioxin-6-yl)-2-oxo-oxazolidin-5-ylmethyl]-[3-(6-methoxy-[1,5]naphthyridin-4-yl)-propyl]-amino}-acetic acid;

3-{[(R)-3-(2,3-dihydro-benzo[1,4]dioxin-6-yl)-2-oxo-oxazolidin-5-ylmethyl]-[3-(6-methoxy-[1,5]naphthyridin-4-yl)-propyl]-amino}-propionic acid;

6-(5-{3-[(6-methoxy-[1,5]naphthyridin-4-ylmethyl)-amino]-propyl}-2-oxo-oxazolidin-3-yl)-4H-benzo[1,4]oxazin-3-one;

6-(5-{3-[(3-methoxy-quinoxalin-5-ylmethyl)-amino]-propyl}-2-oxo-oxazolidin-3-yl)-4H-benzo[1,4]oxazin-3-one;

6-(5-{3-[(6-methoxy-quinolin-4-ylmethyl)-amino]-propyl}-2-oxo-oxazolidin-3-yl)-4H-benzo[1,4]oxazin-3-one;

2-methoxy-8-({3-[2-oxo-3-(3-oxo-3,4-dihydro-2H-benzo[1,4]oxazin-6-yl)-oxazolidin-5-yl]-propylamino}-methyl)-quinoline-5-carboxylic acid methyl ester;

6-(5-{3-[(3-fluoro-6-methoxy-quinolin-4-ylmethyl)-amino]-propyl}-2-oxo-oxazolidin-3-yl)-4H-benzo[1,4]oxazin-3-one;

6-(5-{3-[(3-fluoro-6-methoxy-[1,5]naphthyridin-4-ylmethyl)-amino]-propyl}-2-oxo-oxazolidin-3-yl)-4H-benzo[1,4]oxazin-3-one;

6-(5-{3-[(7-fluoro-2-methoxy-quinolin-8-ylmethyl)-amino]-propyl}-2-oxo-oxazolidin-3-yl)-4H-benzo[1,4]oxazin-3-one;

6-(5-{3-[((R)-2,3-dihydroxy-propyl)-(3-fluoro-6-methoxy-[1,5]naphthyridin-4-ylmethyl)-amino]-propyl}-2-oxo-oxazolidin-3-yl)-4H-benzo[1,4]thiazin-3-one;

6-(5-{3-[((R)-3-chloro-2-hydroxy-propyl)-(3-fluoro-6-methoxy-[1,5]naphthyridin-4-ylmethyl)-amino]-propyl}-2-oxo-oxazolidin-3-yl)-4H-benzo[1,4]thiazin-3-one;

6-(5-{3-[((S)-3-dimethylamino-2-hydroxy-propyl)-(3-fluoro-6-methoxy-[1,5]naphthyridin-4-ylmethyl)-amino]-propyl}-2-oxo-oxazolidin-3-yl)-4H-benzo[1,4]thiazin-3-one;

6-(2-oxo-5-{3-[(quinolin-4-ylmethyl)-amino]-propyl}-oxazolidin-3-yl)-4H-benzo[1,4]thiazin-3-one;

6-(5-{3-[(naphthalen-1-ylmethyl)-amino]-propyl}-2-oxo-oxazolidin-3-yl)-4H-benzo[1,4]thiazin-3-one;

2-methoxy-8-({3-[2-oxo-3-(3-oxo-3,4-dihydro-2H-benzo[1,4]thiazin-6-yl)-oxazolidin-5-yl]-propylamino}-methyl)-quinoline-5-carboxylic acid methyl ester;

6-[5-(3-{[3-methoxy-8-(2-methoxy-ethoxy)-quinoxalin-5-ylmethyl]-amino}-propyl)-2-oxo-oxazolidin-3-yl]-4H-benzo[1,4]thiazin-3-one;

6-(5-{3-[(6-fluoro-quinolin-4-ylmethyl)-amino]-propyl}-2-oxo-oxazolidin-3-yl)-4H-benzo[1,4]thiazin-3-one;

6-(5-{3-[(3-methoxy-quinoxalin-5-ylmethyl)-amino]-propyl}-2-oxo-oxazolidin-3-yl)-4H-benzo[1,4]thiazin-3-one;

6-(5-{3-[(6-methoxy-quinolin-4-ylmethyl)-amino]-propyl}-2-oxo-oxazolidin-3-yl)-4H-benzo[1,4]thiazin-3-one;

6-(5-{3-[(isoquinolin-5-ylmethyl)-amino]-propyl}-2-oxo-oxazolidin-3-yl)-4H-benzo[1,4]thiazin-3-one;

6-(5-{3-[(4-methoxy-naphthalen-1-ylmethyl)-amino]-propyl}-2-oxo-oxazolidin-3-yl)-4H-benzo[1,4]thiazin-3-one;

6-(2-oxo-5-{3-[(quinolin-5-ylmethyl)-amino]-propyl}-oxazolidin-3-yl)-4H-benzo[1,4]thiazin-3-one;

6-(2-oxo-5-{3-[(quinolin-8-ylmethyl)-amino]-propyl}-oxazolidin-3-yl)-4H-benzo[1,4]thiazin-3-one;

6-(5-{3-[(4-hydroxy-naphthalen-1-ylmethyl)-amino]-propyl}-2-oxo-oxazolidin-3-yl)-4H-benzo[1,4]thiazin-3-one;

6-(5-{3-[(2-hydroxy-naphthalen-1-ylmethyl)-amino]-propyl}-2-oxo-oxazolidin-3-yl)-4H-benzo[1,4]thiazin-3-one;

6-(5-{3-[(7-fluoro-2-methoxy-quinolin-8-ylmethyl)-amino]-propyl}-2-oxo-oxazolidin-3-yl)-4H-benzo[1,4]thiazin-3-one;

6-(5-{3-[(2,3-dimethoxy-naphthalen-1-ylmethyl)-amino]-propyl}-2-oxo-oxazolidin-3-yl)-4H-benzo[1,4]thiazin-3-one;

6-(5-{3-[(4,7-dimethoxy-naphthalen-1-ylmethyl)-amino]-propyl}-2-oxo-oxazolidin-3-yl)-4H-benzo[1,4]thiazin-3-one;

((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-acetic acid tert-butyl ester;

3-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-propionic acid methyl ester;

4-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-butyric acid ethyl ester;

((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-acetic acid;

3-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-propionic acid;

4-((6-methoxy-[1,5]naphthyridin-4-ylmethyl)-{3-[2-oxo-3-(3-oxo-3,4-dihydro-2H-benzo[1,4]thiazin-6-yl)-oxazolidin-5-yl]-propyl}-amino)-butyric acid;

6-((R)-5-{3-[(3-fluoro-6-methoxy-[1,5]naphthyridin-4-ylmethyl)-amino]-propyl}-2-oxo-oxazolidin-3-yl)-4H-benzo[1,4]oxazin-3-one;

6-((R)-5-{3-[((S)-2,3-dihydroxy-propyl)-(3-fluoro-6-methoxy-[1,5]naphthyridin-4-ylmethyl)-amino]-propyl}-2-oxo-oxazolidin-3-yl)-4H-benzo[1,4]oxazin-3-one;

6-((R)-5-{3-[((R)-2,3-dihydroxy-propyl)-(3-fluoro-6-methoxy-[1,5]naphthyridin-4-ylmethyl)-amino]-propyl}-2-oxo-oxazolidin-3-yl)-4H-benzo[1,4]oxazin-3-one;

6-((R)-5-{3-[(3-fluoro-6-methoxy-[1,5]naphthyridin-4-ylmethyl)-(2-hydroxy-ethyl)-amino]-propyl}-2-oxo-oxazolidin-3-yl)-4H-benzo[1,4]oxazin-3-one;

(S)-3-(2,3-dihydro-benzo[1,4]dioxin-6-yl)-5-{(1R,2S)-1,2-dihydroxy-3-[(6-methoxy-[1,5]naphthyridin-4-ylmethyl)-amino]-propyl}-oxazolidin-2-one;

(S)-3-(2,3-dihydro-benzo[1,4]dioxin-6-yl)-5-{(1R,2S)-3-[(3-fluoro-6-methoxy-quinolin-4-ylmethyl)-amino]-1,2-dihydroxy-propyl}-oxazolidin-2-one;

(S)-3-(2,3-dihydro-benzo[1,4]dioxin-6-yl)-5-{(1R,2S)-1,2-dihydroxy-3-[(3-methoxy-quinoxalin-5-ylmethyl)-amino]-propyl}-oxazolidin-2-one;

(R)-3-(2,3-dihydro-benzo[1,4]dioxin-6-yl)-5-{(1R,2S)-1,2-dihydroxy-3-[(6-methoxy-[1,5]naphthyridin-4-ylmethyl)-amino]-propyl}-oxazolidin-2-one;

(R)-3-(2,3-dihydro-benzo[1,4]dioxin-6-yl)-5-{(1R,2S)-3-[(3-fluoro-6-methoxy-[1,5]naphthyridin-4-ylmethyl)-amino]-1,2-dihydroxy-propyl}-oxazolidin-2-one;

6-((S)-5-{(1R,2S)-1,2-dihydroxy-3-[(6-methoxy-[1,5]naphthyridin-4-ylmethyl)-amino]-propyl}-2-oxo-oxazolidin-3-yl)-4H-benzo[1,4]thiazin-3-one;

6-((S)-5-{(1R,2S)-3-[(3-fluoro-6-methoxy-[1,5]naphthyridin-4-ylmethyl)-amino]-1,2-dihydroxy-propyl}-2-oxo-oxazolidin-3-yl)-4H-benzo[1,4]thiazin-3-one;

6-((S)-5-{(1R,2S)-3-[(3-fluoro-6-methoxy-quinolin-4-ylmethyl)-amino]-1,2-dihydroxy-propyl}-2-oxo-oxazolidin-3-yl)-4H-benzo[1,4]thiazin-3-one;

(R)-3-(2,3-dihydro-benzo[1,4]dioxin-6-yl)-5-{(1S,2R)-1,2-dihydroxy-3-[(6-methoxy-[1,5]naphthyridin-4-ylmethyl)-amino]-propyl}-oxazolidin-2-one;

(R)-3-(2,3-dihydro-benzo[1,4]dioxin-6-yl)-5-{(1S,2R)-3-[(3-fluoro-6-methoxy-[1,5]naphthyridin-4-ylmethyl)-amino]-1,2-dihydroxy-propyl}-oxazolidin-2-one;

(S)-3-(2,3-dihydro-benzo[1,4]dioxin-6-yl)-5-{(1S,2R)-1,2-dihydroxy-3-[(6-methoxy-[1,5]naphthyridin-4-ylmethyl)-amino]-propyl}-oxazolidin-2-one;

6-((R)-5-{(1S,2R)-1,2-dihydroxy-3-[(6-methoxy-[1,5]naphthyridin-4-ylmethyl)-amino]-propyl}-2-oxo-oxazolidin-3-yl)-4H-benzo[1,4]thiazin-3-one;

6-((R)-5-{(1S,2R)-1,2-dihydroxy-3-[(3-methoxy-quinoxalin-5-ylmethyl)-amino]-propyl}-2-oxo-oxazolidin-3-yl)-4H-benzo[1,4]thiazin-3-one;

6-((R)-5-{(1S,2R)-3-[(3-fluoro-6-methoxy-[1,5]naphthyridin-4-ylmethyl)-amino]-1,2-dihydroxy-propyl}-2-oxo-oxazolidin-3-yl)-4H-benzo[1,4]thiazin-3-one;

6-((R)-5-{(1S,2R)-3-[(3-fluoro-6-methoxy-quinolin-4-ylmethyl)-amino]-1,2-dihydroxy-propyl}-2-oxo-oxazolidin-3-yl)-4H-benzo[1,4]thiazin-3-one;

6-((S)-5-{(1S,2R)-3-[(3-fluoro-6-methoxy-[1,5]naphthyridin-4-ylmethyl)-amino]-1,2-dihydroxy-propyl}-2-oxo-oxazolidin-3-yl)-4H-benzo[1,4]thiazin-3-one;

6-((R)-5-{(1S,2R)-3-[(3-fluoro-6-methoxy-[1,5]naphthyridin-4-ylmethyl)-amino]-1,2-dihydroxy-propyl}-2-oxo-oxazolidin-3-yl)-4H-benzo[1,4]oxazin-3-one;

6-((R)-5-{(1S,2R)-3-[(3-fluoro-6-methoxy-quinolin-4-ylmethyl)-amino]-1,2-dihydroxy-propyl}-2-oxo-oxazolidin-3-yl)-4H-benzo[1,4]oxazin-3-one;

6-((S)-5-{(1S,2R)-3-[(3-fluoro-6-methoxy-[1,5]naphthyridin-4-ylmethyl)-amino]-1,2-dihydroxy-propyl}-2-oxo-oxazolidin-3-yl)-4H-benzo[1,4]oxazin-3-one;

2-(6-methoxy-[1,5]naphthyridin-4-yloxy)-N-[(R)-2-oxo-3-(3-oxo-3,4-dihydro-2H-benzo[1,4]thiazin-6-yl)-oxazolidin-5-ylmethyl]-acetamide;

3-(3-fluoro-4-methyl-phenyl)-5-{2-[2-hydroxy-2-(3-methoxy-quinoxalin-5-yl)-ethylamino]-ethyl}-oxazolidin-2-one;

6-((R)-5-{[2-(6-methoxy-[1,5]naphthyridin-4-ylamino)-ethylamino]-methyl}-2-oxo-oxazolidin-3-yl)-4H-benzo[1,4]thiazin-3-one;

6-((R)-5-{[2-(6-methoxy-[1,5]naphthyridin-4-ylamino)-ethylamino]-methyl}-2-oxo-oxazolidin-3-yl)-4H-benzo[1,4]oxazin-3-one;

6-((S)-5-{3-[(3-fluoro-6-methoxy-[1,5]naphthyridin-4-ylmethyl)-amino]-propyl}-2-oxo-oxazolidin-3-yl)-4H-benzo[1,4]oxazin-3-one;

6-((R)-5-{[3-(6-methoxy-[1,5]naphthyridin-4-yl)-propylamino]-methyl}-2-oxo-oxazolidin-3-yl)-4H-pyrido[3,2-b][1,4]oxazin-3-one;

3-(2,3-dihydro-benzo[1,4]dioxin-6-yl)-5-{[(3-fluoro-6-methoxy-[1,5]naphthyridin-4-ylmethyl)-amino]-2-hydroxy-propyl}-oxazolidin-2-one;

6-((R)-5-{3-[(3-amino-propyl)-(3-fluoro-6-methoxy-[1,5]naphthyridin-4-ylmethyl)-amino]-propyl}-2-oxo-oxazolidin-3-yl)-4H-benzo[1,4]oxazin-3-one;

6-((R)-5-{3-[(3-fluoro-6-methoxy-[1,5]naphthyridin-4-ylmethyl)-(3-hydroxy-propyl)-amino]-propyl}-2-oxo-oxazolidin-3-yl)-4H-benzo[1,4]oxazin-3-one;

6-((S*)-5-{(S*)-3-[(3-fluoro-6-methoxy-[1,5]naphthyridin-4-ylmethyl)-amino]-1-hydroxy-propyl}-2-oxo-oxazolidin-3-yl)-4H-benzo[1,4]oxazin-3-one;

(S*)-5-{(S*)-1-amino-3-[(3-fluoro-6-methoxy-[1,5]naphthyridin-4-ylmethyl)-amino]-propyl}-3-(2,3-dihydro-benzo[1,4]dioxin-6-yl)-oxazolidin-2-one;

6-(5-{3-[(3-fluoro-6-methoxy-[1,5]naphthyridin-4-ylmethyl)-amino]-2-hydroxy-propyl}-2-oxo-oxazolidin-3-yl)-4H-benzo[1,4]thiazin-3-one;

6-(5-{3-[(3-fluoro-6-methoxy-quinolin-4-ylmethyl)-amino]-2-hydroxy-propyl}-2-oxo-oxazolidin-3-yl)-4H-benzo[1,4]thiazin-3-one;

6-(5-{3-[(3-fluoro-6-methoxy-[1,5]naphthyridin-4-ylmethyl)-amino]-2-hydroxy-propyl}-2-oxo-oxazolidin-3-yl)-4H-benzo[1,4]oxazin-3-one;

6-(5-{3-[(3-fluoro-6-methoxy-quinolin-4-ylmethyl)-amino]-2-hydroxy-propyl}-2-oxo-oxazolidin-3-yl)-4H-benzo[1,4]oxazin-3-one; or 6-(5-{3-[(7-fluoro-2-methoxy-quinolin-8-ylmethyl)-amino]-2-hydroxy-propyl}-2-oxo-oxazolidin-3-yl)-4H-benzo[1,4]oxazin-3-one;

or a salt of said compound.

10. A pharmaceutical composition comprising the compound of claim 1, or a pharmaceutically acceptable salt thereof, and at least one therapeutically inert excipient.

11. A method for treating bacterial infection comprising the step of administering to a patient in need thereof a therapeutically effective amount of the compound of claim 1, or a pharmaceutically acceptable salt thereof.

* * * * *